(12) United States Patent
Chuah et al.

(10) Patent No.: US 11,920,149 B2
(45) Date of Patent: Mar. 5, 2024

(54) DIAPHRAGM-SPECIFIC NUCLEIC ACID REGULATORY ELEMENTS AND METHODS AND USE THEREOF

(71) Applicant: VRIJE UNIVERSITEIT BRUSSEL, Brussels (BE)

(72) Inventors: Lay Khim Chuah, Bierbeek (BE); Thierry Vandendriessche, Bierbeek (BE); Warut Tulalamba, Brussels (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 843 days.

(21) Appl. No.: 16/498,690

(22) PCT Filed: Mar. 27, 2018

(86) PCT No.: PCT/EP2018/057753
§ 371 (c)(1),
(2) Date: Sep. 27, 2019

(87) PCT Pub. No.: WO2018/178067
PCT Pub. Date: Oct. 4, 2018

(65) Prior Publication Data
US 2020/0407749 A1    Dec. 31, 2020

(30) Foreign Application Priority Data

Mar. 27, 2017 (EP) .................................. 17163080

(51) Int. Cl.
| C12N 15/86 | (2006.01) |
| A61K 48/00 | (2006.01) |
| A61P 21/00 | (2006.01) |
| C12N 9/24 | (2006.01) |
| C12N 9/26 | (2006.01) |

(52) U.S. Cl.
CPC .............. *C12N 15/86* (2013.01); *A61K 48/00* (2013.01); *A61P 21/00* (2018.01); *C12N 9/2408* (2013.01); *C12Y 302/0102* (2013.01); *C12N 2750/14143* (2013.01); *C12N 2800/22* (2013.01); *C12N 2830/008* (2013.01)

(58) Field of Classification Search
None
See application file for complete search history.

(56) References Cited

U.S. PATENT DOCUMENTS

| 7,655,700 B2 | 2/2010 | Jordan et al. | |
| 2007/0161031 A1* | 7/2007 | Trinklein ............. | C12Q 1/6897 435/6.11 |

FOREIGN PATENT DOCUMENTS

| JP | 2009-519710 | 5/2009 |
| JP | 2017-505126 | 2/2017 |
| JP | 2017-521492 | 8/2017 |
| WO | 2007/025269 | 3/2007 |
| WO | 2007/078599 | 7/2007 |
| WO | 2008/073303 | 6/2008 |
| WO | 2015/110449 | 7/2015 |
| WO | 2015/197869 | 12/2015 |
| WO | 2016/016119 | 2/2016 |

OTHER PUBLICATIONS

Jaenecke and Diaz, Int Microbiol, Mar. 1999, 2(1):29-31. (Year: 1999).*
Powell et al., Discov Med., Jan. 2015, 19(102):49-57. (Year: 2015).*
Rasowo et al., European Scientific Journal, Jun. 2014, 10(18):23-37. (Year: 2014).*
Stuart et al., Am J Physiol Cell Physiol. Mar. 1, 2016; 310(5): C381-C389. (Year: 2016).*
Wei et al., Gene, May 2016, 582(1): 1-13. (Year: 2016).*
International Preliminary Report on Patentability dated Oct. 10, 2019 in International Application No. PCT/EP2018/057753.
Sato et al., "Resequencing of the common marmoset genome improves genome assemblies and gene-coding sequence analysis", Scientific Reports, 2015, vol. 5, No. 1, pp. 1-8.
Sequence 1 from Jordan et al., "Transgenic mouse model and methods for treatment of neuro muscular disease by interfering with androgen-androgen receptor interaction in skeletal muscles", U.S. Pat. No. 7,655,700, issued Feb. 2, 2010, 2 pages.
Sequence from Slepak et al., "Control of cardiac-specific transcription by p300 through myocyte enhancer factor-2D", Journal of Biological Chemistry, 2000, vol. 276, No. 10, pp. 7575-7585, 1 page.
Sequence 4138 from Trinklein et al., "Functional Arrays for High Throughput Characterization of Gene Expression Regulatory Elements", EP Patent 2021499 published as WO 2007/078599, 2013, 1 page.
"Aplha-actin promoter—Vp16-Bagly gene fusion", SEQ ID 84, Mar. 24, 2016. 2 pages.
"Human DNA sequence from clone RP5-1068B5 on chromosome 1q42. 11-43", Mar. 8, 2000, 2 pages.
"Human transcriptional regulatory element SEQ ID No. 7044", Dec. 11, 2008, 3 pages.
Bishopric et al., "Adrenergic regulation of the skeletal α-actin gene promoter during myocardial cell hypertrophy", Proceedings National Academy of Sciences PNAS, 1991, vol. 88, No. 6, pp. 2132-2136.
"Callithrix jacchus DNA, clone: CJB1-183K21, sequence_id: CJB1-183K21.b.", Aug. 25, 2015, 2 pages.

(Continued)

*Primary Examiner* — Nicole Kinsey White
(74) *Attorney, Agent, or Firm* — Wenderoth, Lind & Ponack, L.L.P.

(57) ABSTRACT

The present invention relates to nucleic acid regulatory elements that are able to enhance diaphragm-specific expression of genes, in particular expression in diaphragm as such, or in combination with expression in cardiac muscle and/or skeletal muscle, methods employing these regulatory elements and uses of these elements. Expression cassettes and vectors containing these nucleic acid regulatory elements are also disclosed. The present invention is particularly useful for applications using gene therapy, more particularly diaphragm-directed gene therapy, and for vaccination purposes.

24 Claims, 31 Drawing Sheets

Specification includes a Sequence Listing.

(56) References Cited

OTHER PUBLICATIONS

Mogalle et al., "Quantification of Diaphragm Mechanics in Pompe Disease Using Dynamic 3D MRI", PLOS ONE, 2016, vol. 11, No. 7, pp. 1-24.
International Search Report dated Jul. 23, 2018 in International (PCT) Application No. PCT/EP2018/057753.
Slepak et al., "Control of Cardiac-specific Transcription by p300 through Myocyte Enhancer Factor-2D", Journal of Biological Chemistry, 2000, vol. 276, No. 10, pp. 7575-7585.
Office Action dated Mar. 8, 2022 in corresponding Japanese Patent Application No. 2019-553082, with English Translation, 12 pages.

\* cited by examiner

A

B

C

D

E

F

G

H

K

L

M

MYBPC1

N

ENO3

O

P

A

MYL2

B

MB

C

D

E

F

G

ALDOA

H

TPM1

A)

B)

C)

A)

B)

DIAPHRAGM-SPECIFIC NUCLEIC ACID REGULATORY ELEMENTS AND METHODS AND USE THEREOF

FIELD

The present invention relates to nucleic acid regulatory elements that are able to enhance diaphragm-specific expression of genes, methods employing these regulatory elements and use thereof. The invention further encompasses expression cassettes, vectors and pharmaceutical compositions comprising these regulatory elements. The present invention is particularly useful for applications using gene therapy, more particularly diaphragm-directed gene therapy, or gene editing, and for vaccination purposes.

BACKGROUND

The diaphragm is a sheet of internal skeletal muscle that extends across the bottom of the thoracic cavity. The diaphragm separates the thoracic cavity containing the heart and lungs, from the abdominal cavity and performs an important function in respiration: as the diaphragm contracts, the volume of the thoracic cavity increases, and air is drawn into the lungs. As with any organ or muscle, the diaphragm is subject to disorders and abnormalities, which come in many different forms and can stem from injury or illness. Consequently, diaphragm dysfunction can result in severe respiratory problems with potential fatal consequences. Diaphragmatic weakness and paralysis can be classified according to the anatomic region of abnormality. Diaphragmatic paralysis and weakness may be unilateral or bilateral, temporary or permanent, depending on the cause.

There are currently no effective cures available to treat the potential life-threatening diaphragm dysfunction in many of these and other muscle disorders. Hence, there is a need to establish effective cures by gene therapy to enable robust expression of the cognate therapeutic genes in the diaphragm. This requires the development of potent expression cassettes containing the genes of interest.

Consequently, there is a need to identify robust nucleic acid regulatory elements capable of substantially increasing transcription in the diaphragm. These nucleic acid regulatory elements are critically important for the regulation of gene expression in a tissue-specific manner. They are typically composed of clusters of transcription factor binding site (TFBS) motifs. The types and arrangement of TFBS and epigenetic modification patterns influence gene expression levels and specificity. Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take account of the importance of including evolutionary conserved regulatory motifs into the expression modules, which is particularly relevant for clinical translation.

There remains a need in the art for safe and efficient gene delivery to diaphragm, skeletal muscles and/or heart.

SUMMARY OF THE INVENTION

The present inventors have relied on a computational approach (cf. FIG. 1) to identify robust nucleic acid regulatory elements that boost gene expression at the transcriptional level in the diaphragm (i.e. diaphragm: Dph). This requires the following computational steps: (1) diaphragm-specific genes were identified that are highly and specifically expressed based on expression data from diaphragm; (2) publicly available databases (ENSEMBL) were used for extracting the sequences upstream of the Transcriptional Start Site (TSS) of the selected genes. 3) These sequences were then submitted into UCSC Genome Browser Database for locating the transcription start site in human genome. To extract the corresponding diaphragm nucleic acid regulatory elements, defined herein as nucleic acid regulatory elements, the sequences were selected based on the following criteria: a) rich TFBS content, b) epigenetic signatures associated with high DNase hypersensitivity or chromatin accessibility (i.e. histone modifications), and c) evolutionary conserved clusters of TFBS associated with highly expressed diaphragm-specific genes.

As shown in the experimental section, the inventors identified nucleic acid regulatory elements that will specifically enhance gene expression in diaphragm. In addition, the inventors identified nucleic acid regulatory elements with combined diaphragm-specific and other tissue-specific expression such as for skeletal muscle and cardiac and skeletal muscle expression. Exemplary, but not limiting, muscle- or heart-muscle-specific regulatory elements are those that identified previously in European Patent Applications WO2015/110449A1 and WO2011/051450A1.

This combination approach will hence allow robust expression in diaphragm as well as other tissues that are affected by particular diseases that affect both diaphragm and skeletal muscles such as e.g. MTM. However, for diseases such as GSD-II and DMD which affects different tissues such as the diaphragm, skeletal muscles and heart, a combination of diaphragm nucleic acid regulatory element with the skeletal muscle nucleic acid regulatory element and/or the cardiac nucleic acid element will be developed. The diaphragm regulatory elements and the combination of diaphragm and other tissues elements (skeletal muscle and/or cardiac elements) will subsequently be validated in vivo yielding efficient and multiple tissue-specific gene expression. This approach hence, allows for the use of lower and thus safer vector doses, while maximizing therapeutic efficacy.

The invention therefore provides the following aspects:

In the screening, 89 regulatory elements were identified that can increase the expression of a transgene in a gene therapy delivery system such as in a vector system such as in an AAV vector system, increasing expression in diaphragm tissue. These elements are depicted in Tables 3 and 4 below. Table 3 depicts the Diaphragm cis regulatory elements (denominations "Dph-CREs", "CREs" or "CRMs" or "SH" used herein are the same and interchangeable) (Dph-CREs) which are particularly relevant for increasing expression in diaphragm and skeletal muscle, while Table 4 depicts the Diaphragm CREs (Dph-CREs) which are particularly relevant for increasing expression in diaphragm, skeletal muscle and heart tissue. Seven of these CREs are present in both groups.

In particular, Dph-CRE02, Dph-CRE04, Dph-CRE58, Dph-CRE59, Dph-CRE60, Dph-CRE64, Dph-CRE06, Dph-CRE21, Dph-CRE41 and Dph-CRE18 (Table 3 & FIG. 5) have been validated in vivo for their high expression in diaphragm and skeletal muscle tissue. More particularly, Dph-CRE-02 Dph-CRE-64 and Dph-CRE-21 are preferred. Even more preferably, Dph-CRE64 is used for treating diseases which require upregulation of transgene expression in Diaphragm and skeletal muscle, and less in heart. In a specific embodiment, these Dph-CREs, more preferably the Dph-CRE64 (or Dph-CRE02 or CRE-21) are combined with muscle specific CRE Sk-SH4 (SEQ ID NO; 121). In a more preferred embodiment, said combination of CREs is coupled to the human desmin promoter, more preferably the 1,4 kb variant thereof (SEQ ID NO; 92). For treatment of MTM disease, said CRE-promoter combination is preferably driving the hMTM1 (SEQ ID NO: 95) or more preferably the codon optimized hMTM1 transgene (SEQ ID NO; 96).

Myotubular myopathy (MTM) affects primarily the skeletal muscles and diaphragm, whereas the heart is rarely affected. Hence, ideally expression of the therapeutic MTM1 transgene should be targeted to skeletal muscles and diaphragm but not the heart. Therefore the SK-SH4-hDes1.4 kb expression cassette is referred since in this cassette expression in skeletal muscle is high, while it is much lower in heart when combined with the (Dph-CRE-64) compared to e.g. the CSk-SH5-SPc which result in widespread cardiac gene expression when combined with the top Dph-CREs such as the Dph-CRE-02, -04 & 06.

As an example, the most preferred AAV vector combination for treating MTM is defined by SEQ ID NO: 131, pAAVss-CRE64-Sk-SH4-hDES1.4 kb-MVM-hMTM1co-SynthpA.

Alternatively, Dph-CRE69, 70, 71, 66, 68, 77, 02, 04, 06, 07 (Table 4 and FIG. 5) have been validated in vivo for their high expression in diaphragm, skeletal muscle and heart tissue. More particularly, Dph-CRE-02, Dph-CRE-04 and CRE-06 are preferred. In a specific embodiment, said Dph-CREs, more preferably Dph-CRE-02, Dph-CRE04 (or Dph-CRE06) are combined with skeletal muscle and heart specific CRE CSk-SH5 (SEQ ID NO: 122). In a more preferred embodiment, said combination of CREs is coupled to the SPc5-12 promoter (SEQ ID NO: 124). SPc5-12 (sometimes called SPC-5-12-GTRM, which term is interchangeable). For treatment of e.g. Pompe disease, said CRE-promoter combination is preferably driving the hGAA (SEQ ID NO: 93) or more preferably the codon optimized hGAAco transgene (SEQ ID NO; 94).

The rationale for this design is based on the fact that in Pompe disease the GAA transgene is defective, which affects mainly skeletal muscles, diaphragm and the heart. Hence, ideally expression of the therapeutic GAA gene should be targeted to these affected tissues. The CSk-SH5-SPc combination leads to robust and specific expression in diaphragm, the skeletal muscles and heart and is therefore well suited to target those tissues that are affected in Pompe. As an example, the most preferred AAV vector combination for treating Pompe disease is defined by SEQ ID NO: 130). pAAVss-CRE04-CSk-SH5-SPc5-12GTRM-MVM-hGAAco-SynthpA (SEQ ID NO: 130).

Based on the above arguments, the present invention provides 10 different AAV constructs which were tested for expressing therapeutic genes:

1) pAAVss-hDes1.4 kb-MVM-hMTM1-SynthpA (no diaphragm CRE, no muscle CRE Sk-SH4, only Desmin1.4 kb promoter driving the MTM1 gene expression+MTM1) (SEQ ID NO; 135)

2) pAAVss-hDes1.4 kb-MVM-hMTMco-SynthpA (no diaphragm CRE, no muscle CRE Sk-SH4, +Des1.4 kb+codon opt MTM1) (SEQ ID NO; 134)

3) pAAVss-Sk-SH4-hDes1.4 kb-MVM-hMTM1-SynthpA (no diaphragm CRE,+muscle CRE Sk-SH4+Des1.4 kb+MTM1) (SEQ ID NO; 137)

4) pAAVss-Sk-SH4-hDes1.4 kb-MVM-hMTMco-SynthpA (no diaphragm CRE,+muscle CRE Sk-SH4+Des1.4 kb+codon opt MTM1) (SEQ ID NO; 136)

5) pAAVss-CRE64-Sk-SH4-hDes1.4 kb-MVM-hMTMco-SynthpA (contain best selected Diaphragm CRE64 combined with muscle CRE Sk-SH4) (SEQ ID NO; 131)

6) pAAVss-SPc5-12GTRM-MVM-hGAA-SynthpA (no diaphragm CRE, no muscle CRE, only SPc5-12-GTRM promoter driving the GAA gene expression)) (SEQ ID NO; 139)

7) pAAVss-SPc5-12GTRM-MVM-hGAAco-SynthpA (no diaphragm, no muscle CRE CSk-SH5,+SPc5-12-GTRM+codon opt GAA) (SEQ ID NO; 138)

8) pAAVss-CSK-SH5-SPc5-12GTRM-MVM-hGAA-SynthpA (no diaphragm CRE,+muscle CRE CSk-SH5+SPc5-12-GTRM+GAA) (SEQ ID NO; 133)

9) pAAVss-CSk-SH5-SPc-5-12GTRM-MVM-hGAAco-SynthpA ((no diaphragm CRE,+muscle CRE CSK-SH5+SPc5-12-GTRM+codon opt GAA (SEQ ID NO; 132)

10) pAAVss-CRE04-CSk-SH5-SPc-5-12GTRM-MVM-hGAAco-SynthpA ((contain best selected Diaphragm CRE04 combined with muscle CRE CSk-SH5) (SEQ ID NO; 130)

The invention further provides the following aspects:

Aspect 1: a nucleic acid regulatory element for enhancing diaphragm-specific gene expression comprising, consisting essentially of, or consisting of the sequence selected from the group consisting of: SEQ ID NO:1 to 89, a sequence having at least 80%, preferably at least 85%, more preferably at least 90%, even more preferably at least 95%, such as 95%, 96%, 97%, 98%, or 99%, identity to any of these sequences. This aspect hence preferably provides for a nucleic acid regulatory element for enhancing gene expression in diaphragm, having a maximal length of 1000 nucleotides, preferably 800 nucleotides, more preferably 700 nucleotides, 600 nucleotides or 550 nucleotides, comprising the sequence defined by SEQ ID NO: 4, a sequence having at least 80%, preferably at least 85%, more preferably at least 90%, even more preferably at least 95%, such as 95%, 96%, 97%, 98%, or 99%, identity to any of these sequences, the complement of said sequence, or a sequence hybridizing under stringent conditions to said nucleic acid regulatory element, or the use thereof for enhancing diaphragm-specific gene expression. In either one of these embodiments, SEQ ID NO:4 can be replaced by either one of SEQ ID NO: 1-89.

Aspect 2: the nucleic acid regulatory element according to aspect 1 for enhancing gene expression in the diaphragm and skeletal muscle, comprising consisting essentially of, or consisting of the sequence selected from the group consisting of: SEQ ID NO:1 to 7 and 10 to 65, 82, and 83 (cf. Dph-CRE-1 to 7, 10 to 65, 82, and 83 in Table 3), or a sequence having at least 80%, preferably at least 85%, more preferably at least 90%, even more preferably at least 95%, such as 95%, 96%, 97%, 98%, or 99%, identity to any of these sequences, or the use thereof for enhancing gene expression in the diaphragm and skeletal muscle. In a preferred embodiment of said aspect, said regulatory element is Dph-CRE64 (SEQ ID NO: 64) or Dph-CRE02 (SEQ ID NO: 2) or Dph-CRE21 (SEQ ID NO: 21).

Aspect 3: the nucleic acid regulatory element according to aspect 1 or 2, having a maximal length of 1000 nucleotides, preferably 800 nucleotides, more preferably 700 nucleotides, still comprising the regulatory element defined by any one of SEQ ID NO: 1 to 7, 10 to 65, 82, and 83 (cf. Dph-CRE1 to 7, 10 to 65, 82, and 83 in Table 3). In a preferred embodiment of said aspect, said regulatory element is Dph-CRE64 (SEQ ID NO: 64) or Dph-CRE02 (SEQ ID NO: 2) or Dph-CRE21 (SEQ ID NO: 21).

Aspect 4: the nucleic acid regulatory element according to aspect 1 for enhancing gene expression in diaphragm, skeletal muscle and heart tissue comprising a functional fragment of a sequence selected from the group consisting of: SEQ ID NO: 1 to 9, 66 to 81, and 84 to 89, or a sequence having at least 80%, preferably at least 85%, more preferably at least 90%, even more preferably at least 95%, such as 95%, 96%, 97%, 98%, or 99%, identity to any of these sequences. (cf. Dph-CRE1 to 9, 66 to 81, and 84 to 89 in Table 4), or the use thereof for enhancing gene expression in diaphragm, skeletal muscle and heart tissue. In a preferred embodiment of said aspect, said regulatory element is Dph-CRE04 (SEQ ID NO: 4) or Dph-CRE06 (SEQ ID NO: 6) or Dph-CRE02 (SEQ ID NO: 2).

Aspect 5: the nucleic acid regulatory element according to aspect 1 or 4, having a maximal length of 1000 nucleotides, preferably 800 nucleotides, more preferably 700 nucleotides even more preferably 600 nucleotides, such as 500 nucleotides, still comprising the regulatory element defined by any one of SEQ ID No: 1 to 9, 66 to 81, and 84 to 89. (cf. Dph-CRE1 to 9, 66 to 81, and 84 to 89 in Table 4). In a preferred embodiment of said aspect, said regulatory element is Dph-CRE04 (SEQ ID NO: 4) or Dph-CRE06 (SEQ ID NO: 6) or Dph-CRE02 (SEQ ID NO: 2).

Aspect 6: a nucleic acid regulatory element for enhancing gene expression in diaphragm, skeletal muscle and heart tissue comprising, consisting essentially of, or consisting of the complement of a sequence as defined in any one of aspects 1 to 3, or hybridizing under stringent conditions to the nucleic acid regulatory element according to any one of aspects 1 to 3.

Aspect 7: a nucleic acid regulatory element for enhancing gene expression in diaphragm, skeletal muscle and heart tissue comprising, consisting essentially of, or consisting of the complement of a sequence as defined in any one of aspects 1, 4 or 5, or hybridizing under stringent conditions to the nucleic acid regulatory element according to any one of aspects 1, 4 or 5.

Aspect 8: use of the nucleic acid regulatory element according to any one aspects 1 to 3, and 6 in a nucleic acid expression cassette, or a vector, more particularly for enhancing gene expression in diaphragm and skeletal muscle of said nucleic acid expression cassette or vector.

Aspect 9: use of the nucleic acid regulatory element according to any one aspects 1, 4, 5, and 7 in a nucleic acid expression cassette, or a vector, more particularly for enhancing gene expression in diaphragm, skeletal muscle and heart tissue expression of said nucleic acid expression cassette or vector.

Aspect 10: a nucleic acid expression cassette comprising at least one, such as one, two, three, four, five or more, nucleic acid regulatory elements according to any one of aspects 1 to 7, operably linked to a promoter.

Aspect 11: the nucleic acid expression cassette according to aspect 10, wherein the nucleic acid regulatory element is operably linked to a promoter and a transgene.

Aspect 12: the nucleic acid expression cassette according any one of aspects 10 or 11, wherein the promoter is a diaphragm and skeletal muscle-specific promoter, such as the promotor of any one of the genes defined in Table 3, namely the ACTA1, CKM, TPM2, MYL1, TNNC2, FHL1, TNNT1, TNNI2, MYLPF, TNNT3, MYH2, SLN, MYBPC1, ENO3, CA3, ATP2A1, and MYH1 genes; or wherein the promoter is a diaphragm, skeletal muscle and heart-specific promoter, such as the promotor of any one of the genes defined in Table 4, namely ACTA1, CKM, MYL2, MB, DES, TNNC1, TCAP, MYH7, ALDOA, and TPM1 genes. In preferred embodiments of said aspect, and particularly of aspects 2 and 3, the promoter is the mouse or human Desmin promoter, more preferably the human 1.4 kb Desmin promoter according to SEQ ID NO: 92. In preferred embodiments of said aspect and particularly of aspects 4 and 5, the promoter is the SPc5-12 promoter according to SEQ ID NO: 124.

Aspect 13: the nucleic acid expression cassette according to any one of aspects 10 to 12, wherein the transgene encodes a therapeutic protein or an immunogenic protein.

Aspect 14: the nucleic acid expression cassette according to any one of aspects 9 to 13, wherein the transgene encodes a secretable protein or a structural protein, such as myotubularin (MTM, SEQ ID NO: 95), acid glucosidase (GAA, SEQ ID NO: 93), follistatin, dystrophin, sarcoglycan, or dysferlin. In a preferred embodiment of said aspect, said transgenes are codon-optimised such as MTMco (SEQ ID NO: 96) or GAAco (SEQ ID NO: 94).

Additionally, the Dph-CRE can be supplemented by a further regulatory element (CRE) e.g. resulting in further expression in skeletal muscle or skeletal muscle and heart tissue such as the ones disclosed in WO2015/110449. Said additional CRE can be placed before or after the Dph-CRE (Exemplary vector backbones are depicted in FIG. 8). In a preferred embodiment, the skeletal muscle CRE Sk-SH4 (SEQ ID NO: 121), or the skeletal muscle and cardiac CREs CSk-SH5 (SEQ ID NO: 122) and CSk-SH1 (SEQ ID NO: 123) regulatory elements are used in combination with the Dph-CREs.

Specifically preferred is the combination of Dph-CRE64, 02 or 21 with CRE Sk-SH4, in particular the combination of Dph-CRE64 with CRE Sk-SH4. This embodiment is preferably coupled to the mouse or human Desmin promoter, more preferably the human 1.4 kb Desmin promoter according to SEQ ID NO: 92. Even more preferred, said CRE-promoter combination is driving the MTM1 transgene (SEQ ID NO: 94) or its codon-optimised variant MTM1co (SEQ ID NO: 96). Said combination is particularly interesting for use in treating MTM disease.

Further specifically preferred is the combination of Dph-CRE04, 06 or 02 with CRE CSk-SH5, in particular the combination of Dph-CRE04 with CRE CSk-SH5. This embodiment is preferably coupled to the SPc5-12 promoter according to SEQ ID NO: 124. Even more preferred, said CRE-promoter combination is driving the hGAA (SEQ ID NO:93 transgene or its codon optimised variant hGAAco (SEQ ID NO: 94). Said combination is particularly interesting for use in treating Pompe disease.

Aspect 15: the nucleic acid expression cassette according to any one of aspects 9 to 14, further comprising an intron, preferably the Minute Virus of Mouse (MVM) intron (SEQ ID NO: 125).

Aspect 16: the nucleic acid expression cassette according to any one of aspects 9 to 15, further comprising a polyadenylation signal, preferably the synthetic poly-A site (SEQ ID NO: 127) or the Simian Virus 40 (SV40) polyadenylation signal.

Aspect 17: a vector comprising the nucleic acid regulatory element according to any one of aspects 1 to 7, or the nucleic acid expression cassette according to any one of aspects 10 to 16.

Aspect 18: the vector according to aspect 17, which is a viral vector, preferably an adeno-associated viral (AAV) vector, more preferably an AAV9 vector.

Aspect 19: the vector according to aspect 17, which is a non-viral vector, preferably a plasmid, a minicircle, an episomal vector, or a transposon-based vector, such as a PiggyBac-based vector or a Sleeping Beauty-based vector.

Particularly interesting embodiments of said aspect are the vectors defined by SEQ ID NO: 131 (especially for use in treating MTM disease) or 130 (especially for use in treating Pompe disease).

Aspect 20: a pharmaceutical composition comprising the nucleic acid expression cassette according to any one of aspects 10 to 16, or the vector according to any one of aspects 17 to 19, and a pharmaceutically acceptable carrier.

Aspect 21: the nucleic acid regulatory element according to any one of aspects 1 to 7, the nucleic acid expression cassette according to any one of aspects 10 to 16, the vector according to any one of aspects 17 to 19, or the pharmaceutical composition according to aspect 20 for use in medicine, more preferably for use in gene therapy.

Aspect 22: the nucleic acid regulatory element according to any one of aspects 1 to 3, and 6, the nucleic acid expression cassette according to any one of aspects 10 to 16, the vector according to any one of aspects 17 to 19, or the pharmaceutical composition according to aspect 20, for use in treating MTM.

Aspect 23: the nucleic acid regulatory element according to any one of aspects 1, 4, 5, and 7, the nucleic acid expression cassette according to any one of aspects 10 to 16, the vector according to any one of aspects 17 to 19, or the pharmaceutical composition according to aspect 20, for use in treating Pompe disease.

Alternatively, either one of the following diseases could be treated using the nucleic acid regulatory element according to any one of aspects 1 to 7, the nucleic acid expression cassette according to any one of aspects 10 to 16, the vector according to any one of aspects 17 to 19, or the pharmaceutical composition according to aspect 20: neuromuscular disorders and heart diseases, such as Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystrophic Myotonia (Schwartz-Jampel Syndrome), Chudley Syndrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy), Welander's Distal Myopathy, Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barré Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy, Nuclear Envelop Disease, muscular dystrophy (e.g. Duchenne muscular dystrophy (DMD)/Becker muscular dystrophy (BMD)), motor neuron diseases (MND), such as e.g. Charcot-Marie-Tooth Diseases (CMT) such as CMT Type I, CMT Type II, CMT Type III (Dejerine-Sottas Disease), CMT Type IV (Refsum's Disease), CMT Type V, spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes.

In one embodiment, the diseases and disorders that may benefit from gene therapy using the Dph-CRE Sk-SH4 CRE in combination with, the Desmin promoter (e.g. the human DES 1.4 kb promoter (SEQ ID NO:92) are diseases that affect the skeletal muscle, and include Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystrophic Myotonia (Schwartz-Jampel Syndrome), Chudley Syndrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy) and Welander's Distal Myopathy.

In another embodiment, the diseases and disorders that may benefit from gene therapy using the Dph-CRE CSk- SH5 CRE combination with e.g. the SPc5-12 promoter are diseases that affect both the skeletal muscle and heart, and include Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barré Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy and Nuclear Envelop Disease.

Aspect 24: the nucleic acid regulatory element according to any one of aspects 1 to 7, the nucleic acid expression cassette according to any one of aspects 10 to 16, the vector according to any one of aspects 17 to 19, or the pharmaceutical composition according to aspect 20 for use as a vaccine, preferably a prophylactic vaccine, or for use in vaccination therapy, preferably prophylactic vaccination.

Aspect 25: A method, preferably an in vitro or ex vivo method, for expressing a transgene product in diaphragm and skeletal muscle cells, comprising:
  introducing the nucleic acid expression cassette according to any one of aspects 10 to 16, or the vector according to any one of aspects 17 to 19, comprising the nucleic acid regulatory element according to any one of aspects 1 to 3 and 6, into the cells; and
  expressing the transgene product in the cells.

Aspect 26: A method, preferably an in vitro or ex vivo method, for expressing a transgene product in diaphragm, skeletal muscle, and heart cells, comprising:
  introducing the nucleic acid expression cassette according to any one of aspects 10 to 16, or the vector according to any one of aspects 17 to 19, comprising the nucleic acid regulatory element according to any one of aspects 1, 4, 5, and 7, into the cells; and
  expressing the transgene product in the cells.

Aspect 27: a method for treating MTM comprising the administration of a therapeutically effective amount of the nucleic acid expression cassette according to any one of aspects 10 to 16, the vector according to any one of aspects 17 to 19, or the pharmaceutical composition according to aspect 20, each comprising the nucleic acid regulatory element according to any one of aspects 1 to 3, and 6, to a subject in need thereof.

Aspect 28: a method for treating Pompe disease comprising the administration of a therapeutically effective amount of the nucleic acid expression cassette according to any one of aspects 10 to 16, the vector according to any one of aspects 17 to 19, or the pharmaceutical composition according to aspect 20, each comprising the nucleic acid regulatory element according to any one of aspects 1, 4, 5, and 7, to a subject in need thereof.

Aspect 29: a method for treating any one of the diseases or disorders selected from the group comprising: muscular dystrophy (e.g. Duchenne muscular dystrophy (DMD)/Becker muscular dystrophy (BMD)), myotonic dystrophy, myotonic muscular dystrophy (DM), Duchenne dystrophinopathy, sarcoglycanopathies, Miyoshi myopathy, Fukuyama type congenital muscular dystrophy, dysferlinopathies, neuromuscular disease, motor neuron diseases (MND), such as e.g. Charcot-Marie-Tooth disease (CMT), spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes, comprising the administration of a therapeutically effective amount of the nucleic acid expression cassette according to any one of aspects 10 to 16, the vector according to any one of aspects 17 to 19, or the pharmaceutical composition according to aspect 20, each comprising the nucleic acid regulatory element according to any one of aspects 1 to 7.

Aspect 30. A codon-optimised human GAA gene as defined in SEQ ID NO: 94

Aspect 31. The codon-optimised human GAA gene for use in gene therapy, more particularly for use in treatment of diseases requiring restoration of GAA expression or increase of GAA expression. More preferably, said disease is Pompe disease or Duchenne muscular dystrophy.

Aspect 32. A codon-optimised human MTM1 gene as defined in SEQ ID NO: 96

Aspect 33. The codon-optimised human MTM1 gene for use in gene therapy, more particularly for use in treatment of diseases requiring restoration of MTM1 expression or increase of MTM expression. More preferably, said disease is MTM disease or Duchenne muscular dystrophy.

Aspect 34. A vector comprising the codon-optimised human GAA gene of aspect 30.

Aspect 35. A vector comprising the codon-optimised human MTM1 gene of aspect 32.

Aspect 36. A pharmaceutical composition comprising the vector according to aspect 34 or 35.

Aspect 37. A vector according to any one of aspects 1, and 4 to 5, comprising the codon-optimised human GAA gene of aspect 30.

Aspect 38. A vector according to any one of aspects 1-3, and 5, comprising the codon-optimised human MTM1 gene of aspect 32.

Aspect 39. A method, preferably an in vitro or ex vivo method, for expressing a transgene product in diaphragm, skeletal muscle, and heart cells, comprising:

introducing the nucleic acid expression cassette according to aspects 10 to 16, or the vector according to any one of aspects 17 to 19, comprising a nucleic acid regulatory element having a maximal length of 1000 nucleotides, preferably 800 nucleotides, more preferably 700 nucleotides, 600 nucleotides or 550 nucleotides, comprising the sequence defined by SEQ ID NO: 4 or SEQ ID NO: 64, a sequence having at least 80%, preferably at least 85%, more preferably at least 90%, even more preferably at least 95%, such as 95%, 96%, 97%, 98%, or 99%, identity to said sequence, the complement of said sequence, or a sequence hybridizing under stringent conditions to said nucleic acid regulatory element, into the cells; and expressing the transgene product in the cells.

Figure 1:
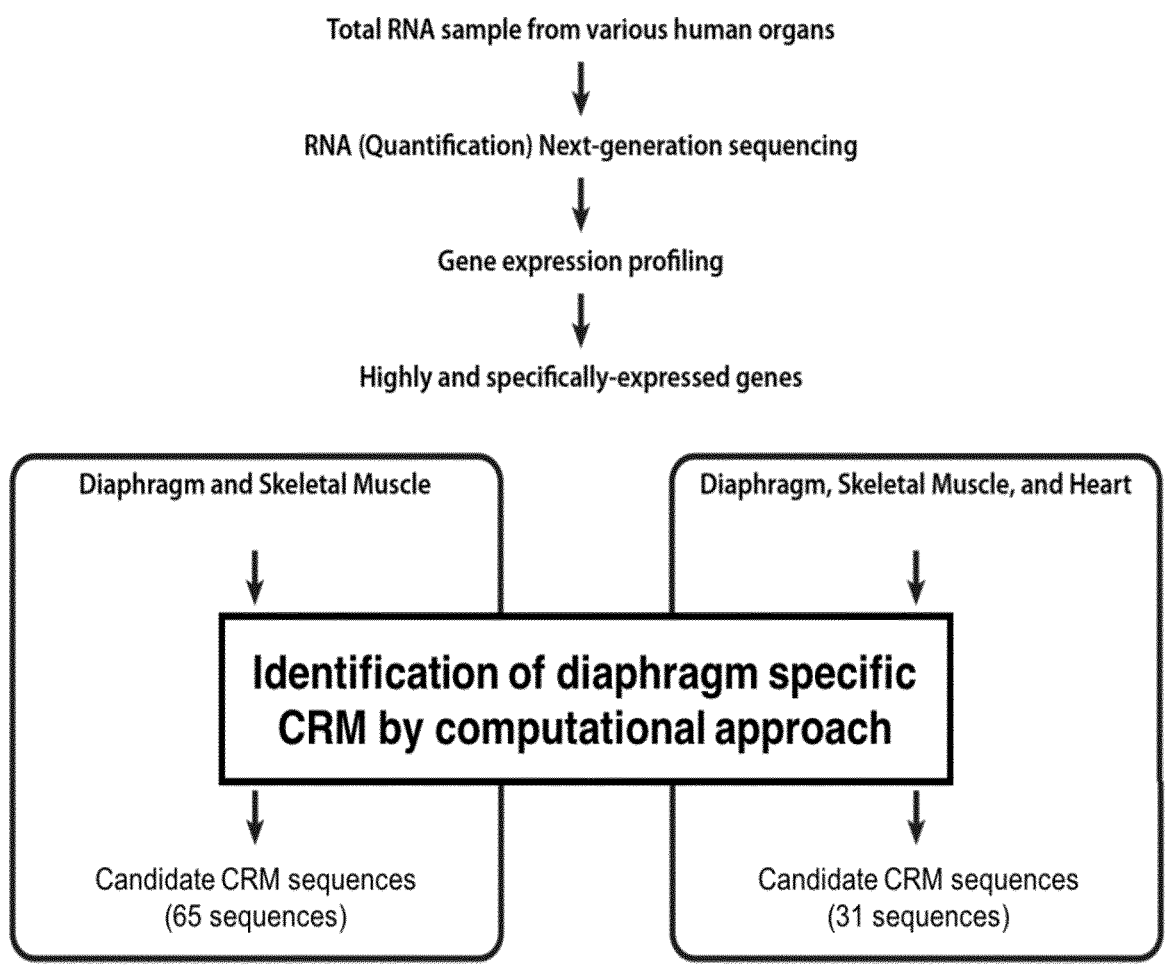
FIG. 1: Flow diagram of the identification of potential nucleic acid regulatory elements specific for diaphragm and skeletal muscle, or specific for diaphragm, skeletal muscle and heart. A computational approach was used to identify the nucleic acid regulatory elements involving the following steps: (1) gene expression profiling of total RNA samples from different human tissues, including human diaphragm tissue, by RNA (Quantification) Next-generation sequencing, (2) comparison of the gene expression profiles to identify genes that are highly and specifically expressed in i) diaphragm and skeletal muscle (17 genes), and ii) diaphragm, skeletal muscle and heart (10 genes), (3) locating the transcription start site of the identified genes using ENSEMBL, and (4) selecting candidate nucleic acid regulatory elements using UCSC Genome Browser database based on i) high DNase hypersensitivity sites; ii) high content of epigenetic markers associated with open chromatin (acetylation, methylation); iii) high content of transcription factor binding sites; iv) strong evolutionary conservation among vertebrates; and v) conserved transcription factor binding sites in 3 species (human, rat, mouse).
Figure 2:
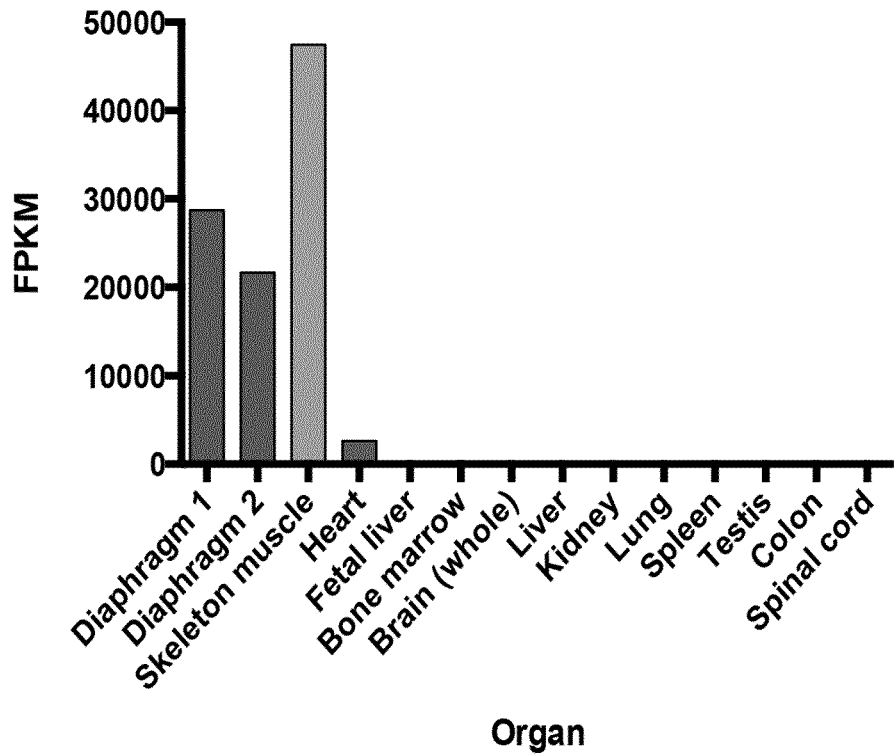
FIG. 2: Expression of the genes ACTA1 (A), CKM (B), TPM2 (C), MYL1 (D), TNNC2 (E), FHL1 (F), TNNT1 (G), TNNI2 (H), MYLPF (I), TNNT3 (J), MYH2 (K), SLN (L), MYBPC1 (M), ENO3 (N), CA3 (O), ATP2A1 (P), MYH1 (Q) in total RNA samples from the recited human tissues. Expression is indicated as Fragments Per Kilobase of transcript per Million mapped reads (FPKM).
Figure 2:
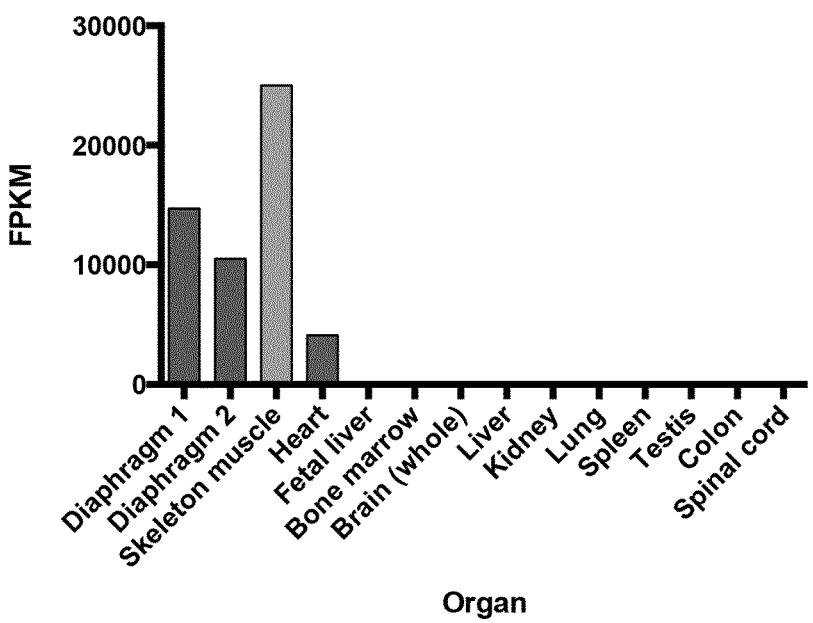
Figure 2:
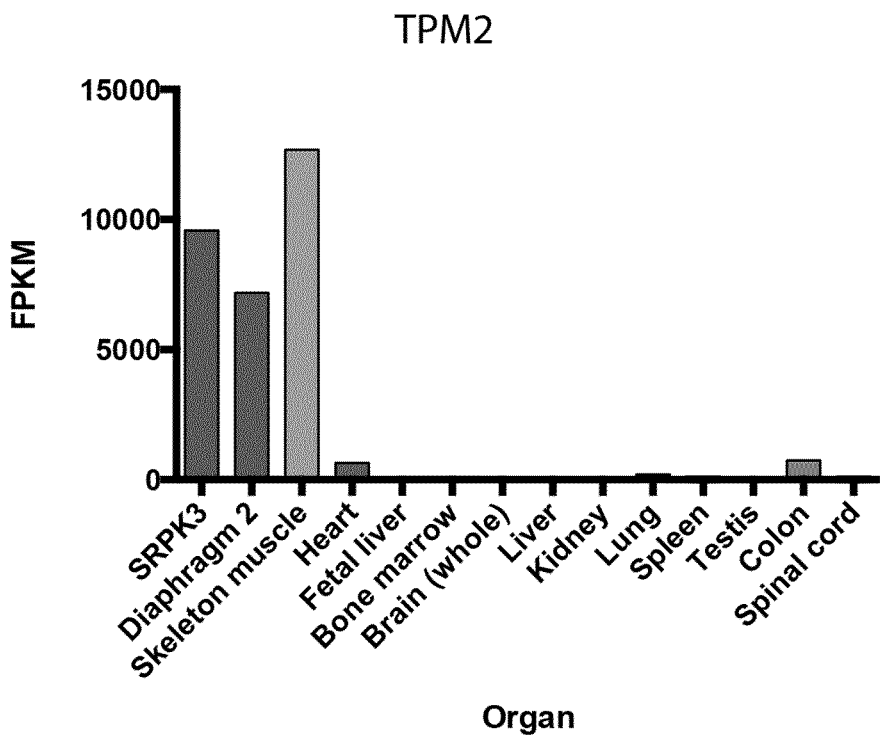
Figure 2:
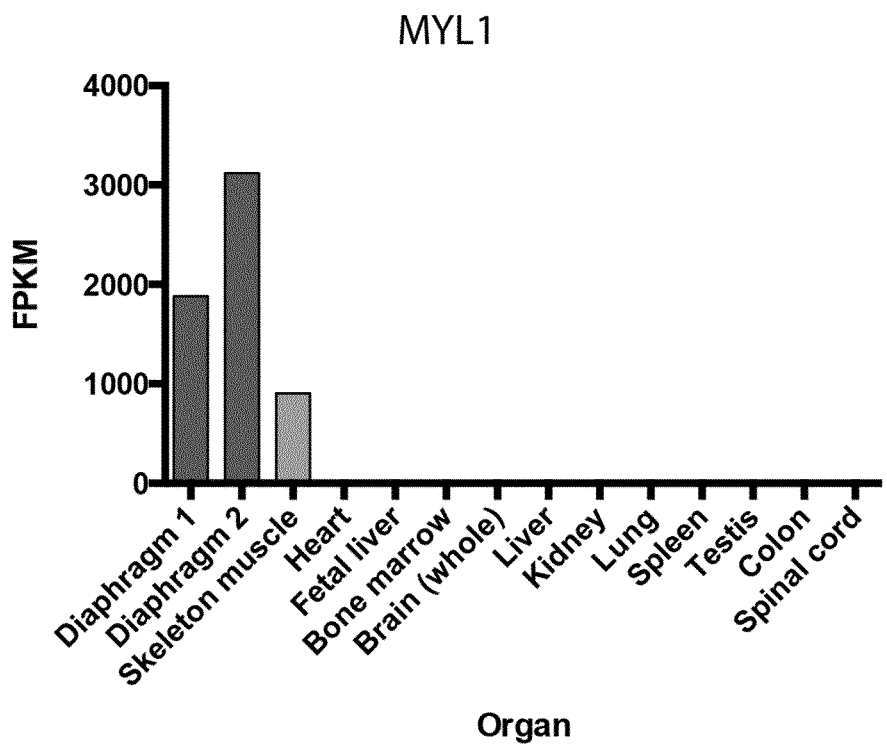
Figure 2:
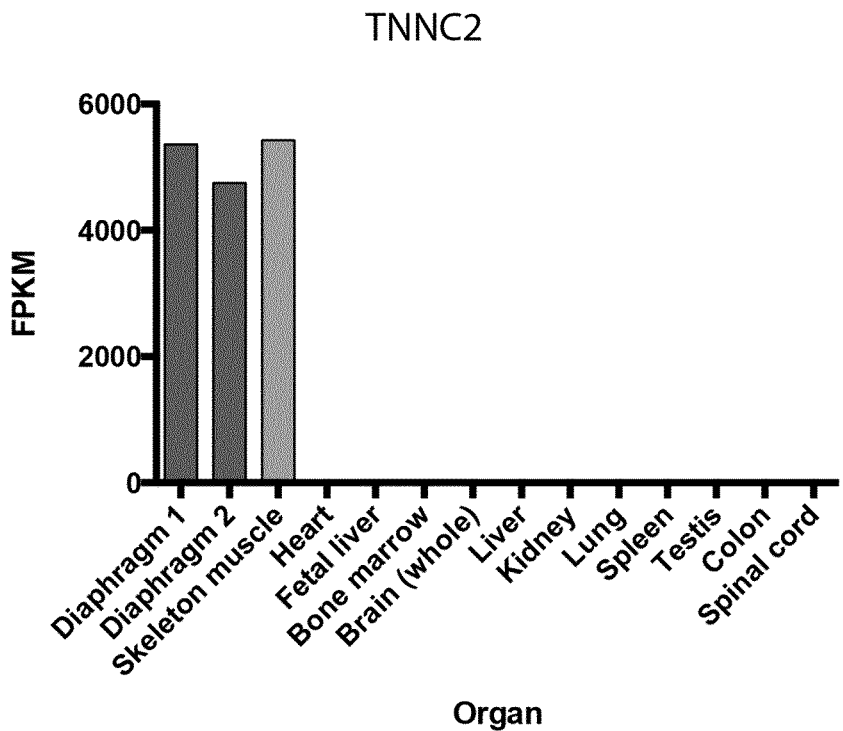
Figure 2:
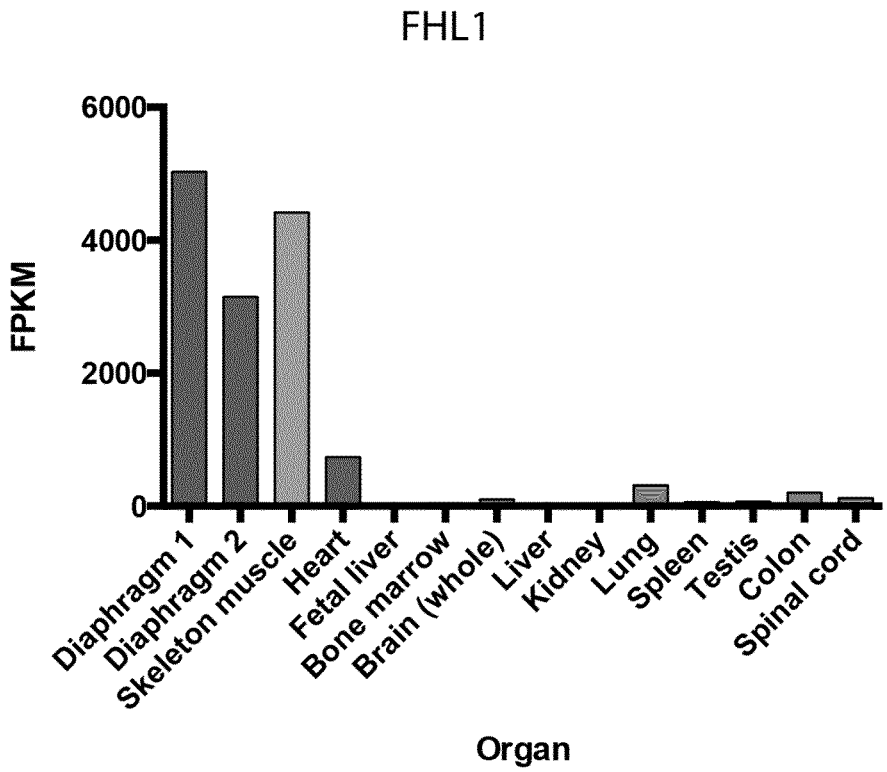
Figure 2:
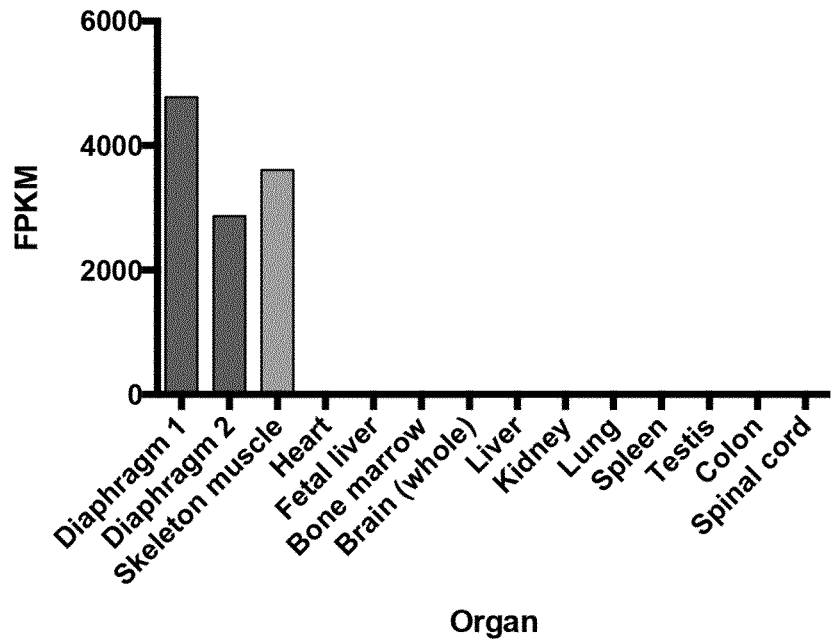
Figure 2:
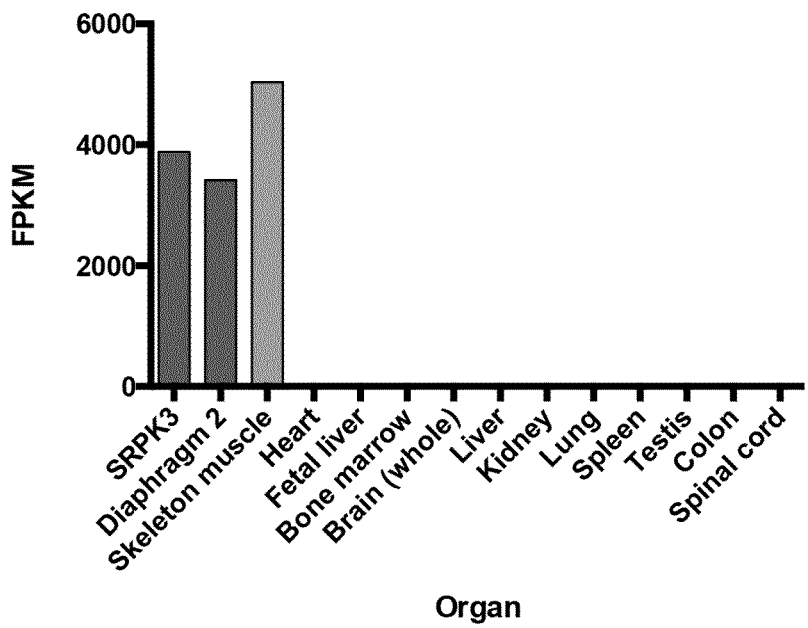
Figure 2:
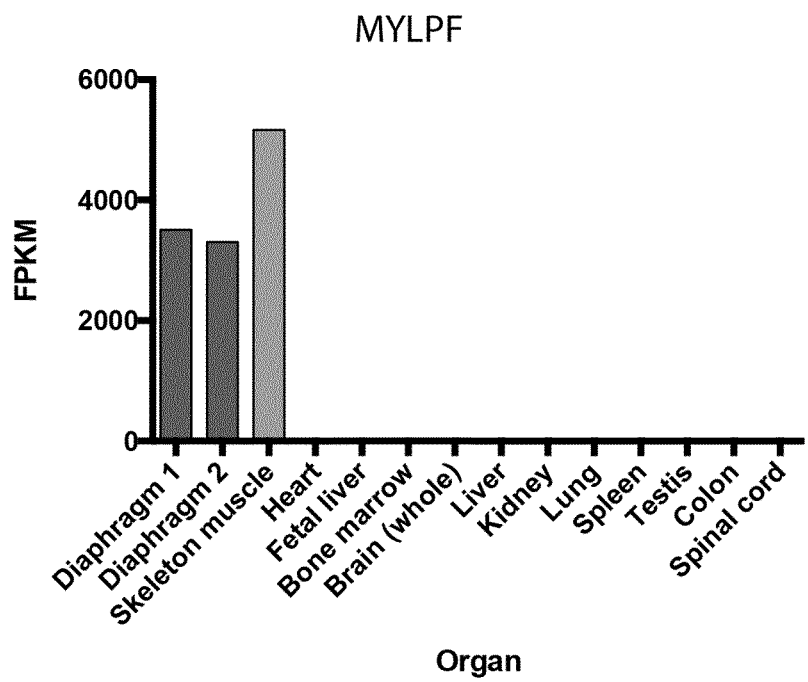
Figure 2:
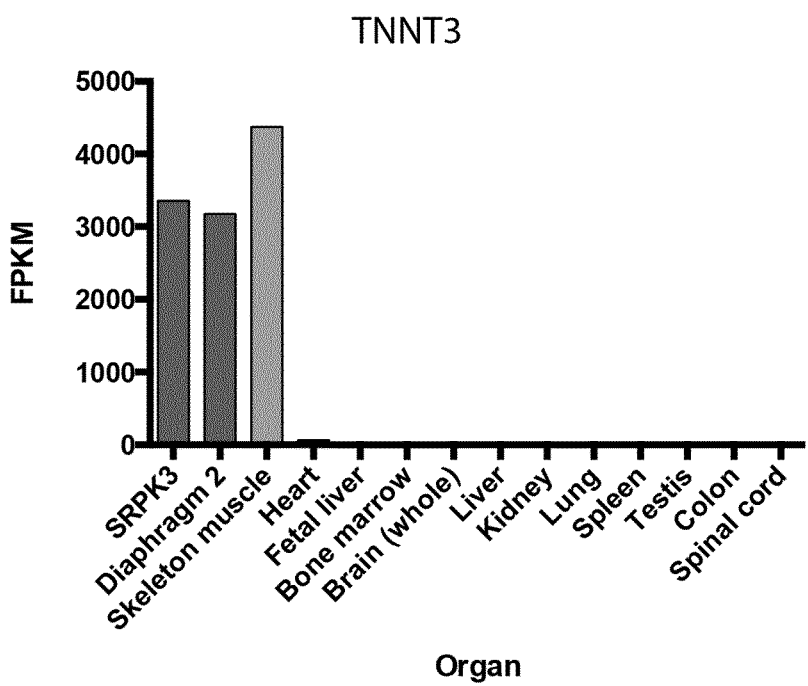
Figure 2:
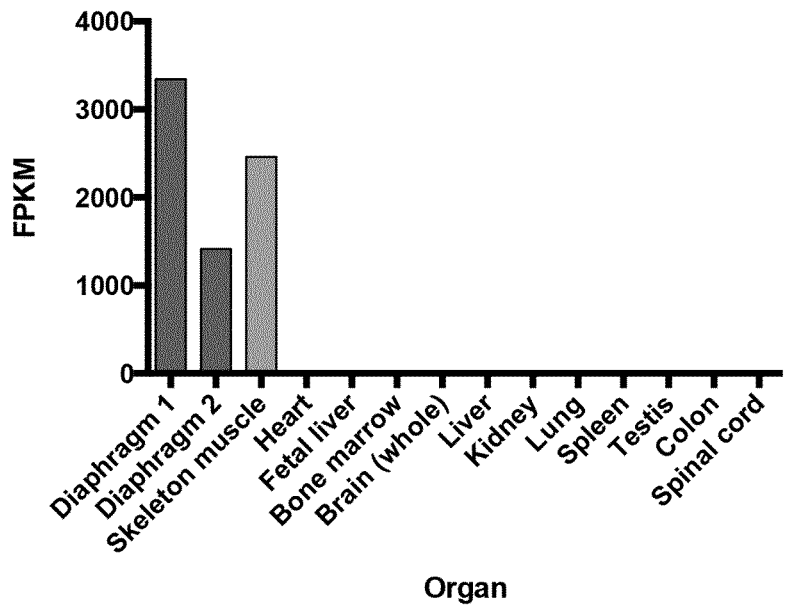
Figure 2:
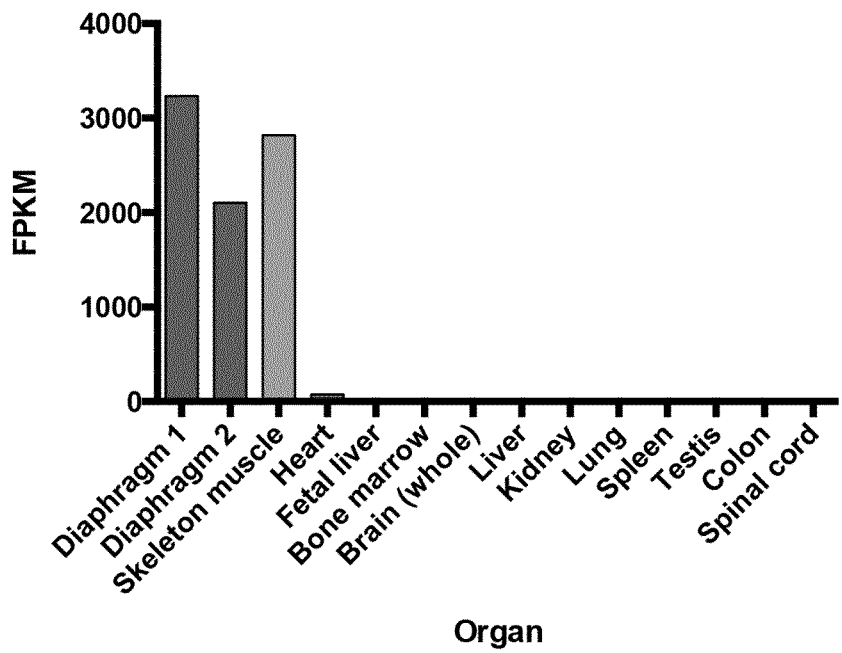
Figure 2:
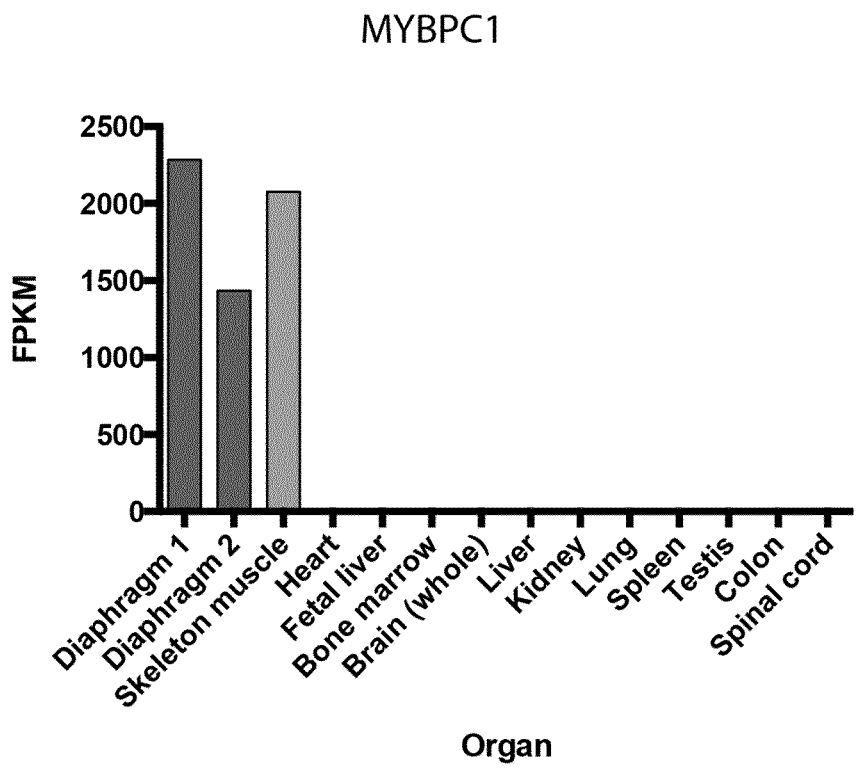
Figure 2:
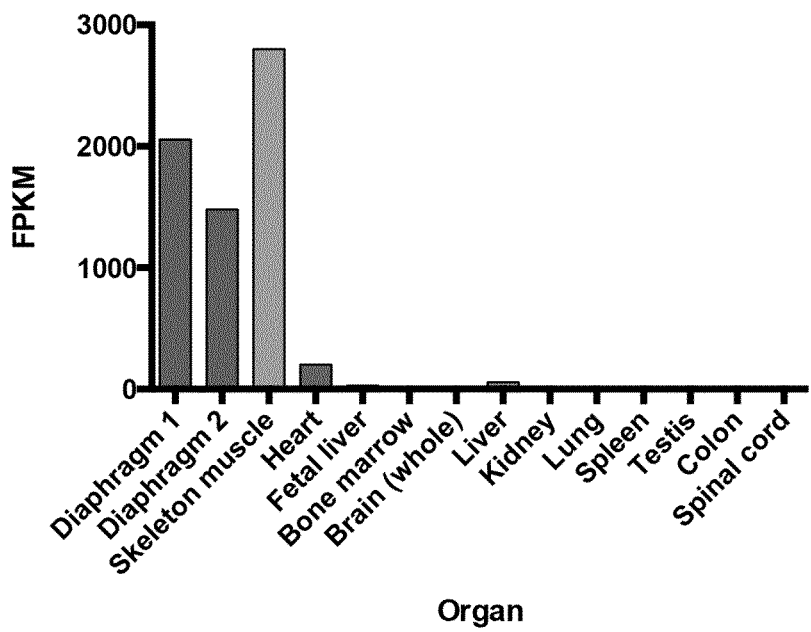
Figure 2:
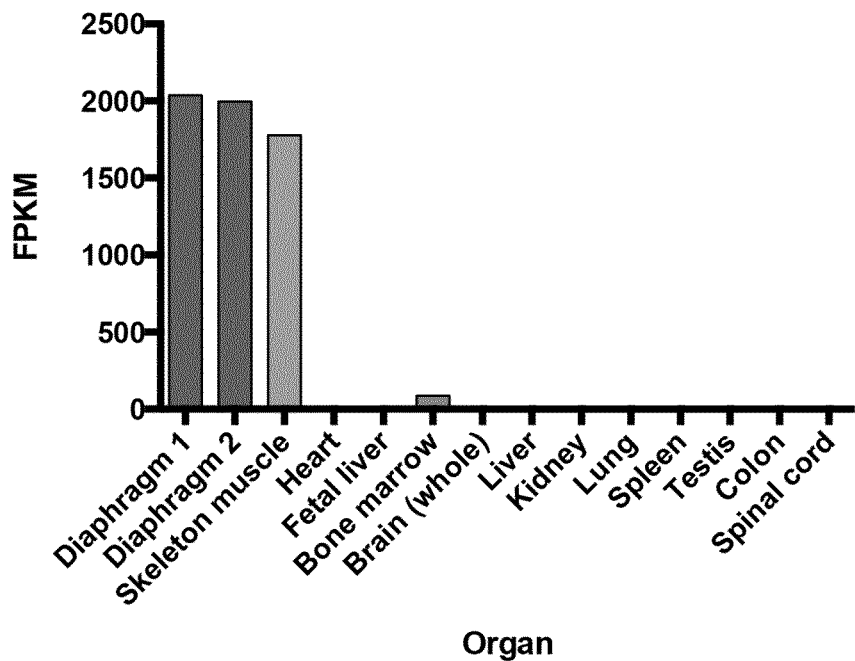
Figure 2:
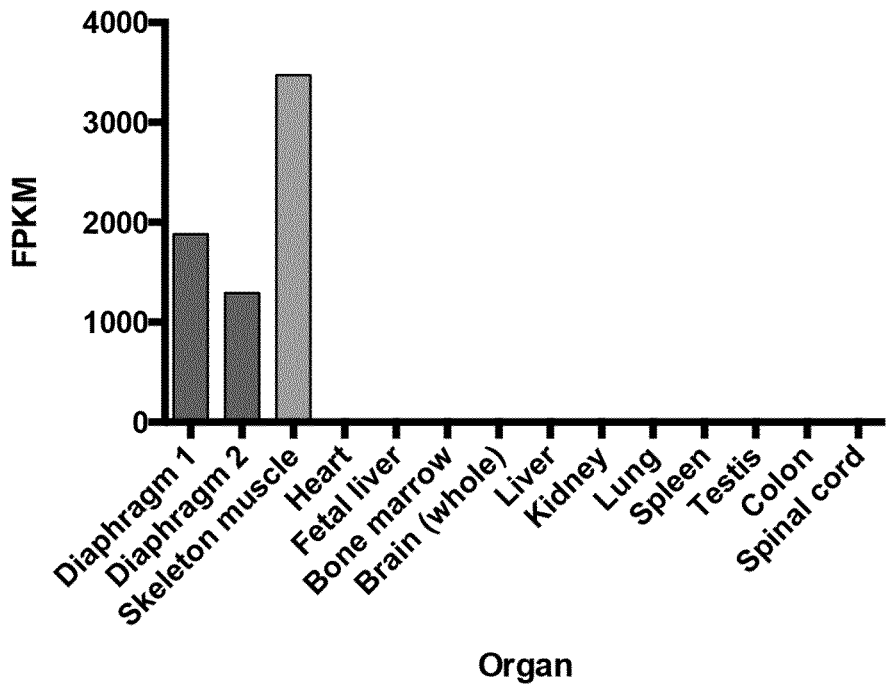
Figure 2:
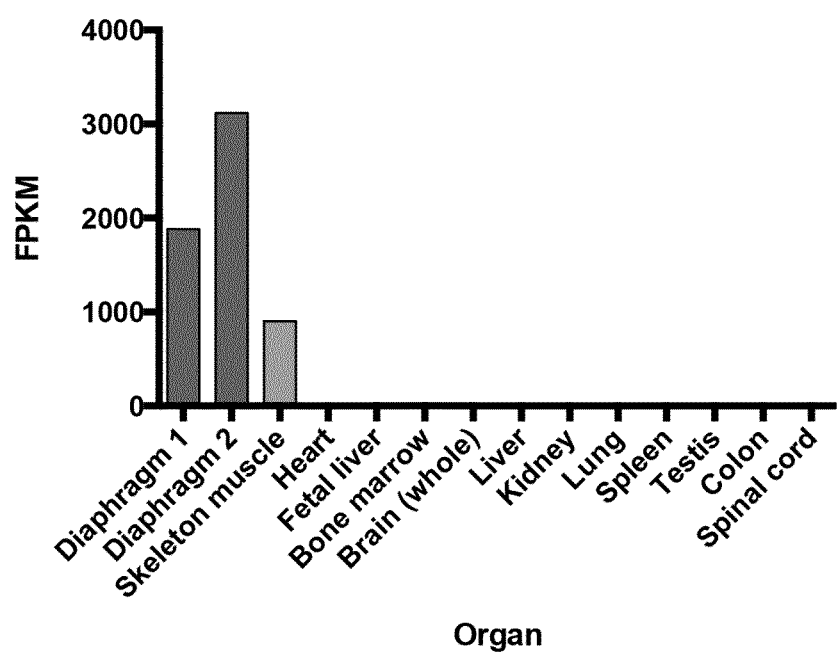
Figure 3:
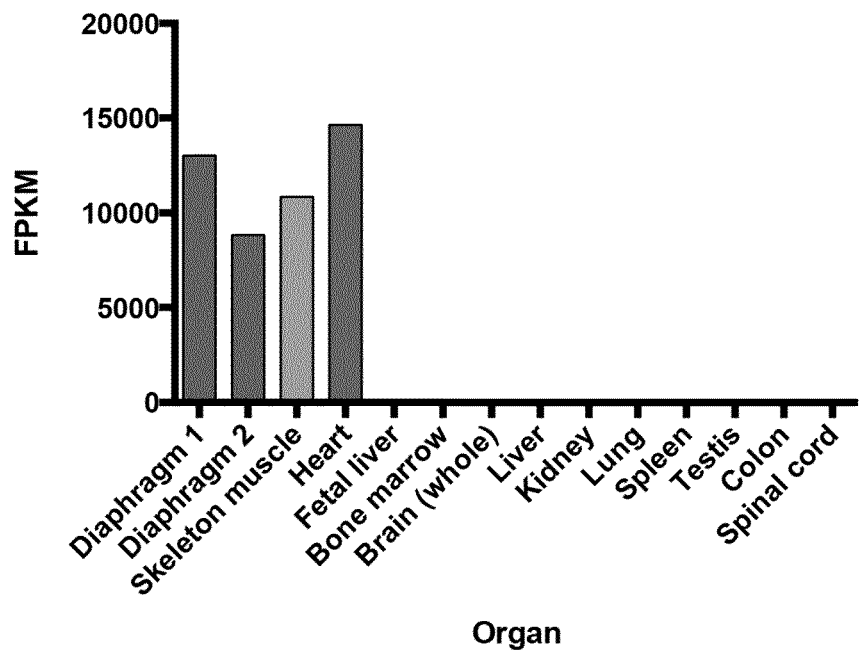
FIG. 3: Expression of the genes MYL2 (A), MB (B), DES (C), TNNC1 (D), TCAP (E), MYH7 (F), ALDOA (G), TPM1 (H) in total RNA samples from the recited human tissues. Expression is indicated as Fragments Per Kilobase of transcript per Million mapped reads (FPKM).
Figure 3:
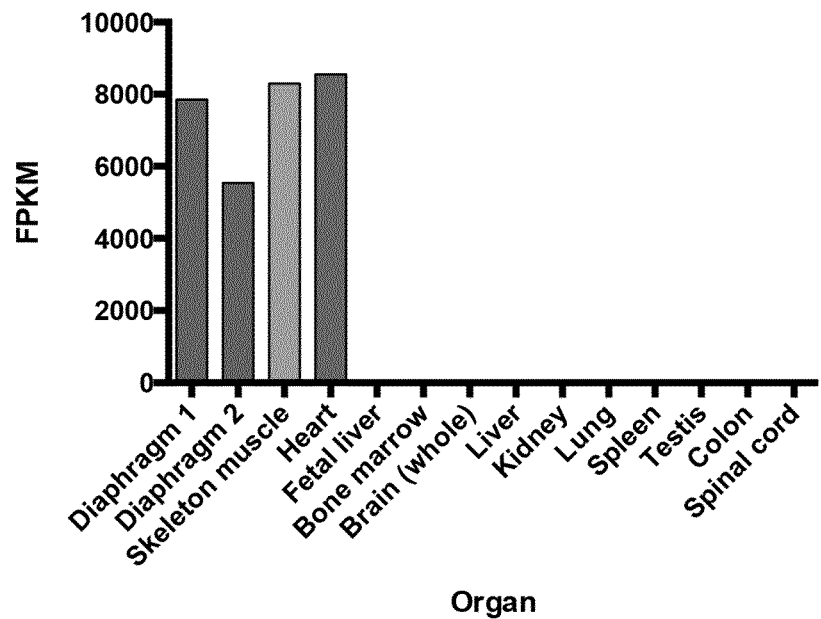
Figure 3:
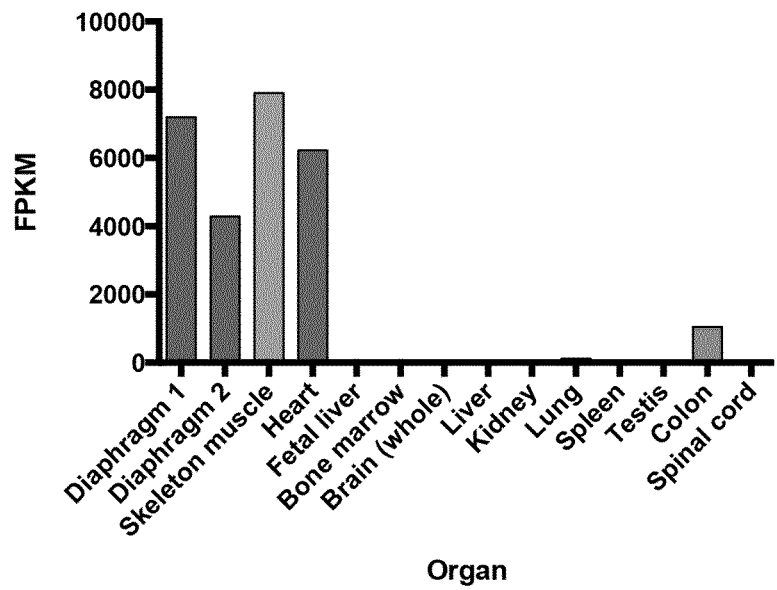
Figure 3:
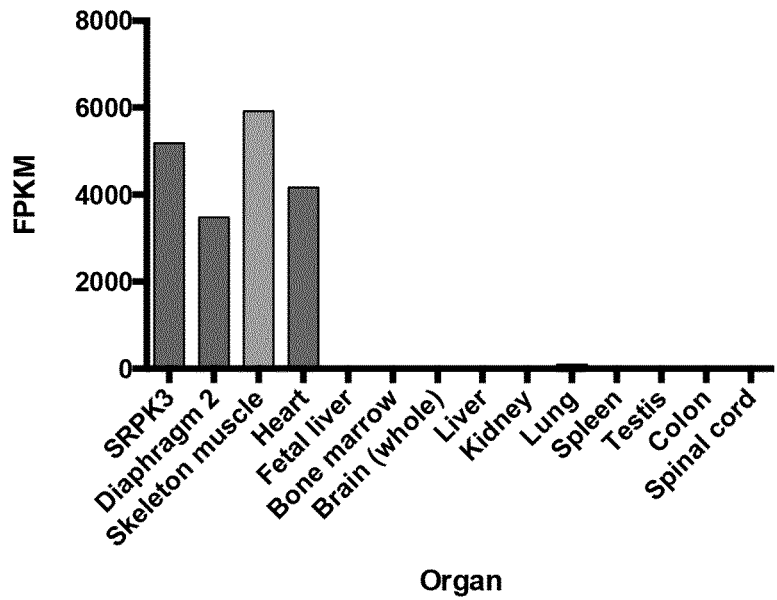
Figure 3:
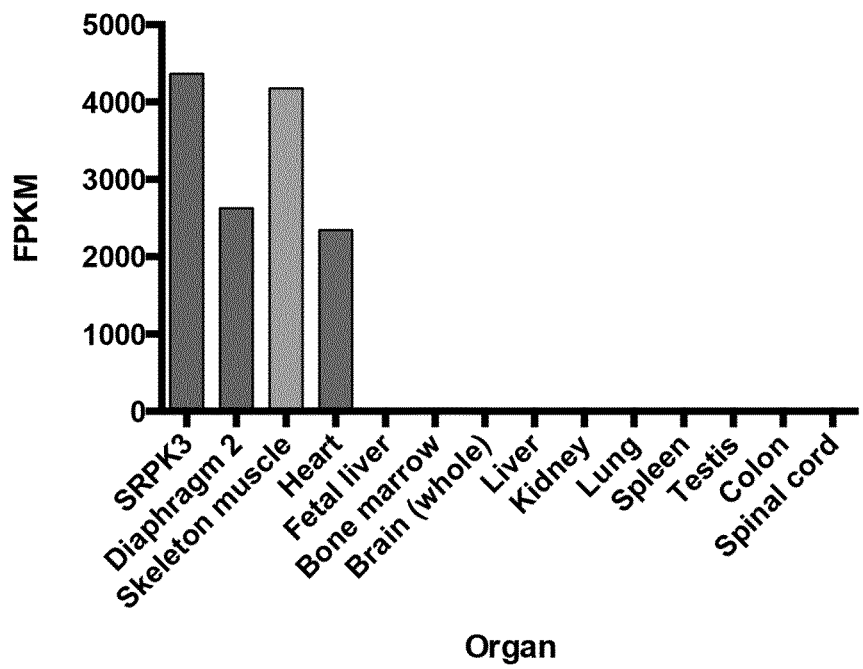
Figure 3:
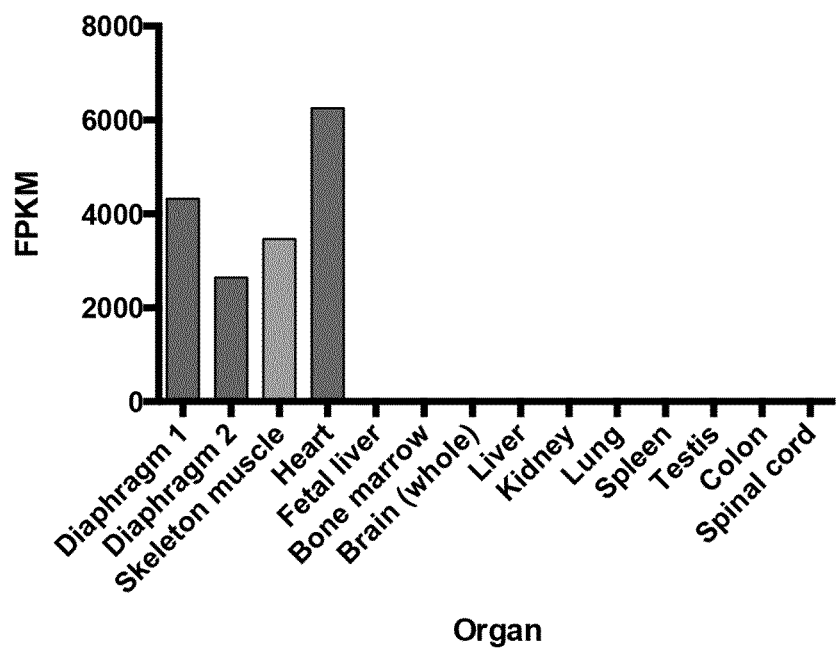
Figure 3:
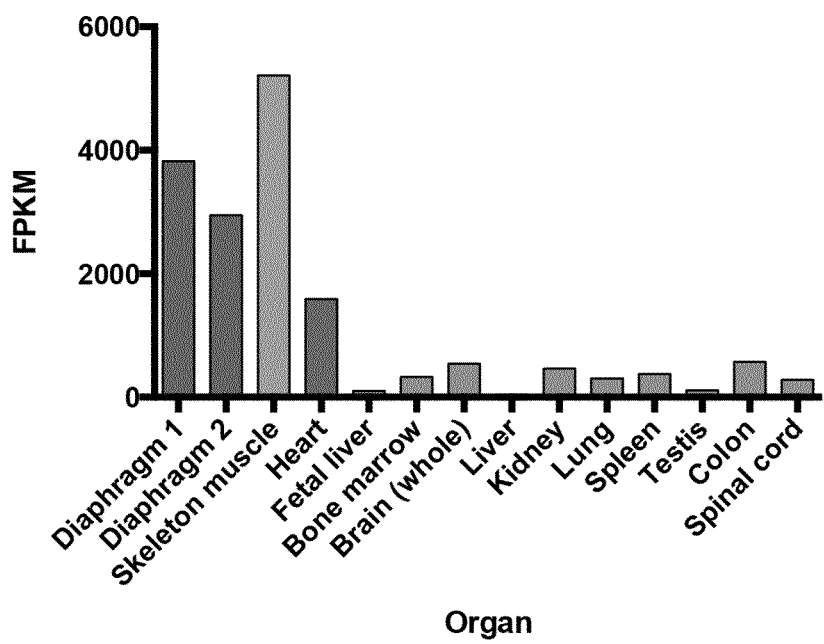
Figure 3:
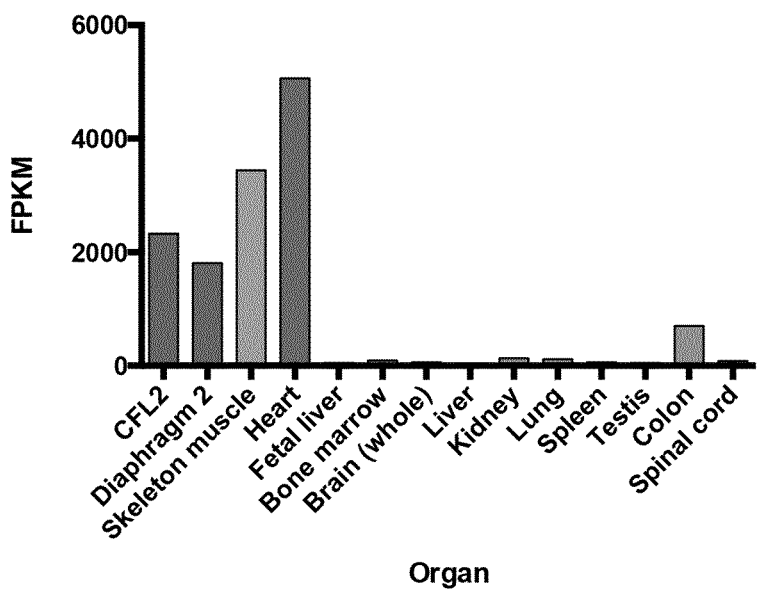

(SEQ ID NO: 121—called SKCRM4 in the figure). The fold-difference indicated on the top of each bar is calculated from relative expression between Dph-CRE-containing AAV (light gray) and its control without Dph-CRE64 and Sk-SH4 (black).

DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

For general methods relating to the invention, reference is made inter alia to well-known textbooks, including, e.g., "Molecular Cloning: A Laboratory Manual, 2nd Ed." (Sambrook et al., 1989), "Current Protocols in Molecular Biology" (Ausubel et al., 1987).

In one aspect, the invention relates to a nucleic acid regulatory element for enhancing gene expression in diaphragm and skeletal muscle cells or tissue or in diaphragm, heart, and skeletal muscle cells or tissue comprising, consisting essentially of (i.e., the regulatory element may for instance additionally comprise sequences used for cloning purposes, but the indicated sequences make up the essential part of the regulatory element, e.g. they do not form part of a larger regulatory region such as a promoter), or consisting of a sequence selected from the group consisting of: SEQ ID NO:1 to 89, a sequence having at least 80%, preferably at least 85%, more preferably at least 90%, even more preferably at least 95%, such as 95%, 96%, 97%, 98%, or 99%, identity to any of these sequences, or a functional fragment of a sequence selected from the group consisting of: SEQ ID NO:1 to 89.

Table 3 below depicts the core nucleotide sequence of the different nucleic acid regulatory elements for enhancing gene expression in diaphragm and skeletal muscle cells or tissue and their corresponding genes and lengths.

TABLE 3

The CREs sequence for high expression in diaphragm and skeletal muscle.

| SEQ ID NO. | Gene | Dph-CRE (CRE) | Size (bp) | Sequence |
|---|---|---|---|---|
| 1 | ACTA1 | Dph-CRE01 | 328 | GGAGACACTCCATATACGGCCCGGCCCGCGTTACCTGGG ACCGGGCCAACCCGCTCCTTCTTTGGTCAACGCAGGGGA CCCGGGCGGGGCCCAGGCCGCGAACCGGCCGAGGGAGG |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | GGGCTCTAGTGCCCAACACCCAAATATGGCTCGAGAAGG GCAGCGACATTCCTGCGGGGTGGCGCGGAGGGAATGCCC GCGGGCTATATAAAACCTGAGCAGAGGGACAAGCGGCCA CCGCAGCGGACAGCGCCAAGTGAAGCCTCGCTTCCCCTC CGCGGCGACCAGGGCCCGAGCCGAGAGTAGCAGTTGTAG CTACCCGCCCAGGTAG |
| 2 | ACTA1 | Dph-CRE02 | 452 | GACAGGTGCGGTTCCCGGAGCGCAGGCGCACACATGCAC CCACCGGCGAACGCGGTGACCCTCGCCCCACCCCATCCC CTCCGGCGGGCAACTGGGTCGGGTCAGGAGGGGCAAACC CGCTAGGGAGACACTCCATATACGGCCCGGCCCGCGTTA CCTGGGACCGGGCCAACCCGCTCCTTCTTTGGTCAACGC AGGGGACCCGGGCGGGGGCCCAGGCCGCGAACCGGCCGA GGGAGGGGGCTCTAGTGCCCAACACCCAAATATGGCTCG AGAAGGGCAGCGACATTCCTGCGGGGTGGCGCGGAGGGA ATGCCCGCGGGCTATATAAAACCTGAGCAGAGGGACAAG CGGCCACCGCAGCGGACAGCGCCAAGTGAAGCCTCGCTT CCCCTCCGCGGCGACCAGGGCCCGAGCCGAGAGTAGCAG TTGTAGCTACCCGCCCAGGTAGG |
| 3 | ACTA1 | Dph-CRE03 | 239 | AGAGAGAGGGACAGGCACCAACTGGGTAACCTCTGCTGA CCCCCACTCTACTTTACCATAAGTAGCTCCAAATCCTTC TAGAAAATCTGAAAGGCATAGCCCCATATATCAGTGATA TAAATAGAACCTGCAGCAGGCTCTGGTAAATGATGACTA CAAGGTGGACTGGGAGGCAGCCCGGCCTTGGCAGGCATC ATCCTCTAAATATAAAGATGAGTTTGTTCAGCCTTTGCA GAAGG |
| 4 | ACTA1 | Dph-CRE04 | 509 | CCTTTTAGAGAATCCACACCTGTCCCAGTTGCTGGGTTC CACTACCAAAAGTGAATTGCAACTATTTTAGGAGCACTT AAGCACATCCGAAAAATGAGTGATTCTGTTCTGGCCCAC ACCACATCACTGATGTACCCCCTTAAAGCATGTCCCTGA GTTCATCACAGAAGACTGCTCCTCCTGTGCCCTCCACAA GGTTAGAACTGTCCTTGTCTTAGGGAAAAAGGAGAGAGA GAGAGAGAGAGAGAGAGAGAGAGAGAGAGAGAGAGAGAG AGAGGGACAGGCACCAACTGGGTAACCTCTGCTGACCCC CACTCTACTTTACCATAAGTAGCTCCAAATCCTTCTAGA AAATCTGAAAGGCATAGCCCCATATATCAGTGATATAAA TAGAACCTGCAGCAGGCTCTGGTAAATGATGACTACAAG GTGGACTGGGAGGCAGCCCGGCCTTGGCAGGCATCATCC TCTAAATATAAAGATGAGTTTGTTCAGCCTTTGCAGAAG GA |
| 5 | ACTA1 | Dph-CRE05 | 169 | CCTTTTAGAGAATCCACACCTGTCCCAGTTGCTGGGTTC CACTACCAAAAGTGAATTGCAACTATTTTAGGAGCACTT AAGCACATCCGAAAAATGAGTGATTCTGTTCTGGCCCAC ACCACATCACTGATGTACCCCCTTAAAGCATGTCCCTGA GTTCATCACAGAA |
| 6 | CKM | Dph-CRE06 | 400 | GGGCCAGGGGACGGTGGCTTCTACGTGCTTGGGACGTTC CCAGCCACCGTCCCATGTTCCCGGCGGGGGGCCAGCTGT CCCCACCGCCAGCCCAACTCAGCACTTGGTCAGGGTATC AGCTTGGTGGGGGGCGTGAGCCCAGCCCCTGGGGCTGGG TCAGCCCATACAAGGCCATGGGGCTGGGCGCAAAGCATG CCTGGGTTCAGGGTGGGTATGGTGCGGGAGCAGGGAGGT GAGAGGCTCAGCTGCCCTCCAGAACTCCTCCCTGGGGAC AACCCCTCCCAGCCAATAGCACAGCCTAGGTCCCCCTAT ATAAGGCCACGGCTGCTGGCCCTTCCTTTGGGTCAGTGT CACCTCCAGGATACAGACAGCCCCCCTTCAGCCCAGCCC AGCCAGGTAC |
| 7 | CKM | Dph-CRE07 | 255 | CCCAGCCCCCTTCCCCGGGAGGTGGGAGCGGCCACCCAG GGCCCCGTGGCTGCCCTTGTAAGGAGGCGAGGCCCGAGG ACACCCGAGACGCCCGGTTATAATTAACCAGGACACGTG GCGAACCCCCTCCAACACCTGCCCCCGAACCCCCCCAT ACCCAGCGCCTCGGGTCTCGGCCTTTGCGGCAGAGGAGA CAGCAAAGCGCCCTCTAAAAATAACTCCTTTCCCGGCGA CCGAGACCCTCCCTGTCCCCC |
| 10 | TPM2 | Dph-CRE10 | 608 | ACTCAGGGTAAACTGAGGCACTCAAACTGCCGAGGAGCT CCGCCTCCCGAGAGACATTTAATCCGGGGGGATTTGCAG GAAACTTCTAAATTAAGGGTAGCGGCTGCTGCAGCTGAG GGGGGGCACGCCGGTCCCTGCGCCCGGGCAGCTGCCGTG AGCTCACGCCCCGAAATAGCCCCAGGGGCCCCAGCCGCA |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | GCTGCCACTGGGTCCGGCTGTCACTCAGAGGAAGCACGG<br>AGCCCCCAGCCCAAGGGTCCCCTCCCCTTCGCATCGCCG<br>GGGTTTTTCCAGCCGACCGTCGGCCACTTTTTCCTCCGA<br>CGGCTGGCAGGGAAGAGGGGGATGGGGCGGGACCCCAA<br>GGGAGGCGGTCCCCAGTGGGTGGGCGAAGGGGGCGGCCG<br>CACCCCCCGGCCGGGCCGTGCTTCTGCCCCTACAAGGTT<br>TGGGCCGAGGTGGGGAGGGTCCTGGTTGCCGGCCCCGC<br>CCGGTCCCTCCCCGCCTTTTAGGCGCCCGCGTGGCCGGG<br>ACGTCCCAGTCCCGCTCCGTCCTCCTCGCCTGCCACCGG<br>TGCACCCAGTCCGCTCACCCAGCCCAGTCCGTCCGGTCC<br>TCACCGCCTGCCGGCCGGCCCAC |
| 11 | TPM2 | Dph-CRE11 | 308 | TTTTTCCTCCGACGGCTGGCAGGGAAGAGGGGGATGGGG<br>GCGGGACCCCAAGGGAGGCGGTCCCCAGTGGGTGGGCGA<br>AGGGGGCGGCCGCACCCCCCGGCCGGGCCGTGCTTCTGC<br>CCCTACAAGGTTTGGGCCGAGGTGGGGAGGGTCCTGGT<br>TGCCGGCCCCGCCCGGTCCCTCCCCGCCTTTTAGGCGCC<br>CGCGTGGCCGGGACGTCCCAGTCCCGCTCCGTCCTCCTC<br>GCCTGCCACCGGTGCACCCAGTCCGCTCACCCAGCCCAG<br>TCCGTCCGGTCCTCACCGCCTGCCGGCCGGCCCAC |
| 12 | TPM2 | Dph-CRE12 | 263 | GACTCAGGGTAAACTGAGGCACTCAAACTGCCGAGGAGC<br>TCCGCCTCCCGAGAGACATTTAATCCGGGGGGATTTGCA<br>GGAAACTTCTAAATTAAGGGGTAGCGGCTGCTGCAGCTGA<br>GGGGGGGCACGCCGGTCCCTGCGCCCGGGCAGCTGCCGT<br>GAGCTCACGCCCCGAAATAGCCCCAGGGGCCCCAGCCGC<br>AGCTGCCACTGGGTCCGGCTGTCACTCAGAGGAAGCACG<br>GAGCCCCCAGCCCAAGGGTCCCCTCCCCT |
| 13 | MYL1 | Dph-CRE13 | 324 | CTCAGGGAATGAGCTGGATACAACTAAAAATCAGCACAT<br>TTTTGTTTGGTTAAAACATTCTTTGTGGTCAATTTCTTT<br>CTAACAGATCGAGTTCTCTAAGGAACAGCAGGATGGTAA<br>GTTTAAAAGCTATGGTTCTTAAATGTGCACACTCATAAA<br>GATGGCATGTGTGAAAACCAACTCCCTTGGGATGAGTTT<br>AGCTCTTCCTAATTATCCCCACTGGTGTTGCCATTCTGA<br>ATATAAATTGCTCTCGATCACTCTAAATATAAATTAGCT<br>CAATCTGAAACCCTTGCTGATACTCAGTAATCAAAGGTT<br>TAACAAACAAAA |
| 14 | MYL1 | Dph-CRE14 | 326 | CATTTAGTTAAATCATTAAGATGCAGAAAGATATTCCCT<br>AATTATCTTTTGCAATAGCTTTTTATGTTCCTAGATTCA<br>AAAGTATCCTAAGGCAACCTTCTAATGCCAAGACACCTA<br>CATAGCTTCCTAAAAATCTCAGAGCAACCAGCACTCATT<br>CTTCTGTCAATGCATTTGAAAGAGTACTAGTTTTTTTTC<br>TTTCTTTCTCTTCTTCGCCACTGCAGTCCTTCAGTGCTG<br>ACCAGATTGCTGGTAAGTGAATTGAGTTTGTCTGCTACA<br>GATGTAGGCACAGCACTGCCTAGTTTCTGCAATATTACT<br>TATCTTCAAGGCAT |
| 15 | MYL1 | Dph-CRE15 | 596 | TTTGTTTGTTAAACCTTTGATTACTGAGTATCAGCAAGG<br>GTTTCAGATTGAGCTAATTTATATTTAGAGTGATCGAGA<br>GCAATTTATATTCAGAATGGCAACACCAGTGGGGATAAT<br>TAGGAAGAGCTAAACTCATCCCAAGGGAGTTGGTTTTCA<br>CACATGCCATCTTTATGAGTGTGCACATTTAAGAACCAT<br>AGCTTTTAAACTTACCATCCTGCTGTTCCTTAGAGAACT<br>CGATCTGTTAGAAAGAAATTGACCACAAAGAATGTTTTA<br>ACCAAACAAAAATGTGCTGATTTTTAGTTGTATCCAGCT<br>CATTCCCTGAGTAATCTTCAAAGTAAGCTCCAAAAGTCA<br>GCCTACTTTTCAGAGTTCAGGCGTAGCTTGGACACTAAC<br>AGGTTAAGCCATAGTGTAACATGCCTTGAAGATAAGTAA<br>TATTGCAGAAACTAGGCAGTGCTGTGCCTACATCTGTAG<br>CAGACAAACTCAATTCACTTACCAGCAATCTGGTCAGCA<br>CTGAAGGACTGCAGTGGCGAAGAAGAGAAAGAAAGAAAA<br>AAAACTAGTACTCTTTCAAATGCATTGACAGAAGAATGA<br>GTGCTGGTTGC |
| 16 | MYL1 | Dph-CRE16 | 290 | AGACCATAAAAGTACCGGCAGGCTTCCATCTCACTATGG<br>CTGTCTACTCCAAGGTTCTGGTCATCTAAAAATAGCTCT<br>CAGGGTACAGATCCATCTTTCCCTTTGCCCTAAGAAAGC<br>TAAAGAACTCTCCAAGGGGTGTGGCAACTTATCTCTGAA<br>ACCTGATGCTAGCTGTGAGGTCAAAGCTTGCCCAGAAAT<br>AAAAGGAAGCCTCAGCCAGGGATGACCCCACTCAGGGAC<br>CGGAGCAGCCCTCAACTCACTCTTCAGCTTCCCTGCTGT<br>GTTGCAGCCCAGCCGCT |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 17 | MYL1 | Dph-CRE17 | 632 | GTGCTCCCTAGAAGGGAAGCCACTTTAAGACATGATGGG CTTTCCTTATACGTCTGCTTTTTTATTTTTAACCACCAC CACCTCTTTGCTGACCAACATTTCCTTGCAAATTATGGC AAGGGGGGAGGAGCATGAGCAAAGGAGCTGTGTGAAAGT TGGTGATACTCCCTGCCAAAATTCCAAGTTGAAATGGAA TCCTTCAGTAAAGTCTCTTAGGCAAGGTGGGAAAAAAAG ATTTACAACTTCAGCAGAACTGTAATTCTACCAAGAAAA AGTACAGTCAATCTACCTCACTGTCACCAAAGGATCTGA AGCTGGCTTTGTCATATATCTTTCTCCTTTATATATGGA GGTGGGGGGGGAGAAAAAAAGGAAAGAGAGTTAAAAAA AATTGATGAAGCCCTGACCCTTTAGATTCCATTTATAGT CTGAGCCGGAATGCCATCCCCCTTGACTAGAGAACTGTC CAATCCAGCCGCATGTGTCAAGATTCTATTAGGCACTAA GTGAAATATATATGCATGCCCTTATGCCGTTTAACACTC TGGGTCCATCTTCAAGACACTGGGCTGTGGATCAACCCA ACCACCACTCCTCTTCCAAGAATCATTTTGACAGGTTCT TTTGGAGG |
| 18 | TNNC2 | Dph-CRE18 | 297 | CCTTTGACTTTTCTTGAAAGGGGAGGGCTGGGATATTCC AGAGATTGATCCTTAAGGCTTGCTGACTGCCTACTCACT TCTGGAAACTTCCAGCAGTGTCATTCATAGACCTGTGAA GAGCTCTTAGCTTGTTTCCTTCACACAGTGGGGACTCTG AGGGGTCAGAGTGAGTCACCCAGCAGGCCAGTGGCAGGG GTGAGCCAGAAGCCTGGCCAAACCCTCCTATCATCATGG AGAGAAGAAAGCCTCCTCCAGAAGACGGGAGGCCGGCAG GGCGTGGGGCCTGCTCAGATGCAG |
| 19 | TNNC2 | Dph-CRE19 | 309 | GGAACAGGGCAGGCCTTCCTCACAAGAATCTAGGACGTC AAGGCCTGCCACCTGCTTGGAGGCTTAAATTTCTCTGCA AGGGCCCTTGGCTAAATTAGGTAATGGGTTCAGACTGTG GGAGGGGTGGGACTCGCTGACCCCAGGATCTGATTGGGC AGGGTCTCCAGTGCTGGGGAGCAGGGAGGTGGGAGGGGA GGGTGCCCCTACAAATCCCGGGGGCTAGAGCAGGCCAGG TCATCTTTGGGTGGTGGAGTGCAAAGGAGGCGACCTGCA ACAGAGGAGTCCCGGTCACCAGCAACCATGGTAAGG |
| 20 | FHL1 | Dph-CRE20 | 267 | AATTGTGACATTTAAGCAGTGACTTTGCAAAATTGGACG TGTCAGTAGGAAAAAGTACTCTTCCCACCTTAAAGATTG ACAGGAACATGAGATGGCTGAAGCTGTTCTGAGCTTTTT TCTGGCAAGAGTACATAGGACAAGAAATACTCTGGAGAG CTCAACATTGAATCACATCATATCATAGTGCATGACTAG TTGCCTTAATCTTGCAGTTGGACTCACTCAGGAGAAATT GTTGGCAGAGGGATTAAGTAGCCTGACAAAATT |
| 21 | FHL1 | Dph-CRE21 | 493 | CTTTTCTTTTCTAATTAGGTCAGTTACTTCATGTCTGTT TTTCTTTTTTGACATGGTTTCTTCTGGCTTTGGCACCAC ATATTTTCCCCATATGTCATTGCCTCTGGAGCTTCATGT TGCAATAGTTTTTCAAGGGGAACGGAGAGCACATTGCTA AGGGTGGGGGATGGCTTTTGCCTCTTTTGCCTGCCCTTT GCTTCAGTGAGTGTTCGTATTTCTGTTGGGCCTAGTTCT GTTTGGTTTTGTAGTCTTCAGAGTCAGTTATGTTTGGAC TGAAAGATACTTAAGTAAAAATAATGGCAAGTCAGAGAT ATGCTGGCAAAGGTGCAGCACATTTGTTAAGGTTACTG GTTTATTTATCTCCCTTGTCTCTATGGTGACTAAATCTG GGTCTGGGATTTAATGGACTTAGTTTTGACCTCTTGTAA CATCTCCTAACTTTTCCCAGCCTCTGATTTAGAAAGAAT TCATTTTCACTTGAGGAGAGAAACT |
| 22 | FHL1 | Dph-CRE22 | 197 | TCATTTGTTTTGATTACCCGGGTGATTGCCAAATGTTAA TTTAAAACTGAAATAGGCCATGAGCTCACTCCCCTAACA ATGCTGAGTGTTTGAGCTAATACGGCTTGATAATGAGGG AGCCAGATCCACTGCCAGTGCTCATGTTATATGATAAAC AGACATTTGGAGAAGTATGCAGAACATCTTGGCAGTTTT CC |
| 23 | FHL1 | Dph-CRE23 | 637 | AAAAATTGGCTTTAAGGTCATGAGCCTCCTTACAGCAGT CCCTCTCACCTTCAGCTGTATTCCCTATTTCAGATATAC TTGTTTCTCTGCTGTAAGTACACTTTTCTTTTCTAATTA GGTCAGTTACTTCATGTCTGTTTTTCTTTTTTGACATGG TTTCTTCTGGCTTTGGCACCACATATTTTCCCCATATGT CATTGCCTCTGGAGCTTCATGTTGCAATAGTTTTTCAAG GGGAACGGAGAGCACATTGCTAAGGGTGGGGGATGGCTT TTGCCTCTTTTGCCTGCCCTTTGCTTCAGTGAGTGTTCG TATTTCTGTTGGGCCTAGTTCTGTTTGGTTTTGTAGTCT TCAGAGTCAGTTATGTTTGGACTGAAAGATACTTAAGTA |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | AAAATAATGGCAAGTCAGAGATATGTCTGGCAAAGGTGC AGCACATTTGTTAAGGTTACTGGTTTATTTATCTCCCTT GTCTCTATGGTGACTAAATCTGGGTCTGGGATTTAATGG ACTTAGTTTTGACCTCTTGTAACATCTCCTAACTTTTCC CAGCCTCTGATTTAGAAAGAATTCATTTTCACTTGAGGA GAGAAACTGTCTCACTTAGAAAAGGGGTCCTAACTGGAC TCTCGAAAAGTGG |
| 24 | FHL1 | Dph-CRE24 | 561 | GTCTGCATCCTAATCCTGCTGTTGATTGGAGATAACTTC AGCGGTCACAGGGCACCTCGTCTCCATGGCAACCCCTCT AAATATTCCTCTAGTGACTTGTGCTCTACATTCTGGCTG GATCAGAGCCCTCCTGTGGCAAAATATTCTAAAGATGTT AAAAGAGAGAGAGAGAAAAAAAAAGGCTCAACTAATAAA TCTATTCTAAACGACTGAGTCATTTGTTTTGATTACCCG GGTGATTGCCAAATGTTAATTTAAAACTGAAATAGGCCA TGAGCTCACTCCCCTAACAATGCTGAGTGTTTGAGCTAA TACGGCTTGATAATGAGGGAGCCAGATCCACTGCCAGTG CTCATGTTATATGATAAACAGACATTTGGAGAAGTATGC AGAACATCTTGGCAGTTTTCCTTTAACTCTAAGGGTTGT AAATACAAAGTAGAATGTGTTACCATGAGCCATTTCATA GGAAGTTGACTTTATTTTTTTAGAATTCAGAACTTTGCT TCTAAAAAGGTAACTTTGCCTCTTGATTCTCATTTTTTT CCCTAACTTAGGCAC |
| 25 | FHL1 | Dph-CRE25 | 511 | AAAGACAGGGAGGTGCAATCTAAGTTAGGAAATTGGTGA CAAATAGTCATAGAACATGGGTCACCTGGCTTCAATTAG TTATGTGACCTTTAAGAAAACAAGTGCCCGTTTCAGAAA AGACTGACCTTTGAGGCTAGAGACATCAAGCTACTCCTC TACTTTTAGGAAAAAACAATGACAGGGTTAATTTAAAAC TCTGATGCAGACAGAGTTGAAAAATCCATGACAGATTTA TATAACGAACGTGGATGGTGTTTTGTTTTCCCAGAATGC AGTTTTAAGGTCAGACCTATGACTCAGAGCTGTGCACTT CCCTGGTGGTATGCATCAGTGACATGTTGCCAGTCTAAT CGTCCAGAAGGGCTTGTGCCCAGCTCGGCTTGCTCCATT ATAATCCCCAGCTGAGAAGCCACCTTTCATTTTTTTTAA ATAGATAAGGAAGACAGCATGAACATTTGAAACTCAAAT ACTATATGTAGTTTATAACTTTTCAGCCTGAAGACTTGA TGCA |
| 26 | FHL1 | Dph-CRE26 | 399 | AATGCAGCATACCAGTGAAGTTGCTAATTACATTGAATC ATTCTGTACACGTTCTATTTTGAAGGGAAAAAACACTTT CTGATTTTTGTATGAAATTGTATGAAAGACTACTTTTCA GCCGTGACTCATGAGCTCCGTCTCATTGCAGCTACTTAG GTATTTATTCCCAAATGTCTGACGACACCTCCAGGTGCA TTAGCATGTCTATTACACAAGTGTCCTATTCATTGGCTA AGGCTTTGCTCCATCTGTTGAATGTTCTGAGGAAAGCAT TATACCCTTTCTTTAGAAGCCAGTGTTTATATGTGGAGT CACTAATGTACTGGTAGGTTGGATTTAGTGAAGAACAGA TCTGAAATAACCTGATTTTTTCCATTTGGGTTGTTGTT CATTGTTTA |
| 27 | TNNT1 | Dph-CRE27 | 360 | CCCAACCTTTGAATGTATATGGGGGAGAAAATAACAGAC AAGGTTGGAGGCGAAGATAAGGGGGGATGGGGTGGTGCT TCTCCGCAAACATCCAACCCTTCTGTAAAGATTCCTCCA GACTGGGGAAGAAGGCTTGGGTGTCGGTCCCTTTAAGAA GGAAGGGAAAGGGTTAAAGCCACTGCGGGGCCATTTCCC TTCCCGGCCCCGAGAGGGCGCAGGAGCTCTCAGGGGCTT AAAGGACCGGGCCTGGGGGCGGGTTATGGGGGCGGAGGG AGGGAAGGGTGGTCTTGGAGGTTGGGGCCCGAGGATATC GGGGGTCCCCCCGGGCCCCCGACATCGGTCTCGGGAAGC GAAGCAGCC |
| 28 | TNNT1 | Dph-CRE28 | 471 | CTCACCTTCCTCCTCCTCCTCCGCAGCCTCCTCTGGAGA TGGGGGCACAGAAGAGAAGGCGTTAGGAGCTGGGGGAGG GATGGGGGCGGTGGCCAGAGACCAGGGTTCCAGTCTCTG CTGGACGGGGGTCCCTCTGGCCTCGGCTGCGATGGGCAC GTTCCCCCTGGCGGTGCAGGGATGGCGCGAGGAGACGCT CCAGACCCGGAGAGGGCGGGCGAGGGCCCGAGGGCTGAG CCGCCCCTTCCCCGCCAAAGTGCCACACTCCTCGCCTCC CCTCCCAAGAGCTCCTGGGCGTGTCCCCATCCCATAGGG CCGGCCCACTCCCTACTCACCTTCCGGCTGCTCCCTGCG GACGGGTGTGGGAGAGAGGAGGGAGGGGAGAGTTAGAC CTGGGGTGGGAGAGCCTCTCCACCACTGCACGCCCCAAC CCCTCCCAGTGCAGCACTCACTCCTCATATTCCTGCTCC TCG |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 29 | TNNI2 | Dph-CRE29 | 393 | GGCCGCCTGGGAAGACCGGGGAGGTGGGGGCCAGAGAGT CGGGACCACATGGGATGGGGCGGGCTAGAGCCAGCCCTG TAGGGACAGAGTGGGCAATGGTGTCTGGGGGCTGGTGAG CATGGAGGGAGGACCCCCAACACCTCAGAGACCTGTGCT GCAGGGCCTTCCCTGCATGAGCAGCAGGGGGCAGCAGAT GCCTTCGGAAGCCGCTGGGGCCTTTAGGGGCTCAGTCCT GGCCGGATGCCCCTCCCAGTCCCCACACATCTGGGCTGC CTTAGCGGCTGGGGCCTCCACGCTGCTGTCTCCTCTGAT CCTCCCCACGGGGCTGCGAAGCCGGCAGGGCTGGGGCCA AGAGCCCCCACTCCGAGAGGGTGCCAAGTCACGGTCCAG GGG |
| 30 | TNNI2 | Dph-CRE30 | 331 | CTGTCCTCAGGCTCCTTACGAGAACGACAGAGGCATCTC CAGCGCGTCACCGAGCCCTAAATAGAGTAGCCCAGCCAC GGCACCCCCACCAAGACTTCTTGGACTGGGCGGCAGCA CGCGGCCAGGCCAGGCGGCCGGACAGGTGGGGAGGTCTC TGTGGCTCTCCACGCCCCCATTGGTCTGAGGAGGACTCT ATGCCCTTTCTGAGCAGGGGCCCAGCCTGGGGGAGGCCA TTTATACCCCTCCCCCTGGGCCCACCAGCCCAACTCGCC GCTGCCGGCCTGACCTCGCTCCCAGCCCTGCTGCCCAGA TTCTAGGTGAGGCCCAGCC |
| 31 | TNNI2 | Dph-CRE31 | 306 | GCTCCCCCAACTCAGCATAGGTCATAGGTCACAGCCTCA AGGCCCTAAGGCCCAGAGAAGATGGCCTGGCCCTCCCCG CTGGCAAAAGTGCCCCACCCACCCACCAAGACGCTGCTG AAAGAGAGGAAGTGGCTGCCCCAAGCCTTCTGGGGCAGG GGAAGTGTGGCTGTGGCCTGGTCACAGGGGAATCACTTC TTCTTTCTGATTCCTGCACTTCCCGCCCCCACCTCACCG GCCGACCTGCCCCCAACTGGCCCTCCTCTCCCCCAGCCT CTGGCCTCCCAGCACCATGTGCCACCTGGCAAA |
| 32 | MYLPF | Dph-CRE32 | 268 | AACTCTGGCACATTCCAGCCCCTCTTTGGGAGAAAGAAC ATCTCTTCTTGCCCAGGCCCTAGTGAGACATGCATCGCA AGACATGCTCCCCCCTTCCTCCCCGCTGGGCTCCAGCTG CTGCCAGCCCTCCAAGAAAGGAGAGGCCCTGAGTTGGGC TATTTTGGTATCTGGGGTGGGCACCCGCAGGGCTAAGGT TACCTTGGTATGTTAAGGGCTCCCTGGGGCAGGACTATA TAACCCCAGAGGGACTGCCCCATGCTGACTCCTT |
| 33 | TNNT3 | Dph-CRE33 | 214 | TACCTGGTGCAGGCCCTCGAGGCCGCTGGTGCCTGCTCT GTGCAGTCCCTGCTACGCCTCAGGCCCAGCGCCCGAGGG GGAGGTCGCCGATACCCAAAATAAAACCTGCCCTATCCC TCTGACCTCAGCTGGCTGGGCGGAGAGCGCCTGCCAAAG CTCCAGGAGCTGGGCGGGCAGCACCTTCCCCTGCTGGCC ACACGGGGCCAGTGCAGGG |
| 34 | TNNT3 | Dph-CRE34 | 129 | TCTTGGGTTTCTGGGCAGAAACGTCTTGCCTATTTCTGG ACT+CCTCAGCTGCCACTGGCTCCTTATAAATAACCCACC CCAGGCGAGGGCCACGCTGCCCCATCTTGTGGCAGCCG ACAGGTGTCTGC |
| 35 | TNNT3 | Dph-CRE35 | 403 | TTACCTGGTGCAGGCCCTCGAGGCCGCTGGTGCCTGCTC TGTGCAGTCCCTGCTACGCCTCAGGCCCAGCGCCCGAGG GGGAGGTCGCCGATACCCAAAATAAAACCTGCCCTATCC CTCTGACCTCAGCTGGCTGGGCGGAGAGCGCCTGCCAAA GCTCCAGGAGCTGGGCGGGCAGCACCTTCCCCTGCTGGC CACACGGGGCCAGTGCAGGGTTATGGCACACCCCACCTTC AGGTGCGCCCCTCAGGACCCCTGGCCTGGGTGAGGGCTT GGGTGGGCACAGGCTTCCTAGGCCTGCAGACTGAACCAC GTGTAACCAGAATGGTGGGCTCAGGGCTCCGTTAGAGAA GCCGGCAGAGCGAGCCTGGAAAAGGAGGTTGGCCCCACC ATGGGAGAGGATG |
| 36 | TNNT3 | Dph-CRE36 | 415 | AGAGTGAATGCATGGGAATGAATAGATGGGTGGATGAAT GGACAACTGTGTGAAATAGCAGACAGCCTGGGGACACCC TCCCTCCTGTCCCTCCTCTCCCAGGTCTTGCACTGGGCC CTGACACTCAGCCCTGCAGCCTTCAGCGTCTGGGAAGTC CCTTCGAGGAGCAGCACCCCAGACTCTGATGTTCTGGAC TTCACTTTGCCATTCCCTTGGGTCCTCACAGCCACTATT TTCTGAAGGCTTCATGTCAAACCCTGCTTGCCTCATGAA TACACACAGTTCAGAAAAGCAAAACCTCGACAGAGCGAC CACCCACACAAGGGAGGTGACGTGCCCCATCCTTTCTC AGATGCCCCAGCCACTGAGAGAGGATCCAGGCCACCCTC CCCAGCTGGGGAACCACCCAGTGAC |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 37 | TNNT3 | Dph-CRE37 | 352 | ACCAATCTGTGCCTGAACCGAAGAGTTCCGCAGACACCA<br>CCGCCCACGCTCAGCCTGTGGGGTCTGAGGGGAGTGAGG<br>GGGTGGGTCAGGGTGCCAGACTGCTCTCCCCCACCTGGT<br>GCCTCAGTTTCCCTGATCCAAGAGGCAGGGTTATCCAAT<br>CTGGTGGCCTCACTGCCAGCATACAGGCCATCAGAGGC<br>CAGGAAGGATGTCTGCTAGTCGGACGGTGCCACCTGGAG<br>TCCTGAGGAAAGAAAACCAGTCTCCACACGCCACAATGA<br>GCCTGTGGGAGATGCTGGCACAGATGGTAACGGCCACTG<br>CGAGTGCCCAGGGTGGGGCCCCAGGGTTAGAAAGGGCCT<br>A |
| 38 | TNNT3 | Dph-CRE38 | 349 | CTCCTCAGCCCATCCAGAATGTACCCGCTGCTGGGAGTA<br>AAAATAGCAGCTGACACCTCCTGGAGGCGGAGGGAGGAC<br>CTTGCCTCCTTCTCCAAGCACGTCCTCTGCATCCTGGCC<br>TCCTTCAGCCTCCTCCTCTGGCCATTCCTATACTTGGTA<br>AGGGGCCTGCACGGGCATAGCCCCCCCCAGCAAGACTCC<br>GCACACACCCCGGCCACCCAGTCACTGGCCAATGGGCTC<br>CTAGGAAGATCAAATGTCACTATAACACGAGGGTGTGAG<br>CCGGGCGCCAGTGCCTGCAGCCGGTGCTGTCCACAGGGA<br>GCTCCAGCCCTTCTCACACTCGACCCGCAGGTGGGTA |
| 82 | MYH2 | Dph-CRE82 | 390 | GAAGCCAGGTATCCTGGCTGCCCAGCCACTGCCTTTATC<br>CACCAGCTTGACTCTTTCAGATCATCTTCTCAAATTATC<br>CATAGGAGATTTATCCACATACTCAATAAGAAAAATATT<br>TCTAATTATATCCAACCATTCTTAATATGAATGAGAATT<br>ATGCGGGGACGCTAGATTGCCAAGAGGTATTTTGCCAAA<br>CAATTCCTTTTGACTTAAGAAAGAAGAGGCAGCTGCATT<br>GTTTCCATAGCTATCCATATAAAAGAGCCCTTGGAATGA<br>GGCTGACTCGTCCTGCTTTAAAAAGCTCCAAGGTAAGTG<br>GGAGCAGGACGGGCCTTTCAAGAGGGACACTGGTCACAC<br>CGCCCAGTGTCAGCAGCAGCTGCTAGTTCTGGTACTGCT |
| 83 | MYH2 | Dph-CRE83 | 294 | CAGCTGCTAGTTCTGGTACTGCTCCTTCTGGAACTGCAC<br>GTTTTACCTCTATGAATTTTGTTACTTCTGTTTACAATA<br>GCAAGCCATGCCATAAATGGGATTTTTTCCCCCTCTTTT<br>TGGTCAACTAATCAAGTGCTTTTCCCTTTTCTTTTATAG<br>AACTGTCTCACTCCCAGGCTACATCTTCTCACTTGCTAA<br>CAAGGTAAGATTTGGACTAACCAGTTCCTGGAGGAGAAT<br>GCAAGAGGCTCTGGGATGGATTTCTGTCACTTAGCAACC<br>TTTCAGAAAGTGCTTGTCTCA |
| 39 | SLN | Dph-CRE39 | 380 | TAACTATGTTTAATGTGCTGAGAGAAAGCCATTTGTTTA<br>CAGAATCTTATTATAGAACAGAAATATACTTGTTCCAGA<br>GAAGAGGAGTTTAATTGGTTCCAAGTCAAATGATGCTAA<br>CAGGCGTCACCTCACCAATCCAGGACTTAAGATGGGTTA<br>TTATAAATAGGAGTAACACATATTTTTTTGGCTCTTTT<br>TCCCACCTGTTATGCAAGACTGCATACCACTATGATGTT<br>CCTCCTGATTATTTCCAGGAACTTTGGGGGTGGCTCACG<br>TGTGCTCATGAACAAGTACTGTCAGGTATCACATACGGT<br>CTGTCATTTTCTTGCTCTTGAGCTCTGGCACTTCTCTGC<br>TGCTGTCTGCTGCTGAGGCCTGCAGAGAT |
| 40 | SLN | Dph-CRE40 | 575 | TTCTCTCTCACTGTAAAAGTGTAAAAGGTTAGGTTACTC<br>CCCAGCCTGTCGAACATGTGCCTGATTGCCTTCTGAGAT<br>AGCACATCCCTAATCCAAAAGAAAACCTAGCCTGGAGCT<br>TGCATCCAGCTAATCTTCTTCCACATTGCTCCAAACAGG<br>GAGTTCAGTTTTCTCATTACTCATACAGAGAGCAGAGAT<br>AGATTTTCATGATTCTTCAGGACTCTGTTCTCTCTGCTT<br>TAATAGCCAAAAGCTAAAGCCAAATGAACTTCTTCACAG<br>AGAACAACAAGCAATTTTATCTAATCCTTATTATTCTTG<br>CTGTAACTGCAATTGTGTTATTCTGACTGACAGATTCCC<br>AGAAGAGATTCAGTGAAAATACCCTTGATCAGATTCACA<br>AAGGAACAGCATATTTCAAGTGGGCGTGTCTGGCTAGAA<br>TCTCCCTGGACAGTTCAGTAACAGCACATCAACAGACTG<br>CTGAATTCTTATTTCCCCGTCCAAAAAATAACAAAGCCA<br>ATCTGAAATCTGGAAGTGTTCTGAGGGCAGATGGTATTA<br>GCCCAGTAGTAAACATATTTTTGGCTGCT |
| 41 | SLN | Dph-CRE41 | 463 | CTACAATAAATATATAACTTTTTTAATTTGACAAAAAAT<br>AATTTTGAGTGGTTACAAAAAGGGACAGGTGTGGCTTGG<br>TAACTAGAAAAACATTCCCAGCCTGGGAAACAATCTAGT<br>GAGAGCTTGGAGGCAGAAGACAGAACTCTGATTACATTC<br>AAGGAGTTTGCCAGATGGCAACAGATAACTGCCAATGTT<br>CGGTTGCACTATAATTATTATACACTCTCTGTCACTTCA<br>GCAAGCGCTCTTTTCACAAGACAAGTGGTGACAGAATGT |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | TGTATTAAGATTACCCGTTGCTAAGCTTATGTTAAAATG<br>AGGAAATGAAATGGAAAGTCTTGTTTTGGTAATGTCTCT<br>GGGGTATGAGGAATGGAGGGAAAGGTTTGACTATGAGCA<br>TAACTGCATAGAGAATTTTGTTTGTTTATGCCTTTTGGG<br>AATGCATTATTTTGATTGACCCTAATTGGGAATT |
| 42 | SLN | Dph-CRE42 | 379 | ATTCATGAAGATGTAAAAGACACATTTAAAACCCACATC<br>AATTGCACTAAAAGTCAACTGGAAACAGAAGGTTTTTAA<br>ATCCTGGTGGTGGCAAATTGGCAGCCAAAGGAACAAAGT<br>CTTAGTCAACATATTTCCATGTCCCCCGAACACAAATAG<br>CCTCGAACCTTCGGAGGGTGTTCCTTTGAGATGTTTCAT<br>CAGTGACATCACAGTGATTGCCAGCTTCCACGGACTACT<br>TTAGGCGCTGCCCAGAGTCCAGGAGTCCAGACAGCCTGG<br>GAGGGGAGAAGGAGTTGGAGCTCAAGTTGGAGACAGCGA<br>GGAGAAACCTGCCATAGCCAGGGTGTGTCTTTGATCCTC<br>TTCAGGTAACTGCAGGATTTTTATGCTT |
| 43 | MYBPC1 | Dph-CRE43 | 250 | AAGAAGGAATACCCTAGGGCAAATGCGTGCTAGAGGGGC<br>TTAATACTTGGCAGAATCCTTCTTTTTCAGTAGCCTGCT<br>TTTATGACTGCTCCGACTGCACCTGTTAGGAAGATAAAT<br>AAAGGACTGGCCAATTCTTTCCTCTGAAGCGCCCTAAAT<br>ATATCACTTTAAAAAGACTTTGGAAAAACAAGTTGTATC<br>CTTACTTCTCACCCAGTAAATCTAAAGAAATTCCCTCTT<br>GTTCCCAGGCCTTTCA |
| 44 | MYBPC1 | Dph-CRE44 | 194 | CCACATAACTAAAGCATGATGCTATTGAGTTCTAAGTCT<br>AGTTTCCACCCTTATATGAAAAGTCAGCTTGGCACAGAG<br>TTTGGTAGAGCTAAGTCTGACCAGCTGCACTCTCAGCCA<br>CAAGGGAAATTAGACGAGACAGTGTGGCTGCTTCAGTAC<br>CAATCAATCAAAGTTTTTGAAAATTATCTTGAAAACAC |
| 45 | MYBPC1 | Dph-CRE45 | 264 | ACTTTCTCTGTGGATTGCAATATTTCCTGGCATATGTTC<br>ACTTCAGTAAGACGATCAGTGTATTAAAAACCCAATGGG<br>GTTTCTGCAGAAGCCAATGATGGCATGGCACCTCTTTTG<br>TGGCATGTGTGAAATCTGCCCTTCGCTGTAAACATTCTT<br>ATGCAACATGACACTCTGCCCTATGTCCATTTCATATGT<br>GGTGTTCAGTGTGCTGGGAATGCTGAAAAAAACAATTCT<br>CTCTTAGAGATTTCCCAAGTAGAATCACAG |
| 46 | MYBPC1 | Dph-CRE46 | 427 | AGAAGGAATACCCTAGGGCAAATGCGTGCTAGAGGGGCT<br>TAATACTTGGCAGAATCCTTCTTTTTCAGTAGCCTGCTT<br>TTATGACTGCTCCGACTGCACCTGTTAGGAAGATAAATA<br>AAGGACTGGCCAATTCTTTCCTCTGAAGCGCCCTAAATA<br>TATCACTTTAAAAAGACTTTGGAAAAACAAGTTGTATCC<br>TTACTTCTCACCCAGTAAATCTAAAGAAATTCCCTCTTG<br>TTCCCAGGCCTTTCAAACAGTGAAGTCAGGAGTAAGGGA<br>GACTGTGGACTGGTCAAAGGTGGAAGTTAGACTCACTAG<br>CTGGTCTAAGGAATCCAGGAGGGTGGAAAACATGAAGAA<br>CTTACAATCCTTTATGCTCTCAATGACTCACTTTATTTT<br>GGCCATGAGACACAGCCTTGAAACTTTTTTTTTTTT |
| 47 | MYBPC1 | Dph-CRE47 | 436 | GGTCATAAAATACTTTCTCTGTGGATTGCAATATTTCCT<br>GGCATATGTTCACTTCAGTAAGACGATCAGTGTATTAAA<br>AACCCAATGGGGTTTCTGCAGAAGCCAATGATGGCATGG<br>CACCTCTTTTGTGGCATGTGTGAAATCTGCCCTTCGCTG<br>TAAACATTCTTATGCAACATGACACTCTGCCCTATGTCC<br>ATTTCATATGTGGTGTTCAGTGTGCTGGGAATGCTGAAA<br>AAAACAATTCTCTCTTAGAGATTTCCCAAGTAGAATCAC<br>AGTGTTAAACCTATCAGCAGCCTCCAAGATCATTTTTTT<br>TAAGCCCCTCATTTTACACAAAAAGAAACTGAGGCCCAG<br>AAAGCCCCCTGACTTTCTCAGAGTAACTAAGCTGGTTAA<br>TGATAGATCCAGAAATAGAACCCAAGGGACCAACTTCAG<br>ATTCTAG |
| 48 | MYBPC1 | Dph-CRE48 | 359 | CTGAGTCAGCACATGCATCTGTCAGAGAGAGAAGAGCAA<br>GACGGAGCACGAGGCTGCAGCTGAATTTAGAAAGTTAGA<br>GGTGTTCTCATCAGCCACATGAGATGGGCAGGAGATTCC<br>TTCCAGTAGGCGAGAGAGCAGAGTGCAGACAACAGATGT<br>GAGAAAGGTCCCCATAGCTGTCAAGTTCCTGCATCCTTG<br>TGCTGAAGAAAGGGAGGTGCCATCATGATTGATGTTCAG<br>AGGCAGTATAAAAGCACTGGGTTTCTCCCCAACTGCTTG<br>TCACACCGACCTGCACCATCTCTCGCCTGCCTGTGGGGT<br>TTCTGTCAACTAGTCGTGAGGGAAGGAGACTCTTTAAA<br>GAATAACA |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 49 | MYBPC1 | Dph-CRE49 | 353 | GAGATTTCATCACATTTTAAAGTTTTGCCAAGCCAAAAA GCTACCTGAATGTAGAGCAGCATTCATCCCTCTTGCCT ATTTCTAAGCATTTCTCAGGGCTTAGTCATCCATCAGAA AAGGACCTCCCTTGATGGGAAAACTCCTTCTCATATCTC TTCTTTGACCTTCAGTTTCTACCTGCAAGAGAGTGAATG GCCTATTTCAAACACCGAAATCAATTTGTCTTTGGAAAG TCATCTTATATACAAATATTATCCTTACCTCAAATTGGG GAAAGGTTAATAATTTATGCAGAAAACTAAGAGAAAGGA ATAGGGGAGGAGGAAAGATAGTTTATCAAGGGCAATTGT TT |
| 50 | MYBPC1 | Dph-CRE50 | 354 | TCAAAAGTCTTTTAAACATATTTTCTTTATATAATTAAG TAACCAGTGTTGACAGGCTGTGGTGATCAGTTTACAGGT TGGCCTTACTTAGTGGCAGAGGGCATTGATGGATGAAGT CTTTCACCCAAAATAACCACACCAAATGCATGTATTAAT ATGGGAACTTAATCCTGACTGTCAGGCAGGGAGTCCAAC CCCTGCTAAAGTATCTTATTTGTAATGCAAATGATTTAC GTGTGTACTAAGTGTCCTTTTTATCTGCTCTGTCACTTT AACCTCTCCGAAGTGTACCCAGAAGCAATACATTCTACC ATGTTTCCAAACTGGAAACACAATATTGTTTTAATTATT CTG |
| 51 | ENO3 | Dph-CRE51 | 351 | GCTGTCCCAGCGTTATCAGTCGGGCGCCTTGCCAGCCGA AAGGGCCTGTCTAAATTCGTTTCCTGTCCCCTAACTCAT CCCGGCGCTGGCTGGCCTGGAGAGGGTAGGATGGGGCGG CGCCGAGAATGGCCGTTATGAGGACCCTAAGAGGTGAGA CCCTCTCGCCTTCTGGGGTGGGGGGTCCCGTCCTTTCCC CCACTGAGGACAGAGGCCCGCCCAGCGATCTGAGCATGT GTGGACGTCAATCTTGCAGCCCCTCTTCCAGGCCCCCTC CCCAGCCTTGCAGGGCTCAGGTTACCCCTGGCCTTTCCT AAAGGTCACTCATTCCTCTTGACGTTTGCAAAAGGGGAA |
| 52 | ENO3 | Dph-CRE52 | 607 | TGTCCCAGCGTTATCAGTCGGGCGCCTTGCCAGCCGAAA GGGCCTGTCTAAATTCGTTTCCTGTCCCCTAACTCATCC CGGCGCTGGCTGGCCTGGAGAGGGTAGGATGGGGCGGCG CCGAGAATGGCCGTTATGAGGACCCTAAGAGGTGAGACC CTCTCGCCTTCTGGGGTGGGGGGTCCCGTCCTTTCCCCC ACTGAGGACAGAGGCCCGCCCAGCGATCTGAGCATGTGT GGACGTCAATCTTGCAGCCCCTCTTCCAGGCCCCCTCCC CAGCCTTGCAGGGCTCAGGTTACCCCTGGCCTTTCCTAA AGGTCACTCATTCCTCTTGACGTTTGCAAAAGGGGAATG TAATCCTGGGGTGGGGGGAGACCCCTCATCTGTAGCCCC TCCCTTGCTCCTCCCAAAGGGTGGAATTAGAACAGGGAC TGTTATTGGGAGACAGAAAGTGGGGGATAGTAGTTGACC TTTGGTAAGGGGGCAGGTGCCCAGGGCCAGAGGCTTCTG CTTCAGGCTGTAGTGGGCACTTGGCTGCCAGCCCAGTGT GAAGGGGGAGGATGGAGAGAAAGAGAGGCGGGGCTGGC TGGGGACCGAGTGGCTCAGGGA |
| 53 | ENO3 | Dph-CRE53 | 469 | AGGGCTGGGCGGCTTCCGGAGCCTGGGCTAGGGGCAAGG GGTCACCGAGCGCGGCCCGGGCGGAAAGGGGGTTGGTTT TCTCTCTCCTCCCGAGCGCGGCGCGCATCCCTGGCGTCC ACGCCGAATCCCACAGTCCCCGACGCCCCTCGAGTCCGT GTTCCTCGACAGCCGCGCGGCTGAGTCACTGGCGGGCTC GGGCGGGGCCGCACCCGGGCACGTGGCGGCGCTCCCCGC CCGCCATCTCCTGACCCCTGGCCCACCGCACCCCTACCC CAGGGTGGAAAAATCCCGGGAGGAGCGGCCTGAGATGAG GGGGCGGGGCGAGAGGGGAGACTGGACGGGTGGCGGGGC AGGTGGCCTGGGGTGGGGGCTGGGAGGCCGCGCGGGCCG GCGGGGCGGGGAGCAGGGGTGGGGAGAGGGCGGCGGGGG TGAGTCACCGGGCGCGCGCTGCCCCGGCGCCGACGGGAA G |
| 54 | ENO3 | Dph-CRE54 | 332 | TGGGTTCACCAGGGCCCATTCTCAGTCTAGAGGATTGTC CCTTCTCTGGATCGGCTCTAGCCCAGGGCCTCACCCGAC ATCCCAGCCCCGCCCGCCCCAGGCAGGCAATGTCTGGAT CACCGGCCGTGCCCCTTGGCCTGTGTCTGCAGAGGTCAC AGAGCGCGGACACCCGCGGGGCTTAACAGGCGGGGCTAT TTTTCGAGGCGGAAGAATACTCAAGTTGCAAGAGTGGCA ACTTTTTCAAGAAGGGGAAAGTCCCACTTCGGGCCCTTT GGGTTTCTTCGCAGTCAGATGTGCGCTCACAGCCACCTG GGGAGGGCGGGACGGGCGGG |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 55 | CA3 | Dph-CRE55 | 206 | TACATTCCAGGGAGGGAGACCAGTTGGGACAAGGCCTAG<br>GCTGCTCTCCTACAAATTTGCCATGAACAGGAGCCAAAC<br>TCTAAGACCTGATTCAAGTGGCCCAGCTGTCACTGGTGA<br>CACACTCAGGGGCTGGGCCTATCATGTTCTTATACAACC<br>TAGTGAGTCAAGCTTTGGAAAATAACATTGTCAGGGAAG<br>AACGTAAAAGT |
| 56 | CA3 | Dph-CRE56 | 289 | GGAGCTGAGAGTTTAAGGGCATTTGTTTACTATGTTTGC<br>TTGGATTTTCCGAACTGCCTTAGTTCCTGATTCCACACT<br>GCTATTGTGTGGATCAAATAATCCCTTGTCACAAAAATA<br>CCCTGGGGAATGACTCCCCTGGCGTCCAGGTTATGAGTG<br>TGGTCAGTCATTCCACATGCCTTAGGGATGAGCTATCTG<br>TGCCATGACGAGCGATTTCCTTTTCGAGTTTTGTAATCC<br>CCAAATACTAAATACTATTATCAATAAAAGTTAATTAAG<br>GAAATGTATATCGAAA |
| 57 | CA3 | Dph-CRE57 | 195 | GACAGCTGTCCCGCTCTTGGAATTCATTGGCTTCCTCTA<br>CCCGGCCTCCCAAACACCACCCCAATCTAGTTTAGCCCC<br>CCGCCCCACCCTCGCTGACCTAATAAGGCCATGCAGTGT<br>GCGGGGGAGCTACATAAAAGCGCGGGCTCGCGGCGACTC<br>TGCACCACGCAGGGGAAGAGAAAGCAGGAGCCGTCCAGC |
| 58 | ATP2A1 | Dph-CRE58 | 345 | CCCCTCAGCTTCAGCCCCCACCTCCAGGAGGCCCTACCC<br>ACGCTCATGACCTTGCTATTCTGGGCCTTGTGTCCTGTA<br>GGGAGATGGACAGGAGACAGCTGGGCTTCCAGGCCACCC<br>AGGCGGGGGGCTAGCCGAGGGAAGCCTGCTGGCTCTCCT<br>GCTTGCTCTAATTTCTGGGGCTCCCCAAACCTTGGCCTC<br>AGGAGACTGGGGATAGGACCGGCCTTGAAAGTGGGGGAA<br>GCTTTGGAGAGCCGGGTGCTGGGTTCTTAGTGAGATGGC<br>CAGTGAAGGCTGTGGTGCCCCGAGGTAAGCAGGGCCTGA<br>TCCCCTCCTAATCTTCCAGCAGCAACTGGTGCT |
| 59 | ATP2A1 | Dph-CRE59 | 220 | CTCCTCCAGCAGCTGCCCTGGTGGTAACCAAGAGACGCC<br>CCCATCCTGGAGCAGGGGTGGGAGGGGCAGCTCAGAGC<br>AGCTGCTTCTCTGAGGAAGCTGACACCAAGGCCAGCATT<br>CAGCAACAACTTGTGGCTTTGCACCCAGCGCCGGGGTCC<br>CCGCCCACCTGGCTCCCTGCTGTCCCTCTTCCCCACTGC<br>TGCTCGGACTTCCCTCTGACCCTGG |
| 60 | ATP2A1 | Dph-CRE60 | 663 | CTTTGCTCCCTGGGAGGGCCTGGCCCTGTGGGCATTTGA<br>GTTTATAACACCACCCCATTGTGGCACACCCCTCCACC<br>CCGTAAAACACAGGCTCTGCTCTTGGAATCAGTCTTCCT<br>GATCTGTGGCTGTGCCCTCCAACAGAGGGCACCCCTGGG<br>CTTCCCAGCTCTGGGGGTAGTGGGTGCCAACAAGGAGGG<br>GCCTGGGGCTGAAGAATCCCACCCGCTGAGCTCGGCCTT<br>CTCCCTTCCCCACTGTCCAGCTCCGCCTTTCAGCATCCT<br>GCCTCACTCCCCGCCCAGGCAGCAAGGAGCCCACACCCT<br>CATGCCCCTCAGCTTCAGCCCCCACCTCCAGGAGGCCCT<br>ACCCACGCTCATGACCTTGCTATTCTGGGCCTTGTGTCC<br>TGTAGGGAGATGGACAGGAGACAGCTGGGCTTCCAGGCC<br>ACCCAGGCGGGGGGCTAGCCGAGGGAAGCCTGCTGGCTC<br>TCCTGCTTGCTCTAATTTCTGGGGCTCCCCAAACCTTGG<br>CCTCAGGAGACTGGGGATAGGACCGGCCTTGAAAGTGGG<br>GGAAGCTTTGGAGAGCCGGGTGCTGGGTTCTTAGTGAGA<br>TGGCCAGTGAAGGCTGTGGTGCCCCGAGGTAAGCAGGGC<br>CTGATCCCCTCCTAATCTTCCAGCAGCAACTGGTGCTCT |
| 61 | ATP2A1 | Dph-CRE61 | 594 | CAGCAGCTGCCCTGGTGGTAACCAAGAGACGCCCCCATC<br>CTGGAGCAGGGGTGGGAGGGGCAGCTCAGAGCAGCTGC<br>TTCTCTGAGGAAGCTGACACCAAGGCCAGCATTCAGCAA<br>CAACTTGTGGCTTTGCACCCAGCGCCGGGGTCCCCGCCC<br>ACCTGGCTCCCTGCTGTCCCTCTTCCCCACTGCTGCTCG<br>GACTTCCCTCTGACCCTGGTGGCTCTGTGTCTCTGCTCC<br>CTTTCCCCCTAGGTCTAGACATCTGTCCTTATTTCCCCC<br>AGACCTGTCCCCAGAAGTCCACCCTTCCCCATTCCTTTG<br>GTCTGGAGCCCCTGCTTGGTCCAGCTTCCCCAGGCCCCG<br>ACACCTTTCTGTGGGGTCTGCCTAGCTCCTGCACGGACA<br>CAGCATGGGCCTGATCCTGTTCCCCTCGTGGACAGATGC<br>AGCAGGGCAGAGTGCAGCGCAGACCACAGGCCTCTGGGG<br>CTGGCCACAGAAACCCCGTTGGTTAGAGCACAGTGTGGG<br>ATGAGGTGACCCTCAGTGCACGACTTGGGGTGACCCCTG<br>CCCCCATCCTGAGACAGTTACCCCTCCCCCTCTGCCATC<br>AGCACATTC |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 62 | ATP2A1 | Dph-CRE62 | 634 | CCTTCCCCATTCCTTTGGTCTGGAGCCCCTGCTTGGTCC AGCTTCCCCAGGCCCCGACACCTTTCTGTGGGGTCTGCC TAGCTCCTGCACGCACACAGCATGGGCCTGATCCTGTTC CCCTCGTGGACAGATGCAGCAGGGCAGAGTGCAGCGCAG ACCACAGGCCTCTGGGGCTGGCCACAGAAACCCCGTTGG TTAGAGCACAGTGTGGGATGAGGTGACCCTCAGTGCACG ACTTGGGGTGACCCCTGCCCCCATCCTGAGACAGTTACC CCTCCCCCTCTGCCATCAGCACATTCTGTAGCCTCTTGG GTTACTTGGCTGCCTTGGTGTCCCATTTTCTTGGGGGTG GGGTGGGGATTCCCTATCCAGGATGGGGGGGCCCTCAGG GCTCTGTTCCCAGAGGCTGAGTTAGAGCGATGGGGAAGG GGGGGGGCAGTTTTGGGGAGAGACAGGCAGTGCTGGCTT TGCTCACCAGGGCCTGGACACTAAATCCCTTGTTGATGG CTGTGGCAACCCCTCCCTAGGGTAGGGTTACCATCTTCG GCCCTGTCCCCTTGACTCTCTCCCCTCACTTCCCCTTGT CCCTCTAGGAGCCACTCACTTCCTCTAGCCCCCAAAAGA TGTTCTCCCT |
| 63 | ATP2A1 | Dph-CRE63 | 445 | CCTCCCCTGCACCCCAGAGGCAGGTTTTATTTTAAGCTT TAAGGGTGTTCTCAGCCAAAACACCGAAGCTAAGCCACC CTCGCGGCTTCAAGAGCTTGGAGAGCTCGGGTTACCCAC CCGAACTCCGGGCTCCGGTCCCGCCGCGATGCCGGCTG CGGCGCGGGGGCCACTGCCACTCCCGGCATGCGCCGGG CGGACGGCCGCTCCACCAATCCCCGCGCCCGTCGGCGCC CCTGCCCCGCCCTCCCCAGCCTCCTGACGCTGATTGGTC GAGGGGAGGACTCGCTCCTAGTGGCGGGAAAGCGCGGCG GTGTGATGATGACTCCAAGGAGCCCGGCGCCCGGTCAGG GAGGGCACTGGCATCCCTCATTACCCGCCCAGCCTGGCC TTAGCCCTTCCCCGCGCTCCCTAGGCACCCCCACCCCCG CAGGGCATCTCCAGGG |
| 64 | ATP2A1 | Dph-CRE64 | 408 | GTCTCCGAACGCAGGCCCCGTCGCGTTAAGCACAAGCTG GCAGGGCCTCTCCTCTCCCTTCTCAGATTTGCTCCTTGA CATTTGCCTGCTGCCTGGCGGTGGCAACAGCTGGGGCGG GGCGCGCGCAGGAGGCCCCGTAACCCTATCCCCGCTCCG GCTCCCTCGTGAAACCGGAGCTTCCCTGCCTTGGCCGAG GGGGAGGGCTGCGGGGGCCAGACCGCCTGCGAAGACCAC AGGGTTTTTCCTCTCGGGTTTTGGCTCCCGTGGGATGGA TGTGGCTGTGCGGGGGTTGGCCTGAGCTTCGCTTCTAA GCCAGCAGCTTGGTCAGGGAAACCTGAAAGCATTCCCAG CTAATCCCCCAAGTGGTGCAAGTCTGTGCGCGCCCATCC CGCTGAGTAAGGCGGTGG |
| 65 | MYH1 | Dph-CRE65 | 496 | GGCAACAAAGTCCAGGGATTCCAGAACTTAGCTGTCTTT GAAACAACACCTTACATTCCAAAGGCCAACAACTTTAAG ATTGCCAACGACTCAAATTATTTATAGGAGATTGATTCA TATACTTAACCCAATATGAGAGGAAATATTTCTAATTAT ATCCAAACATCTTTAATATGAGGGGAATTAGGCTTGGAG ACCTTCAATGCCAAAAACATGTTTTGCCAAATATGTTTT AAGAAAGAGGAGGAGGTTACGTGTTTTCCATATTTGAGC CTATAAAAGTACCCTTGGAATGAGTATGACTTGTCTCTC CTCATAAAGCTTCAAGGTAAGTGTGTGTGAGGACAGGGC TCTGTCTGGAGGACGGTAAGGGATGTCTGGCTGCCCGCG TGCATGCCACACATCCTGGCTCCCACTGTCCCTGGCAGC CCTGCCAGTGAAGCACCAGCTTACTCCGTAGCAATTTTA ATTAGATGTTGTAGTCTTCCCAGTCATT |

Table 4 below depicts the core nucleotide sequence of the different nucleic acid regulatory elements for enhancing gene expression in diaphragm, heart and skeletal muscle cells or tissue and their corresponding genes and lengths.

TABLE 4

The CREs sequence for highly expression in diaphragm, skeletal muscle, and heart.

| SEQ ID NO. | Gene | Dph-CRE (CRE) | Size (bp) | Sequence |
|---|---|---|---|---|
| 1 | ACTA1 | Dph-CRE01 | 328 | GGAGACACTCCATATACGGCCCGGCCCGCGTTACCTGG GACCGGGCCAACCCGCTCCTTCTTTGGTCAACGCAGGG GACCCGGGCGGGGCCCAGGCCGCGAACCGGCCGAGGG AGGGGGCTCTAGTGCCCAACACCCAAATATGGCTCGAG |

TABLE 4-continued

The CREs sequence for highly expression in diaphragm, skeletal muscle, and heart.

| SEQ ID NO. | Gene | Dph-CRE (CRE) | Size (bp) | Sequence |
|---|---|---|---|---|
| | | | | AAGGGCAGCGACATTCCTGCGGGGTGGCGCGGAGGGAA<br>TGCCCGCGGGCTATATAAAACCTGAGCAGAGGGACAAG<br>CGGCCACCGCAGCGGACAGCGCCAAGTGAAGCCTCGCT<br>TCCCCTCCGCGGCGACCAGGGCCCGAGCCGAGAGTAGC<br>AGTTGTAGCTACCCGCCCAGGTAG |
| 2 | ACTA1 | Dph-CRE02 | 452 | GACAGGTGCGGTTCCCGGAGCGCAGGCGCACACATGCA<br>CCCACCGGCGAACGCGGTGACCCTCGCCCCACCCCATC<br>CCCTCCGGCGGGCAACTGGGTCGGGTCAGGAGGGGCAA<br>ACCCGCTAGGGAGACACTCCATATACGGCCCGGCCCGC<br>GTTACCTGGGACCGGGCCAACCCGCTCCTTCTTTGGTC<br>AACGCAGGGGACCCGGGCGGGGCCCAGGCCGCGAACC<br>GGCCGAGGGAGGGGGCTCTAGTGCCCAACACCCAAATA<br>TGGCTCGAGAAGGGCAGCGACATTCCTGCGGGGTGGCG<br>CGGAGGGAATGCCCGCGGGCTATATAAAACCTGAGCAG<br>AGGGACAAGCGGCCACCGCAGCGGACAGCGCCAAGTGA<br>AGCCTCGCTTCCCCTCCGCGGCGACCAGGGCCCGAGCC<br>GAGAGTAGCAGTTGTAGCTACCCGCCCAGGTAGG |
| 3 | ACTA1 | Dph-CRE03 | 239 | AGAGAGAGGGACAGGCACCAACTGGGTAACCTCTGCTG<br>ACCCCCACTCTACTTTACCATAAGTAGCTCCAAATCCT<br>TCTAGAAAATCTGAAAGGCATAGCCCCATATATCAGTG<br>ATATAAATAGAACCTGCAGCAGGCTCTGGTAAATGATG<br>ACTACAAGGTGGACTGGGAGGCAGCCCGGCCTTGGCAG<br>GCATCATCCTCTAAATATAAAGATGAGTTTGTTCAGCC<br>TTTGCAGAAGG |
| 4 | ACTA1 | Dph-CRE04 | 509 | CCTTTTAGAGAATCCACACCTGTCCCAGTTGCTGGGTT<br>CCACTACCAAAAGTGAATTGCAACTATTTTAGGAGCAC<br>TTAAGCACATCCGAAAAATGAGTGATTCTGTTCTGGCC<br>CACACCACATCACTGATGTACCCCCTTAAAGCATGTCC<br>CTGAGTTCATCACAGAAGACTGCTCCTCCTGTGCCCTC<br>CACAAGGTTAGAACTGTCCTTGTCTTAGGGAAAAAGGA<br>GAGAGAGAGAGAGAGAGAGAGAGAGAGAGAGAGAGAGA<br>GAGAGAGAGAGGGACAGGCACCAACTGGGTAACCTCTG<br>CTGACCCCCACTCTACTTTACCATAAGTAGCTCCAAAT<br>CCTTCTAGAAAATCTGAAAGGCATAGCCCCATATATCA<br>GTGATATAAATAGAACCTGCAGCAGGCTCTGGTAAATG<br>ATGACTACAAGGTGGACTGGGAGGCAGCCCGGCCTTGG<br>CAGGCATCATCCTCTAAATATAAAGATGAGTTTGTTCA<br>GCCTTTGCAGAAGGA |
| 5 | ACTA1 | Dph-CRE05 | 169 | CCTTTTAGAGAATCCACACCTGTCCCAGTTGCTGGGTT<br>CCACTACCAAAAGT1AATTGCAACTATTTTAGGAGCAC<br>TTAAGCACATCCGAAAAATGAGTGATTCTGTTCTGGCC<br>CACACCACATCACTGATGTACCCCCTTAAAGCATGTCC<br>CTGAGTTCATCACAGAA |
| 6 | CKM | Dph-CRE06 | 400 | GGGCCAGGGGACGGTGGCTTCTACGTGCTTGGGACGTT<br>CCCAGCCACCGTCCCATGTTCCCGGCGGGGGGCCAGCT<br>GTCCCCACCGCCAGCCCAACTCAGCACTTGGTCAGGGT<br>ATCAGCTTGGTGGGGGGCGTGAGCCCAGCCCCTGGGG<br>CGGCTCAGCCCATACAAGGCCATGGGGCTGGGCGCAAA<br>GCATGCCTGGGTTCAGGGTGGGTATGGTGCGGGAGCAG<br>GGAGGTGAGAGGCTCAGCTGCCCTCCAGAACTCCTCCC<br>TGGGGACAACCCCTCCCAGCCAATAGCACAGCCTAGGT<br>CCCCCTATATAAGGCCACGGCTGCTGGCCCTTCCTTTG<br>GGTCAGTGTCACCTCCAGGATACAGACAGCCCCCCTTC<br>AGCCCAGCCCAGCCAGGTAC |
| 7 | CKM | Dph-CRE07 | 255 | CCCAGCCCCCTTCCCCGGGAGGTGGGAGCGGCCACCCA<br>GGGCCCCGTGGCTGCCCTTGTAAGGAGGCGAGGCCCGA<br>GGACACCCGAGACGCCCGGTTATAATTAACCAGGACAC<br>GTGGCGAACCCCCTCCAACACCTGCCCCCGAACCCCC<br>CCATACCCAGCGCCTCGGGTCTCGGCCTTTGCGGCAGA<br>GGGAGACAGCAAAGCGCCCTCTAAAAATAACTCCTTTCC<br>CGGCGACCGAGACCCTCCCTGTCCCCC |
| 8 | MYL2 | Dph-CRE08 | 354 | CTCCTGGGCTCGAGCAATTCTCCTGCCTTGACCTCCCA<br>AAGTGCTGGGATTACAGGCATGAGCCACTACACCCTGC<br>CCTAGTGTGCTTTATATCAAAGGGGA/vACCATTTGGGG<br>CTTCCAAACAGGAAATGAACAGTCGTACCTTTTGTCCT<br>CACTAACATTCAGATTGCAGGAATGCCGTGTCCCATAG<br>GGAAAGAGAAATTCCTGAGGCAAGTGTGYTATCTGAAC |

TABLE 4-continued

The CREs sequence for highly expression in diaphragm, skeletal muscle, and heart.

| SEQ ID NO. | Gene | Dph-CRE (CRE) | Size (bp) | Sequence |
|---|---|---|---|---|
| | | | | TTGAGATAGTCACCTTCCAGGCAGAAAGCTACACCCGC CTCTTTTCCCAGCCTCTGGCATCAGCTGCCGGCGGTGT GGGTAAGGGATGCAAAGAACTCAAAACATGTAGCCAGG ATTCCCCATTTG |
| 9 | MYL2 | Dph-CRE09 | 297 | TGACAAGCACAAGTGTCCCCGGCCCAAGCACCGCAGAG AGCGCGCAGCATCTCTCCCCGTGACCATGACCCAGCTA CTGCCTCTTTAACCTTGAATGCCTTTTTGGGGGCTCAC GTGTCACCCAGTGGCGAGTGAGCCACCCTTACTTCAGA AGAACGGCATGGGGTGGGGGGGCCTTAGGTGGTGCCCG CCTCACCTATGACTGCCAAAAGCGGTCATGGGGTTATT TTTAAACATGGGGAGGAAGTATTTATTGTTCCTGGGCT GCAGAGAGCTGGGCGGAGTGTGGAATTCTTC |
| 66 | MB | Dph-CRE66 | 319 | CCAGGTGACAGGTGGATGGTGGAGCTGGAGGAGCCACT CGGAGCCTCCAAGGCTGGGGAGGGTGGAGGGGGAGGC AGGTCGGTGTCCCAGGCCACACCTGTTGACTAAGGGAT TAGGATGTTGTGTCCCTGCCAGCCCTCCTCCAATAAGC CCCTCTGGGCCTGCAGGGAGAGGAGGAGCCTTGCCATG TAAACTGTATTTTTAGTTCCCTGTGCCTCTCCCCGGCT GCTATAAGACACCTCTCCCCACCCCCAGCCCTGGCCGC TTGGCTGGAGGCTCTGCGAGGACAGCTGGGGAGAAGGG GAGCTGTGGTCAGTA |
| 67 | MB | Uph-CRE67 | 372 | TCATCTTCTAATAATTTGGCAAGCCATCCATGGTCTTC TAAGCAAGGCGCCATGAATATAACGAATATAGAGACAG AAAAAGACCCCTCCCCACTGGCTGGGTTGAGGGACTGG AGAGCCCAGATGGAAGGGCAGAGGTGCAGGCTTTTTTC CTTGTTGCCACTAGATGGCAGTAGGGCACCCGTTGTCA GCCCTGGGGCAAGGTCACCGACTGTCTTTGCCTTTGCC TCCAGCAAGCCAAAACCCTGGGCAGACTCAATCCAAAA ATAAACAATCAAAGAGCATGTTGGCCTGGTCCTTTGCT AGGTACTGTAGAGCAGGTGAGAGAGTGAGGGGGAAGGA CTCCAAATTAGACCAGTTCTTAGCCATGAA |
| 68 | MB | Dph-CRE68 | 293 | AGAAAGGAGCTGCCCTGGGGATGGCTGTGTATCCCTAC AACTGCCAGGCACATGCCCCTTGAACACCCGATGCTAC GTGTCCCAAAGGAAACTGGTCTCCACCCACCCCCCGGCC CGTCCTCGTCCTGGGTACCCCACCTTAGTAAATGGCGC CACCATCTGCCCGGTCACTCAGCGAGAAACTCAACTCC TGGCAGCAGATGACGGGCACTCTGGTTAAATGACTCTC TCCAGCCTCCAAGTTCAACCTGCAGGGAAGCCCTGGAA ATCCTGTCTCCCTCTGCCCTGCCTCTC |
| 69 | DES | Dph-CRE69 | 482 | GAAACATGGCTTCCACAGGTTCCAGTTGAAGAATCCCA GTTCCGTCTATAAATTCCAGGGAAGGTCTCTGATTGGC CCTGCTCATTCCCAGGCCCATTCCTTGACCCAGTCACT GAAGTCAGGGAGATGCAGTAATAAGACTGGCTGGAATC AGGGTCTTTAGGGGTGGAGGGATGGGGAGGAGGCACAG CATGTCATCAAAATAAGGAAATTGCAAAAGAAAGCTTG CAGGCTACTTTGAATGACAATGAGAAAGACGGTGCTGC CTGAGTGTGTTAAGGATCCACATGGTCTCCAAAATCCT CCAGGAGCATACAGTCTAGTCTGGGAGATGAGACACAA AAATAACCAGAACACAACAGCTTGCACTGACTCGAGGG CTGGATAAGAATATCTGGAACTCCCCCATCTATTTCAG AAGCTTGTCTCTTGGATGAAAATTAGACACTTAATGGG AAAGGGCTTTGAAAAGAGTGCAGTAA |
| 70 | DES | Dph-CRE70 | 398 | CCTCAGGTACCCCCTGCCCCCCACAGCTCCTCTCCTGT GCCTTGTTTCCCAGCGATGCGTTCTCCTCTATAAATAC CCGCTCTGGTATTTGGGGTTGGCAGCTGTTGCTGCCAG GGAGATGGTTGGGTTGACATGCGGCTCCTGACAAAACA CAAACCCCTGGTGTGTGTGGGCGTGGGTGGTGTGAGTA GGGGGGATGAATCAGGGAGGGGCGGGGGACCCAGGGGG CAGGAGCCACACAAAGTCTGTGCGGGGGTGGGAGCGCA CATAGCAATTGGAAACTGAAAGCTTATCAGACCCTTTC TGGAAATCAGCCCACTGTTTATAAACTTGAGGCCCCAC CCTCGACAGTACCGGGGAGGAAGAGGGCCTGCACTAGT CCAGAGGGAAACTGAGGC |
| 71 | DES | Dph-CRE71 | 241 | CAGGGGCGCAGGCCTCTTGCGGGGGAGCTGGCCTCCCC GCCCCCACGCCCACGGGCCGCCCTTTCCTGGCAGGACA GCGGGATCTTGCAGCTGTCAGGGGAGGGGAGGCGGGGG CTGATGTCAGGAGGGATACAAATAGTGCCGACGGCTGG |

TABLE 4-continued

The CREs sequence for highly expression in diaphragm, skeletal muscle, and heart.

| SEQ ID NO. | Gene | Dph-CRE (CRE) | Size (bp) | Sequence |
|---|---|---|---|---|
| | | | | GGGCCCTGTCTCCCCTCGCCGCATCCACTCTCCGGCCG GCCGCCTGCCCGCCGCCTCCTCCGTGCGCCCGCCAGCC TCGCCCGCGCCGT |
| 72 | TNNC1 | Dph-CRE72 | 238 | CCCCCAGGCAGCGGCACGGTGGACTTTGATGAGTTCCT GGTCATGATGGTTCGGTGCATGAAGGACGACAGCAAAG GGAAATCTGAGGAGGAGCTGTCTGACCTCTTCCGCATG TTTGACAAGTGAGCACGTGACCCTTGACCTCTGACCCT GACCCACACTCAAGCCGAGCTGTACAGGAGGGCAGTCT CAGATTCCAGGCCTAGGGACCCTGTGGCCTCTGCCTGA TAGGGGAGAG |
| 73 | TNNC1 | Dph-CRE73 | 465 | AGCCAGCTCTGGGGGCACGCCTGCTTATCCTGTGGGAG TCCATGGAGCCGGGGTTGGGACAGCCCTCCACCCAGTG CCCATACAAGGCCTGGCGGAGTTGGGGACTAATTTTGG CTTCTGAGGCGGCACTAGCAGGCCAGGGGGCCAGATAA CGCTGCCCCACCCCCTGCATGCCAAAGTCCCCAGAACA ATCACCAGGTTTAACTTTGTTCCTCGTTAAAAATAGCC CAGTGGCCACCCTGGTCAGGTTACCGTGGGTGGCTTGC CTGCCTCCACACTGGTTTTATTATCCCAACTTGAGGGA CAGCTGTCCTTCGGGCCACCCAGCTTGAGTTTCATCAG GGGCCGAAAGGGCATTGAGTGGTCACTGACTATTGTTA CTGAGGGTCACCTTGGTCCTGAAGGGGGTGCCCACCTG TCACCCTGGCCCTGAGCCCAGTCGCAGTGAGGCCAGCT GGGTCACGT |
| 74 | TNNC1 | Dph-CRE74 | 285 | TTTTCATTCATTCCAGAAACCTTTTCAGAGAGTCCCTT TGGGGAGTGTGGGGACAGGAGGGAAAGAAACCTGGTC CTTGTAGCCGTTCGTCTGCTCCCTGCCCTGGGCAGAGG ACGTGGGGACTCAGGCCAGCCTGAGATCACTGGGACCA GAGGAGGGGCTGGAGGATACTACACGCAGGGGTGGGCT GGGCTGGGCTGGGCTGGGCCAGGAATGCAGCGGGGCAG GGCTATTTAAGTCAAGGGCCGGCTGGCAACCCCAGCAA GCTGTCCTGTGAGCCGCCA |
| 75 | TCAP | Dph-CRE75 | 332 | TGCTCTGTTTACAGACAAGCTGCTGTCCTCCCTGCAAA GGGGAGTGGGTGGGGCAGAGGGCAAGTGCCAGGGGGGC ACAAGGCTGGGCATGTGGCTGGCATGAGACGGTGTCTG AGTAATGTCAGGCACCTGGAGGCATTGACCCCAGGACC TTGGACCCCAGACCTCTGACCGGGGGCAGCCAGCGTC CAGGTACCCCAACCCCTGCCCTGGGTCCGGCGTCCCCC CATTAGTGAGTCTTGGCTCTACTTATAGCATCTGACAC CAGAGGGGCCGAAAATAGCCCCTGGAGAAGGGGGAGGA GGGGGCTATTTAAAGGGCCTGGGAGGGG |
| 76 | MYH7 | Dph-CRE76 | 381 | GCCTGTGGTCTTGGTGGTCGTGGTCAGTTCCCTCTCCT GCCAGCTGTGGAATGTGAGGCCTGGCCTGGGAGATATT TTTGCTGCACTTTGAGCCACCCCGCCCCCTGGAACTCA GACCCTGCACAGTCCATGCCATAACAATGACGACCACT TCCAATTGTTTCCTAGCTGGAGAGGCGGGGAGGGGAGC ACTGTTTGGGAAGGGGGGGAGCCTGGGGGAAATGCTTC TAGTGACAACAGCCCTTTCTAAATCCGGCTAGGGACTG GGTGCCGTTGGGGGTGGGGGTGCCCTGCTGCCCCATAT ATACAGCCCCTGAGACCAGGTCTGGCTCCACAGCTCTG TCCTGCTCTGTGTCTTTCCCTGCTGCTCTCAGGTAGGA G |
| 77 | MYH7 | Dph-CRE77 | 316 | GGAATACCCTACCTTAAAAACAAAACAAACCGTGCTAC TTGGCCCTCTTCCCTTGAGTTGTTGTCTAATCTCATTC ATTTCACTGCCAAACTCCTCAAATGCATGGTGTACACC CACTGCTTCCACTTCCTGTCCACTCATCTTTTTCCTCA TTAACTCCCTGTGGCCTGGCTTTGCCTGTGACACTACA CAAGCTGCTTGCTCCAAGATAATCCAAGTTCTTTTCTC TGTCTTCCTGATACACAGGCTTTCTTTGGCATCTGACA CTGCTGGCCACCTGCTCTTCTTGAAATGCTTCTTTTGG CTTCTAGGAAAC |
| 78 | ALDOA | Dph-CRE78 | 401 | CCAAGTGGTGGGTGTAGCCTGGGGGTTCAATCCTCCTG TGGCGCCCCAGAACCCGGTGCCTCCTCCAACGTCCGGC ATCTGATGAGGATCCGACCCAGGCGGGCGGCGGCGGGA TTCGCTCTTCCCCTTCGCTCCCCGCGAGAAAGCCCCGA GGGCCGCGGCGGCGCAGAGCCGGTGACAGTTGAAGCTT AGGCGGGAAGAGGGAGGCGCGAGGCGGGAAGAGGGAGT TTGGGCCTCGGCAGCCGCCGTACAAACACCGCTCTGGT |

TABLE 4-continued

The CREs sequence for highly expression in diaphragm, skeletal muscle, and heart.

| SEQ ID NO. | Dph-CRE Gene (CRE) | Size (bp) | Sequence |
|---|---|---|---|
| | | | CACCATGGCAACAGCGGGATGCCGCGAACGGCTTCTGG GCGGGGCCGGTCCCTCGGACGATTGGACCTAGCTTGGC GCGGAATCCGTGAATTGCCCGCGGCCCGAGGGTGCAGG TGATGGGTGCTGACCGACTGG |
| 79 | ALDOADph-CRE79 | 281 | GACTACAACCTGCCAGCTCAGGACGAGAGCTGTCAGGA AGAGTCCAGGAATGGACTTCCCACGGGAGGGCACATTT CTGGTATTCCTGGCAAGATAAGGAGTTGACTAAGTAAT CCACGAGAAAAGGCATTTCCGGCAGAGGAAACAGTCTG GGGGTGAGAGGGAGGCTGCAGCATTTGGGGAACTGCTA GGGCTATCGTGTGTTTGGAAGAGGGGGAGGGAGAGAGG TAGGCAGGGCTAAATTGGGAATTTTGTCACTGACATAA ATTTTAAGTGCCAGG |
| 80 | ALDOADph-CRE80 | 393 | CGTTTTGTGGTACCAGGGGGTCCCTCCTCTCCTGTCCC CAGCCAAACCTTTTCCTTTCCCCTCGGGAAAGCTGCCT TGGCTGTCACTACCTGCTGCCTATTCCACATCCTGAAC CCTGTGACCTAGGCCCAGGGCTGCTGCGCGGACGGTAG CTCCCCCTGCAGGAAGCAAGGTTCCTCCGGGCCCCCAG ACTGCTGCTGGACCTGTGCAGAAGCCTGCAACTTTCCT CTGCCTAGCCCGGCCCACTTCCTGGATGCTTGCTGCCC CCAGCCCACCAGAGCTGTGAGTTCCATTCCTACCCCCT GCCCCACTGAGCCCTGATCTAGGTATGATCGGTGCATT CATTTTTTTGCTCAACAACATTTATTACTGAGCACCTT CTCAAGGCCAGGC |
| 81 | ALDOADph-CRE81 | 169 | CCTAGGCCCAGGGCTGCTGCGCGGACGGTAGCTCCCCC TGCAGGAAGCAAGGTTCCTCCGGGCCCCCAGACTGCTG CTGGACCTGTGCAGAAGCCTGCAACTTTCCTCTGCCTA GCCCGGCCCACTTCCTGGATGCTTGCTGCCCCCAGCCC ACCAGAGCTGTGAGTTC |
| 84 | TPM1 Dph-CRE84 | 460 | TAAAGACCTTTCTCAGAGATCCAAACCAGCCCCACCCC CCGCCCCCAGGAAGCATAGCATATTTTCTGTGAGGCCT TGATGGTAGCATCACAAACCCTTGGGAAACACAACTCC CAGTGTTTGAGGAGAGCATGCCGTATCTTGTTCCAGGG ACACTGAGTCGTGAGCATAAAACGCTGCATTCCAAAAG AGACGAAGAAGCAGTCGTCTCTCCATTTAATTATAGAT TCTTCACTTTCCCTTAATTGCTTCAGTCAGCACTGTTG ACTCTGGGGAGTCACAGTACACCGGCAGGGCTATTGC TGTTAAACAAGGGGTGACTATCAGGTAATGAGGTTTTC ATTTTGTTTTTTCAAACAAACAAACCCTGATGTACATA TTCAAGTGGGCATTCCTGTTAAAGGTGTCACATTGGGA AATGATGCTCATGTTGACTCTCCTTTGTAACCAAATAT TGAT |
| 85 | TPM1 Dph-CRE85 | 292 | TAGGAAGGAACAAGAAGAGGTAGAAATGAAATGGCTCC CAAAAGAAAAACCTCCCTTGGGTGGTATTTTAGGACAT TAGCTCAGGCTGCCTTGTCCTCAGTCATCTCAGTGGCA TTTAAGTAGCCCCTTGGGTTACAGATCACGGCAGGTGC TGGGAAGTGAAGAAGGCCATGCTAAAAATACTGGCCTC TTCTGGAACTCTGCCGGCAGCCCTGATGGAGCTCCCTC CTCAAGCAGCAGTACCTCAGCAAAAGAACAGTTTCCTC CGCCTTAAGCAGTAAGAAAAGTCTGG |
| 86 | TPM1 Dph-CRE86 | 472 | AAGAAAGGGTCTTTACAAAACCAAAAGAAAGCCCATTG CTTACTTTTAATAACCTAGGCCCACCCATAGGCCTCTA AATCAAATAACCTCCACTGAGAATTAAGCTGTTAGCAC TAGGTCTGGCATAGGTGCAGAAACAAAAGTTTAGAAAT CCTAATCTTGAATTTACCTAACACGGCTGCCTCCTAGA GCCTGAGTGGGTTGTAGCGAGACCTCAAGTAGAGGAGA GGCACCTGGGCCATCCGCCTCCATGGGCTTTTTTTTTT TTGCATCGAATTTCATGGTCTGCAAAGTAAGGGTGGGG CTTTACTTGCCATTCAGGAGGTTGCAAAGGTCACCTCC ACATATGTTCCTGTTAAGGACATCAGCAGAAACTTGAG AAGCAAGTATAAAAATATAAAAATGAGCAGGTGGCATT CAATAGGAAAAGAATGCAGGGTTTGCTGGGAAGTCATG ATTGAAACCAGTCCAA |
| 87 | TFM1 Dph-CRE87 | 476 | AAGGAAGTGACCAGGCCAGGTCTGGATCCCTGGAACTG ACTCCTAACTCCCTATTCTTGCCTCCTCTGCTGAGCTC CAACCTGGGGAGTCAGCTCCCTGGAGTCCACGCATCTG GATATCGTCCACATGCCTGGAACTTTGTCACTGTTCCG GTGGCTGGGTTGACACACCGTGATTAAAGGGCTCTGGT |

TABLE 4-continued

The CREs sequence for highly expression in diaphragm, skeletal muscle, and heart.

| SEQ ID NO. | Gene | Dph-CRE (CRE) | Size (bp) | Sequence |
|---|---|---|---|---|
| | | | | CAATTTCTGTGCCACGCAGCCCCTATGCTAATGGTCAG ATCTAATGTTCTGACCATTAGGTCAGTGTATCTTTTCC CTCCTGGGCAGTTAGGTTAGTGGAAGAAACCCGATAAA ATCTTGGAGAGGAATTTGATCATTCTCTGAAGGACTTA CAAGTTGTTTGGCCTGCCTAATCTGCTCAGATACCGTC CGGGGAATATTTGGTAACCATGCAGTACAGACTGTGAA TTATTCTGTGGGGACTATTAACAAGACCCTCACCAACC CTGCCTCAGCTGATCTCAGG |
| 88 | TPM1 | Dph-CRE88 | 459 | ACAGACCAAATTGCCTGAGTCTAAACTCAATGTTCTTT CCCCTTAGACTGCCACCCGCACACACACGCACACATGC ACACCTTTTTGGAGGCACTGCACAGCAAGCACAGAAGT ACGCCACTGAGTCCTGTGTCCCTAAAGTATTTGACTGT CCCTCCGCTGGGGAAAGGGCAGGCAGAAAACAAGACT CCGTGTGCTGTCGCTGTGCCGCCCCCTGCCTCTCTGAC CCGCGCCCGCAGAGAAAGTCTCAAGAGCCGCCCCAGGC TTTCTCCCACGTTCTCCCTTTCTCTGCTGCAGTTGAGT TTCCAGAGCGTGAGCGCGCAGGATGACACCTGGCTGGC TGAGAGCTGCCGGGGAGGCGCTGGCGGGTGCCGAGAGC GCACTGACCCTGACGCGGGGTGCAGCACGGCTGGGAAG CCCCCGGGCCTTTGGCTAAGCGCGCCGGGGGACGGCAC AGG |
| 89 | TPM1 | Dph-CRE89 | 378 | GCCCCAACGCCCTCTCCCTGGCGCGCAGGTTTAGAAAC AGGGCGGCCTCTCCGGCCGCCGCCTCGGCGGCTCGGGT CCCCATATATAGTCATATCCACCGTCAACTGGGAGGCC GGCGGCCGGCAGCGAATGGGCGAGCGGCCCCCGCGGGA GGAGCGGGGAGGGGGCACGGGGCGGAGGGAGGAGAGGA GGAAGGGGGCAGGAGAAAAAAGCTTTTCCAAAAAAGT ATTGGCTGTCTTGAGGAATGCGGTCGCCCCCTTGGGAA AGTACATATCTGGGAGAAGCAGGCGGCTCCGCGCTCGC ACTCCCGCTCCTCCGCCCGACCGCGCGCTCGCCCCGCC GCTCCTGCTGCAGCCCCAGGGCCCCTCGCCGCCGCC |

A 'nucleic acid regulatory element' or 'regulatory element', also called "CRE" (cis-regulatory element), "CRM" (cis-regulatory module), or "SH" as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a muscle-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory elements hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for transcription factor 3, also known as TCF3 or E2A; binding sites for nuclear factor I, also known as NF; binding sites for CCAAT-enhancer-binding protein, also known as C/EBP; binding sites for myogenic differentiation, also known as MyoD; binding sites for sterol regulatory element-binding protein, also known as SREBP; binding sites for leukemia/lymphoma-related factor, also known as LRF; binding sites for protein 53, also known as p53; binding sites for hepatocyte nuclear factor 3-alpha, also known as HNF3a; binding sites for hepatocyte nuclear factor 3-beta, also known as HNF3b; binding sites for hepatocyte nuclear factor 4, also known as HNF4; binding sites for myocyte-specific enhancer factor 2A, also known as MEF2A or RSRFC4; binding sites for peroxisome proliferator-activated receptor, also known as PPAR; binding sites for serum response factor, also known as SRF; binding sites for transcription activator-like protein 1b, also known as Tal1_b. Transcription factor binding sites may be found in databases such as Transfac®.

Sequences disclosed herein may be part of sequences of regulatory elements capable of controlling transcription of diaphragm-, and skeletal muscles-specific genes in vivo. Particular examples for diaphragm and skeletal muscle specific regulatory elements may in particular be controlling the following genes (cf. Table 2): ACTA1, CKM, TPM2, MYL1, TNNC2, FHL1, TNNT1, TNNI2, MYLPF, TNNT3, MYH2, SLN, MYBPC1, ENO3, CA3, ATP2A1, or MYH1.

Accordingly, in embodiments, the nucleic acid regulatory elements disclosed herein comprise a sequence from ACTA1 regulatory elements, i.e. regulatory elements that control expression of the ACTA1 gene (Alpha-actin-1 gene) in vivo, e.g. regulatory elements comprising any one or more of SEQ ID NOs: 1 to 5, or functional fragments thereof. In other embodiments, the nucleic acid regulatory elements disclosed herein comprise a sequence from CKM regulatory elements, i.e. regulatory elements that control expression of the CKM gene (Muscle Creatine Kinase gene) in vivo, e.g. regulatory elements comprising any one or more of SEQ ID NOs: 6 or 7, or functional fragments thereof. In other embodiments, the nucleic acid regulatory elements disclosed herein comprise a sequence from MYL2 regulatory elements, i.e. regulatory elements that control expression of the MYL2 (Myosin, Light Chain 2 gene) gene in vivo, e.g. regulatory elements comprising any one or more of SEQ ID NOs: 8 or 9, or functional fragments thereof. In other embodiments, the nucleic acid regulatory elements disclosed herein comprise a sequence from TPM2 regulatory elements, i.e. regulatory elements that control expression of the TPM2 gene (Tropomyosin 2 gene) in vivo, e.g. regulatory elements comprising any one or more of SEQ ID NOs: 10 to 12, or functional fragments thereof. In other embodiments, the nucleic acid regulatory elements disclosed herein comprise a sequence from MYL1 regulatory elements, i.e. regulatory elements that control expression of the MYL1 gene (gene) in vivo, e.g. regulatory elements comprising any one or more of SEQ ID NOs: 13 to 17, or functional fragments thereof. In other embodiments, the nucleic acid regulatory elements disclosed herein comprise a sequence from TNNC2 regulatory elements, i.e. regulatory elements that control expression of the TNNC2 gene (Troponin T2, Cardiac Type gene) in vivo, e.g. regulatory elements comprising any one or more of SEQ ID NOs: 18 or 19, or functional fragments thereof. In other embodiments, the nucleic acid regulatory elements disclosed herein comprise a sequence from FHL1 regulatory elements, i.e. regulatory elements that control expression of the FHL1 gene (Four And A Half LIM Domains 1 gene) in vivo, e.g. regulatory elements comprising any one or more of SEQ ID NOs: 20 to 26, or functional fragments thereof. In other embodiments, the nucleic acid regulatory elements disclosed herein comprise a sequence from TNNT1 regulatory elements, i.e. regulatory elements that control expression of the TNNT1 gene (Troponin T Type 1 gene) in vivo, e.g. regulatory elements comprising any one or more of SEQ ID NOs: 27 or 28, or functional fragments thereof. In other embodiments, the nucleic acid regulatory elements disclosed herein comprise a sequence from TNNI2 regulatory elements, i.e. regulatory elements that control expression of the TNNI2 gene (Troponin I Type 2 gene) in vivo, e.g. regulatory elements comprising any one or more of SEQ ID NOs: 29 to 31, or functional fragments thereof. In other embodiments, the nucleic acid regulatory elements disclosed herein comprise a sequence from MYLPF regulatory elements, i.e. regulatory elements that control expression of the MYLPF gene (Myosin Light Chain, Phosphorylatable, Fast Skeletal Muscle gene) in vivo, e.g. regulatory elements comprising SEQ ID NO: 32, or functional fragments thereof. In other embodiments, the nucleic acid regulatory elements disclosed herein comprise a sequence from TNNT3 regulatory elements, i.e. regulatory elements that control expression of the TNNT3 gene (Troponin T Type 3 gene) in vivo, e.g. regulatory elements comprising any one or more of SEQ ID NOs: 33 to 38, or functional fragments thereof. In other embodiments, the nucleic acid regulatory elements disclosed herein comprise a sequence from MYH2 regulatory elements, i.e. regulatory elements that control expression of the MYH2 gene (Myosin, Heavy Chain 2 gene) in vivo, e.g. regulatory elements comprising any one or more of SEQ ID NOs: 82 or 83, or functional fragments thereof. In other embodiments, the nucleic acid regulatory elements disclosed herein comprise a sequence from SLN regulatory elements, i.e. regulatory elements that control expression of the SLN gene (Sarcolipin gene) in vivo, e.g. regulatory elements comprising any one or more of SEQ ID NOs: 39 to 42, or functional fragments thereof. In other embodiments, the nucleic acid regulatory elements disclosed herein comprise a sequence from MYBPC1 regulatory elements, i.e. regulatory elements that control expression of the MYBPC1 gene (Myosin Binding Protein C, Slow Type gene) in vivo, e.g. regulatory elements comprising any one or more of SEQ ID NOs: 43 to 50, or functional fragments thereof. In other embodiments, the nucleic acid regulatory elements disclosed herein comprise a sequence from ENO3 regulatory elements, i.e. regulatory elements that control expression of the ENO3 gene (Enolase 3 gene) in vivo, e.g. regulatory elements comprising any one or more of SEQ ID NOs: 51 to 54, or functional fragments thereof. In other embodiments, the nucleic acid regulatory elements disclosed herein comprise a sequence from CA3 regulatory elements, i.e. regulatory elements that control expression of the CA3 gene (Carbonic Anhydrase III gene) in vivo, e.g. regulatory elements comprising any one or more of SEQ ID NOs: 55 to 57, or functional fragments thereof. In other embodiments, the nucleic acid regulatory elements disclosed herein comprise a sequence from ATP2A1 regulatory elements, i.e. regulatory elements that control expression of the ATP2A1 gene (ATPase, Ca++Transporting, Cardiac Muscle, Fast Twitch 1 gene or Sarcoplasmic/endoplasmic reticulum calcium ATPase 1 gene) in vivo, e.g. regulatory elements comprising any one or more of SEQ ID NOs: 58 to 64, or functional fragments thereof. In other embodiments, the nucleic acid regulatory elements disclosed herein comprise a sequence from MYH1 regulatory elements, i.e. regulatory elements that control expression of the MYH1 gene (Myosin, Heavy Chain 1 gene) in vivo, e.g. regulatory elements comprising SEQ ID NO: 65, or functional fragments thereof. Sequences disclosed herein may be part of sequences of regulatory elements capable of controlling transcription of diaphragm-, skeletal muscle and heart-specific genes in vivo. Particular examples for diaphragm-, skeletal muscle and heart specific regulatory elements may in particular be controlling the following genes: ACTA1, CKM, MYL2, MB, DES, TNNC1, TCAP, MYH7, ALDOA, or TPM1. Accordingly, in embodiments, the nucleic acid regulatory elements disclosed herein comprise a sequence from ACTA1 regulatory elements, i.e. regulatory elements that control expression of the ACTA1 gene (Alpha-actin-1 gene) in vivo, e.g. regulatory elements comprising any one or more of SEQ ID NOs: 1 to 5, or functional fragments thereof. In other embodiments, the nucleic acid regulatory elements disclosed herein comprise a sequence from CKM regulatory elements, i.e. regulatory elements that control expression of the CKM gene (Muscle Creatine Kinase gene) in vivo, e.g. regulatory elements comprising any one or more of SEQ ID NOs: 6 or 7, or functional fragments thereof. In other embodiments, the nucleic acid regulatory elements disclosed herein comprise a sequence from MYL2 regulatory elements, i.e. regulatory elements that control expression of the MYL2 (Myosin, Light Chain 2 gene) gene in vivo, e.g. regulatory elements comprising any one or more of SEQ ID NOs: 8 or 9, or functional fragments thereof. In other embodiments, the nucleic acid regulatory elements disclosed herein comprise a sequence from MB regulatory elements, i.e. regulatory elements that control expression of the MB gene (Myoglobin gene) in vivo, e.g. regulatory elements comprising any one or more of SEQ ID NOs: 66 to 68, or functional fragments thereof. In other embodiments, the nucleic acid regulatory elements disclosed herein comprise a sequence from DES regulatory elements, i.e. regulatory elements that control expression of the DES gene (Desmin gene) in vivo, e.g. regulatory elements comprising any one or more of SEQ ID NOs: 69 to 71, or functional fragments thereof. In other embodiments, the nucleic acid regulatory elements disclosed herein comprise a sequence from TNNC1 regulatory elements, i.e. regulatory elements that control expression of the TNNC1 gene (Troponin C Type 1 gene) in vivo, e.g. regulatory elements comprising any one or more of SEQ ID NOs: 72 to 74, or functional fragments thereof. In other embodiments, the nucleic acid regulatory elements disclosed herein comprise a sequence from TCAP regulatory elements, i.e. regulatory elements that control expression of the TCAP gene (Titin-Cap gene) in vivo, e.g. regulatory elements comprising SEQ ID NOs: 75, or functional fragments thereof. In other embodiments, the nucleic acid regulatory elements disclosed herein comprise a sequence from MYH7 regulatory elements, i.e. regulatory elements that control expression of the MYH7 gene (Myosin, Heavy Chain 7 gene) in vivo, e.g. regulatory elements comprising any one or more of SEQ ID NOs: 76 or 77, or functional fragments thereof. In other embodiments, the nucleic acid regulatory elements disclosed herein comprise a sequence from ALDOA regulatory elements, i.e. regulatory elements that control expression of the ALDOA gene (Aldolase A gene) in vivo, e.g. regulatory elements comprising any one or more of SEQ ID NOs: 78 to 81, or functional fragments thereof. In other embodiments, the nucleic acid regulatory elements disclosed herein comprise a sequence from TPM1 regulatory elements, i.e. regulatory elements that control expression of the TPM1 gene (Tropomyosin 1 gene) in vivo, e.g. regulatory elements comprising any one or more of SEQ ID NOs: 84 to 89, or functional fragments thereof.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term 'functional fragment' as used in the application refers to fragments of the regulatory element sequences disclosed herein that retain the capability of regulating muscle-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

"Diaphragm and skeletal muscle-specific expression" as used in the application, refers to the preferential or predominant expression of a (trans)gene (as RNA and/or polypeptide) in diaphragm and skeletal muscle cells or diaphragm or skeletal muscle tissue, as compared to other (i.e. non-diaphragm or skeletal muscle) tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm and/or skeletal muscle cells or tissue. According to a particular embodiment, diaphragm and skeletal muscle specific expression entails that there is less than 10%, less than 5%, less than 2% or even less than 1% 'leakage' of expressed gene product to other organs or tissue than muscle, such as lung, liver, brain, kidney and/or spleen.

As used herein "diaphragm, skeletal muscle and cardiac-specific expression" refers to the preferential or predominant expression of a (trans)gene in diaphragm, heart, skeletal muscle cells or tissue and in particular heart muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm, skeletal muscle cells and heart tissue. Thus, according to particular embodiments, less than 10%, less than 5%, less than 2% or even less than 1% of the (trans)gene expression occurs in an organ or tissue other than diaphragm, heart and skeletal muscle.

The same applies mutatis mutandis for myocyte-specific and myoblast-specific expression, which may be considered as a particular form of muscle-specific expression. Throughout the application, where muscle-specific is mentioned in the context of expression, myocyte-specific and myoblast-specific expression are also explicitly envisaged. Similarly, where cardiac and skeletal muscle-specific expression is used in the application, cardiomyocyte and skeletal myocyte-specific expression and cardiac myoblast and skeletal myoblast-specific expression is also explicitly envisaged. Similarly, where skeletal muscle-specific expression is used in the application, skeletal myocyte-specific and skeletal myoblast-specific expression is also explicitly envisaged.

As used herein, the terms "heart muscle" or "cardiac muscle" refer to the automatically regulated, striated muscle type found in the heart.

As used herein, the term "skeletal muscle" refers to the voluntarily controlled, striated muscle type that is attached to the skeleton. Non-limiting examples of skeletal muscle include the biceps, the triceps, the quadriceps, the tibialis interior, and the gastrocnemius muscle.

The term "myocyte," as used herein, refers to a cell that has been differentiated from a progenitor myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The term "myoblast" as used herein, refers to an embryonic cell in the mesoderm that differentiates to give rise to a muscle cell or myocyte. The term includes cells in vivo and cells cultured ex vivo regardless of whether such cells are primary or passaged.

In embodiments, the invention relates to a nucleic acid regulatory element for enhancing gene expression in diaphragm and skeletal muscle comprising, consisting essentially of, or consisting of a sequence selected from the group consisting of: SEQ ID NO:1 to 7, 10 to 65, 82, and 83 (cf. Dph-CRE1 to 7, 10 to 65, 82, and 83 in Table 3); a sequence having at least 80%, preferably at least 85%, more preferably at least 90%, even more preferably at least 95%, such as 95%, 96%, 97%, 98%, or 99%, identity to any of the sequences selected from the group consisting of SEQ ID NO: 1 to 7, 10 to 65, 82, and 83 (cf. Dph-CRE1 to 7, 10 to 65, 82, and 83 in Table 3); or a functional fragment thereof, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In further embodiments, the invention relates to a nucleic acid regulatory element for enhancing gene expression in diaphragm, skeletal muscle and cardiac comprising, consisting essentially of, or consisting of a sequence selected from the group consisting of: SEQ ID No: 1 to 9, 66 to 81, and 84 to 89. (cf. Dph-CRE1 to 9, 66 to 81, and 84 to 89 in Table 4); or a sequence having at least 80%, preferably at least 85%, more preferably at least 90%, even more preferably at least 95%, such as 95%, 96%, 97%, 98%, or 99%, identity to any one of the sequences selected from the group consisting of SEQ ID No: 1 to 9, 66 to 81, and 84 to 89. (cf. Dph-CRE1 to 9, 66 to 81, and 84 to 89 in Table 4); or a functional fragment thereof, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

It is also possible to make nucleic acid regulatory elements that comprise an artificial sequence by combining two or more identical or different sequences disclosed herein or functional fragments thereof. Accordingly, in certain embodiments a nucleic acid regulatory element for enhancing gene expression in diaphragm, and skeletal muscle cells or tissue is provided comprising at least two sequences selected from the group consisting of: SEQ ID NO:1 to 7, 10 to 65, 82, and 83 (cf. Dph-CRE1 to 7, 10 to 65, 82, and 83 in Table 3).

Alternatively, in certain embodiments a nucleic acid regulatory element for enhancing gene expression in diaphragm, skeletal muscle and heart cells or tissue is provided comprising at least two sequences selected from the group consisting of: SEQ ID No: 1 to 9, 66 to 81, and 84 to 89. (cf. Dph-CRE1 to 9, 66 to 81, and 84 to 89 in Table 4).

For example, disclosed herein is a nucleic acid regulatory element comprising, consisting essentially of, or consisting of 2, 3, 4, or 5 repeats, e.g. tandem repeats, of any one of SEQ ID NOs:1 to 89, or combinations thereof.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing muscle-specific gene expression, in particular cardiac and skeletal muscle-specific gene expression, comprising binding sites for E2A, HNH1, NF1, C/EBP, LRF, MyoD, and SREBP; or for E2A, NF1, p53, C/EBP, LRF, and SREBP; or for E2A, HNH1, HNF3a, HNF3b, NF1, C/EBP, LRF, MyoD, and SREBP; or E2A, HNF3a, NF1, C/EBP, LRF, MyoD, and SREBP; or for E2A, HNF3a, NF1, CEBP, LRF, MyoD, and SREBP; or for HNF4, NF1, RSRFC4, C/EBP, LRF, and MyoD, or NF1, PPAR, p53, C/EBP, LRF, and MyoD. Further for example, also disclosed herein is a nucleic acid regulatory element for enhancing diaphragm and skeletal muscle-specific gene expression, in particular comprising binding sites for one or more of: NFYA, SIN3A, TCF12, PHF8, IRF1 and combinations thereof, such as NFYA, SIN3A, TCF12, PHF8, and IRF1. Further for example, also disclosed herein is a nucleic acid regulatory element for enhancing diaphragm, heart, and skeletal muscle-specific gene expression, in particular comprising binding sites for one or more of: MAFF, FOXA2, TAL1, CEBPB, RFX5, HSF1, SRF and combinations thereof, such as MAFF, FOXA2, TAL1, CEBPB, RFX5, HSF1, and SRF. In some embodiments, these nucleic acid regulatory elements comprise at least two, such as 2, 3, 4, or more copies of any one or more of the recited TFBSs.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing muscle-specific gene expression comprising, consisting essentially of, or consisting of the complement of a sequence described herein, in particular a sequence selected from the group consisting of: SEQ ID NOs:1 to 89; a sequence having at least 80%, preferably at least 85%, more preferably at least 90%, even more preferably at least 95%, such as 95%, 96%, 97%, 98%, or 99%, identity to any of these sequences; or a functional fragment thereof.

Also disclosed herein is a nucleic acid regulatory element for enhancing muscle-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NOs:1 to 89; a sequence having at least 90%, preferably at least 95%, such as 95%, 96%, 97%, 98%, or 99%, identity to any of these sequences; a functional fragment thereof; or to its complement. Said nucleic acid regulatory elements do not need to be of equal length as the sequence they hybridize to. In preferred embodiments, the size of said hybridizing nucleic acid regulatory element does not differ more than 25% in length, in particular 20% in length, more in particular 15% in length, most in particular 10% in length from the sequence it hybridizes to.

The expression 'hybridize under stringent conditions' refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 1500 nucleotides or less, 1000 nucleotides or less, 900 nucleotides or less, 800 nucleotides or less, 700 nucleotides or less, more preferably 600 nucleotides or less, such as 550 nucleotides or less, 500 nucleotides or less, 450 nucleotides or less, 400 nucleotides or less, 350 nucleotides or less, or 300 nucleotides or less (i.e. the nucleic acid regulatory element has a maximal length of 1500 nucleotides, 1000 nucleotides, 900 nucleotides, 800 nucleotides, 700 nucleotides, preferably 600 nucleotides, such as 550 nucleotides, 500 nucleotides, 450 nucleotides, 400 nucleotides, 350 nucleotides, or 300 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 200 nucleotides, 250 nucleotides, 300 nucleotides, 350 nucleotides or 400 nucleotides.

In certain embodiments, the invention provides for a nucleic acid regulatory element of 1000 nucleotides or less, preferably 900 nucleotides or less, preferably 800 nucleotides or less, preferably 700 nucleotides or less of a sequence selected from the group consisting of: SEQ ID NOs:1 to 89; a sequence having at least 80%, preferably at least 85%, more preferably at least 90%, even more preferably at least 95%, such as 95%, 96%, 97%, 98%, or 99%, identity to any of said sequences; or a functional fragment thereof.

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein. In alternative embodiments, the nucleic acid expression cassette comprises two or more, such as, e.g., 2, 3, 4, 5, 6, 7, 8, 9, or 10, nucleic acid regulatory elements as described herein, i.e. they are combined modularly to enhance their regulatory (and/or enhancing) effect. In further embodiments, at least two of the two or more nucleic acid regulatory elements are identical or substantially identical. In yet further embodiments, all of the two or more regulatory elements are identical or substantially identical. The copies of the identical or substantially identical nucleic acid regulatory elements may be provided as tandem repeats in the nucleic acid expression cassette. In alternative further embodiments, at least two of the two or more nucleic acid regulatory elements are different from each other, that is to say, are defined by a different SEQ ID NO. The nucleic acid expression cassette may also comprise a combination of identical and substantially identical nucleic acid regulatory elements and non-identical nucleic acid regulatory elements.

For example, the nucleic acid expression cassette may comprise a nucleic acid regulatory element comprising SEQ ID NO:1, and a nucleic acid regulatory element comprising any one or more of SEQ ID Nos: 2 to 689; or the nucleic acid expression cassette may comprise a nucleic acid regulatory element comprising any one or more of SEQ ID NO: 1-89 and a nucleic acid regulatory element (cis-regulatory element, CRE, CRM, or SH) specific for another tissue type such as e.g. the ones disclosed in previous applications from the same authors: WO2015110449; WO2009130208; WO2009071679; WO2011051450; WO2016146757; WO2014063753; or WO2014064277. Alternatively, this can be done for remaining regulatory elements defined by SEQ ID NOs: 2 to 89 respectively. In a specific embodiment, the muscle-specific regulatory element designated Sk-SH4 (SEQ ID NO:121) or CSk-SH5 (SEQ ID NO:122) can be used in combination with any one of the Diaphragm cis-regulatory elements defined by SEQ ID NOs: 1 to 89.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of diaphragm-specific, in particular diaphragm and skeletal muscle-specific or diaphragm, cardiac and skeletal muscle-specific, expression in vivo (and/or in vitro in cell lines derived from cardiac, diaphragm, and skeletal muscle cells or tissue) of the transgene, and/or (2) can increase the level of expression of the transgene in diaphragm and skeletal muscle or in diaphragm, cardiac and skeletal muscle (and/or in vitro in cell lines derived from cardiac, diaphragm, and skeletal muscle cells or tissue).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

Non-limiting exemplary skeletal muscle and/or diaphragm-specific promoter are the Desmin promotor, other muscle specific promoters such as muscle creatine kinase promoter (MCK) (Wang B et al, Gene Ther, 2008), alpha-myosin heavy chain (a-MHC), myosin light chain (MLC-2), cardiac troponin C (cTnC), myogenin MYF4 promoters (Pacak C. A. et al., Genet Vaccines Ther, 2008), viral promoters such as murine stem cell virus (MSCV) promoter (Suga T et al., Plos One, 2011), and all potential promoters that can be used to cloned downstream of the diaphragm nucleic acid regulatory elements. The regulatory elements disclosed herein can be used in nucleic acid expression cassettes in conjunction with their natural promoter, as well as with another promoter.

Preferably, the nucleic acid expression cassettes disclosed herein comprise a diaphragm, heart, and/or skeletal muscle-specific promoter, in order to increase diaphragm, heart, and/or skeletal muscle-specificity and/or avoid leakage of expression in other tissues. Examples of such promotors are diaphragm and/or skeletal muscle-specific promoters, such as the promotor of one of the genes defined in Table 3, namely the ACTA1, CKM, TPM2, MYL1, TNNC2, FHL1, TNNT1, TNNI2, MYLPF, TNNT3, MYH2, SLN, MYBPC1, ENO3, CA3, ATP2A1, and MYH1 genes; or diaphragm-, skeletal muscle- and heart-specific promoters, such as the promotor of any one of the genes defined in Table 4, namely ACTA1, CKM, MYL2, MB, DES, TNNC1, TCAP, MYH7, ALDOA, and TPM1 genes. Non-limiting examples of muscle-specific promoters include the desmin (DES) promoter, the synthetic SPc-5-12 promoter (SPc5-12-GTRM), the alpha-actin1 promoter (ACTA1), the Creatine kinase, muscle (CKM) promoter, the Four and a half LIM domains protein 1 (FHL1) promoter, the alpha 2 actinin (ACTN2) promoter, the filamin-C(FLNC) promoter, the sarcoplasmic/endoplasmic reticulum calcium ATPase 1 (ATP2A1) promoter, the troponin I type 1 (TNNI1) promoter, the myosin-1 (MYH1) promoter, the phosphorylatable, fast skeletal muscle myosin light chain (MYLPF) promoter, the alpha-3 chain tropomyosin (TPM3) promoter, the ankyrin repeat domain-containing protein 2 (ANKRD2) promoter the myosin heavy-chain (MHC) promoter, the myosin light-chain (MLC) promoter, the muscle creatine kinase (MCK) promoter, synthetic muscle promoters as described in Li et al. (1999, Nat Biotechnol. 17:241-245), such as the SPc5-12 promoter, the muscle creatine kinase (MCK) promoter, the dMCK promoter and the tMCK promoter consisting of respectively, a double or triple tandem of the MCK enhancer to the MCK basal promoter as described in Wang et al. (2008, Gene Ther, 15:1489-1499).

In particularly preferred embodiments, the promoter is a mammalian promoter, in particular a murine or human promoter.

In preferred embodiments, the promoter is from the desmin gene, in particular the murine desmin gene, such as the promoter as defined in SEQ ID NO: 90 (cf. FIG. 4), or the human desmin gene, such as the promoter as defined in SEQ ID NO: 91 (1.0 kb) or SEQ ID NO: 92 (1.4 kb). In preferred embodiments, the desmin promoter is the 1.4 kb promoter of SEQ ID NO: 92 which has been shown to further increase expression levels (cf. examples) For example, the murine desmin promoter is commercially available as pDRIVE-mDesmin (Invivogen). The desmin promoter is expressed in both cardiac muscle and skeletal muscle. In embodiments, the promoter is a skeletal muscle-specific promoter, in particular a muscle creatine kinase (MCK) promoter, more particularly the double MCK promoter or triple MCK promoter consisting of a double or triple tandem of MCK enhancer and MCK basal promoter as described in Wang et al. (2008, Gene Ther, 15:1489-1499). Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less.

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, antisense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular a mammal or human, in which it is introduced, e.g. in cases where the nucleic acid expression cassette is used for gene therapy).

The transgene may be a full-length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein. The therapeutic protein may be a secretable protein. Non-limiting examples of secretable proteins, in particular secretable therapeutic proteins, include glucosidase, follistatin, clotting factors, such as factor VIII or factor IX, insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, include myotubularin, dysferlin, follistatin, microdystrophin 1, dystrophin and sarcoglycans. In preferred embodiments, the transgene comprises the microdystrophin 1 (MD1 & MD2) gene or the follistatin (FST) gene, preferably the exon-skipping construct of follistatin. A non-exhaustive and non-limiting list of transgenes envisaged in the application includes angiogenic factors for therapeutic angiogenesis such as VEGF, PlGF, or guidance molecules such as ephrins, semaphorins, Slits and netrins or their cognate receptors; cytokines and/or growth factors such as erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), proteins involved in calcium handling such as SERCA (Sarco/Endoplasmic Reticulum Ca2+-ATPase), calcineurin, microdystrophin 1 (MD1), follistatin (FST), alpha-glucosidase (GAA), myotubularin 1 (MTM1), transgenes encoding antibodies, nanobodies, antiviral dominant-negative proteins, and fragments, subunits or mutants thereof.

In embodiments, the transgene encodes an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron.

Preferably, the intron is MVM intron.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit ·-globin (mRBG) gene, and the synthetic polyA s(SPA) site as described in Levitt et al. (1989, Genes Dev 3:1019-1025).

Preferably, the polyadenylation signal is derived from SV40 (i.e. SV40 pA).

In particular embodiments, the invention provides a nucleic acid expression cassette comprising, consisting essentially of, or consisting of a nucleic acid regulatory element selected from the group consisting of SEQ ID NO: 1 to 89 or a sequence having 95% identity to said sequence, operably linked to a promoter, preferably a promoter selected from the group consisting of the promoter from the desmin gene or the SPc5-12 promoter, and a transgene, preferably a transgene encoding a luciferase. In further embodiments, the nucleic acid expression cassette further comprises an MVM intron. In yet further embodiments the nucleic acid expression cassette further comprises a polyadenylation signal, preferably a polyadenylation signal derived from synthetic polyA (SynthpA: SEQ ID: 127 & FIGS. 9 A & B).

In particular embodiments, the invention provides a nucleic acid expression cassette comprising, consisting essentially of, or consisting of a nucleic acid regulatory element selected from the group consisting of SEQ ID NO: 1 to 89, or a sequence having 95% identity to said sequence, operably linked to a promoter, preferably the promoter from the desmin gene, and a transgene, preferably a transgene encoding microdystrophin, exon-skipping construct or follistatin. In further embodiments, the nucleic acid expression cassette further comprises an MVM intron. In yet further embodiments, the nucleic acid expression cassette further comprises a polyadenylation signal. Alternatively, any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1) gene or the follistatin (FST) gene, preferably the exon-skipping construct of follistatin.

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

Figure 9:
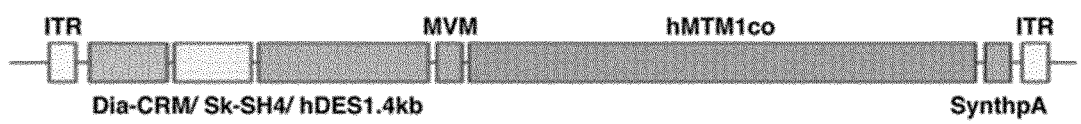
FIG. 9: Schematic view of AAV vectors for expression of A) hMTMco or B) hGAAco transgene. Vector A) further comprises one of the Dph-CREs (called Dia-CRM), the Sk-SH4-CRE (SEQ ID NO: 121), the hDes1.4 kb promoter, the MVM intron, the hMTM1co transgene, and a synthetic poly-A site, cloned between the ITRs of an AAV vector. Vector B) further comprises one of the Dph-CREs (called Dia-CRM), the CSk-SH5-CRE (SEQ ID NO: 122), the SPc5-12 promoter, the MVM intron, the hGAAco transgene, and a synthetic poly-A site, cloned between the ITRs of an AAV vector.
Figure 9:
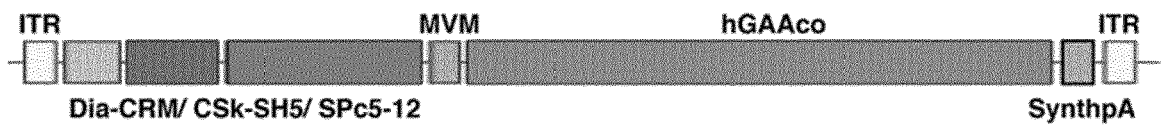

In preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), and also the use of single-stranded AAV vectors (ssAAV) are also encompassed herein (FIGS. 9 A & B).

AAV serotype 9 (AAV9) is ideally suited to achieve efficient transduction in heart and skeletal muscle. Accordingly, in particularly preferred embodiments, the vector is an AAV9 vector.

Production of AAV vector particles can e.g. be achieved by transient co-transfection of AAV-reporter and AAV helper constructs, encoding AAV serotype 9 capsids into HEK293 cells, followed by a purification step based on cesium chloride (CsCl) density gradient ultracentrifugation, as described (Vanden Driessche et al., 2007).

Since the nucleic acid regulatory elements are de facto modular, also combinations of the best diaphragm-specific nucleic acid regulatory elements with any other muscle-specific and/or cardiac specific nucleic acid regulatory elements to maximize expression in the desired target tissue are tested. Consequently, this can lead to the generation of a versatile muscle-specific nucleic acid regulatory element platform tailor-made for diseases that affect skeletal muscle, diaphragm and in some cases also heart (e.g. MTM or GSD II). Furthermore, the diaphragm-specific nucleic acid regulatory elements can also be combined with other promoters or nucleic acid regulatory elements active in other target tissues.

In other embodiments, the vector is a non-viral vector, preferably a plasmid, a minicircle, or a transposon-based vector, such as a Sleeping Beauty(SB)-based vector or piggyBac(PB)-based vector.

In yet other embodiments, the vector comprises viral and non-viral elements.

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 89 a promoter, preferably the promoter from the desmin gene, an MVM intron, a transgene, preferably a transgene encoding microdystrophin 1/2 or an exon-skipping construct thereof, and a polyadenylation signal. Alternatively, any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1 or 2) gene or the follistatin (FST) gene, preferably the exon-skipping construct of follistatin.

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 89, a promoter, preferably the promoter from the desmin gene, an MVM intron, a transgene, preferably a transgene encoding follistatin, and a polyadenylation signal. Alternatively, any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1 or 2) gene or the follistatin (FST) gene, preferably the exon-skipping construct of follistatin.

The nucleic acid expression cassettes and vectors disclosed herein may be used, for example, to express proteins that are normally expressed and utilized in muscle (i.e. structural proteins), or to express proteins that are expressed in muscle and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement. In embodiments, the nucleic acid regulatory elements according to any one of SEQ ID NO:1 to 7, 10 to 65, 82, and 83 (cf. Dph-CRE1 to 7, 10 to 65, 82, and 83 in Table 3), the nucleic acid expression cassettes, the vectors, or the pharmaceutical compositions described herein may be for use in gene therapy, in particular diaphragm and skeletal muscle-directed gene therapy. Alternatively, the nucleic acid regulatory elements according to any one of SEQ ID No: 1 to 9, 66 to 81, and 84 to 89. (cf. Dph-CRE1 to 9, 66 to 81, and 84 to 89 in Table 4). the nucleic acid expression cassettes, the vectors, or the pharmaceutical compositions described herein may be for use in gene therapy, in particular diaphragm-, skeletal muscle- and heart-directed gene therapy.

Also disclosed herein is the use of the nucleic acid regulatory elements according to any one of SEQ ID NO: 1 to 7, 10 to 65, 82, and 83 (cf. Dph-CRE1 to 7, 10 to 65, 82, and 83 in Table 3), the nucleic acid expression cassettes, the vectors, or the pharmaceutical compositions described herein for the manufacture of a medicament for gene therapy, in particular diaphragm and skeletal muscle-directed gene therapy.

Also disclosed herein is the use of the nucleic acid regulatory elements according to any one of SEQ ID No: 1 to 9, 66 to 81, and 84 to 89. (cf. Dph-CRE1 to 9, 66 to 81, and 84 to 89 in Table 4)., the nucleic acid expression cassettes, the vectors, or the pharmaceutical compositions described herein for the manufacture of a medicament for gene therapy, in particular diaphragm-, skeletal muscle- and heart-directed gene therapy.

Also disclosed herein is a method for gene therapy, in particular diaphragm and skeletal muscle-directed gene therapy in a subject in need of said gene therapy comprising:
  introducing in the subject, in particular in diaphragm and/or skeletal muscle tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID NO: 1 to 7, 10 to 65, 82, and 83 (cf. Dph-CRE1 to 7, 10 to 65, 82, and 83 in Table 3), operably linked to a promoter and a transgene; and
  expressing a therapeutically effective amount of the transgene product in the subject, in particular in diaphragm and/or skeletal muscle tissue or cells of the subject.

Also disclosed herein is a method for gene therapy, in particular diaphragm-, skeletal muscle- and heart-directed gene therapy in a subject in need of said gene therapy comprising:
  introducing in the subject, in particular in diaphragm-, skeletal muscle- and heart-tissue or cells of the subject a nucleic acid expression cassette, a vector or a pharmaceutical composition described herein, wherein the nucleic acid expression cassette, the vector or the pharmaceutical composition comprises a nucleic acid regulatory element according to any one of SEQ ID No: 1 to 9, 66 to 81, and 84 to 89. (cf. Dph-CRE1 to 9, 66 to 81, and 84 to 89 in Table 4), operably linked to a promoter and a transgene; and
  expressing a therapeutically effective amount of the transgene product in the subject, in particular in diaphragm-, skeletal muscle-, and heart-tissue or cells of the subject.

The transgene product may be any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1 or 2) gene or the follistatin (FST) gene, preferably the exon-skipping construct of follistatin. In particular embodiments, the transgene product is follistatin or microdystrophin, in particular microdystrophin 1 (MTM1). Alternatively, the transgene product may be RNA, such as siRNA.

Exemplary diseases and disorders that may benefit from gene therapy using the nucleic acid regulatory elements, the nucleic acid expression cassettes, the vectors, or the pharmaceutical compositions described herein include myotubular myopathy (MTM), Pompe disease, muscular dystrophy (e.g. Duchenne muscular dystrophy (DMD)/Becker muscular dystrophy (BMD)), myotonic dystrophy, Myotonic Muscular Dystrophy (DM), Miyoshi myopathy, Fukuyama type congenital, muscular dystrophy, dysferlinopathies neuromuscular disease, motor neuron diseases (MND), such as e.g. Charcot-Marie-Tooth disease (CMT), spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes. In addition, many neuromuscular disorders affect respiratory function due to weakening of the diaphragm and respiratory muscles (www.medscape.com/viewarticle/805299_3) Semin Respir Crit Care Med. 2002 June; 23(3):191-200). Causes of diseases of the diaphragm vary, but they can be due to gene defects that influence diaphragm function directly. In particular, there are multiple genetic disorders that are due to mutations in genes that affect the function of the diaphragm, often in combination with abnormalities at the level of skeletal muscles and/or heart. For example, myotubular myopathy (MTM) is due to mutations in the myotubularin gene and affects the skeletal muscle and diaphragm. Patients suffering from MTM typically present with hypotonia, generalized muscle weakness and respiratory failure at birth. Survival beyond the postnatal period requires intensive support, often including gastrostomy feeding and mechanical ventilation. Because of their severe breathing problems, patients suffering from MTM typically do not live past age 2. For MTM, muscle-directed gene therapy is currently the only clinically relevant option. Alternatively, Pompe's disease (also referred to as glycogen storage disorder type II or GSD II) mainly affects skeletal muscle, diaphragm and heart. GSD II results in deficiency of the lysosomal enzyme acid α-glucosidase (GAA) that leads to a lysosomal storage defect. In GSD II patients, glycogen cannot be broken down effectively into glucose. The accumulation of glycogen in GSD II patients causes myopathy with progressive muscle weakness. Without medical intervention, patients suffering from the most severe form of GSD II die because of respiratory failure within the first year of life. Other muscle diseases such as Duchenne muscular dystrophy (DMD) afflicts approximately one in 3500 live male births. The disease leads to a progressive destruction of skeletal muscles, including the diaphragm, the most affected individuals die of ventilatory failure in the third decade of life. Many other myopathies also affect pulmonary function, including—but not limited to—polymyositis/dermatomyositis, hereditary channel disorders, mitochondrial encephalomyopathies, acid maltase deficiency, and congenital myopathy, disuse atrophy. Other diseases affecting diaphragm include Congenital Muscular Dystrophy (CMD), Becker Muscular Dystrophy (BMD), Facioscapulohumeral Muscular Dystrophy (FSHD), Limb Girdle Muscular Dystrophy (LGMD), Myotonic Muscular Dystrophy (DM), Miyoshi myopathy, Fukuyama type congenital muscular dystrophy, dysferlinopathies. Also many neuropathic disorders weaken the diaphragm and respiratory muscles. This includes amyotrophic lateral sclerosis, poliomyelitis, postpolio syndrome, Kennedy syndrome, stroke, multiple sclerosis, spinal muscular atrophy, syringomyelia, neuralgic neuropathy, and motor neuron diseases. Brachial plexitis and isolated unilateral or bilateral phrenic neuropathies can also weaken the diaphragm significantly. Peripheral neuropathies affecting respiration are primarily acute disorders such as Guillain-Barré syndrome, porphyria, and critical illness neuropathy, but chronic diseases such as chronic inflammatory demyelinating polyneuropathy (CIDP) and Charcot-Marie-Tooth disease (CMT) can also cause respiratory insufficiency. Disorders of neuromuscular transmission such as Lambert-Eaton syndrome, and myasthenia gravis often affect respiration. Alternatively, diaphragm dysfunction can be the result of congenital defects resulting in anatomical abnormalities (e.g. Arnold-Chiari malformation) or acquired defects, which occur as the result of an injury, trauma, infection (e.g. West Nile virus, botulism), exposure to, organophosphates, radiation therapy, malnutrition, tumour compression or surgery. Cold cardioplegia used in cardiac surgery is another common cause of phrenic nerve injury. In addition, radiation therapy can affect the phrenic nerve resulting in diaphragmatic dysfunction. Obstructive airway diseases that affect the lungs, such as chronic obstructive pulmonary disease (COPD) and asthma, can result in significant hyperinflation resulting in diaphragmatic disadvantage and weakness. Finally, it is known that lupus and thyroid disorders can also contribute to diaphragm dysfunction.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993). In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of medicament or a vaccine, in particular for the manufacture of a prophylactic vaccine.

Also disclosed herein is a method of vaccination, in particular prophylactic vaccination, of a subject in need of said vaccination comprising:
  introducing in the subject, in particular in diaphragm-, and skeletal muscle-tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID NO:1 to 7, 10 to 65, 82, and 83 (cf. Dph-CRE1 to 7, 10 to 65, 82, and 83 in Table 3), operably linked to a promoter and a transgene; and
  expressing an immunologically effective amount of the transgene product in the subject, in particular in diaphragm- and skeletal muscle-cells or tissue of the subject.

Also disclosed herein is a method of vaccination, in particular prophylactic vaccination, of a subject in need of said vaccination comprising:

introducing in the subject, in particular in diaphragm, skeletal muscle- and heart-tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID No: 1 to 9, 66 to 81, and 84 to 89. (cf. Dph-CRE1 to 9, 66 to 81, and 84 to 89 in Table 4), operably linked to a promoter and a transgene; and expressing an immunologically effective amount of the transgene product in the subject, in particular in diaphragm-, skeletal muscle- and heart-cells or tissue of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g. by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Preferably, the higher expression remains specific to diaphragm, heart and skeletal muscle tissues or cells. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

Also disclosed herein is the use of the nucleic acid regulatory elements according to SEQ ID NO:1 to 7, 10 to 65, 82, and 83 (cf. Dph-CRE1 to 7, 10 to 65, 82, and 83 in Table 3), or the nucleic acid expression cassettes, or the vectors disclosed herein comprising said nucleic acid regulatory elements, for transfecting or transducing diaphragm, and/or skeletal muscle cells.

Also disclosed herein is the use of the nucleic acid regulatory elements according to SEQ ID No: 1 to 9, 66 to 81, and 84 to 89. (cf. Dph-CRE1 to 9, 66 to 81, and 84 to 89 in Table 4), or the nucleic acid expression cassettes, or the vectors disclosed herein comprising said nucleic acid regulatory elements, for transfecting or transducing diaphragm, skeletal muscle and/or heart, cells.

Further disclosed herein is the use of the nucleic acid expression cassettes or the vectors disclosed herein comprising the nucleic acid regulatory elements according to SEQ ID NO:1 to 7, 10 to 65, 82, and 83 (cf. Dph-CRE1 to 7, 10 to 65, 82, and 83 in Table 3), for expressing a transgene product in diaphragm and/or skeletal muscle cells, wherein the nucleic acid expression cassette or the vector comprises a nucleic acid regulatory element disclosed herein operably linked to a promoter and a transgene.

Further disclosed herein is the use of the nucleic acid expression cassettes or the vectors disclosed herein comprising the nucleic acid regulatory elements according to SEQ ID No: 1 to 9, 66 to 81, and 84 to 89. (cf. Dph-CRE1 to 9, 66 to 81, and 84 to 89 in Table 4), for expressing a transgene product in diaphragm, skeletal muscle, and heart cells, wherein the nucleic acid expression cassette or the vector comprises a nucleic acid regulatory element disclosed herein operably linked to a promoter and a transgene.

Further disclosed herein is a method for expressing a transgene product in diaphragm, and/or skeletal muscle cells, comprising:
transfecting or transducing said cells with a nucleic acid expression cassette or a vector disclosed herein, wherein the nucleic acid expression cassette or the vector comprises a nucleic acid regulatory element according to any one of SEQ ID NO:1 to 7, 10 to 65, 82, and 83 (cf. Dph-CRE1 to 7, 10 to 65, 82, and 83 in Table 3), operably linked to a promoter and a transgene; and
expressing the transgene product in said cells.

Further disclosed herein is a method for expressing a transgene product in diaphragm, skeletal muscle and heart cells, comprising:
transfecting or transducing said cells with a nucleic acid expression cassette or a vector disclosed herein, wherein the nucleic acid expression cassette or the vector comprises a nucleic acid regulatory element according to any one of SEQ ID No: 1 to 9, 66 to 81, and 84 to 89. (cf. Dph-CRE1 to 9, 66 to 81, and 84 to 89 in Table 4) operably linked to a promoter and a transgene; and expressing the transgene product in said cells.

Non-viral transfection or viral vector-mediated transduction of diaphragm, heart, and/or skeletal muscle cells may be performed by in vitro, ex vivo or in vivo procedures. The in vitro approach requires the in vitro transfection or transduction of diaphragm, heart, and/or skeletal muscle cells, e.g. cells previously harvested from a subject, cell lines or cells differentiated from e.g. induced pluripotent stem cells or embryonic cells. The ex vivo approach requires harvesting of the diaphragm, skeletal muscle and heart, cells from a subject, in vitro transfection or transduction, and optionally re-introduction of the transfected cells into the subject. The in vivo approach requires the administration of the nucleic acid expression cassette or the vector disclosed herein into a subject. In preferred embodiments, the transfection of the diaphragm, skeletal muscle, and heart cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into diaphragm, skeletal muscle, and heart cells, transgenic models for over-expression of proteins in diaphragm, skeletal muscle, and heart etc.

The invention is further explained by the following non-limiting examples

EXAMPLES

Example 1: Identification of Diaphragm-Specific Nucleic Acid Regulatory Elements To identify the diaphragm genes that are highly expressed, the gene expression profiling of the human diaphragm tissue has been investigated compared to that of other tissues such as skeletal muscle, heart, liver, spleen, and kidneys etc. The total RNA samples extracted from each tissue were purchased commercially (Table 1).

TABLE 1 overview of RNA samples

Diaphragm RNA samples (from Biochain, #R1234169-10)

| | |
|---|---|
| Diaphragm sample 1 | Male 26 years |
| Diaphragm sample 2 | Male 24 years |

Other organs RNA samples (from Clontech, #636643)

| | |
|---|---|
| Fetal liver | pooled from 3 males/females, age 20-38 weeks |
| Bone marrow | pooled from 4 males/female, age 58-76 |
| Brain (whole) | pooled from 4 males, age 21-29 |
| Kidney | pooled from 1 female, age 40 |
| Liver | pooled from 3 males, age 24-64 |
| Lung | pooled from 3 males/females, age 32-61 |
| Skeletal muscle | pooled from 1 male, age 20 |
| Heart | pooled from 3 males, age 30, 30, 39 |
| Spleen | pooled from 15 males/females, age 22-69 |
| Testis | pooled from 7 males, age 24-87 |
| Colon | pooled from 3 males, age 24-29 |
| Spinal cord | pooled from 7 males, age 20-59 |

Gene expression profiling was performed by RNA next-generation sequencing (RNA-seq). This method provides deep coverage and base pair-level resolution. RNA sequencing quantification is proven to be an efficient alternative to microarray technique in gene expression studies, and it is a critical technology in differential expression analysis.

In this study, RNA-sequencing was achieved using Illumina™ Hiseq 4000 sequencing 50SE (20 clean reads per sample) by BGI (Hong Kong). All samples showed good to excellent quality as high RNA integrity number (RIN) index.

Initially, the gene expression level in diaphragm samples was ranked from highest to lowest values based on the RNA-seq data. The 25 highest expressed genes in the diaphragm were selected. The gene expression profiles were then compared between diaphragm, skeletal muscle, with or without heart versus other tissues to identify only highly and specifically expressed genes in i) diaphragm and skeletal muscle (Dph+SkM) or ii) diaphragm, skeletal muscle, and heart(Dph+SkM+Hrt). Based on this comparison, 18 genes were identified (Table 3), which are highly and specifically expressed in diaphragm and skeletal muscle and 8 genes (Table 4) that are highly expressed in diaphragm, skeletal muscle, and heart. All 25 genes (17 genes for Dph+SkM and 10 genes for Dph+SkM+Hrt: 2 genes ACTA1 and CKM are overlapping with the Dph+SkM group) were analyzed using ENSEMBL for locating the transcription start site (TSS). Subsequently, these TSS were mapped into UCSC Genome Browser Database for nucleic acid regulatory element identification. The nucleic acid regulatory elements were selected based on i) high DNase hypersensitivity sites ii) high content of epigenetic markers associated with open chromatin (i.e. acetylation, methylation) iii) high content of transcription factor binding sites iv) strong evolutionary conservation among vertebrates and v) conserved transcription factor binding sites in 3 species (human, rat, mouse) (FIG. 1). Finally, based on these 5 criteria, 89 nucleic acid regulatory elements were identified from 25 genes. 65 nucleic acid regulatory elements sequenced were identified for high expression in diaphragm and skeletal muscle (Tabl 3) and 31 nucleic acid regulatory elements sequenced were identified for high expression in diaphragm, skeletal muscle and heart (Table 4). 7 of these are common CREs and are therefore present in both tables.

TABLE 2 list of genes highly expressed in Diaphragm and Skeletal Muscle or Diaphragm, Skeletal Muscle and Heart (cf. also Table 3 & 4)

| High expressed genes in Diaphragm and Skeletal Muscle | High expressed genes in Diaphragm and Skeletal Muscle and Heart |
|---|---|
| 1) ACTA1 | 1) MYL2 |
| 2) CKM | 2) MB |
| 3) TPM2 | 3) DES |
| 4) MYL1 | 4) TNNC1 |
| 5) TNNC2 | 5) TCAP |
| 6) FHL1 | 6) MYH7 |
| 7) TNNT1 | 7) ALDOA |
| 8) TNNI2 | 8) TPM1 |
| 9) MYLPF | 9) ACTA1 |
| 10) TNNT3 | 10) CKM |
| 11) MYH2 | |
| 12) SLN | |
| 13) MYBPC1 | |
| 14) CA3 | |
| 15) ATP2A1 | |
| 16) MYH1 | |
| 17) ENO3 | |

Example 2: In Vivo Comparison of Desmin Promoters

Experimental Procedures

AAV vectors comprising the muscle-specific regulatory element Sk-SH4 were generated according to the protocol described in Example 3. Briefly, the muscle-specific regulatory element Sk-SH4 was synthesized by conventional oligonucleotide synthesis and cloned upstream of the human desmin 1.4 kb promoter (SEQ ID NO: 92), the human desmin 1.0 kb promoter (SEQ ID NO: 91) or the murine desmin promoter (SEQ ID NO: 90) in the context of the AAV vector backbone of AAVsc-hDes1.4 kb-MVM-Luc, AAVsc-hDes1.0 kb-MVM-Luc or AAVsc-mDes-MVM-Luc, respectively.

Adult CB17/IcrTac/PrkdcSCID (SCID, severe combined immunodeficient) mice were intravenously injected (n=5) at a dose of $1 \times 10^{10}$ vg/mouse.

Mice were sacrificed at two weeks and four weeks after injection of the vectors and the different muscle types (biceps, diaphragm, gastrocnemius, heart, quadriceps, tibialis and triceps) were isolated and quantified using bioluminescence imaging as described in Keyaerts M1, Caveliers V, Lahoutte T. Trends Mol Med. 2012 March; 18(3):164-72. doi: 10.1016/j.molmed.2012.01.005. Epub 2012 Feb. 8. Bioluminescence imaging: looking beyond the light.

Results

Figure 4:
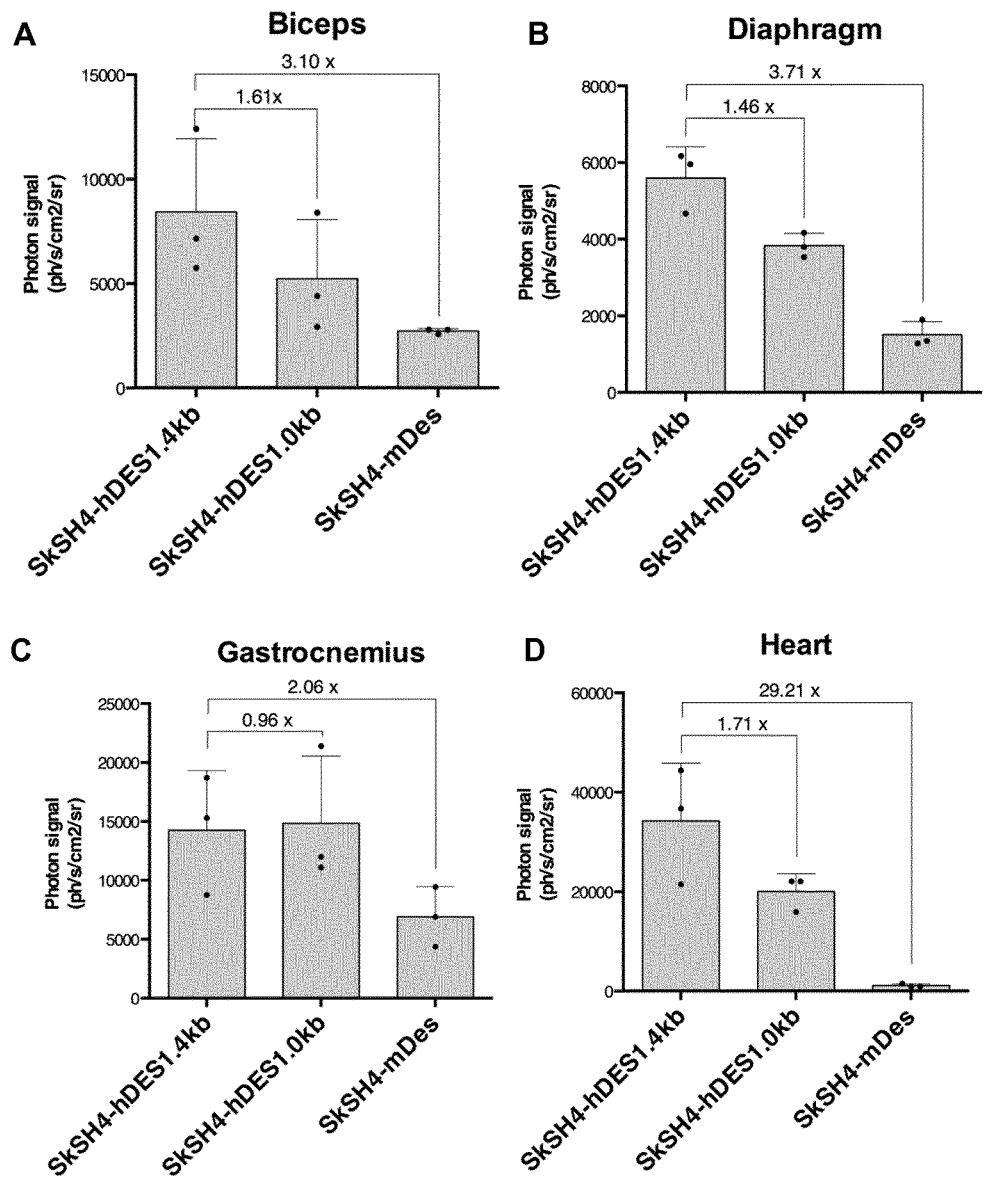
FIG. 4: In vivo comparison of desmin promoters. SCID mice were injected with $1 \times 10^{10}$ vg/mouse of AAV9-luciferase vector containing the most robust skeletal muscle specific CRE (designated as Sk-SH4) in combination with different desmin promoters: Sk-SH4-hDES1.4 kb, (SEQ ID NO: 92) Sk-SH4-hDES1.0 kb & (SEQ ID NO: 91) Sk-SH4-mDES (SEQ ID NO: 90), quantified as Photons signal, in murine Biceps (A), diaphragm (B), gastrocnemius (C), heart (D), quadriceps (E), tibialis (F) and triceps (G).
Figure 4:
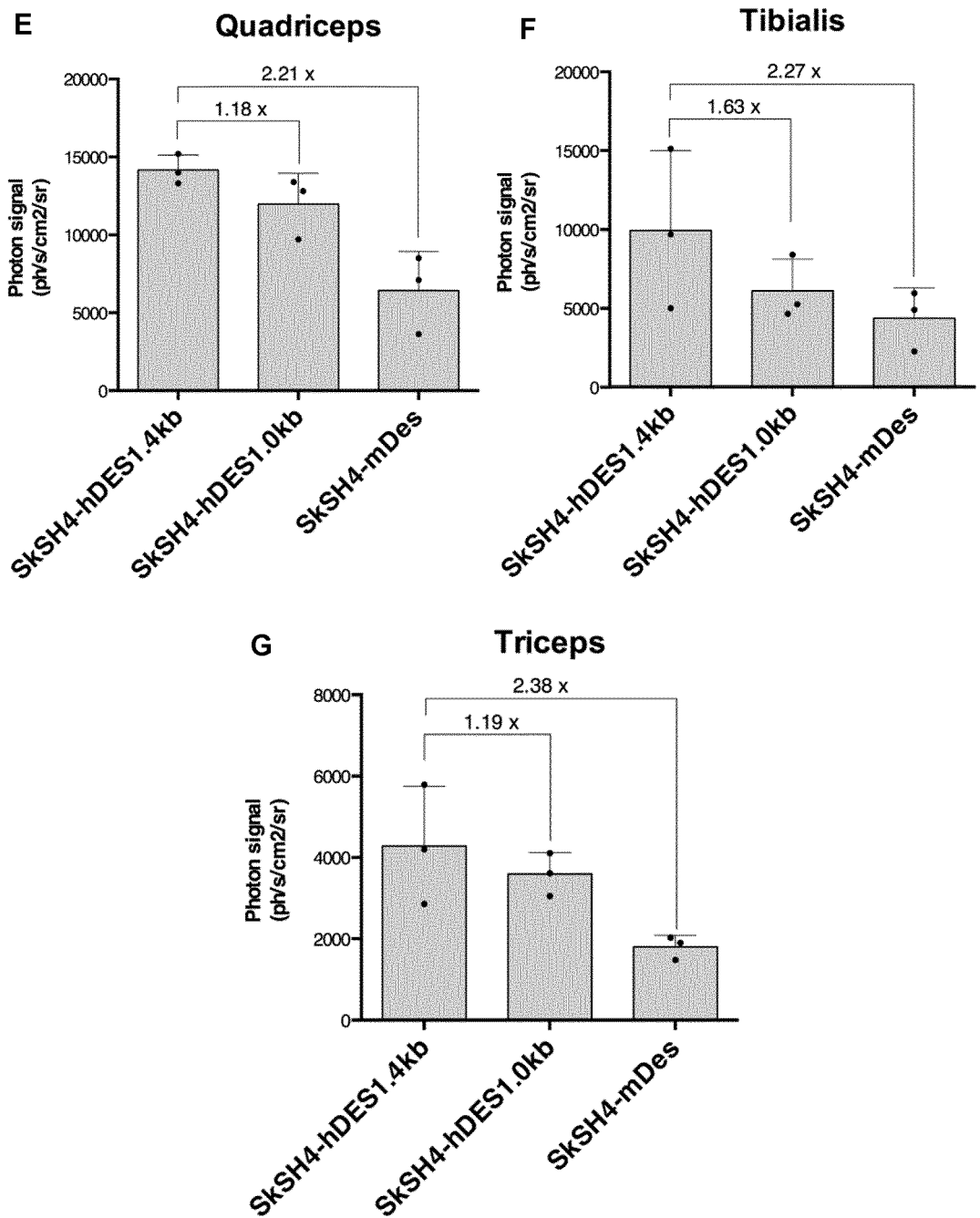

Comparison of the luciferase expression induced by the different AAV vectors quantified as Photons signal shows that the expression cassette comprising Sk-SH4-hDES1.0 kb or Sk-SH4-hDES1.4 kb, especially Sk-SH4-hDES1.4 kb, leads to a higher luciferase expression in the different muscle types of mice (Biceps, diaphragm, gastrocnemius, heart, quadriceps, tibialis and triceps) compared to the expression cassette comprising Sk-SH4-mDES (FIG. 4).

Example 3: In Vivo Validation of Dph-CREs

The selected top diaphragm-specific nucleic acid regulatory elements (cf. Table 3 & 4) were cloned upstream of a promoter which is active in muscle, diaphragm and optionally heart tissue (e.g. mouse or human desmin promoter (DES, more preferably mDES, hDES1.0 kb, or hDES1,4 kb as depicted in SEQ ID NO: 90-92 respectively), or the SPc5-12 promoter (SEQ ID NO: 124), to drive expression of a reporter gene in an AAV vector backbone (e.g. pAAV$_{SC}$ or pAAV$_{SS}$). Other promotors of genes highly expressed in diaphragm can also be used. In addition, other muscle specific promoters such as muscle creatine kinase promoter (MCK) (Wang B et al., 2008) alpha-myosin heavy chain (a-MHC), myosin light chain (MLC-2) or cardiac troponin C (cTnC), myogenin MYF4 promoters ((Pacak C. A. et al; 2008) or viral promoters such as murine stem cell virus (MSCV) promoter (Suga T et al., Plos One 2011) are all potential promoters that can be used to cloned downstream of the diaphragm nucleic acid regulatory elements.

Figure 8:
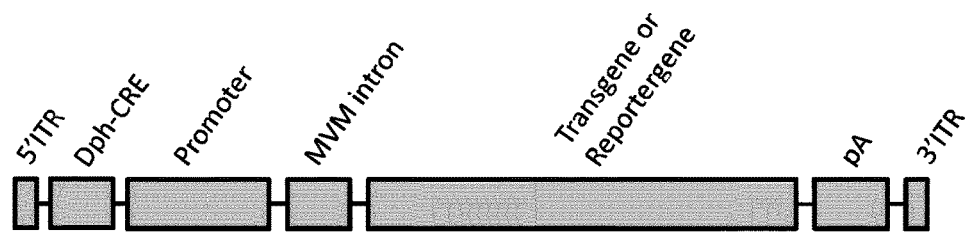
FIG. 8: Schematic view of AAV vector backbone. A) reference backbone with Dph-CREs coupled to a promotor, MVM intron, a transgene or reporter gene, and a polyA site. B-C) Same as A), but with an additional muscle CRE (Sk-CRE) or heart-muscle CRE (CSk-CRE) coupled after B) the Dph-CRE or before C) the Dph-CRE.
Figure 8:
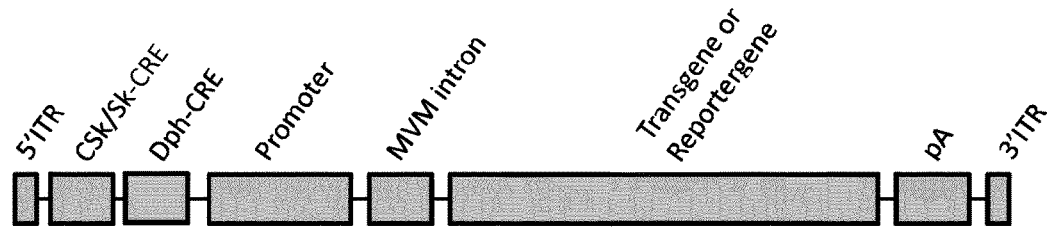
Figure 8:
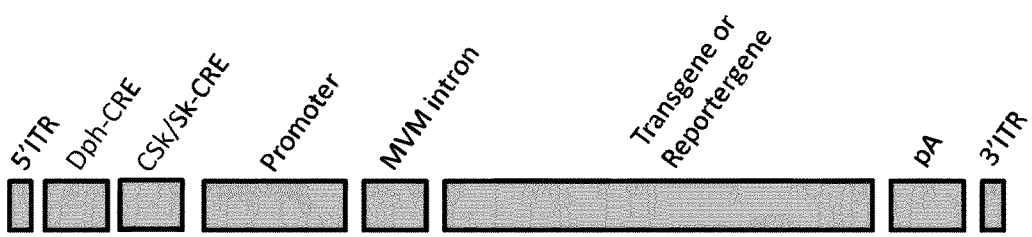

The plasmids also contain a Minute Virus of Mouse (MVM) intron (SEQ ID NO: 125) and a polyadenylation site (pA), e.g. the Simian Virus 40 polyadenylation site (SEQ ID NO: 126) or a synthetic poly-A site (SEQ ID NO: 127). This leads to the general AAV backbone pAAV-Dph-CRE01to89-Des/SPc-promoter-MVM-intron-Transgene/Reportergene-pA (FIG. 8A). Some of these backbones were further complemented with a muscle/heart-CRE such as the ones disclosed in WO2015/110449. This leads to the AAV backbone pAAV-CSk/Sk-CRE-Dph-CRE01to89-Des/SPc-promoter-MVM-intron-Transgene/Reportergene-pA (FIG. 8B) or pAAV-Dph-CRE01to89-Sk/CSk-CRE-Des/SPc-promoter-MVM-intron-Transgene/Reportergene-pA (FIG. 8c), wherein the Sk-CRE/CSk-CRE is either one of the CRE's disclosed in WO2015/110449, preferably skeletal muscle CRE Sk-SH4 (SEQ ID NO: 121), or the skeletal muscle and cardiac CREs CSk-SH5 (SEQ ID NO: 122) and CSk-SH1 (SEQ ID NO: 123) regulatory elements.

The reporter gene is preferably a Luciferase reporter gene and the transgenes tested below are the human GAA and MTM1 genes or their codon-optimised variants (cf. example 4).

For studying the effect of the Dph-CREs on tissue specific expression, the following AAV vector backbones were used:
for the Dph-CREs from Table 3: pAAVss-Sk-SH4-hDES1.4 kb-MVM-Luciferase-pA
for the Dph-CREs from Table 4: pAAVss-CSk-SH5-SPc5-12GTRM-MVM-Luciferase-pA, Wherein the different Dph-CREs are cloned before or after the Sk-SH4 or CSk-SH5 CRE.

Production of the AAV vector particles is achieved by transient co-transfection of AAV-reporter and AAV helper constructs, encoding AAV serotype 9 capsids into HEK293 cells, followed by a purification step based on cesium chloride (CsCl) density gradient ultracentrifugation, as described previously (Vanden Driessche et al., 2007 J Thromb Haemost 5:16-24), which is specifically incorporated by reference herein.

Briefly, two days post transfection, cells were harvested and vector particles were purified using isopycnic centrifugation methods. Harvested cells were lysed by successive freeze/thaw cycles and sonication, treated with benzonase (Novagen, Madison, WI) and deoxycholic acid (Sigma-Aldrich, St. Louis, MO) and subsequently subjected to 3 successive rounds of cesium chloride (Invitrogen Corp, Carlsbad, CA) density gradient ultracentrifugation. Fractions containing the AAV vector were collected, concentrated in 1 mM MgCl$_2$ in Dulbecco's phosphate buffered saline (PBS) (Gibco, BRL) and stored at −80° C.

Vector titers (in viral genomes (vg)/ml) were determined by quantitative real-time PCR using SYBR Green mix (which included SYBR Green dye, Taqman polymerase, ROX and dNTP's all in one) and luciferase specific primers on an ABI 7500 Real-Time PCR System (Applied Biosystem, Foster city, CA, USA). The forward and reverse primers used were 5'-CCCACCGTCGTATTCGTGAG-3' (SEQ ID NO: 128) and 5'-TCAGGGCGATGGTTTTGTCCC-3' (SEQ ID NO: 129), respectively.

Typically, for all vectors titers in the range of $1.5-6.1 \times 10^{11}$ vg/ml were achieved from a small production batch of 20 petri dishes of producer cells. If higher number of petri dishes such as 60 dishes of producer cells were used, a higher titer typically in the range of $10^{12}-10^{13}$ gc/ml of AAV particles were achieved. Known copy numbers ($10^2-10^7$) of the respective vector plasmids used to generate the corresponding AAV vectors, carrying the appropriate cDNAs were used to generate the standard curves.

All animal procedures were approved by the institutional animal ethics committee of the Free University of Brussels (VUB) (Brussels, Belgium). All mice were housed under specific pathogen-free conditions; food and water were provided ad libitum.

The purified AAV vectors are injected intravenously (i.v.) in 4 weeks old immunodeficient CB17-SCID mice (Janvier, France) at different vector doses, allowing the identification of the most robust diaphragm-specific nucleic acid regulatory elements by quantifying the reporter gene expression.

In different muscle tissues (biceps, diaphragm, gastrocnemius, heart, quadriceps, tibialis and triceps) were quantified using bioluminescence imaging. Whole body bioluminescence was performed approx. 1 week post-AAV injection and organs bioluminescence approx. 3 weeks post-AAV injection.

Luciferase expression induced by the different AAV vectors quantified as Photons signal are shown in FIGS. 5a to 5i for Dph-CRE-02, -58, -59, -60, -64, -21, -41, -18, -04, -06 for the Sk-SH4 backbone) and Dph-CRE-77, -02, -04, -06, -69, -70, -71, -66, -68, and -07 for the CSk-SH5 backbone). All 20 tested Dph-CREs show an increased expression versus the base line expression using a Sk-SH4-hDES1,4 kb or CSk-SH5-SPc5-12 backbone. 100% of the diaphragm CREs tested showed enhanced luciferase expression. In particular, Dph-CRE-02, 21 and 64 show a particularly higher expression levels compared to the Sk-SH4-hDES1,4 kb backbone, while Dph-CRE-04, -02 and -06 show a particularly higher expression level compared to the CSk-SH5-SPc5-12 kb backbone.

The individual screening of the 20 diaphragm CREs clearly demonstrated the successful generation of synergistic CRE combinations (Diaphragm CRE+Skeletal muscle CREs) and (Diaphragm CRE+Skeletal muscle/Heart CREs) that led to robust gene expression in the diaphragm and, skeletal muscle and/or heart, higher than with any conventional vector designs that are either currently being used in clinical trials or being considered for future trials.

The experiments show that the skeletal muscle specific-CRE (Sk-SH4) leads to a robust increase in reporter (or transgene) expression in vivo when compared to control without muscle specific CRE (hDES1.4 kb). In particular, the diaphragm specific CRE (Dph-CRE64, CRE02, and CRE21) coupled to the muscle specific CRE (Sk-SH4) act synergistically as a combined module, leading to an extremely high level of enhancement of luciferase expression in vivo. The other Dph CREs (60, 58, 04, 18, 41, 69, 06) also showed moderate augmentation of luciferase gene expression.

Similarly, the combined cardiac/skeletal muscle specific-CRE (CSk-SH5) led to robust increased in luciferase expression in vivo when compared to control without CSk-SH5 CRE but just the SPc5-12-GTRM promotor driving the luciferase gene. In addition, we showed that the diaphragm specific CRE (Dph-CRE04, 02, 06) when coupled to the combined cardiac/skeletal muscle specific CRE (CSk-SH5) act synergistically, leading to an extremely high level of enhancement of luciferase expression in vivo. Other Dph CREs (77, 70, 66, 71, 69, 68, 07) showed moderate level of augmentation of luciferase gene expression.

Dph-CRE64 showed the highest increase in luciferase gene expressed when combined to the Sk-SH4 muscle CRE driven from the human Desmin 1.4 kb promoter. There is a clear synergistic effect of the Diaphragm CRE in combination with the muscle CRE.

Dph-CRE04 showed the highest increase in luciferase gene expressed when combined to the CSk-SH5 muscle CRE driven from the synthetic SPc5-12 promoter. There is a clear synergistic effect of the Diaphragm CRE in combination with the muscle CRE.

This demonstrates that the CREs can act synergistically in a modular fashion.

The individual organ data confirmed the data of the whole body. In the diaphragm tissues, for the group of diaphragm CREs combined with the Sk-SH4-hDes1.4 kb expression cassette, the diaphragm CREs that are the most robust are: CRE02, CRE64 CRE60 and CRE21 leading to an augmentation of 400-600 fold luciferase expression when compared to luciferase expression driven from just the human Desmin 1.4 kb promoter (normalized to hDes1.4 kb, fold difference depicted in lower numbers above graphs in FIG. 5a left-hand). This 400-600 fold increased in luciferase expression is the contribution of the diaphragm CRE combined with the muscle CRE (Sk-SH4). When normalized to Sk-SH4-hDes1.4 kb, up to 10 fold enhancement of luciferase expression can be detected from these 4 robust diaphragm CREs (fold difference upper numbers above graphs in FIG. 5a left-hand). This 10 fold difference is the contribution of the individual diaphragm CRE driven from this expression cassette.

Similarly, for the group of diaphragm CREs combined with the CSk-SH5-SPc5-12-GTRM expression cassette, the diaphragm CREs that are the most robust are: CRE02, CRE04, CRE06) leading to an augmentation of about 300 fold luciferase expression when compared to luciferase expression driven from just the SPc5-12-GTRM promoter (normalized to SPc5-12-GTRM, fold difference depicted in lower numbers above graphs in FIG. 5a right-hand). This 300 fold increased in luciferase expression is the contribution of the diaphragm CRE combined with the muscle/heart CRE (CSk-SH5). When normalized to CSk-SH5-SPc5-12-GTRM, up to 23-25 fold enhancement of luciferase expression can be detected from these 3 robust diaphragm CREs (fold difference upper numbers above graphs in FIG. 5a right-hand). This 23-25 fold enhancement is the sole contribution from the individual diaphragm CRE.

Figure 5A:
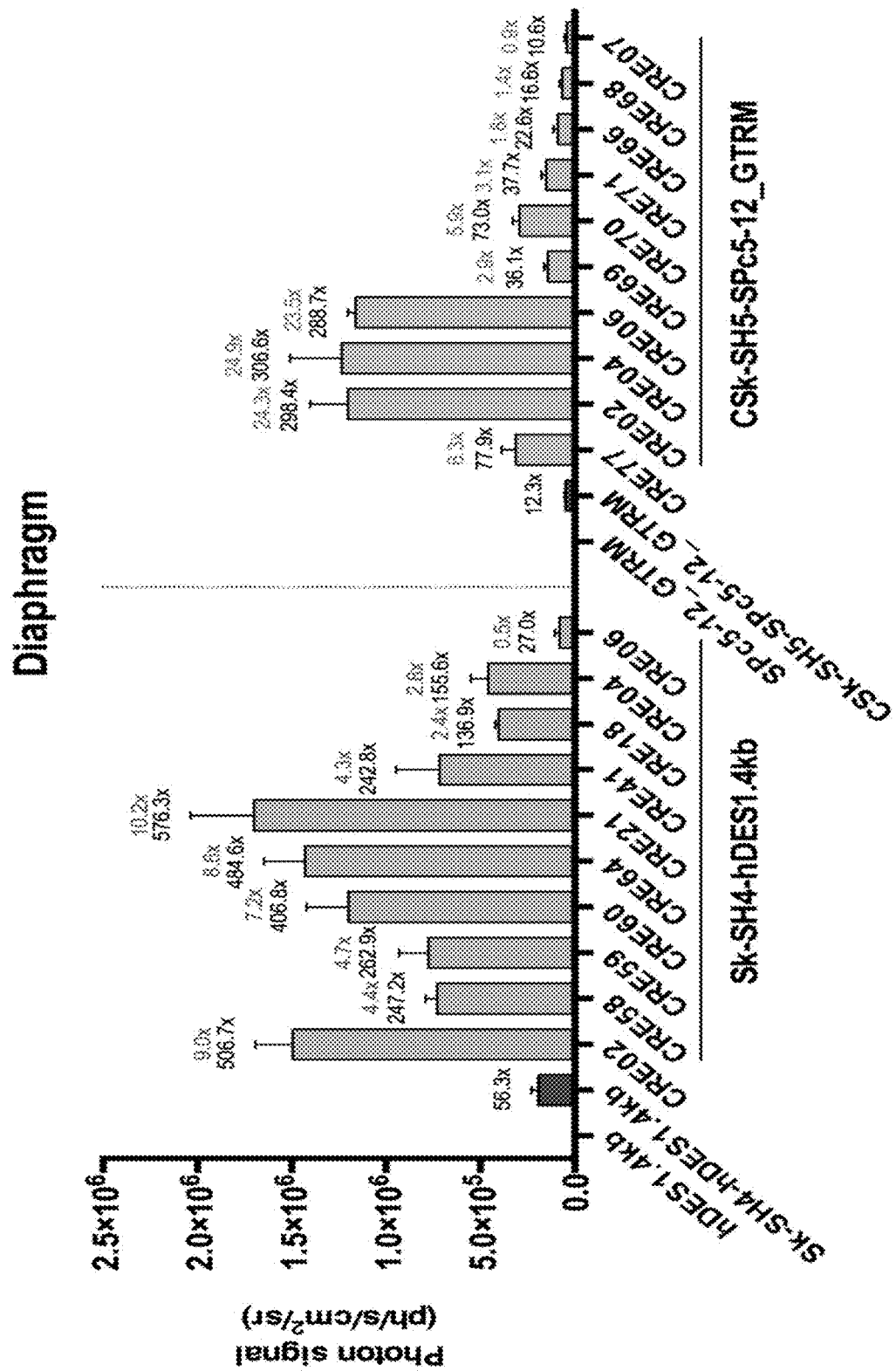
FIG. 5: Comparison of tissue expression levels in absence or presence of Diaphragm CREs (Dph-CREs) according to the invention. a) Expression in Diaphragm b) Expression in Quadricep c) Expression in Gastrocnemius d) Expression in Tibialis e) Expression in Bicep f) Expression in Tricep g) Expression in total skeletal muscle tissues h) Expression in heart. In the left-hand graphs, the fold difference in expression of the different new Diaphragm CREs (Dph-CREs) in a vector backbone comprising the hDES1.4 kb promoter and a muscle-specific CRE Sk-SH4 (SEQ ID NO: 121) is indicated versus the same vector backbone with hDES1.4 kb promoter only (bottom numbers) and versus the same vector backbone without the new CREs (upper numbers). In the right-hand graphs, the fold difference in expression of the different new Diaphragm CREs in a vector backbone comprising the SPc5-12 promoter and a muscle-specific CRE CSk-SH5 (SEQ ID NO: 122) is indicated versus the same vector backbone with SPc5-12 promoter only (bottom numbers) and versus the same vector backbone without the new CRE's (upper numbers) i) Specificity of Diaphragm CREs (mainly expressed in diaphragm, skeletal muscle and heart but not in other tissues. The numbers of the Diaphragm CREs correspond to the numbering of Tables 3 and 4.
Figure 5B:
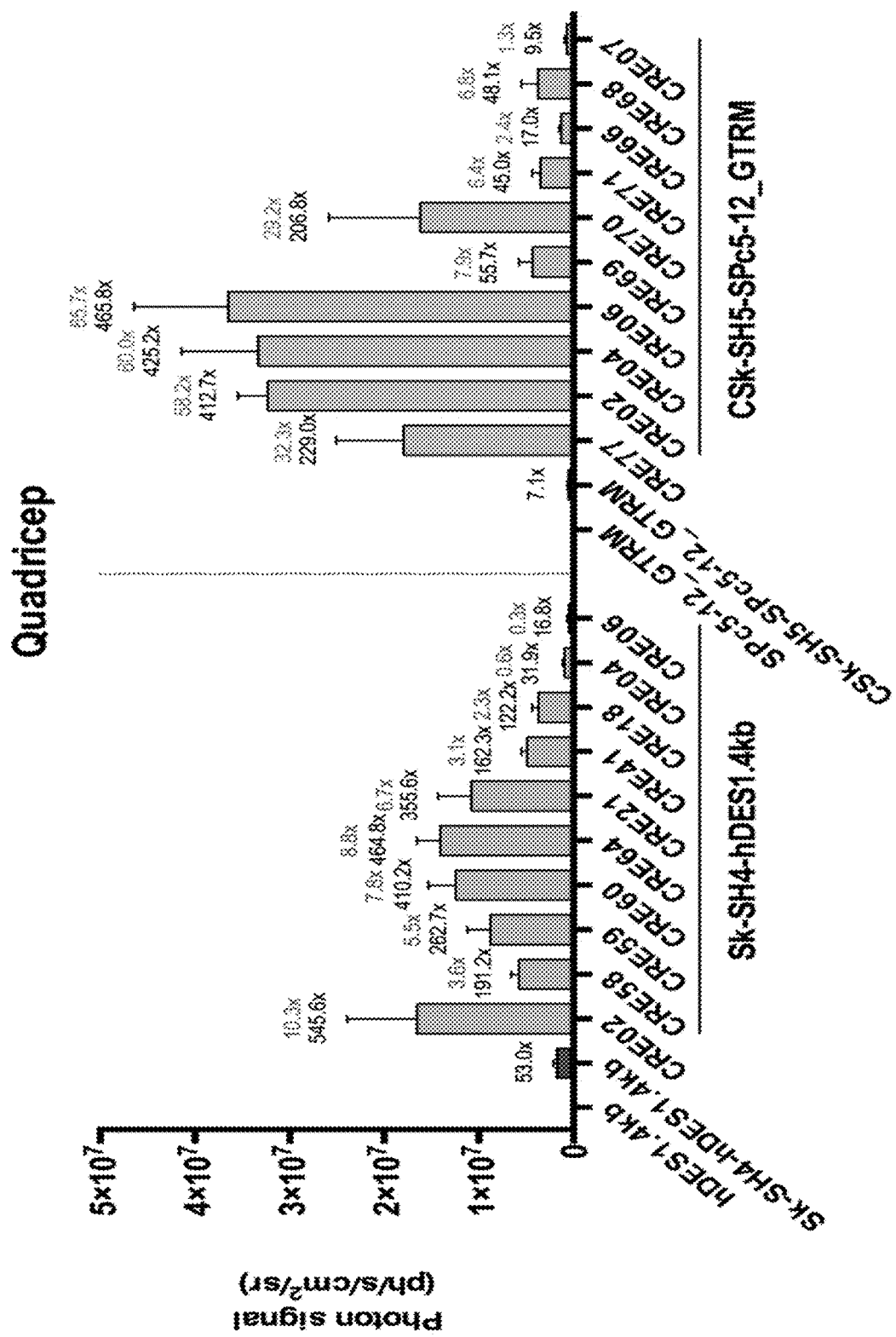
Figure 5C:
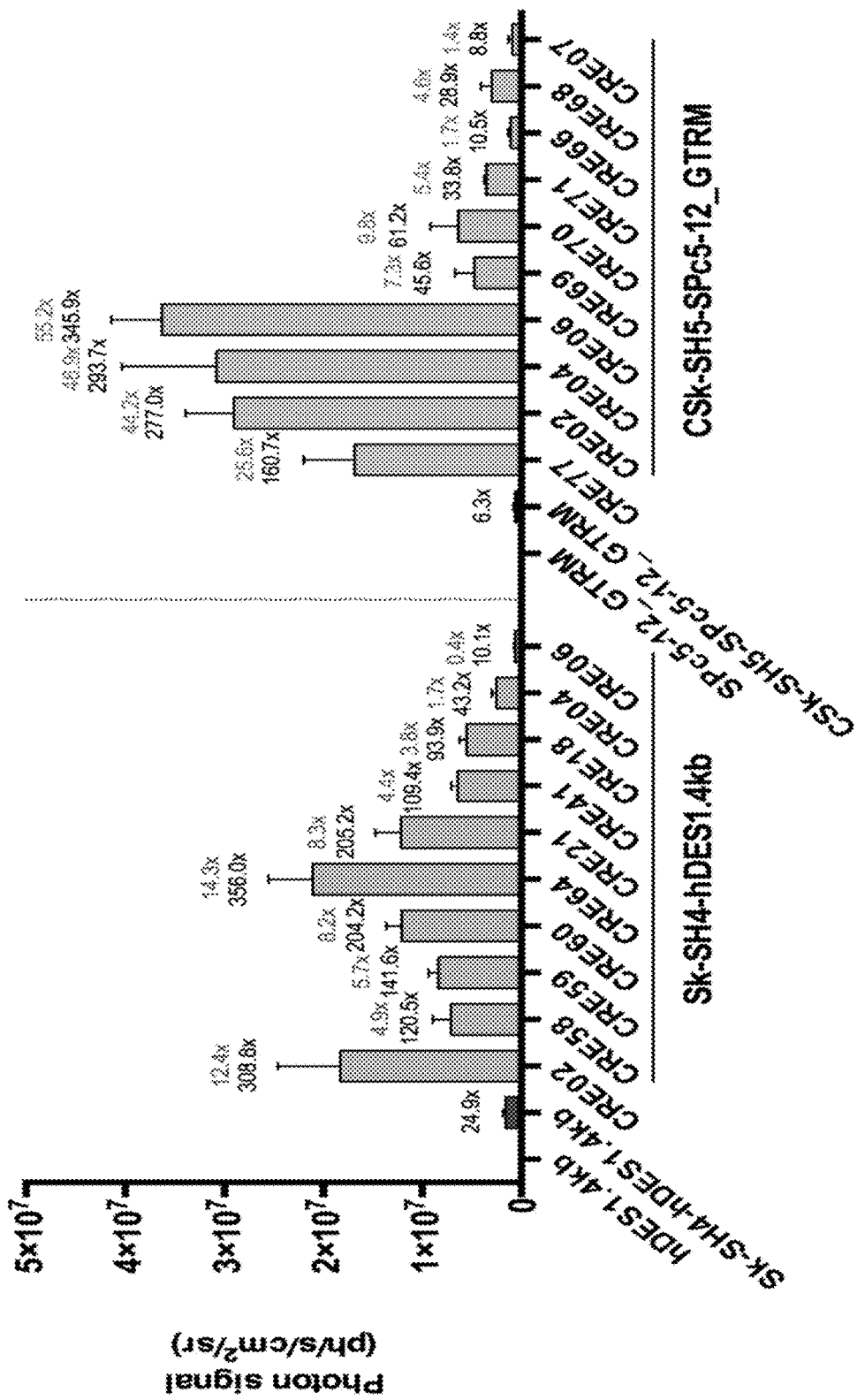
Figure 5D:
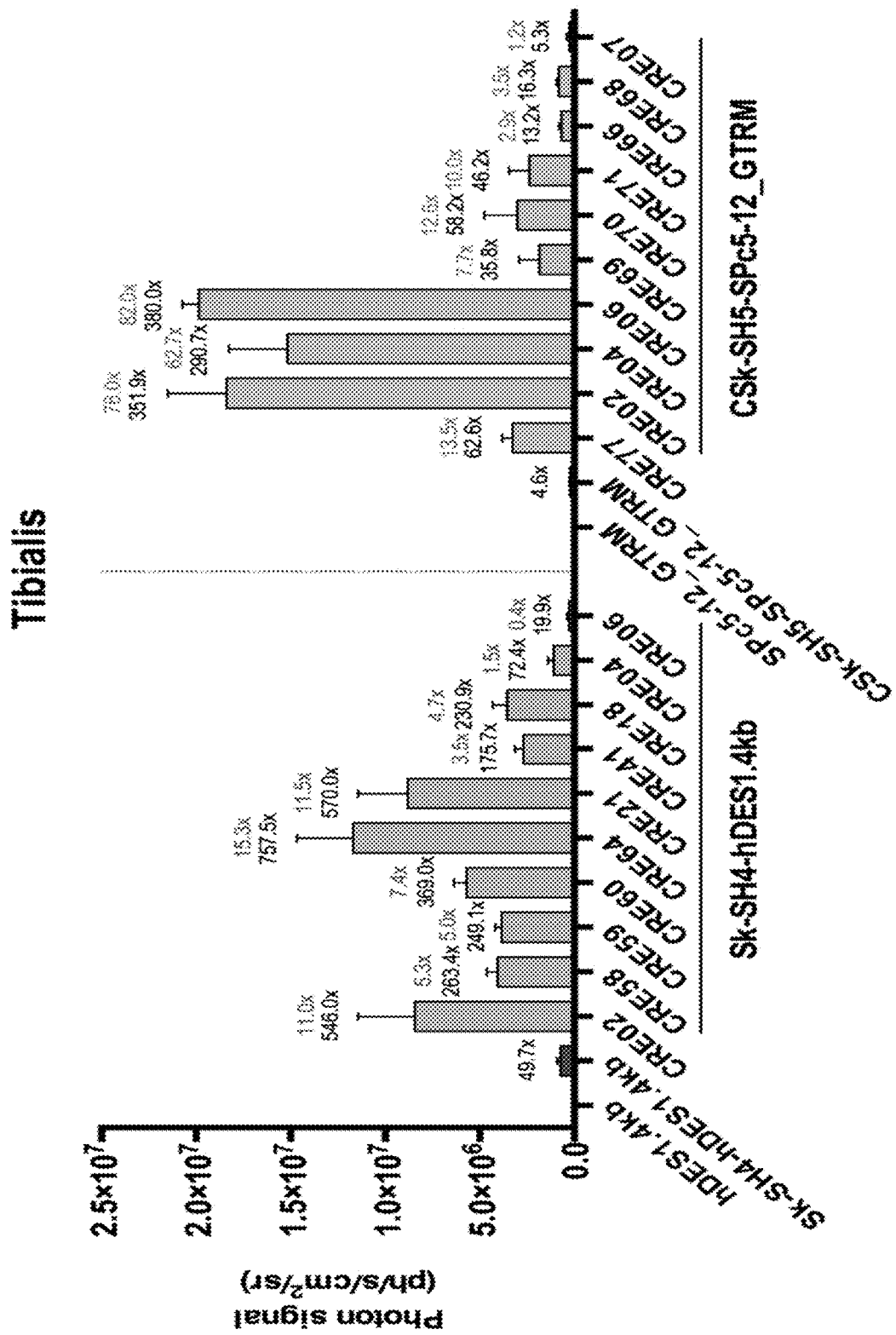
Figure 5E:
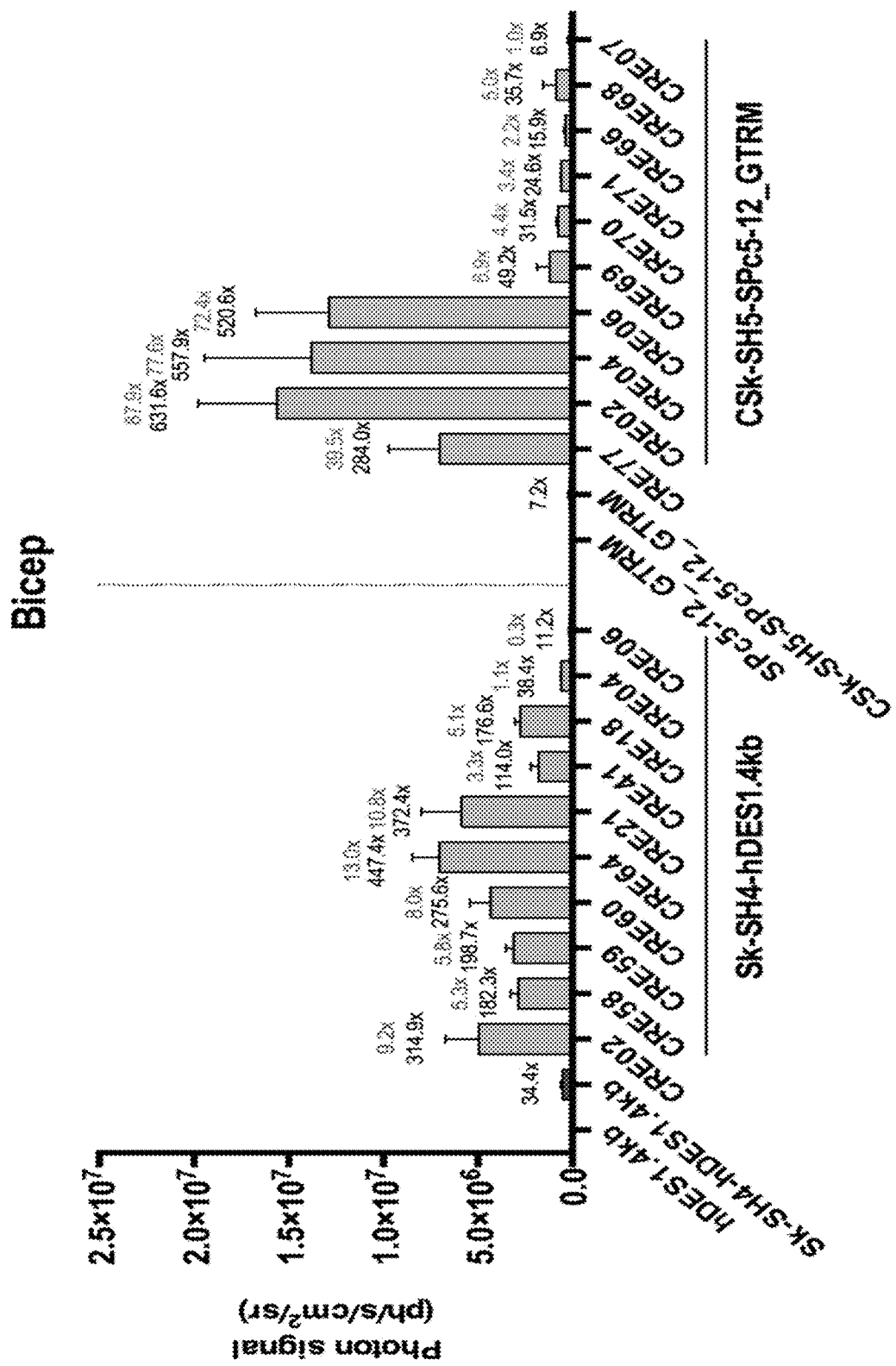
Figure 5F:
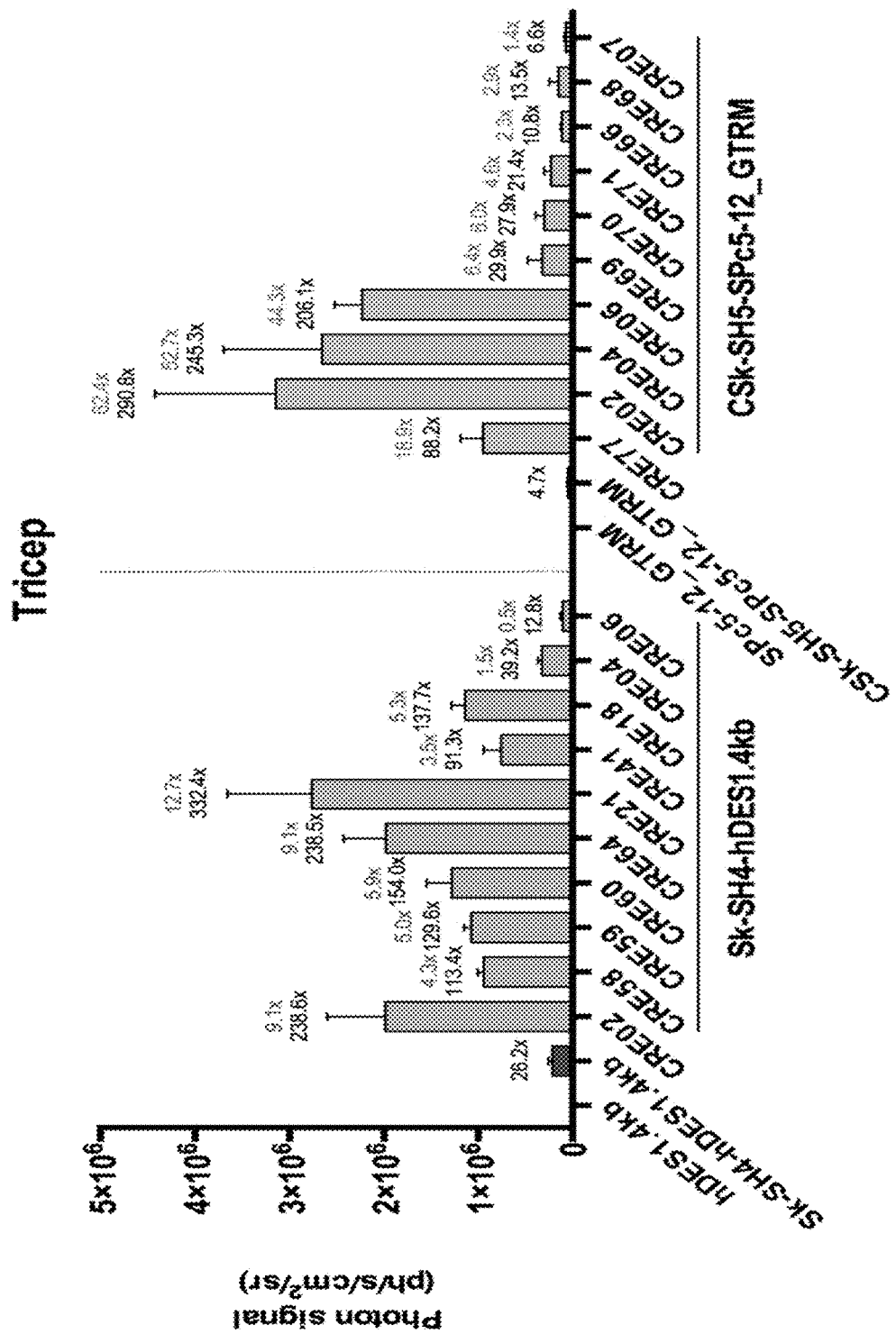
Figure 5G:
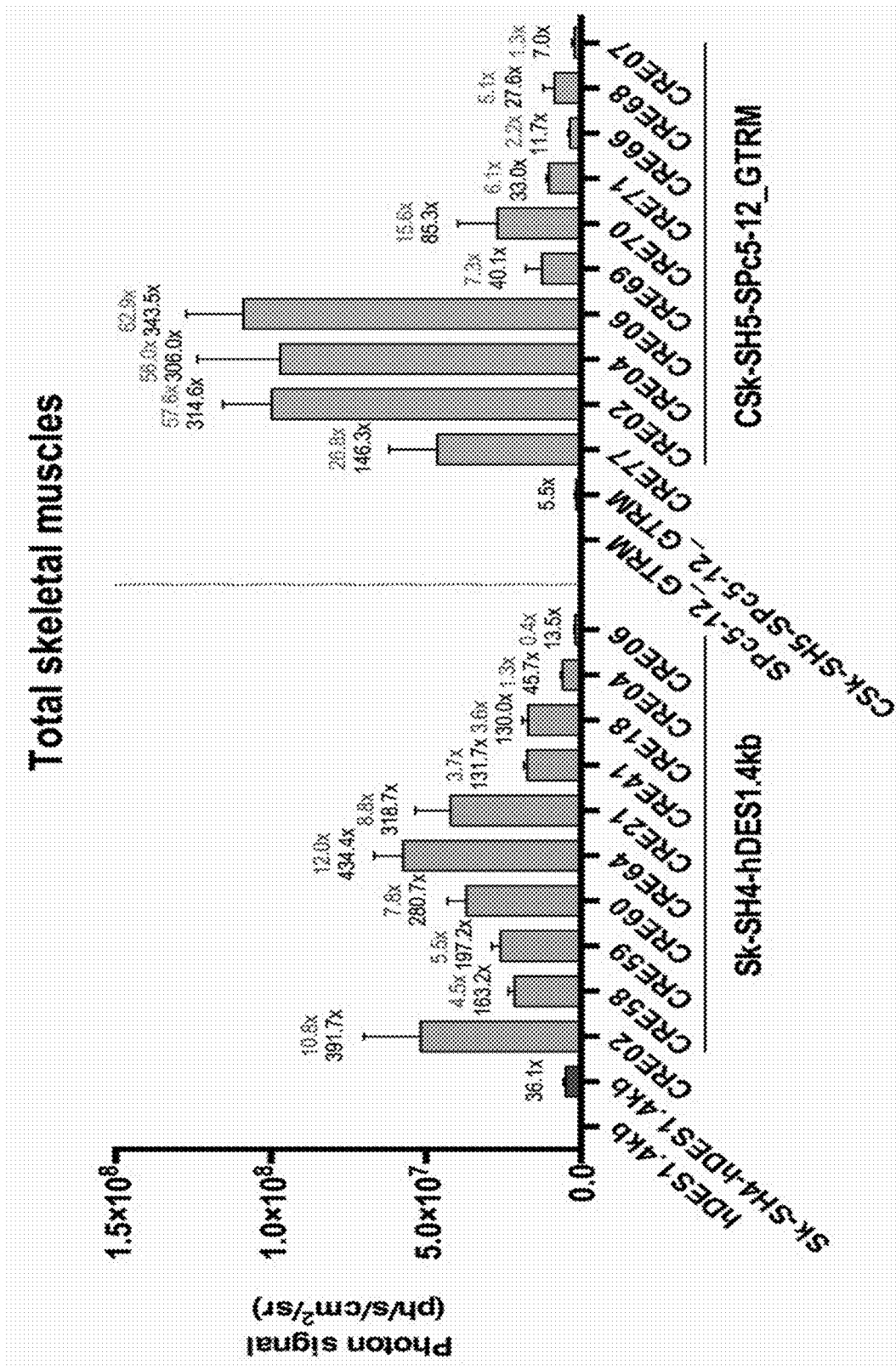
Figure 5H:
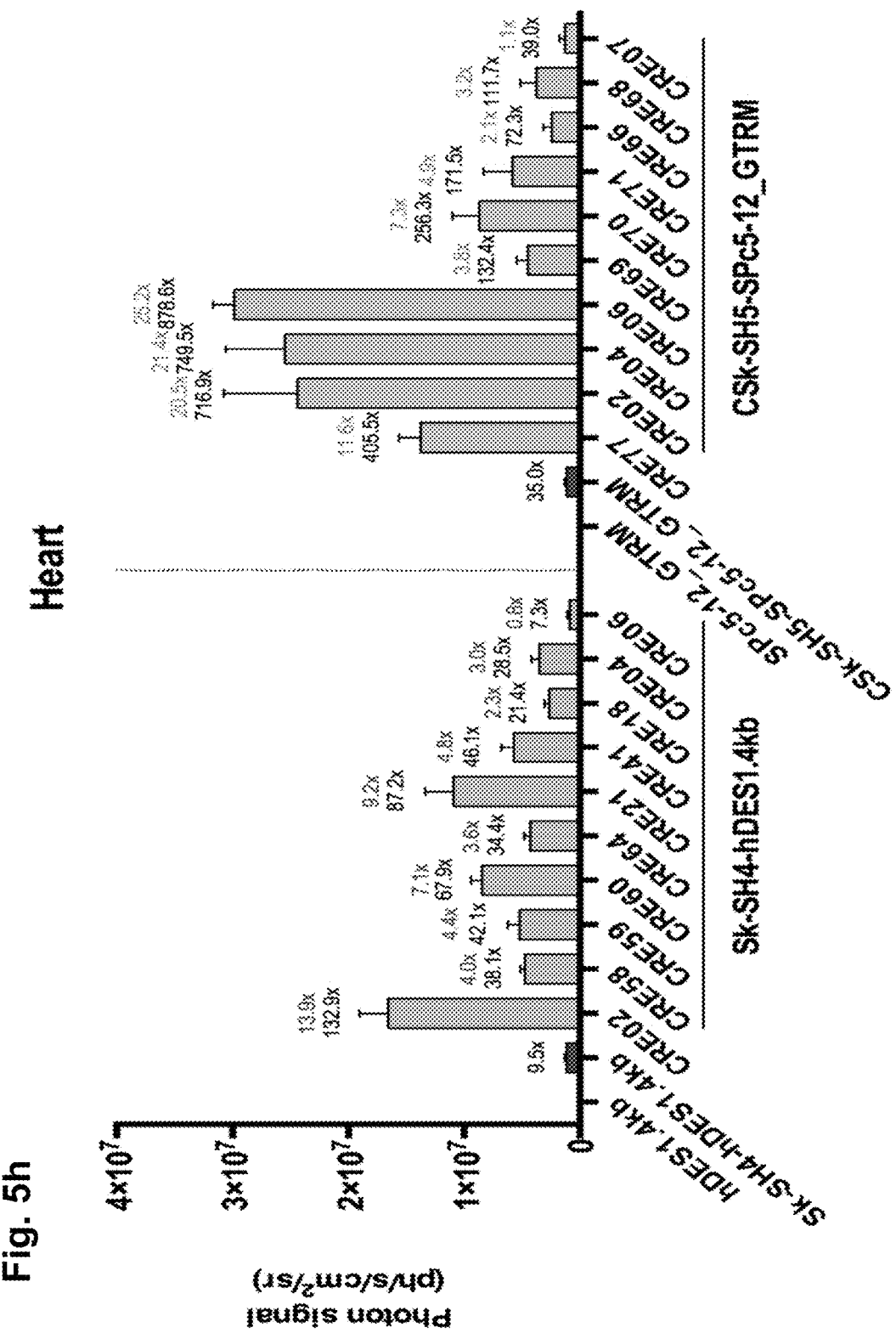
Figure 5I:
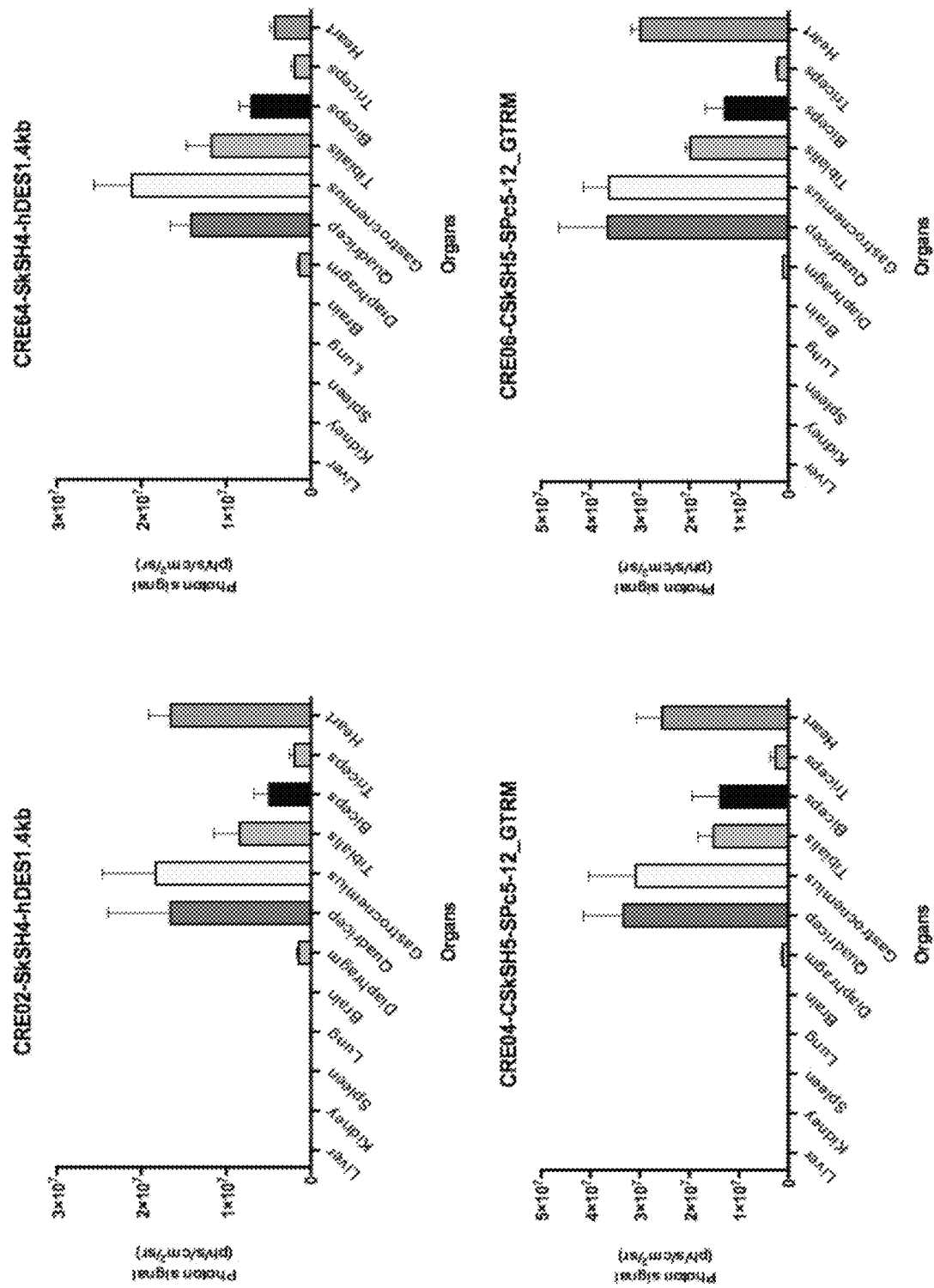

Similar comparisons are made for other muscle tissues: FIG. 5b) Expression in Quadricep FIG. 5c) Expression in Gastrocnemius FIG. 5d) Expression in Tibialis FIG. 5e) Expression in Bicep FIG. 5f) Expression in Tricep FIG. 5g), Expression in heart FIG. 5h), Specificity of Diaphragm CREs (mainly expressed in diaphragm, skeletal muscle and heart but not in other tissues. The numbers of the Diaphragm CREs correspond to the numbering of Tables 3 & 4 FIG. 5i).

Example 4: Codon-Optimisation of Therapeutic Genes GAA and MTM1

Experimental Procedures
Generation of the AAV Plasmid Constructs
The human alpha-glucosidase (hGAA) gene and the human myotubularin 1 (hMTM1) gene were codon-optimized using the Gene optimizer (GeneArt, Life technologies, Germany).

The wild-type human alpha-glucosidase (hGAA; SEQ ID NO: 93) and codon-optimized hGAA genes (hGAAco; SEQ ID NO: 94) flanked by BsiWI and XmaJI restriction sites at the 5' and 3' ends, were cloned and driven from the SPc5-12 promoter, which was operably linked to the regulatory element CSk-SH5.

On the other hand, the wild-type human myotubularin 1 (hMTM1; SEQ ID NO: 95) and codon-optimized hMTM1 (hMTMco; SEQ ID NO: 96) genes flanked by BsiWI and XmaJI restriction sites at the 5' and 3' ends were cloned and driven from the hDES1.4 kb (SEQ ID NO: 92), which was operably linked to the regulatory element Sk-SH4 (SEQ ID NO: 121).

The Sk-SH4 regulatory element (SEQ ID NO: 121) operably linked to the hDES1.4 kb promoter (SEQ ID NO: 92), or the CSk-SH5 regulatory element (SEQ ID NO: 122) operably linked to the SPc5-12 promoter (SEQ ID NO: 124), were cloned upstream of the MVM intron (SEQ ID NO: 125) in the context of a single stranded adeno-associated viral vector (AAVss) backbone. The vector also contained a 49 bp synthetic polyadenylation site (Levitt N et al, 1989) (SEQ ID NO: 127). The generated constructs were designated as pAAVss-Sk-SH4-hDES1.4 kb-MVM-hMTM1
pAAVss-Sk-SH4-hDES1.4 kb-MVM-hMTM1co
pAAVss-CSk-SH5-SPc5-12-MVM-hGAA
pAAVss-CSk-SH5-SPc5-12-MVM-hGAAco.

AAV Vector Production and Purification

AAV vector production and purification were carried out as described in Example 2.

Animal Studies

All animal procedures were approved by the institutional animal ethics committee of the Free University of Brussels (VUB) (Brussels, Belgium). All mice were housed under specific pathogen-free conditions; food and water were provided ad libitum.

The concentrated vectors ($5\times10^{11}$ vg/mouse) were injected into the tail-vein of 4 weeks old CB.17-SCID mice (Janvier, France). Four to five weeks post injection, the mice were euthanized and individual organs were analyzed to evaluate mRNA and protein expression.

hGAA(Co) and hMTM1(Co) ELISA

For all GAA and MTM1 ELISA, the protocol will follow as indicated by manufacturer's instruction. Both kits (MyBiosources) require PBS as the protein extraction cocktails. The protease inhibitor cocktail (Invitrogen, USA) is added to inhibit the protease activity and maximise the quality of the samples.

For each ELISA, 50 mg of the tissue was taken from frozen storage. Then 500 uL of cold PBS with protease inhibitor were added to the tissue and then homoginized with Matrix D (MPBio) for 3 cycles of 20 s. Afterward, the lysates were centrifuged at 13,000 rpm for 5 mins at 4 C. The supernatants were collected and processed as mentioned in each ELISA kits or stored at −20 C until analysis.

mRNA Analysis

For qRT-PCR, the 30-50 mg of the samples were removed from the frozen storage. The samples were homogenised using Matrix D (MPBio) for 2 cycles of 20 s. Then the RNA were extracted using RNA Nucleospin (Macherey-Nagel). The cDNAs were synthesised using SuperScript III cDNA synthesis kit (Invitrogen, USA) according to the manufacture's protocol. Next, the cDNA was amplified by quantitative qPCR on an ABI 7700 (Applied Biosystems, USA). The primer sequences for each gene are listed table below.

| Target | Primer | Sequence | Amplicon size (bp) | SEQ ID |
|---|---|---|---|---|
| hGAA | F | TGCCCTCGCAGTATATCACAG | 129 | 140 |
|  | R | GAGACCCGTAGAGGTTCGC |  | 141 |
| hGAAco | F | ACCCCTTCATGCCTCCTTAT | 148 | 142 |
|  | R | TCCATGTAGTCCAGGTCGTT |  | 143 |
| hMTM1 | F | GTTTGAGATCCTCACGAGATACG | 96 | 144 |
|  | R | GTCCATCCATCCACGTTAAACTT |  | 145 |

| Target | Primer | Sequence | Amplicon size (bp) | SEQ ID |
|---|---|---|---|---|
| hMTM1co | F | GGCAAGAGAAACAAGGACGA | 150 | 146 |
|  | R | GGCATCGTCGGACTCATATC |  | 147 |

Results hGAA(Co) Expression

Figure 6A:
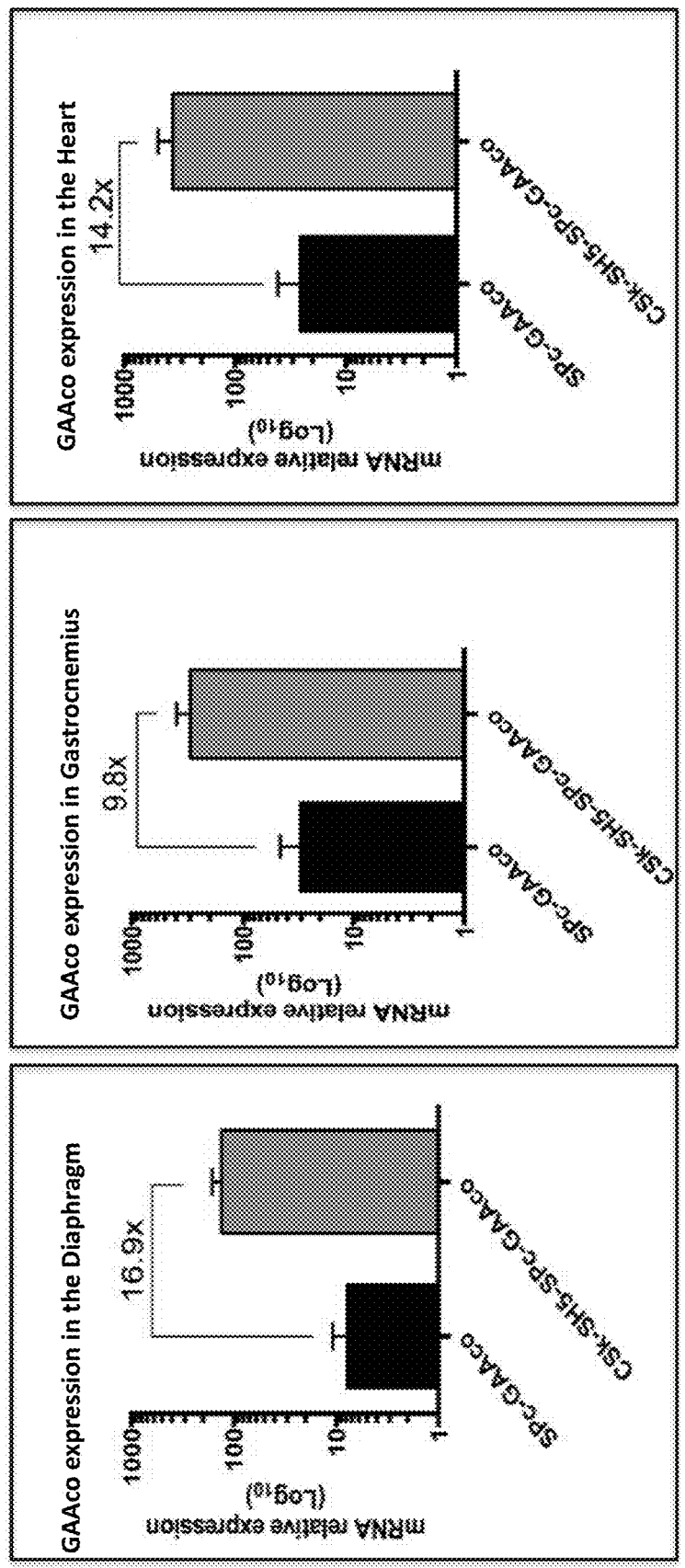
FIG. 6: a) Effect of the muscle-specific CRE (CSk-SH5-SEQ ID NO: 122) on the mRNA expression of human codon optimized GAA gene. b) The increasing of GAA protein expression. The total proteins from the mice organs were extracted according to the manufacturer's protocol. The total proteins were diluted with the samples buffer and loaded into the hGAA ELISA plate. The background was subtracted with non-injected mice. The results show that codon-optimized hGAA sequence can improve the translation efficiency resulting in 2-3 folds higher expression.
Figure 6B:
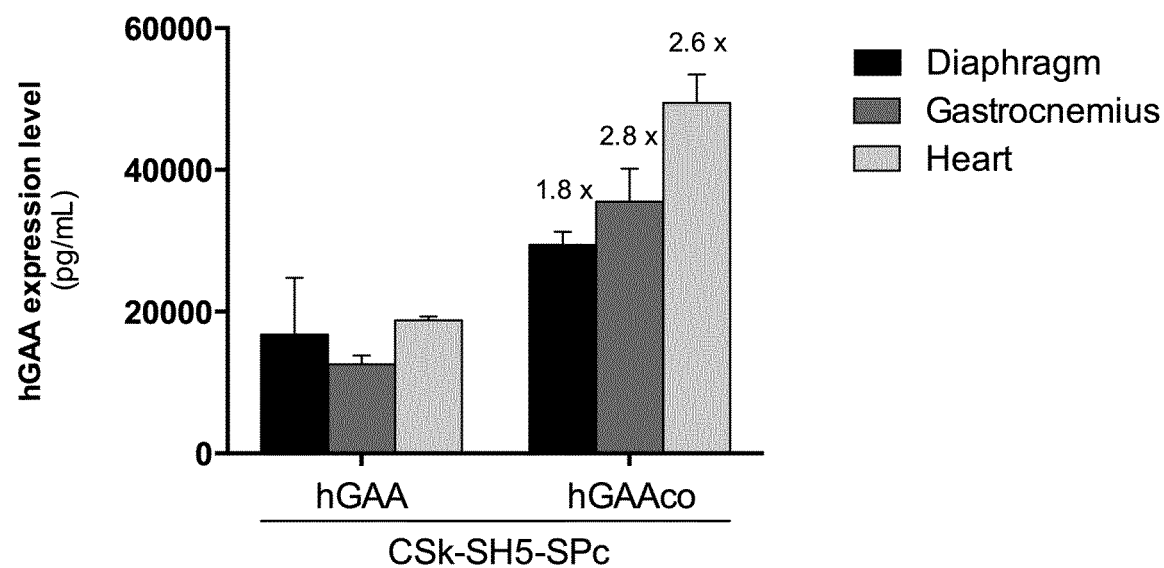

Using quantitative RT-PCR, the expression of the hGAA and hGAAco genes in diaphragm, gastrocnemius, and heart of CB.17-SCID mice injected with the SPc-hGAAco, CSk-SH5-SPc-hGAAco and CSk-SH5-SPc-hGAA constructs was assessed. The results show that CSk-SH5 can increase the hGAAco mRNA expression 16.9, 9.8, and 14.2 times respectively in diaphragm, gastrocnemius, and heart of CB.17-SCID mice (FIG. 6a) Furthermore, FIG. 6b shows that codon-optimized hGAA sequence itself improves the translation efficiency resulting in >2 folds higher hGAA protein expression in diaphragm, gastrocnemius, and heart of CB.17-SCID mice, compared to wild type hGAA.

hMTM1(Co) Expression

Figure 7A:
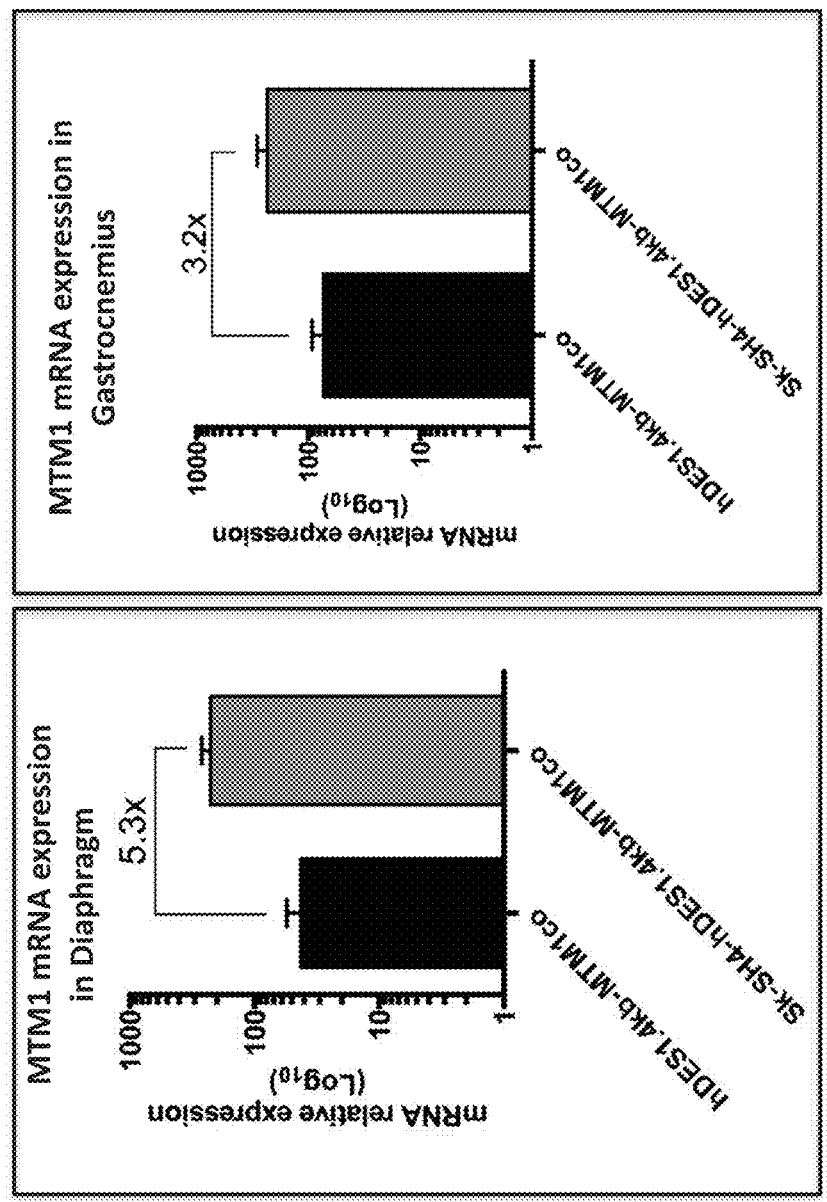
FIG. 7: a) Effect of the skeletal muscle specific CRE (Sk-SH4-SEQ ID NO: 121) on the mRNA expression of human codon optimized MTM1 gene. b) Codon optimization led to an increase of 2.2 to 3.8 folds of hMTM1 protein expression in gastrocnemius and diaphragm respectively.
Figure 7B:
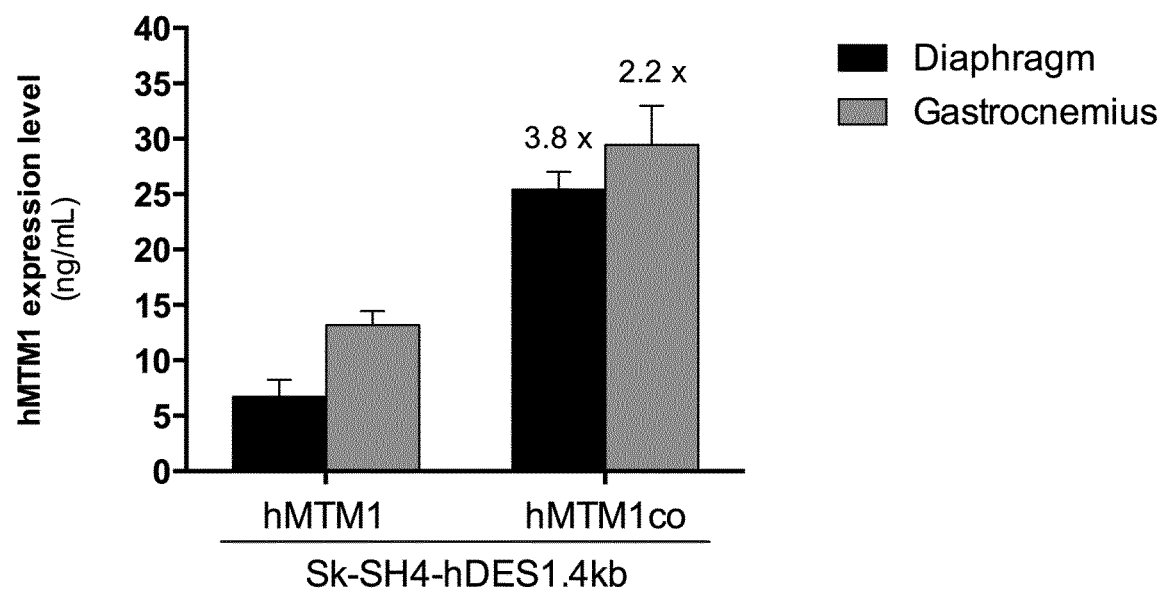

Using quantitative RT-PCR and ELISA, the expression of the hMTM1 and hMTM1co genes in diaphragm and gastrocnemius of CB.17-SCID mice injected with the hDES1.4 kb-hMTM1co, Sk-SH4-hDES1.4 kb-hMTMco and Sk-SH4-hDES1.4 kb-hMTM1 construct was assessed. The results show that Sk-SH4 can increase the hMTM1co mRNA expression 5.3 and 3.2 times respectively in diaphragm and gastrocnemius of CB.17-SCID mice (FIG. 7a). Furthermore, FIG. 7b shows that codon-optimized hMTM1 sequence alone can improve the translation efficiency resulting in 2-4 fold higher hMTM1 protein expression in diaphragm and gastrocnemius of CB.17-SCID mice, compared to wild type hMTM1.

Example 5: Prototype AAV Vectors for MTM and GSD-II for Potential Clinical Trial for MTM and GSD II Related Diseases The prototype AAV vector for MTM (FIG. 9a) was designed to maximize transcription and translation of MTM1. Transcription was enhanced by coupling the diaphragm-CRE (Dia-CRE) to the previously identified skeletal muscle CRE (Sk-SH4). These elements were cloned upstream of a 1.4 kb human desmin promoter to drive expression of a human bias codon-usage optimized human MTM1 gene (hMTMco), in combination with the minute virus of mouse (MVM) intron and a synthetic polyadenylation site (Synth poly A).

The prototype AAV vector for GSD-II (FIG. 9b) was designed to maximize transcription and translation of GAA. Transcription was enhanced by coupling the diaphragm-CRE (Dia-CRE) to the previously identified cardiac/skeletal muscle CRE (CSk-SH5). These elements were cloned upstream of a synthetic SPc5-12-GTRM promoter to drive expression of a human bias codon-usage optimized human GAA gene (hGAAco), in combination with the minute virus of mouse (MVM) intron and the human acid α-glucosidase gene (hGAAco) and a synthetic polyadenylation site (Synth poly A).

The following 10 different AAV constructs have been evaluated for expressing therapeutic genes in vivo in mouse and the best performing ones will be the subject of a pre-clinical or phase I clinical trial:

1) pAAVss-hDes1.4 kb-MVM-hMTM1-SynthpA (no diaphragm CRE, no muscle CRE Sk-SH4, only Desmin1.4 kb promoter driving the MTM1 gene expression+MTM1) (SEQ ID NO; 135)

2) pAAVss-hDes1.4 kb-MVM-hMTMco-SynthpA (no diaphragm CRE, no muscle CRE Sk-SH4, +Des1.4 kb+codon opt MTM1) (SEQ ID NO; 134)

3) pAAVss-Sk-SH4-hDes1.4 kb-MVM-hMTM1-SynthpA (no diaphragm CRE,+muscle CRE Sk-SH4+Des1.4 kb+MTM1) (SEQ ID NO; 137)

4) pAAVss-Sk-SH4-hDes1.4 kb-MVM-hMTMco-SynthpA (no diaphragm CRE,+muscle CRE Sk-SH4+Des1.4 kb+codon opt MTM1) (SEQ ID NO; 136)

5) pAAVss-CRE64-Sk-SH4-hDes1.4 kb-MVM-hMTM1co-SynthpA (contain best selected Diaphragm CRE64 combined with muscle CRE Sk-SH4) (SEQ ID NO; 131)

6) pAAVss-SPc5-12GTRM-MVM-hGAA-SynthpA (no diaphragm CRE, no muscle CRE, only SPc5-12-GTRM promoter driving the GAA gene expression)) (SEQ ID NO; 139)

7) pAAVss-SPc5-12GTRM-MVM-hGAAco-SynthpA (no diaphragm, no muscle CRE CSk-SH5,+SPc5-12-GTRM+codon opt GAA) (SEQ ID NO; 138)

8) pAAVss-CSk-SH5-SPc5-12GTRM-MVM-hGAA-SynthpA (no diaphragm CRE,+muscle CRE CSk-SH5+SPc5-12-GTRM+GAA) (SEQ ID NO; 133)

9) pAAVss-CSk-SH5-SPc-5-12GTRM-MVM-hGAAco-SynthpA ((no diaphragm CRE,+muscle CRE CSk-SH5+SPc5-12-GTRM+codon opt GAA) (SEQ ID NO; 132)

10) pAAVss-CRE04-CSk-SH5-SPc-5-12GTRM-MVM-hGAAco-SynthpA ((contain best selected Diaphragm CRE04 combined with muscle CRE CSk-SH5) (SEQ ID NO; 130)

Since Myotubular myopathy (MTM) patients do not have heart problems, it is not intended to target the heart for treating this disease. For this, the Sk-SH4 CRE with human Desmin 1,4 kb promoter cassette was used in combination with Dia-CRE64 to express the MTM1 gene or codon optimised MTM1co in diaphragm and skeletal muscle tissue.

Since Pompe patients also suffer from heart problems, it is important to also target the heart. For this the CSk-SH5 CRE in combination with Dia-CRE04 is used with the synthetic SPc5-12 promoter cassette to express the therapeutic GAA gene or codon optimised GAAco gene because this combination leads to very robust expression in diaphragm, skeletal muscles and heart tissue.

Figure 10:
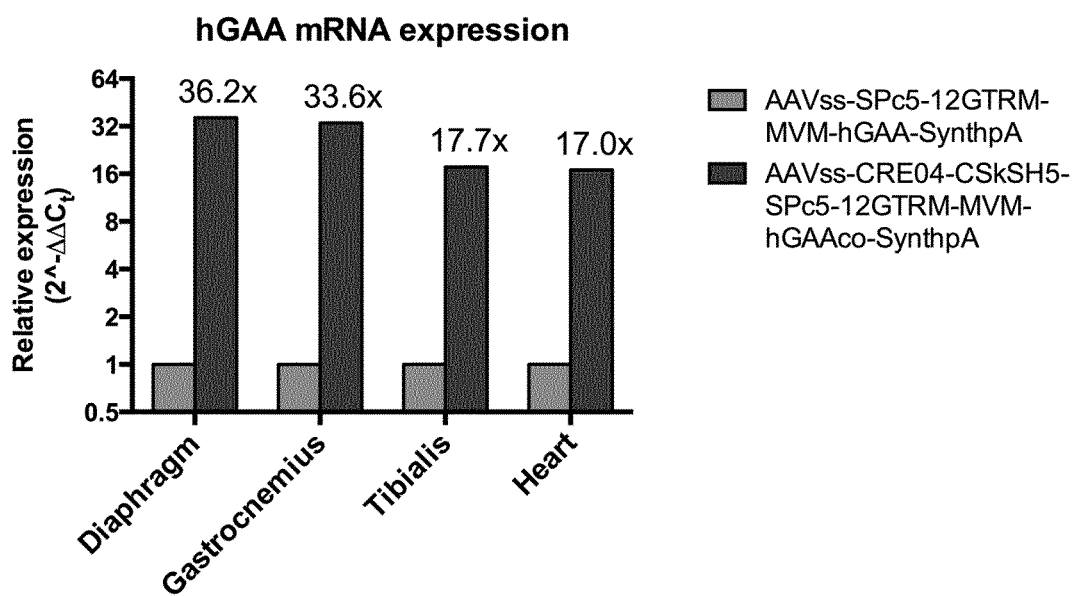
FIG. 10: Increase of GAA therapeutic gene transcription using diaphragm-specific cis-regulatory element (Dph-CRE) CRE04 (SEQ ID NO: 4) in combination with CSk-SH5 (SEQ ID NO: 122). The fold-difference indicated on the top of each bar is calculated from relative expression between Dph-CRE-containing AAV (dark gray) and its control without Dph-CRE04 and CSk-SH5 (light gray).

Example 6: In Vivo Validation of Prototype AAV Vectors pAAVss-CRE04-CSk-SH5-SPc-5-12GTRM-MVM-hGAAco-SynthpA and pAAVss-CRE64-Sk-SH4-hDes1.4 kb-MVM-hMTM1co-SynthpA AAV backbones comprising the diaphragm-specific regulatory element CRE04 (defined by SEQ ID NO:4) or CRE64 (defined by SEQ ID NO:64) combined respectively with a muscle-specific Sk-SH4 (SEQ ID NO:121) or a cardiac/muscle-specific CSk-SH5 (SEQ ID NO:122) regulatory element were injected into CB17-SCID pups at dose of $5\times10^{10}$ vg/mouse. At 8-week post-injection time point, the organs were removed for total RNA extraction using AllPrep DNA/RNA mini kit (Qaigen) according to manufacturer's instruction. The RNAs were reversed-transcribed using Superscript VI cDNA synthesis kit (ThermoFisher). Afterwards, cDNA from each organ was subjected to perform qRT-PCR using hGAA, hGAAco, hMTM1 or hMTM1co therapeutic gene-specific primers. The mGapdh gene was used as internal control to normalize resulting in relative expression ($2^{\Delta\Delta Ct}$) AAV containing a combination of diaphragm-specific CRE04 and skeletal muscle and heart specific CSk-SH5 (AAVss-CRE04-CskSH5-SPc5-12GTRM-MVM-hGAAco-SynthpA (SEQ ID NO:130)) increased the expression of hGAAco in the diaphragm, gastrocnemius, tibialis and heart at least 17-fold compared to control (FIG. 10).

Figure 11:
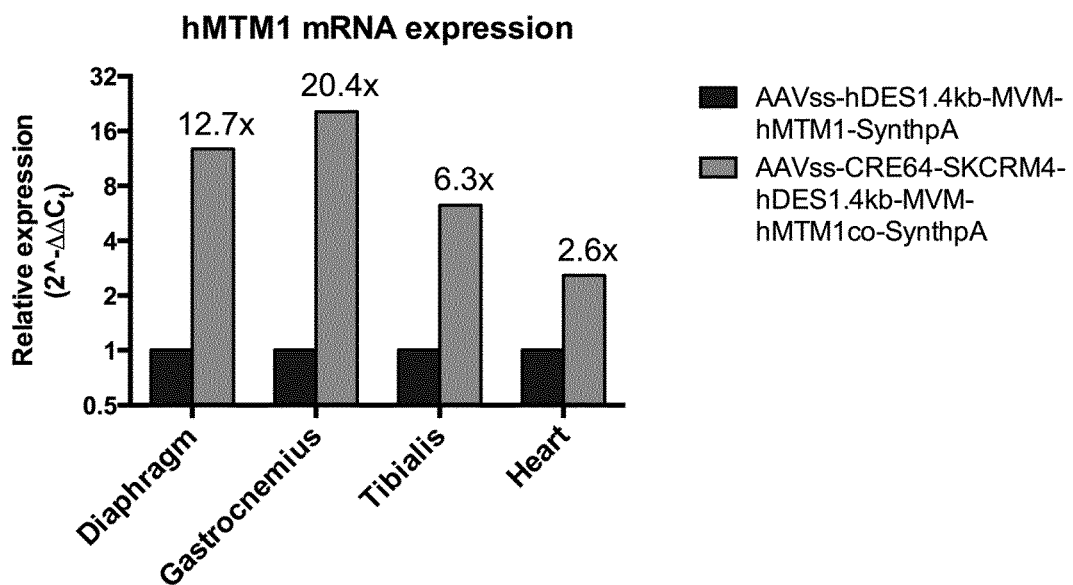
FIG. 11: Increase of MTM1 therapeutic gene transcription using diaphragm-specific cis-regulatory element (Dph-CRE) CRE64 (SEQ ID NO:64) in combination with Sk-SH4

AAV containing a combination of diaphragm-specific CRE64 and Sk-SH4 (called Sk-CRM4 in the figure—AAVss-CRE64-Sk-SH4-hDes1.4 kb-MVM-hMTMco-SynthpA (SEQ ID NO:131)) increased the expression of hMTMco in the diaphragm, gastrocnemius, tibialis and heart at least 2.6-fold compared to control (FIG. 11).

The invention claimed is:

1. A method for enhancing gene expression in diaphragm, skeletal muscle and heart tissue comprising administering to a subject in need thereof, a nucleic acid regulatory element having a maximal length of 1000 nucleotides and comprising the sequence defined by SEQ ID NO: 4, the complement of said sequence, or a sequence hybridizing under stringent conditions to said nucleic acid regulatory element.

2. A nucleic acid expression cassette comprising at least one nucleic acid regulatory element wherein the nucleic acid regulatory element has a maximal length of 1000 nucleotides and comprises the sequence defined by SEQ ID NO: 4, the complement of said sequence, or a sequence hybridizing under stringent conditions to said nucleic acid regulatory element, operably linked to a promoter other than an alpha-actin-1 (ACTA1), wherein the promoter is a diaphragm, heart, and/or skeletal muscle-specific promoter.

3. The nucleic acid expression cassette according to claim 2, wherein the nucleic acid regulatory element is operably linked to the promoter and a transgene.

4. The nucleic acid expression cassette according to claim 2, wherein the promoter is selected from the group consisting of: an SPc5-12 promoter, an MYL2 promoter, an MB promoter, a DES promoter, a TNNC1 promoter, a TCAP promoter, an MYH7 promoter, an ALDA promoter, and a TPM1 promoter.

5. The nucleic acid expression cassette according to claim 3, wherein the transgene encodes a therapeutic protein or an immunogenic protein.

6. The nucleic acid expression cassette according to claim 3, wherein the transgene encodes a secretable protein or a structural protein selected from the group consisting of acid glucosidase (GAA), myotubularin (MTM1), follistatin, dystrophin, sarcoglycan, and dysferlin.

7. The nucleic acid expression cassette according to claim 3, wherein the transgene encodes acid glucosidase (GAA) as defined by SEQ ID NO: 93 or the codon-optimised human acid glucosidase gene (hGAAco) as defined by SEQ ID NO: 94.

8. The nucleic acid expression cassette according to claim 2, further comprising a Minute Virus of Mouse (MVM) intron.

9. The nucleic acid expression cassette according to claim 2, further comprising a polyadenylation signal selected from a synthetic polyadenylation signal (SEQ ID NO: 127) or the Simian Virus 40 (SV40) polyadenylation signal.

10. A vector comprising the nucleic acid expression cassette according to claim 2.

11. The vector according to claim 10, which is a viral vector.

12. The vector according to claim 10, which is a non-viral vector selected from the group consisting of a plasmid, a minicircle, an episomal vector, and a transposon-based vector.

13. The vector according to claim 10, further comprising a heart-muscle specific CRE CSk-SH5 regulatory element as defined in SEQ ID NO: 122 before or after said nucleic acid regulatory element.

14. The vector according to claim 10, comprising a CRE-CSk-SH5 regulatory element, a nucleic acid regulatory element having a maximal length of 1000 nucleotides and comprising the sequence defined by SEQ ID NO: 4, the complement of said sequence, or a sequence hybridizing under stringent conditions to said nucleic acid regulatory element, an MVM intron, an SPc5-12 promoter, a human GAA transgene (SEQ ID NO: 93) or a codon-optimised variant thereof (SEQ ID NO: 94), and a synthetic poly A site (SEQ ID NO: 127).

15. A pharmaceutical composition comprising the vector according to claim 10 and a pharmaceutically acceptable carrier.

16. A method of treating a disease affecting the diaphragm comprising administering a therapeutically effective amount of the pharmaceutical composition according to claim 15 to a subject in need thereof, wherein the vector comprises a CRE-CSk-SH5 regulatory element (SEQ ID NO: 122), a nucleic acid regulatory element having a maximal length of 1000 nucleotides and comprising the sequence defined by SEQ ID NO: 4, the complement of said sequence, or a sequence hybridizing under stringent conditions to said nucleic acid regulatory element, an SPc5-12 promoter, and a human transgene that affects the function of the diaphragm when being defective or a codon-optimised variant thereof.

17. A method of treating Pompe disease comprising administering a therapeutically effective amount of the pharmaceutical composition according to claim 15 to a subject in need thereof, wherein the vector comprises a CRE-CSk-SH5 regulatory element (SEQ ID NO: 122), a nucleic acid regulatory element having a maximal length of 1000 nucleotides and comprising the sequence defined by SEQ ID NO: 4, the complement of said sequence, or a sequence hybridizing under stringent conditions to said nucleic acid regulatory element, an SPc5-12 promoter, and a human GAA transgene (SEQ ID NO: 93) or a codon-optimised variant thereof (SEQ ID NO: 94).

18. A method for expressing a transgene product in diaphragm, skeletal muscle, and heart cells, comprising:
    introducing the vector according to claim 10, wherein the nucleic acid regulatory element is operably linked to the promoter and a transgene, into said cells; and
    expressing the transgene product in the cells.

19. The nucleic acid expression cassette according to claim 2, wherein the nucleic acid regulatory element has a maximal length of 600 nucleotides.

20. The method according to claim 1, wherein the subject is suffering from a disease affecting the diaphragm.

21. The method according to claim 1, wherein the subject is suffering from Pompe disease.

22. The method according to claim 17, wherein the vector further comprises an MVM intron and a synthetic poly A site (SEQ ID NO: 127).

23. The method according to claim 17, wherein the vector is an adeno-associated viral (AAV) vector and further comprises an MVM intron and a synthetic poly A site (SEQ ID NO: 127).

24. The method according to claim 17, wherein the vector is defined by SEQ ID NO: 130).

* * * * *

SEQUENCE LISTING

<160> NUMBER OF SEQ ID NOS: 147

<210> SEQ ID NO 1
<211> LENGTH: 328
<212> TYPE: DNA
<213> ORGANISM: Artificial Sequence
<220> FEATURE:
<223> OTHER INFORMATION: Dph-CRE01

<400> SEQUENCE: 1

```
ggagacactc catatacggc ccggcccgcg ttacctggga ccgggccaac ccgctccttc      60
tttggtcaac gcagggacc cgggcggggg cccaggccgc gaaccggccg agggaggggg     120
ctctagtgcc caacacccaa atatggctcg agaagggcag cgacattcct gcgggtggc     180 gcggagggaa tgcccgcggg ctatataaaa cctgagcaga gggacaagcg gccaccgcag    240
cggacagcgc caagtgaagc ctcgcttccc ctccgcggcg accagggccc gagccgagag    300
tagcagttgt agctacccgc ccaggtag                                        328
```

<210> SEQ ID NO 2
<211> LENGTH: 452
<212> TYPE: DNA
<213> ORGANISM: Artificial Sequence
<220> FEATURE:
<223> OTHER INFORMATION: Dph-CRE02

<400> SEQUENCE: 2

```
gacaggtgcg gttcccggag cgcaggcgca cacatgcacc caccggcgaa cgcggtgacc      60
ctcgccccac cccatcccct ccggcgggca actgggtcgg gtcaggaggg gcaaacccgc     120
tagggagaca ctccatatac ggcccggccc gcgttacctg gaccgggcc aacccgctcc      180
ttctttggtc aacgcagggg acccgggcgg gggcccaggc cgcgaaccgg ccgagggagg     240
gggctctagt gcccaacacc caaatatggc tcgagaaggg cagcgacatt cctgcgggt      300
ggcgcggagg gaatgcccgc gggctatata aacctgagc agagggacaa gcggccaccg     360
cagcggacag cgccaagtga agcctcgctt ccctccgcg gcgaccaggg cccgagccga     420
gagtagcagt tgtagctacc cgcccaggta gg                                  452
```

<210> SEQ ID NO 3
<211> LENGTH: 239
<212> TYPE: DNA
<213> ORGANISM: Artificial Sequence
<220> FEATURE:
<223> OTHER INFORMATION: Dph-CRE03

<400> SEQUENCE: 3

```
agagagaggg acaggcacca actgggtaac ctctgctgac ccccactcta ctttaccata     60
agtagctcca aatccttcta gaaaatctga aaggcatagc cccatatatc agtgatataa    120
atagaacctg cagcaggctc tggtaaatga tgactacaag gtggactggg aggcagcccg    180
gccttggcag gcatcatcct ctaaatataa agatgagttt gttcagcctt tgcagaagg     239
```

<210> SEQ ID NO 4
<211> LENGTH: 509
<212> TYPE: DNA
<213> ORGANISM: Artificial Sequence
<220> FEATURE:
<223> OTHER INFORMATION: Dph-CRE04

<400> SEQUENCE: 4

```
ccttttagag aatccacacc tgtcccagtt gctgggttcc actaccaaaa gtgaattgca     60
actattttag gagcacttaa gcacatccga aaaatgagtg attctgttct ggcccacacc    120
acatcactga tgtaccccct taaagcatgt ccctgagttc atcacagaag actgctcctc    180
ctgtgccctc acaaggtta gaactgtcct tgtcttaggg aaaaaggaga gagagagaga    240
gagagagaga gagagagaga gagagagaga gagagaggga caggcaccaa ctgggtaacc    300
tctgctgacc cccactctac tttaccataa gtagctccaa atccttctag aaaatctgaa    360
aggcatagcc ccatatatca gtgatataaa tagaacctgc agcaggctct ggtaaatgat    420
gactacaagg tggactggga ggcagcccgg ccttggcagg catcatcctc taaatataaa    480
gatgagtttg ttcagccttt gcagaagga                                      509
```

<210> SEQ ID NO 5
<211> LENGTH: 169
<212> TYPE: DNA
<213> ORGANISM: Artificial Sequence
<220> FEATURE:
<223> OTHER INFORMATION: Dph-CRE05

<400> SEQUENCE: 5

```
cctttagag aatccacacc tgtcccagtt gctgggttcc actaccaaaa gtgaattgca    60
actattttag gagcacttaa gcacatccga aaaatgagtg attctgttct ggcccacacc   120
acatcactga tgtacccccct taaagcatgt ccctgagttc atcacagaa             169
```

<210> SEQ ID NO 6
<211> LENGTH: 400
<212> TYPE: DNA
<213> ORGANISM: Artificial Sequence
<220> FEATURE:
<223> OTHER INFORMATION: Dph-CRE06

<400> SEQUENCE: 6

```
gggccagggg acgtggcttt ctacgtgctt gggacgttcc cagccaccgt cccatgttcc    60
cggcggggg ccagctgtcc ccaccgccag cccaactcag cacttggtca gggtatcagc   120
ttggtggggg ggcgtgagcc cagccctgg ggcggctcag cccatacaag gccatggggc   180
tgggcgcaaa gcatgcctgg gttcagggtg gtatggtgc gggagcaggg aggtgagagg   240
ctcagctgcc ctccagaact cctccctggg acaaccccct cccagccaat agcacagcct   300
aggtccccct atataaggcc acggctgctg gccttcctt tgggtcagtg tcacctccag    360
gatacagaca gccccccttc agcccagccc agccaggtac                        400
```

<210> SEQ ID NO 7
<211> LENGTH: 255
<212> TYPE: DNA
<213> ORGANISM: Artificial Sequence
<220> FEATURE:
<223> OTHER INFORMATION: Dph-CRE07

<400> SEQUENCE: 7

```
cccagccccc ttccccggga ggtgggagcg gccacccagg gccccgtggc tgcccttgta    60
aggaggcgag gccgaggac acccgagacg cccggttata attaaccagg acacgtggcg   120
aaccccctc caacacctgc ccccgaaccc cccataccc agcgcctcgg gtctcggcct    180
ttgcggcaga ggagacagca aagcgccctc taaaaataac tcctttcccg gcgaccgaga   240
ccctccctgt ccccc                                                   255
```

<210> SEQ ID NO 8
<211> LENGTH: 354
<212> TYPE: DNA
<213> ORGANISM: Artificial Sequence
<220> FEATURE:
<223> OTHER INFORMATION: Dph-CRE08

<400> SEQUENCE: 8

```
ctcctgggct cgagcaattc tcctgccttg acctcccaaa gtgctgggat tacaggcatg    60
agccactaca ccctgcccta gtgtgcttta tatcaaaggg gaaaccattt ggggcttcca   120
aacaggaaat gaacagtcgt accttttgtc ctcactaaca ttcagattgc aggaatgccg   180
tgtcccatag ggaaagagaa attcctgagg caagtgtcat atctgaactt gagatagtca   240
ccttccaggc agaaagctac acccgcctct tttcccagcc tctggcatca gctgccggcg   300
gtgtgggtaa gggatgcaaa gaactcaaaa catgtagcca ggattcccca tttg         354
```

<210> SEQ ID NO 9
<211> LENGTH: 297
<212> TYPE: DNA

<213> ORGANISM: Artificial Sequence
<220> FEATURE:
<223> OTHER INFORMATION: Dph-CRE09

<400> SEQUENCE: 9

| | | | | | |
|---|---|---|---|---|---|
| tgacaagcac | aagtgtcccc | ggcccaagca | ccgcagagag | cgcgcagcat | ctctcccgt | 60 |
| gaccatgacc | cagctactgc | ctctttaacc | ttgaatgcct | ttttgggggc | tcacgtgtca | 120 |
| cccagtggcg | agtgagccac | ccttacttca | gaagaacggc | atggggtggg | ggggccttag | 180 |
| gtggtgcccg | cctcacctat | gactgccaaa | agcggtcatg | gggttatttt | taaacatggg | 240 |
| gaggaagtat | ttattgttcc | tgggctgcag | agagctgggc | ggagtgtgga | attcttc | 297 |

<210> SEQ ID NO 10
<211> LENGTH: 608
<212> TYPE: DNA
<213> ORGANISM: Artificial Sequence
<220> FEATURE:
<223> OTHER INFORMATION: Dph-CRE10

<400> SEQUENCE: 10

| | | | | | |
|---|---|---|---|---|---|
| actcagggta | aactgaggca | ctcaaactgc | cgaggagctc | cgcctcccga | gagacattta | 60 |
| atccgggggg | atttgcagga | aacttctaaa | ttaaggtag | cggctgctgc | agctgagggg | 120 |
| gggcacgccg | gtccctgcgc | ccgggcagct | gccgtgagct | cacgccccga | aatagcccca | 180 |
| ggggccccag | ccgcagctgc | cactgggtcc | ggctgtcact | cagaggaagc | acggagcccc | 240 |
| cagcccaagg | gtcccctccc | cttcgcatcg | ccggggtttt | tccagccgac | cgtcggccac | 300 |
| ttttcctcc | gacggctggc | agggaagagg | gggatggggg | cgggacccca | agggaggcgg | 360 |
| tccccagtgg | gtgggcgaag | ggggcggccg | cacccccgg | ccgggccgtg | cttctgcccc | 420 |
| tacaaggttt | gggccgaggt | gggggagggt | cctggttgcc | ggccccgccc | ggtccctccc | 480 |
| cgccttttag | gcgcccgcgt | ggccgggacg | tcccagtccc | gctccgtcct | cctcgcctgc | 540 |
| caccggtgca | cccagtccgc | tcacccagcc | cagtccgtcc | ggtcctcacc | gcctgccggc | 600 |
| cggcccac | | | | | | 608 |

<210> SEQ ID NO 11
<211> LENGTH: 308
<212> TYPE: DNA
<213> ORGANISM: Artificial Sequence
<220> FEATURE:
<223> OTHER INFORMATION: Dph-CRE11

<400> SEQUENCE: 11

| | | | | | |
|---|---|---|---|---|---|
| ttttcctcc | gacggctggc | agggaagagg | gggatggggg | cgggacccca | agggaggcgg | 60 |
| tccccagtgg | gtgggcgaag | ggggcggccg | cacccccgg | ccgggccgtg | cttctgcccc | 120 |
| tacaaggttt | gggccgaggt | gggggagggt | cctggttgcc | ggccccgccc | ggtccctccc | 180 |
| cgccttttag | gcgcccgcgt | ggccgggacg | tcccagtccc | gctccgtcct | cctcgcctgc | 240 |
| caccggtgca | cccagtccgc | tcacccagcc | cagtccgtcc | ggtcctcacc | gcctgccggc | 300 |
| cggcccac | | | | | | 308 |

<210> SEQ ID NO 12
<211> LENGTH: 263
<212> TYPE: DNA
<213> ORGANISM: Artificial Sequence
<220> FEATURE:
<223> OTHER INFORMATION: Dph-CRE12

<400> SEQUENCE: 12

```
gactcagggt aaactgaggc actcaaactg ccgaggagct ccgcctcccg agagacattt    60
aatccggggg gatttgcagg aaacttctaa attaagggta gcggctgctg cagctgaggg   120
ggggcacgcc ggtccctgcg cccgggcagc tgccgtgagc tcacgccccg aaatagcccc   180
aggggcccca gccgcagctg ccactgggtc cggctgtcac tcagaggaag cacggagccc   240
ccagcccaag ggtcccctcc cct                                            263

<210> SEQ ID NO 13
<211> LENGTH: 324
<212> TYPE: DNA
<213> ORGANISM: Artificial Sequence
<220> FEATURE:
<223> OTHER INFORMATION: Dph-CRE13

<400> SEQUENCE: 13
ctcagggaat gagctggata caactaaaaa tcagcacatt tttgtttggt taaaacattc    60
tttgtggtca atttctttct aacagatcga gttctctaag gaacagcagg atggtaagtt   120
taaaagctat ggttcttaaa tgtgcacact cataaagatg gcatgtgtga aaaccaactc   180
ccttgggatg agtttagctc ttcctaatta tccccactgg tgttgccatt ctgaatataa   240
attgctctcg atcactctaa atataaatta gctcaatctg aaaccccttgc tgatactcag   300 taatcaaagg tttaacaaac aaaa                                           324

<210> SEQ ID NO 14
<211> LENGTH: 326
<212> TYPE: DNA
<213> ORGANISM: Artificial Sequence
<220> FEATURE:
<223> OTHER INFORMATION: Dph-CRE14

<400> SEQUENCE: 14
catttagtta aatcattaag atgcagaaag atattcccta attatctttt gcaatagctt    60
tttatgttcc tagattcaaa agtatcctaa ggcaaccttc taatgccaag acacctacat   120
agcttcctaa aaatctcaga gcaaccagca ctcattcttc tgtcaatgca tttgaaagag   180
tactagtttt ttttctttct ttctcttctt cgccactgca gtccttcagt gctgaccaga   240
ttgctggtaa gtgaattgag tttgtctgct acagatgtag gcacagcact gcctagtttc   300
tgcaatatta cttatcttca aggcat                                         326

<210> SEQ ID NO 15
<211> LENGTH: 596
<212> TYPE: DNA
<213> ORGANISM: Artificial Sequence
<220> FEATURE:
<223> OTHER INFORMATION: Dph-CRE15

<400> SEQUENCE: 15
tttgtttgtt aaacctttga ttactgagta tcagcaaggg tttcagattg agctaattta    60
tatttagagt gatcgagagc aatttatatt cagaatggca acaccagtgg ggataattag   120
gaagagctaa actcatccca agggagttgg ttttcacaca tgccatcttt atgagtgtgc   180
acatttaaga accatagctt ttaaacttac catcctgctg ttccttagag aactcgatct   240
gttagaaaga aattgaccac aaagaatgtt ttaaccaaac aaaaatgtgc tgattttag    300 ttgtatccag ctcattccct gagtaatctt caaagtaagc tccaaaagtc agcctacttt   360
tcagagttca ggcgtagctt ggacactaac aggttaagcc atagtgtaac atgccttgaa   420
```

```
gataagtaat attgcagaaa ctaggcagtg ctgtgcctac atctgtagca gacaaactca      480
attcacttac cagcaatctg gtcagcactg aaggactgca gtggcgaaga agagaaagaa      540
agaaaaaaaa ctagtactct ttcaaatgca ttgacagaag aatgagtgct ggttgc          596
```

<210> SEQ ID NO 16
<211> LENGTH: 290
<212> TYPE: DNA
<213> ORGANISM: Artificial Sequence
<220> FEATURE:
<223> OTHER INFORMATION: Dph-CRE16

<400> SEQUENCE: 16

```
agaccataaa agtaccggca ggcttccatc tcactatggc tgtctactcc aaggttctgg       60
tcatctaaaa atagctctca gggtacagat ccatctttcc ctttgcccta agaaagctaa      120
agaactctcc aagggtgtg gcaacttatc tctgaaacct gatgctagct gtgaggtcaa       180
agcttgccca gaaataaaag gaagcctcag ccagggatga ccccactcag ggaccggagc      240
agccctcaac tcactcttca gcttccctgc tgtgttgcag cccagccgct                 290
```

<210> SEQ ID NO 17
<211> LENGTH: 632
<212> TYPE: DNA
<213> ORGANISM: Artificial Sequence
<220> FEATURE:
<223> OTHER INFORMATION: Dph-CRE17

<400> SEQUENCE: 17

```
gtgctcccta aagggaagc cactttaaga catgatgggc tttccttata cgtctgcttt        60 tttatttta accaccacca cctctttgct gaccaacatt tccttgcaaa ttatggcaag       120
gggggaggag catgagcaaa ggagctgtgt gaaagttggt gatactccct gccaaaattc      180
caagttgaaa tggaatcctt cagtaaagtc tcttaggcaa ggtgggaaaa aaagatttac      240
aacttcagca gaactgtaat tctaccaaga aaaagtacag tcaatctacc tcactgtcac      300
caaaggatct gaagctggct ttgtcatata tctttctcct ttatatatgg aggtgggggg      360
gggagaaaaa aaggaaagag agttaaaaaa aattgatgaa gccctgaccc tttagattcc      420
atttatagtc tgagccggaa tgccatcccc cttgactaga gaactgtcca atccagccgc      480
atgtgtcaag attctattag gcactaagtg aaatatatat gcatgccctt atgccgttta      540
acactctggg tccatcttca agacactggg ctgtggatca acccaaccac cactcctctt      600
ccaagaatca ttttgacagg ttcttttgga gg                                    632
```

<210> SEQ ID NO 18
<211> LENGTH: 297
<212> TYPE: DNA
<213> ORGANISM: Artificial Sequence
<220> FEATURE:
<223> OTHER INFORMATION: Dph-CRE18

<400> SEQUENCE: 18

```
cctttgactt ttcttgaaag gggagggctg ggatattcca gagattgatc cttaaggctt       60
gctgactgcc tactcacttc tggaaacttc cagcagtgtc attcatagac ctgtgaagag      120
ctcttagctt gtttccttca cacagtgggg actctgaggg gtcagagtga gtcacccagc      180
aggccagtgg caggggtgag ccagaagcct ggccaaaccc tcctatcatc atggagagaa      240
gaaagcctcc tccagaagac gggaggccgg cagggcgtgg ggcctgctca gatgcag        297
```

<210> SEQ ID NO 19
<211> LENGTH: 309
<212> TYPE: DNA
<213> ORGANISM: Artificial Sequence
<220> FEATURE:
<223> OTHER INFORMATION: Dph-CRE19

<400> SEQUENCE: 19

```
ggaacagggc aggccttcct cacaagaatc taggacgtca aggcctgcca cctgcttgga    60
ggcttaaatt tctctgcaag ggcccttggc taaattaggt aatgggttca gactgtggga   120
ggggtgggac tcgctgaccc caggatctga ttgggcaggg tctccagtgc tggggagcag   180
ggaggtggga gggagggtg  ccctacaaa  tcccgggggc tagagcaggc caggtcatct   240
ttgggtggtg gagtgcaaag gaggcgacct gcaacagagg agtcccggtc accagcaacc   300
atggtaagg                                                          309
```

<210> SEQ ID NO 20
<211> LENGTH: 267
<212> TYPE: DNA
<213> ORGANISM: Artificial Sequence
<220> FEATURE:
<223> OTHER INFORMATION: Dph-CRE20

<400> SEQUENCE: 20

```
aattgtgaca tttaagcagt gactttgcaa aattggacgt gtcagtagga aaaagtactc    60
ttcccacctt aaagattgac aggaacatga gatggctgaa gctgttctga gcttttttct   120
ggcaagagta cataggacaa gaaatactct ggagagctca acattgaatc acatcatatc   180
atagtgcatg actagttgcc ttaatcttgc agttggactc actcaggaga aattgttggc   240
agagggatta agtagcctga caaaatt                                      267
```

<210> SEQ ID NO 21
<211> LENGTH: 493
<212> TYPE: DNA
<213> ORGANISM: Artificial Sequence
<220> FEATURE:
<223> OTHER INFORMATION: Dph-CRE21

<400> SEQUENCE: 21

```
cttttctttt ctaattaggt cagttacttc atgtctgttt ttcttttttg acatggtttc    60
ttctggcttt ggcaccacat attttcccca tatgtcattg cctctggagc ttcatgttgc   120
aatagttttt caaggggaac ggagagcaca ttgctaaggg tgggggatgg cttttgcctc   180
ttttgcctgc cctttgcttc agtgagtgtt cgtatttctg ttgggcctag ttctgtttgg   240
ttttgtagtc ttcagagtca gttatgtttg gactgaaaga tacttaagta aaaataatgg   300
caagtcagag atatgtctgg caaaggtgca gcacatttgt taaggttact ggtttatttta  360
tctcccttgt ctctatggtg actaaatctg ggtctgggat ttaatggact agttttgac   420
ctcttgtaac atctccctaac ttttcccagc ctctgattta gaaagaattc attttcactt   480
gaggagagaa act                                                     493
```

<210> SEQ ID NO 22
<211> LENGTH: 197
<212> TYPE: DNA
<213> ORGANISM: Artificial Sequence
<220> FEATURE:
<223> OTHER INFORMATION: Dph-CRE22

<400> SEQUENCE: 22

| tcatttgttt tgattacccg ggtgattgcc aaatgttaat ttaaaactga ataggccat | 60 |
| gagctcactc ccctaacaat gctgagtgtt tgagctaata cggcttgata atgagggagc | 120 |
| cagatccact gccagtgctc atgttatatg ataaacagac atttggagaa gtatgcagaa | 180 |
| catcttggca gttttcc | 197 |

<210> SEQ ID NO 23
<211> LENGTH: 637
<212> TYPE: DNA
<213> ORGANISM: Artificial Sequence
<220> FEATURE:
<223> OTHER INFORMATION: Dph-CRE23

<400> SEQUENCE: 23

| aaaaattggc tttaaggtca tgagcctcct tacagcagtc cctctcacct tcagctgtat | 60 |
| tccctatttc agatatactt gtttctctgc tgtaagtaca cttttctttt ctaattaggt | 120 |
| cagttacttc atgtctgttt ttcttttttg acatggtttc ttctggcttt ggcaccacat | 180 |
| attttcccca tatgtcattg cctctggagc ttcatgttgc aatagttttt caagggggaac | 240 |
| ggagagcaca ttgctaaggg tgggggatgg cttttgcctc ttttgcctgc cctttgcttc | 300 |
| agtgagtgtt cgtatttctg ttgggcctag ttctgtttgg ttttgtagtc ttcagagtca | 360 |
| gttatgtttg gactgaaaga tacttaagta aaaataatgg caagtcagag atatgtctgg | 420 |
| caaaggtgca gcacatttgt taaggttact ggtttattta tctcccttgt ctctatggtg | 480 |
| actaaatctg ggtctgggat ttaatggact tagttttgac ctcttgtaac atctcctaac | 540 |
| ttttcccagc ctctgattta gaaagaattc attttcactt gaggagagaa actgtctcac | 600 |
| ttagaaaagg ggtcctaact ggactctcga aaagtgg | 637 |

<210> SEQ ID NO 24
<211> LENGTH: 561
<212> TYPE: DNA
<213> ORGANISM: Artificial Sequence
<220> FEATURE:
<223> OTHER INFORMATION: Dph-CRE24

<400> SEQUENCE: 24

| gtctgcatcc taatcctgct gttgattgga gataacttca gcggtcacag ggcacctcgt | 60 |
| ctccatggca acccctctaa atattcctct agtgacttgt gctctacatt ctggctggat | 120 |
| cagagccctc ctgtggcaaa atattctaaa gatgttaaaa gagagagaga gaaaaaaaaa | 180 |
| ggctcaacta ataaatctat tctaaacgac tgagtcattt gttttgatta cccgggtgat | 240 |
| tgccaaatgt taatttaaaa ctgaaatagg ccatgagctc actcccctaa caatgctgag | 300 |
| tgtttgagct aatacggctt gataatgagg gagccagatc cactgccagt gctcatgtta | 360 |
| tatgataaac agacatttgg agaagtatgc agaacatctt ggcagttttc ctttaactct | 420 |
| aagggttgta aatacaaagt agaatgtgtt accatgagcc atttcatagg aagttgactt | 480 |
| tattttttta gaattcagaa ctttgcttct aaaaaggtaa ctttgcctct tgattctcat | 540 |
| tttttttccct aacttaggca c | 561 |

<210> SEQ ID NO 25
<211> LENGTH: 511
<212> TYPE: DNA
<213> ORGANISM: Artificial Sequence
<220> FEATURE:
<223> OTHER INFORMATION: Dph-CRE25

<400> SEQUENCE: 25

```
aaagacaggg aggtgcaatc taagttagga aattggtgac aaatagtcat agaacatggg    60
tcacctggct tcaattagtt atgtgacctt taagaaaaca agtgcccgtt tcagaaaaga   120
ctgacctttg aggctagaga catcaagcta ctcctctact tttaggaaaa acaatgaca    180 gggttaattt aaaactctga tgcagacaga gttgaaaaat ccatgacaga tttatataac   240
gaacgtggat ggtgttttgt tttcccagaa tgcagtttta aggtcagacc tatgactcag   300
agctgtgcac ttccctggtg gtatgcatca gtgacatgtt gccagtctaa tcgtccagaa   360
gggcttgtgc ccagctcggc ttgctccatt ataatcccca gctgagaagc cacctttcat   420
tttttttaaa tagataagga agacagcatg aacatttgaa actcaaatac tatatgtagt   480
ttataacttt tcagcctgaa gacttgatgc a                                  511

<210> SEQ ID NO 26
<211> LENGTH: 399
<212> TYPE: DNA
<213> ORGANISM: Artificial Sequence
<220> FEATURE:
<223> OTHER INFORMATION: Dph-CRE26

<400> SEQUENCE: 26
aatgcagcat accagtgaag ttgctaatta cattgaatca ttctgtacac gttctatttt    60
gaagggaaaa aacactttct gattttgta tgaaattgta tgaaagacta cttttcagcc   120
gtgactcatg agctccgtct cattgcagct acttaggtat ttattcccaa atgtctgacg   180
acacctccag gtgcattagc atgtctatta cacaagtgtc ctattcattg gctaaggctt   240
tgctccatct gttgaatgtt ctgaggaaag cattataccc tttctttaga agccagtgtt   300
tatatgtgga gtcactaatg tactggtagg ttggatttag tgaagaacag atctgaaata   360
acctgatttt tttccatttg ggttgttgtt cattgttta                          399

<210> SEQ ID NO 27
<211> LENGTH: 360
<212> TYPE: DNA
<213> ORGANISM: Artificial Sequence
<220> FEATURE:
<223> OTHER INFORMATION: Dph-CRE27

<400> SEQUENCE: 27
cccaaccttt gaatgtatat gggggagaaa ataacagaca aggttggagg cgaagataag    60
gggggatggg gtggtgcttc tccgcaaaca tccaaccctt ctgtaaagat tcctccagac   120
tggggaagaa ggcttgggtg tcggtccctt taagaaggaa gggaagggt taaagccact   180 gcggggccat ttcccttccc ggccccgaga gggcgcagga gctctcaggg gcttaaagga   240
ccgggcctgg gggcgggtta tggggcggga gggagggaag ggtggtcttg gaggttgggg   300
cccgaggata tcgggggtcc ccccgggccc ccgacatcgg tctcggaag cgaagcagcc   360

<210> SEQ ID NO 28
<211> LENGTH: 471
<212> TYPE: DNA
<213> ORGANISM: Artificial Sequence
<220> FEATURE:
<223> OTHER INFORMATION: Dph-CRE28

<400> SEQUENCE: 28
ctcaccttcc tcctcctcct ccgcagcctc ctctggagat gggggcacag aagagaaggc    60
gttaggagct gggggaggga tgggggcggt ggccagagac cagggttcca gtctctgctg   120
```

```
gacggggtc cctctggcct cggctgcgat gggcacgttc ccctggcgg tgcagggatg    180 gcgcgaggag acgctccaga cccggagagg cgggcgagg gcccgagggc tgagccgccc    240
cttccccgcc aaagtgccac actcctcgcc tcccctccca agagctcctg ggcgtgtccc    300
catcccatag ggccggccca ctccctactc accttccggc tgctccctgc ggacgggtgt    360
ggggagagag gagggagggg agagttagac ctggggtggg agagcctctc caccactgca    420
cgccccaacc cctcccagtg cagcactcac tcctcatatt cctgctcctc g             471
```

<210> SEQ ID NO 29
<211> LENGTH: 393
<212> TYPE: DNA
<213> ORGANISM: Artificial Sequence
<220> FEATURE:
<223> OTHER INFORMATION: Dph-CRE29

<400> SEQUENCE: 29

```
ggccgcctgg gaagaccggg gaggtgggg ccagagagtc gggaccacat gggatggggc    60
gggctagagc cagccctgta gggacagagt gggcaatggt gtctgggggc tggtgagcat   120
ggagggagga ccccaacac ctcagagacc tgtgctgcag ggccttccct gcatgagcag   180 caggggggcag cagatgcctt cggaagccgc tggggccttt agggctcag tcctggccgg   240 atgccctcc cagtccccac acatctgggc tgccttagcg gctggggcct ccacgctgct   300
gtctcctctg atcctcccca cggggctgcg aagccggcag ggctggggcc aagagccccc   360
actccgagag ggtgccaagt cacggtccag ggg                                393
```

<210> SEQ ID NO 30
<211> LENGTH: 331
<212> TYPE: DNA
<213> ORGANISM: Artificial Sequence
<220> FEATURE:
<223> OTHER INFORMATION: Dph-CRE30

<400> SEQUENCE: 30

```
ctgtcctcag gctccttacg agaacgacag aggcatctcc agcgcgtcac cgagccctaa    60
atagagtagc ccagccacgg cacccccac caagacttct tggactgggc ggcagcacgc   120
ggccaggcca ggcggccgga caggtgggga ggtctctgtg gctctccacg ccccattgg    180 tctgaggagg actctatgcc cttttctgagc aggggcccag cctgggggag gccattata    240 cccctccccc tgggcccacc agcccaactc gccgctgccg gcctgacctc gctcccagcc   300
ctgctgccca gattctaggt gaggcccagc c                                   331
```

<210> SEQ ID NO 31
<211> LENGTH: 306
<212> TYPE: DNA
<213> ORGANISM: Artificial Sequence
<220> FEATURE:
<223> OTHER INFORMATION: Dph-CRE31

<400> SEQUENCE: 31

```
gctcccccaa ctcagcatag gtcataggtc acagcctcaa ggccctaagg cccagagaag    60
atggcctggc cctccccgct ggcaaaagtg ccccacccac ccaccaagac gctgctgaaa   120
gagaggaagt ggctgcccca agccttctgg ggcaggggaa gtgtggctgt ggcctggtca   180
caggggaatc acttcttctt tctgattcct gcacttcccg ccccccacctc accggccgac   240 ctgccccaa ctggccctcc tctccccag cctctggcct cccagcacca tgtgccacct     300
ggcaaa                                                               306
```

<210> SEQ ID NO 32
<211> LENGTH: 268
<212> TYPE: DNA
<213> ORGANISM: Artificial Sequence
<220> FEATURE:
<223> OTHER INFORMATION: Dph-CRE32

<400> SEQUENCE: 32

| | | | | | |
|---|---|---|---|---|---|
| aactctggca | cattccagcc | cctctttggg | agaaagaaca | tctcttcttg | cccaggccct | 60 |
| agtgagacat | gcatcgcaag | acatgctccc | cccttcctcc | ccgctgggct | ccagctgctg | 120 |
| ccagccctcc | aagaaaggag | aggccctgag | ttgggctatt | ttggtatctg | ggtgggcac | 180 |
| ccgcagggct | aaggttacct | tggtatgtta | agggctccct | ggggcaggac | tatataaccc | 240 |
| cagagggact | gccccatgct | gactcctt | | | | 268 |

<210> SEQ ID NO 33
<211> LENGTH: 214
<212> TYPE: DNA
<213> ORGANISM: Artificial Sequence
<220> FEATURE:
<223> OTHER INFORMATION: Dph-CRE33

<400> SEQUENCE: 33

| | | | | | |
|---|---|---|---|---|---|
| tacctggtgc | aggccctcga | ggccgctggt | gcctgctctg | tgcagtccct | gctacgcctc | 60 |
| aggcccagcg | cccgaggggg | aggtcgccga | tacccaaaat | aaaacctgcc | ctatccctct | 120 |
| gacctcagct | ggctgggcgg | agagcgcctg | ccaaagctcc | aggagctggg | cgggcagcac | 180 |
| cttcccctgc | tggccacacg | gggccagtgc | aggg | | | 214 |

<210> SEQ ID NO 34
<211> LENGTH: 129
<212> TYPE: DNA
<213> ORGANISM: Artificial Sequence
<220> FEATURE:
<223> OTHER INFORMATION: Dph-CRE34

<400> SEQUENCE: 34

| | | | | | |
|---|---|---|---|---|---|
| tcttgggttt | ctgggcagaa | acgtcttgcc | tatttctgga | cacctcagct | gccactggct | 60 |
| ccttataaat | aacccacccc | aggcgagggc | cacgctgccc | ccatcttgtg | gcagccgaca | 120 |
| ggtgtctgc | | | | | | 129 |

<210> SEQ ID NO 35
<211> LENGTH: 403
<212> TYPE: DNA
<213> ORGANISM: Artificial Sequence
<220> FEATURE:
<223> OTHER INFORMATION: Dph-CRE35

<400> SEQUENCE: 35

| | | | | | |
|---|---|---|---|---|---|
| ttacctggtg | caggccctcg | aggccgctgg | tgcctgctct | gtgcagtccc | tgctacgcct | 60 |
| caggcccagc | gcccgagggg | gaggtcgccg | atacccaaaa | taaaacctgc | cctatccctc | 120 |
| tgacctcagc | tggctgggcg | gagagcgcct | gccaaagctc | aggagctgg | gcgggcagca | 180 |
| ccttcccctg | ctggccacac | ggggccagtg | cagggttatg | gcacacccac | cttcaggtgc | 240 |
| gcccctcagg | acccctggcc | tgggtgaggg | cttgggtggg | cacaggcttc | ctaggcctgc | 300 |
| agactgaacc | acgtgtaacc | agaatggtgg | gctcagggct | ccgttagaga | agccggcaga | 360 |
| gcgagcctgg | aaaaggaggt | tggccccacc | atgggagagg | atg | | 403 |

<210> SEQ ID NO 36
<211> LENGTH: 415
<212> TYPE: DNA
<213> ORGANISM: Artificial Sequence
<220> FEATURE:
<223> OTHER INFORMATION: Dph-CRE36

<400> SEQUENCE: 36

```
agagtgaatg catgggaatg aatagatggg tggatgaatg acaactgtg tgaaatagca      60 gacagcctgg ggacaccctc cctcctgtcc ctcctctccc aggtcttgca ctgggccctg     120
acactcagcc ctgcagcctt cagcgtctgg gaagtccctt cgaggagcag caccccagac    180
tctgatgttc tggacttcac tttgccattc ccttgggtcc tcacagccac tattttctga    240
aggcttcatg tcaaacccctg cttgcctcat gaatacacac agttcagaaa agcaaaacct   300
cgacagagcc accacccaca caagggaggt gacgtgcccc catcctttct cagatgcccc    360
agccactgag agaggatcca ggccaccctc cccagctggg gaaccaccca gtgac          415
```

<210> SEQ ID NO 37
<211> LENGTH: 352
<212> TYPE: DNA
<213> ORGANISM: Artificial Sequence
<220> FEATURE:
<223> OTHER INFORMATION: Dph-CRE37

<400> SEQUENCE: 37

```
accaatctgt gcctgaaccg aagagttccg cagacaccac cgcccacgct cagcctgtgg     60
ggtctgaggg gagtgagggg gtgggtcagg gtgccagact gctctccccc acctggtgcc    120
tcagtttccc tgatccaaga ggcagggtta tccaatctgg tggcctcact ggccagcata   180
caggccatca gaggccagga aggatgtctg ctagtcggac ggtgccacct ggagtcctga   240
ggaaagaaaa ccagtctcca cacgccacaa tgagcctgtg ggagatgctg gcacagatgg   300
taacggccac tgcgagtgcc cagggtgggg ccccagggtt agaaagggcc ta             352
```

<210> SEQ ID NO 38
<211> LENGTH: 349
<212> TYPE: DNA
<213> ORGANISM: Artificial Sequence
<220> FEATURE:
<223> OTHER INFORMATION: Dph-CRE38

<400> SEQUENCE: 38

```
ctcctcagcc catccagaat gtacccgctg ctgggagtaa aaatagcagc tgacacctcc     60
tggaggcgga gggaggacct tgcctccttc tccaagcacg tcctctgcat cctggcctcc    120
ttcagcctcc tcctctggcc attcctatac ttggtaaggg gcctgcacgg gcatagcccc    180
ccccagcaag actccgcaca caccccggcc acccagtcac tggccaatgg gctcctagga   240
agatcaaatg tcactataac acgagggtgt gagccgggcg ccagtgcctg cagccggtgc    300
tgtccacagg gagctccagc ccttctcaca ctcgacccgc aggtgggta                 349
```

<210> SEQ ID NO 39
<211> LENGTH: 380
<212> TYPE: DNA
<213> ORGANISM: Artificial Sequence
<220> FEATURE:
<223> OTHER INFORMATION: Dph-CRE39

<400> SEQUENCE: 39

```
taactatgtt taatgtgctg agagaaagcc atttgtttac agaatcttat tatagaacag     60
```

```
aaatatactt gttccagaga agaggagttt aattggttcc aagtcaaatg atgctaacag      120
gcgtcacctc accaatccag gacttaagat gggttattat aaataggagt aacacatatt      180 tttttggct cttttcccca cctgttatgc aagactgcat accactatga tgttcctcct       240
gattatttcc agcaactttg ggggtggctc acgtgtgctc atgaacaagt actgtcaggt      300
atcacatacg gtctgtcatt ttcttgctct tgagctctgg cacttctctg ctgctgtctg      360
ctgctgaggc ctgcagagat                                                  380

<210> SEQ ID NO 40
<211> LENGTH: 575
<212> TYPE: DNA
<213> ORGANISM: Artificial Sequence
<220> FEATURE:
<223> OTHER INFORMATION: Dph-CRE40

<400> SEQUENCE: 40
ttctctctca ctgtaaaagt gtaaaaggtt aggttactcc ccagcctgtc gaacatgtgc       60
ctgattgcct tctgagatag cacatcccta atccaaaaga aaacctagcc tggagcttgc      120
atccagctaa tcttcttcca cattgctcca acagggagt tcagttttct cattactcat       180
acagagagca gagatagatt ttcatgattc ttcaggactc tgttctctct gctttaatag      240
ccaaaagcta agccaaatg aacttcttca cagagaacaa caagcaattt tatctaatcc       300
ttattattct tgctgtaact gcaattgtgt tattctgact gacagattcc cagaagagat      360
tcagtgaaaa taccccttgat cagattcaca aaggaacagc atatttcaag tgggcgtgtc    420
tggctagaat ctccctggac agttcagtaa cagcacatca acagactgct gaattcttat      480
ttccccgtcc aaaaaataac aaagccaatc tgaaatctgg aagtgttctg agggcagatg     540
gtattagccc agtagtaaac atattttttgg ctgct                               575

<210> SEQ ID NO 41
<211> LENGTH: 463
<212> TYPE: DNA
<213> ORGANISM: Artificial Sequence
<220> FEATURE:
<223> OTHER INFORMATION: Dph-CRE41

<400> SEQUENCE: 41
ctacaataaa tatataactt ttttaatttg acaaaaaata attttgagtg gttacaaaaa       60
gggacaggtg tggcttggta actagaaaaa cattcccagc ctgggaaaca atctagtgag      120
agcttggagg cagaagacag aactctgatt acattcaagg agtttgccag atggcaacag      180
ataactgcca atgttcggtt gcactataat tattatacac tctctgtcac ttcagcaagc      240
gctcttttca caagacaagt ggtgacagaa tgttgtatta agattacccg ttgctaagct      300
tatgttaaaa tgaggaaatg aaatggaaag tcttgttttg gtaatgtctc tggggtatga      360
ggaatggagg gaaaggtttg actatgagca taactgcata gagaatttg tttgtttatg     420 ccttttggga atgcattatt ttgattgacc ctaattggga att                       463

<210> SEQ ID NO 42
<211> LENGTH: 379
<212> TYPE: DNA
<213> ORGANISM: Artificial Sequence
<220> FEATURE:
<223> OTHER INFORMATION: Dph-CRE42

<400> SEQUENCE: 42
```

```
attcatgaag atgtaaaaga cacatttaaa acccacatca attgcactaa aagtcaactg    60
gaaacagaag gttttttaaat cctggtggtg gcaaattggc agccaaagga acaaagtctt   120
agtcaacata tttccatgtc ccccgaacac aaatagcctc gaaccttcgg agggtgttcc    180
tttgagatgt ttcatcagtg acatcacagt gattgccagc ttccacggac tactttaggc   240
gctgcccaga gtccaggagt ccagacagcc tgggagggga aaggagttg gagctcaagt     300 tggagacagc gaggagaaac ctgccatagc cagggtgtgt cttttgatcct cttcaggtaa   360 ctgcaggatt tttatgctt                                                 379

<210> SEQ ID NO 43
<211> LENGTH: 250
<212> TYPE: DNA
<213> ORGANISM: Artificial Sequence
<220> FEATURE:
<223> OTHER INFORMATION: Dph-CRE43

<400> SEQUENCE: 43
aagaaggaat accctagggc aaatgcgtgc tagaggggct taatacttgg cagaatcctt    60 cttttttcagt agcctgcttt tatgactgct ccgactgcac ctgttaggaa gataaataaa   120
ggactggcca attctttcct ctgaagcgcc ctaaatatat cactttaaaa agactttgga   180
aaaacaagtt gtatccttac ttctcaccca gtaaatctaa agaaattccc tcttgttccc   240
aggcctttca                                                           250

<210> SEQ ID NO 44
<211> LENGTH: 194
<212> TYPE: DNA
<213> ORGANISM: Artificial Sequence
<220> FEATURE:
<223> OTHER INFORMATION: Dph-CRE44

<400> SEQUENCE: 44
ccacataact aaagcatgat gctattgagt tctaagtcta gtttccaccc ttatatgaaa    60
agtcagcttg gcacagagtt tggtagagct aagtctgacc agctgcactc tcagccacaa   120
gggaaattag acgagacagt gtggctgctt cagtaccaat caatcaaagt ttttgaaaat   180
tatcttgaaa acac                                                      194

<210> SEQ ID NO 45
<211> LENGTH: 264
<212> TYPE: DNA
<213> ORGANISM: Artificial Sequence
<220> FEATURE:
<223> OTHER INFORMATION: Dph-CRE45

<400> SEQUENCE: 45
actttctctg tggattgcaa tatttcctgg catatgttca cttcagtaag acgatcagtg    60
tattaaaaac ccaatggggt ttctgcagaa gccaatgatg gcatggcacc tcttttgtgg   120
catgtgtgaa atctgccctt cgctgtaaac attcttatgc aacatgacac tctgccctat   180
gtccatttca tatgtggtgt tcagtgtgct gggaatgctg aaaaaaacaa ttctctctta   240
gagatttccc aagtagaatc acag                                           264

<210> SEQ ID NO 46
<211> LENGTH: 427
<212> TYPE: DNA
<213> ORGANISM: Artificial Sequence
<220> FEATURE:
<223> OTHER INFORMATION: Dph-CRE46
```

<400> SEQUENCE: 46

```
agaaggaata cccctagggca aatgcgtgct agaggggctt aatacttggc agaatccttc    60
tttttcagta gcctgctttt atgactgctc cgactgcacc tgttaggaag ataaataaag   120
gactggccaa ttctttcctc tgaagcgccc taaatatatc actttaaaaa gactttggaa   180
aaacaagttg tatccttact tctcacccag taaatctaaa gaaattccct cttgttccca   240
ggcctttcaa acagtgaagt caggagtaag ggagactgtg gactggtcaa aggtggaagt   300
tagactcact agctggtcta aggaatccag gagggtggaa acatgaaga acttacaatc    360
ctttatgctc tcaatgactc actttatttt ggccatgaga cacagccttg aaactttttt   420
ttttttt                                                             427
```

<210> SEQ ID NO 47
<211> LENGTH: 436
<212> TYPE: DNA
<213> ORGANISM: Artificial Sequence
<220> FEATURE:
<223> OTHER INFORMATION: Dph-CRE47

<400> SEQUENCE: 47

```
ggtcataaaa tactttctct gtggattgca atatttcctg gcatatgttc acttcagtaa    60
gacgatcagt gtattaaaaa cccaatgggg tttctgcaga agccaatgat ggcatggcac   120
ctcttttgtg gcatgtgtga aatctgccct tcgctgtaaa cattcttatg caacatgaca   180
ctctgcccta tgtccatttc atatgtggtg ttcagtgtgc tgggaatgct gaaaaaaaca   240
attctctctt agagatttcc caagtagaat cacagtgtta aacctatcag cagcctccaa   300
gatcattttt tttaagcccc tcattttaca caaaaagaaa ctgaggccca gaaagccccc   360
tgactttctc agagtaacta agctggttaa tgatagatcc agaaatagaa cccaagggac   420
caacttcaga ttctag                                                   436
```

<210> SEQ ID NO 48
<211> LENGTH: 359
<212> TYPE: DNA
<213> ORGANISM: Artificial Sequence
<220> FEATURE:
<223> OTHER INFORMATION: Dph-CRE48

<400> SEQUENCE: 48

```
ctgagtcagc acatgcatct gtcagagaga gaagagcaag acggagcacg aggctgcagc    60
tgaatttaga aagttagagg tgttctcatc agccacatga gatgggcagg agattccttc   120
cagtaggcga gagagcagag tgcagacaac agatgtgaga aggtccccca tagctgtcaa   180
gttcctgcat ccttgtgctg aagaaaggga ggtgccatca tgattgatgt tcagaggcag   240
tataaaagca ctgggtttct ccccaactgc ttgtcacacc gacctgcacc atctctcgcc   300
tgcctgtggg gttctgtcga actagtcgtg gagggaagga gactctttaa agaataaca    359
```

<210> SEQ ID NO 49
<211> LENGTH: 353
<212> TYPE: DNA
<213> ORGANISM: Artificial Sequence
<220> FEATURE:
<223> OTHER INFORMATION: Dph-CRE49

<400> SEQUENCE: 49

```
gagatttcat cacattttaa agttttgcca agccaaaaag ctacctgaat gtagagcagc    60
```

| | |
|---|---|
| attcatccccc tcttgcctat ttctaagcat ttctcagggc ttagtcatcc atcagaaaag | 120 |
| gacctccctt gatgggaaaa ctccttctca tatctcttct ttgaccttca gtttctacct | 180 |
| gcaagagagt gaatggccta tttcaaacac cgaaatcaat ttgtctttgg aaagtcatct | 240 |
| tatatacaaa tattatcctt acctcaaatt ggggaaaggt taataattta tgcagaaaac | 300 |
| taagagaaag gaataggggga ggaggaaaga tagtttatca agggcaattg ttt | 353 |

<210> SEQ ID NO 50
<211> LENGTH: 354
<212> TYPE: DNA
<213> ORGANISM: Artificial Sequence
<220> FEATURE:
<223> OTHER INFORMATION: Dph-CRE50

<400> SEQUENCE: 50

| | |
|---|---|
| tcaaaagtct tttaaacata ttttctttat ataattaagt aaccagtgtt gacaggctgt | 60 |
| ggtgatcagt ttacaggttg gccttactta gtggcagagg gcattgatgg atgaagtctt | 120 |
| tcacccaaaa taaccacacc aaatgcatgt attaatatgg gaacttaatc ctgactgtca | 180 |
| ggcagggagt ccaaccccctg ctaaagtatc ttatttgtaa tgcaaatgat ttacgtgtgt | 240 |
| actaagtgtc cttttatct gctctgtcac tttaacctct ccgaagtgta cccagaagca | 300 |
| atacattcta ccatgtttcc aaactggaaa cacaatattg ttttaattat tctg | 354 |

<210> SEQ ID NO 51
<211> LENGTH: 351
<212> TYPE: DNA
<213> ORGANISM: Artificial Sequence
<220> FEATURE:
<223> OTHER INFORMATION: Dph-CRE51

<400> SEQUENCE: 51

| | |
|---|---|
| gctgtcccag cgttatcagt cgggcgcctt gccagccgaa agggcctgtc taaattcgtt | 60 |
| tcctgtcccc taactcatcc cggcgctggc tggcctggag agggtaggat ggggcggcgc | 120 |
| cgagaatggc cgttatgagg accctaagag gtgagaccct ctcgccttct ggggtggggg | 180 |
| gtcccgtcct ttcccccact gaggacagag cccgcccag cgatctgagc atgtgtggac | 240 |
| gtcaatcttg cagcccctct tccaggcccc ctccccagcc ttgcagggct caggttaccc | 300 |
| ctggcctttc ctaaaggtca ctcattcctc ttgacgtttg caaaagggga a | 351 |

<210> SEQ ID NO 52
<211> LENGTH: 607
<212> TYPE: DNA
<213> ORGANISM: Artificial Sequence
<220> FEATURE:
<223> OTHER INFORMATION: Dph-CRE52

<400> SEQUENCE: 52

| | |
|---|---|
| tgtcccagcg ttatcagtcg ggcgccttgc cagccgaaag ggcctgtcta aattcgtttc | 60 |
| ctgtccccta actcatcccg gcgctggctg gcctggagag gtaggatgg ggcggcgccg | 120 |
| agaatggccg ttatgaggac cctaagaggt gagaccctct cgccttctgg ggtgggggt | 180 |
| cccgtccttt cccccactga ggacagagcc cgcccagcg atctgagcat gtgtggacgt | 240 |
| caatcttgca gcccctcttc caggcccccct ccccagcctt gcagggctca ggttacccct | 300 |
| ggcctttcct aaaggtcact cattcctctt gacgtttgca aaaggggaat gtaatcctgg | 360 |
| ggtgggggga gaccctcat ctgtagcccc tcccttgctc ctcccaaagg gtggaattag | 420 |
| aacagggact gttattggga gacagaaagt gggggatagt agttgacctt tggtaagggg | 480 |

-continued

```
gcaggtgccc agggccagag gcttctgctt caggctgtag tgggcacttg gctgccagcc    540
cagtgtgaag gggggaggat ggagagaaag agaggcgggg ctggctgggg accgagtggc    600
tcaggga                                                               607
```

<210> SEQ ID NO 53
<211> LENGTH: 469
<212> TYPE: DNA
<213> ORGANISM: Artificial Sequence
<220> FEATURE:
<223> OTHER INFORMATION: Dph-CRE53

<400> SEQUENCE: 53

```
agggctgggc ggcttccgga gcctgggcta ggggcaaggg gtcaccgagc gcggcccggg     60
cggaaagggg gttggttttc tctctcctcc cgagcgcggc gcgcatccct ggcgtccacg    120
ccgaatccca cagtccccga cgcccctcga gtccgtgttc ctcgacagcc gcgcggctga    180
gtcactggcg ggctcgggcg gggccgcacc cgggcacgtg gcggcgctcc ccgcccgcca    240
tctcctgacc cctggcccac cgcaccccta ccccagggtg gaaaaatccc gggaggagcg    300
gcctgagatg agggggcggg gcgagagggg agactggacg ggtggcgggg caggtggcct    360
ggggtggggg ctgggaggcc gcgcgggccg gcggggcggg gagcaggggt ggggagaggg    420 cggcggggt gagtcaccgg gcgcgcgctg ccccggcgcc gacgggaag              469
```

<210> SEQ ID NO 54
<211> LENGTH: 332
<212> TYPE: DNA
<213> ORGANISM: Artificial Sequence
<220> FEATURE:
<223> OTHER INFORMATION: Dph-CRE54

<400> SEQUENCE: 54

```
tgggttcacc agggcccatt ctcagtctag aggattgtcc cttctctgga tcggctctag     60
cccagggcct caccccacat cccagccccg cccgccccag gcaggcaatg tctggatcac    120
cggccgtgcc ccttggcctg tgtctgcaga ggtcacagag gcgggacacc cgcggggctt    180
aacaggcggg gctattttc gaggcggaag aatactcaag ttgcaagagt ggcaactttt    240
tcaagaaggg gaaagtccca cttcgggccc tttgggtttc ttcgcagtca gatgtgcgct    300
cacagccacc tggggagggc gggacgggcg gg                                  332
```

<210> SEQ ID NO 55
<211> LENGTH: 206
<212> TYPE: DNA
<213> ORGANISM: Artificial Sequence
<220> FEATURE:
<223> OTHER INFORMATION: Dph-CRE55

<400> SEQUENCE: 55

```
tacattccag ggagggagac cagttgggac aaggcctagg ctgctctcct acaaatttgc     60
catgaacagg agccaaactc taagacctga ttcaagtggc ccagctgtca ctggtgacac    120
actcaggggc tgggcctatc atgttcttat acaacctagt gagtcaagct ttggaaaata    180
acattgtcag ggaagaacgt aaaagt                                         206
```

<210> SEQ ID NO 56
<211> LENGTH: 289
<212> TYPE: DNA
<213> ORGANISM: Artificial Sequence
<220> FEATURE:

<223> OTHER INFORMATION: Dph-CRE56

<400> SEQUENCE: 56

```
ggagctgaga gtttaagggc atttgtttac tatgtttgct tggatttttcc gaactgcctt    60 agttcctgat tccacactgc tattgtgtgg atcaaataat cccttgtcac aaaaataccc   120
tggggaatga ctcccctggc gtccaggtta tgagtgtggt cagtcattcc acatgcctta   180
gggatgagct atctgtgcca tgacgagcga tttcctttttc gagttttgta atccccaaat   240
actaaatact attatcaata aaagttaatt aaggaaatgt atatcgaaa               289
```

<210> SEQ ID NO 57
<211> LENGTH: 195
<212> TYPE: DNA
<213> ORGANISM: Artificial Sequence
<220> FEATURE:
<223> OTHER INFORMATION: Dph-CRE57

<400> SEQUENCE: 57

```
gacagctgtc ccgctcttgg aattcattgg cttcctctac ccggcctccc aaacaccacc    60
ccaatctagt ttagcccccc gccccaccct cgctgaccta ataaggccat gcagtgtgcg   120
ggggagctac ataaaagcgc gggctcgcgg cgactctgca ccacgcaggg aagagaaag   180 caggagccgt ccagc                                                    195
```

<210> SEQ ID NO 58
<211> LENGTH: 345
<212> TYPE: DNA
<213> ORGANISM: Artificial Sequence
<220> FEATURE:
<223> OTHER INFORMATION: Dph-CRE58

<400> SEQUENCE: 58

```
cccctcagct tcagccccca cctccaggag gccctaccca cgctcatgac cttgctattc    60
tgggccttgt gtcctgtagg gagatggaca ggagacagct gggcttccag gccacccagg   120 cgggggggcta gccgagggaa gcctgctggc tctcctgctt gctctaatttt ctggggctcc  180 ccaaaccttg gcctcaggag actggggata ggaccggcct tgaaagtggg ggaagctttg   240
gagagccggg tgctgggttc ttagtgagat ggccagtgaa ggctgtggtg ccccgaggta   300
agcagggcct gatcccctcc taatcttcca gcagcaactg gtgct                   345
```

<210> SEQ ID NO 59
<211> LENGTH: 220
<212> TYPE: DNA
<213> ORGANISM: Artificial Sequence
<220> FEATURE:
<223> OTHER INFORMATION: Dph-CRE59

<400> SEQUENCE: 59

```
ctcctccagc agctgccctg gtggtaacca agagacgccc ccatcctgga gcaggggtgg    60
ggaggggcag ctcagagcag ctgcttctct gaggaagctg acaccaaggc cagcattcag   120
caacaacttg tggctttgca cccagcgccg gggtccccgc ccacctggct ccctgctgtc   180
cctcttcccc actgctgctc ggacttccct ctgaccctgg                         220
```

<210> SEQ ID NO 60
<211> LENGTH: 663
<212> TYPE: DNA
<213> ORGANISM: Artificial Sequence
<220> FEATURE:
<223> OTHER INFORMATION: Dph-CRE60

<400> SEQUENCE: 60

```
ctttgctccc tgggagggcc tggccctgtg ggcatttgag tttataacac caccccatt       60
gtggcacacc cctccacccc gtaaaacaca ggctctgctc ttggaatcag tcttcctgat     120
ctgtggctgt gccctccaac agagggcacc cctgggcttc ccagtctgg gggtagtggg      180
tgccaacaag gagggcctg gggctgaaga atcccacccg ctgagctcgg ccttctccct     240
tccccactgt ccagctccgc ctttcagcat cctgcctcac tccccgccca ggcagcaagg     300
agcccacacc ctcatgcccc tcagcttcag cccccacctc caggaggccc tacccacgct     360
catgaccttg ctattctggg ccttgtgtcc tgtaggagaa tggacaggag acagctgggc     420
ttccaggcca cccaggcggg gggctagccg agggaagcct gctggctctc ctgcttgctc     480
taatttctgg ggctccccaa accttggcct caggagactg gggataggac cggccttgaa     540
agtgggggaa gctttggaga gccgggtgct gggttcttag tgagatggcc agtgaaggct     600
gtggtgcccc gaggtaagca gggcctgatc ccctcctaat cttccagcag caactggtgc     660
tct                                                                    663
```

<210> SEQ ID NO 61
<211> LENGTH: 594
<212> TYPE: DNA
<213> ORGANISM: Artificial Sequence
<220> FEATURE:
<223> OTHER INFORMATION: Dph-CRE61

<400> SEQUENCE: 61

```
cagcagctgc cctggtggta accaagagac gcccccatcc tggagcaggg gtggggaggg       60
gcagctcaga gcagctgctt ctctgaggaa gctgacacca aggccagcat tcagcaacaa     120
cttgtggctt tgcacccagc gccggggtcc ccgcccacct ggctccctgc tgtccctctt     180
ccccactgct gctcggactt ccctctgacc ctggtggctc tgtgtctctg ctcccttttcc     240
ccctaggtct agacatctgt ccttatttcc cccagacctg tccccagaag tccaccttc      300
cccattcctt tggtctggag ccctgcttg gtccagcttc cccaggcccc gacacctttc     360
tgtggggtct gcctagctcc tgcacgcaca cagcatgggc ctgatcctgt tcccctcgtg     420
gacagatgca gcagggcaga gtgcagcgca gaccacaggc ctctggggct ggccacagaa     480
accccgttgg ttagagcaca gtgtgggatg aggtgaccct cagtgcacga cttgggtgaa     540
cccctgcccc catcctgaga cagttaccccc tcccctctg ccatcagcac attc            594
```

<210> SEQ ID NO 62
<211> LENGTH: 634
<212> TYPE: DNA
<213> ORGANISM: Artificial Sequence
<220> FEATURE:
<223> OTHER INFORMATION: Dph-CRE62

<400> SEQUENCE: 62

```
ccttccccat tcctttggtc tggagcccct gcttggtcca gcttccccag gccccgacac       60
ctttctgtgg ggtctgccta gctcctgcac gcacacagca tgggcctgat cctgttcccc     120
tcgtggacag atgcagcagg gcagagtgca gcgcagacca caggcctctg ggctggcca      180
cagaaacccc gttggttaga gcacagtgtg ggatgaggtg accctcagtg cacgacttgg     240
ggtgacccct gccccatcc tgagacagtt acccctcccc ctctgccatc agcacattct     300
gtagcctctt gggttacttg gctgccttgg tgtcccattt tcttggggt ggggtgggga      360
```

```
ttccctatcc aggatggggg ggccctcagg gctctgttcc cagaggctga gttagagcga    420
tggggaaggg gggggcagt tttggggaga gacaggcagt gctggctttg ctcaccaggg     480
cctggacact aaatcccttg ttgatggctg tggcaacccc tccctagggt agggttacca    540
tcttcggccc tgtcccttg actctctccc ctcacttccc cttgtccctc taggagccac     600
tcacttcctc tagcccccaa agatgttct ccct                                 634
```

```
<210> SEQ ID NO 63
<211> LENGTH: 445
<212> TYPE: DNA
<213> ORGANISM: Artificial Sequence
<220> FEATURE:
<223> OTHER INFORMATION: Dph-CRE63

<400> SEQUENCE: 63
cctcccctgc accccagagg caggttttat tttaagcttt aagggtgttc tcagccaaaa     60
caccgaagct aagccaccct cgcggcttca agagcttgga gagctcgggt tacccacccg    120
aactccgggc tccgggtccc gccgcgatgc cggctgcggc gcggggggcc actgccactc    180
ccggcatgcg ccgggcggac ggccgctcca ccaatccccg cgccgtcgg cgcccctgcc     240 ccgccctccc cagcctcctg acgctgattg gtcgagggga ggactcgctc ctagtggcgg    300
gaaagcgcgg cggtgtgatg atgactccaa ggagcccggc gcccggtcag ggagggcact    360 ggcatcctc attacccgcc cagcctggcc ttagcccttc ccgcgctcc ctaggcaccc      420 ccacccccgc agggcatctc caggg                                          445
```

```
<210> SEQ ID NO 64
<211> LENGTH: 408
<212> TYPE: DNA
<213> ORGANISM: Artificial Sequence
<220> FEATURE:
<223> OTHER INFORMATION: Dph-CRE64

<400> SEQUENCE: 64
gtctccgaac gcaggcccg tcgcgttaag cacaagctgg cagggcctct cctctccctt     60
ctcagatttg ctccttgaca tttgcctgct gcctggcggt ggcaacagct ggggcggggc    120
gcgcgcagga ggccccgtaa ccctatcccc gctccggctc cctcgtgaaa ccggagcttc    180
cctgccttgg ccgaggggga gggctgcggg ggccagaccg cctgcgaaga ccacaggggt    240
tttcctctcg ggttttggct cccgtgggat ggatgtggct gtgcgggggg ttggcctgag    300
cttcgcttct aagccagcag cttggtcagg gaaacctgaa agcattccca gctaatcccc    360
caagtggtgc aagtctgtgc gcgcccatcc cgctgagtaa ggcggtgg                 408
```

```
<210> SEQ ID NO 65
<211> LENGTH: 496
<212> TYPE: DNA
<213> ORGANISM: Artificial Sequence
<220> FEATURE:
<223> OTHER INFORMATION: Dph-CRE65

<400> SEQUENCE: 65
ggcaacaaag tccagggatt ccagaactta gctgtctttg aaacaacacc ttacattcca     60
aaggccaaca actttaagat tgccaacgac tcaaattatt tataggagat tgattcatat    120
acttaaccca atatgagagg aaatatttct aattatatcc aaacatcttt aatatgaggg    180
gaattaggct tggagacctt caatgccaaa aacatgtttt gccaaatatg ttttaagaaa    240
gaggaggagg ttacgtgttt tccatatttg agcctataaa agtacccttg gaatgagtat    300
```

```
gacttgtctc tcctcataaa gcttcaaggt aagtgtgtgt gaggacaggg ctctgtctgg    360
aggacggtaa gggatgtctg gctgcccgcg tgcatgccac acatcctggc tcccactgtc    420
cctggcagcc ctgccagtga agcaccagct tactccgtag caatttaat tagatgttgt     480 agtcttccca gtcatt                                                    496

<210> SEQ ID NO 66
<211> LENGTH: 319
<212> TYPE: DNA
<213> ORGANISM: Artificial Sequence
<220> FEATURE:
<223> OTHER INFORMATION: Dph-CRE66

<400> SEQUENCE: 66
ccaggtgaca ggtggatggt ggagctggag gagccactcg gagcctccaa ggctggggag     60
ggtggagggg ggaggcaggt cggtgtccca ggccacacct gttgactaag ggattaggat    120
gttgtgtccc tgccagccct cctccaataa gccctctgg gcctgcaggg agaggaggag    180
ccttgccatg taaactgtat ttttagttcc ctgtgcctct ccccggctgc tataagacac    240
ctctccccac cccagccct ggccgcttgg ctggaggctc tgcgaggaca gctggggaga    300
aggggagctg tggtcagta                                                319

<210> SEQ ID NO 67
<211> LENGTH: 372
<212> TYPE: DNA
<213> ORGANISM: Artificial Sequence
<220> FEATURE:
<223> OTHER INFORMATION: Dph-CRE67

<400> SEQUENCE: 67
tcatcttcta ataatttggc aagccatcca tggtcttcta agcaaggcgc catgaatata     60
acgaatatag agacagaaaa agaccctcc ccactggctg ggttgaggga ctggagagcc    120
cagatggaag ggcagaggtg caggcttttt tccttgttgc cactagatgg cagtagggca    180
cccgttgtca gccctgggc aaggtcaccg actgtctttg cctttgcctc agcaagcca    240 aaaccctggg cagactcaat ccaaaaataa acaatcaaag agcatgttgg cctggtcctt    300
tgctaggtac tgtagagcag gtgagagagt gaggggggaag gactccaaat tagaccagtt    360
cttagccatg aa                                                       372

<210> SEQ ID NO 68
<211> LENGTH: 293
<212> TYPE: DNA
<213> ORGANISM: Artificial Sequence
<220> FEATURE:
<223> OTHER INFORMATION: Dph-CRE68

<400> SEQUENCE: 68
agaaaggagc tgccctgggg atggctgtgt atccctacaa ctgccaggca catgcccctt     60
gaacacccga tgctacgtgt cccaaaggaa actggtctcc acccaccccc ggcccgtcct    120
cgtcctgggt accccacctt agtaaatggc gccaccatct gcccggtcac tcagcgagaa    180
actcaactcc tggcagcaga tgacgggcac tctggttaaa tgactctctc cagcctccaa    240
gttcaacctg cagggaagcc ctggaaatcc tgtctccctc tgccctgcct ctc          293

<210> SEQ ID NO 69
<211> LENGTH: 482
<212> TYPE: DNA
```

<210> SEQ ID NO 69
<211> LENGTH: 482
<212> TYPE: DNA
<213> ORGANISM: Artificial Sequence
<220> FEATURE:
<223> OTHER INFORMATION: Dph-CRE69

<400> SEQUENCE: 69

```
gaaacatggc ttccacaggt tccagttgaa gaatcccagt tccgtctata aattccaggg    60
aaggtctctg attggccctg ctcattccca ggcccattcc ttgacccagt cactgaagtc   120
agggagatgc agtaataaga ctggctggaa tcagggtctt taggggtgga gggatgggga   180
ggaggcacag catgtcatca aaataaggaa attgcaaaag aaagcttgca ggctactttg   240
aatgacaatg agaaagacgg tgctgcctga gtgtgttaag gatccacatg gtctccaaaa   300
tcctccagga gcatacagtc tagtctggga gatgagacac aaaaataacc agaacacaac   360
agcttgcact gactcgaggg ctggataaga atatctggaa ctcccccatc tatttcagaa   420
gcttgtctct tggatgaaaa ttagacactt aatgggaaag ggctttgaaa agagtgcagt   480
aa                                                                 482
```

<210> SEQ ID NO 70
<211> LENGTH: 398
<212> TYPE: DNA
<213> ORGANISM: Artificial Sequence
<220> FEATURE:
<223> OTHER INFORMATION: Dph-CRE70

<400> SEQUENCE: 70

```
cctcaggtac ccctgcccc ccacagctcc tctcctgtgc cttgtttccc agccatgcgt     60
tctcctctat aaatacccgc tctggtattt ggggttggca gctgttgctg ccagggagat   120
ggttgggttg acatgcggct cctgacaaaa cacaaacccc tggtgtgtgt gggcgtgggt   180
ggtgtgagta gggggatgaa tcaggagggg gcgggggac ccaggggca ggagccacac     240
aaagtctgtg cggggtggg agcgcacata gcaattggaa actgaaagct tatcagaccc    300
tttctggaaa tcagcccact gtttataaac ttgaggcccc accctcgaca gtaccgggga   360
ggaagagggc ctgcactagt ccagagggaa actgaggc                           398
```

<210> SEQ ID NO 71
<211> LENGTH: 241
<212> TYPE: DNA
<213> ORGANISM: Artificial Sequence
<220> FEATURE:
<223> OTHER INFORMATION: Dph-CRE71

<400> SEQUENCE: 71

```
caggggcgca ggcctcttgc gggggagctg gcctccccgc cccacggcc acgggccgcc     60
ctttcctggc aggacagcgg gatcttgcag ctgtcagggg aggggaggcg ggggctgatg   120
tcaggaggga tacaaatagt gccgacggct gggggccctg tctcccctcg ccgcatccac   180
tctccggccg ccgcctgcc cgccgcctcc tccgtgcgcc cgccagcctc gcccgcgccg    240
t                                                                   241
```

<210> SEQ ID NO 72
<211> LENGTH: 238
<212> TYPE: DNA
<213> ORGANISM: Artificial Sequence
<220> FEATURE:
<223> OTHER INFORMATION: Dph-CRE72

<400> SEQUENCE: 72

```
cccccaggca gcggcacggt ggactttgat gagttcctgg tcatgatggt tcggtgcatg     60
```

```
aaggacgaca gcaaagggaa atctgaggag gagctgtctg acctcttccg catgtttgac      120
aagtgagcac gtgacccttg acctctgacc ctgacccaca ctcaagccga gctgtacagg      180
agggcagtct cagattccag gcctagggac cctgtggcct ctgcctgata ggggagag       238
```

<210> SEQ ID NO 73
<211> LENGTH: 465
<212> TYPE: DNA
<213> ORGANISM: Artificial Sequence
<220> FEATURE:
<223> OTHER INFORMATION: Dph-CRE73

<400> SEQUENCE: 73

```
agccagctct gggggcacgc ctgcttatcc tgtgggagtc catggagccg ggggttgggac      60 agccctccac ccagtgccca tacaaggcct ggcggagttg gggactaatt ttggcttctg     120
aggcggcact agcaggccag ggggccagat aacgctgccc caccccctgc atgccaaagt     180
ccccagaaca atcaccaggt ttaactttgt tcctcgttaa aaatagccca gtggccaccc     240
tggtcaggtt accgtgggtg gcttgcctgc ctccacactg gttttattat cccaacttga     300
gggacagctg tccttcgggc cacccagctt gagtttcatc aggggccgaa agggcattga     360
gtggtcactg actattgtta ctgagggtca ccttggtcct gaaggggggtg cccacctgtc     420 accctggccc tgagcccagt cgcagtgagg ccagctgggt cacgt                      465
```

<210> SEQ ID NO 74
<211> LENGTH: 285
<212> TYPE: DNA
<213> ORGANISM: Artificial Sequence
<220> FEATURE:
<223> OTHER INFORMATION: Dph-CRE74

<400> SEQUENCE: 74

```
ttttcattca ttccagaaac cttttcagag agtccctttg gggagtgtgg gggacaggag      60
ggaaagaaac ctggtccttg tagccgttcg tctgctccct gccctgggca gaggacgtgg     120
ggactcaggc cagcctgaga tcactgggac cagaggaggg gctggaggat actacacgca     180
ggggtgggct gggctgggct gggctgggcc aggaatgcag cggggcaggg ctatttaagt     240
caagggccgg ctggcaaccc cagcaagctg tcctgtgagc cgcca                     285
```

<210> SEQ ID NO 75
<211> LENGTH: 332
<212> TYPE: DNA
<213> ORGANISM: Artificial Sequence
<220> FEATURE:
<223> OTHER INFORMATION: Dph-CRE75

<400> SEQUENCE: 75

```
tgctctgttt acagacaagc tgctgtcctc cctgcaaagg ggagtgggtg gggcagaggg      60
caagtgccag gggggcacaa ggctgggcat gtggctggca tgagacggtg tctgagtaat     120
gtcaggcacc tggaggcatt gaccccagga ccttggaccc cagacctctg accgggggc      180 agccagcgtc caggtacccc aaccctgcc ctgggtccgg cgtcccccca ttagtgagtc      240
ttggctctac ttatagcatc tgacaccaga ggggccgaaa atagccctg gagaagggg      300 aggagggggc tatttaaagg gcctgggagg gg                                   332
```

<210> SEQ ID NO 76
<211> LENGTH: 381
<212> TYPE: DNA

<213> ORGANISM: Artificial Sequence
<220> FEATURE:
<223> OTHER INFORMATION: Dph-CRE76

<400> SEQUENCE: 76

| | | | | | |
|---|---|---|---|---|---|
| gcctgtggtc | ttggtggtcg | tggtcagttc | cctctcctgc | cagctgtgga | atgtgaggcc | 60 |
| tggcctggga | gatattttg | ctgcactttg | agccaccccg | ccccctggaa | ctcagaccct | 120 |
| gcacagtcca | tgccataaca | atgacgacca | cttccaattg | tttcctagct | ggagaggcgg | 180 |
| ggagggagc | actgtttggg | aagggggga | gcctgggga | aatgcttcta | gtgacaacag | 240 |
| cccttctaa | atccggctag | ggactgggtg | ccgttggggg | tggggtgcc | ctgctgcccc | 300 |
| atatatacag | cccctgagac | caggtctggc | tccacagctc | tgtcctgctc | tgtgtctttc | 360 |
| cctgctgctc | tcaggtagga | g | | | | 381 |

<210> SEQ ID NO 77
<211> LENGTH: 316
<212> TYPE: DNA
<213> ORGANISM: Artificial Sequence
<220> FEATURE:
<223> OTHER INFORMATION: Dph-CRE77

<400> SEQUENCE: 77

| | | | | | |
|---|---|---|---|---|---|
| ggaataccct | accttaaaaa | caaaacaaac | cgtgctactt | ggccctcttc | ccttgagttg | 60 |
| ttgtctaatc | tcattcattt | cactgccaaa | ctcctcaaat | gcatggtgta | cacccactgc | 120 |
| ttccacttcc | tgtccactca | tcttttcct | cattaactcc | ctgtggcctg | gctttgcctg | 180 |
| tgacactaca | caagctgctt | gctccaagat | aatccaagtt | cttttctctg | tcttcctgat | 240 |
| acacaggctt | tctttggcat | ctgacactgc | tggccacctg | ctcttcttga | aatgcttctt | 300 |
| ttggcttcta | ggaaac | | | | | 316 |

<210> SEQ ID NO 78
<211> LENGTH: 401
<212> TYPE: DNA
<213> ORGANISM: Artificial Sequence
<220> FEATURE:
<223> OTHER INFORMATION: Dph-CRE78

<400> SEQUENCE: 78

| | | | | | |
|---|---|---|---|---|---|
| ccaagtggtg | ggtgtagcct | gggggttcaa | tcctcctgtg | gcgccccaga | acccggtgcc | 60 |
| tcctccaacg | tccggcatct | gatgaggatc | cgacccaggc | gggcggcggc | gggattcgct | 120 |
| cttccccttc | gctccccgcg | agaaagcccc | gagggccgcg | gcggcgcaga | gccggtgaca | 180 |
| gttgaagctt | aggcgggaag | agggaggcgc | gaggcgggaa | gagggagttt | gggcctcggc | 240 |
| agccgccgta | caaacaccgc | tctggtcacc | atggcaacag | cgggatgccg | cgaacggctt | 300 |
| ctgggcgggg | ccggtccctc | ggacgattgg | acctagcttg | gcgcggaatc | cgtgaattgc | 360 |
| ccgcggcccg | agggtgcagg | tgatgggtgc | tgaccgactg | g | | 401 |

<210> SEQ ID NO 79
<211> LENGTH: 281
<212> TYPE: DNA
<213> ORGANISM: Artificial Sequence
<220> FEATURE:
<223> OTHER INFORMATION: Dph-CRE79

<400> SEQUENCE: 79

| | | | | | |
|---|---|---|---|---|---|
| gactacaacc | tgccagctca | ggacgagagc | tgtcaggaag | agtccaggaa | tggacttccc | 60 |
| acgggagggc | acatttctgg | tattcctggc | aagataagga | gttgactaag | taatccacga | 120 |

```
gaaaaggcat tccggcaga ggaaacagtc tgggggtgag agggaggctg cagcatttgg      180
ggaactgcta gggctatcgt gtgtttggaa gaggggagg gagagaggta ggcagggcta      240
aattgggaat tttgtcactg acataaattt taagtgccag g                        281
```

<210> SEQ ID NO 80
<211> LENGTH: 393
<212> TYPE: DNA
<213> ORGANISM: Artificial Sequence
<220> FEATURE:
<223> OTHER INFORMATION: Dph-CRE80

<400> SEQUENCE: 80

```
cgttttgtgg taccaggggg tccctcctct cctgtcccca gccaaacctt ttcctttccc     60
ctcgggaaag ctgccttggc tgtcactacc tgctgcctat tccacatcct gaaccctgtg    120
acctaggccc agggctgctg cgcggacggt agctcccccct gcaggaagca aggttcctcc   180 ggcccccag actgctgctg gacctgtgca aagcctgca actttcctct gcctagcccg      240
gcccacttcc tggatgcttg ctgcccccag cccaccagag ctgtgagttc cattcctacc    300
ccctgcccca ctgagccctg atctaggtat gatcggtgca ttcatttttt tgctcaacaa    360
catttattac tgagcaccttt ctcaaggcca ggc                                393
```

<210> SEQ ID NO 81
<211> LENGTH: 169
<212> TYPE: DNA
<213> ORGANISM: Artificial Sequence
<220> FEATURE:
<223> OTHER INFORMATION: Dph-CRE81

<400> SEQUENCE: 81

```
cctaggccca gggctgctgc gcggacggta gctcccccctg caggaagcaa ggttcctccg    60
ggcccccaga ctgctgctgg acctgtgcag aagcctgcaa ctttcctctg cctagcccgg   120
cccacttcct ggatgcttgc tgcccccagc ccaccagagc tgtgagttc                169
```

<210> SEQ ID NO 82
<211> LENGTH: 390
<212> TYPE: DNA
<213> ORGANISM: Artificial Sequence
<220> FEATURE:
<223> OTHER INFORMATION: Dph-CRE82

<400> SEQUENCE: 82

```
gaagccaggt atcctggctg cccagccact gcctttatcc accagcttga ctctttcaga    60
tcatcttctc aaattatcca taggagattt atccacatac tcaataagaa aaatatttct   120
aattatatcc aaccattctt aatatgaatg agaattatgc ggggacgcta gattgccaag   180
aggtattttg ccaaacaatt cctttttgact taagaaagaa gaggcagctg cattgtttcc   240
atagctatcc atataaaaga gcccttggaa tgaggctgac tcgtcctgct ttaaaaagct    300
ccaaggtaag tgggagcagg acgggccttt caagagggac actggtcaca ccgcccagtg    360
tcagcagcag ctgctagttc tggtactgct                                    390
```

<210> SEQ ID NO 83
<211> LENGTH: 294
<212> TYPE: DNA
<213> ORGANISM: Artificial Sequence
<220> FEATURE:
<223> OTHER INFORMATION: Dph-CRE83

<400> SEQUENCE: 83

```
cagctgctag ttctggtact gctccttctg gaactgcacg ttttacctct atgaattttg      60
ttacttctgt ttacaatagc aagccatgcc ataaatggga ttttttcccc ctcttttttgg    120
tcaactaatc aagtgctttt ccctttttctt ttatagaact gtctcactcc caggctacat    180
cttctcactt gctaacaagg taagatttgg actaaccagt tcctggagga gaatgcaaga    240
ggctctggga tggatttctg tcacttagca acctttcaga aagtgcttgt ctca           294
```

<210> SEQ ID NO 84
<211> LENGTH: 460
<212> TYPE: DNA
<213> ORGANISM: Artificial Sequence
<220> FEATURE:
<223> OTHER INFORMATION: Dph-CRE84

<400> SEQUENCE: 84

```
taaagacctt tctcagagat ccaaaccagc cccacccccc gccccagga agcatagcat       60
atttttctgtg aggccttgat ggtagcatca caaacccttg ggaaacacaa ctcccagtgt   120
ttgaggagag catgccgtat cttgttccag ggacactgag tcgtgagcat aaaacgctgc    180
attccaaaag agacgaagaa gcagtcgtct ctccatttaa ttatagattc ttcactttcc    240
cttaattgct tcagtcagca ctgttgactc tggggagtc acagtacacc ggcagggcta    300
ttgctgttaa acaaggggtg actatcaggt aatgaggttt tcattttgtt ttttcaaaca    360
aacaaaccct gatgtacata ttcaagtggg cattcctgtt aaaggtgtca cattgggaaa   420
tgatgctcat gttgactctc ctttgtaacc aaatattgat                           460
```

<210> SEQ ID NO 85
<211> LENGTH: 292
<212> TYPE: DNA
<213> ORGANISM: Artificial Sequence
<220> FEATURE:
<223> OTHER INFORMATION: Dph-CRE85

<400> SEQUENCE: 85

```
taggaaggaa caagaagagg tagaaatgaa atggctccca aaagaaaaac ctcccttggg      60
tggtatttta ggacattagc tcaggctgcc ttgtcctcag tcatctcagt ggcatttaag    120
tagccccttg ggttacagat cacggcaggt gctgggaagt gaagaaggcc atgctaaaaa    180
tactggcctc ttctggaact ctgccggcag ccctgatgga gctccctcct caagcagcag    240
tacctcagca aaagaacagt ttcctccgcc ttaagcagta agaaaagtct gg             292
```

<210> SEQ ID NO 86
<211> LENGTH: 472
<212> TYPE: DNA
<213> ORGANISM: Artificial Sequence
<220> FEATURE:
<223> OTHER INFORMATION: Dph-CRE86

<400> SEQUENCE: 86

```
aagaaagggt ctttacaaaa ccaaaagaaa gcccattgct tactttaat aacctaggcc       60
cacccatagg cctctaaatc aaataacctc cactgagaat taagctgtta gcactaggtc   120
tggcataggt gcagaaacaa aagtttagaa atcctaatct tgaatttacc taacacggct   180
gcctcctaga gcctgagtgg gttgtagcga gacctcaagt agaggagagg cacctgggcc   240
atccgcctcc atgggctttt tttttttgc atcgaatttc atggtctgca aagtaagggt   300
ggggctttac ttgccattca ggaggttgca aaggtcacct ccacatatgt tcctgttaag   360
```

```
gacatcagca gaaacttgag aagcaagtat aaaaatataa aaatgagcag gtggcattca    420
ataggaaaag aatgcagggt ttgctgggaa gtcatgattg aaaccagtcc aa            472

<210> SEQ ID NO 87
<211> LENGTH: 476
<212> TYPE: DNA
<213> ORGANISM: Artificial Sequence
<220> FEATURE:
<223> OTHER INFORMATION: Dph-CRE87

<400> SEQUENCE: 87
aaggaagtga ccaggccagg tctggatccc tggaactgac tcctaactcc ctattcttgc    60
ctcctctgct gagctccaac ctggggagtc agctccctgg agtccacgca tctggatatc    120
gtccacatgc ctggaacttt gtcactgttc cggtggctgg gttgacacac cgtgattaaa    180
gggctctggt caatttctgt gccacgcagc ccctatgcta atggtcagat ctaatgttct    240
gaccattagg tcagtgtatc ttttccctcc tgggcagtta ggttagtgga agaaacccga    300
taaaatcttg gagaggaatt tgatcattct ctgaaggact acaagttgt ttggcctgcc    360 taatctgctc agataccgtc cggggaatat ttggtaacca tgcagtacag actgtgaatt    420
attctgtggg gactattaac aagaccctca ccaaccctgc ctcagctgat ctcagg       476

<210> SEQ ID NO 88
<211> LENGTH: 459
<212> TYPE: DNA
<213> ORGANISM: Artificial Sequence
<220> FEATURE:
<223> OTHER INFORMATION: Dph-CRE88

<400> SEQUENCE: 88
acagaccaaa ttgcctgagt ctaaactcaa tgttctttcc ccttagactg ccacccgcac    60
acacacgcac acatgcacac cttttggag gcactgcaca gcaagcacag aagtacgcca     120
ctgagtcctg tgtccctaaa gtatttgact gtccctccgc tgggggaaag ggcaggcaga    180
aaacaagact ccgtgtgctg tgctgtgcc gccccctgcc tctctgaccc cgcgcccgcag     240 agaaagtctc aagagccgcc ccaggctttc tcccacgttc tcccttttctc tgctgcagtt    300 gagtttccag agcgtgagcg cgcaggatga cacctggctg gctgagagct gccggggagg    360
cgctggcggg tgccgagagc gcactgaccc tgacgcgggg tgcagcacgg ctgggaagcc    420
cccgggcctt tggctaagcg cgccggggga cggcacagg                          459

<210> SEQ ID NO 89
<211> LENGTH: 378
<212> TYPE: DNA
<213> ORGANISM: Artificial Sequence
<220> FEATURE:
<223> OTHER INFORMATION: Dph-CRE89

<400> SEQUENCE: 89
gccccaacgc cctctccctg gcgcgcaggt ttagaaacag ggcggcctct ccggccgccg    60
cctcggcggc tcgggtcccc atatatagtc atatccaccg tcaactggga ggccggcggc    120
cggcagcgaa tgggcgagcg gccccccgcgg gaggagcggg gagggggcac ggggcggagg    180
gaggagagga ggaagggggg caggagaaaa aagcttttcc aaaaaagtat tggctgtctt    240
gaggaatgcg gtcgcccccct tgggaaagta catatctggg agaagcaggc ggctccgcgc    300
tcgcactccc gctcctccgc ccgaccgcgc gctcgccccg ccgctcctgc tgcagcccca    360
```

```
gggcccctcg ccgccgcc                                                  378
```

<210> SEQ ID NO 90
<211> LENGTH: 983
<212> TYPE: DNA
<213> ORGANISM: Artificial Sequence
<220> FEATURE:
<223> OTHER INFORMATION: mouse desmin promotor

<400> SEQUENCE: 90

```
accttgcttc ctagctgggc ctttccttct cctctataaa taccagctct ggtatttcgc    60
cttggcagct gttgctgcta gggagacggc tggcttgaca tgcatctcct gacaaaacac   120
aaacccgtgg tgtgagtggg tgtgggcggt gtgagtaggg ggatgaatca gagagggggc   180
gagggagaca ggggcgcagg agtcaggcaa aggcgatgcg ggggtgcgac tacacgcagt   240
tggaaacagt cgtcagaaga ttctggaaac tatcttgctg gctataaact tgagggaagc   300
agaaggccaa cattcctccc aagggaaact gaggctcaga gttaaaaccc aggtatcagt   360
gatatgcatg tgccccggcc agggtcactc tctgactaac cggtacctac cctacaggcc   420
tacctagaga ctcttttgaa aggatggtag agacctgtcc gggctttgcc cacagtcgtt   480
ggaaacctca gcattttcta gcaacttgt gcgaataaaa cacttcgggg gtccttcttg    540
ttcattccaa taacctaaaa cctctcctcg gagaaaatag ggggcctcaa acaaacgaaa   600
ttctctagcc cgctttcccc aggataaggc aggcatccaa atggaaaaaa aggggccggc   660
cgggggtctc ctgtcagctc cttgccctgt gaaacccagc aggcctgcct gtcttctgtc   720
ctcttggggc tgtccagggg cgcaggcctc ttgcggggga gctggcctcc ccgcccctc    780
gcctgtggcc gccctttttcc tggcaggaca gagggatcct gcagctgtca ggggaggggc   840
gccggggggt gatgtcagga gggctacaaa tagtgcagac agctaagggg ctccgtcacc    900
catcttcaca tccactccag ccggctgccc gcccgctgcc tcctctgtgc gtccgcccag    960
ccagcctcgt ccacgccgcc acc                                           983
```

<210> SEQ ID NO 91
<211> LENGTH: 1099
<212> TYPE: DNA
<213> ORGANISM: Artificial Sequence
<220> FEATURE:
<223> OTHER INFORMATION: human 1.0kb desmin promoter

<400> SEQUENCE: 91

```
tgtacaacgc gttacgcctc aggtaccccc tgcccccac agctcctctc ctgtgccttg     60
tttcccagcc atgcgttctc ctctataaat acccgctctg gtatttgggg ttggcagctg   120
ttgctgccag ggagatggtt gggttgacat gcggctcctg acaaaacaca aaccctggt    180
gtgtgtgggc gtgggtggtg tgagtagggg gatgaatcag ggaggggcg ggggacccag    240
ggggcaggag ccacacaaag tctgtgcggg ggtgggagcg cacatagcaa ttggaaactg   300
aaagcttatc agacccttc tggaaatcag cccactgttt ataaacttga ggccccaccc    360
tcgacagtac cggggaggaa gagggcctgc actagtccag agggaaactg aggctcaggg   420
ctagctcgcc catagacata catggcaggc aggctttggc caggatccct ccgcctgcca   480
ggcgtctccc tgccctccct tcctgcctag agaccccac cctcaagcct ggctggtctt    540
tgcctgagac ccaaacctct tcgacttcaa gagaatattt aggaacaagg tggtttaggg   600
cctttcctgg gaacaggcct tgacccttta agaaatgacc caaagtctct ccttgaccaa   660
aaggggacc ctcaaactaa agggaagcct ctcttctgct gtctccctg acccccactcc    720
```

| | | |
|---|---|---|
| cccccacccc aggacgagga gataaccagg gctgaaagag gcccgcctgg gggctgcaga | 780 | |
| catgcttgct gcctgccctg gcgaaggatt ggcaggcttg cccgtcacag gaccccgct | 840 | |
| ggctgactca ggggcgcagg cctcttgcgg gggagctggc ctccccgccc ccacggccac | 900 | |
| gggccgccct ttcctggcag gacagcggga tcttgcagct gtcaggggag gggaggcggg | 960 | |
| ggctgatgtc aggagggata caaatagtgc cgacggctgg gggccctgtc tccctcgcc | 1020 | |
| gcatccactc tccggccggc cgcctgcccg ccgcctcctc cgtgcgcccg ccagcctcgc | 1080 | |
| ccgcgccgtc acctctaga | 1099 | |

<210> SEQ ID NO 92
<211> LENGTH: 1426
<212> TYPE: DNA
<213> ORGANISM: Artificial Sequence
<220> FEATURE:
<223> OTHER INFORMATION: human 1.4kb desmin promotor

<400> SEQUENCE: 92

| | | |
|---|---|---|
| acacacctac tagtaacccc tccagctggt gatggcaggt ctagggtagg accagtgact | 60 | |
| ggctcctaat cgagcactct attttcaggg tttgcattcc aaaagggtca ggtccaagag | 120 | |
| ggacctggag tgccaagtgg aggtgtagag gcacggccag tacccatgga gaatggtgga | 180 | |
| tgtccttagg ggttagcaag tgccgtgtgc taaggagggg gctttggagg ttgggcaggc | 240 | |
| cctctgtggg gctccatttt tgtggggtg ggggctggag cattataggg ggtgggaagt | 300 | |
| gattggggct gtcaccctag ccttccttat ctgacgccca cccatgcctc ctcaggtacc | 360 | |
| ccctgccccc cacagctcct ctcctgtgcc ttgtttccca gccatgcgtt ctcctctata | 420 | |
| aatacccgct ctggtatttg gggttggcag ctgttgctgc cagggagatg gttgggttga | 480 | |
| catgcggctc ctgacaaaac acaaacccct ggtgtgtgtg ggcgtgggtg gtgtgagtag | 540 | |
| ggggatgaat cagggagggg gcgggggacc caggggcag gagccacaca aagtctgtgc | 600 | |
| gggggtggga gcgcacatag caattggaaa ctgaaagctt atcagaccct ttctggaaat | 660 | |
| cagcccactg tttataaact tgaggcccca ccctcgacag taccggggag gaagagggcc | 720 | |
| tgcactagtc cagagggaaa ctgaggctca ggctagctc gcccatagac atacatggca | 780 | |
| ggcaggcttt ggccaggatc cctccgcctg ccaggcgtct ccctgccctc ccttcctgcc | 840 | |
| tagagacccc cacccctcaag cctggctggt ctttgcctga acccaaacc tcttcgactt | 900 | |
| caagagaata tttaggaaca aggtggttta gggccttttcc tgggaacagg ccttgaccct | 960 | |
| ttaagaaatg acccaaagtc tctccttgac caaaaagggg accctcaaac taagggaag | 1020 | |
| cctctcttct gctgtctccc ctgaccccac tccccccac cccaggacga ggagataacc | 1080 | |
| agggctgaaa gaggcccgcc tggggggctgc agacatgctt gctgcctgcc ctggcgaagg | 1140 | |
| attggcaggc ttgcccgtca caggaccccc gctggctgac tcagggggcgc aggcctcttg | 1200 | |
| cgggggagct ggcctccccg ccccacggc cacgggccgc cctttcctgg caggacagcg | 1260 | |
| ggatcttgca gctgtcaggg gaggggaggc ggggggctgat gtcaggaggg atacaaatag | 1320 | |
| tgccgacggc tgggggccct gtctcccctc gccgcatcca ctctccggcc ggccgcctgc | 1380 | |
| ccgccgcctc ctccgtgcgc ccgccagcct cgcccgcgcc gtcacc | 1426 | |

<210> SEQ ID NO 93
<211> LENGTH: 2859
<212> TYPE: DNA
<213> ORGANISM: Artificial Sequence
<220> FEATURE:

<223> OTHER INFORMATION: human GAA sequence

<400> SEQUENCE: 93

```
atgggagtga ggcacccgcc ctgctcccac cggctcctgg ccgtctgcgc cctcgtgtcc      60
ttggcaaccg ctgcactcct ggggcacatc ctactccatg atttcctgct ggttccccga     120
gagctgagtg gctcctcccc agtcctggag gagactcacc cagctcacca gcagggagcc     180
agcagaccag gcccccggga tgcccaggca caccccggcc gtcccagagc agtgcccaca     240
cagtgcgacg tcccccccaa cagccgcttc gattgcgccc ctgacaaggc catcacccag     300
gaacagtgcg aggcccgcgg ctgttgctac atccctgcaa agcaggggct gcagggagcc     360
cagatggggc agccctggtg cttcttccca cccagctacc ccagctacaa gctggagaac     420
ctgagctcct ctgaaatggg ctacacggcc accctgaccc gtaccacccc caccttcttc     480
cccaaggaca tcctgaccct gcggctggac gtgatgatgg agactgagaa ccgcctccac     540
ttcacgatca agatccagc taacaggcgc tacgaggtgc ccttggagac ccgcatgtc      600
cacagccggg caccgtcccc actctacagc gtggagttct ccgaggagcc cttcggggtg     660
atcgtgcgcc ggcagctgga cggccgcgtg ctgctgaaca cgacggtggc gcccctgttc     720
tttgcggacc agttccttca gctgtccacc tcgctgccct cgcagtatat cacaggcctc     780
gccgagcacc tcagtcccct gatgctcagc accagctgga ccaggatcac cctgtggaac     840
cgggaccttg cgcccacgcc cggtgcgaac ctctacgggt ctcacccttt ctacctggcg     900
ctggaggacg gcgggtcggc acacggggtg ttcctgctaa acagcaatgc catggatgtg     960
gtcctgcagc cgagccctgc ccttagctgg aggtcgacag gtgggatcct ggatgtctac    1020
atcttcctgg gccagagccc aagagcgtg gtgcagcagt acctggacgt tgtgggatac    1080
ccgttcatgc cgccatactg gggcctgggc ttccacctgt gccgctgggg ctactcctcc    1140
accgctatca cccgccaggt ggtggagaac atgaccaggg cccacttccc cctggacgtc    1200
cagtggaacg acctggacta catggactcc cggaggact tcacgttcaa caaggatggc    1260
ttccgggact ccccggccat ggtgcaggag ctgcaccagg gcggccggcg ctacatgatg    1320
atcgtggatc ctgccatcag cagctcgggc cctgccggga gctacaggcc ctacgacgag    1380
ggtctgcgga gggggttttt catcaccaac gagaccggcc agccgctgat tgggaaggta    1440
tggccccggc caactgcctt cccccgactt caccaaccc cagccctggc ctggtgggag    1500
gacatggtgg ctgagttcca tgaccaggtg cccttcgacg gcatgtggat tgacatgaac    1560
gagccttcca acttcatcag gggctctgag gacggctgcc ccaacaatga gctggagaac    1620
ccaccctacg tgcctggggt ggttgggggg accctccagg cggccaccat ctgtgcctcc    1680
agccaccagt ttctctccac acactacaac ctgcacaacc tctacggcct gaccgaagcc    1740
atcgcctccc acagggcgct ggtgaaggct cggggacac gcccatttgt gatctcccgc    1800
tcgacctttg ctggccacgg ccgatacgcc ggccactgga cgggggacgt gtggagctcc    1860
tgggagcagc tcgcctcctc cgtgccagaa atcctgcagt taacctgct gggggtgcct    1920
ctggtcgggg ccgacgtctg cggcttcctg ggcaacacct cagaggagct gtgtgtgcgc    1980
tggacccagc tggggccctt ctaccccttc atgcggaacc acaacagcct gctcagtctg    2040
ccccaggagc cgtacagctt cagcgagccg gcccagcagg ccatgaggaa ggccctcacc    2100
ctgcgctacg cactcctccc ccacctctac acactgttcc accaggccca cgtcgcgggg    2160
gagaccgtgg cccggcccct cttcctggag ttccccaagg actctagcac ctggactgtg    2220
gaccaccagc tcctgtgggg ggaggccctg ctcatcaccc cagtgctcca ggccgggaag    2280
```

| | |
|---|---|
| gccgaagtga ctggctactt ccccttgggc acatggtacg acctgcagac ggtgccagta | 2340 |
| gaggcccttg gcagcctccc acccccacct gcagctcccc gtgagccagc catccacagc | 2400 |
| gaggggcagt gggtgacgct gccggccccc ctggacacca tcaacgtcca cctccgggct | 2460 |
| gggtacatca tccccctgca gggccctggc ctcacaacca cagagtcccg ccagcagccc | 2520 |
| atggccctgg ctgtggccct gaccaagggt ggggaggccc gagggagct gttctgggac | 2580 |
| gatggagaga gcctggaagt gctggagcga ggggcctaca cacaggtcat cttcctggcc | 2640 |
| aggaataaca cgatcgtgaa tgagctggta cgtgtgacca gtgagggagc tggcctgcag | 2700 |
| ctgcagaagg tgactgtcct gggcgtggcc acggcgcccc agcaggtcct ctccaacggt | 2760 |
| gtccctgtct ccaacttcac ctacagcccc gacaccaagg tcctggacat ctgtgtctcg | 2820 |
| ctgttgatgg gagagcagtt tctcgtcagc tggtgttag | 2859 |

<210> SEQ ID NO 94
<211> LENGTH: 2859
<212> TYPE: DNA
<213> ORGANISM: Artificial Sequence
<220> FEATURE:
<223> OTHER INFORMATION: human GAAco sequence

<400> SEQUENCE: 94

| | |
|---|---|
| atgggcgtca gacatcctcc atgttctcac agactgctgg ccgtgtgtgc tctggtgtct | 60 |
| cttgctacag ctgccctgct gggacatatc ctgctgcacg attttctgct ggtgccagag | 120 |
| gagctgtctg gcagctctcc tgtgctggaa gaaacacacc tgcacatca gcagggcgcc | 180 |
| tctagacctg gacctagaga tgctcaagcc catcctggca gacctagagc cgtgcctaca | 240 |
| cagtgtgacg tgccacctaa cagcagattc gactgcgccc ctgacaaggc catcacacaa | 300 |
| gagcagtgtg aagccagagg ctgctgctac attcctgcca acaaggact gcagggcgct | 360 |
| cagatgggac agccttggtg cttcttccca ccatcttacc ccagctacaa gctggaaaac | 420 |
| ctgagcagca gcgagatggg ctacaccgcc acactgacca gaaccacacc tacattcttc | 480 |
| ccaaaggaca tcctgacact gcggctggac gtgatgatgg aaaccgagaa ccggctgcac | 540 |
| ttcaccatca aggaccccgc caatagaaga tacgaggtgc ccctggaaac ccctcacgtg | 600 |
| cactctagag ccccatctcc actgtacagc gtggaattca gcgaggaacc ctttggcgtg | 660 |
| atcgtgcgga gacagctgga tgcagagtg ctgctgaata ccacagtggc ccctctgttc | 720 |
| ttcgccgacc agtttctgca gctgagcaca agcctgccta gccagtatat cacaggcctg | 780 |
| gccgaacacc tgtctccact gatgctgagc accagctgga ccagaatcac cctgtggaac | 840 |
| agagatctgg ccctacacc tggcgccaat ctgtacggct ctcaccctt ttatctggcc | 900 |
| ctggaagatg gcgaagcgc ccacggtgtc tttctgctga acagcaacgc catggacgtg | 960 |
| gtgctgcaac atctcctgc tctgtcttgg agaagcaccg gcggcatcct ggacgtgtac | 1020 |
| atctttctgg acccgagcc taagagcgtg gtgcagcagt atctggatgt cgtgggctac | 1080 |
| cccttcatgc ctccttattg gggcctgggc ttccacctgt gtagatgggg atacagctcc | 1140 |
| accgccatca ccagacaggt ggtggaaaac atgacccggg ctcacttccc actggatgtg | 1200 |
| cagtggaacg acctggacta catggactcc agacgggact tcacctttaa caaggacggc | 1260 |
| ttcagagact tccccgccat ggtgcaagaa ctgcatcaag cggcagacg gtacatgatg | 1320 |
| atcgtggatc ctgccatctc ttctagcggc cctgccggaa gctacagacc ttatgatgag | 1380 |
| ggcctgagaa gaggcgtgtt catcaccaat gagacaggcc agcctctgat cggcaaagtg | 1440 |

```
tggcctggaa gcaccgcctt tccagacttc accaatccaa ccgctctggc ttggtgggaa      1500
gatatggtgg ccgagttcca cgatcaggtg cccttcgatg catgtggat cgacatgaac      1560 gagcccagca acttcatcag gggcagcgag gatggctgcc ccaacaacga actggaaaat    1620
cctccttacg tgccaggcgt tgtcggagga acactgcagg ccgccacaat tgtgccagc     1680 agccatcagt ttctgagcac ccactacaac ctgcacaacc tgtacggcct gaccgaggcc    1740
attgcctctc atagagccct ggttaaggcc agaggcaccc ggccttttgt gatcagcaga    1800
agcacatttg ccggccacgg cagatatgcc ggacattgga caggggacgt tggtctagt    1860 tgggagcagc tggcctctag cgtgcccgag atcctgcagt ttaatctgct gggagtgccc   1920
ctcgtgggag ccgatgtttg tggatttctg ggcaacacct ccgaggaact gtgcgtcaga   1980
tggacacagc tgggcgcctt ctatcccttc atgagaaacc acaacagcct gctgagcctg   2040
cctcaagagc cttacagctt tagcgaaccc gcacagcagg ccatgagaaa ggccctgact   2100
ctgagatacg ctctgctgcc ccacctgtac accctgtttc atcaagctca tgtggccggc   2160
gagacagtgg ccagaccact gtttctggaa ttccccaagg acagcagcac ctggacagtg   2220
gatcatcagc tgctctgggg agaagccctg ctcattacac ctgtgctgca ggctggcaag   2280
gccgaagtga caggatactt tcccctcggc acttggtacg acctgcagac agttcctgtg   2340
gaagctctgg gatctctgcc tccacctcct gctgctccta gagagcctgc cattcactct   2400
gaaggccagt gggttacact gcccgctcca ctggacacca tcaatgtgca cctgagagcc   2460
ggctacatca tccctctgca aggccctgga ctgaccacaa ccgaaagcag acagcagcca   2520
atggctctgg ccgtggctct gacaaaaggc ggagaagcta gaggcgaact gttctgggat   2580
gacggcgaga gcctggaagt gctggaacgg ggagcctaca cacaagtgat cttcctcgcc   2640
cggaacaaca ccatcgtgaa cgaactcgtc agagtgacca gtgaaggtgc cggactgcag   2700
ctccagaaag tgacagtgct tggagtggcc acagcacccc agcaggtttt gtctaatggc   2760
gtgcccgtgt ccaacttcac atacagccct gacaccaagg tgctggacat ctgtgtgtct   2820
ctgctgatgg gcgagcagtt cctggtgtcc tggtgttga                           2859
```

<210> SEQ ID NO 95
<211> LENGTH: 1812
<212> TYPE: DNA
<213> ORGANISM: Artificial Sequence
<220> FEATURE:
<223> OTHER INFORMATION: human MTM1 sequence

<400> SEQUENCE: 95

```
atggcttctg catcaacttc taaatataat tcacactcct tggagaatga gtctattaag     60
aggacgtctc gagatggagt caatcgagat ctcactgagg ctgttcctcg acttccagga   120
gaaacactaa tcactgacaa agaagttatt tacatatgtc ctttcaatgg ccccattaag   180
ggaagagttt acatcacaaa ttatcgtctt tatttaagaa gtttggaaac ggattcttct   240
ctaatacttg atgttcctct gggtgtgatc tcgagaattg aaaaaatggg aggcgcgaca   300
agtagaggag aaaattccta tggtctagat attacttgta agacatgag aaacctgagg   360 ttcgctttga acaggaagg ccacagcaga agagatatgt tgagatcct cacgagatac    420 gcgtttcccc tggctcacag tctgccatta tttgcatttt taaatgaaga aaagtttaac    480
gtggatggat ggcagtttta caatccagtg aagaataca ggaggcaggg cttgcccaat    540
caccattgga gaataacttt tattaataag tgctatgagc tctgtgacac ttaccctgct    600
cttttggtgg ttccgtatcg tgcctcagat gatgacctcc ggagagttgc aactttagg    660
```

```
tcccgaaatc gaattccagt gctgtcatgg attcatccag aaaataagac ggtcattgtg    720
cgttgcagtc agcctcttgt cggtatgagt gggaaacgaa ataaagatga tgagaaatat    780
ctcgatgtta tcaggagac taataaacaa atttctaaac tcaccattta tgatgcaaga    840
cccagcgtaa atgcagtggc caacaaggca acaggaggag gatatgaaag tgatgatgca    900
tatcataacg ccgaactttt cttcttagac attcataata ttcatgttat gcgggaatct    960
ttaaaaaaag tgaaggacat tgtttatcct aatgtagaag aatctcattg gttgtccagt   1020
ttggagtcta ctcattggtt agaacatatc aagctcgttt tgacaggagc cattcaagta   1080
gcagacaaag tttcttcagg gaagagttca gtgcttgtgc attgcagtga cggatgggac   1140
aggactgctc agctgacatc cttggccatg ctgatgttgg atagcttcta taggagcatt   1200
gaagggttcg aaatactggt acaaaaaaaa tggataagtt ttggacataa atttgcatct   1260
cgaataggtc atggtgataa aaaccacacc gatgctgacc gttctcctat ttttctccag   1320
tttattgatt gtgtgtggca aatgtcaaaa cagttcccta cagcttttga attcaatgaa   1380 caattttga ttataatttt ggatcatctg tatagttgcc gatttggtac tttcttattc   1440
aactgtgaat ctgctcgaga aagacagaag gttacagaaa ggactgtttc tttatggtca   1500
ctgataaaca gtaataaaga aaaattcaaa aaccccttct atactaaaga aatcaatcga   1560
gttttatatc cagttgccag tatgcgtcac ttggaactct gggtgaatta ctacattaga   1620
tggaacccca ggatcaagca acaacagccg aatccagtgg agcagcgtta catggagctc   1680
ttagccttac gcgacgaata cataaagcgg cttgaggaac tgcagctcgc caactctgcc   1740
aagctttctg atcccccaac ttcaccttcc agtccttcgc aaatgatgcc ccatgtgcaa   1800
actcacttct ga                                                       1812
```

<210> SEQ ID NO 96
<211> LENGTH: 1812
<212> TYPE: DNA
<213> ORGANISM: Artificial Sequence
<220> FEATURE:
<223> OTHER INFORMATION: human MTM1co sequence

<400> SEQUENCE: 96

```
atggccagcg ccagcacaag caagtacaac agccacagcc tggaaaacga gagcatcaag     60
cggaccagca gagatggcgt gaacagagat ctgaccgagg ccgttcctag actgcctggc    120
gagacactga tcaccgacaa agaagtgatc tacatctgcc ccttcaacgg ccccatcaag    180
ggaagagtgt acatccaccaa ctaccggctg tacctgcggt ccctggaaac cgatagcagc    240
ctgattctgg atgtgccccct gggcgtgatc agccggattg aaaaaatggg cggagccacc    300
tccagaggcg agaatagcta tggcctggat atcacatgca aggacatgcg gaacctgaga    360
ttcgccctga gcaagagggg ccacagcaga cgggacatgt cgagatcct gaccagatac    420 gcctttcctc tggctcactc tctgcccctg ttcgccttcc tgaacgaaga aagttcaac    480 gtggacggct ggaccgtgta caaccccgtg gaagagtata cggcaggg actgcccaat    540 caccactggc ggatcacctt catcaacaag tgctacgagc tgtgcgacac ataccccgca    600
ctgctggtgg tgccttacag agcctctgac gacgatctga agagtggc cacctttcgg    660 agccggaaca gaatccctgt gctgagctgg attcaccccg agaacaagac cgtgatcgtg    720
cggtgttctc agcctctcgt gggcatgagc ggcaagagaa acaaggacga cgagaagtac    780
ctggacgtga tccgcgagac aaacaagcag atcagcaagc tgaccatcta cgacgccaga    840
```

```
ccttctgtga acgccgtggc caacaaagcc acaggcggcg atatgagtc cgacgatgcc     900
tatcacaacg ccgagctgtt cttcctggac attcacaaca tccatgtgat gcgcgagagc    960
ctgaagaaag tgaaggacat cgtgtacccc aatgtggaag agagccactg gctgtctagc   1020
ctggaatcca cacactggct ggaacacatc aagctggtgc tgacaggcgc catccaggtg   1080
gcagacaaag tgtctagcgg caagtctagc gtgctggtgc actgtagcga cggatgggat   1140
agaacagccc agctgacatc cctggccatg ctgatgctgg acagcttcta cagatccatc   1200
gagggctttg agatcctggt gcagaagaag tggatcagct tcggccacaa gttcgcctct   1260
agaatcggac acggcgacaa gaaccacacc gacgccgata aagcccccat cttcctgcag   1320
ttcatcgact gcgtgtggca gatgtccaag cagttcccta ccgccttcga gttcaacgag   1380
cagttcctga tcatcatcct ggaccacctg tactcttgca gattcggcac cttcctgttc   1440
aactgcgaga gcgccagaga acggcagaaa gtgaccgaga aaccgtgtc tctgtggtcc    1500
ctgatcaaca gcaacaaaga gaaattcaag aacccttct acaccaaaga aatcaaccgg   1560
gtgctgtacc ccgtggccag catgagacat ctggaactgt gggtcaacta ctacatccgg   1620
tggaaccca gaatcaagca gcagcagccc aatcctgtgg aacagcggta tatggaactg   1680
ctggcccgtg gggacgagta catcaagaga ctggaagaac tgcagctggc caacagcgcc   1740
aagctgagcg atcctcctac aagccctagc agcccctctc agatgatgcc ccatgtgcag   1800
acccactttt ga                                                       1812

<210> SEQ ID NO 97
<211> LENGTH: 6024
<212> TYPE: DNA
<213> ORGANISM: Artificial Sequence
<220> FEATURE:
<223> OTHER INFORMATION: plasmid pAAVss-CRE02-CSkSH5-SPc5-12_GTRM-Luc2

<400> SEQUENCE: 97
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgac aggtgcggtt cccggagcgc aggcgcacac   180
atgcacccac cggcgaacgc ggtgaccctc gccccacccc atccctccg gcgggcaact   240
gggtcgggtc aggaggggca aacccgctag ggagacactc catatacggc ccggcccgcg   300
ttacctggga ccgggccaac ccgctccttc tttggtcaac gcaggggacc cgggcggggg   360
cccaggccgc gaaccggccg agggagggg ctctagtgcc caacacccaa atatggctcg   420
agaagggcag cgacattcct gcggggtggc gcggagggaa tgcccgcggg ctatataaaa   480
cctgagcaga gggacaagcg gccaccgcag cggacagcgc caagtgaagc ctcgcttccc   540
ctccgcggcg accagggccc gagccgagag tagcagttgt agctaccgc ccaggtaggg    600
gcgcgccacg cgtcagttta ctcaccaggg attcagaggc agcactgctg aaccctgagc   660
ccttggcaca tcaggttggc tgtcagaagt cggccttgt acatacacag ttcccttgtg    720
aggcccagct gcgtgtccta ggagcggggc ctctctccac agcagagctc agcctctcaa   780
gtgtatggac agcacgggtg cctgatgggt ggatttagcc atgagttgaa ggtgccttgg   840
ggagaatgag agttctagag atagggagaa ggggttgcca ataggagagt ggaattcctg   900
agcacctcgt cacaggcagc cgacagaaca tgagccgcag ggcccaggct atttatacct   960
cgcctgtcac tatcagggtc cccacagctc cccccacctc cagccacaca cagcaggtcc   1020
ttttgctctt tctggtccct tctctactcc tccccctccc tacctaaggt acccaacgcg   1080
```

```
ttacgtggcc accgccttcg gcaccatcct cacgacaccc aaatatggcg acgggtgagg    1140
aatggtgggg agttattttt agagcggtga ggaaggtggg caggcagcag gtgttggcgc    1200
tctaaaaata actcccggga gttattttta gagcggagga atggtggaca cccaaatatg    1260
gcgacggttc ctcacccgtc gccatatttg ggtgtccgcc ctcggccggg gccgcattcc    1320
tgggggccgg gcggtgctcc cgcccgcctc gataaaaggc tccggggccg gcggcggccc    1380
acgagctacc cggaggagcg ggaggcgcca agctctagat ctagaaagag gtaagggttt    1440
aagggatggt tggttggtgg ggtattaatg tttaattacc tggagcacct gcctgaaatc    1500
acttttttc aggttggaag cttatggaag atgccaaaaa cattaagaag ggcccagcgc    1560
cattctaccc actcgaggac gggaccgccg gcgagcagct gcacaaagcc atgaagcgct    1620
acgccctggt gccggcacc atcgccttta ccgacgcaca tatcgaggtg gacattacct    1680
acgccgagta cttcgagatg agcgttcggc tggcagaagc tatgaagcgc tatgggctga    1740
atacaaacca tcggatcgtg gtgtgcagcg agaatagctt gcagttcttc atgcccgtgt    1800
tgggtgccct gttcatcggt gtggctgtgg ccccagctaa cgacatctac aacgagcgcg    1860
agctgctgaa cagcatgggc atcagccagc ccaccgtcgt attcgtgagc aagaaagggc    1920
tgcaaaagat cctcaacgtg caaaagaagc taccgatcat acaaaagatc atcatcatgg    1980
atagcaagac cgactaccag ggcttccaaa gcatgtacac cttcgtgact tcccatttgc    2040
cacccggctt caacgagtac gacttcgtgc ccgagagctt cgaccgggac aaaaccatcg    2100
ccctgatcat gaacagtagt ggcagtaccg gattgcccaa gggcgtagcc ctaccgcacc    2160
gcaccgcttg tgtccgattc agtcatgccc gcgacccat cttcggcaac cagatcatcc    2220
ccgacaccgc tatcctcagc gtggtgccat tcaccacgg cttcggcatg ttcaccacgc    2280
tgggctactt gatctgcggc tttcgggtcg tgctcatgta ccgcttcgag gaggagctat    2340
tcttgcgcag cttgcaagac tataagattc aatctgccct gctggtgccc acactattta    2400
gcttcttcgc taagagcact ctcatcgaca agtacgacct aagcaacttg cacgagatcg    2460
ccagcggcgg ggcgccgctc agcaaggagg taggtgaggc cgtggccaaa cgcttccacc    2520
taccaggcat ccgccagggc tacggcctga cagaaacaac cagcgccatt ctgatcaccc    2580
ccgaagggga cgacaagcct ggcgcagtag gcaaggtggt gcccttcttc gaggctaagg    2640
tggtggactt ggacaccggt aagacactgg gtgtgaacca gcgcggcgag ctgtgcgtcc    2700
gtggccccat gatcatgagc ggctacgtta caaccccga ggctacaaac gctctcatcg    2760
acaaggacgg ctggctgcac agcggcgaca tcgcctactg ggacgaggac gagcacttct    2820
tcatcgtgga ccggctgaag agcctgatca aatacaaggg ctaccaggta gccccagccg    2880
aactggagag catcctgctg caacacccca acatcttcga cgccggggtc gccggcctgc    2940
ccgacgacga tgccggcgag ctgcccgccg cagtcgtcgt gctggaacac ggtaaaacca    3000
tgaccgagaa ggagatcgtg gactatgtgg ccagccaggt tacaaccgcc aagaagctgc    3060
gcggtggtgt tgtgttcgtg gacgaggtgc ctaaaggact gaccggcaag ttggacgccc    3120
gcaagatccg cgagattctc attaaggcca agaagggcgg caagatcgcc gtgtaattcg    3180
aaacgtcaag tccatcttga gcatctgact tctggctaaa taaagatct ttattttcat    3240
tagatctgtg tgttggtttt ttgtgtgcgt cgagatccac ggccgcagga accctagtg    3300
atggagttgg ccactccctc tctgcgcgct cgctcgctca ctgaggccgg gcgaccaaag    3360
gtcgcccgac gcccgggctt tgcccgggcg gcctcagtga gcgagcgagc gcgcagctgc    3420
```

```
ctgcaggggc gcctgatgcg gtattttctc cttacgcatc tgtgcggtat ttcacaccgc   3480
atacgtcaaa gcaaccatag tacgcgccct gtagcggcgc attaagcgcg gcgggtgtgg   3540
tggttacgcg cagcgtgacc gctacacttg ccagcgccct agcgcccgct cctttcgctt   3600
tcttcccttc ctttctcgcc acgttcgccg gctttccccg tcaagctcta atcgggggc    3660 tccctttagg gttccgattt agtgctttac ggcacctcga ccccaaaaaa cttgatttgg   3720
gtgatggttc acgtagtggg ccatcgccct gatagacgtt ttttcgccct ttgacgttgg   3780
agtccacgtt ctttaatagt ggactcttgt tccaaactgg aacaacactc aaccctatct   3840
cgggctattc ttttgattta aagggatttt gccgatttc ggcctattgg ttaaaaaatg     3900
agctgattta acaaaaattt aacgcgaatt ttaacaaaat attaacgttt acaattttat   3960
ggtgcactct cagtacaatc tgctctgatg ccgcatagtt aagccagccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgagacgaaa gggcctcgtg atacgcctat ttttataggt taatgtcatg ataataatgg   4200
tttcttagac gtcaggtggc acttttcggg gaaatgtgcg cggaacccct atttgtttat   4260
ttttctaaat acattcaaat atgtatccgc tcatgagaca ataaccctga taaatgcttc   4320
aataatattg aaaaggaag agtatgagta ttcaacattt ccgtgtcgcc cttattccct    4380
tttttgcggc attttgcctt cctgtttttg ctcacccaga aacgctggtg aaagtaaaag   4440
atgctgaaga tcagttgggt gcacgagtgg gttacatcga actggatctc aacagcggta   4500
agatccttga gagttttcgc cccgaagaac gttttccaat gatgagcact tttaaagttc   4560
tgctatgtgg cgcggtatta tcccgtattg acgccgggca agagcaactc ggtcgccgca   4620
tacactattc tcagaatgac ttggttgagt actcaccagt cacagaaaag catcttacgg   4680
atggcatgac agtaagagaa ttatgcagtg ctgccataac catgagtgat aacactgcgg   4740
ccaacttact tctgacaacg atcggaggac cgaaggagct aaccgctttt ttgcacaaca   4800
tgggggatca tgtaactcgc cttgatcgtt gggaaccgga gctgaatgaa gccataccaa   4860
acgacgagcg tgacaccacg atgcctgtag caatggcaac aacgttgcgc aaactattaa   4920
ctggcgaact acttactcta gcttcccggc aacaattaat agactggatg gaggcggata   4980
aagttgcagg accacttctg cgctcggccc ttccggctgg ctggtttatt gctgataaat   5040
ctggagccgg tgagcgtggg tctcgcggta tcattgcagc actggggcca gatggtaagc   5100
cctcccgtat cgtagttatc tacacgacgg ggagtcaggc aactatggat gaacgaaata   5160
gacagatcgc tgagataggt gcctcactga ttaagcattg gtaactgtca gaccaagttt   5220
actcatatat actttagatt gatttaaaac ttcattttta atttaaaagg atctaggtga   5280
agatcctttt tgataatctc atgaccaaaa tcccttaacg tgagttttcg ttccactgag   5340
cgtcagaccc cgtagaaaag atcaaaggat cttcttgaga tcctttttt ctgcgcgtaa    5400 tctgctgctt gcaaacaaaa aaaccaccgc taccagcggt ggtttgtttg ccggatcaag   5460
agctaccaac tcttttccg aaggtaactg gcttcagcag agcgcagata ccaaatactg    5520
tccttctagt gtagccgtag ttaggccacc acttcaagaa ctctgtagca ccgcctacat   5580
acctcgctct gctaatcctg ttaccagtgg ctgctgccag tggcgataag tcgtgtctta   5640
ccgggttgga ctcaagacga tagttaccgg ataaggcgca gcggtcgggc tgaacggggg   5700
gttcgtgcac acagcccagc ttggagcgaa cgacctacac cgaactgaga tacctacagc   5760
gtgagctatg agaaagcgcc acgcttcccg aagggagaaa ggcggacagg tatccggtaa   5820
```

```
gcggcagggt cggaacagga gagcgcacga gggagcttcc aggggggaaac gcctggtatc    5880 tttatagtcc tgtcgggttt cgccacctct gacttgagcg tcgattttg tgatgctcgt     5940 caggggggcg gagcctatgg aaaaacgcca gcaacgcggc ctttttacgg ttcctggcct    6000
tttgctggcc ttttgctcac atgt                                           6024

<210> SEQ ID NO 98
<211> LENGTH: 6081
<212> TYPE: DNA
<213> ORGANISM: Artificial Sequence
<220> FEATURE:
<223> OTHER INFORMATION: plasmid pAAVss-CRE04-CSkSH5-SPc5-12_GTRM-Luc2

<400> SEQUENCE: 98
acatgtcctg caggcagctg cgcgctcgct cgctcactga ggccgcccgg gcaaagcccg     60
ggcgtcgggc gacctttggt cgcccggcct cagtgagcga gcgagcgcgc agagagggag    120
tggccaactc catcactagg ggttcctgcg gccccttta gagaatccac acctgtccca    180
gttgctgggt tccactacca aaagtgaatt gcaactattt taggagcact taagcacatc    240
cgaaaaatga gtgattctgt tctggcccac accacatcac tgatgtaccc ccttaaagca    300
tgtccctgag ttcatcacag aagactgctc ctcctgtgcc ctccacaagg ttagaactgt    360
ccttgtctta gggaaaaagg agagagagag agagagagag agagagagag agagagagag    420
agagagagag ggacaggcac caactgggta acctctgctg accccactc tactttacca    480 taagtagctc caaatccttc tagaaaatct gaaaggcata gccccatata tcagtgatat    540
aaatagaacc tgcagcaggc tctggtaaat gatgactaca aggtggactg ggaggcagcc    600
cggccttggc aggcatcatc ctctaaatat aaagatgagt ttgttcagcc tttgcagaag    660
gaggcgcgcc acgcgtcagt ttactcacca gggattcaga ggcagcactg ctgaaccctg    720
agcccttggc acatcaggtt ggctgtcaga agtcggcctt tgtacataca cagttccctt    780
gtgaggccca gctgcgtgtc ctaggagcgg ggcctctctc cacagcagag ctcagcctct    840
caagtgtatg acagcacgg gtgcctgatg ggtggattta gccatgagtt gaaggtggct    900
tggggagaat gagagttcta gagatagggga gaagggggttg ccaataggag agtggaattc    960
ctgagcacct cgtcacaggc agccgacaga acatgagccg cagggcccag gctatttata   1020
cctcgcctgt cactatcagg gtccccacag ctccccccac ctccagccac acacagcagg   1080 tcctttttgct ctttctggtc ccttctctac tcctccccct ccctacctaa ggtacccaac   1140
gcgttacgtg gccaccgcct tcggcaccat cctcacgaca cccaaatatg gcgacgggtg   1200
aggaatggtg gggagttatt tttagagcgg tgaggaaggt gggcaggcag caggtgttgg   1260
cgctctaaaa ataactcccg ggagttattt ttagagcgga ggaatggtgg acacccaaat   1320
atggcgacgg ttcctcaccc gtcgccatat ttgggtgtcc gccctcggcc ggggccgcat   1380 tcctggggc cggcggtgc tcccgcccgc ctcgataaaa ggctccgggg ccggcggcg    1440 cccacgagct acccggagga gcgggaggcg ccaagctcta gatctagaaa gaggtaaggg   1500
tttaagggat ggttggttgg tgggtatta atgtttaatt acctggagca cctgcctgaa   1560 atcactttt ttcaggttgg aagcttatgg aagatgccaa aaacattaag aagggcccag   1620
cgccattcta cccactcgag gacgggaccg ccggcgagca gctgcacaaa gccatgaagc   1680
gctacgccct ggtgcccggc accatcgcct taccgacgc acatatcgag gtggacatta   1740
cctacgccga gtacttcgag atgagcgttc ggctggcaga agctatgaag cgctatgggc   1800
```

```
tgaatacaaa ccatcggatc gtggtgtgca gcgagaatag cttgcagttc ttcatgcccg    1860
tgttgggtgc cctgttcatc ggtgtggctg tggccccagc taacgacatc tacaacgagc    1920
gcgagctgct gaacagcatg ggcatcagcc agcccaccgt cgtattcgtg agcaagaaag    1980
ggctgcaaaa gatcctcaac gtgcaaaaga agctaccgat catacaaaag atcatcatca    2040
tggatagcaa gaccgactac cagggcttcc aaagcatgta caccttcgtg acttcccatt    2100
tgccacccgg cttcaacgag tacgacttcg tgcccgagag cttcgaccgg gacaaaacca    2160
tcgccctgat catgaacagt agtggcagta ccggattgcc caagggcgta gccctaccgc    2220
accgcaccgc ttgtgtccga ttcagtcatg cccgcgaccc catcttcggc aaccagatca    2280
tccccgacac cgctatcctc agcgtggtgc catttcacca cggcttcggc atgttcacca    2340
cgctgggcta cttgatctgc ggctttcggg tcgtgctcat gtaccgcttc gaggaggagc    2400
tattcttgcg cagcttgcaa gactataaga ttcaatctgc cctgctggtg cccacactat    2460
ttagcttctt cgctaagagc actctcatcg acaagtacga cctaagcaac ttgcacgaga    2520
tcgccagcgg cggggcgccg ctcagcaagg aggtaggtga ggccgtggcc aaacgcttcc    2580
acctaccagg catccgccag ggctacggcc tgacagaaac aaccagcgcc attctgatca    2640
cccccgaagg ggacgacaag cctggcgcag taggcaaggt ggtgcccttc ttcgaggcta    2700
aggtggtgga cttggacacc ggtaagacac tgggtgtgaa ccagcgcggc gagctgtgcg    2760
tccgtggccc catgatcatg agcggctacg ttaacaaccc cgaggctaca aacgctctca    2820
tcgacaagga cggctggctg cacagcggcg acatcgccta ctgggacgag gacgagcact    2880
tcttcatcgt ggaccggctg aagagcctga tcaaatacaa gggctaccag gtagccccag    2940
ccgaactgga gagcatcctg ctgcaacacc ccaacatctt cgacgccggg gtcgccggcc    3000
tgcccgacga cgatgccggc gagctgcccg ccgcagtcgt cgtgctggaa cacggtaaaa    3060
ccatgaccga aaggagatc gtggactatg tggccagcca ggttacaacc gccaagaagc    3120
tgcgcggtgg tgttgtgttc gtggacgagg tgcctaaagg actgaccggc aagttggacg    3180
cccgcaagat ccgcgagatt ctcattaagg ccaagaaggg cggcaagatc gccgtgtaat    3240
tcgaaacgtc acgtccatct tgagcatctg acttctggct aaataaaaga tctttatttt    3300
cattagatct gtgtgttggt ttttgtgtg cgtcgagatc cacggccgca ggaacccta    3360
gtgatggagt tggccactcc ctctctgcgc gctcgctcgc tcactgaggc cgggcgacca    3420
aaggtcgccc gacgcccggg cttttgcccgg gcggcctcag tgagcgagcg agcgcgcagc    3480
tgcctgcagg ggcgcctgat gcggtatttt ctccttacgc atctgtgcgg tatttcacac    3540
cgcatacgtc aaagcaacca tagtacgcgc cctgtagcgg cgcattaagc gcggcgggtg    3600
tggtggttac gcgcagcgtg accgctacac ttgccagcgc cctagcgccc gctcctttcg    3660
ctttcttccc ttcctttctc gccacgttcg ccggctttcc ccgtcaagct ctaaatcggg    3720
ggctcccttt agggttccga tttagtgctt tacggcacct cgaccccaaa aaacttgatt    3780
tgggtgatgg ttcacgtagt gggccatcgc cctgatagac ggtttttcgc cctttgacgt    3840
tggagtccac gttctttaat agtggactct tgttccaaac tggaacaaca ctcaacccta    3900
tctcgggcta ttcttttgat ttataaggga ttttgccgat ttcggcctat tggttaaaaa    3960
atgagctgat ttaacaaaaa tttaacgcga attttaacaa aatattaacg tttacaattt    4020
tatggtgcac tctcagtaca atctgctctg atgccgcata gttaagccag ccccgacacc    4080
cgccaacacc cgctgacgcg ccctgacggg cttgtctgct cccggcatcc gcttacagac    4140
aagctgtgac cgtctccggg agctgcatgt gtcagaggtt ttcaccgtca tcaccgaaac    4200
```

-continued

```
gcgcgagacg aaagggcctc gtgatacgcc tattttata ggttaatgtc atgataataa    4260
tggtttctta gacgtcaggt ggcactttc ggggaaatgt gcgcggaacc cctatttgtt    4320
tattttcta aatacattca aatatgtatc cgctcatgag acaataaccc tgataaatgc    4380
ttcaataata ttgaaaaagg aagagtatga gtattcaaca tttccgtgtc gcccttattc    4440
ccttttttgc ggcatttgc cttcctgttt tgctcaccc agaaacgctg gtgaaagtaa    4500
aagatgctga agatcagttg ggtgcacgag tgggttacat cgaactggat ctcaacagcg    4560
gtaagatcct tgagagtttt cgccccgaag aacgttttcc aatgatgagc acttttaaag    4620
ttctgctatg tggcgcggta ttatcccgta ttgacgccgg gcaagagcaa ctcggtcgcc    4680
gcatacacta ttctcagaat gacttggttg agtactcacc agtcacagaa aagcatctta    4740
cggatggcat gacagtaaga gaattatgca gtgctgccat aaccatgagt gataacactg    4800
cggccaactt acttctgaca acgatcggag gaccgaagga gctaaccgct ttttgcaca    4860
acatggggga tcatgtaact cgccttgatc gttgggaacc ggagctgaat gaagccatac    4920
caaacgacga gcgtgacacc acgatgcctg tagcaatggc aacaacgttg cgcaaactat    4980
taactggcga actacttact ctagcttccc ggcaacaatt aatagactgg atggaggcgg    5040
ataaagttgc aggaccactt ctgcgctcgg cccttccggc tggctggttt attgctgata    5100
aatctggagc cggtgagcgt gggtctcgcg gtatcattgc agcactgggg ccagatggta    5160
agccctcccg tatcgtagtt atctacacga cggggagtca ggcaactatg gatgaacgaa    5220
atagacagat cgctgagata ggtgcctcac tgattaagca ttggtaactg tcagaccaag    5280
tttactcata tatactttag attgatttaa aacttcattt ttaatttaaa aggatctagg    5340
tgaagatcct ttttgataat ctcatgacca aaatccctta acgtgagttt tcgttccact    5400
gagcgtcaga ccccgtagaa aagatcaaag gatcttcttg agatcctttt tttctgcgcg    5460
taatctgctg cttgcaaaca aaaaaaccac cgctaccagc ggtggtttgt ttgccggatc    5520
aagagctacc aactctttt ccgaaggtaa ctggcttcag cagagcgcag ataccaaata    5580
ctgtccttct agtgtagccg tagttaggcc accacttcaa gaactctgta gcaccgccta    5640
catacctcgc tctgctaatc ctgttaccag tggctgctgc cagtggcgat aagtcgtgtc    5700
ttaccgggtt ggactcaaga cgatagttac cggataaggc gcagcggtcg ggctgaacgg    5760
ggggttcgtg cacacagccc agcttggagc gaacgaccta ccgaactg agataccta    5820
agcgtgagct atgagaaagc gccacgcttc ccgaagggag aaaggcggac aggtatccgg    5880
taagcggcag ggtcggaaca ggagagcgca cgagggagct tccaggggga aacgcctggt    5940
atctttatag tcctgtcggg tttcgccacc tctgacttga gcgtcgattt tgtgatgct    6000
cgtcaggggg gcggagccta tggaaaaacg ccagcaacgc ggcctttta cggttcctgg    6060
ccttttgctg gccttttgct c                                              6081
```

<210> SEQ ID NO 99
<211> LENGTH: 5972
<212> TYPE: DNA
<213> ORGANISM: Artificial Sequence
<220> FEATURE:
<223> OTHER INFORMATION: plasmid pAAVss-CRE06-CSkSH5-SPc5-12_GTRM-Luc2

<400> SEQUENCE: 99

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
```

| | |
|---|---|
| actccatcac tagggttcc tgcggccggg ccaggggacg gtggcttcta cgtgcttggg | 180 |
| acgttcccag ccaccgtccc atgttccgg cggggggcca gctgtcccca ccgccagccc | 240 |
| aactcagcac ttggtcaggg tatcagcttg gtggggggc gtgagcccag ccctggggc | 300 |
| ggctcagccc atacaaggcc atgggctgg gcgcaaagca tgcctgggtt cagggtgggt | 360 |
| atggtgcggg agcagggagg tgagaggctc agctgccctc cagaactcct ccctggggac | 420 |
| aacccctccc agccaatagc acagcctagg tccccctata taaggccacg gctgctggcc | 480 |
| cttcctttgg gtcagtgtca cctccaggat acagacagcc ccccttcagc ccagcccagc | 540 |
| caggtacggc gcgccacgcg tcagtttact caccagggat tcagaggcag cactgctgaa | 600 |
| ccctgagccc ttggcacatc aggttggctg tcagaagtcg gcctttgtac atacacagtt | 660 |
| cccttgtgag gccagctgc gtgtcctagg agcggggcct ctctccacag cagagctcag | 720 |
| cctctcaagt gtatggacag cacgggtgcc tgatgggtgg atttagccat gagttgaagg | 780 |
| tggcttgggg agaatgagag ttctagagat agggagaagg ggttgccaat aggagagtgg | 840 |
| aattcctgag cacctcgtca caggcagccg acagaacatg agccgcaggg cccaggctat | 900 |
| ttatacctcg cctgtcacta tcagggtccc cacagctccc cccacctcca gccacacaca | 960 |
| gcaggtcctt ttgctctttc tggtcccttc tctactcctc cccctcccta cctaaggtac | 1020 |
| ccaacgcgtt acgtggccac cgccttcggc accatcctca cgacacccaa atatggcgac | 1080 |
| gggtgaggaa tggtggggag ttatttttag agcggtgagg aaggtgggca ggcagcaggt | 1140 |
| gttggcgctc taaaaataac tcccgggagt tattttaga gcggaggaat ggtggacacc | 1200 |
| caaatatggc gacggttcct cacccgtcgc catatttggg tgtccgccct cggccggggc | 1260 |
| cgcattcctg ggggccgggc ggtgctcccg cccgcctcga taaaaggctc cggggccggc | 1320 |
| ggcggcccac gagctacccg gaggagcggg aggcgccaag ctctagatct agaaagaggt | 1380 |
| aagggtttaa gggatggttg gttggtgggg tattaatgtt taattacctg gagcacctgc | 1440 |
| ctgaaatcac ttttttttcag gttggaagct tatggaagat gccaaaaaca ttaagaaggg | 1500 |
| cccagcgcca ttctacccac tcgaggacgg gaccgccggc gagcagctgc acaaagccat | 1560 |
| gaagcgctac gccctggtgc ccggcaccat cgccttttacc gacgcacata tcgaggtgga | 1620 |
| cattacctac gccgagtact tcgagatgag cgttcggctg gcagaagcta tgaagcgcta | 1680 |
| tgggctgaat acaaaccatc ggatcgtggt gtgcagcgag aatagcttgc agttcttcat | 1740 |
| gcccgtgttg ggtgccctgt tcatcggtgt ggctgtggcc ccagctaacg acatctacaa | 1800 |
| cgagcgcgag ctgctgaaca gcatgggcat cagccagccc accgtcgtat tcgtgagcaa | 1860 |
| gaaagggctg caaaagatcc tcaacgtgca aaagaagcta ccgatcatac aaaagatcat | 1920 |
| catcatggat agcaagaccg actaccaggg cttccaaagc atgtacacct tcgtgacttc | 1980 |
| ccatttgcca cccggcttca acgagtacga cttcgtgccc gagagcttcg accgggacaa | 2040 |
| aaccatcgcc ctgatcatga acagtagtgg cagtaccgga ttgcccaagg gcgtagccct | 2100 |
| accgcaccgc accgcttgtg tccgattcag tcatgcccgc gacccatct tcggcaacca | 2160 |
| gatcatcccc gacaccgcta tcctcagcgt ggtgccattt caccacggct tcggcatgtt | 2220 |
| caccacgctg ggctacttga tctgcggctt tcgggtcgtg ctcatgtacc gcttcgagga | 2280 |
| ggagctattc ttgcgcagct tgcaagacta taagattcaa tctgccctgc tggtgcccac | 2340 |
| actatttagc ttcttcgcta agagcactct catcgacaag tacgacctaa gcaacttgca | 2400 |
| cgagatcgcc agcggcgggg cgccgctcag caaggaggta ggtgaggccg tggccaaacg | 2460 |
| cttccaccta ccaggcatcc gccagggcta cggcctgaca gaaacaacca gcgccattct | 2520 |

```
gatcacccccc gaaggggacg acaagcctgg cgcagtaggc aaggtggtgc ccttcttcga   2580
ggctaaggtg gtggacttgg acaccggtaa gacactgggt gtgaaccagc gcggcgagct   2640
gtgcgtccgt ggccccatga tcatgagcgg ctacgttaac aaccccgagg ctacaaacgc   2700
tctcatcgac aaggacggct ggctgcacag cggcgacatc gcctactggg acgaggacga   2760
gcacttcttc atcgtggacc ggctgaagag cctgatcaaa tacaagggct accaggtagc   2820
cccagccgaa ctggagagca tcctgctgca cacccccaac atcttcgacg ccggggtcgc   2880
cggcctgccc gacgacgatg ccggcgagct gcccgccgca gtcgtcgtgc tggaacacgg   2940
taaaaccatg accgagaagg agatcgtgga ctatgtggcc agccaggtta caaccgccaa   3000
gaagctgcgc ggtggtgttg tgttcgtgga cgaggtgcct aaaggactga ccggcaagtt   3060
ggacgcccgc aagatccgcg agattctcat taaggccaag aagggcggca agatcgccgt   3120
gtaattcgaa acgtctagtc catcttgagc atctgacttc tggctaaata aaagatcttt   3180
attttcatta gatctgtgtg ttggtttttt gtgtgcgtcg agatccacgg ccgcaggaac   3240
ccctagtgat ggagttggcc actccctctc tgcgcgctcg ctcgctcact gaggccgggc   3300
gaccaaaggt cgcccgacgc ccgggctttg cccgggcggc ctcagtgagc gagcgagcgc   3360
gcagctgcct gcagggggcgc ctgatgcggt attttctcct tacgcatctg tgcggtattt   3420
cacaccgcat acgtcaaagc aaccatagta cgcgccctgt agcggcgcat taagcgcggc   3480
gggtgtggtg gttacgcgca gcgtgaccgc tacacttgcc agcgccctag cgcccgctcc   3540
tttcgctttc ttcccttcct ttctcgccac gttcgccggc tttccccgtc aagctctaaa   3600 tcggggggctc cctttagggt tccgatttag tgctttacgg cacctcgacc ccaaaaaact   3660
tgatttgggt gatggttcac gtagtgggcc atcgccctga tagacggttt ttcgcccttt   3720
gacgttggag tccacgttct ttaatagtgg actcttgttc caaactggaa caacactcaa   3780
ccctatctcg gctattctt ttgatttata agggattttg ccgatttcgg cctattggtt   3840
aaaaaatgag ctgatttaac aaaaatttaa cgcgaatttt aacaaaatat taacgtttac   3900
aattttatgg tgcactctca gtacaatctg ctctgatgcc gcatagttaa gccagccccg   3960
acacccgcca cacccgctg acgcgccctg acgggcttgt ctgctcccgg catccgctta   4020
cagacaagct gtgaccgtct ccgggagctg catgtgtcag aggttttcac cgtcatcacc   4080
gaaacgcgcg agacgaaagg gcctcgtgat acgcctattt ttataggtta atgtcatgat   4140
aataatggtt tcttagacgt caggtggcac ttttcgggga atgtgcgcg aacccctat   4200 ttgttatttt ttctaaatac attcaaatat gtatccgctc atgagacaat aaccctgata   4260
aatgcttcaa taatattgaa aaaggaagag tatgagtatt caacatttcc gtgtcgccct   4320
tattcccttt tttgcggcat tttgccttcc tgttttgtct cacccagaaa cgctggtgaa   4380
agtaaaagat gctgaagatc agttgggtgc acgagtgggt tacatcgaac tggatctcaa   4440
cagcggtaag atccttgaga gttttcgccc cgaagaacgt tttccaatga tgagcacttt   4500
taaagttctg ctatgtggcg cggtattatc ccgtattgac gccgggcaag agcaactcgg   4560
tcgccgcata cactattctc agaatgactt ggttgagtac tcaccagtca cagaaaagca   4620
tcttacggat ggcatgacag taagagaatt atgcagtgct gccataacca tgagtgataa   4680
cactgcggcc aacttacttc tgacaacgat cggaggaccg aaggagctaa ccgcttttttt   4740 gcacaacatg ggggatcatg taactcgcct tgatcgttgg gaaccggagc tgaatgaagc   4800
cataccaaac gacgagcgtg acaccacgat gcctgtagca atggcaacaa cgttgcgcaa   4860
```

```
actattaact ggcgaactac ttactctagc ttcccggcaa caattaatag actggatgga    4920
ggcggataaa gttgcaggac cacttctgcg ctcggccctt ccggctggct ggtttattgc    4980
tgataaatct ggagccggtg agcgtgggtc tcgcggtatc attgcagcac tggggccaga    5040
tggtaagccc tcccgtatcg tagttatcta cacgacgggg agtcaggcaa ctatggatga    5100
acgaaataga cagatcgctg agataggtgc ctcactgatt aagcattggt aactgtcaga    5160
ccaagtttac tcatatatac tttagattga tttaaaactt cattttaat ttaaaaggat    5220 ctaggtgaag atccttttg ataatctcat gaccaaaatc ccttaacgtg agttttcgtt    5280
ccactgagcg tcagacccg tagaaaagat caaaggatct tcttgagatc cttttttct    5340 gcgcgtaatc tgctgcttgc aaacaaaaaa accaccgcta ccagcggtgg tttgtttgcc    5400
ggatcaagag ctaccaactc tttttccgaa ggtaactggc ttcagcagag cgcagatacc    5460
aaatactgtc cttctagtgt agccgtagtt aggccaccac ttcaagaact ctgtagcacc    5520
gcctacatac ctcgctctgc taatcctgtt accagtggct gctgccagtg gcgataagtc    5580
gtgtcttacc gggttggact caagacgata gttaccggat aaggcgcagc ggtcgggctg    5640
aacggggggt tcgtgcacac agcccagctt ggagcgaacg acctacaccg aactgagata    5700
cctacagcgt gagctatgag aaagcgccac gcttcccgaa gggagaaagg cggacaggta    5760
tccggtaagc ggcagggtcg gaacaggaga gcgcacgagg gagcttccag ggggaaacgc    5820
ctggtatctt tatagtcctg tcgggtttcg ccacctctga cttgagcgtc gatttttgtg    5880
atgctcgtca gggggggcgga gcctatggaa aaacgccagc aacgcggcct ttttacggtt    5940
cctggccttt tgctggcctt ttgctcacat gt                                 5972

<210> SEQ ID NO 100
<211> LENGTH: 5827
<212> TYPE: DNA
<213> ORGANISM: Artificial Sequence
<220> FEATURE:
<223> OTHER INFORMATION: plasmid pAAVss-CRE07-CSkSH5-SPc5-12_GTRM-Luc2

<400> SEQUENCE: 100
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccccc agccccttc cccggaggt gggagcggcc     180 acccagggcc ccgtggctgc ccttgtaagg aggcgaggcc cgaggacacc cgagacgccc     240
ggttataatt aaccaggaca cgtggcgaac cccctccaa cacctgcccc cgaacccccc     300
catacccagc gcctcgggtc tcggcctttg cggcagagga gacagcaaag cgccctctaa     360
aaataactcc tttcccggcg accgagaccc tccctgtccc ccggcgcgcc acgcgtcagt     420
ttactcacca gggattcaga ggcagcactg ctgaaccctg agcccttggc acatcaggtt     480
ggctgtcaga agtcggcctt tgtacataca cagttccctt gtgaggccca gctgcgtgtc     540
ctaggagcgg ggcctctctc cacagcagag ctcagcctct caagtgtatg acagcacgg     600 gtgcctgatg ggtggattta gccatgagtt gaaggtggct tggggagaat gagagttcta     660 gagatagga gaaggggttg ccaataggag agtggaattc ctgagcacct cgtcacaggc     720
agccgacaga acatgagccg cagggcccag gctatttata cctcgcctgt cactatcagg     780
gtccccacag ctccccccac ctccagccac acacagcagg tccttttgct ctttctggtc     840
ccttctctac tcctcccct ccctacctaa ggtacccaac gcgttacgtg gccaccgcct     900
tcggcaccat cctcacgaca cccaaatatg gcgacgggtg aggaatggtg gggagttatt     960
```

-continued

```
tttagagcgg tgaggaaggt gggcaggcag caggtgttgg cgctctaaaa ataactcccg    1020
ggagttattt ttagagcgga ggaatggtgg acacccaaat atggcgacgg ttcctcaccc    1080
gtcgccatat ttgggtgtcc gccctcggcc ggggccgcat tcctggggc  cgggcggtgc    1140
tcccgcccgc ctcgataaaa ggctccgggg ccggcggcgg cccacgagct acccggagga    1200
gcgggaggcg ccaagctcta gatctagaaa gaggtaaggg tttaagggat ggttggttgg    1260
tggggtatta atgtttaatt acctggagca cctgcctgaa atcacttttt ttcaggttgg    1320
aagcttatgg aagatgccaa aaacattaag aagggcccag cgccattcta cccactcgag    1380
gacgggaccg ccggcgagca gctgcacaaa gccatgaagc gctacgccct ggtgcccggc    1440
accatcgcct ttaccgacgc acatatcgag gtggacatta cctacgccga gtacttcgag    1500
atgagcgttc ggctggcaga agctatgaag cgctatgggc tgaatacaaa ccatcggatc    1560
gtggtgtgca gcgagaatag cttgcagttc ttcatgcccg tgttgggtgc cctgttcatc    1620
ggtgtggctg tggccccagc taacgacatc tacaacgagc gcgagctgct gaacagcatg    1680
ggcatcagcc agcccaccgt cgtattcgtg agcaagaaag ggctgcaaaa gatcctcaac    1740
gtgcaaaaga gctaccgat  catacaaaag atcatcatca tggatagcaa gaccgactac    1800
cagggcttcc aaagcatgta caccttcgtg acttcccatt tgccaccgg  cttcaacgag    1860
tacgacttcg tgcccgagag cttcgaccgg gacaaaacca tcgccctgat catgaacagt    1920
agtggcagta ccggattgcc caagggcgta gccctaccgc accgcaccgc ttgtgtccga    1980
ttcagtcatg cccgcgaccc catcttcggc aaccagatca tccccgacac cgctatcctc    2040
agcgtggtgc catttcacca cggcttcggc atgttcacca cgctgggcta cttgatctgc    2100
ggctttcggg tcgtgctcat gtaccgcttc gaggaggagc tattcttgcg cagcttgcaa    2160
gactataaga ttcaatctgc cctgctggtg cccacactat ttagcttctt cgctaagagc    2220
actctcatcg acaagtacga cctaagcaac ttgcacgaga tcgccagcgg cggggcgccg    2280
ctcagcaagg aggtaggtga ggccgtggcc aaacgcttcc acctaccagg catccgccag    2340
ggctacggcc tgacagaaac aaccagcgcc attctgatca cccccgaagg ggacgacaag    2400
cctggcgcag taggcaaggt ggtgcccttc ttcgaggcta aggtggtgga cttggacacc    2460
ggtaagacac tgggtgtgaa ccagcgcggc gagctgtgcg tccgtggccc catgatcatg    2520
agcggctacg ttaacaaccc cgaggctaca acgctctca  tcgacaagga cggctggctg    2580
cacagcggcg acatcgccta ctgggacgag gacgagcact tcttcatcgt ggaccggctg    2640
aagagcctga tcaaatacaa gggctaccag gtagccccag ccgaactgga gagcatcctg    2700
ctgcaacacc ccaacatctt cgacgccggg gtcgccggcc tgcccgacga cgatgccggc    2760
gagctgcccg ccgcagtcgt cgtgctggaa cacggtaaaa ccatgaccga agg gagatc    2820
gtggactatg tggccagcca ggttacaacc gccaagaagc tgcgcggtgg tgttgtgttc    2880
gtggacgagg tgcctaaagg actgaccggc aagttggacg cccgcaagat ccgcgagatt    2940
ctcattaagg ccaagaaggg cggcaagatc gccgtgtaat tcgaaacgtc ttgtccatct    3000
tgagcatctg acttctggct aaataaaaga tctttatttt cattagatct gtgtgttggt    3060
tttttgtgtg cgtcgagatc cacggccgca ggaaccccta gtgatggagt tggccactcc    3120
ctctctgcgc gctcgctcgc tcactgaggc cgggcgacca aggtcgccc  gacgcccggg    3180
ctttgccccgg gcggcctcag tgagcgagcg agcgcgcagc tgcctgcagg ggcgcctgat    3240
gcggtatttt ctccttacgc atctgtgcgg tatttcacac cgcatacgtc aaagcaacca    3300
```

```
tagtacgcgc cctgtagcgg cgcattaagc gcggcgggtg tggtggttac gcgcagcgtg      3360
accgctacac ttgccagcgc cctagcgccc gctcctttcg ctttcttccc ttcctttctc      3420
gccacgttcg ccggctttcc ccgtcaagct ctaaatcggg ggctcccttt agggttccga      3480
tttagtgctt tacggcacct cgaccccaaa aaacttgatt tgggtgatgg ttcacgtagt      3540
gggccatcgc cctgatagac ggttttcgc cctttgacgt tggagtccac gttctttaat      3600
agtggactct tgttccaaac tggaacaaca ctcaaccta tctcgggcta ttctttgat       3660 ttataaggga ttttgccgat tcggcctat tggttaaaaa atgagctgat ttaacaaaaa      3720
tttaacgcga attttaacaa aatattaacg tttacaattt tatggtgcac tctcagtaca      3780
atctgctctg atgccgcata gttaagccag ccccgacacc cgccaacacc cgctgacgcg      3840
ccctgacggg cttgtctgct cccggcatcc gcttacagac aagctgtgac cgtctccggg      3900
agctgcatgt gtcagaggtt ttcaccgtca tcaccgaaac gcgcgagacg aaagggcctc      3960
gtgatacgcc tatttttata ggttaatgtc atgataataa tggtttctta gacgtcaggt      4020
ggcacttttc ggggaaatgt gcgcggaacc cctatttgtt tattttcta aatacattca      4080 aatatgtatc cgctcatgag acaataaccc tgataaatgc ttcaataata ttgaaaaagg      4140
aagagtatga gtattcaaca tttccgtgtc gcccttattc cctttttgc ggcatttgc       4200 cttcctgttt ttgctcaccc agaaacgctg gtgaaagtaa agatgctga agatcagttg      4260 ggtgcacgag tgggttacat cgaactggat ctcaacagcg gtaagatcct tgagagtttt      4320
cgccccgaag aacgttttcc aatgatgagc acttttaaag ttctgctatg tggcgcggta      4380
ttatcccgta ttgacgccgg gcaagagcaa ctcggtcgcc gcatacacta ttctcagaat      4440
gacttggttg agtactcacc agtcacagaa aagcatctta cggatggcat gacagtaaga      4500
gaattatgca gtgctgccat aaccatgagt gataacactg cggccaactt acttctgaca      4560
acgatcggag gaccgaagga gctaaccgct ttttgcaca acatggggga tcatgtaact      4620
cgccttgatc gttgggaacc ggagctgaat gaagccatac caaacgacga gcgtgacacc      4680
acgatgcctg tagcaatggc aacaacgttg cgcaaactat taactggcga actacttact      4740
ctagcttccc ggcaacaatt aatagactgg atggaggcgg ataaagttgc aggaccactt      4800
ctgcgctcgg cccttccggc tggctggttt attgctgata aatctggagc cggtgagcgt      4860
gggtctcgcg gtatcattgc agcactgggg ccagatggta agccctcccg tatcgtagtt      4920
atctacacga cggggagtca ggcaactatg gatgaacgaa atagacagat cgctgagata      4980
ggtgcctcac tgattaagca ttggtaactg tcagaccaag tttactcata tactttag       5040 attgatttaa aacttcattt ttaatttaaa aggatctagg tgaagatcct ttttgataat      5100
ctcatgacca aaatccctta acgtgagttt tcgttccact gagcgtcaga ccccgtagaa      5160
aagatcaaag gatcttcttg agatcctttt tttctgcgcg taatctgctg cttgcaaaca      5220
aaaaaaccac cgctaccagc ggtggtttgt ttgccggatc aagagctacc aactcttttt      5280
ccgaaggtaa ctggcttcag cagagcgcag ataccaaata ctgtccttct agtgtagccg      5340
tagttaggcc accacttcaa gaactctgta gcaccgccta catacctcgc tctgctaatc      5400
ctgttaccag tggctgctgc cagtggcgat aagtcgtgtc ttaccgggtt ggactcaaga      5460
cgatagttac cggataaggc gcagcggtcg ggctgaacgg ggggttcgtg cacacagccc      5520
agcttggagc gaacgaccta caccgaactg agatacctac agcgtgagct atgagaaagc      5580
gccacgcttc ccgaagggag aaaggcggac aggtatccgg taagcggcag gtcggaaca       5640 ggagagcgca cgagggagct tccaggggga aacgcctggt atctttatag tcctgtcggg      5700
```

```
tttcgccacc tctgacttga gcgtcgattt ttgtgatgct cgtcaggggg gcggagccta    5760
tggaaaaacg ccagcaacgc ggcctttttta cggttcctgg ccttttgctg gccttttgct    5820
cacatgt                                                                5827
```

<210> SEQ ID NO 101
<211> LENGTH: 5891
<212> TYPE: DNA
<213> ORGANISM: Artificial Sequence
<220> FEATURE:
<223> OTHER INFORMATION: plasmid pAAVss-CRE66-CSkSH5-SPc5-12_GTRM-Luc2

<400> SEQUENCE: 101

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggcccca ggtgacaggt ggatggtgga gctggaggag    180
ccactcggag cctccaaggc tggggagggt ggaggggga ggcaggtcgg tgtcccaggc      240
cacacctgtt gactaaggga ttaggatgtt gtgtccctgc cagccctcct ccaataagcc     300
cctctgggcc tgcagggaga ggaggagcct tgccatgtaa actgtatttt tagttccctg     360
tgcctctccc cggctgctat aagacacctc tccccacccc cagccctggc cgcttggctg     420
gaggctctgc gaggacagct ggggagaagg ggagctgtgg tcagtaggcg cgccacgcgt     480
cagtttactc accagggatt cagaggcagc actgctgaac cctgagccct ggcacatca     540 ggttggctgt cagaagtcgg cctttgtaca tacacagttc ccttgtgagg cccagctgcg    600
tgtcctagga gcggggcctc tctccacagc agagctcagc ctctcaagtg tatggacagc    660
acgggtgcct gatgggtgga tttagccatg agttgaaggt ggcttgggga gaatgagagt    720
tctagagata gggagaaggg gttgccaata ggagagtgga attcctgagc acctcgtcac    780
aggcagccga cagaacatga ccgcagggc ccaggctatt tatacctcgc ctgtcactat    840
cagggtcccc acagctcccc ccacctccag ccacacacag caggtccttt tgctctttct   900
ggtcccttct ctactcctcc ccctccctac ctaaggtacc caacgcgtta cgtggccacc    960
gccttcggca ccatcctcac gacacccaaa tatggcgacg ggtgaggaat ggtggggagt   1020 tattttaga gcggtgagga aggtgggcag gcagcaggtg ttggcgctct aaaaataact   1080
cccgggagtt attttagag cggaggaatg gtggacaccc aaatatggcg acggttcctc    1140
acccgtcgcc atatttgggt gtccgccctc ggccggggcc gcattcctgg gggccgggcg   1200
gtgctcccgc ccgcctcgat aaaaggctcc ggggccggcg gcggcccacg agctacccgg   1260
aggagcggga ggcgccaagc tctagatcta gaaagaggta agggtttaag ggatggttgg   1320
ttggtggggt attaatgttt aattacctgg agcacctgcc tgaaatcact ttttttcagg    1380
ttggaagctt atggaagatg ccaaaaacat taagaagggc ccagcgccat tctacccact    1440
cgaggacggg accgccggcg agcagctgca caaagccatg aagcgctacg ccctggtgcc    1500
cggcaccatc gcctttaccg acgcacatat cgaggtggac attacctacg ccgagtactt    1560
cgagatgagc gttcggctgg cagaagctat gaagcgctat gggctgaata caaaccatcg    1620
gatcgtggtg tgcagcgaga atagcttgca gttcttcatg cccgtgttgg tgccctgtt    1680 catcggtgtg gctgtggccc agctaacga catctacaac gagcgcgagc tgctgaacag   1740
catgggcatc agccagccca ccgtcgtatt cgtgagcaag aaagggctgc aaaagatcct   1800
caacgtgcaa aagaagctac cgatcataca aaagatcatc atcatggata gcaagaccga   1860
```

```
ctaccagggc ttccaaagca tgtacacctt cgtgacttcc catttgccac ccggcttcaa    1920
cgagtacgac ttcgtgcccg agagcttcga ccgggacaaa accatcgccc tgatcatgaa    1980
cagtagtggc agtaccggat tgcccaaggg cgtagcccta ccgcaccgca ccgcttgtgt    2040
ccgattcagt catgcccgcg acccccatct tcggcaaccag atcatccccg acaccgctat   2100
cctcagcgtg gtgccatttc accacggctt cggcatgttc accacgctgg gctacttgat    2160
ctgcggcttt cgggtcgtgc tcatgtaccg cttcgaggag gagctattct tgcgcagctt    2220
gcaagactat aagattcaat ctgccctgct ggtgcccaca ctatttagct tcttcgctaa    2280
gagcactctc atcgacaagt acgacctaag caacttgcac gagatcgcca gcggcggggc    2340
gccgctcagc aaggaggtag gtgaggccgt ggccaaacgc ttccacctac caggcatccg    2400
ccagggctac ggcctgacag aaacaaccag cgccattctg atcaccccg aaggggacga     2460 caagcctggc gcagtaggca aggtggtgcc cttcttcgag gctaaggtgg tggacttgga    2520
caccggtaag acactgggtg tgaaccagcg cggcgagctg tgcgtccgtg gccccatgat    2580
catgagcggc tacgttaaca ccccgaggc tacaaacgct ctcatcgaca aggacggctg     2640
gctgcacagc ggcgacatcg cctactggga cgaggacgag cacttcttca tcgtggaccg    2700
gctgaagagc ctgatcaaat acaagggcta ccaggtagcc ccagccgaac tggagagcat    2760
cctgctgcaa caccccaaca tcttcgacgc cggggtcgcc ggcctgcccg acgacgatgc    2820
cggcgagctg cccgccgcag tcgtcgtgct ggaacacggt aaaaccatga ccgagaagga    2880
gatcgtggac tatgtggcca gccaggttac aaccgccaag aagctgcgcg tggtgttgt     2940 gttcgtggac gaggtgccta aaggactgac cggcaagttg gacgcccgca agatccgcga    3000
gattctcatt aaggccaaga agggcggcaa gatcgccgtg taattcgaaa cgtactgtcc    3060
atcttgagca tctgacttct ggctaaataa aagatcttta ttttcattag atctgtgtgt    3120 tggtttttg tgtgcgtcga gatccacggc cgcaggaacc cctagtgatg gagttggcca    3180
ctccctctct gcgcgctcgc tcgctcactg aggccgggcg accaaaggtc gcccgacgcc    3240
cgggctttgc ccgggcggcc tcagtgagcg agcgagcgcg cagctgcctg cagggcgcc    3300 tgatgcggta ttttctcctt acgcatctgt gcggtatttc acaccgcata cgtcaaagca    3360
accatagtac gcgccctgta gcggcgcatt aagcgcggcg ggtgtggtgg ttacgcgcag    3420
cgtgaccgct acacttgcca gcgccctagc gcccgctcct ttcgctttct tcccttcctt    3480
tctcgccacg ttcgccggct ttccccgtca agctctaaat cggggctcc ctttagggtt     3540 ccgatttagt gctttacggc acctcgaccc caaaaaactt gatttgggtg atggttcacg    3600
tagtgggcca tcgccctgat agacggtttt tcgccctttg acgttggagt ccacgttctt    3660
taatagtgga ctcttgttcc aaactggaac aacactcaac cctatctcgg gctattcttt    3720
tgatttataa gggattttgc cgatttcggc ctattggtta aaaaatgagc tgatttaaca    3780
aaaatttaac gcgaatttta caaaatatt aacgtttaca attttatggt gcactctcag     3840
tacaatctgc tctgatgccg catagttaag ccagccccga cacccgccaa cacccgctga    3900
cgcgccctga cgggcttgtc tgctcccggc atccgcttac agacaagctg tgaccgtctc    3960
cgggagctga tgtgtcaga ggttttcacc gtcatcaccg aaacgcgcga cacgaaaggg     4020
cctcgtgata cgcctatttt tataggttaa tgtcatgata ataatggttt cttagacgtc    4080
aggtggcact tttcggggaa atgtgcgcgg aaccctatt tgtttatttt tctaaataca     4140
ttcaaatatg tatccgctca tgagacaata accctgataa atgcttcaat aatattgaaa    4200
aaggaagagt atgagtattc aacatttccg tgtcgccctt attccttttt tgcggcatt    4260
```

```
ttgccttcct gttttttgctc acccagaaac gctggtgaaa gtaaaagatg ctgaagatca    4320
gttgggtgca cgagtgggtt acatcgaact ggatctcaac agcggtaaga tccttgagag    4380
ttttcgcccc gaagaacgtt ttccaatgat gagcactttt aaagttctgc tatgtggcgc    4440
ggtattatcc cgtattgacg ccgggcaaga gcaactcggt cgccgcatac actattctca    4500
gaatgacttg gttgagtact caccagtcac agaaaagcat cttacggatg gcatgacagt    4560
aagagaatta tgcagtgctg ccataaccat gagtgataac actgcggcca acttacttct    4620
gacaacgatc ggaggaccga aggagctaac cgcttttttg cacaacatgg ggatcatgt     4680 aactcgcctt gatcgttggg aaccggagct gaatgaagcc ataccaaacg acgagcgtga    4740
caccacgatg cctgtagcaa tggcaacaac gttgcgcaaa ctattaactg gcgaactact    4800
tactctagct tcccggcaac aattaataga ctggatggag gcggataaag ttgcaggacc    4860
acttctgcgc tcggcccttc cggctggctg gtttattgct gataaatctg gagccggtga    4920
gcgtgggtct cgcggtatca ttgcagcact ggggccagat ggtaagccct cccgtatcgt    4980
agttatctac acgacgggga gtcaggcaac tatggatgaa cgaaatagac agatcgctga    5040
gataggtgcc tcactgatta agcattggta actgtcagac caagtttact catatatact    5100
ttagattgat ttaaaacttc attttttaatt taaaaggatc taggtgaaga tcctttttga    5160
taatctcatg accaaaatcc cttaacgtga gttttcgttc cactgagcgt cagaccccgt    5220
agaaaagatc aaaggatctt cttgagatcc tttttttctg cgcgtaatct gctgcttgca    5280
aacaaaaaaa ccaccgctac cagcggtggt ttgtttgccg gatcaagagc taccaactct    5340
ttttccgaag gtaactggct tcagcagagc gcagatacca atactgtcc ttctagtgta     5400 gccgtagtta ggccaccact tcaagaactc tgtagcaccg cctacatacc tcgctctgct    5460
aatcctgtta ccagtggctg ctgccagtgg cgataagtcg tgtcttaccg ggttggactc    5520
aagacgatag ttaccggata aggcgcagcg gtcgggctga acggggggtt cgtgcacaca    5580
gcccagcttg gagcgaacga cctacaccga actgagatac ctacagcgtg agctatgaga    5640
aagcgccacg cttcccgaag ggagaaaggc ggacaggtat ccggtaagcg cagggtcgg     5700 aacaggagag cgcacgaggg agcttccagg gggaaacgcc tggtatcttt atagtcctgt    5760
cgggtttcgc cacctctgac ttgagcgtcg attttttgtga tgctcgtcag ggggggcggag  5820 cctatggaaa aacgccagca acgcggcctt tttacggttc ctggccttttt gctggccttt   5880 tgctcacatg t                                                         5891
```

<210> SEQ ID NO 102
<211> LENGTH: 5865
<212> TYPE: DNA
<213> ORGANISM: Artificial Sequence
<220> FEATURE:
<223> OTHER INFORMATION: plasmid pAAVss-CRE68-CSkSH5-SPc5-12_GTRM-Luc2

<400> SEQUENCE: 102

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccaga aaggagctgc cctggggatg gctgtgtatc     180
cctacaactg ccaggcacat gccccttgaa cacccgatgc tacgtgtccc aaaggaaact     240
ggtctccacc cacccccggc ccgtcctcgt cctgggtacc ccaccttagt aaatggcgcc     300
accatctgcc cggtcactca gcgagaaact caactcctgg cagcagatga cgggcactct     360
```

| | |
|---|---|
| ggttaaatga ctctctccag cctccaagtt caacctgcag ggaagccctg gaaatcctgt | 420 |
| ctccctctgc cctgcctctc ggcgcgccac gcgtcagttt actcaccagg gattcagagg | 480 |
| cagcactgct gaaccctgag cccttggcac atcaggttgg ctgtcagaag tcggcctttg | 540 |
| tacatacaca gttcccttgt gaggcccagc tgcgtgtcct aggagcgggg cctctctcca | 600 |
| cagcagagct cagcctctca agtgtatgga cagcacgggt gcctgatggg tggatttagc | 660 |
| catgagttga aggtggcttg gggagaatga gagttctaga gatagggaga aggggttgcc | 720 |
| aataggagag tggaattcct gagcacctcg tcacaggcag ccgacagaac atgagccgca | 780 |
| gggcccaggc tatttatacc tcgcctgtca ctatcagggt ccccacagct cccccacct | 840 |
| ccagccacac acagcaggtc cttttgctct ttctggtccc ttctctactc ctcccctcc | 900 |
| ctacctaagg tacccaacgc gttacgtggc caccgccttc ggcaccatcc tcacgacacc | 960 |
| caaatatggc gacgggtgag aatggtgggg gagttatttt tagagcggtg aggaaggtgg | 1020 |
| gcaggcagca ggtgttggcg ctctaaaaat aactcccggg agttattttt agagcggagg | 1080 |
| aatggtggac acccaaatat ggcgacggtt cctcacccgt cgccatattt gggtgtccgc | 1140 |
| cctcggccgg ggccgcattc ctggggccg ggcggtgctc ccgcccgcct cgataaaagg | 1200 |
| ctccggggcc ggcggcggcc cacgagctac ccggaggagc gggaggcgcc aagctctaga | 1260 |
| tctagaaaga ggtaagggtt taagggatgg ttggttggtg gggtattaat gtttaattac | 1320 |
| ctggagcacc tgcctgaaat cacttttttt caggttggaa gcttatggaa gatgccaaaa | 1380 |
| acattaagaa gggcccagcg ccattctacc cactcgagga cgggaccgcc ggcgagcagc | 1440 |
| tgcacaaagc catgaagcgc tacgccctgg tgcccggcac catcgccttt accgacgcac | 1500 |
| atatcgaggt ggacattacc tacgccgagt acttcgagat gagcgttcgg ctggcagaag | 1560 |
| ctatgaagcg ctatgggctg aatacaaacc atcggatcgt ggtgtgcagc gagaatagct | 1620 |
| tgcagttctt catgcccgtg ttgggtgccc tgttcatcgg tgtggctgtg ccccagcta | 1680 |
| acgacatcta caacgagcgc gagctgctga acagcatggg catcagccag cccaccgtcg | 1740 |
| tattcgtgag caagaagggg ctgcaaaaga tcctcaacgt gcaaaagaag ctaccgatca | 1800 |
| tacaaaagat catcatcatg gatagcaaga ccgactacca gggcttccaa agcatgtaca | 1860 |
| ccttcgtgac ttcccatttg ccacccggct tcaacgagta cgacttcgtg cccgagagct | 1920 |
| tcgaccggga caaaaccatc gccctgatca tgaacagtag tggcagtacc ggattgccca | 1980 |
| agggcgtagc cctaccgcac cgcaccgctt gtgtccgatt cagtcatgcc cgcgacccca | 2040 |
| tcttcggcaa ccagatcatc cccgacaccg ctatcctcag cgtggtgcca tttcaccacg | 2100 |
| gcttcggcat gttcaccacg ctgggctact tgatctgcgg ctttcgggtc gtgctcatgt | 2160 |
| accgcttcga ggaggagcta ttcttgcgca gcttgcaaga ctataagatt caatctgccc | 2220 |
| tgctggtgcc cacactattt agcttcttcg ctaagagcac tctcatcgac aagtacgacc | 2280 |
| taagcaactt gcacgagatc gccagcggcg gggcgccgct cagcaaggag gtaggtgagg | 2340 |
| ccgtggccaa acgcttccac ctaccaggca tccgccaggg ctacgcctg acagaaacaa | 2400 |
| ccagcgccat tctgatcacc cccgaagggg acgacaagcc tggcgcagta ggcaaggtgg | 2460 |
| tgcccttctt cgaggctaag gtggtggact tggacaccgg taagacactg ggtgtgaacc | 2520 |
| agcgcggcga gctgtgcgtc cgtggcccca tgatcatgag cggctacgtt aacaaccccg | 2580 |
| aggctacaaa cgctctcatc gacaaggacg gctggctgca cagcggcgac atcgcctact | 2640 |
| gggacgagga cgagcacttc ttcatcgtgg accggctgaa gagcctgatc aaatacaagg | 2700 |
| gctaccaggt agccccagcc gaactggaga gcatcctgct gcaacacccc aacatcttcg | 2760 |

```
acgccggggt cgccggcctg cccgacgacg atgccggcga gctgcccgcc gcagtcgtcg   2820
tgctggaaca cggtaaaacc atgaccgaga aggagatcgt ggactatgtg ccagccagg    2880 ttacaaccgc caagaagctg cgcggtggtg ttgtgttcgt ggacgaggtg cctaaaggac   2940
tgaccggcaa gttggacgcc cgcaagatcc gcgagattct cattaaggcc aagaagggcg   3000
gcaagatcgc cgtgtaattc gaaacgtacg gtccatcttg agcatctgac ttctggctaa   3060
ataaaagatc tttattttca ttagatctgt gtgttggttt tttgtgtgcg tcagatcca    3120 cggccgcagg aaccctagt gatggagttg ccactccct ctctgcgcgc tcgctcgctc     3180
actgaggccg ggcgaccaaa ggtcgcccga cgcccgggct tgcccgggc ggcctcagtg    3240 agcgagcgag cgcgcagctg cctgcagggg cgcctgatgc ggtattttct ccttacgcat   3300
ctgtgcggta tttcacaccg catacgtcaa agcaaccata gtacgcgccc tgtagcggcg   3360
cattaagcgc ggcgggtgtg gtggttacgc gcagcgtgac cgctacactt gccagcgccc   3420
tagcgcccgc tcctttcgct ttcttccctt cctttctcgc cacgttcgcc ggctttcccc   3480
gtcaagctct aaatcggggg ctccctttag ggttccgatt tagtgcttta cggcacctcg   3540
accccaaaaa acttgatttg ggtgatggtt cacgtagtgg gccatcgccc tgatagacgg   3600
tttttcgccc tttgacgttg gagtccacgt tctttaatag tggactcttg ttccaaactg   3660
gaacaacact caaccctatc tcgggctatt cttttgattt ataagggatt ttgccgattt   3720
cggcctattg gttaaaaaat gagctgattt aacaaaaatt taacgcgaat tttaacaaaa   3780
tattaacgtt tacaatttta tggtgcactc tcagtacaat ctgctctgat gccgcatagt   3840
taagccagcc ccgacacccg ccaacacccg ctgacgcgcc ctgacgggct tgtctgctcc   3900
cggcatccgc ttacagacaa gctgtgaccg tctccgggag ctgcatgtgt cagaggtttt   3960
caccgtcatc accgaaacgc gcgagacgaa agggcctcgt gatacgccta ttttttatagg   4020 ttaatgtcat gataataatg gtttcttaga cgtcaggtgg cacttttcgg ggaaatgtgc    4080
gcggaacccc tatttgttta ttttttctaaa tacattcaaa tatgtatccg ctcatgagac   4140
aataaccctg ataaatgctt caataatatt gaaaaaggaa gagtatgagt attcaacatt   4200
tccgtgtcgc ccttattccc ttttttgcgg cattttgcct tcctgttttt gctcacccag   4260
aaacgctggt gaaagtaaaa gatgctgaag atcagttggg tgcacgagtg ggttacatcg   4320
aactggatct caacagcggt aagatccttg agagttttcg ccccgaagaa cgttttccaa   4380
tgatgagcac ttttaaagtt ctgctatgtg gcgcggtatt atcccgtatt gacgccgggc   4440
aagagcaact cggtcgccgc atacactatt ctcagaatga cttggttgag tactcaccag   4500
tcacagaaaa gcatcttacg gatggcatga cagtaagaga attatgcagt gctgccataa   4560
ccatgagtga taacactgcg gccaacttac ttctgacaac gatcggagga ccgaaggagc   4620
taaccgcttt tttgcacaac atgggggatc atgtaactcg ccttgatcgt tgggaaccgg   4680
agctgaatga agccatacca aacgacgagc gtgacaccac gatgcctgta gcaatggcaa   4740
caacgttgcg caaactatta actggcgaac tacttactct agcttcccgg caacaattaa   4800
tagactggat ggaggcggat aaagttgcag gaccacttct gcgctcggcc cttccggctg   4860
gctggtttat tgctgataaa tctggagccg gtgagcgtgg gtctcgcggt atcattgcag   4920
cactggggcc agatggtaag ccctcccgta tcgtagttat ctacacgacg gggagtcagg   4980
caactatgga tgaacgaaat agacagatcg ctgagatagg tgcctcactg attaagcatt   5040
ggtaactgtc agaccaagtt tactcatata ctttagat tgatttaaaa cttcatttt      5100
```

```
aatttaaaag gatctaggtg aagatccttt ttgataatct catgaccaaa atcccttaac    5160
gtgagttttc gttccactga gcgtcagacc ccgtagaaaa gatcaaagga tcttcttgag    5220
atcctttttt tctgcgcgta atctgctgct tgcaaacaaa aaaaccaccg ctaccagcgg    5280
tggtttgttt gccggatcaa gagctaccaa ctcttttttcc gaaggtaact ggcttcagca    5340
gagcgcagat accaaatact gtccttctag tgtagccgta gttaggccac cacttcaaga    5400
actctgtagc accgcctaca tacctcgctc tgctaatcct gttaccagtg gctgctgcca    5460
gtggcgataa gtcgtgtctt accgggttgg actcaagacg atagttaccg gataaggcgc    5520
agcggtcggg ctgaacgggg ggttcgtgca cacagcccag cttggagcga acgacctaca    5580
ccgaactgag atacctacag cgtgagctat gagaaagcgc cacgcttccc gaagggagaa    5640
aggcggacag gtatccggta agcggcaggg tcggaacagg agagcgcacg agggagcttc    5700 caggggggaaa cgcctggtat ctttatagtc ctgtcgggtt tcgccacctc tgacttgagc    5760
gtcgattttt gtgatgctcg tcaggggggc ggagcctatg gaaaaacgcc agcaacgcgg    5820
cctttttacg gttcctggcc ttttgctggc cttttgctca catgt             5865
```

<210> SEQ ID NO 103
<211> LENGTH: 6054
<212> TYPE: DNA
<213> ORGANISM: Artificial Sequence
<220> FEATURE:
<223> OTHER INFORMATION: plasmid pAAVss-CRE69-CSkSH5-SPc5-12_GTRM-Luc2

<400> SEQUENCE: 103

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgaa acatggcttc cacaggttcc agttgaagaa     180
tcccagttcc gtctataaat tccagggaag gtctctgatt ggccctgctc attcccaggc     240
ccattccttg acccagtcac tgaagtcagg agatgcagt aataagactg ctggaatca     300 gggtctttag gggtggaggg atggggagga ggcacagcat gtcatcaaaa taaggaaatt     360
gcaaaagaaa gcttgcaggc tactttgaat gacaatgaga aagacggtgc tgcctgagtg     420
tgttaaggat ccacatggtc tccaaaatcc tccaggagca tacagtctag tctgggagat     480
gagacacaaa ataaccaga acacaacagc ttgcactgac tcgagggctg ataagaata     540 tctggaactc ccccatctat ttcagaagct tgtctcttgg atgaaaatta gacacttaat     600
gggaaagggc tttgaaaaga gtgcagtaag gcgcgccacg cgtcagttta ctcaccaggg     660
attcagaggc agcactgctg aaccctgagc ccttggcaca tcaggttggc tgtcagaagt     720
cggcctttgt acatacacag ttcccttgtg aggcccagct gcgtgtccta ggagcggggc     780
ctctctccac agcagagctc agcctctcaa gtgtatggac agcacgggtg cctgatgggt     840
ggatttagcc atgagttgaa ggtggcttgg ggagaatgag agttctagag atagggagaa     900
ggggttgcca ataggagagt ggaattcctg agcacctcgt cacaggcagc cgacagaaca     960
tgagccgcag ggcccaggct atttatacct cgcctgtcac tatcagggtc cccacagctc    1020
cccccacctc cagccacaca cagcaggtcc ttttgctctt tctggtccct tctctactcc    1080
tccccctccc tacctaaggt acccaacgcg ttacgtggcc accgcttcg gcaccatcct    1140 cacgacaccc aaatatggcg acgggtgagg aatggtgggg agttattttt agagcggtga    1200
ggaaggtggg caggcagcag gtgttggcgc tctaaaaata actcccggga gttattttta    1260
gagcggagga atggtggaca cccaaatatg cgacggttc ctcacccgtc gccatatttg    1320
```

```
ggtgtccgcc ctcggccggg gccgcattcc tggggccgg gcggtgctcc cgcccgcctc    1380
gataaaaggc tccggggccg gcggcggccc acgagctacc cggaggagcg ggaggcgcca    1440
agctctagat ctagaaagag gtaagggttt aagggatggt tggttggtgg ggtattaatg    1500
tttaattacc tggagcacct gcctgaaatc acttttttc aggttggaag cttatgaag     1560
atgccaaaaa cattaagaag ggcccagcgc cattctaccc actcgaggac gggaccgccg    1620
gcgagcagct gcacaaagcc atgaagcgct acgccctggt gcccggcacc atcgccttta    1680
ccgacgcaca tatcgaggtg gacattacct acgccgagta cttcgagatg agcgttcggc    1740
tggcagaagc tatgaagcgc tatgggctga atacaaacca tcggatcgtg gtgtgcagcg    1800
agaatagctt gcagttcttc atgcccgtgt tgggtgccct gttcatcggt gtggctgtgg    1860
ccccagctaa cgacatctac aacgagcgcg agctgctgaa cagcatgggc atcagccagc    1920
ccaccgtcgt attcgtgagc aagaaagggc tgcaaaagat cctcaacgtg caaagaagc     1980
taccgatcat acaaaagatc atcatcatgg atagcaagac cgactaccag ggcttccaaa    2040
gcatgtacac cttcgtgact tcccatttgc cacccggctt caacgagtac gacttcgtgc    2100
ccgagagctt cgaccgggac aaaaccatcg ccctgatcat gaacagtagt ggcagtaccg    2160
gattgcccaa gggcgtagcc ctaccgcacc gcaccgcttg tgtccgattc agtcatgccc    2220
gcgaccccat cttcggcaac cagatcatcc ccgacaccgc tatcctcagc gtggtgccat    2280
ttcaccacgg cttcggcatg ttcaccacgc tgggctactt gatctgcggc tttcgggtcg    2340
tgctcatgta ccgcttcgag gaggagctat tcttgcgcag cttgcaagac tataagattc    2400
aatctgccct gctggtgccc acactattta gcttcttcgc taagagcact ctcatcgaca    2460
agtacgacct aagcaacttg cacgagatcg ccagcggcgg ggcgccgctc agcaaggagg    2520
taggtgaggc cgtggccaaa cgcttccacc taccaggcat ccgccagggc tacggcctga    2580
cagaaacaac cagcgccatt ctgatcaccc ccgaagggga cgacaagcct ggcgcagtag    2640
gcaaggtggt gcccttcttc gaggctaagg tggtggactt ggacaccggt aagacactgg    2700
gtgtgaacca gcgcggcgag ctgtgcgtcc gtggccccat gatcatgagc ggctacgtta    2760
acaaccccga ggctacaaac gctctcatcg acaaggacgc tggctgcac agcggcgaca    2820
tcgcctactg ggacgaggac gagcacttct tcatcgtgga ccggctgaag agcctgatca    2880
aatacaaggg ctaccaggta gccccagccg aactggagag catcctgctg caacacccca    2940
acatcttcga cgccggggtc gccggcctgc ccgacgacga tgccggcgag ctgcccgccg    3000
cagtcgtcgt gctggaacac ggtaaaacca tgaccgagaa ggagatcgtg gactatgtgg    3060
ccagccaggt tacaaccgcc aagaagctgc gcggtggtgt tgtgttcgtg gacgaggtgc    3120
ctaaaggact gaccggcaag ttggacgccc gcaagatccg cgagattctc attaaggcca    3180
agaagggcgg caagatcgcc gtgtaattcg aaacgtatcg tccatcttga gcatctgact    3240
tctggctaaa taaagatct ttattttcat tagatctgtg tgttggtttt ttgtgtgcgt     3300
cgagatccac ggccgcagga accctagtg atggagttgg ccactccctc tctgcgcgct     3360
cgctcgctca ctgaggccgg gcgaccaaag gtcgcccgac gcccgggctt tgcccgggcg    3420
gcctcagtga gcgagcgagc gcgcagctgc ctgcagggc gcctgatgcg gtattttctc     3480
cttacgcatc tgtgcggtat ttcacaccgc atacgtcaaa gcaaccatag tacgcgccct    3540
gtagcggcgc attaagcgcg gcgggtgtgg tggttacgcg cagcgtgacc gctacacttg    3600
ccagcgccct agcgcccgct cctttcgctt tcttcccttc ctttctcgcc acgttcgccg    3660
```

-continued

```
gctttccccg tcaagctcta aatcggggc tccctttagg gttccgattt agtgctttac    3720
ggcacctcga ccccaaaaaa cttgatttgg gtgatggttc acgtagtggg ccatcgccct    3780
gatagacggt ttttcgccct ttgacgttgg agtccacgtt ctttaatagt ggactcttgt    3840
tccaaactgg aacaacactc aaccctatct cgggctattc ttttgattta aagggattt    3900
tgccgatttc ggcctattgg ttaaaaaatg agctgattta caaaaatttt aacgcgaatt    3960
ttaacaaaat attaacgttt acaattttat ggtgcactct cagtacaatc tgctctgatg    4020
ccgcatagtt aagccagccc cgacacccgc caacacccgc tgacgcgccc tgacgggctt    4080
gtctgctccc ggcatccgct tacagacaag ctgtgaccgt ctccgggagc tgcatgtgtc    4140
agaggttttc accgtcatca ccgaaacgcg cgagacgaaa gggcctcgtg atacgcctat    4200
ttttataggt taatgtcatg ataataatgg tttcttagac gtcaggtggc acttttcggg    4260
gaaatgtgcg cggaacccct atttgtttat ttttctaaat acattcaaat atgtatccgc    4320
tcatgagaca ataaccctga taaatgcttc aataatattg aaaaaggaag agtatgagta    4380
ttcaacattt ccgtgtcgcc cttattccct ttttttgcggc attttgcctt cctgtttttg    4440
ctcacccaga aacgctggtg aaagtaaaag atgctgaaga tcagttgggt gcacgagtgg    4500
gttacatcga actggatctc aacagcggta agatccttga gttttcgc cccgaagaac    4560
gttttccaat gatgagcact tttaaagttc tgctatgtgg cgcggtatta cccgtattg    4620
acgccgggca agagcaactc ggtcgccgca tacactattc tcagaatgac ttggttgagt    4680
actcaccagt cacagaaaag catcttacgg atggcatgac agtaagagaa ttatgcagtg    4740
ctgccataac catgagtgat aacactgcgg ccaacttact tctgacaacg atcggaggac    4800
cgaaggagct aaccgctttt ttgcacaaca tgggggatca tgtaactcgc cttgatcgtt    4860
gggaaccgga gctgaatgaa gccataccaa acgacgagcg tgacaccacg atgcctgtag    4920
caatggcaac aacgttgcgc aaactattaa ctggcgaact acttactcta gcttcccggc    4980
aacaattaat agactggatg gaggcggata aagttgcagg accacttctg cgctcggccc    5040
ttccggctgg ctggtttatt gctgataaat ctggagccgg tgagcgtggg tctcgcggta    5100
tcattgcagc actggggcca gatggtaagc cctcccgtat cgtagttatc tacacgacgg    5160
ggagtcaggc aactatggat gaacgaaata gacagatcgc tgagataggt gcctcactga    5220
ttaagcattg gtaactgtca gaccaagttt actcatatat actttagatt gatttaaaac    5280
ttcatttta atttaaaagg atctaggtga agatccttt tgataatctc atgaccaaaa    5340
tcccttaacg tgagttttcg ttccactgag cgtcagaccc cgtagaaaag atcaaaggat    5400
cttcttgaga tcctttttt ctgcgcgtaa tctgctgctt gcaaacaaaa aaaccaccgc    5460
taccagcggt ggtttgtttg ccggatcaag agctaccaac tctttttccg aaggtaactg    5520
gcttcagcag agcgcagata ccaaatactg tccttctagt gtagccgtag ttaggccacc    5580
acttcaagaa ctctgtagca ccgcctacat acctcgctct gctaatcctg ttaccagtgg    5640
ctgctgccag tggcgataag tcgtgtctta ccgggttgga ctcaagacga tagttaccgg    5700
ataaggcgca gcggtcgggc tgaacggggg gttcgtgcac acagcccagc ttggagcgaa    5760
cgacctacac cgaactgaga tacctacagc gtgagctatg agaaagcgcc acgcttcccg    5820
aagggagaaa ggcggacagg tatccggtaa gcggcagggt cggaacagga gagcgcacga    5880
gggagcttcc agggggaaac gcctggtatc tttatagtcc tgtcgggttt cgccacctct    5940
gacttgagcg tcgatttttg tgatgctcgt caggggggcg gagcctatgg aaaaacgcca    6000
gcaacgcggc cttttacgg ttcctggcct tttgctggcc ttttgctcac atgt           6054
```

<210> SEQ ID NO 104
<211> LENGTH: 5970
<212> TYPE: DNA
<213> ORGANISM: Artificial Sequence
<220> FEATURE:
<223> OTHER INFORMATION: plasmid pAAVss-CRE70-CSkSH5-SPc5-12_GTRM-Luc2

<400> SEQUENCE: 104

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggcccct caggtacccc ctgcccccca cagctcctct     180
cctgtgcctt gtttcccagc catgcgttct cctctataaa tacccgctct ggtatttggg     240
gttggcagct gttgctgcca gggagatggt tgggttgaca tgcggctcct gacaaaacac     300
aaaccctgg tgtgtgtggg cgtgggtggt gtgagtaggg ggatgaatca gggaggggc     360
gggggaccca gggggcagga gccacacaaa gtctgtgcgg gggtgggagc gcacatagca     420
attggaaact gaaagcttat cagacccttt ctggaaatca gcccactgtt tataaacttg     480
aggccccacc ctcgacagta ccggggagga agagggcctg cactagtcca gagggaaact     540
gaggcggcgc gccacgcgtc agtttactca ccagggattc agaggcagca ctgctgaacc     600
ctgagccctt ggcacatcag gttggctgtc agaagtcggc cttttgtacat acacagttcc     660
cttgtgaggc ccagctgcgt gtcctaggag cggggcctct ctccacagca gagctcagcc     720
tctcaagtgt atggacagca cgggtgcctg atgggtggat ttagccatga gttgaaggtg     780
gcttgggag aatgagagtt ctagagatag ggagaagggg ttgccaatag gagagtggaa     840
ttcctgagca cctcgtcaca gcagccgac agaacatgag ccgcagggcc caggctattt     900
atacctcgcc tgtcactatc agggtcccca cagctcccc cacctccagc cacacacagc     960
aggtcctttt gctctttctg gtcccttctc tactcctccc cctccctacc taaggtaccc    1020
aacgcgttac gtgccaccg ccttcggcac catcctcacg acacccaaat atggcgacgg    1080
gtgaggaatg gtggggagtt attttagag cggtgaggaa ggtgggcagg cagcaggtgt    1140
tggcgctcta aaataactc ccgggagtta ttttagagc ggaggaatgg tggacacca    1200
aatatggcga cggttcctca cccgtcgcca tatttgggtg tccgccctcg gccggggccg    1260
cattcctggg ggccgggcgg tgctcccgcc cgcctcgata aaaggctccg gggccggcgg    1320
cggcccacga gctacccgga ggagcgggag gcgccaagct ctagatctag aaagaggtaa    1380
gggtttaagg gatggttggt tggtgggta ttaatgtta attacctgga gcacctgcct    1440
gaaatcactt ttttttcaggt tggaagctta tggaagatgc caaaaacatt aagaagggcc    1500
cagcgccatt ctaccactc gaggacggga ccgccggcga gcagctgcac aaagccatga    1560
agcgctacgc cctggtgccc ggcaccatcg cctttaccga cgcacatatc gaggtggaca    1620
ttacctacgc cgagtacttc gagatgagcg ttcggctggc agaagctatg aagcgctatg    1680
ggctgaatac aaaccatcgg atcgtggtgt gcagcgagaa tagcttgcag ttcttcatgc    1740
ccgtgttggg tgccctgttc atcggtgtgg ctgtggcccc agctaacgac atctacaacg    1800
agcgcgagct gctgaacagc atgggcatca gccagcccac cgtcgtattc gtgagcaaga    1860
aagggctgca aaagatcctc aacgtgcaaa agaagctacc gatcatacaa aagatcatca    1920
tcatggatag caagaccgac taccagggct tccaaagcat gtacaccttc gtgacttccc    1980
atttgccacc cggcttcaac gagtacgact tcgtgcccga gagcttcgac cgggacaaaa    2040
```

-continued

```
ccatcgccct gatcatgaac agtagtggca gtaccggatt gcccaagggc gtagccctac    2100
cgcaccgcac cgcttgtgtc cgattcagtc atgcccgcga ccccatcttc ggcaaccaga    2160
tcatccccga caccgctatc ctcagcgtgg tgccatttca ccacggcttc ggcatgttca    2220
ccacgctggg ctacttgatc tgcggctttc gggtcgtgct catgtaccgc ttcgaggagg    2280
agctattctt gcgcagcttg caagactata agattcaatc tgccctgctg gtgcccacac    2340
tatttagctt cttcgctaag agcactctca tcgacaagta cgacctaagc aacttgcacg    2400
agatcgccag cggcggggcg ccgctcagca aggaggtagg tgaggccgtg gccaaacgct    2460
tccacctacc aggcatccgc cagggctacg gcctgacaga acaaccagc gccattctga    2520 tcaccccga aggggacgac aagcctggcg cagtaggcaa ggtggtgccc ttcttcgagg    2580
ctaaggtggt ggacttggac accggtaaga cactgggtgt gaaccagcgc ggcgagctgt    2640
gcgtccgtgg ccccatgatc atgagcggct acgttaacaa ccccgaggct acaaacgctc    2700
tcatcgacaa ggacgctgg ctgcacagcg gcgacatcgc ctactgggac gaggacgagc    2760
acttcttcat cgtggaccgg ctgaagagcc tgatcaaata caagggctac caggtagccc    2820
cagccgaact ggagagcatc ctgctgcaac accccaacat cttcgacgcc ggggtcgccg    2880
gcctgcccga cgacgatgcc ggcgagctgc ccgccgcagt cgtcgtgctg aacacggta    2940 aaaccatgac cgagaaggag atcgtggact atgtggccag ccaggttaca accgccaaga    3000
agctgcgcgg tggtgttgtg ttcgtggacg aggtgcctaa aggactgacc ggcaagttgg    3060
acgcccgcaa gatccgcgag attctcatta aggccaagaa gggcggcaag atcgccgtgt    3120
aattcgaaac gtatggtcca tcttgagcat ctgacttctg gctaaataaa agatctttat    3180
tttcattaga tctgtgtgtt ggttttttgt gtgcgtcgag atccacggcc gcaggaaccc    3240
ctagtgatgg agttggccac tccctctctg cgcgctcgct cgctcactga ggccgggcga    3300
ccaaaggtcg cccgacgccc gggctttgcc cgggcggcct cagtgagcga gcgagcgcgc    3360
agctgcctgc aggggcgcct gatgcggtat tttctcctta cgcatctgtg cggtatttca    3420
caccgcatac gtcaaagcaa ccatagtacg cgccctgtag cggcgcatta agcgcggcgg    3480
gtgtggtggt tacgcgcagc gtgaccgcta cacttgccag cgccctagcg cccgctcctt    3540
tcgctttctt cccttccttt ctcgccacgt tcgccggctt tccccgtcaa gctctaaatc    3600
gggggctccc tttagggttc cgatttagtg ctttacggca cctcgacccc aaaaaacttg    3660
atttgggtga tggttcacgt agtgggccat cgccctgata cggttttt cgccctttga    3720 cgttggagtc cacgttcttt aatagtggac tcttgttcca aactggaaca cactcaacc    3780 ctatctcggg ctattctttt gatttataag ggattttgcc gatttcggcc tattggttaa    3840
aaaatgagct gatttaacaa aaatttaacg cgaattttaa caaaatatta acgtttacaa    3900
ttttatggtg cactctcagt acaatctgct ctgatgccgc atagttaagc cagccccgac    3960
acccgccaac acccgctgac gcgccctgac gggcttgtct gctcccggca tccgcttaca    4020
gacaagctgt gaccgtctcc gggagctgca tgtgtcagag gttttcaccg tcatcaccga    4080
aacgcgcgag acgaaagggc ctcgtgatac gcctattttt ataggttaat gtcatgataa    4140
taatggtttc ttagacgtca ggtggcactt ttcggggaaa tgtgcgcgga acccctattt    4200 gtttatttt ctaaatacat tcaaatatgt atccgctcat gagacaataa ccctgataaa    4260
tgcttcaata atattgaaaa aggaagagta tgagtattca acatttccgt gtcgccctta    4320
ttcccttttt tgcggcattt tgccttcctg ttttgctca cccagaaacg ctggtgaaag    4380
taaaagatgc tgaagatcag ttgggtgcac gagtgggtta catcgaactg gatctcaaca    4440
```

```
gcggtaagat ccttgagagt tttcgccccg aagaacgttt tccaatgatg agcacttta    4500 aagttctgct atgtggcgcg gtattatccc gtattgacgc cgggcaagag caactcggtc    4560
gccgcataca ctattctcag aatgacttgg ttgagtactc accagtcaca gaaaagcatc    4620
ttacggatgg catgacagta agagaattat gcagtgctgc cataaccatg agtgataaca    4680
ctgcggccaa cttacttctg acaacgatcg gaggaccgaa ggagctaacc gcttttttgc    4740
acaacatggg ggatcatgta actcgccttg atcgttggga accggagctg aatgaagcca    4800
taccaaacga cgagcgtgac accacgatgc ctgtagcaat ggcaacaacg ttgcgcaaac    4860
tattaactgg cgaactactt actctagctt cccggcaaca attaatagac tggatggagg    4920
cggataaagt tgcaggacca cttctgcgct cggcccttcc ggctggctgg tttattgctg    4980
ataaatctgg agccggtgag cgtgggtctc gcggtatcat tgcagcactg gggccagatg    5040
gtaagccctc ccgtatcgta gttatctaca cgacggggag tcaggcaact atggatgaac    5100
gaaatagaca gatcgctgag ataggtgcct cactgattaa gcattggtaa ctgtcagacc    5160
aagtttactc atatatactt tagattgatt taaaacttca ttttaattt aaaaggatct    5220 aggtgaagat cctttttgat aatctcatga ccaaaatccc ttaacgtgag ttttcgttcc    5280
actgagcgtc agacccgta gaaaagatca aaggatcttc ttgagatcct ttttttctgc    5340
gcgtaatctg ctgcttgcaa acaaaaaaac caccgctacc agcggtggtt tgtttgccgg    5400
atcaagagct accaactctt tttccgaagg taactggctt cagcagagcg cagataccaa    5460
atactgtcct tctagtgtag ccgtagttag gccaccactt caagaactct gtagcaccgc    5520
ctacatacct cgctctgcta atcctgttac cagtggctgc tgccagtggc gataagtcgt    5580
gtcttaccgg gttggactca agacgatagt taccggataa ggcgcagcgg tcgggctgaa    5640
cggggggttc gtgcacacag cccagcttgg agcgaacgac ctacaccgaa ctgagatacc    5700
tacagcgtga gctatgagaa agcgccacgc ttcccgaagg gagaaaggcg gacaggtatc    5760
cggtaagcgg cagggtcgga acaggagagc gcacgaggga gcttccaggg ggaaacgcct    5820
ggtatcttta tagtcctgtc gggtttcgcc acctctgact tgagcgtcga ttttgtgat    5880 gctcgtcagg gggcggagc ctatggaaaa acgccagcaa cgcggccttt ttacggttcc    5940 tggcctttg ctggccttt gctcacatgt                                        5970
```

<210> SEQ ID NO 105
<211> LENGTH: 5813
<212> TYPE: DNA
<213> ORGANISM: Artificial Sequence
<220> FEATURE:
<223> OTHER INFORMATION: plasmid pAAVss-CRE71-CSkSH5-SPc5-12_GTRM-Luc2

<400> SEQUENCE: 105

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggcccag gggcgcaggc ctcttgcggg ggagctggcc    180
tccccgcccc cacggccacg ggccgcccct tcctggcagg acagcgggat cttgcagctg    240
tcaggggagg ggaggcgggg gctgatgtca ggagggatac aaatagtgcc gacggctggg    300
ggccctgtct cccctcgccg catccactct ccggccggcc gcctgccgc cgcctcctcc      360 gtgcgcccgc cagcctcgcc cgcgcgtgg cgcgccacgc gtcagtttac tcaccaggga    420
ttcagaggca gcactgctga accctgagcc cttggcacat caggttggct gtcagaagtc    480
```

```
ggcctttgta catacacagt tcccttgtga ggcccagctg cgtgtcctag gagcggggcc       540
tctctccaca gcagagctca gcctctcaag tgtatggaca gcacgggtgc ctgatgggtg       600
gatttagcca tgagttgaag gtggcttggg gagaatgaga gttctagaga tagggagaag      660
gggttgccaa taggagagtg gaattcctga gcacctcgtc acaggcagcc gacagaacat      720
gagccgcagg gcccaggcta tttatacctc gcctgtcact atcagggtcc ccacagctcc      780
ccccacctcc agccacacac agcaggtcct tttgctcttt ctggtccctt ctctactcct      840 cccccctccct acctaaggta cccaacgcgt tacgtggcca ccgccttcgg caccatcctc     900
acgacaccca aatatggcga cgggtgagga atggtgggga gttattttta gagcggtgag     960
gaaggtgggc aggcagcagg tgttggcgct ctaaaaataa ctcccgggag ttattttag      1020 agcggaggaa tggtggacac ccaaatatgg cgacggttcc tcacccgtcg ccatatttgg     1080
gtgtccgccc tcggccgggg ccgcattcct gggggccggg cggtgctccc gcccgcctcg     1140
ataaaaggct ccggggccgg cggcggccca cgagctaccc ggaggagcgg gaggcgccaa     1200
gctctagatc tagaaagagg taagggttta agggatggtt ggttggtggg gtattaatgt     1260
ttaattacct ggagcacctg cctgaaatca cttttttttca ggttggaagc ttatggaaga    1320
tgccaaaaac attaagaagg gcccagcgcc attctaccca ctcgaggacg ggaccgccgg     1380
cgagcagctg cacaaagcca tgaagcgcta cgccctggtg cccggcacca tcgcctttac      1440
cgacgcacat atcgaggtgg acattaccta cgccgagtac ttcgagatga cgttcggct     1500 ggcagaagct atgaagcgct atgggctgaa tacaaaccat cggatcgtgg tgtgcagcga    1560
gaatagcttg cagttcttca tgcccgtgtt gggtgccctg ttcatcggtg tggctgtggc     1620
cccagctaac gacatctaca cgagcgcga gctgctgaac agcatgggca tcagccagcc     1680
caccgtcgta ttcgtgagca gaaagggct gcaaaagatc ctcaacgtgc aaaagaagct     1740
accgatcata caaaagatca tcatcatgga tagcaagacc gactaccagg cttccaaag     1800 catgtacacc ttcgtgactt cccatttgcc accggcttc aacgagtacg acttcgtgcc      1860
cgagagcttc gaccgggaca aaaccatcgc cctgatcatg aacagtagtg cagtaccgg     1920 attgcccaag ggcgtagccc taccgcaccg caccgcttgt gtccgattca gtcatgcccg     1980
cgaccccatc ttcggcaacc agatcatccc cgacaccgct atcctcagcg tggtgccatt     2040
tcaccacggc ttcggcatgt tcaccacgct gggctacttg atctgcggct ttcgggtcgt    2100
gctcatgtac cgcttcgagg aggagctatt cttgcgcagc ttgcaagact ataagattca    2160
atctgccctg ctggtgccca cactatttag cttcttcgct aagagcactc tcatcgacaa    2220
gtacgaccta agcaacttgc acgagatcgc cagcggcggg gcgccgctca gcaaggaggt    2280
aggtgaggcc gtggccaaac gcttccacct accaggcatc cgccaggct acggcctgac    2340 agaaacaacc agcgccattc tgatcacccc cgaaggggac gacaagcctg gcgcagtagg    2400
caaggtggtg cccttcttcg aggctaaggt ggtggacttg gacaccggta agacactggg    2460
tgtgaaccag cgcggcgagc tgtgcgtccg tggccccatg atcatgagcg ctacgttaa     2520 caaccccgag gctacaaacg ctctcatcga caaggacggc tggctgcaca gcggcgacat    2580
cgcctactgg gacgaggacg agcacttctt catcgtggac cggctgaaga gcctgatcaa    2640
atacaagggc taccaggtag ccccagccga actggagagc atcctgctgc aacacccaa     2700 catcttcgac gccggggtcg ccggcctgcc cgacgacgat gccggcgagc tgccccgcgc    2760
agtcgtcgtg ctgaacacg gtaaaaccat gaccgagaag gagatcgtgg actatgtggc    2820
cagccaggtt acaaccgcca agaagctgcg cggtggtgtt gtgttcgtgg acgaggtgcc    2880
```

```
taaaggactg accggcaagt tggacgcccg caagatccgc gagattctca ttaaggccaa    2940
gaagggcggc aagatcgccg tgtaattcga acgtacagt ccatcttgag catctgactt     3000
ctggctaaat aaaagatctt tattttcatt agatctgtgt gttggttttt tgtgtgcgtc    3060
gagatccacg gccgcaggaa cccctagtga tggagttggc cactccctct ctgcgcgctc    3120
gctcgctcac tgaggccggg cgaccaaagg tcgcccgacg cccgggcttt gcccgggcgg    3180
cctcagtgag cgagcgagcg cgcagctgcc tgcaggggcg cctgatgcgg tattttctcc    3240
ttacgcatct gtgcggtatt tcacaccgca tacgtcaaag caaccatagt acgcgccctg    3300
tagcggcgca ttaagcgcgg cgggtgtggt ggttacgcgc agcgtgaccg ctacacttgc    3360
cagcgcccta gcgcccgctc ctttcgcttt cttcccttcc tttctcgcca cgttcgccgg    3420
ctttccccgt caagctctaa atcggggct cccttaggg ttccgattta gtgctttacg      3480
gcacctcgac cccaaaaaac ttgatttggg tgatggttca cgtagtgggc catcgccctg    3540
atagacggtt tttcgccctt tgacgttgga gtccacgttc tttaatagtg gactcttgtt    3600
ccaaactgga acaacactca accctatctc gggctattct tttgatttat aagggatttt    3660
gccgatttcg gcctattggt taaaaaatga gctgatttaa caaaaattta cgcgaatttt    3720
taacaaaata ttaacgttta caattttatg gtgcactctc agtacaatct gctctgatgc    3780
cgcatagtta agccagcccc gacacccgcc aacaccgct gacgcgccct gacgggcttg     3840
tctgctcccg gcatccgctt acagacaagc tgtgaccgtc tccgggagct gcatgtgtca    3900
gaggttttca ccgtcatcac cgaaacgcgc gagacgaaag gcctcgtga tacgcctatt     3960
tttataggtt aatgtcatga taataatggt ttcttagacg tcaggtggca cttttcgggg    4020
aaatgtgcgc ggaaccccta tttgtttatt tttctaaata cattcaaata tgtatccgct    4080
catgagacaa taaccctgat aaatgcttca ataatattga aaaaggaaga gtatgagtat    4140
tcaacatttc cgtgtcgccc ttattccctt ttttgcggca ttttgccttc ctgttttgc     4200
tcacccagaa acgctggtga agtaaaaga tgctgaagat cagttgggtg cacgagtggg    4260
ttacatcgaa ctggatctca acagcggtaa gatccttgag agttttcgcc ccgaagaacg    4320
ttttccaatg atgagcactt ttaaagttct gctatgtggc gcggtattat cccgtattga    4380
cgccgggcaa gagcaactcg gtcgccgcat acactattct cagaatgact tggttgagta    4440
ctcaccagtc acagaaaagc atcttacgga tggcatgaca gtaagagaat tatgcagtgc    4500
tgccataacc atgagtgata acactgcggc caacttactt ctgacaacga tcggaggacc    4560
gaaggagcta accgcttttt tgcacaacat ggggggatcat gtaactcgcc ttgatcgttg    4620
ggaaccggag ctgaatgaag ccataccaaa cgacgagcgt gacaccacga tgcctgtagc    4680
aatggcaaca acgttgcgca aactattaac tggcgaacta cttactctag cttcccggca    4740
acaattaata gactggatgg aggcggataa agttgcagga ccacttctgc gctcggccct    4800
tccggctggc tggtttattg ctgataaatc tggagccggt gagcgtgggt ctcgcggtat    4860
cattgcagca ctggggccag atggtaagcc ctcccgtatc gtagttatct acacgacggg    4920
gagtcaggca actatggatg aacgaaatag acagatcgct gagataggtg cctcactgat    4980
taagcattgg taactgtcag accaagttta ctcatatata ctttagattg atttaaaact    5040
tcatttttaa tttaaaagga tctaggtgaa gatccttttt gataatctca tgaccaaaat    5100
cccttaacgt gagttttcgt tccactgagc gtcagacccc gtagaaaaga tcaaaggatc    5160
ttcttgagat cctttttttc tgcgcgtaat ctgctgcttg caaacaaaaa aaccaccgct    5220
```

```
accagcggtg gtttgtttgc cggatcaaga gctaccaact cttttttccga aggtaactgg      5280 cttcagcaga gcgcagatac caaatactgt ccttctagtg tagccgtagt taggccacca      5340
cttcaagaac tctgtagcac cgcctacata cctcgctctg ctaatcctgt taccagtggc      5400
tgctgccagt ggcgataagt cgtgtcttac cgggttggac tcaagacgat agttaccgga      5460
taaggcgcag cggtcgggct gaacgggggg ttcgtgcaca cagcccagct tggagcgaac      5520
gacctacacc gaactgagat acctacagcg tgagctatga gaaagcgcca cgcttcccga      5580
agggagaaag gcggacaggt atccggtaag cggcagggtc ggaacaggag agcgcacgag      5640
ggagcttcca gggggaaacg cctggtatct ttatagtcct gtcgggtttc gccacctctg      5700
acttgagcgt cgatttttgt gatgctcgtc aggggggcgg agcctatgga aaaacgccag      5760
caacgcggcc ttttttacggt tcctggcctt ttgctggcct tttgctcaca tgt            5813
```

<210> SEQ ID NO 106
<211> LENGTH: 5888
<212> TYPE: DNA
<213> ORGANISM: Artificial Sequence
<220> FEATURE:
<223> OTHER INFORMATION: plasmid pAAVss-CRE77-CSkSH5-SPc5-12_GTRM-Luc2

<400> SEQUENCE: 106

```
acatgtcctg caggcagctg cgcgctcgct cgctcactga ggccgcccgg gcaaagcccg       60
ggcgtcgggc gacctttggt cgcccggcct cagtgagcga gcgagcgcgc agagagggag      120
tggccaactc catcactagg ggttcctgcg gccggaatac cctaccttaa aaacaaaaca      180
aaccgtgcta cttggccctc ttcccttgag ttgttgtcta atctcattca tttcactgcc      240
aaactcctca aatgcatggt gtacacccac tgcttccact tcctgtccac tcatcttttt      300
cctcattaac tccctgtggc ctggctttgc ctgtgacact acacaagctg cttgctccaa      360
gataatccaa gttctttttct ctgtcttcct gatacacagg cttttctttgg catctgacac      420 tgctggccac ctgctcttct tgaaatgctt cttttggctt ctaggaaacg gcgcgccacg      480
cgtcagttta ctcaccaggg attcagaggc agcactgctg aaccctgagc ccttggcaca      540
tcaggttggc tgtcagaagt cggcctttgt acatacacag ttcccttgtg aggcccagct      600
gcgtgtccta ggagcggggc ctctctccac agcagagctc agcctctcaa gtgtatggac      660
agcacgggtg cctgatgggt ggatttagcc atgagttgaa ggtggcttgg ggagaatgag      720
agttctagag atagggagaa ggggttgcca ataggagagt ggaattcctg agcacctcgt      780
cacaggcagc cgacagaaca tgagccgcag ggcccaggct atttataccct cgcctgtcac      840 tatcagggtc cccacagctc ccccccacctc cagccacaca cagcaggtcc ttttgctctt      900
tctggtccct tctctactcc tccccctccc tacctaaggt acccaacgcg ttacgtggcc      960
accgccttcg gcaccatcct cacgacaccc aaatatggcg acgggtgagg aatggtgggg     1020 agttatttttt agagcggtga ggaaggtggg caggcagcag gtgttggcgc tctaaaaata     1080
actcccggga gttatttttta gagcggagga atggtggaca cccaaatatg gcgacggttc     1140
ctcacccgtc gccatatttg ggtgtccgcc ctcggccggg gccgcattcc tggggggccgg     1200 gcggtgctcc cgcccgcctc gataaaaggc tccggggccg gcggcggccc acgagctacc     1260
cggaggagcg ggaggcgcca agctctagat ctagaaagag gtaagggttt aagggatggt     1320
tggttggtgg ggtattaatg tttaattacc tggagcacct gcctgaaatc acttttttttc     1380 aggttggaag cttatggaag atgccaaaaa cattaagaag ggcccagcgc cattctaccc     1440
actcgaggac gggaccgccg gcgagcagct gcacaaagcc atgaagcgct acgccctggt     1500
```

```
gcccggcacc atcgccttta ccgacgcaca tatcgaggtg gacattacct acgccgagta   1560
cttcgagatg agcgttcggc tggcagaagc tatgaagcgc tatgggctga atacaaacca   1620
tcggatcgtg gtgtgcagcg agaatagctt gcagttcttc atgcccgtgt tgggtgccct   1680
gttcatcggt gtggctgtgg ccccagctaa cgacatctac aacgagcgcg agctgctgaa   1740
cagcatgggc atcagccagc ccaccgtcgt attcgtgagc aagaaggggc tgcaaaagat   1800
cctcaacgtg caaaagaagc taccgatcat acaaaagatc atcatcatgg atagcaagac   1860
cgactaccag ggcttccaaa gcatgtacac cttcgtgact tcccatttgc cacccggctt   1920
caacgagtac gacttcgtgc ccgagagctt cgaccgggac aaaaccatcg ccctgatcat   1980
gaacagtagt ggcagtaccg gattgcccaa gggcgtagcc ctaccgcacc gcaccgcttg   2040
tgtccgattc agtcatgccc gcgacccat cttcggcaac cagatcatcc ccgacaccgc   2100
tatcctcagc gtggtgccat ttcaccacgg cttcggcatg ttcaccacgc tgggctactt   2160
gatctgcggc tttcgggtcg tgctcatgta ccgcttcgag gaggagctat tcttgcgcag   2220
cttgcaagac tataagattc aatctgccct gctggtgccc acactattta gcttcttcgc   2280
taagagcact ctcatcgaca gtacgacct aagcaacttg cacgagatcg ccagcggcgg   2340
ggcgccgctc agcaaggagg taggtgaggc cgtggccaaa cgcttccacc taccaggcat   2400
ccgccagggc tacggcctga cagaaacaac cagcgccatt ctgatcaccc ccgaagggga   2460
cgacaagcct ggcgcagtag gcaaggtggt gcccttcttc gaggctaagg tggtggactt   2520
ggacaccggt aagacactgg gtgtgaacca gcgcggcgag ctgtgcgtcc gtggccccat   2580
gatcatgagc ggctacgtta caacccccga ggctacaaac gctctcatcg acaaggacgg   2640
ctggctgcac agcggcgaca tcgcctactg ggacgaggac gagcacttct tcatcgtgga   2700
ccggctgaag agcctgatca aatacaaggg ctaccaggta gccccagccg aactggagag   2760
catcctgctg caacacccca acatcttcga cgccggggtc gccggcctgc ccgacgacga   2820
tgccggcgag ctgcccgccg cagtcgtcgt gctggaacac ggtaaaacca tgaccgagaa   2880
ggagatcgtg gactatgtgg ccagccaggt tacaaccgcc aagaagctgc gcggtggtgt   2940
tgtgttcgtg gacgaggtgc ctaaaggact gaccggcaag ttggacgccc gcaagatccg   3000
cgagattctc attaaggcca agaagggcgg caagatcgcc gtgtaattcg aaacgtaggg   3060
tccatcttga gcatctgact tctggctaaa taaaagatct ttattttcat tagatctgtg   3120
tgttggtttt ttgtgtgcgt cgagatccac ggccgcagga accctagtg atggagttgg   3180 ccactcccte tctgcgcgct cgctcgctca ctgaggccgg gcgaccaaag gtcgcccgac   3240
gcccgggctt tgcccgggcg gcctcagtga gcgagcgagc gcgcagctgc ctgcaggggc   3300
gcctgatgcg gtattttctc cttacgcatc tgtgcggtat ttcacaccgc atacgtcaaa   3360
gcaaccatag tacgcgccct gtagcggcgc attaagcgcg gcgggtgtgg tggttacgcg   3420
cagcgtgacc gctacacttg ccagcgccct agcgcccgct cctttcgctt tcttcccttc   3480
ctttctcgcc acgttcgccg gctttccccg tcaagctcta aatcgggggc tccctttagg   3540
gttccgattt agtgctttac ggcacctcga ccccaaaaaa cttgatttgg gtgatggttc   3600
acgtagtggg ccatcgccct gatagacggt ttttcgccct tgacgttgg agtccacgtt   3660 ctttaatagt ggactcttgt tccaaactgg aacaacactc aaccctatct cgggctattc   3720
ttttgattta agggattt tgccgatttc ggcctattgg ttaaaaaatg agctgattta   3780
acaaaaattt aacgcgaatt ttaacaaaat attaacgttt acaattttat ggtgcactct   3840
```

```
cagtacaatc tgctctgatg ccgcatagtt aagccagccc cgacacccgc caacacccgc    3900
tgacgcgccc tgacgggctt gtctgctccc ggcatccgct tacagacaag ctgtgaccgt    3960
ctccgggagc tgcatgtgtc agaggttttc accgtcatca ccgaaacgcg cgagacgaaa    4020
gggcctcgtg atacgcctat ttttataggt taatgtcatg ataataatgg tttcttagac    4080
gtcaggtggc acttttcggg gaaatgtgcg cggaacccct atttgtttat ttttctaaat    4140
acattcaaat atgtatccgc tcatgagaca ataaccctga taaatgcttc aataatattg    4200
aaaaaggaag agtatgagta ttcaacattt ccgtgtcgcc cttattccct ttttgcggc     4260
attttgcctt cctgttttg ctcacccaga acgctggtg aaagtaaaag atgctgaaga     4320
tcagttgggt gcacgagtgg gttacatcga actggatctc aacagcggta agatccttga    4380
gagttttcgc cccgaagaac gttttccaat gatgagcact tttaaagttc tgctatgtgg    4440
cgcggtatta tcccgtattg acgccgggca agagcaactc ggtcgccgca tacactattc    4500
tcagaatgac ttggttgagt actcaccagt cacagaaaag catcttacgg atggcatgac    4560
agtaagagaa ttatgcagtg ctgccataac catgagtgat aacactgcgg ccaacttact    4620
tctgacaacg atcggaggac cgaaggagct aaccgctttt ttgcacaaca tgggggatca    4680
tgtaactcgc cttgatcgtt gggaaccgga gctgaatgaa gccataccaa acgacgagcg    4740
tgacaccacg atgcctgtag caatggcaac aacgttgcgc aaactattaa ctggcgaact    4800
acttactcta gcttcccggc aacaattaat agactggatg gaggcggata agttgcagg    4860
accacttctg cgctcggccc ttccggctgg ctggtttatt gctgataaat ctggagccgg    4920
tgagcgtggg tctcgcggta tcattgcagc actggggcca gatggtaagc cctcccgtat    4980
cgtagttatc tacacgacgg ggagtcaggc aactatggat gaacgaaata gacagatcgc    5040
tgagataggt gcctcactga ttaagcattg gtaactgtca gaccaagttt actcatatat    5100
actttagatt gatttaaaac ttcattttta atttaaaagg atctaggtga agatccttt     5160
tgataatctc atgaccaaaa tcccttaacg tgagttttcg ttccactgag cgtcagaccc    5220
cgtagaaaag atcaaaggat cttcttgaga tcctttttt ctgcgcgtaa tctgctgctt     5280
gcaaacaaaa aaaccaccgc taccagcggt ggtttgtttg ccggatcaag agctaccaac    5340
tcttttttccg aaggtaactg gcttcagcag agcgcagata ccaaatactg tccttctagt    5400
gtagccgtag ttaggccacc acttcaagaa ctctgtagca ccgcctacat acctcgctct    5460
gctaatcctg ttaccagtgg ctgctgccag tggcgataag tcgtgtctta ccgggttgga    5520
ctcaagacga tagttaccgg ataaggcgca gcggtcgggc tgaacggggg gttcgtgcac    5580
acagcccagc ttggagcgaa cgacctacac cgaactgaga tacctacagc gtgagctatg    5640
agaaagcgcc acgcttcccg aagggagaaa ggcggacagg tatccggtaa gcggcagggt    5700
cggaacagga gagcgcacga gggagcttcc agggggaaac gcctggtatc tttatagtcc    5760
tgtcgggttt cgccacctct gacttgagcg tcgatttttg tgatgctcgt caggggggcg    5820
gagcctatgg aaaaacgcca gcaacgcggc ctttttacgg ttcctggcct tttgctggcc    5880
ttttgctc                                                             5888
```

<210> SEQ ID NO 107
<211> LENGTH: 5572
<212> TYPE: DNA
<213> ORGANISM: Artificial Sequence
<220> FEATURE:
<223> OTHER INFORMATION: plasmid pAAVss-CSkSH5-SPc5-12_GTRM-Luc2

<400> SEQUENCE: 107

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gccggcgcgc cacgcgtcag tttactcacc     180
agggattcag aggcagcact gctgaaccct gagcccttgg cacatcaggt tggctgtcag     240
aagtcggcct ttgtacatac acagttccct tgtgaggccc agctgcgtgt cctaggagcg     300
gggcctctct ccacagcaga gctcagcctc tcaagtgtat ggacagcacg ggtgcctgat     360
gggtggattt agccatgagt tgaaggtggc ttggggagaa tgagagttct agagataggg     420
agaaggggtt gccaatagga gagtggaatt cctgagcacc tcgtcacagg cagccgacag     480
aacatgagcc gcagggccca ggctatttat acctcgcctg tcactatcag ggtccccaca     540
gctcccccca cctccagcca cacacagcag gtccttttgc tctttctggt cccttctcta     600
ctcctccccc tccctaccta aggtacccaa cgcgttacgt ggccaccgcc ttcggcacca     660
tcctcacgac acccaaatat ggcgacgggg aggaatggt ggggagttat ttttagagcg      720
gtgaggaagg tgggcaggca gcaggtgttg gcgctctaaa aataactccc gggagttatt     780
tttagagcgg aggaatggtg gacacccaaa tatggcgacg gttcctcacc cgtcgccata     840
tttgggtgtc cgccctcggc cggggccgca ttcctggggg ccgggcggtg ctcccgcccg     900
cctcgataaa aggctccggg gccggcgcg gcccacgagc tacccggagg agcgggaggc      960
gccaagctct agatctagaa agaggtaagg gtttaaggga tggttggttg gtggggtatt    1020
aatgtttaat tacctggagc acctgcctga aatcactttt tttcaggttg gaagcttatg    1080
gaagatgcca aaaacattaa gaagggccca gcgccattct acccactcga ggacgggacc    1140
gccggcgagc agctgcacaa agccatgaag cgctacgccc tggtgcccgg caccatcgcc    1200
tttaccgacg cacatatcga ggtggacatt acctacgccg agtacttcga gatgagcgtt    1260
cggctggcag aagctatgaa gcgctatggg ctgaatacaa accatcggat cgtggtgtgc    1320
agcgagaata gcttgcagtt cttcatgccc gtgttgggtg ccctgttcat cggtgtggct    1380
gtggccccag ctaacgacat ctacaacgag cgcgagctgc tgaacagcat gggcatcagc    1440
cagcccaccg tcgtattcgt gagcaagaaa gggctgcaaa agatcctcaa cgtgcaaaag    1500
aagctaccga tcatacaaaa gatcatcatc atggatagca agaccgacta ccagggcttc    1560
caaagcatgt acaccttcgt gacttcccat ttgccacccg gcttcaacga gtacgacttc    1620
gtgcccgaga gcttcgaccg ggacaaaacc atcgccctga tcatgaacag tagtggcagt    1680
accggattgc ccaagggcgt agccctaccg caccgcaccg cttgtgtccg attcagtcat    1740
gcccgcgacc ccatcttcgg caaccagatc atccccgaca ccgctatcct cagcgtggtg    1800
ccatttcacc acgcttcgg catgttcacc acgctgggct acttgatctg cggctttcgg     1860
gtcgtgctca tgtaccgctt cgaggaggag ctattcttgc gcagcttgca agactataag    1920
attcaatctg ccctgctggt gcccacacta tttagcttct tcgctaagag cactctcatc    1980
gacaagtacg acctaagcaa cttgcacgag atcgccagcg gcggggcgcc gctcagcaag    2040
gaggtaggtg aggccgtggc caaacgcttc cacctaccag gcatccgcca gggctacggc    2100
ctgacagaaa caaccagcgc cattctgatc accccgaag gggacgacaa gcctggcgca    2160
gtaggcaagg tggtgccctt cttcgaggct aaggtggtgg acttggacac cggtaagaca    2220
ctgggtgtga accagcgcgg cgagctgtgc gtccgtggcc ccatgatcat gagcggctac    2280
gttaacaacc ccgaggctac aaacgctctc atcgacaagg acggctggct gcacagcggc    2340
```

```
gacatcgcct actgggacga ggacgagcac ttcttcatcg tggaccggct gaagagcctg    2400
atcaaataca agggctacca ggtagcccca gccgaactgg agagcatcct gctgcaacac    2460
cccaacatct tcgacgccgg ggtcgccggc ctgcccgacg acgatgccgg cgagctgccc    2520
gccgcagtcg tcgtgctgga acacggtaaa accatgaccg agaaggagat cgtggactat    2580
gtggccagcc aggttacaac cgccaagaag ctgcgcggtg gtgttgtgtt cgtggacgag    2640
gtgcctaaag gactgaccgg caagttggac gcccgcaaga tccgcgagat tctcattaag    2700
gccaagaagg gcggcaagat cgccgtgtaa ttcgaaacgt tcggtccatc ttgagcatct    2760
gacttctggc taaataaaag atctttattt tcattagatc tgtgtgttgg ttttttgtgt    2820
gcgtcgagat ccacggccgc aggaacccct agtgatggag ttggccactc cctctctgcg    2880
cgctcgctcg ctcactgagg ccgggcgacc aaaggtcgcc cgacgcccgg gctttgcccg    2940
ggcggcctca gtgagcgagc gagcgcgcag ctgcctgcag gggcgcctga tgcggtattt    3000
tctccttacg catctgtgcg gtatttcaca ccgcatacgt caaagcaacc atagtacgcg    3060
ccctgtagcg gcgcattaag cgcggcgggt gtggtggtta cgcgcagcgt gaccgctaca    3120
cttgccagcg ccctagcgcc cgctccttt c gctttcttcc cttcctttct cgccacgttc    3180
gccggctttc cccgtcaagc tctaaatcgg gggctccctt tagggttccg atttagtgct    3240
ttacggcacc tcgaccccaa aaaacttgat ttgggtgatg gttcacgtag tgggccatcg    3300
ccctgataga cggttttttcg ccctttgacg ttggagtcca cgttctttaa tagtggactc    3360
ttgttccaaa ctggaacaac actcaaccct atctcgggct attcttttga tttataaggg    3420
attttgccga tttcggccta ttggttaaaa aatgagctga tttaacaaaa atttaacgcg    3480
aattttaaca aaatattaac gtttacaatt ttatggtgca ctctcagtac aatctgctct    3540
gatgccgcat agttaagcca gccccgacac ccgccaacac ccgctgacgc gccctgacgg    3600
gcttgtctgc tcccggcatc cgcttacaga caagctgtga ccgtctccgg agctgcatg    3660
tgtcagaggt tttcaccgtc atcaccgaaa cgcgcgagac gaaagggcct cgtgatacgc    3720
ctatttttat aggttaatgt catgataata atggtttctt agacgtcagg tggcactttt    3780
cggggaaatg tgcgcggaac ccctatttgt ttatttttct aaatacattc aaatatgtat    3840
ccgctcatga gacaataacc ctgataaatg cttcaataat attgaaaaag gaagagtatg    3900
agtattcaac atttccgtgt cgcccttatt cccttttttg cggcattttg ccttcctgtt    3960
tttgctcacc cagaaacgct ggtgaaagta aaagatgctg aagatcagtt gggtgcacga    4020
gtgggttaca tcgaactgga tctcaacagc ggtaagatcc ttgagagttt tcgccccgaa    4080
gaacgttttc caatgatgag cacttttaaa gttctgctat gtggcgcggt attatcccgt    4140
attgacgccg ggcaagagca actcggtcgc cgcatacact attctcagaa tgacttggtt    4200
gagtactcac cagtcacaga aaagcatctt acggatggca tgacagtaag agaattatgc    4260
agtgctgcca taaccatgag tgataacact gcggccaact tacttctgac aacgatcgga    4320
ggaccgaagg agctaaccgc ttttttgcac aacatggggg atcatgtaac tcgccttgat    4380
cgttgggaac cggagctgaa tgaagccata ccaaacgacg agcgtgacac cacgatgcct    4440
gtagcaatgg caacaacgtt gcgcaaacta ttaactggcg aactacttac tctagcttcc    4500
cggcaacaat taatagactg gatggaggcg gataaagttg caggaccact tctgcgctcg    4560
gcccttccgg ctggctggtt tattgctgat aaatctggag ccggtgagcg tgggtctcgc    4620
ggtatcattg cagcactggg gccagatggt aagccctccc gtatcgtagt tatctacacg    4680
acggggagtc aggcaactat ggatgaacga aatagacaga tcgctgagat aggtgcctca    4740
```

```
ctgattaagc attggtaact gtcagaccaa gtttactcat atatacttta gattgattta    4800
aaacttcatt tttaatttaa aaggatctag gtgaagatcc ttttttgataa tctcatgacc    4860
aaaatccctt aacgtgagtt ttcgttccac tgagcgtcag accccgtaga aaagatcaaa    4920
ggatcttctt gagatccttt ttttctgcgc gtaatctgct gcttgcaaac aaaaaaacca    4980
ccgctaccag cggtggtttg tttgccggat caagagctac caactctttt tccgaaggta    5040
actggcttca gcagagcgca gataccaaat actgtccttc tagtgtagcc gtagttaggc    5100
caccacttca agaactctgt agcaccgcct acatacctcg ctctgctaat cctgttacca    5160
gtggctgctg ccagtggcga taagtcgtgt cttaccgggt tggactcaag acgatagtta    5220
ccggataagg cgcagcggtc gggctgaacg gggggttcgt gcacacagcc cagcttggag    5280
cgaacgacct acaccgaact gagatacctta cagcgtgagc tatgagaaag cgccacgctt    5340
cccgaaggga gaaaggcgga caggtatccg gtaagcggca gggtcggaac aggagagcgc    5400
acgagggagc ttccaggggg aaacgcctgg tatctttata gtcctgtcgg gtttcgccac    5460
ctctgacttg agcgtcgatt tttgtgatgc tcgtcagggg ggcggagcct atggaaaaac    5520
gccagcaacg cggccttttt acggttcctg gccttttgct ggccttttgc tc            5572
```

<210> SEQ ID NO 108
<211> LENGTH: 5118
<212> TYPE: DNA
<213> ORGANISM: Artificial Sequence
<220> FEATURE:
<223> OTHER INFORMATION: plasmid pAAVss-SPc5-12_GTRM-Luc2

<400> SEQUENCE: 108

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gccggcgcgc cacgcgtggt acccaacgcg     180
ttacgtggcc accgccttcg gcaccatcct cacgacaccc aaatatggcg acgggtgagg     240
aatggtgggg agttattttt agagcggtga ggaaggtggg caggcagcag gtgttggcgc     300
tctaaaaata actcccggga gttatttta gagcggagga atggtggaca cccaaatatg     360
gcgacggttc ctcacccgtc gccatatttg ggtgtccgcc ctcggccggg gccgcattcc     420
tgggggccgg gcggtgctcc cgcccgcctc gataaaaggc tccggggccg gcggcggccc     480
acgagctacc cggaggagcg ggaggcgcca agctctagat ctagaaagag gtaagggttt     540
aagggatggt tggttggtgg ggtattaatg tttaattacc tggagcacct gcctgaaatc     600
acttttttc aggttggaag cttatggaag atgccaaaaa cattaagaag ggcccagcgc     660
cattctaccc actcgaagac gggaccgccg gcgagcagct gcacaaagcc atgaagcgct     720
acgccctggt gcccggcacc atcgccttta ccgacgcaca tatcgaggtg gacattacct     780
acgccgagta cttcgagatg agcgttcggc tggcagaagc tatgaagcgc tatgggctga     840
atacaaacca tcggatcgtg gtgtgcagcg agaatagctt gcagttcttc atgcccgtgt     900
tgggtgccct gttcatcggt gtggctgtgg cccagctaa cgacatctac aacgagcgcg     960
agctgctgaa cagcatgggc atcagccagc ccaccgtcgt attcgtgagc aagaaagggc    1020
tgcaaaagat cctcaacgtg caaaagaagc taccgatcat acaaaagatc atcatcatgg    1080
atagcaagac cgactaccag ggcttccaaa gcatgtacac cttcgtgact tcccatttgc    1140
cacccggctt caacgagtac gacttcgtgc ccgagagctt cgaccgggac aaaaccatcg    1200
```

```
ccctgatcat gaacagtagt ggcagtaccg gattgcccaa gggcgtagcc ctaccgcacc    1260
gcaccgcttg tgtccgattc agtcatgccc gcgaccccat cttcggcaac cagatcatcc    1320
ccgacaccgc tatcctcagc gtggtgccat tcaccacgg cttcggcatg ttcaccacgc     1380
tgggctactt gatctgcggc tttcgggtcg tgctcatgta ccgcttcgag gaggagctat    1440
tcttgcgcag cttgcaagac tataagattc aatctgccct gctggtgccc acactattta   1500
gcttcttcgc taagagcact ctcatcgaca agtacgacct aagcaacttg cacgagatcg    1560
ccagcggcgg ggcgccgctc agcaaggagg taggtgaggc cgtggccaaa cgcttccacc    1620
taccaggcat ccgccagggc tacggcctga cagaaacaac cagcgccatt ctgatcaccc    1680
ccgaagggga cgacaagcct ggcgcagtag gcaaggtggt gcccttcttc gaggctaagg    1740
tggtggactt ggacaccggt aagacactgg gtgtgaacca gcgcggcgag ctgtgcgtcc    1800
gtggccccat gatcatgagc ggctacgtta caaccccga ggctacaaac gctctcatcg     1860
acaaggacgg ctggctgcac agcggcgaca tcgcctactg ggacgaggac gagcacttct    1920
tcatcgtgga ccggctgaag agcctgatca aatacaaggg ctaccaggta gccccagccg    1980
aactggagag catcctgctg caacacccca acatcttcga cgccggggtc gccggcctgc    2040
ccgacgacga tgccggcgag ctgccccgcg cagtcgtcgt gctggaacac ggtaaaacca    2100
tgaccgagaa ggagatcgtg gactatgtgg ccagccaggt tacaaccgcc aagaagctgc    2160
gcggtggtgt tgtgttcgtg gacgaggtgc ctaaaggact gaccggcaag ttggacgccc    2220
gcaagatccg cgagattctc attaaggcca agaagggcgg caagatcgcc gtgtaattcg    2280
aaacgttgtg tccatcttga gcatctgact tctggctaaa taaagatct ttattttcat     2340
tagatctgtg tgttggtttt ttgtgtgcgt cgagatccac ggccgcagga cccctagtg     2400
atggagttgg ccactccctc tctgcgcgct cgctcgctca ctgaggccgg gcgaccaaag    2460
gtcgcccgac gcccgggctt tgcccgggcg gcctcagtga gcgagcgagc gcgcagctgc    2520
ctgcaggggc gcctgatgcg gtattttctc cttacgcatc tgtgcggtat ttcacaccgc    2580
atacgtcaaa gcaaccatag tacgcgccct gtagcggcgc attaagcgcg gcgggtgtgg    2640
tggttacgcg cagcgtgacc gctacacttg ccagcgccct agcgcccgct cctttcgctt    2700
tcttcccttc ctttctcgcc acgttcgccg gctttccccg tcaagctcta aatcggggc     2760
tcccttagg gttccgattt agtgctttac ggcacctcga ccccaaaaaa cttgatttgg     2820
gtgatggttc acgtagtggg ccatcgccct gatagacggt ttttcgccct tgacgttgg     2880
agtccacgtt ctttaatagt ggactcttgt tccaaactgg aacaacactc aaccctatct    2940
cgggctattc ttttgattta agggatttt gccgatttc ggcctattgg ttaaaaaatg      3000
agctgattta acaaaaattt aacgcgaatt ttaacaaaat attaacgttt acaattttat    3060
ggtgcactct cagtacaatc tgctctgatg ccgcatagtt aagccagccc cgacacccgc    3120
caacacccgc tgacgcgccc tgacgggctt gtctgctccc ggcatccgct tacagacaag    3180
ctgtgaccgt ctccgggagc tgcatgtgtc agaggttttc accgtcatca ccgaaacgcg    3240
cgagacgaaa gggcctcgtg atacgcctat ttttataggt taatgtcatg ataataatgg    3300
tttcttagac gtcaggtggc acttttcggg gaaatgtgcg cggaaccct atttgtttat     3360
ttttctaaat acattcaaat atgtatccgc tcatgagaca ataaccctga taatgcttc     3420
aataatattg aaaaggaag agtatgagta ttcaacattt ccgtgtcgcc cttattcct      3480
tttttgcgg attttgcctt cctgtttttg ctcacccaga aacgctggtg aaagtaaaag    3540
atgctgaaga tcagttgggt gcacgagtgg gttacatcga actggatctc aacagcggta    3600
```

| | |
|---|---|
| agatccttga gagttttcgc cccgaagaac gttttccaat gatgagcact tttaaagttc | 3660 |
| tgctatgtgg cgcggtatta tcccgtattg acgccgggca agagcaactc ggtcgccgca | 3720 |
| tacactattc tcagaatgac ttggttgagt actcaccagt cacagaaaag catcttacgg | 3780 |
| atggcatgac agtaagagaa ttatgcagtg ctgccataac catgagtgat aacactgcgg | 3840 |
| ccaacttact tctgacaacg atcggaggac cgaaggagct aaccgctttt ttgcacaaca | 3900 |
| tgggggatca tgtaactcgc cttgatcgtt gggaaccgga gctgaatgaa gccataccaa | 3960 |
| acgacgagcg tgacaccacg atgcctgtag caatggcaac aacgttgcgc aaactattaa | 4020 |
| ctggcgaact acttactcta gcttcccggc aacaattaat agactggatg gaggcggata | 4080 |
| aagttgcagg accacttctg cgctcggccc ttccggctgg ctggtttatt gctgataaat | 4140 |
| ctggagccgg tgagcgtggg tctcgcggta tcattgcagc actggggcca gatggtaagc | 4200 |
| cctcccgtat cgtagttatc tacacgacgg ggagtcaggc aactatggat gaacgaaata | 4260 |
| gacagatcgc tgagataggt gcctcactga ttaagcattg gtaactgtca gaccaagttt | 4320 |
| actcatatat actttagatt gatttaaaac ttcattttta atttaaaagg atctaggtga | 4380 |
| agatccttttt tgataatctc atgaccaaaa tcccttaacg tgagttttcg ttccactgag | 4440 |
| cgtcagaccc cgtagaaaag atcaaaggat cttcttgaga tccttttttt ctgcgcgtaa | 4500 |
| tctgctgctt gcaaacaaaa aaaccaccgc taccagcggt ggtttgtttg ccggatcaag | 4560 |
| agctaccaac tctttttccg aaggtaactg gcttcagcag agcgcagata ccaaatactg | 4620 |
| tccttctagt gtagccgtag ttaggccacc acttcaagaa ctctgtagca ccgcctacat | 4680 |
| acctcgctct gctaatcctg ttaccagtgg ctgctgccag tggcgataag tcgtgtctta | 4740 |
| ccgggttgga ctcaagacga tagttaccgg ataaggcgca gcggtcgggc tgaacggggg | 4800 |
| gttcgtgcac acagcccagc ttggagcgaa cgacctacac cgaactgaga tacctacagc | 4860 |
| gtgagctatg agaaagcgcc acgcttcccg aagggagaaa ggcggacagg tatccggtaa | 4920 |
| gcggcagggt cggaacagga gagcgcacga gggagcttcc agggggaaac gcctggtatc | 4980 |
| tttatagtcc tgtcgggttt cgccacctct gacttgagcg tcgatttttg tgatgctcgt | 5040 |
| caggggggcg gagcctatgg aaaaacgcca gcaacgcggc ctttttacgg ttcctggcct | 5100 |
| tttgctggcc ttttgctc | 5118 |

<210> SEQ ID NO 109
<211> LENGTH: 7097
<212> TYPE: DNA
<213> ORGANISM: Artificial Sequence
<220> FEATURE:
<223> OTHER INFORMATION: plasmid pAAVss-CRE02-SkSH4-hDES1.4kb-Luc2

<400> SEQUENCE: 109

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgac aggtgcggtt cccggagcgc aggcgcacac | 180 |
| atgcacccac cggcgaacgc ggtgaccctc gccccacccc atcccctccg gcgggcaact | 240 |
| gggtcgggtc aggaggggca aacccgctag ggagacactc catatacggc ccggcccgcg | 300 |
| ttacctggga ccgggccaac ccgctccttc tttggtcaac gcaggggacc cggcgggggg | 360 |
| cccaggccgc gaaccggccg agggagggggg ctctagtgcc caacacccaa atatggctcg | 420 |
| agaagggcag cgacattcct gcggggtggc gcggagggaa tgcccgcggg ctatataaaa | 480 |

```
cctgagcaga gggacaagcg gccaccgcag cggacagcgc caagtgaagc ctcgcttccc    540
ctccgcggcg accagggccc gagccgagag tagcagttgt agctacccgc ccaggtaggg    600
gcgcgccacg cgtttctgag tcctctaagg tccctcactc ccaactcagc cccatgtcct    660
gtcaattccc actcagtgtc tgatctcctt ctcctcacct ttcccatctc ccgtttgacc    720
caagcttcct gagctctcct cccattcccc tttttggagt cctcctcctc tcccagaacc    780
cagtaataag tgggctcctc cctggcctgg accccgtgg taaccctata aggcgaggca    840
gctgctgtct gaggcaggga ggggctggtg tgggaggcta agggcagctg ctaagtttag    900
ggtggctcct tctctcttct tagagacaac aggtggctgg ggcctcagtg cccagaaaag    960
aaaatgtctt agaggtatcg gcatgggcct ggaggagggg ggacagggca gggggaggca   1020
tcttcctcag gacatcgggt cctagagggg tacccaacgg gttacgcac acctactagt    1080
aacccctcca gctggtgatg gcaggtctag ggtaggacca gtgactggct cctaatcgag   1140
cactctattt tcagggtttg cattccaaaa gggtcaggtc caagagggac ctggagtgcc   1200
aagtggaggt gtagaggcac ggccagtacc catggagaat ggtggatgtc cttagggggtt   1260
agcaagtgcc gtgtgctaag gagggggctt tggaggttgg gcaggccctc tgtgggctc    1320
cattttgtg ggggtggggg ctggagcatt ataggggtg ggaagtgatt ggggctgtca     1380
ccctagcctt ccttatctga cgcccaccca tgcctcctca ggtaccccct gccccccaca   1440
gctcctctcc tgtgccttgt ttcccagcca tgcgttctcc tctataaata cccgctctgg   1500
tatttggggt tggcagctgt tgctgccagg gagatggttg ggttgacatg cggctcctga   1560
caaaacacaa accccctggtg tgtgtgggcg tgggtggtgt gagtaggggg atgaatcagg   1620
gaggggggcgg gggacccagg gggcaggagc cacacaaagt ctgtgcgggg gtgggagcgc   1680
acatagcaat tggaaactga aagcttatca gaccctttct ggaaatcagc ccactgttta   1740
taaacttgag gccccaccct cgacagtacc ggggaggaag agggcctgca ctagtccaga   1800
gggaaactga ggctcagggc tagctcgccc atagacatac atggcaggca ggctttggcc   1860
aggatccctc cgcctgccag gcgtctccct gccctccctt cctgcctaga gaccccccacc   1920
ctcaagcctg gctggtcttt gcctgagacc caaacctctt cgacttcaag agaatattta   1980
ggaacaaggt ggtttagggc cttttcctggg aacaggcctt gaccctttaa gaaatgaccc   2040
aaagtctctc cttgaccaaa aaggggaccc tcaaactaaa gggaagcctc tcttctgctg   2100
tctcccctga ccccactccc ccccacccca ggacgaggag ataaccaggg ctgaaagagg   2160
cccgcctggg ggctgcagac atgcttgctg cctgccctgg cgaaggattg gcaggcttgc   2220
ccgtcacagg accccgctg gctgactcag gggcgcaggc ctcttgcggg ggagctggcc   2280
tccccgcccc cacggccacg ggccgccctt tcctggcagg acagcgggat cttgcagctg   2340
tcagggagg ggaggcgggg gctgatgtca ggagggatac aaatagtgcc gacggctggg   2400
ggccctgtct ccctcgccg catccactct ccggccggcc gctgccgc cgcctcctcc      2460
gtgcgcccgc cagcctcgcc cgcgccgtca cctctagaaa gaggtaaggg tttaagggat   2520
ggttggttgg tggggtatta atgtttaatt acctggagca cctgcctgaa atcacttttt   2580
ttcaggttgg aagcttatgg aagatgccaa aaacattaag aagggcccag cgccattcta   2640
cccactcgag gacgggaccg ccggcgagca gctgcacaaa gccatgaagc gctacgccct   2700
ggtgcccgga accatcgcct ttaccgacgc acatatcgag gtggacatta cctacgccga   2760
gtacttcgag atgagcgttc ggctggcaga agctatgaag cgctatgggc tgaatacaaa   2820
ccatcggatc gtggtgtgca gcgagaatag cttgcagttc ttcatgcccg tgttgggtgc   2880
```

```
cctgttcatc ggtgtggctg tggccccagc taacgacatc tacaacgagc gcgagctgct   2940
gaacagcatg ggcatcagcc agcccaccgt cgtattcgtg agcaagaaag ggctgcaaaa   3000
gatcctcaac gtgcaaaaga agctaccgat catacaaaag atcatcatca tggatagcaa   3060
gaccgactac cagggcttcc aaagcatgta caccttcgtg acttcccatt tgccacccgg   3120
cttcaacgag tacgacttcg tgcccgagag cttcgaccgg gacaaaacca tcgccctgat   3180
catgaacagt agtggcagta ccggattgcc caagggcgta gccctaccgc accgcaccgc   3240
ttgtgtccga ttcagtcatg cccgcgaccc catcttcggc aaccagatca tccccgacac   3300
cgctatcctc agcgtggtgc catttcacca cggcttcggc atgttcacca cgctgggcta   3360
cttgatctgc ggctttcggg tcgtgctcat gtaccgcttc gaggaggagc tattcttgcg   3420
cagcttgcaa gactataaga ttcaatctgc cctgctggtg cccacactat ttagcttctt   3480
cgctaagagc actctcatcg acaagtacga cctaagcaac ttgcacgaga tcgccagcgg   3540
cggggcgccg ctcagcaagg aggtaggtga ggccgtggcc aaacgcttcc acctaccagg   3600
catccgccag ggctacggcc tgacagaaac aaccagcgcc attctgatca ccccccgaagg   3660
ggacgacaag cctggcgcag taggcaaggt ggtgcccttc ttcgaggcta aggtggtgga   3720
cttggacacc ggtaagacac tgggtgtgaa ccagcgcggc gagctgtgcg tccgtggccc   3780
catgatcatg agcggctacg ttaacaaccc cgaggctaca aacgctctca tcgacaagga   3840
cggctggctg cacagcggcg acatcgccta ctgggacgag gacgagcact tcttcatcgt   3900
ggaccggctg aagagcctga tcaaatacaa gggctaccag gtagcccag ccgaactgga   3960
gagcatcctg ctgcaacacc ccaacatctt cgacgccggg gtcgccggcc tgcccgacga   4020
cgatgccggc gagctgcccg ccgcagtcgt cgtgctggaa cacggtaaaa ccatgaccga   4080
gaaggagatc gtggactatg tggccagcca ggttacaacc gccaagaagc tgcgcggtgg   4140
tgttgtgttc gtggacgagg tgcctaaagg actgaccggc aagttggacg cccgcaagat   4200
ccgcgagatt ctcattaagg ccaagaaggg cggcaagatc gccgtgtaat cgaaacgaa   4260
atgtccatct tgagcatctg acttctggct aaataaaaga tctttatttt cattagatct   4320
gtgtgttggt tttttgtgtg cgtcgagatc cacgccgca ggaaccccta gtgatggagt   4380
tggccactcc ctctctgcgc gctcgctcgc tcactgaggc cgggcgacca aaggtcgccc   4440
gacgcccggg ctttgcccgg gcggcctcag tgagcgagca gcgcgcagc tgcctgcagg   4500
ggcgcctgat gcggtatttt ctccttacgc atctgtgcgg tatttcacac cgcatacgtc   4560
aaagcaacca tagtacgcgc cctgtagcgg cgcattaagc gcggcgggtg tggtggttac   4620
gcgcagcgtg accgctacac ttgccagcgc cctagcgccc gctcctttcg ctttcttccc   4680
ttcctttctc gccacgttcg ccggctttcc ccgtcaagct ctaaatcggg ggctcccttt   4740
agggttccga tttagtgctt tacggcacct cgaccccaaa aaacttgatt tgggtgatgg   4800
ttcacgtagt gggccatcgc cctgatagac ggttttcgc cctttgacgt tggagtccac   4860
gttctttaat agtggactct tgttccaaac tggaacaaca ctcaacccta tctcgggcta   4920
ttcttttgat ttataaggga ttttgccgat ttcggcctat tggttaaaaa atgagctgat   4980
ttaacaaaaa tttaacgcga attttaacaa aatattaacg tttacaattt tatggtgcac   5040
tctcagtaca atctgctctg atgccgcata gttaagccag ccccgacacc cgccaacacc   5100
cgctgacgcg ccctgacggg cttgtctgct cccggcatcc gcttacagac aagctgtgac   5160
cgtctccggg agctgcatgt gtcagaggtt ttcaccgtca tcaccgaaac gcgcgagacg   5220
```

```
aaagggcctc gtgatacgcc tattttata ggttaatgtc atgataataa tggtttctta      5280
gacgtcaggt ggcacttttc ggggaaatgt gcgcggaacc cctatttgtt tatttttcta      5340
aatacattca aatatgtatc cgctcatgag acaataaccc tgataaatgc ttcaataata      5400
ttgaaaaagg aagagtatga gtattcaaca tttccgtgtc gcccttattc ccttttttgc      5460
ggcattttgc cttcctgttt ttgctcaccc agaaacgctg gtgaaagtaa aagatgctga      5520
agatcagttg ggtgcacgag tgggttacat cgaactggat ctcaacagcg gtaagatcct      5580
tgagagtttt cgccccgaag aacgttttcc aatgatgagc acttttaaag ttctgctatg      5640
tggcgcggta ttatcccgta ttgacgccgg gcaagagcaa ctcggtcgcc gcatacacta      5700
ttctcagaat gacttggttg agtactcacc agtcacagaa aagcatctta cggatggcat      5760
gacagtaaga gaattatgca gtgctgccat aaccatgagt gataacactg cggccaactt      5820
acttctgaca acgatcggag gaccgaagga gctaaccgct ttttgcaca acatggggga      5880
tcatgtaact cgccttgatc gttgggaacc ggagctgaat gaagccatac caaacgacga      5940
gcgtgacacc acgatgcctg tagcaatggc aacaacgttg cgcaaactat taactggcga      6000
actacttact ctagcttccc ggcaacaatt aatagactgg atggaggcgg ataaagttgc      6060
aggaccactt ctgcgctcgg cccttccggc tggctggttt attgctgata atctggagc      6120
cggtgagcgt gggtctcgcg gtatcattgc agcactgggg ccagatggta agccctcccg      6180
tatcgtagtt atctacacga cggggagtca ggcaactatg gatgaacgaa atagacagat      6240
cgctgagata ggtgcctcac tgattaagca ttggtaactg tcagaccaag tttactcata      6300
tatactttag attgatttaa aacttcattt ttaatttaaa aggatctagg tgaagatcct      6360
ttttgataat ctcatgacca aaatccctta acgtgagttt tcgttccact gagcgtcaga      6420
ccccgtagaa aagatcaaag gatcttcttg agatcctttt tttctgcgcg taatctgctg      6480
cttgcaaaca aaaaaaccac cgctaccagc ggtggtttgt ttgccggatc aagagctacc      6540
aactcttttt ccgaaggtaa ctggcttcag cagagcgcag ataccaaata ctgtccttct      6600
agtgtagccg tagttaggcc accacttcaa gaactctgta gcaccgccta catacctcgc      6660
tctgctaatc ctgttaccag tggctgctgc cagtggcgat aagtcgtgtc ttaccgggtt      6720
ggactcaaga cgatagttac cggataaggc gcagcggtcg ggctgaacgg ggggttcgtg      6780
cacacagccc agcttggagc gaacgaccta caccgaactg agatacctac agcgtgagct      6840
atgagaaagc gccacgcttc ccgaagggag aaaggcggac aggtatccgg taagcggcag      6900
ggtcggaaca ggagagcgca cgagggagct tccaggggga aacgcctggt atctttatag      6960
tcctgtcggg tttcgccacc tctgacttga gcgtcgattt ttgtgatgct cgtcaggggg      7020
gcggagccta tggaaaaacg ccagcaacgc ggcctttta cggttcctgg ccttttgctg      7080
gccttttgct cacatgt                                                     7097
```

<210> SEQ ID NO 110
<211> LENGTH: 7154
<212> TYPE: DNA
<213> ORGANISM: Artificial Sequence
<220> FEATURE:
<223> OTHER INFORMATION: plasmid pAAVss-CRE04-SkSH4-hDES1.4kb-Luc2

<400> SEQUENCE: 110

```
acatgtcctg caggcagctg cgcgctcgct cgctcactga ggccgcccgg gcaaagcccg        60
ggcgtcgggc gacctttggt cgcccggcct cagtgagcga gcgagcgcgc agagagggag       120
tggccaactc catcactagg ggttcctgcg gcccctttta gagaatccac acctgtccca       180
```

-continued

```
gttgctgggt tccactacca aaagtgaatt gcaactattt taggagcact taagcacatc     240
cgaaaaatga gtgattctgt tctggcccac accacatcac tgatgtaccc ccttaaagca     300
tgtccctgag ttcatcacag aagactgctc ctcctgtgcc ctccacaagg ttagaactgt     360
ccttgtctta gggaaaaagg agagagagag agagagagag agagagagag agagagagag     420
agagagagag ggacaggcac caactgggta acctctgctg accccactc tactttacca      480 taagtagctc caaatccttc tagaaaatct gaaaggcata gccccatata tcagtgatat     540
aaatagaacc tgcagcaggc tctggtaaat gatgactaca aggtggactg ggaggcagcc     600
cggccttggc aggcatcatc ctctaaatat aaagatgagt ttgttcagcc tttgcagaag     660
gaggcgcgcc acgcgtttct gagtcctcta aggtccctca ctcccaactc agccccatgt     720
cctgtcaatt cccactcagt gtctgatctc cttctcctca cctttcccat ctcccgtttg     780
acccaagctt cctgagctct cctcccattc ccttttttgg agtcctcctc ctctcccaga     840
acccagtaat aagtgggctc ctccctggcc tggaccccg tggtaaccct ataaggcgag      900
gcagctgctg tctgaggcag ggaggggctg tgtgtgggagg ctaagggcag ctgctaagtt    960
tagggtggct ccttctctct tcttagagac aacaggtggc tggggcctca gtgcccagaa    1020
aagaaaatgt cttagaggta tcggcatggg cctggaggag ggggacagg gcaggggag      1080 gcatcttcct caggacatcg ggtcctagag gggtacccaa cgggttacga cacacctact    1140
agtaacccct ccagctggtg atggcaggtc tagggtagga ccagtgactg gctcctaatc    1200
gagcactcta ttttcagggt ttgcattcca aaagggtcag gtccaagagg gacctggagt    1260
gccaagtgga ggtgtagagg cacggccagt acccatggag aatggtggat gtccttaggg    1320
gttagcaagt gccgtgtgct aaggaggggg cttttggaggt tgggcaggcc ctctgtgggg    1380
ctccattttt gtggggtgg gggctggagc attataggg gtgggaagtg attggggctg      1440
tcaccctagc cttccttatc tgacgcccac ccatgcctcc tcaggtaccc cctgccccc     1500 acagctcctc tcctgtgcct tgtttcccag ccatgcgttc tcctctataa atacccgctc    1560
tggtatttgg ggttggcagc tgttgctgcc agggagatgg ttgggttgac atgcggctcc    1620
tgacaaaaca caaacccctg gtgtgtgtgg gcgtgggtgg tgtgagtagg gggatgaatc    1680 agggagggg cggggaccc aggggcagg agccacacaa agtctgtgcg ggggtgggag       1740
cgcacatagc aattgaaac tgaaagctta tcagacccctt tctggaaatc agcccactgt     1800
ttataaactt gaggccccac cctcgacagt accggggagg aagagggcct gcactagtcc    1860
agagggaaac tgaggctcag ggctagctcg cccatagaca tacatggcag gcaggctttg    1920
gccaggatcc ctccgcctgc caggcgtctc cctgccctcc cttcctgcct agagacccc     1980 accctcaagc ctggctggtc tttgcctgag acccaaacct cttcgacttc aagagaatat    2040
ttaggaacaa ggtggtttag ggcctttcct gggaacaggc cttgacccctt taagaaatga    2100 cccaaagtct ctccttgacc aaaaagggga ccctcaaact aaagggaagc ctctcttctg    2160
ctgtctcccc tgaccccact cccccccacc ccaggacgag gagataacca gggctgaaag    2220
aggcccgcct gggggctgca gacatgcttg ctgcctgccc tggcgaagga ttggcaggct    2280
tgcccgtcac aggaccccg ctggctgact caggggcgca ggcctcttgc ggggagctg      2340 gcctccccgc cccacggcc acgggccgcc ctttcctggc aggacagcgg gatcttgcag     2400
ctgtcagggg aggggaggcg ggggctgatg tcaggaggga tacaaatagt gccgacggct    2460 ggggccctg tctcccctcg ccgcatccac tctccggccg gccgcctgcc cgccgcctcc     2520
```

```
tccgtgcgcc cgccagcctc gcccgcgccg tcacctctag aaagaggtaa gggtttaagg    2580
gatggttggt tggtggggta ttaatgttta attacctgga gcacctgcct gaaatcactt    2640
tttttcaggt tggaagctta tggaagatgc caaaaacatt aagaagggcc cagcgccatt    2700
ctacccactc gaggacggga ccgccggcga gcagctgcac aaagccatga agcgctacgc    2760
cctggtgccc ggcaccatcg cctttaccga cgcacatatc gaggtggaca ttacctacgc    2820
cgagtacttc gagatgagcg ttcggctggc agaagctatg aagcgctatg gctgaatac     2880 aaaccatcgg atcgtggtgt gcagcgagaa tagcttgcag ttcttcatgc ccgtgttggg    2940
tgccctgttc atcggtgtgg ctgtggcccc agctaacgac atctacaacg agcgcgagct    3000
gctgaacagc atgggcatca gccagcccac cgtcgtattc gtgagcaaga aagggctgca    3060
aaagatcctc aacgtgcaaa agaagctacc gatcatacaa aagatcatca tcatggatag    3120
caagaccgac taccagggct ccaaagcat gtacaccttc gtgacttccc atttgccacc     3180
cggcttcaac gagtacgact tcgtgcccga gagcttcgac cgggacaaaa ccatcgccct    3240
gatcatgaac agtagtggca gtaccggatt gcccaagggc gtagccctac cgcaccgcac    3300
cgcttgtgtc cgattcagtc atgcccgcga ccccatcttc ggcaaccaga tcatccccga    3360
caccgctatc ctcagcgtgg tgccatttca ccacggcttc ggcatgttca ccacgctggg    3420
ctacttgatc tgcggctttc gggtcgtgct catgtaccgc ttcgaggagg agctattctt    3480
gcgcagcttg caagactata agattcaatc tgccctgctg gtgcccacac tatttagctt    3540
cttcgctaag agcactctca tcgacaagta cgacctaagc aacttgcacg agatcgccag    3600
cggcggggcg ccgctcagca aggaggtagg tgaggccgtg gccaaacgct tccacctacc    3660
aggcatccgc cagggctacg gcctgacaga acaaccagc gccattctga tcaccccga      3720 aggggacgaa aagcctggcg cagtaggcaa ggtggtgccc ttcttcgagg ctaaggtggt    3780
ggacttggac accggtaaga cactgggtgt gaaccagcgc ggcgagctgt cgtccgtgg     3840 ccccatgatc atgagcggct acgttaacaa ccccgaggct acaaacgctc tcatcgacaa    3900
ggacggctgg ctgcacagcg gcgacatcgc ctactgggac gaggacgagc acttcttcat    3960
cgtggaccgg ctgaagagcc tgatcaaata caagggctac caggtagccc cagccgaact    4020
ggagagcatc ctgctgcaac accccaacat cttcgacgcc ggggtcgccg gcctgcccga    4080
cgacgatgcc ggcgagctgc cgccgcagt cgtcgtgctg gaacacggta aaaccatgac     4140
cgagaaggag atcgtggact atgtggccag ccaggttaca accgccaaga agctgcgcgg    4200
tggtgttgtg ttcgtggacg aggtgcctaa aggactgacc ggcaagttgg acgcccgcaa    4260
gatccgcgag attctcatta aggccaagaa gggcggcaag atcgccgtgt aattcgaaac    4320
gaaaggtcca tcttgagcat ctgacttctg gctaaataaa agatctttat tttcattaga    4380
tctgtgtgtt ggttttttgt gtgcgtcgag atccacggcc gcaggaaccc ctagtgatgg    4440
agttggccac tccctctctg cgcgctcgct cgctcactga ggccgggcga ccaaaggtcg    4500
cccgacgccc gggctttgcc cgggcggcct cagtgagcga gcgagcgcgc agctgcctgc    4560 agggggcgcct gatgcggtat tttctcctta cgcatctgtg cggtatttca caccgcatac    4620
gtcaaagcaa ccatagtacg cgccctgtag cggcgcatta agcgcggcgg gtgtggtggt    4680
tacgcgcagc gtgaccgcta cacttgccag cgccctagcg cccgctcctt tcgctttctt    4740
cccttccttt ctcgccacgt tcgccggctt tccccgtcaa gctctaaatc ggggggctccc   4800 tttagggttc cgatttagtg ctttacggca cctcgacccc aaaaaacttg atttgggtga    4860
tggttcacgt agtgggccat cgccctgata gacggttttt cgccctttga cgttggagtc    4920
```

```
cacgttcttt aatagtggac tcttgttcca aactggaaca acactcaacc ctatctcggg    4980
ctattctttt gatttataag ggattttgcc gatttcggcc tattggttaa aaaatgagct    5040
gatttaacaa aaatttaacg cgaattttaa caaaatatta acgtttacaa ttttatggtg    5100
cactctcagt acaatctgct ctgatgccgc atagttaagc cagccccgac acccgccaac    5160
acccgctgac gcgccctgac gggcttgtct gctcccggca tccgcttaca gacaagctgt    5220
gaccgtctcc gggagctgca tgtgtcagag gttttcaccg tcatcaccga aacgcgcgag    5280
acgaaagggc ctcgtgatac gcctattttt ataggttaat gtcatgataa taatggtttc    5340
ttagacgtca ggtggcactt ttcggggaaa tgtgcgcgga acccctattt gtttattttt    5400
ctaaatacat tcaaatatgt atccgctcat gagacaataa ccctgataaa tgcttcaata    5460
atattgaaaa aggaagagta tgagtattca acatttccgt gtcgccctta ttcccttttt    5520
tgcggcattt tgccttcctg ttttttgctca cccagaaacg ctggtgaaag taaaagatgc    5580
tgaagatcag ttgggtgcac gagtgggtta catcgaactg gatctcaaca gcggtaagat    5640
ccttgagagt tttcgccccg aagaacgttt tccaatgatg agcacttttta aagttctgct    5700 atgtggcgcg gtattatccc gtattgacgc cgggcaagag caactcggtc gccgcataca    5760
ctattctcag aatgacttgg ttgagtactc accagtcaca gaaaagcatc ttacggatgg    5820
catgacagta agagaattat gcagtgctgc cataaccatg agtgataaca ctgcggccaa    5880
cttacttctg acaacgatcg gaggaccgaa ggagctaacc gcttttttgc acaacatggg    5940
ggatcatgta actcgccttg atcgttggga accggagctg aatgaagcca taccaaacga    6000
cgagcgtgac accacgatgc ctgtagcaat ggcaacaacg ttgcgcaaac tattaactgg    6060
cgaactactt actctagctt cccggcaaca attaatagac tggatggagg cggataaagt    6120
tgcaggacca cttctgcgct cggcccttcc ggctggctgg tttattgctg ataaatctgg    6180
agccggtgag cgtgggtctc gcggtatcat tgcagcactg gggccagatg gtaagccctc    6240
ccgtatcgta gttatctaca cgacggggag tcaggcaact atggatgaac gaaatagaca    6300
gatcgctgag ataggtgcct cactgattaa gcattggtaa ctgtcagacc aagtttactc    6360
atatatactt tagattgatt taaaacttca ttttaatttt aaaaggatct aggtgaagat    6420
cctttttgat aatctcatga ccaaaatccc ttaacgtgag ttttcgttcc actgagcgtc    6480
agaccccgta gaaaagatca aaggatcttc ttgagatcct ttttttctgc gcgtaatctg    6540
ctgcttgcaa acaaaaaaac caccgctacc agcggtggtt tgtttgccgg atcaagagct    6600
accaactctt tttccgaagg taactggctt cagcagagcg cagataccaa atactgtcct    6660
tctagtgtag ccgtagttag gccaccactt caagaactct gtagcaccgc ctacatacct    6720
cgctctgcta atcctgttac cagtggctgc tgccagtggc gataagtcgt gtcttaccgg    6780
gttggactca agacgatagt taccggataa ggcgcagcgg tcgggctgaa cggggggttc    6840
gtgcacacag cccagcttgg agcgaacgac ctacaccgaa ctgagatacc tacagcgtga    6900
gctatgagaa agcgccacgc ttcccgaagg gagaaaggcg gacaggtatc cggtaagcgg    6960
cagggtcgga acaggagagc gcacgaggga gcttccaggg ggaaacgcct ggtatcttta    7020
tagtcctgtc gggtttcgcc acctctgact tgagcgtcga ttttttgtgat gctcgtcagg    7080 ggggcggagc ctatggaaaa acgccagcaa cgcggccttt ttacggttcc tggccttttg    7140
ctggcctttt gctc                                                     7154
```

<210> SEQ ID NO 111

<211> LENGTH: 7045
<212> TYPE: DNA
<213> ORGANISM: Artificial Sequence
<220> FEATURE:
<223> OTHER INFORMATION: plasmid pAAVss-CRE06-SkSH4-hDES1.4kb-Luc2

<400> SEQUENCE: 111

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | taggggttcc | tgcggccggg | ccaggggacg | gtggcttcta | cgtgcttggg | 180 |
| acgttcccag | ccaccgtccc | atgttccggg | cgggggggcca | gctgtcccca | ccgccagccc | 240 |
| aactcagcac | ttggtcaggg | tatcagcttg | gtggggggc | gtgagcccag | ccctggggc | 300 |
| ggctcagccc | atacaaggcc | atggggctgg | gcgcaaagca | tgcctgggtt | cagggtgggt | 360 |
| atggtgcggg | agcagggagg | tgagaggctc | agctgccctc | cagaactcct | ccctggggac | 420 |
| aaccctcc | agccaatagc | acagcctagg | tccccctata | taaggccacg | gctgctggcc | 480 |
| cttcctttgg | gtcagtgtca | cctccaggat | acagacagcc | cccttcagc | ccagcccagc | 540 |
| caggtacggc | gcgccacgcg | tttctgagtc | ctctaaggtc | cctcactccc | aactcagccc | 600 |
| catgtcctgt | caattcccac | tcagtgtctg | atctccttct | cctcacctt | ccatctcccc | 660 |
| gtttgaccca | agcttcctga | gctctcctcc | cattcccctt | tttggagtcc | tcctcctctc | 720 |
| ccagaaccca | gtaataagtg | ggctcctccc | tggcctggac | ccccgtggta | accctataag | 780 |
| gcgaggcagc | tgctgtctga | ggcagggagg | ggctggtgtg | ggaggctaag | ggcagctgct | 840 |
| aagtttaggg | tggctccttc | tctcttctta | gagacaacag | gtggctgggg | cctcagtgcc | 900 |
| cagaaaagaa | aatgtcttag | aggtatcggc | atgggcctgg | aggagggggg | acagggcagg | 960 |
| gggaggcatc | ttcctcagga | catcgggtcc | tagaggggta | cccaacgggt | tacgacacac | 1020 |
| ctactagtaa | cccctccagc | tggtgatggc | aggtctaggg | taggaccagt | gactggctcc | 1080 |
| taatcgagca | ctctattttc | agggtttgca | ttccaaaagg | gtcaggtcca | agagggacct | 1140 |
| ggagtgccaa | gtggaggtgt | agaggcacgg | ccagtaccca | tggagaatgg | tggatgtcct | 1200 |
| taggggttag | caagtgccgt | gtgctaagga | ggggggctttg | gaggttgggc | aggccctctg | 1260 |
| tggggctcca | ttttttgtggg | ggtgggggct | ggagcattat | aggggggtggg | aagtgattgg | 1320 |
| ggctgtcacc | ctagccttcc | ttatctgacg | cccacccatg | cctcctcagg | tacccccctgc | 1380 |
| ccccacagc | tcctctcctg | tgccttgttt | cccagccatg | cgttctcctc | tataaatacc | 1440 |
| cgctctggta | tttggggttg | gcagctgttg | ctgccaggga | gatggttggg | ttgacatgcg | 1500 |
| gctcctgaca | aaacacaaac | ccctggtgtg | tgtgggcgtg | ggtggtgtga | gtaggggat | 1560 |
| gaatcaggga | gggggcgggg | gacccagggg | gcaggagcca | cacaaagtct | gtgcgggggt | 1620 |
| gggagcgcac | atagcaattg | gaaactgaaa | gcttatcaga | ccctttctgg | aaatcagccc | 1680 |
| actgttttata | aacttgaggc | cccaccctcg | acagtaccgg | ggaggaagag | ggcctgcact | 1740 |
| agtccagagg | gaaactgagg | ctcagggcta | gctcgcccat | agacatacat | ggcaggcagg | 1800 |
| ctttggccag | gatccctccg | cctgccaggc | gtctccctgc | cctcccttcc | tgcctagaga | 1860 |
| cccccaccct | caagcctggc | tggtctttgc | ctgagaccca | aacctcttcg | acttcaagag | 1920 |
| aatatttagg | aacaaggtgg | tttagggcct | ttcctgggaa | caggccttga | ccctttaaga | 1980 |
| aatgacccaa | agtctctcct | tgaccaaaaa | gggaccctc | aaactaaagg | gaagcctctc | 2040 |
| ttctgctgtc | tcccctgacc | ccactccccc | ccacccagg | acgaggagat | aaccagggct | 2100 |
| gaaagaggcc | cgcctggggg | ctgcagacat | gcttgctgcc | tgccctggcg | aaggattggc | 2160 |

```
aggcttgccc gtcacaggac ccccgctggc tgactcaggg gcgcaggcct cttgcggggg    2220
agctggcctc cccgccccca cggccacggg ccgcccttc ctggcaggac agcgggatct     2280
tgcagctgtc aggggagggg aggcggggc tgatgtcagg agggatacaa atagtgccga     2340
cggctggggg ccctgtctcc cctcgccgca tccactctcc ggccggccgc ctgcccgccg    2400
cctcctccgt gcgcccgcca gcctcgcccg cgccgtcacc tctagaaaga ggtaagggtt    2460
taagggatgg ttggttggtg gggtattaat gtttaattac ctggagcacc tgcctgaaat    2520
cacttttttt caggttggaa gcttatggaa gatgccaaaa acattaagaa gggcccagcg    2580
ccattctacc cactcgagga cgggaccgcc ggcgagcagc tgcacaaagc catgaagcgc    2640
tacgccctgg tgcccggcac catcgccttt accgacgcac atatcgaggt ggacattacc    2700
tacgccgagt acttcgagat gagcgttcgg ctggcagaag ctatgaagcg ctatgggctg    2760
aatacaaacc atcggatcgt ggtgtgcagc gagaatagct tgcagttctt catgcccgtg    2820
ttgggtgccc tgttcatcgg tgtggctgtg gccccagcta acgacatcta caacgagcgc    2880
gagctgctga acagcatggg catcagccag cccaccgtcg tattcgtgag caagaaaggg    2940
ctgcaaaaga tcctcaacgt gcaaaagaag ctaccgatca tacaaaagat catcatcatg    3000
gatagcaaga ccgactacca gggcttccaa agcatgtaca ccttcgtgac ttcccatttg    3060
ccacccggct tcaacgagta cgacttcgtg cccgagagct tcgaccggga caaaaccatc    3120
gccctgatca tgaacagtag tggcagtacc ggattgccca agggcgtagc cctaccgcac    3180
cgcaccgctt gtgtccgatt cagtcatgcc cgcgaccca tcttcggcaa ccagatcatc    3240
cccgacaccg ctatcctcag cgtggtgcca tttcaccacg gcttcggcat gttcaccacg    3300
ctgggctact tgatctgcgg ctttcgggtc gtgctcatgt accgcttcga ggaggagcta    3360
ttcttgcgca gcttgcaaga ctataagatt caatctgccc tgctggtgcc cacactattt    3420
agcttcttcg ctaagagcac tctcatcgac aagtacgacc taagcaactt gcacgagatc    3480
gccagcggcg gggcgccgct cagcaaggag gtaggtgagg ccgtggccaa acgcttccac    3540
ctaccaggca tccgcagggg ctacggcctg acagaaacaa ccagcgccat tctgatcacc    3600
cccgaagggg acgacaagcc tggcgcagta ggcaaggtgg tgcccttctt cgaggctaag    3660
gtggtggact tggacaccgg taagacactg ggtgtgaacc agcgcggcga gctgtgcgtc    3720
cgtggcccca tgatcatgag cggctacgtt aacaaccccg aggctacaaa cgctctcatc    3780
gacaaggacg gctggctgca cagcggcgac atcgcctact gggacgagga cgagcacttc    3840
ttcatcgtgg accggctgaa gagcctgatc aaatacaagg ctaccaggt agccccagcc    3900 gaactggaga gcatcctgct gcaacacccc aacatcttcg acgccggggt cgccggcctg    3960 cccgacacg atgccggcga gctgcccgcc gcagtcgtcg tgctggaaca cggtaaaacc    4020
atgaccgaga aggagatcgt ggactatgtg gccagccagg ttacaaccgc caagaagctg    4080
cgcggtggtg ttgtgttcgt ggacgaggtg cctaaaggac tgaccggcaa gttggacgcc    4140
cgcaagatcc gcgagattct cattaaggcc aagaagggcg gcaagatcgc cgtgtaattc    4200
gaaacgaagg gtccatcttg agcatctgac ttctggctaa ataaaagatc tttatttca    4260 ttagatctgt gtgttggttt tttgtgtgcg tcgagatcca cggccgcagg aacccctagt    4320
gatggagttg gccactccct ctctgcgcgc tcgctcgctc actgaggccg ggcgaccaaa    4380
ggtcgcccga cgcccgggct ttgcccggc ggcctcagtg agcgagcgag cgcgcagctg    4440
cctgcagggg cgcctgatgc ggtatttct ccttacgcat ctgtgcggta tttcacaccg    4500
```

```
catacgtcaa agcaaccata gtacgcgccc tgtagcggcg cattaagcgc ggcgggtgtg    4560
gtggttacgc gcagcgtgac cgctacactt gccagcgccc tagcgcccgc tcctttcgct    4620 ttcttcectt cctttctcgc cacgttcgcc ggctttcccc gtcaagctct aaatcggggg    4680 ctcccttag ggttccgatt tagtgcttta cggcacctcg accccaaaaa acttgatttg    4740
ggtgatggtt cacgtagtgg gccatcgccc tgatagacgg ttttcgccc tttgacgttg    4800 gagtccacgt tctttaatag tggactcttg ttccaaactg gaacaacact caaccctatc    4860
tcgggctatt cttttgattt ataagggatt ttgccgattt cggcctattg gttaaaaaat    4920
gagctgattt aacaaaaatt taacgcgaat tttaacaaaa tattaacgtt tacaatttta    4980
tggtgcactc tcagtacaat ctgctctgat gccgcatagt taagccagcc ccgacacccg    5040
ccaacacccg ctgacgcgcc ctgacgggct tgtctgctcc cggcatccgc ttacagacaa    5100
gctgtgaccg tctccgggag ctgcatgtgt cagaggtttt caccgtcatc accgaaacgc    5160
gcgagacgaa agggcctcgt gatacgccta ttttatagg ttaatgtcat gataataatg    5220
gtttcttaga cgtcaggtgg cacttttcgg ggaaatgtgc gcggaacccc tatttgttta    5280
tttttctaaa tacattcaaa tatgtatccg ctcatgagac aataaccctg ataaatgctt    5340
caataatatt gaaaaggaa gagtatgagt attcaacatt tccgtgtcgc ccttattccc    5400
ttttttgcgg catttgcct tcctgttttt gctcacccag aaacgctggt gaaagtaaaa    5460
gatgctgaag atcagttggg tgcacgagtg gttacatcg aactggatct caacagcggt    5520
aagatccttg agagttttcg ccccgaagaa cgttttccaa tgatgagcac ttttaaagtt    5580
ctgctatgtg gcgcggtatt atcccgtatt gacgccgggc aagagcaact cggtcgccgc    5640
atacactatt ctcagaatga cttggttgag tactcaccag tcacagaaaa gcatcttacg    5700
gatggcatga cagtaagaga attatgcagt gctgccataa ccatgagtga taacactgcg    5760
gccaacttac ttctgacaac gatcggagga ccgaaggagc taaccgcttt tttgcacaac    5820 atggggatc atgtaactcg ccttgatcgt tgggaaccgg agctgaatga agccatacca    5880
aacgacgagc gtgacaccac gatgcctgta gcaatggcaa caacgttgcg caaactatta    5940
actggcgaac tacttactct agcttcccgg caacaattaa tagactggat ggaggcggat    6000
aaagttgcag gaccacttct gcgctcggcc cttccggctg gctggtttat tgctgataaa    6060
tctggagccg gtgagcgtgg gtctcgcggt atcattgcag cactgggcc agatggtaag    6120 ccctcccgta tcgtagttat ctacacgacg gggagtcagg caactatgga tgaacgaaat    6180
agacagatcg ctgagatagg tgcctcactg attaagcatt ggtaactgtc agaccaagtt    6240
tactcatata ctttagat tgatttaaaa cttcatttt aatttaaaag gatctaggtg    6300
aagatccttt ttgataatct catgaccaaa atcccttaac gtgagttttc gttccactga    6360
gcgtcagacc ccgtagaaaa gatcaaagga tcttcttgag atccttttt tctgcgcgta    6420 atctgctgct tgcaaacaaa aaaaccaccg ctaccagcgg tggtttgttt gccggatcaa    6480
gagctaccaa ctcttttcc gaaggtaact ggcttcagca gagcgcagat accaaatact    6540
gtccttctag tgtagccgta gttaggccac cacttcaaga actctgtagc accgcctaca    6600
tacctcgctc tgctaatcct gttaccagtg ctgctgcca gtggcgataa gtcgtgtctt    6660
accgggttgg actcaagacg atagttaccg gataaggcgc agcggtcggg ctgaacgggg    6720
ggttcgtgca cacagcccag cttggagcga acgacctaca ccgaactgag atacctacag    6780
cgtgagctat gagaaagcgc cacgcttccc gaagggagaa aggcggacag gtatccgta    6840 agcggcaggg tcggaacagg agagcgcacg agggagcttc caggggaaa cgcctggtat    6900
```

```
ctttatagtc ctgtcgggtt tcgccacctc tgacttgagc gtcgatttt  gtgatgctcg    6960 tcagggggc  ggagcctatg gaaaaacgcc agcaacgcgg ccttttacg  gttcctggcc    7020 ttttgctggc cttttgctca catgt                                          7045

<210> SEQ ID NO 112
<211> LENGTH: 6942
<212> TYPE: DNA
<213> ORGANISM: Artificial Sequence
<220> FEATURE:
<223> OTHER INFORMATION: plasmid pAAVss-CRE18-SkSH4-hDES1.4kb-Luc2

<400> SEQUENCE: 112
cctgcaggca gctgcgcgct cgctcgctca ctgaggccgc ccgggcaaag cccgggcgtc      60
gggcgacctt tggtcgcccg gcctcagtga gcgagcgagc gcgagagag  ggagtggcca    120 actccatcac tagggttcc  tgcggcccct ttgacttttc ttgaagggg  agggctggga    180 tattccagag attgatcctt aaggcttgct gactgcctac tcacttctgg aaacttccag    240
cagtgtcatt catagacctg tgaagagctc ttagcttgtt tccttcacac agtggggact    300
ctgaggggtc agagtgagtc acccagcagg ccagtggcag gggtgagcca gaagcctggc    360
caaaccctcc tatcatcatg gagagaagaa agcctcctcc agaagacggg aggccggcag    420
ggcgtggggc ctgctcagat gcagggcgcg ccacgcgttt ctgagtcctc taaggtccct    480
cactcccaac tcagccccat gtcctgtcaa ttcccactca gtgtctgatc tccttctcct    540
cacctttccc atctcccgtt tgacccaagc ttcctgagct ctcctcccat tcccctttt     600 ggagtcctcc tcctctccca gaacccagta ataagtgggc tcctccctgg cctggacccc    660
cgtggtaacc ctataaggcg aggcagctgc tgtctgaggc agggaggggc tggtgtggga    720
ggctaagggc agctgctaag tttagggtgg ctccttctct cttcttagag acaacaggtg    780 gctgggcct  cagtgcccag aaaagaaaat gtcttagagg tatcggcatg ggcctggagg    840 agggggggaca gggcaggggg aggcatcttc ctcaggacat cgggtcctag aggggtaccc    900
aacgggttac gacacaccta ctagtaaccc ctccagctgg tgatggcagg tctagggtag    960
gaccagtgac tggctcctaa tcgagcactc tattttcagg gtttgcattc caaagggtc    1020 aggtccaaga gggacctgga gtgccaagtg gaggtgtaga ggcacggcca gtacccatgg    1080
agaatggtgg atgtccttag ggggttagcaa gtgccgtgtg ctaaggaggg ggctttggag    1140
gttgggcagg ccctctgtgg ggctccattt ttgtgggggt ggggctgga  gcattatagg    1200 gggtgggaag tgattgggc  tgtcacccta gccttcctta tctgacgccc acccatgcct    1260
cctcaggtac cccctgcccc ccacagctcc tctcctgtgc cttgtttccc agccatgcgt    1320
tctcctctat aaatacccgc tctggtattt ggggttggca gctgttgctg ccagggagat    1380
ggttgggttg acatgcggct cctgacaaaa cacaaacccc tggtgtgtgt gggcgtgggt    1440
ggtgtgagta gggggatgaa tcaggagggg ggcggggac  ccagggggca ggagccacac    1500
aaagtctgtg cggggtgggg agcgcacata gcaattggaa actgaaagct tatcagaccc    1560
tttctggaaa tcagcccact gtttataaac ttgaggcccc accctcgaca gtaccgggga    1620
ggaagagggc ctgcactagt ccagagggaa actgaggctc agggctagct cgcccataga    1680
catacatggc aggcaggctt tggccaggat ccctccgcct gccaggcgtc tccctgccct    1740
cccttcctgc ctagagaccc ccaccctcaa gcctggctgg tctttgcctg agacccaaac    1800
ctcttcgact tcaagagaat atttaggaac aaggtggttt agggcctttc ctgggaacag    1860
```

```
gccttgaccc tttaagaaat gacccaaagt ctctccttga ccaaaaaggg gaccctcaaa   1920
ctaaagggaa gcctctcttc tgctgtctcc cctgacccca ctcccccca ccccaggacg    1980
aggagataac cagggctgaa agaggcccgc ctggggctg cagacatgct tgctgcctgc    2040
cctggcgaag gattgcagg cttgcccgtc acaggacccc cgctggctga ctcaggggcg    2100
caggcctctt gcggggagc tggcctcccc gccccacgg ccacgggccg cccttttcctg    2160
gcaggacagc gggatcttgc agctgtcagg ggaggggagg cggggggctga tgtcaggagg  2220
gatacaaata gtgccgacgg ctgggggccc tgtctcccct cgccgcatcc actctccggc  2280
cggccgcctg cccgccgcct cctccgtgcg cccgccagcc tcgcccgcgc cgtcacctct   2340
agaaagaggt aagggtttaa gggatggttg gttggtgggg tattaatgtt taattacctg   2400
gagcacctgc ctgaaatcac ttttttttcag gttggaagct tatggaagat gccaaaaaca  2460
ttaagaaggg cccagcgcca ttctacccac tcgaggacgg gaccgccggc gagcagctgc   2520
acaaagccat gaagcgctac gccctggtgc ccggcaccat cgcctttacc gacgcacata   2580
tcgaggtgga cattacctac gccgagtact tcgagatgag cgttcggctg gcagaagcta   2640
tgaagcgcta tgggctgaat acaaaccatc ggatcgtggt gtgcagcgag aatagcttgc   2700
agttcttcat gccgtgttg ggtgcccgt tcatcggtgt ggctgtggcc ccagctaacg     2760
acatctacaa cgagcgcgag ctgctgaaca gcatgggcat cagccagccc accgtcgtat   2820
tcgtgagcaa gaaagggctg caaaagatcc tcaacgtgca aaagaagcta ccgatcatac   2880
aaaagatcat catcatggat agcaagaccg actaccaggg cttccaaagc atgtacacct   2940
tcgtgacttc ccatttgcca cccggcttca acgagtacga cttcgtgccc gagagcttcg   3000
accgggacaa aaccatcgcc ctgatcatga acagtagtgg cagtaccgga ttgcccaagg   3060
gcgtagccct accgcaccgc accgcttgtg tccgattcag tcatgcccgc gaccccatct   3120
tcggcaacca gatcatcccc gacaccgcta tcctcagcgt ggtgccattt caccacggct   3180
tcggcatgtt caccacgctg gctacttga tctgcggctt tcgggtcgtg ctcatgtacc    3240
gcttcgagga ggagctattc ttgcgcagct tgcaagacta taagattcaa tctgccctgc   3300
tggtgcccac actatttagc ttcttcgcta agagcactct catcgacaag tacgacctaa   3360
gcaacttgca cgagatcgcc agcggcgggg cgccgctcag caaggaggta ggtgaggccg   3420
tggccaaacg cttccaccta ccaggcatcc gccaggcta cggcctgaca gaaacaacca   3480
gcgccattct gatcaccccc gaaggggacg acaagcctgg cgcagtaggc aaggtggtgc   3540
ccttcttcga ggctaaggtg gtggacttgg acaccggtaa gacactgggt gtgaaccagc   3600
gcggcgagct gtgcgtccgt ggccccatga tcatgagcgg ctacgttaac aaccccgagg   3660
ctacaaacgc tctcatcgac aaggacggct ggctgcacag cggcgacatc gcctactggg   3720
acgaggacga gcacttcttc atcgtggacc ggctgaagag cctgatcaaa tacaagggct   3780
accaggtagc cccagccgaa ctggagagca tcctgctgca acaccccaac atcttcgacg   3840
ccggggtcgc cggcctgccc gacgacgatg ccggcgagct gcccgccgca gtcgtcgtgc   3900
tggaacacgg taaaaccatg accgagaagg agatcgtgga ctatgtggcc agccaggtta   3960
caaccgccaa gaagctgcgc ggtggtgttg tgttcgtgga cgaggtgcct aaaggactga   4020
ccggcaagtt ggacgcccgc aagatccgcg agattctcat taaggccaag aagggcggca   4080
agatcgccgt gtaattcgaa acgagacgtc catcttgagc atctgacttc tggctaaata   4140
aaagatcttt attttcatta gatctgtgtg ttggttttt gtgtgcgtcg agatccacgg    4200
ccgcaggaac ccctagtgat ggagttggcc actccctctc tgcgcgctcg ctcgctcact   4260
```

```
gaggccgggc gaccaaaggt cgcccgacgc ccgggctttg cccggcggc ctcagtgagc    4320
gagcgagcgc gcagctgcct gcagggggcgc ctgatgcggt attttctcct tacgcatctg    4380
tgcggtattt cacaccgcat acgtcaaagc aaccatagta cgcgccctgt agcggcgcat    4440
taagcgcggg gggtgtggtg gttacgcgca gcgtgaccgc tacacttgcc agcgccctag    4500
cgcccgctcc tttcgctttc ttcccttcct ttctcgccac gttcgccggc tttccccgtc    4560
aagctctaaa tcgggggctc cctttagggt tccgatttag tgctttacgg cacctcgacc    4620
ccaaaaaact tgatttgggt gatggttcac gtagtgggcc atcgccctga tagacggttt    4680
ttcgcccttt gacgttggag tccacgttct taatagtgg actcttgttc caaactggaa    4740
caacactcaa ccctatctcg gctattctt ttgatttata agggattttg ccgatttcgg    4800
cctattggtt aaaaaatgag ctgatttaac aaaaatttaa cgcgaatttt aacaaaatat    4860
taacgtttac aattttatgg tgcactctca gtacaatctg ctctgatgcc gcatagttaa    4920
gccagccccg acaccgcca acaccgctg acgcgccctg acgggcttgt ctgctcccgg    4980
catccgctta cagacaagct gtgaccgtct ccgggagctg catgtgtcag aggttttcac    5040
cgtcatcacc gaaacgcgcg agacgaaagg gcctcgtgat acgcctattt ttataggtta    5100
atgtcatgat aataatggtt tcttagacgt caggtggcac ttttcgggga aatgtgcgcg    5160
gaaccctat ttgtttattt ttctaaatac attcaaatat gtatccgctc atgagacaat    5220
aaccctgata aatgcttcaa taatattgaa aaaggaagag tatgagtatt caacatttcc    5280
gtgtcgccct tattcccttt tttgcggcat tttgccttcc tgttttgct cacccagaaa    5340
cgctggtgaa agtaaaagat gctgaagatc agttgggtgc acgagtgggt tacatcgaac    5400
tggatctcaa cagcggtaag atccttgaga gttttcgccc cgaagaacgt tttccaatga    5460
tgagcacttt taaagttctg ctatgtggcg cggtattatc ccgtattgac gccgggcaag    5520
agcaactcgg tcgccgcata cactattctc agaatgactt ggttgagtac tcaccagtca    5580
cagaaaagca tcttacggat ggcatgacag taagagaatt atgcagtgct gccataacca    5640
tgagtgataa cactgcggcc aacttacttc tgacaacgat cggaggaccg aaggagctaa    5700
ccgcttttt gcacaacatg ggggatcatg taactcgcct tgatcgttgg gaaccggagc    5760
tgaatgaagc cataccaaac gacgagcgtg acaccacgat gcctgtagca atggcaacaa    5820
cgttgcgcaa actattaact ggcgaactac ttactctagc ttcccggcaa caattaatag    5880
actggatgga ggcggataaa gttgcaggac cacttctgcg ctcggccctt ccggctggct    5940
ggtttattgc tgataaatct ggagccggtg agcgtgggtc tcgcggtatc attgcagcac    6000
tggggccaga tggtaagccc tcccgtatcg tagttatcta cacgacgggg agtcaggcaa    6060
ctatggatga acgaaataga cagatcgctg agataggtgc ctcactgatt aagcattggt    6120
aactgtcaga ccaagtttac tcatatatac tttagattga tttaaaactt catttttaat    6180
ttaaaaggat ctaggtgaag atccttttg ataatctcat gaccaaaatc ccttaacgtg    6240
agttttcgtt ccactgagcg tcagaccccg tagaaaagat caaggatctc ttgagatc    6300
ctttttttct gcgcgtaatc tgctgcttgc aaacaaaaaa accaccgcta ccagcggtgg    6360
tttgtttgcc ggatcaagag ctaccaactc tttttccgaa ggtaactggc ttcagcagag    6420
cgcagatacc aaatactgtc cttctagtgt agccgtagtt aggccaccac ttcaagaact    6480
ctgtagcacc gcctacatac ctcgctctgc taatcctgtt accagtggct gctgccagtg    6540
gcgataagtc gtgtcttacc gggttggact caagacgata gttaccggat aaggcgcagc    6600
```

```
ggtcgggctg aacgggtggt tcgtgcacac agcccagctt ggagcgaacg acctacaccg    6660
aactgagata cctacagcgt gagctatgag aaagcgccac gcttcccgaa gggagaaagg    6720
cggacaggta tccggtaagc ggcagggtcg gaacaggaga gcgcacgagg gagcttccag    6780
ggggaaacgc ctggtatctt tatagtcctg tcgggtttcg ccacctctga cttgagcgtc    6840 gattttgtg atgctcgtca ggggggcgga gcctatggaa aaacgccagc aacgcggcct    6900
ttttacggtt cctggccttt tgctggcctt ttgctcacat gt                      6942

<210> SEQ ID NO 113
<211> LENGTH: 7138
<212> TYPE: DNA
<213> ORGANISM: Artificial Sequence
<220> FEATURE:
<223> OTHER INFORMATION: plasmid pAAVss-CRE21-SkSH4-hDES1.4kb-Luc2

<400> SEQUENCE: 113
acatgtcctg caggcagctg cgcgctcgct cgctcactga ggccgcccgg gcaaagcccg      60
ggcgtcgggc gacctttggt cgcccggcct cagtgagcga gcgagcgcgc agagaggag     120 tggccaactc catcactagg ggttcctgcg ccctttttct tttctaatta ggtcagttac    180
ttcatgtctg ttttctttt ttgacatggt ttcttctggc tttggcacca catatttcc     240 ccatatgtca ttgcctctgg agcttcatgt tgcaatagtt tttcaagggg aacggagagc    300
acattgctaa gggtgggga tggcttttgc ctcttttgcc tgcccttgc ttcagtgagt    360 gttcgtattt ctgttgggcc tagttctgtt tggttttgta gtcttcagag tcagttatgt    420
ttggactgaa agatacttaa gtaaaaataa tggcaagtca gagatatgtc tggcaaaggt    480
gcagcacatt tgttaaggtt actggtttat ttatctccct tgtctctatg gtgactaaat    540
ctgggtctgg gatttaatgg acttagtttt gacctcttgt aacatctcct aacttttccc    600
agcctctgat ttagaaagaa ttcatttca cttgaggaga gaaactggcg cgccacgcgt    660
ttctgagtcc tctaaggtcc ctcactccca actcagcccc atgtcctgtc aattcccact    720
cagtgtctga tctccttctc ctcacctttc ccatctcccg tttgacccaa gcttcctgag    780
ctctcctccc attccccttt ttggagtcct cctcctctcc cagaacccag taataagtgg    840
gctcctccct ggcctggacc cccgtggtaa ccctataagg cgaggcagct gctgtctgag    900
gcagggaggg gctggtgtgg gaggctaagg gcagctgcta agtttagggt ggctccttct    960
ctcttcttag agacaacagg tggctgggc ctcagtgccc agaaaagaaa atgtcttaga   1020
ggtatcggca tgggcctgga ggagggggga cagggcaggg ggaggcatct tcctcaggac   1080
atcgggtcct agaggggtac ccaacgggtt acgacacacc tactagtaac ccctccagct   1140
ggtgatggca ggtctagggt aggaccagtg actggctcct aatcgagcac tctatttca   1200 gggtttgcat tccaaaaggg tcaggtccaa gagggacctg gagtgccaag tggaggtgta   1260
gaggcacggc cagtacccat ggagaatggt ggatgtcctt aggggttagc aagtgccgtg   1320
tgctaaggag gggctttgg aggttgggca ggccctctgt ggggctccat ttttgtgggg   1380
gtgggggctg gagcattata gggggtggga agtgattggg gctgtcaccc tagccttcct   1440
tatctgacgc ccacccatgc ctcctcaggt acccctgcc ccccacagct cctctcctgt   1500
gccttgtttc ccagccatgc gttctcctct ataaatacc gctctggtat ttggggttgg   1560
cagctgttgc tgccagggag atggttgggt tgacatgcgg ctcctgacaa aacacaaacc   1620
cctggtgtgt gtgggcgtgg gtggtgtgag taggggatg aatcagggag ggggcggggg   1680
acccaggggg caggagccac acaaagtctg tgcggggtg ggagcgcaca tagcaattgg   1740
```

```
aaactgaaag cttatcagac cctttctgga aatcagccca ctgtttataa acttgaggcc    1800
ccaccctcga cagtaccggg gaggaagagg gcctgcacta gtccagaggg aaactgaggc    1860
tcagggctag ctcgcccata gacatacatg gcaggcaggc tttggccagg atccctccgc    1920
ctgccaggcg tctccctgcc ctcccttcct gcctagagac ccccaccctc aagcctggct    1980
ggtctttgcc tgagacccaa acctcttcga cttcaagaga atatttagga acaaggtggt    2040
ttagggcctt tcctgggaac aggccttgac cctttaagaa atgacccaaa gtctctcctt    2100
gaccaaaaag gggaccctca aactaaaggg aagcctctct tctgctgtct ccctgaccc    2160
cactccccc caccccagga cgaggagata accagggctg aaagaggccc gcctggggc     2220
tgcagacatg cttgctgcct gccctggcga aggattggca ggcttgcccg tcacaggacc    2280
cccgctggct gactcagggg cgcaggcctc ttgcggggga gctggcctcc ccgccccac    2340
ggccacgggc cgccctttcc tggcaggaca gcgggatctt gcagctgtca ggggagggga    2400
ggcgggggct gatgtcagga gggatacaaa tagtgccgac ggctgggggc cctgtctccc    2460
ctcgccgcat ccactctccg gccggccgcc tgcccgccgc ctcctccgtg cgcccgccag    2520
cctcgcccgc gccgtcacct ctagaaagag gtaagggttt aagggatggt tggttggtgg    2580
ggtattaatg tttaattacc tggagcacct gcctgaaatc actttttttc aggttggaag    2640
cttatggaag atgccaaaaa cattaagaag ggcccagcgc cattctaccc actcgaggac    2700
gggaccgccg gcgagcagct gcacaaagcc atgaagcgct acgccctggt gcccggcacc    2760
atcgccttta ccgacgcaca tatcgagtg acattacct acgccgagta cttcgagatg    2820
agcgttcggc tggcagaagc tatgaagcgc tatgggctga atacaaacca tcggatcgtg    2880
gtgtgcagcg agaatagctt gcagttcttc atgcccgtgt tgggtgccct gttcatcggt    2940
gtggctgtgg ccccagctaa cgacatctac aacgagcgcg agctgctgaa cagcatgggc    3000
atcagccagc ccaccgtcgt attcgtgagc aagaaagggc tgcaaaagat cctcaacgtg    3060
caaaagaagc taccgatcat acaaaagatc atcatcatgg atagcaagac cgactaccag    3120
ggcttccaaa gcatgtacac cttcgtgact tcccatttgc cacccggctt caacgagtac    3180
gacttcgtgc ccgagagctt cgaccgggac aaaaccatcg ccctgatcat gaacagtagt    3240
ggcagtaccg gattgcccaa gggcgtagcc ctaccgcacc gcaccgcttg tgtccgattc    3300
agtcatgccc gcgaccccat cttcggcaac cagatcatcc ccgacaccgc tatcctcagc    3360
gtggtgccat tcaccacgg cttcggcatg ttcaccacgc tgggctactt gatctgcggc    3420
tttcgggtcg tgctcatgta ccgcttcgag gaggagctat tcttgcgcag cttgcaagac    3480
tataagattc aatctgccct gctggtgccc acactattta gcttcttcgc taagagcact    3540
ctcatcgaca agtacgacct aagcaacttg cacgagatcg ccagcggcgg ggcgccgctc    3600
agcaaggagg taggtgaggc cgtggccaaa cgcttccacc taccaggcat ccgccagggc    3660
tacgccctga cagaaacaac cagcgccatt ctgatcaccc ccgaagggga cgacaagcct    3720
ggcgcagtag gcaaggtggt gcccttcttc gaggctaagg tggtggactt ggacaccggt    3780
aagacactgg gtgtgaacca gcgcggcgag ctgtgcgtcc gtggccccat gatcatgagc    3840
ggctacgtta caaccccga ggctacaaac gctctcatcg acaaggacgg ctggctgcac    3900
agcggcgaca tcgcctactg ggacgaggac gagcacttct tcatcgtgga ccggctgaag    3960
agcctgatca aatacaaggg ctaccaggta gccccagccg aactggagag catcctgctg    4020
caacaccca acatcttcga cgccggggtc gccggcctgc ccgacgacga tgccggcgag    4080
```

```
ctgcccgccg cagtcgtcgt gctggaacac ggtaaaacca tgaccgagaa ggagatcgtg    4140
gactatgtgg ccagccaggt tacaaccgcc aagaagctgc gcggtggtgt tgtgttcgtg    4200
gacgaggtgc ctaaaggact gaccggcaag ttggacgccc gcaagatccg cgagattctc    4260
attaaggcca agaagggcgg caagatcgcc gtgtaattcg aaacgattcg tccatcttga    4320
gcatctgact tctggctaaa taaaagatct ttatttcat tagatctgtg tgttggtttt    4380
ttgtgtgcgt cgagatccac ggccgcagga acccctagtg atggagttgg ccactccctc    4440
tctgcgcgct cgctcgctca ctgaggccgg gcgaccaaag gtcgcccgac gcccgggctt    4500
tgcccgggcg gcctcagtga gcgagcgagc gcgcagctgc ctgcaggggc gcctgatgcg    4560
gtattttctc cttacgcatc tgtgcggtat ttcacaccgc atacgtcaaa gcaaccatag    4620
tacgcgccct gtagcggcgc attaagcgcg gcggtgtgg tggttacgcg cagcgtgacc    4680
gctacacttg ccagcgccct agcgcccgct cctttcgctt tcttcccttc ctttctcgcc    4740
acgttcgccg gctttccccg tcaagctcta atcgggggc tccctttagg gttccgattt    4800
agtgctttac ggcacctcga ccccaaaaaa cttgatttgg gtgatggttc acgtagtggg    4860
ccatcgccct gatagacggt ttttcgccct ttgacgttgg agtccacgtt ctttaatagt    4920
ggactcttgt tccaaactgg aacaacactc aaccctatct cgggctattc ttttgattta    4980
taagggattt tgccgatttc ggcctattgg ttaaaaatg agctgattta caaaaattt    5040 aacgcgaatt ttaacaaaat attaacgttt acaattttat ggtgcactct cagtacaatc    5100
tgctctgatg ccgcatagtt aagccagccc cgacacccgc caacacccgc tgacgcgccc    5160
tgacgggctt gtctgctccc ggcatccgct tacagacaag ctgtgaccgt ctccgggagc    5220
tgcatgtgtc agaggttttc accgtcatca ccgaaacgcg cgagacgaaa gggcctcgtg    5280
atacgcctat ttttataggt taatgtcatg ataataatgg tttcttagac gtcaggtggc    5340
acttttcggg gaaatgtgcg cggaacccct atttgtttat ttttctaaat acattcaaat    5400
atgtatccgc tcatgagaca ataaccctga taaatgcttc aataatattg aaaaaggaag    5460
agtatgagta ttcaacattt ccgtgtcgcc cttattccct tttttgcggc attttgcctt    5520
cctgtttttg ctcacccaga aacgctggtg aaagtaaaag atgctgaaga tcagttgggt    5580
gcacgagtgg gttacatcga actggatctc aacagcggta agatccttga gttttcgc    5640 cccgaagaac gttttccaat gatgagcact tttaaagttc tgctatgtgg cgcggtatta    5700
tcccgtattg acgccgggca agagcaactc ggtcgccgca tacactattc tcagaatgac    5760
ttggttgagt actcaccagt cacagaaaag catcttacgg atggcatgac agtaagagaa    5820
ttatgcagtg ctgccataac catgagtgat aacactgcgg ccaacttact tctgacaacg    5880
atcggaggac cgaaggagct aaccgctttt ttgcacaaca tgggggatca tgtaactcgc    5940
cttgatcgtt gggaaccgga gctgaatgaa gccataccaa acgacgagcg tgacaccacg    6000
atgcctgtag caatggcaac aacgttgcgc aaactattaa ctggcgaact acttactcta    6060
gcttcccggc aacaattaat agactggatg gaggcggata agttgcagg accacttctg    6120 cgctcggccc ttccggctgg ctggtttatt gctgataaat ctggagccgg tgagcgtggg    6180
tctcgcggta tcattgcagc actggggcca gatggtaagc cctcccgtat cgtagttatc    6240
tacacgacgg ggagtcaggc aactatggat gaacgaaata gacagatcgc tgagataggt    6300
gcctcactga ttaagcattg gtaactgtca gaccaagttt actcatatat actttagatt    6360
gatttaaaac ttcattttta atttaaaagg atctaggtga agatcctttt tgataatctc    6420
atgaccaaaa tcccttaacg tgagttttcg ttccactgag cgtcagaccc cgtagaaaag    6480
```

```
atcaaaggat cttcttgaga tccttttttt ctgcgcgtaa tctgctgctt gcaaacaaaa    6540
aaaccaccgc taccagcggt ggtttgtttg ccggatcaag agctaccaac tcttttttccg   6600 aaggtaactg gcttcagcag agcgcagata ccaaatactg tccttctagt gtagccgtag    6660
ttaggccacc acttcaagaa ctctgtagca ccgcctacat acctcgctct gctaatcctg    6720
ttaccagtgg ctgctgccag tggcgataag tcgtgtctta ccgggttgga ctcaagacga    6780
tagttaccgg ataaggcgca gcggtcgggc tgaacggggg gttcgtgcac acagcccagc    6840
ttggagcgaa cgacctacac cgaactgaga tacctacagc gtgagctatg agaaagcgcc    6900
acgcttcccg aagggagaaa ggcggacagg tatccgtaa gcggcagggt cggaacagga    6960
gagcgcacga gggagcttcc agggggaaac gcctggtatc tttatagtcc tgtcgggttt    7020
cgccacctct gacttgagcg tcgatttttg tgatgctcgt caggggggcg agcctatgg    7080 aaaaacgcca gcaacgcggc ctttttacgg ttcctggcct tttgctggcc ttttgctc      7138
```

<210> SEQ ID NO 114
<211> LENGTH: 7108
<212> TYPE: DNA
<213> ORGANISM: Artificial Sequence
<220> FEATURE:
<223> OTHER INFORMATION: plasmid pAAVss-CRE41-SkSH4-hDES1.4kb-Luc2

<400> SEQUENCE: 114

```
acatgtcctg caggcagctg cgcgctcgct cgctcactga ggccgcccgg gcaaagcccg     60
ggcgtcgggc gacctttggt cgcccggcct cagtgagcga gcgagcgcgc agagagggag    120
tggccaactc catcactagg ggttcctgcg gcctacaat aaatatataa cttttttaat    180
ttgacaaaaa ataattttga gtggttacaa aaagggacag gtgtggcttg gtaactagaa    240
aaacattccc agcctgggaa acaatctagt gagagcttgg aggcagaaga cagaactctg    300
attacattca aggagtttgc cagatggcaa cagataactg ccaatgttcg gttgcactat    360
aattattata cactctctgt cacttcagca agcgctcttt tcacaagaca agtggtgaca    420
gaatgttgta ttaagattac ccgttgctaa gcttatgtta aaatgaggaa atgaaatgga    480
aagtcttgtt ttggtaatgt ctctggggta tgaggaatgg agggaaaggt ttgactatga    540
gcataactgc atagagaatt ttgttttgttt atgccttttg ggaatgcatt attttgattg    600
accctaattg ggaattggcg cgccacgcgt ttctgagtcc tctaaggtcc ctcactccca    660
actcagcccc atgtcctgtc aattcccact cagtgtctga tctccttctc ctcacctttc    720
ccatctcccg tttgacccaa gcttcctgag ctctcctccc attccccttt ttggagtcct    780
cctcctctcc cagaacccag taataagtgg gctcctccct ggcctggacc ccgtggtaa    840 ccctataagg cgaggcagct gctgtctgag gcagggaggg gctggtgtgg gaggctaagg    900
gcagctgcta agtttagggt ggctccttct ctcttcttag agacaacagg tggctggggc    960
ctcagtgccc agaaaagaaa atgtcttaga ggtatcggca tgggcctgga ggagggggga   1020
cagggcaggg ggaggcatct tcctcaggac atcgggtcct agagggtac ccaacgggtt    1080 acgacacacc tactagtaac ccctccagct ggtgatggca ggtctagggt aggaccagtg   1140
actggctcct aatcgagcac tctattttca gggtttgcat tccaaagg tcaggtccaa    1200 gagggacctg gagtgccaag tggaggtgta gaggcacggc cagtacccat ggagaatggt   1260
ggatgtcctt agggggttagc aagtgccgtg tgctaaggag ggggctttgg aggttgggca   1320
ggccctctgt ggggctccat ttttgtgggg gtggggggctg gagcattata gggggtggga   1380
```

```
agtgattggg gctgtcaccc tagccttcct tatctgacgc ccacccatgc ctcctcaggt    1440
accccctgcc ccccacagct cctctcctgt gccttgtttc ccagccatgc gttctcctct    1500
ataaataccc gctctggtat ttggggttgg cagctgttgc tgccagggag atggttgggt    1560
tgacatgcgg ctcctgacaa aacacaaacc cctggtgtgt gtgggcgtgg gtggtgtgag    1620 taggggatg aatcagggag ggggcggggg acccagggg caggagccac acaaagtctg    1680 tgcggggtg ggagcgcaca tagcaattgg aaactgaaag cttatcagac cctttctgga    1740
aatcagccca ctgtttataa acttgaggcc ccaccctcga cagtaccggg gaggaagagg    1800
gcctgcacta gtccagaggg aaactgaggc tcagggctag ctcgcccata gacatacatg    1860
gcaggcaggc tttggccagg atccctccgc ctgccaggcg tctccctgcc ctcccttcct    1920
gcctagagac ccccaccctc aagcctggct ggtctttgcc tgagacccaa acctcttcga    1980
cttcaagaga atatttagga acaaggtggt ttagggcctt cctgggaac aggccttgac    2040 cctttaagaa atgacccaaa gtctctcctt gaccaaaaag gggaccctca aactaagggg    2100
aagcctctct tctgctgtct cccctgaccc cactcccccc cacccagga cgaggagata    2160 accagggctg aaagaggccc gcctgggggc tgcagacatg cttgctgcct gccctggcga    2220
aggattggca ggcttgcccg tcacaggacc cccgctggct gactcagggg cgcaggcctc    2280
ttgcggggga gctggcctcc ccgccccac ggccacgggc cgcccttcc tggcaggaca    2340 gcgggatctt gcagctgtca ggggagggga ggcgggggct gatgtcagga gggatacaaa    2400
tagtgccgac ggctggggc cctgtctccc ctcgccgcat ccactctccg gccggccgcc    2460
tgcccgccgc ctcctccgtg cgcccgccag cctcgcccgc gccgtcacct ctagaaagag    2520
gtaagggttt aagggatggt tggttggtgg ggtattaatg tttaattacc tggagcacct    2580
gcctgaaatc acttttttc aggttggaag cttatggaag atgccaaaaa cattaagaag    2640
ggcccagcgc cattctaccc actcgaggac gggaccgccg gcgagcagct gcacaaagcc    2700
atgaagcgct acgccctggt gcccggcacc atcgccttta ccgacgcaca tatcgaggtg    2760
gacattacct acgccgagta cttcgagatg agcgttcggc tggcagaagc tatgaagcgc    2820
tatgggctga atacaaacca tcggatcgtg gtgtgcagcg agaatagctt gcagttcttc    2880
atgcccgtgt tgggtgccct gttcatcggt gtggctgtgg ccccagctaa cgacatctac    2940
aacgagcgcg agctgctgaa cagcatgggc atcagccagc ccaccgtcgt attcgtgagc    3000 aagaagggc tgcaaaagat cctcaacgtg caaaagaagc taccgatcat acaaaagatc    3060
atcatcatgg atagcaagac cgactaccag ggcttccaaa gcatgtacac cttcgtgact    3120
tcccatttgc cacccggctt caacgagtac gacttcgtgc ccgagagctt cgaccgggac    3180
aaaaccatcg ccctgatcat gaacagtagt ggcagtaccg gattgcccaa gggcgtagcc    3240
ctaccgcacc gcaccgcttg tgtccgattc agtcatgccc gcgacccat cttcggcaac    3300 cagatcatcc ccgacaccgc tatcctcagc gtggtgccat ttcaccacgg cttcggcatg    3360
ttcaccacgc tgggctactt gatctgcggc tttcgggtcg tgctcatgta ccgcttcgag    3420
gaggagctat tcttgcgcag cttgcaagac tataagattc aatctgccct gctggtgccc    3480
acactattta gcttcttcgc taagagcact ctcatcgaca gtacgacct aagcaacttg    3540 cacgagatcg ccagcggcgg ggcgccgctc agcaaggagg taggtgaggc cgtggccaaa    3600
cgcttccacc taccaggcat ccgccagggc tacggcctga cagaaacaac cagcgccatt    3660
ctgatcaccc ccgaaggga cgacaagcct ggcgcagtag gcaaggtggt gcccttcttc    3720
gaggctaagg tggtggactt ggacaccggt aagacactgg gtgtgaacca gcgcggcgag    3780
```

| | |
|---|---|
| ctgtgcgtcc gtggcccat gatcatgagc ggctacgtta acaacccga ggctacaaac | 3840 |
| gctctcatcg acaaggacgg ctggctgcac agcggcgaca tcgcctactg ggacgaggac | 3900 |
| gagcacttct tcatcgtgga ccggctgaag agcctgatca aatacaaggg ctaccaggta | 3960 |
| gccccagccg aactgagag catcctgctg caacacccca acatcttcga cgccggggtc | 4020 |
| gccggcctgc ccgacgacga tgccggcgag ctgcccgccg cagtcgtcgt gctggaacac | 4080 |
| ggtaaaacca tgaccgagaa ggagatcgtg gactatgtgg ccagccaggt tacaaccgcc | 4140 |
| aagaagctgc gcggtggtgt tgtgttcgtg gacgaggtgc ctaaaggact gaccggcaag | 4200 |
| ttggacgccc gcaagatccg cgagattctc attaaggcca agaagggcgg caagatcgcc | 4260 |
| gtgtaattcg aaacgagaag tccatcttga gcatctgact tctggctaaa taaaagatct | 4320 |
| ttattttcat tagatctgtg tgttggtttt ttgtgtgcgt cgagatccac ggccgcagga | 4380 |
| acccctagtg atggagttgg ccactccctc tctgcgcgct cgctcgctca ctgaggccgg | 4440 |
| gcgaccaaag gtcgcccgac gcccgggctt tgcccgggcg gcctcagtga gcgagcgagc | 4500 |
| gcgcagctgc ctgcaggggc gcctgatgcg gtattttctc cttacgcatc tgtgcggtat | 4560 |
| ttcacaccgc atacgtcaaa gcaaccatag tacgcgccct gtagcggcgc attaagcgcg | 4620 |
| gcgggtgtgg tggttacgcg cagcgtgacc gctacacttg ccagcgccct agcgcccgct | 4680 |
| cctttcgctt tcttcccttc ctttctcgcc acgttcgccg gctttccccg tcaagctcta | 4740 |
| aatcggggc tcccttagg gttccgattt agtgctttac ggcacctcga ccccaaaaaa | 4800 |
| cttgatttgg gtgatggttc acgtagtggg ccatcgccct gatagacggt ttttcgccct | 4860 |
| ttgacgttgg agtccacgtt ctttaatagt ggactcttgt tccaaactgg aacaacactc | 4920 |
| aaccctatct cggctattc ttttgattta aagggattt tgccgatttc ggcctattgg | 4980 |
| ttaaaaatg agctgattta caaaaatt aacgcgaatt ttaacaaaat attaacgttt | 5040 |
| acaattttat ggtgcactct cagtacaatc tgctctgatg ccgcatagtt aagccagccc | 5100 |
| cgacacccgc caacacccgc tgacgcgccc tgacgggctt gtctgctccc ggcatccgct | 5160 |
| tacagacaag ctgtgaccgt ctccgggagc tgcatgtgtc agaggttttc accgtcatca | 5220 |
| ccgaaacgcg cgagacgaaa gggcctcgtg atacgcctat ttttataggt taatgtcatg | 5280 |
| ataataatgg tttcttagac gtcaggtggc acttttcggg gaaatgtgcg cggaacccct | 5340 |
| atttgtttat ttttctaaat acattcaaat atgtatccgc tcatgagaca ataaccctga | 5400 |
| taaatgcttc aataatattg aaaaaggaag agtatgagta ttcaacattt ccgtgtcgcc | 5460 |
| cttattccct tttttgcggc attttgcctt cctgtttttg ctcacccaga aacgctggtg | 5520 |
| aaagtaaaag atgctgaaga tcagttgggt gcacgagtgg gttacatcga actggatctc | 5580 |
| aacagcggta agatccttga gagttttcgc cccgaagaac gttttccaat gatgagcact | 5640 |
| tttaaagttc tgctatgtgg cgcggtatta tcccgtattg acgccgggca agagcaactc | 5700 |
| ggtcgccgca tacactattc tcagaatgac ttggttgagt actcaccagt cacagaaaag | 5760 |
| catcttacgg atggcatgac agtaagagaa ttatgcagtg ctgccataac catgagtgat | 5820 |
| aacactgcgg ccaacttact tctgacaacg atcggaggac cgaaggagct aaccgctttt | 5880 |
| ttgcacaaca tgggggatca tgtaactcgc cttgatcgtt gggaaccgga gctgaatgaa | 5940 |
| gccataccaa acgacgagcg tgacaccacg atgcctgtag caatggcaac aacgttgcgc | 6000 |
| aaactattaa ctggcgaact acttactcta gcttcccggc aacaattaat agactggatg | 6060 |
| gaggcggata agttgcagg accacttctg cgctcggccc ttccggctgg ctggtttatt | 6120 |

| | |
|---|---|
| gctgataaat ctggagccgg tgagcgtggg tctcgcggta tcattgcagc actgggccca | 6180 |
| gatggtaagc cctcccgtat cgtagttatc tacacgacgg ggagtcaggc aactatggat | 6240 |
| gaacgaaata gacagatcgc tgagataggt gcctcactga ttaagcattg gtaactgtca | 6300 |
| gaccaagttt actcatatat acttagatt gatttaaaac ttcatttta atttaaaagg | 6360 |
| atctaggtga agatcctttt tgataatctc atgaccaaaa tcccttaacg tgagttttcg | 6420 |
| ttccactgag cgtcagaccc cgtagaaaag atcaaaggat cttcttgaga tcctttttt | 6480 |
| ctgcgcgtaa tctgctgctt gcaaacaaaa aaaccaccgc taccagcggt ggtttgtttg | 6540 |
| ccggatcaag agctaccaac tcttttccg aaggtaactg gcttcagcag agcgcagata | 6600 |
| ccaaatactg tccttctagt gtagccgtag ttaggccacc acttcaagaa ctctgtagca | 6660 |
| ccgcctacat acctcgctct gctaatcctg ttaccagtgg ctgctgccag tggcgataag | 6720 |
| tcgtgtctta ccgggttgga ctcaagacga tagttaccgg ataaggcgca gcggtcgggc | 6780 |
| tgaacggggg gttcgtgcac acagcccagc ttggagcgaa cgacctacac cgaactgaga | 6840 |
| tacctacagc gtgagctatg agaaagcgcc acgcttcccg aagggagaaa ggcggacagg | 6900 |
| tatccggtaa gcggcagggt cggaacagga gagcgcacga gggagcttcc agggggaaac | 6960 |
| gcctggtatc tttatagtcc tgtcgggttt cgccacctct gacttgagcg tcgatttttg | 7020 |
| tgatgctcgt caggggggcg gagcctatgg aaaaacgcca gcaacgcggc cttttacgg | 7080 |
| ttcctggcct tttgctggcc ttttgctc | 7108 |

<210> SEQ ID NO 115
<211> LENGTH: 6990
<212> TYPE: DNA
<213> ORGANISM: Artificial Sequence
<220> FEATURE:
<223> OTHER INFORMATION: plasmid pAAVss-CRE58-SkSH4-hDES1.4kb-Luc2

<400> SEQUENCE: 115

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggttcc tgcggccccc ctcagcttca gccccacct ccaggaggcc | 180 |
| ctacccacgc tcatgacctt gctattctgg gccttgtgtc ctgtagggag atggacagga | 240 |
| gacagctggg cttccaggcc acccaggcgg gggctagcc gagggaagcc tgctggctct | 300 |
| cctgcttgct ctaatttctg gggctcccca aaccttggcc tcaggagact ggggatagga | 360 |
| ccggccttga aagtggggga agcttttggag agcgggtgc tgggttctta gtgagatggc | 420 |
| cagtgaaggc tgtggtgccc cgaggtaagc agggcctgat ccctcctaa tcttccagca | 480 |
| gcaactggtg ctgcgcgcc acgcgtttct gagtcctcta aggtccctca ctcccaactc | 540 |
| agccccatgt cctgtcaatt cccactcagt gtctgatctc cttctcctca cctttcccat | 600 |
| ctcccgtttg acccaagctt cctgagctct cctcccattc cccttttgg agtcctcctc | 660 |
| ctctcccaga acccagtaat aagtgggctc ctccctgggcc tggaccccccg tggtaaccct | 720 |
| ataaggcgag gcagctgctg tctgaggcag ggaggggctg gtgtgggagg ctaagggcag | 780 |
| ctgctaagtt tagggtggct ccttctctct tcttagagac aacaggtggc tggggcctca | 840 |
| gtgcccagaa aagaaaatgt cttagaggta tcggcatggg cctggaggag ggggacagg | 900 |
| gcagggggag gcatcttcct caggacatcg ggtcctagag gggtacccaa cgggttacga | 960 |
| cacacctact agtaaccct ccagctggtg atggcaggtc tagggtagga ccagtgactg | 1020 |
| gctcctaatc gagcactcta ttttcagggt ttgcattcca aaagggtcag gtccaagagg | 1080 |

```
gacctggagt gccaagtgga ggtgtagagg cacggccagt acccatggag aatggtggat    1140
gtccttaggg gttagcaagt gccgtgtgct aaggagggggg ctttggaggt tgggcaggcc    1200
ctctgtgggg ctccattttt gtggggtgg gggctggagc attataggggg gtgggaagtg    1260 attggggctg tcaccctagc cttccttatc tgacgcccac ccatgcctcc tcaggtaccc    1320 cctgccccccc acagctcctc tcctgtgcct tgtttcccag ccatgcgttc tcctctataa    1380
atacccgctc tggtatttgg ggttggcagc tgttgctgcc agggagatgg ttgggttgac    1440
atgcggctcc tgacaaaaca caaacccctg gtgtgtgtgg gcgtgggtgg tgtgagtagg    1500
gggatgaatc agggaggggg cggggaccc agggggcagg agccacacaa agtctgtgcg    1560
ggggtgggag cgcacatagc aattggaaac tgaaagctta tcagacccctt tctggaaatc    1620 agcccactgt ttataaactt gaggcccccac cctcgacagt accggggagg aagagggcct    1680
gcactagtcc agagggaaac tgaggctcag ggctagctcg cccatagaca tacatggcag    1740
gcaggctttg gccaggatcc ctccgcctgc caggcgtctc cctgccctcc cttcctgcct    1800
agagaccccc accctcaagc ctggctggtc tttgcctgag acccaaacct cttcgacttc    1860
aagagaatat ttaggaacaa ggtggtttag ggcctttcct gggaacaggc cttgaccctt    1920
taagaaatga cccaaagtct ctccttgacc aaaaagggga ccctcaaact aagggaagc    1980 ctctcttctg ctgtctcccc tgacccccact cccccccacc ccaggacgag gagataacca    2040
gggctgaaag aggcccgcct gggggctgca gacatgcttg ctgcctgccc tggcgaagga    2100
ttggcaggct tgcccgtcac aggaccccg ctggctgact caggggcgca ggcctcttgc    2160 ggggagctg gcctccccgc ccccacggcc acgggccgcc ctttcctggc aggacagcgg    2220
gatcttgcag ctgtcagggg agggggaggcg ggggctgatg tcaggaggga tacaaatagt    2280
gccgacggct gggggccctg tctccctcg ccgcatccac tctccggccg ccgcctgcc    2340 cgccgcctcc tccgtgcgcc cgccagcctc gcccgcgccg tcacctctag aaagaggtaa    2400
gggtttaagg gatggttggt tggtgggggta ttaatgttta attacctgga gcacctgcct    2460
gaaatcactt ttttttcaggt tggaagctta tggaagatgc caaaaacatt aagaagggcc    2520
cagcgccatt ctacccactc gaggacggga ccgccggcga gcagctgcac aaagccatga    2580
agcgctacgc cctggtgccc ggcaccatcg ccttaccga cgcacatatc gaggtggaca    2640
ttacctacgc cgagtacttc gagatgagcg ttcggctggc agaagctatg aagcgctatg    2700
ggctgaatac aaaccatcgg atcgtggtgt gcagcgagaa tagcttgcag ttcttcatgc    2760
ccgtgttggg tgccctgttc atcggtgtgg ctgtggcccc agctaacgac atctacaacg    2820
agcgcgagct gctgaacagc atgggcatca gccagcccac cgtcgtattc gtgagcaaga    2880
aagggctgca aaagatcctc aacgtgcaaa agaagctacc gatcatacaa agatcatca    2940 tcatggatag caagaccgac taccagggct ccaaagcat gtacaccttc gtgacttccc    3000
atttgccacc cggcttcaac gagtacgact tcgtgcccga gagcttcgac cgggacaaaa    3060
ccatcgccct gatcatgaac agtagtggca gtaccggatt gcccaagggc gtagccctac    3120
cgcaccgcac cgcttgtgtc cgattcagtc atgcccgcga ccccatcttc ggcaaccaga    3180
tcatccccga caccgctatc ctcagcgtgg tgccatttca ccacgcttc ggcatgttca    3240 ccacgctggg ctacttgatc tgcggctttc gggtcgtgct catgtaccgc ttcgaggagg    3300
agctattctt gcgcagcttg caagactata agattcaatc tgccctgctg gtgcccacac    3360
tatttagctt cttcgctaag agcactctca tcgacaagta cgacctaagc aacttgcacg    3420
```

```
agatcgccag cggcggggcg ccgctcagca aggaggtagg tgaggccgtg gccaaacgct    3480
tccacctacc aggcatccgc cagggctacg gcctgacaga aacaaccagc gccattctga    3540 tcaccccga  aggggacgac aagcctggcg cagtaggcaa ggtggtgccc ttcttcgagg    3600
ctaaggtggt ggacttggac accggtaaga cactgggtgt gaaccagcgc ggcgagctgt    3660
gcgtccgtgg ccccatgatc atgagcggct acgttaacaa ccccgaggct acaaacgctc    3720
tcatcgacaa ggacggctgg ctgcacagcg gcgacatcgc ctactgggac gaggacgagc    3780
acttcttcat cgtggaccgg ctgaagagcc tgatcaaata caagggctac caggtagccc    3840
cagccgaact ggagagcatc ctgctgcaac accccaacat cttcgacgcc ggggtcgccg    3900
gcctgcccga cgacgatgcc ggcgagctgc ccgccgcagt cgtcgtgctg aacacggta     3960 aaaccatgac cgagaaggag atcgtggact atgtggccag ccaggttaca accgccaaga    4020
agctgcgcgg tggtgttgtg ttcgtggacg aggtgcctaa aggactgacc ggcaagttgg    4080
acgcccgcaa gatccgcgag attctcatta aggccaagaa gggcggcaag atcgccgtgt    4140
aattcgaaac gaattgtcca tcttgagcat ctgacttctg gctaaataaa agatcttat     4200 tttcattaga tctgtgtgtt ggttttttgt gtgcgtcgag atccacggcc gcaggaaccc    4260
ctagtgatgg agttggccac tccctctctg cgcgctcgct cgctcactga ggccgggcga    4320
ccaaaggtcg cccgacgccc gggctttgcc cgggcggcct cagtgagcga gcgagcgcgc    4380
agctgcctgc aggggcgcct gatgcggtat tttctcctta cgcatctgtg cggtatttca    4440
caccgcatac gtcaaagcaa ccatagtacg cgccctgtag cggcgcatta agcgcggcgg    4500
gtgtggtggt tacgcgcagc gtgaccgcta cacttgccag cgccctagcg cccgctcctt    4560
tcgctttctt cccttccttt ctcgccacgt tcgccggctt tccccgtcaa gctctaaatc    4620
gggggctccc tttagggttc cgatttagtg ctttacggca cctcgacccc aaaaaacttg    4680
atttgggtga tggttcacgt agtgggccat cgccctgata cggttttt cgcccttga      4740 cgttggagtc cacgttcttt aatagtggac tcttgttcca aactggaaca cactcaacc     4800 ctatctcggg ctattctttt gatttataag ggattttgcc gatttcggcc tattggttaa    4860
aaaatgagct gatttaacaa aaatttaacg cgaattttaa caaatatta acgtttacaa     4920 ttttatggtg cactctcagt acaatctgct ctgatgccgc atagttaagc cagccccgac    4980
acccgccaac cccgctgac  gcgccctgac gggcttgtct gctcccggca tccgcttaca    5040
gacaagctgt gaccgtctcc gggagctgca tgtgtcagag gttttcaccg tcatcaccga    5100
aacgcgcgag acgaaaggc  ctcgtgatac gcctattttt ataggttaat gtcatgataa    5160
taatggtttc ttagacgtca ggtggcactt ttcggggaaa tgtgcgcgga accctatttt    5220
gtttattttt ctaaatacat tcaaatatgt atccgctcat gagacaataa ccctgataaa    5280
tgcttcaata atattgaaaa aggaagagta tgagtattca acatttccgt gtcgccctta    5340
ttcccttttt tgcggcattt tgccttcctg tttttgctca cccagaaacg ctggtgaaag    5400 taaagatgc  tgaagatcag ttgggtgcac gagtgggtta catcgaactg gatctcaaca    5460
gcggtaagat ccttgagagt tttcgccccg aagaacgttt tccaatgatg agcactttta    5520
aagttctgct atgtggcgcg gtattatccc gtattgacgc cgggcaagag caactcggtc    5580
gccgcataca ctattctcag aatgacttgg ttgagtactc accagtcaca gaaaagcatc    5640
ttacggatgg catgacagta agagaattat gcagtgctgc cataaccatg agtgataaca    5700
ctgcggccaa cttacttctg acaacgatcg gaggaccgaa ggagctaacc gcttttttgc    5760
acaacatggg ggatcatgta actcgccttg atcgttggga accggagctg aatgaagcca    5820
```

```
taccaaacga cgagcgtgac accacgatgc ctgtagcaat ggcaacaacg ttgcgcaaac    5880
tattaactgg cgaactactt actctagctt cccggcaaca attaatagac tggatggagg    5940
cggataaagt tgcaggacca cttctgcgct cggcccttcc ggctggctgg tttattgctg    6000
ataaatctgg agccggtgag cgtgggtctc gcggtatcat tgcagcactg gggccagatg    6060
gtaagccctc ccgtatcgta gttatctaca cgacgggag tcaggcaact atggatgaac     6120
gaaatagaca gatcgctgag ataggtgcct cactgattaa gcattggtaa ctgtcagacc    6180
aagtttactc atatatactt tagattgatt taaaacttca ttttttaattt aaaaggatct    6240 aggtgaagat cctttttgat aatctcatga ccaaaatccc ttaacgtgag ttttcgttcc    6300
actgagcgtc agacccgta gaaaagatca aggatcttc ttgagatcct ttttttctgc      6360
gcgtaatctg ctgcttgcaa acaaaaaaac caccgctacc agcggtggtt tgtttgccgg    6420
atcaagagct accaactctt tttccgaagg taactggctt cagcagagcg cagataccaa    6480
atactgtcct tctagtgtag ccgtagttag gccaccactt caagaactct gtagcaccgc    6540
ctacatacct cgctctgcta atcctgttac cagtggctgc tgccagtggc gataagtcgt    6600
gtcttaccgg gttggactca agacgatagt taccggataa ggcgcagcgg tcgggctgaa    6660
cggggggttc gtgcacacag cccagcttgg agcgaacgac ctacaccgaa ctgagatacc    6720
tacagcgtga gctatgagaa agcgccacgc ttcccgaagg gagaaaggcg gacaggtatc    6780
cggtaagcgg cagggtcgga acaggagagc gcacgaggga gcttccaggg ggaaacgcct    6840
ggtatcttta tagtcctgtc gggtttcgcc acctctgact tgagcgtcga ttttttgtgat  6900 gctcgtcagg ggggcggagc ctatggaaaa acgccagcaa cgcggccttt ttacggttcc   6960
tggccttttg ctggcctttt gctcacatgt                                     6990
```

<210> SEQ ID NO 116
<211> LENGTH: 6865
<212> TYPE: DNA
<213> ORGANISM: Artificial Sequence
<220> FEATURE:
<223> OTHER INFORMATION: plasmid pAAVss-CRE59-SkSH4-hDES1.4kb-Luc2

<400> SEQUENCE: 116

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccctc ctccagcagc tgccctggtg gtaaccaaga   180
gacgccccca tcctggagca gggggtgggga ggggcagctc agagcagctg cttctctgag   240
gaagctgaca ccaaggccag cattcagcaa caacttgtgg ctttgcaccc agcgccgggg    300
tccccgccca cctggctccc tgctgtccct cttccccact gctgctcgga cttccctctg    360
accctggggc gcgccacgcg tttctgagtc ctctaaggtc cctcactccc aactcagccc    420
catgtcctgt caattcccac tcagtgtctg atctcctttct cctcacctttt cccatctccc   480 gtttgaccca agcttcctga gctctcctcc cattcccctt tttggagtcc tcctcctctc    540
ccagaaccca gtaataagtg ggctcctccc tggcctggac cccgtggta accctataag     600 gcgaggcagc tgctgtctga ggcagggagg ggctggtgtg ggaggctaag ggcagctgct   660
aagtttaggg tggctccttc tctcttctta gagacaacag gtggctgggg cctcagtgcc    720
cagaaaagaa aatgtcttag aggtatcggc atgggcctgg aggagggggg acagggcagg   780
gggaggcatc ttcctcagga catcgggtcc tagagggta cccaacgggt tacgacacac      840
```

```
ctactagtaa cccctccagc tggtgatggc aggtctaggg taggaccagt gactggctcc      900
taatcgagca ctctattttc agggtttgca ttccaaaagg gtcaggtcca agagggacct      960
ggagtgccaa gtggaggtgt agaggcacgg ccagtaccca tggagaatgg tggatgtcct     1020
taggggttag caagtgccgt gtgctaagga gggggctttg gaggttgggc aggccctctg     1080
tggggctcca tttttgtggg ggtgggggct ggagcattat aggggtggg aagtgattgg      1140
ggctgtcacc ctagccttcc ttatctgacg cccacccatg cctcctcagg taccccctgc     1200
cccccacagc tcctctcctg tgccttgttt cccagccatg cgttctcctc tataaatacc     1260
cgctctggta tttggggttg gcagctgttg ctgccaggga gatggttggg ttgacatgcg     1320
gctcctgaca aaacacaaac ccctggtgtg tgtgggcgtg ggtggtgtga gtaggggat      1380
gaatcaggga gggggcgggg gacccagggg gcaggagcca cacaaagtct gtgcgggggt     1440
gggagcgcac atagcaattg gaaactgaaa gcttatcaga ccctttctgg aaatcagccc     1500
actgttata aacttgaggc cccaccctcg acagtaccgg ggaggaagag ggcctgcact      1560
agtccagagg gaaactgagg ctcagggcta gctcgcccat agacatacat ggcaggcagg     1620
ctttggccag gatccctccg cctgccaggc gtctccctgc cctcccttcc tgcctagaga     1680
cccccaccct caagcctggc tggtctttgc ctgagaccca aacctcttcg acttcaagag     1740
aatatttagg aacaaggtgg tttagggcct ttcctgggaa caggccttga ccctttaaga     1800
aatgacccaa agtctctcct tgaccaaaaa ggggaccctc aaactaaagg gaagcctctc     1860
ttctgctgtc tccctgacc ccactccccc ccaccccagg acgaggagat aaccagggct     1920
gaaagaggcc cgcctggggg ctgcagacat gcttgctgcc tgccctggcg aaggattggc     1980
aggcttgccc gtcacaggac ccccgctggc tgactcaggg gcgcaggcct cttgcggggg     2040
agctggcctc cccgccccca cggccacggg ccgccctttc ctggcaggac agcgggatct     2100
tgcagctgtc aggggagggg aggcgggggc tgatgtcagg agggatacaa atagtgccga     2160
cggctggggg ccctgtctcc cctcgccgca tccactctcc ggccggccgc ctgcccgccg     2220
cctcctccgt gcgcccgcca gcctcgcccg cgccgtcacc tctagaaaga ggtaagggtt     2280
taagggatgg ttggttggtg gggtattaat gtttaattac ctggagcacc tgcctgaaat     2340
cacttttttt caggttggaa gcttatggaa gatgccaaaa acattaagaa gggcccagcg     2400
ccattctacc cactcgagga cgggaccgcc ggcgagcagc tgcacaaagc catgaagcgc     2460
tacgccctgg tgcccggcac catcgccttt accgacgcac atatcgaggt ggacattacc     2520
tacgccgagt acttcgagat gagcgttcgg ctggcagaag ctatgaagcg ctatgggctg     2580
aatacaaacc atcggatcgt ggtgtgcagc gagaatagct tgcagttctt catgcccgtg     2640
ttgggtgccc tgttcatcgg tgtggctgtg gccccagcta cgacatcta caacgagcgc     2700
gagctgctga acagcatggg catcagccag cccaccgtcg tattcgtgag caagaaaggg     2760
ctgcaaaaga tcctcaacgt gcaaaagaag ctaccgatca tacaaaagat catcatcatg     2820
gatagcaaga ccgactacca gggcttccaa agcatgtaca ccttcgtgac ttcccatttg     2880
ccacccggct tcaacgagta cgacttcgtg cccgagagct tcgaccggga caaaaccatc     2940
gccctgatca tgaacagtag tggcagtacc ggattgccaa agggcgtagc cctaccgcac     3000
cgcaccgctt gtgtccgatt cagtcatgcc cgcgacccca tcttcggcaa ccagatcatc     3060
cccgacaccg ctatcctcag cgtggtgcca tttcaccacg gcttcggcat gttcaccacg     3120
ctgggctact tgatctgcgg cttccgggtc gtgctcatgt accgcttcga ggaggagcta     3180
ttcttgcgca gcttgcaaga ctataagatt caatctgccc tgctggtgcc cacactattt     3240
```

```
agcttcttcg ctaagagcac tctcatcgac aagtacgacc taagcaactt gcacgagatc   3300
gccagcggcg gggcgccgct cagcaaggag gtaggtgagg ccgtggccaa acgcttccac   3360
ctaccaggca tccgccaggg ctacggcctg acagaaacaa ccagcgccat tctgatcacc   3420
cccgaagggg acgacaagcc tggcgcagta ggcaaggtgg tgcccttctt cgaggctaag   3480
gtggtggact tggacaccgg taagacactg ggtgtgaacc agcgcggcga gctgtgcgtc   3540
cgtggcccca tgatcatgag cggctacgtt aacaaccccg aggctacaaa cgctctcatc   3600
gacaaggacg gctggctgca cagcggcgac atcgcctact gggacgagga cgagcacttc   3660
ttcatcgtgg accggctgaa gagcctgatc aaatacaagg gctaccaggt agccccagcc   3720
gaactggaga gcatcctgct gcaacacccc aacatcttcg acgccggggt cgccggcctg   3780
cccgacgacg atgccggcga gctgcccgcc gcagtcgtcg tgctgaaaca cggtaaaacc   3840
atgaccgaga aggagatcgt ggactatgtg gccagccagg ttacaaccgc caagaagctg   3900
cgcggtggtg ttgtgttcgt ggacgaggtg cctaaaggac tgaccggcaa gttggacgcc   3960
cgcaagatcc gcgagattct cattaaggcc aagaagggcg gcaagatcgc cgtgtaattc   4020
gaaacgaatc gtccatcttg agcatctgac ttctggctaa ataaaagatc tttattttca   4080
ttagatctgt gtgttggttt tttgtgtgcg tcgagatcca cggccgcagg aacccctagt   4140 gatgagttg gccactccct ctctgcgcgc tcgctcgctc actgaggccg ggcgaccaaa   4200
ggtcgcccga cgcccgggct tgccgggcgg gcctcagtg agcgagcgag cgcgcagctg   4260
cctgcagggg cgcctgatgc ggtatttct ccttacgcat ctgtgcggta tttcacaccg   4320
catacgtcaa agcaaccata gtacgcgccc tgtagcggcg cattaagcgc ggcgggtgtg   4380
gtggttacgc gcagcgtgac cgctacactt gccagcgccc tagcgcccgc tcctttcgct   4440
ttcttccctt cctttctcgc cacgttcgcc ggctttcccc gtcaagctct aaatcggggg   4500
ctccctttag ggttccgatt tagtgcttta cggcacctcg accccaaaaa acttgatttg   4560
ggtgatggtt cacgtagtgg gccatcgccc tgatagacgg ttttcgccc tttgacgttg   4620 gagtccacgt tctttaatag tggactcttg ttccaaactg gaacaacact caaccctatc   4680
tcgggctatt cttttgattt ataagggatt ttgccgattt cggcctattg gttaaaaaat   4740
gagctgattt aacaaaaatt taacgcgaat tttaacaaaa tattaacgtt acaattttta   4800
tggtgcactc tcagtacaat ctgctctgat gccgcatagt taagccagcc ccgacacccg   4860
ccaacacccg ctgacgcgcc ctgacgggct tgtctgctcc cggcatccgc ttacagacaa   4920
gctgtgaccg tctccgggag ctgcatgtgt cagaggtttt caccgtcatc accgaaacgc   4980
gcgagacgaa agggcctcgt gatacgccta tttttatagg ttaatgtcat gataataatg   5040
gtttcttaga cgtcaggtgg cacttttcgg ggaaatgtgc gcggaacccc tatttgttta   5100
tttttctaaa tacattcaaa tatgtatccg ctcatgagac aataaccctg ataaatgctt   5160
caataatatt gaaaaggaa gagtatgagt attcaacatt tccgtgtcgc ccttattccc   5220
ttttttgcgg cattttgcct tcctgttttt gctcacccag aaacgctggt gaaagtaaaa   5280
gatgctgaag atcagttggg tgcacgagtg ggttacatcg aactggatct caacagcggt   5340
aagatccttg agagttttcg ccccgaagaa cgttttccaa tgatgagcac ttttaaagtt   5400
ctgctatgtg gcgcggtatt atcccgtatt gacgccgggc aagagcaact cggtcgccgc   5460
atacactatt ctcagaatga cttggttgag tactcaccag tcacagaaaa gcatcttacg   5520
gatggcatga cagtaagaga attatgcagt gctgccataa ccatgagtga taacactgcg   5580
```

```
gccaacttac ttctgacaac gatcggagga ccgaaggagc taaccgcttt tttgcacaac    5640
atggggatc atgtaactcg ccttgatcgt tgggaaccgg agctgaatga agccatacca     5700
aacgacgagc gtgacaccac gatgcctgta gcaatggcaa caacgttgcg caaactatta    5760
actggcgaac tacttactct agcttcccgg caacaattaa tagactggat ggaggcggat    5820
aaagttgcag gaccacttct gcgctcggcc cttccggctg gctggtttat tgctgataaa    5880
tctggagccg gtgagcgtgg gtctcgcggt atcattgcag cactgggcc agatggtaag    5940
ccctcccgta tcgtagttat ctacacgacg gggagtcagg caactatgga tgaacgaaat    6000
agacagatcg ctgagatagg tgcctcactg attaagcatt ggtaactgtc agaccaagtt    6060
tactcatata ctttagat tgatttaaaa cttcattttt aatttaaaag gatctaggtg      6120
aagatccttt ttgataatct catgaccaaa atcccttaac gtgagttttc gttccactga    6180
gcgtcagacc ccgtagaaaa gatcaaagga tcttcttgag atccttttt tctgcgcgta     6240
atctgctgct tgcaaacaaa aaaccaccg ctaccagcgg tggtttgttt gccggatcaa     6300
gagctaccaa ctcttttcc gaaggtaact ggcttcagca gagcgcagat accaaatact     6360
gtccttctag tgtagccgta gttaggccac cacttcaaga actctgtagc accgcctaca    6420
tacctcgctc tgctaatcct gttaccagtg gctgctgcca gtggcgataa gtcgtgtctt    6480
accgggttgg actcaagacg atagttaccg gataaggcgc agcggtcggg ctgaacgggg    6540
ggttcgtgca cacagcccag cttggagcga acgacctaca ccgaactgag atacctacag    6600
cgtgagctat gagaaagcgc cacgcttccc gaagggagaa aggcggacag gtatccggta    6660
agcggcaggg tcgaacagg agagcgcacg agggagcttc caggggaaa cgcctggtat     6720
ctttatagtc ctgtcgggtt tcgccacctc tgacttgagc gtcgatttt gtgatgctcg     6780
tcaggggggc ggagcctatg gaaaaacgcc agcaacgcgg ccttttacg gttcctggcc     6840
ttttgctggc cttttgctca catgt                                           6865

<210> SEQ ID NO 117
<211> LENGTH: 7308
<212> TYPE: DNA
<213> ORGANISM: Artificial Sequence
<220> FEATURE:
<223> OTHER INFORMATION: plasmid pAAVss-CRE60-SkSH4-hDES1.4kb-Luc2

<400> SEQUENCE: 117
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag    120
tggccaactc catcactagg ggttcctgcg gcctttgct ccctgggagg gcctggccct     180
gtgggcattt gagtttataa caccaccccc attgtggcac accctccac cccgtaaaac     240
acaggctctg ctcttggaat cagtcttcct gatctgtggc tgtgccctcc aacagagggc    300
acccctgggc ttcccagctc tgggggtagt gggtgccaac aaggaggggc ctggggctga    360
agaatcccac ccgctgagct cggccttctc ccttccccac tgtccagctc cgcctttcag    420
catcctgcct cactcccgc ccaggcagca aggagcccac accctcatgc cctcagctt     480
cagccccac ctccaggagg ccctacccac gctcatgacc ttgctattct gggccttgtg    540
tcctgtaggg agatggacag gagacagctg ggcttccagg ccacccaggc gggggctag     600
ccgagggaag cctgctggct ctcctgcttg ctctaatttc tggggctccc caaaccttgg    660
cctcaggaga ctggggatag gaccggcctt gaaagtgggg gaagctttgg agagccgggt    720
gctgggttct tagtgagatg gccagtgaag gctgtggtgc cccgaggtaa gcagggcctg    780
```

```
atcccctcct aatcttccag cagcaactgg tgctctggcg cgccacgcgt ttctgagtcc    840
tctaaggtcc ctcactccca actcagcccc atgtcctgtc aattcccact cagtgtctga    900
tctccttctc ctcaccttc ccatctcccg tttgacccaa gcttcctgag ctctcctccc     960 attcccctttt ttggagtcct cctcctctcc cagaacccag taataagtgg gctcctccct   1020
ggcctggacc cccgtggtaa ccctataagg cgaggcagct gctgtctgag gcagggaggg    1080
gctggtgtgg gaggctaagg gcagctgcta agtttagggt ggctccttct ctcttcttag    1140
agacaacagg tggctggggc ctcagtgccc agaaaagaaa atgtcttaga ggtatcggca    1200
tgggcctgga ggaggggga cagggcaggg ggaggcatct tcctcaggac atcgggtcct     1260
agaggggtac ccaacgggtt acgacacacc tactagtaac ccctccagct ggtgatggca    1320
ggtctagggt aggaccagtg actggctcct aatcgagcac tctattttca gggtttgcat    1380
tccaaaaggg tcaggtccaa gagggacctg gagtgccaag tggaggtgta gaggcacggc    1440
cagtacccat ggagaatggt ggatgtcctt aggggttagc aagtgccgtg tgctaaggag    1500
ggggctttgg aggttgggca ggccctctgt ggggctccat ttttgtgggg gtgggggctg    1560
gagcattata gggggtggga agtgattggg gctgtcaccc tagccttcct tatctgacgc    1620
ccacccatgc ctcctcaggt accccctgcc ccccacagct cctctcctgt gccttgtttc    1680
ccagccatgc gttctcctct ataaataccc gctctggtat ttggggttgg cagctgttgc    1740
tgccagggag atggttgggt tgacatgcgg ctcctgacaa acacaaaacc cctggtgtgt    1800
gtgggcgtgg gtggtgtgag taggggatg aatcagggag ggggcggggg acccaggggg     1860
caggagccac acaaagtctg tgcggggtg ggagcgcaca tagcaattgg aaactgaaag     1920
cttatcagac cctttctgga aatcagccca ctgtttataa acttgaggcc ccaccctcga    1980
cagtaccggg gaggaagagg gcctgcacta gtccagaggg aaactgaggc tcagggctag    2040
ctcgcccata gacatacatg gcaggcaggc tttggccagg atccctccgc ctgccaggcg    2100
tctccctgcc ctcccttcct gcctagagac ccccaccctc aagcctggct ggtctttgcc    2160
tgagacccaa acctcttcga cttcaagaga atatttagga acaaggtggt ttagggcctt    2220
tcctgggaac aggccttgac cctttaagaa atgacccaaa gtctctcctt gaccaaaaag    2280
gggaccctca aactaaaggg aagcctctct tctgctgtct cccctgaccc cactccccc    2340 cacccccagga cgaggagata accagggctg aaagaggccc gctgggggc tgcagacatg    2400 cttgctgcct gccctggcga aggattggca ggcttgcccg tcacaggacc cccgctggct    2460
gactcagggg cgcaggcctc ttgcggggga gctggcctcc ccgcccccac ggccacgggc    2520
cgccctttcc tggcaggaca gcgggatctt gcagctgtca ggggagggga ggcgggggct    2580
gatgtcagga gggatacaaa tagtgccgac ggctgggggc cctgtctccc ctcgccgcat    2640
ccactctccg gccggccgcc tgcccgccgc ctcctccgtg cgcccgccag cctcgcccgc    2700
gccgtcacct ctagaaagag gtaagggttt aagggatggt tggttggtgg ggtattaatg    2760
tttaattacc tggagcacct gcctgaaatc acttttttc aggttggaag cttatggaag     2820
atgccaaaaa cattaagaag ggcccagcgc cattctaccc actcgaggac gggaccgccg    2880
gcgagcagct gcacaaagcc atgaagcgct acgccctggt gccggcacc atcgccttta     2940 ccgacgcaca tatcgaggtg gacattacct acgccgagta cttcgagatg agcgttcggc    3000
tggcagaagc tatgaagcgc tatgggctga atacaaacca tcggatcgtg gtgtgcagcg    3060
agaatagctt gcagttcttc atgcccgtgt tgggtgccct gttcatcggt gtggctgtgg    3120
```

```
ccccagctaa cgacatctac aacgagcgcg agctgctgaa cagcatgggc atcagccagc    3180
ccaccgtcgt attcgtgagc aagaaagggc tgcaaaagat cctcaacgtg caaagaagc     3240
taccgatcat acaaaagatc atcatcatgg atagcaagac cgactaccag ggcttccaaa    3300
gcatgtacac cttcgtgact tcccatttgc caccgggctt caacgagtac gacttcgtgc    3360
ccgagagctt cgaccgggac aaaaccatcg ccctgatcat gaacagtagt ggcagtaccg    3420
gattgcccaa gggcgtagcc ctaccgcacc gcaccgcttg tgtccgattc agtcatgccc    3480
gcgacccat  cttcggcaac cagatcatcc ccgacaccgc tatcctcagc gtggtgccat    3540
ttcaccacgg cttcggcatg ttcaccacgc tgggctactt gatctgcggc tttcgggtcg    3600
tgctcatgta ccgcttcgag gaggagctat tcttgcgcag cttgcaagac tataagattc    3660
aatctgccct gctggtgccc acactattta gcttcttcgc taagagcact ctcatcgaca    3720
agtacgacct aagcaacttg cacgagatcg ccagcggcgg ggcgccgctc agcaaggagg    3780
taggtgaggc cgtggccaaa cgcttccacc taccaggcat ccgccagggc tacggcctga    3840
cagaaacaac cagcgccatt ctgatcaccc ccgaagggga cgacaagcct ggcgcagtag    3900
gcaaggtggt gcccttcttc gaggctaagg tggtggactt ggacaccggt aagacactgg    3960
gtgtgaacca cgcggcgag  ctgtgcgtcc gtggccccat gatcatgagc ggctacgtta    4020
acaaccccga ggctacaaac gctctcatcg acaaggacgg ctggctgcac agcggcgaca    4080
tcgcctactg ggacgaggac gagcacttct tcatcgtgga ccggctgaag agcctgatca    4140
aatacaaggg ctaccaggta gccccagccg aactggagag catcctgctg caacacccca    4200
acatcttcga cgccggggtc gccggcctgc ccgacgacga tgccggcgag ctgcccgccg    4260
cagtcgtcgt gctggaacac ggtaaaaacca tgaccgagaa ggagatcgtg gactatgtgg    4320
ccagccaggt tacaaccgcc aagaagctgc gcggtggtgt tgtgttcgtg gacgaggtgc    4380
ctaaaggact gaccggcaag ttggacgccc gcaagatccg cgagattctc attaaggcca    4440
agaagggcgg caagatcgcc gtgtaattcg aaacgaatgg tccatcttga gcatctgact    4500
tctggctaaa taaaagatct ttattttcat tagatctgtg tgttggtttt ttgtgtgcgt    4560
cgagatccac ggccgcagga accctagtg atggagttgg ccactccctc tctgcgcgct    4620
cgctcgctca ctgaggccgg gcgaccaaag gtcgcccgac gcccgggctt tgcccgggcg    4680
gcctcagtga gcgagcgagc gcgcagctgc ctgcaggggc gcctgatgcg gtattttctc    4740
cttacgcatc tgtgcggtat ttcacaccgc atacgtcaaa gcaaccatag tacgcgccct    4800
gtagcggcgc attaagcgcg gcgggtgtgg tggttacgcg cagcgtgacc gctacacttg    4860
ccagcgccct agcgcccgct cctttcgctt tcttcccttc ctttctcgcc acgttcgccg    4920
gctttccccg tcaagctcta aatcgggggc tccctttagg gttccgattt agtgctttac    4980
ggcacctcga ccccaaaaaa cttgatttgg gtgatggttc acgtagtggg ccatcgccct    5040
gatagacggt ttttcgccct tgacgttgg  agtccacgtt ctttaatagt ggactcttgt    5100
tccaaactgg aacaacactc aaccctatct cgggctattc ttttgattta agggatttt    5160
tgccgatttc ggcctattgg ttaaaaaatg agctgatta  acaaaatttt aacgcgaatt    5220
ttaacaaaat attaacgttt acaatttat  ggtgcactct cagtacaatc tgctctgatg    5280
ccgcatagtt aagccagccc cgacacccgc caacacccgc tgacgcgccc tgacgggctt    5340
gtctgctccc ggcatccgct tacagacaag ctgtgaccgt ctccgggagc tgcatgtgtc    5400
agaggttttc accgtcatca ccgaaacgcg cgagacgaaa gggcctcgtg atacgcctat    5460
ttttataggt taatgtcatg ataataatgg tttcttagac gtcaggtggc acttttcggg    5520
```

```
gaaatgtgcg cggaacccct atttgtttat ttttctaaat acattcaaat atgtatccgc    5580
tcatgagaca ataaccctga taaatgcttc aataatattg aaaaaggaag agtatgagta    5640
ttcaacattt ccgtgtcgcc cttattccct tttttgcggc attttgcctt cctgtttttg    5700
ctcacccaga aacgctggtg aaagtaaaag atgctgaaga tcagttgggt gcacgagtgg    5760
gttacatcga actggatctc aacagcggta agatccttga gttttcgc cccgaagaac     5820 gttttccaat gatgagcact tttaaagttc tgctatgtgg cgcggtatta tcccgtattg    5880
acgccgggca agagcaactc ggtcgccgca tacactattc tcagaatgac ttggttgagt    5940
actcaccagt cacagaaaag catcttacgg atggcatgac agtaagagaa ttatgcagtg    6000
ctgccataac catgagtgat aacactgcgg ccaacttact tctgacaacg atcggaggac    6060
cgaaggagct aaccgctttt ttgcacaaca tgggggatca tgtaactcgc cttgatcgtt    6120
gggaaccgga gctgaatgaa gccataccaa acgacgagcg tgacaccacg atgcctgtag    6180
caatggcaac aacgttgcgc aaactattaa ctggcgaact acttactcta gcttcccggc    6240
aacaattaat agactggatg gaggcggata agttgcagg accacttctg cgctcggccc    6300
ttccggctgg ctggtttatt gctgataaat ctggagccgg tgagcgtggg tctcgcggta    6360
tcattgcagc actggggcca gatggtaagc cctcccgtat cgtagttatc tacacgacgg    6420
ggagtcaggc aactatggat gaacgaaata gacagatcgc tgagataggt gcctcactga    6480
ttaagcattg gtaactgtca gaccaagttt actcatatat actttagatt gatttaaaac    6540
ttcattttta atttaaaagg atctaggtga agatcctttt tgataatctc atgaccaaaa    6600
tcccttaacg tgagttttcg ttccactgag cgtcagaccc cgtagaaaag atcaaaggat    6660
cttcttgaga tccttttttt ctgcgcgtaa tctgctgctt gcaaacaaaa aaaccaccgc    6720
taccagcggt ggtttgtttg ccggatcaag agctaccaac tcttttccg aaggtaactg     6780 gcttcagcag agcgcagata ccaaatactg tccttctagt gtagccgtag ttaggccacc    6840
acttcaagaa ctctgtagca ccgcctacat acctcgctct gctaatcctg ttaccagtgg    6900
ctgctgccag tggcgataag tcgtgtctta ccgggttgga ctcaagacga tagttaccgg    6960
ataaggcgca gcggtcgggc tgaacggggg gttcgtgcac acagcccagc ttggagcgaa    7020
cgacctacac cgaactgaga tacctacagc gtgagctatg agaaagcgcc acgcttcccg    7080
aagggagaaa ggcggacagg tatccggtaa gcggcagggt cggaacagga gagcgcacga    7140
gggagcttcc agggggaaac gcctggtatc tttatagtcc tgtcgggttt cgccacctct    7200
gacttgagcg tcgatttttg tgatgctcgt caggggggcg gagcctatgg aaaaacgcca    7260
gcaacgcggc cttttacgg ttcctggcct tttgctggcc ttttgctc                  7308
```

<210> SEQ ID NO 118
<211> LENGTH: 7053
<212> TYPE: DNA
<213> ORGANISM: Artificial Sequence
<220> FEATURE:
<223> OTHER INFORMATION: plasmid pAAVss-CRE64-SkSH4-hDES1.4kb-Luc2

<400> SEQUENCE: 118

```
acatgtcctg caggcagctg cgcgctcgct cgctcactga ggccgcccgg gcaaagcccg     60
ggcgtcgggc gacctttggt cgcccggcct cagtgagcga gcgagcgcgc agagagggag    120
tggccaactc catcactagg ggttcctgcg gccgtctccg aacgcaggcc ccgtcgcgtt    180
aagcacaagc tggcagggcc tctcctctcc cttctcagat ttgctccttg acatttgcct    240
```

-continued

```
gctgcctggc ggtggcaaca gctggggcgg ggcgcgcgca ggaggccccg taaccctatc    300
cccgctccgg ctccctcgtg aaaccggagc ttccctgcct tggccgaggg ggagggctgc    360
gggggccaga ccgcctgcga agaccacagg gttttttcctc tcgggttttg gctcccgtgg   420
gatggatgtg gctgtgcggg gggttggcct gagcttcgct tctaagccag cagcttggtc    480
agggaaacct gaaagcattc ccagctaatc ccccaagtgg tgcaagtctg tgcgcgccca    540
tcccgctgag taaggcggtg gggcgcgcca cgcgtttctg agtcctctaa ggtccctcac    600
tcccaactca gccccatgtc ctgtcaattc ccactcagtg tctgatctcc ttctcctcac    660 cttttcccatc tcccgtttga cccaagcttc ctgagctctc ctcccattcc ccttttttgga  720 gtcctcctcc tctcccagaa cccagtaata agtgggctcc tccctggcct ggaccccgt     780 ggtaacccta taaggcgagg cagctgctgt ctgaggcagg gaggggctgg tgtgggaggc    840
taagggcagc tgctaagttt agggtggctc cttctctctt cttagagaca acaggtggct    900
ggggcctcag tgcccagaaa agaaaatgtc ttagaggtat cggcatgggc ctggaggagg    960
ggggacaggg caggggagg catcttcctc aggacatcgg gtcctagagg ggtacccaac    1020
gggttacgac acacctacta gtaacccctc cagctggtga tggcaggtct agggtaggac    1080
cagtgactgg ctcctaatcg agcactctat tttcagggtt tgcattccaa aagggtcagg   1140
tccaagaggg acctggagtg ccaagtggag gtgtagaggc acggccagta cccatggaga   1200
atggtggatg tccttagggg ttagcaagtg ccgtgtgcta aggaggggc tttggaggtt    1260 gggcaggccc tctgtgggc tccatttttg tggggtggg ggctggagca ttataggggg     1320
tgggaagtga ttggggctgt caccctagcc ttccttatct gacgcccacc catgcctcct   1380
caggtacccc ctgccccca cagctcctct cctgtgcctt gtttcccagc catgcgttct    1440
cctctataaa tacccgctct ggtatttggg gttggcagct gttgctgcca gggagatggt   1500
tgggttgaca tgcggctcct gacaaaacac aaaccctgg tgtgtgtggg cgtgggtggt    1560
gtgagtaggg ggatgaatca gggagggggc ggggaccca gggggcagga gccacacaaa    1620
gtctgtgcgg gggtgggagc gcacatagca attggaaact gaaagcttat cagacccttt   1680
ctggaaatca gcccactgtt tataaacttg aggcccacc ctcgacagta ccggggagga    1740
agagggcctg cactagtcca gagggaaact gaggctcagg gctagctcgc ccatagacat   1800
acatggcagg caggctttgg ccaggatccc tccgcctgcc aggcgtctcc ctgccctccc   1860
ttcctgccta gagacccca ccctcaagcc tggctggtct ttgcctgaga cccaaacctc   1920
ttcgacttca agagaatatt taggaacaag gtggtttagg gcctttcctg gaacaggcc    1980 ttgaccctt aagaaatgac ccaaagtctc tccttgacca aaaagggac cctcaaacta     2040 aagggaagcc tctcttctgc tgtctcccct gaccccactc ccccccaccc caggacgagg   2100
agataaccag ggctgaaaga ggcccgcctg ggggctgcag acatgcttgc tgcctgccct   2160
ggcgaaggat tggcaggctt gcccgtcaca ggaccccgc tggctgactc aggggcgcag    2220
gcctcttgcg ggggagctgg cctccccgcc cccacgccaa cggccgccc tttcctggca    2280 ggacagcggg atcttgcagc tgtcagggga ggggaggcgg gggctgatgt caggagggat    2340
acaaatagtg ccgacggctg ggggccctgt ctccctcgc cgcatccact ctccggccgg    2400
ccgcctgccc gccgcctcct ccgtgcgccc gccagcctcg cccgcgccgt cacctctaga   2460
aagaggtaag ggtttaaggg atggttggtt ggtgggtat taatgtttaa ttacctggag    2520
cacctgccta aaatcacttt ttttcaggtt ggaagcttat ggaagatgcc aaaaacatta   2580
agaagggccc agcgccattc tacccactcg aggacggac cgccggcgag cagctgcaca   2640
```

```
aagccatgaa gcgctacgcc ctggtgcccg gcaccatcgc ctttaccgac gcacatatcg    2700
aggtggacat tacctacgcc gagtacttcg agatgagcgt tcggctggca gaagctatga    2760
agcgctatgg gctgaataca aaccatcgga tcgtggtgtg cagcgagaat agcttgcagt    2820
tcttcatgcc cgtgttgggt gccctgttca tcggtgtggc tgtggcccca gctaacgaca    2880
tctacaacga gcgcgagctg ctgaacagca tgggcatcag ccagcccacc gtcgtattcg    2940
tgagcaagaa agggctgcaa aagatcctca acgtgcaaaa gaagctaccg atcatacaaa    3000
agatcatcat catggatagc aagaccgact accagggctt ccaaagcatg tacaccttcg    3060
tgacttccca tttgccaccc ggcttcaacg agtacgactt cgtgcccgag agcttcgacc    3120
gggacaaaac catcgccctg atcatgaaca gtagtggcag taccggattg cccaagggcg    3180
tagccctacc gcaccgcacc gcttgtgtcc gattcagtca tgcccgcgac ccatcttcg    3240 gcaaccagat catccccgac accgctatcc tcagcgtggt gccatttcac cacggcttcg    3300
gcatgttcac cacgctgggc tacttgatct gcggctttcg ggtcgtgctc atgtaccgct    3360
tcgaggagga gctattcttg cgcagcttgc aagactataa gattcaatct gccctgctgg    3420
tgccacacac atttagcttc ttcgctaaga gcactctcat cgacaagtac gacctaagca    3480
acttgcacga gatcgccagc ggcggggcgc cgctcagcaa ggaggtaggt gaggccgtgg    3540
ccaaacgctt ccacctacca ggcatccgcc agggctacgg cctgacagaa caaccagcg    3600 ccattctgat cacccccgaa ggggacgaca agcctggcgc agtaggcaag gtggtgccct    3660
tcttcgaggc taaggtggtg gacttggaca ccggtaagac actgggtgtg aaccagcgcg    3720
gcgagctgtg cgtccgtggc cccatgatca tgagcggcta cgttaacaac cccgaggcta    3780
caaacgctct catcgacaag gacggctggc tgcacagcgg cgacatcgcc tactgggacg    3840
aggacgagca cttcttcatc gtggaccggc tgaagagcct gatcaaatac aagggctacc    3900
aggtagcccc agccgaactg gagagcatcc tgctgcaaca ccccaacatc ttcgacgccg    3960
gggtcgccgg cctgcccgac gacgatgccg gcgagctgcc cgccgcagtc gtcgtgctgg    4020
aacacggtaa aaccatgacc gagaaggaga tcgtggacta tgtggccagc caggttacaa    4080
ccgccaagaa gctgcgcggt ggtgttgtgt tcgtggacga ggtgcctaaa ggactgaccg    4140
gcaagttgga cgcccgcaag atccgcgaga ttctcattaa ggccaagaag ggcggcaaga    4200
tcgccgtgta attcgaaacg aacggtccat cttgagcatc tgacttctgg ctaaataaaa    4260
gatctttatt ttcattagat ctgtgtgttg gttttttgtg tgcgtcgaga tccacggccg    4320 caggaaccc tagtgatgga gttggccact ccctctctgc gcgctcgctc gctcactgag    4380
gccgggcgac caaaggtcgc ccgacgcccg ggctttgccc gggcggcctc agtgagcgag    4440
cgagcgcgca gctgcctgca ggggcgcctg atgcggtatt ttctccttac gcatctgtgc    4500
ggtatttcac accgcatacg tcaaagcaac catagtacgc gccctgtagc ggcgcattaa    4560
gcgcggcggg tgtggtggtt acgcgcagcg tgaccgctac acttgccagc gccctagcgc    4620
ccgctccttt cgctttcttc ccttcctttc tcgccacgtt cgccggcttt ccccgtcaag    4680
ctctaaatcg ggggctccct ttagggttcc gatttagtgc tttacggcac ctcgacccca    4740
aaaaacttga tttgggtgat ggttcacgta gtgggccatc gccctgatag acggttttc    4800 gccctttgac gttggagtcc acgttcttta atagtggact cttgttccaa actggaacaa    4860
cactcaaccc tatctcgggc tattctttg atttataagg gattttgccg atttcggcct    4920
attggttaaa aaatgagctg atttaacaaa aatttaacgc gaattttaac aaaatattaa    4980
```

| | | | | | |
|---|---|---|---|---|---|
| cgtttacaat | tttatggtgc | actctcagta | caatctgctc | tgatgccgca | tagttaagcc | 5040 |
| agccccgaca | cccgccaaca | cccgctgacg | cgccctgacg | ggcttgtctg | ctcccggcat | 5100 |
| ccgcttacag | acaagctgtg | accgtctccg | ggagctgcat | gtgtcagagg | ttttcaccgt | 5160 |
| catcaccgaa | acgcgcgaga | cgaaagggcc | tcgtgatacg | cctattttta | taggttaatg | 5220 |
| tcatgataat | aatggtttct | tagacgtcag | gtggcacttt | tcggggaaat | gtgcgcggaa | 5280 |
| cccctatttg | tttatttttc | taaatacatt | caaatatgta | tccgctcatg | agacaataac | 5340 |
| cctgataaat | gcttcaataa | tattgaaaaa | ggaagagtat | gagtattcaa | catttccgtg | 5400 |
| tcgcccttat | tcccttttt | gcggcatttt | gccttcctgt | ttttgctcac | ccagaaacgc | 5460 |
| tggtgaaagt | aaaagatgct | gaagatcagt | tgggtgcacg | agtgggttac | atcgaactgg | 5520 |
| atctcaacag | cggtaagatc | cttgagagtt | ttcgccccga | agaacgtttt | ccaatgatga | 5580 |
| gcacttttaa | agttctgcta | tgtggcgcgg | tattatcccg | tattgacgcc | gggcaagagc | 5640 |
| aactcggtcg | ccgcatacac | tattctcaga | atgacttggt | tgagtactca | ccagtcacag | 5700 |
| aaaagcatct | tacggatggc | atgacagtaa | gagaattatg | cagtgctgcc | ataaccatga | 5760 |
| gtgataacac | tgcggccaac | ttacttctga | caacgatcgg | aggaccgaag | gagctaaccg | 5820 |
| cttttttgca | caacatgggg | gatcatgtaa | ctcgccttga | tcgttgggaa | ccggagctga | 5880 |
| atgaagccat | accaaacgac | gagcgtgaca | ccacgatgcc | tgtagcaatg | gcaacaacgt | 5940 |
| tgcgcaaact | attaactggc | gaactactta | ctctagcttc | ccggcaacaa | ttaatagact | 6000 |
| ggatggaggc | ggataaagtt | gcaggaccac | ttctgcgctc | ggcccttccg | gctggctggt | 6060 |
| ttattgctga | taaatctgga | gccggtgagc | gtgggtctcg | cggtatcatt | gcagcactgg | 6120 |
| ggccagatgg | taagccctcc | cgtatcgtag | ttatctacac | gacggggagt | caggcaacta | 6180 |
| tggatgaacg | aaatagacag | atcgctgaga | taggtgcctc | actgattaag | cattggtaac | 6240 |
| tgtcagacca | agtttactca | tatatacttt | agattgattt | aaaacttcat | ttttaattta | 6300 |
| aaaggatcta | ggtgaagatc | ctttttgata | atctcatgac | caaaatccct | taacgtgagt | 6360 |
| tttcgttcca | ctgagcgtca | gaccccgtag | aaaagatcaa | aggatcttct | tgagatcctt | 6420 |
| tttttctgcg | cgtaatctgc | tgcttgcaaa | caaaaaaacc | accgctacca | gcggtggttt | 6480 |
| gtttgccgga | tcaagagcta | ccaactcttt | ttccgaaggt | aactggcttc | agcagagcgc | 6540 |
| agataccaaa | tactgtcctt | ctagtgtagc | cgtagttagg | ccaccacttc | aagaactctg | 6600 |
| tagcaccgcc | tacatacctc | gctctgctaa | tcctgttacc | agtggctgct | gccagtggcg | 6660 |
| ataagtcgtg | tcttaccggg | ttggactcaa | gacgatagtt | accggataag | gcgcagcggt | 6720 |
| cgggctgaac | ggggggttcg | tgcacacagc | ccagcttgga | gcgaacgacc | tacaccgaac | 6780 |
| tgagatacct | acagcgtgag | ctatgagaaa | gcgccacgct | tcccgaaggg | agaaaggcgg | 6840 |
| acaggtatcc | ggtaagcggc | agggtcggaa | caggagagcg | cacgagggag | cttccagggg | 6900 |
| gaaacgcctg | gtatctttat | agtcctgtcg | ggtttcgcca | cctctgactt | gagcgtcgat | 6960 |
| ttttgtgatg | ctcgtcaggg | gggcggagcc | tatggaaaaa | cgccagcaac | gcggcctttt | 7020 |
| tacggttcct | ggccttttgc | tggccttttg | ctc | | | 7053 |

<210> SEQ ID NO 119
<211> LENGTH: 6210
<212> TYPE: DNA
<213> ORGANISM: Artificial Sequence
<220> FEATURE:
<223> OTHER INFORMATION: plasmid pAAVss-hDES1.4kb-Luc2

<400> SEQUENCE: 119

```
acatgtcctg caggcagctg cgcgctcgct cgctcactga ggccgcccgg gcaaagcccg    60
ggcgtcgggc gacctttggt cgcccggcct cagtgagcga gcgagcgcgc agagagggag   120
tggccaactc catcactagg ggttcctgcg gccggcgcgc cacgcgtggt acccaacggg   180
ttacgacaca cctactagta acccctccag ctggtgatgg caggtctagg gtaggaccag   240
tgactggctc ctaatcgagc actctatttt cagggtttgc attccaaaag ggtcaggtcc   300
aagagggacc tggagtgcca agtggaggtg tagaggcacg gccagtaccc atggagaatg   360
gtggatgtcc ttaggggtta gcaagtgccg tgtgctaagg agggggcttt ggaggttggg   420
caggccctct gtggggctcc attttgtggg gggtggggc tggagcatta taggggtgg    480 gaagtgattg ggctgtcac cctagccttc cttatctgac gcccacccat gcctcctcag    540
gtaccccctg cccccacag ctcctctcct gtgccttgtt tcccagccat gcgttctcct    600
ctataaatac ccgctctggt atttggggtt ggcagctgtt gctgccaggg agatggttgg   660
gttgacatgc ggctcctgac aaaacacaaa cccctggtgt gtgtgggcgt gggtggtgtg   720
agtaggggga tgaatcaggg aggggcggg ggacccaggg ggcaggagcc acacaaagtc    780
tgtgcggggg tgggagcgca catagcaatt ggaaactgaa agcttatcag accctttctg   840
gaaatcagcc cactgtttat aaacttgagg ccccacccta cagtaccg gggaggaaga     900 gggcctgcac tagtccagag ggaaactgag gctcagggct agctcgccca tagacataca   960
tggcaggcag gctttggcca ggatccctcc gcctgccagg cgtctccctg ccctcccttc  1020
ctgcctagag acccccaccc tcaagcctgg ctggtctttg cctgagaccc aaacctcttc  1080
gacttcaaga gaatatttag gaacaaggtg gtttagggcc tttcctggga acaggccttg  1140 acccttttaag aaatgaccca aagtctctcc ttgaccaaaa aggggacccct caaactaaag  1200 ggaagcctct cttctgctgt ctcccctgac cccactcccc cccaccccag gacgaggaga  1260
taaccagggc tgaaagaggc ccgcctgggg gctgcagaca tgcttgctgc ctgccctggc  1320
gaaggattgg caggcttgcc cgtcacagga ccccgctgg ctgactcagg ggcgcaggcc   1380
tcttgcgggg gagctggcct ccccgccccc acggccacgg gccgcccttt cctggcagga  1440
cagcgggatc ttgcagctgt caggggaggg gaggcggggg ctgatgtcag gagggataca  1500
aatagtgccg acggctgggg gccctgtctc ccctcgccgc atccactctc cggccggccg  1560
cctgcccgcc gcctcctccg tgcgcccgcc agcctcgccc gcgccgtcac ctctagaaag  1620
aggtaagggt ttaagggatg gttggttggt ggggtattaa tgtttaatta cctggagcac  1680
ctgcctgaaa tcactttttt tcaggttgga agcttatgga agatgccaaa aacattaaga  1740
agggcccagc gccattctac ccactcgaag acgggaccgc cggcgagcag ctgcacaaag  1800
ccatgaagcg ctacgccctg gtgccggca ccatcgcctt taccgacgca catatcgagg   1860
tggacattac ctacgccgag tacttcgaga tgagcgttcg gctggcagaa gctatgaagc  1920
gctatgggct gaatacaaac catcggatcg tggtgtgcag cgagaatagc ttgcagttct  1980
tcatgcccgt gttgggtgcc ctgttcatcg gtgtggctgt ggccccagct aacgacatct  2040
acaacgagcg cgagctgctg aacagcatgg gcatcagcca gcccaccgtc gtattcgtga  2100
gcaagaaagg gctgcaaaag atcctcaacg tgcaaaagaa gctaccgatc atacaaaaga  2160
tcatcatcat ggatagcaag accgactacc agggcttcca aagcatgtac accttcgtga  2220
cttcccattt gccacccggc ttcaacgagt acgacttcgt gcccgagagc ttcgaccggg  2280
acaaaaccat cgccctgatc atgaacagta gtggcagtac cggattgccc aagggcgtag  2340
```

```
ccctaccgca ccgcaccgct tgtgtccgat tcagtcatgc ccgcgacccc atcttcggca    2400
accagatcat ccccgacacc gctatcctca gcgtggtgcc atttcaccac ggcttcggca    2460
tgttcaccac gctgggctac ttgatctgcg gctttcgggt cgtgctcatg taccgcttcg    2520
aggaggagct attcttgcgc agcttgcaag actataagat tcaatctgcc ctgctggtgc    2580
ccacactatt tagcttcttc gctaagagca ctctcatcga caagtacgac ctaagcaact    2640
tgcacgagat cgccagcggc ggggcgccgc tcagcaagga ggtaggtgag gccgtggcca    2700
aacgcttcca cctaccaggc atccgccagg gctacggcct gacagaaaca accagcgcca    2760
ttctgatcac ccccgaaggg gacgacaagc ctggcgcagt aggcaaggtg gtgcccttct    2820
tcgaggctaa ggtggtggac ttggacaccg gtaagacact gggtgtgaac cagcgcggcg    2880
agctgtgcgt ccgtggcccc atgatcatga gcggctacgt taacaacccc gaggctacaa    2940
acgctctcat cgacaaggac ggctggctgc acagcggcga catcgcctac tgggacgagg    3000
acgagcactt cttcatcgtg gaccggctga gagcctgat caaatacaag ggctaccagg    3060
tagccccagc cgaactggag agcatcctgc tgcaacaccc caacatcttc gacgccgggg    3120
tcgccggcct gcccgacgac gatgccggcg agctgcccgc cgcagtcgtc gtgctggaac    3180
acggtaaaac catgaccgag aaggagatcg tggactatgt ggccagccag gttacaaccg    3240
ccaagaagct gcgcggtggt gttgtgttcg tggacgaggt gcctaaagga ctgaccggca    3300
agttggacgc ccgcaagatc cgcgagattc tcattaaggc caagaagggc ggcaagatcg    3360
ccgtgtaatt cgaaacgttg agtccatctt gagcatctga cttctggcta aataaaagat    3420
ctttattttc attagatctg tgtgttggtt ttttgtgtgc gtcagatcc acggccgcag    3480 gaaccctag tgatggagtt ggccactccc tctctgcgcg ctcgctcgct cactgaggcc    3540
gggcgaccaa aggtcgcccg acgcccgggc tttgcccggg cggcctcagt gagcgagcga    3600
gcgcgcagct gcctgcaggg gcgcctgatg cggtattttc tccttacgca tctgtgcggt    3660
atttcacacc gcatacgtca aagcaaccat agtacgcgcc ctgtagcggc gcattaagcg    3720
cggcgggtgt ggtggttacg cgcagcgtga ccgctacact tgccagcgcc ctagcgcccg    3780
ctcctttcgc tttcttccct tcctttctcg ccacgttcgc cggctttccc cgtcaagctc    3840
taaatcgggg gctcccttta gggttccgat ttagtgcttt acggcacctc gaccccaaaa    3900
aacttgattt gggtgatggt tcacgtagtg ggccatcgcc ctgatagacg ttttttcgcc    3960
ctttgacgtt ggagtccacg ttctttaata gtggactctt gttccaaact ggaacaacac    4020
tcaaccctat ctcgggctat tcttttgatt tataagggat tttgccgatt tcggcctatt    4080
ggttaaaaaa tgagctgatt taacaaaaat ttaacgcgaa ttttaacaaa atattaacgt    4140
ttacaatttt atggtgcact ctcagtacaa tctgctctga tgccgcatag ttaagccagc    4200
cccgacaccc gccaacaccc gctgacgcgc cctgacgggc ttgtctgctc ccggcatccg    4260
cttacagaca agctgtgacc gtctccggga gctgcatgtg tcagaggttt tcaccgtcat    4320
caccgaaacg cgcgagacga agggcctcg tgatacgcct atttttatag gttaatgtca    4380
tgataataat ggtttcttag acgtcaggtg gcacttttcg gggaaatgtg cgcggaaccc    4440
ctatttgttt attttctaa atacattcaa atatgtatcc gctcatgaga caataaccct    4500
gataaatgct tcaataatat tgaaaaagga agagtatgag tattcaacat ttccgtgtcg    4560
cccttattcc cttttttgcg gcattttgcc ttcctgtttt tgctcaccca gaaacgctgg    4620
tgaaagtaaa agatgctgaa gatcagttgg gtgcacgagt gggttacatc gaactggatc    4680
tcaacagcgg taagatcctt gagagttttc gccccgaaga acgttttcca atgatgagca    4740
```

```
cttttaaagt tctgctatgt ggcgcggtat tatcccgtat tgacgccggg caagagcaac    4800
tcggtcgccg catacactat tctcagaatg acttggttga gtactcacca gtcacagaaa    4860
agcatcttac ggatggcatg acagtaagag aattatgcag tgctgccata accatgagtg    4920
ataacactgc ggccaactta cttctgacaa cgatcggagg accgaaggag ctaaccgctt    4980
ttttgcacaa catgggggat catgtaactc gccttgatcg ttgggaaccg gagctgaatg    5040
aagccatacc aaacgacgag cgtgacacca cgatgcctgt agcaatggca acaacgttgc    5100
gcaaactatt aactggcgaa ctacttactc tagcttcccg gcaacaatta atagactgga    5160
tggaggcgga taaagttgca ggaccacttc tgcgctcggc ccttccggct ggctggttta    5220
ttgctgataa atctggagcc ggtgagcgtg ggtctcgcgg tatcattgca gcactggggc    5280
cagatggtaa gccctcccgt atcgtagtta tctacacgac ggggagtcag gcaactatgg    5340
atgaacgaaa tagacagatc gctgagatag gtgcctcact gattaagcat tggtaactgt    5400
cagaccaagt ttactcatat atactttaga ttgatttaaa acttcatttt taatttaaaa    5460
ggatctaggt gaagatcctt tttgataatc tcatgaccaa aatcccttaa cgtgagtttt    5520
cgttccactg agcgtcagac cccgtagaaa agatcaaagg atcttcttga tccttttttt    5580
ttctgcgcgt aatctgctgc ttgcaaacaa aaaaaccacc gctaccagcg gtggtttgtt    5640
tgccggatca agagctacca actctttttc cgaaggtaac tggcttcagc agagcgcaga    5700
taccaaatac tgtccttcta gtgtagccgt agttaggcca ccacttcaag aactctgtag    5760
caccgcctac atacctcgct ctgctaatcc tgttaccagt ggctgctgcc agtggcgata    5820
agtcgtgtct taccgggttg gactcaagac gatagttacc ggataaggcg cagcggtcgg    5880
gctgaacggg gggttcgtgc acacagccca gcttggagcg aacgacctac accgaactga    5940
gatacctaca gcgtgagcta tgagaaagcg ccacgcttcc cgaagggaga aaggcggaca    6000
ggtatccggt aagcggcagg gtcggaacag gagagcgcac gagggagctt ccagggggaa    6060
acgcctggta tctttatagt cctgtcgggt ttcgccacct ctgacttgag cgtcgatttt    6120
tgtgatgctc gtcaggggggg cggagcctat ggaaaaacgc cagcaacgcg gcctttttac    6180
ggttcctggc cttttgctgg ccttttgctc                                    6210
```

<210> SEQ ID NO 120
<211> LENGTH: 6645
<212> TYPE: DNA
<213> ORGANISM: Artificial Sequence
<220> FEATURE:
<223> OTHER INFORMATION: plasmid pAAVss-SkSH4-hDES1.4kb-Luc2

<400> SEQUENCE: 120

```
acatgtcctg caggcagctg cgcgctcgct cgctcactga ggccgcccgg gcaaagcccg      60
ggcgtcgggc gacctttggt cgcccggcct cagtgagcga gcgagcgcgc agagagggag     120
tggccaactc catcactagg ggttcctgcg gccggcgcgc cacgcgtttc tgagtcctct     180
aaggtccctc actcccaact cagccccatg tcctgtcaat tcccactcag tgtctgatct     240
ccttctcctc acctttccca tctcccgttt gacccaagct tcctgagctc tcctcccatt     300
ccccttttg gagtcctcct cctctcccag aaccagtaa taagtgggct cctccctggc      360
ctggaccccc gtggtaaccc tataaggcga ggcagctgct gtctgaggca gggaggggct     420
ggtgtgggag gctaagggca gctgctaagt ttagggtggc tccttctctc ttcttagaga     480
caacaggtgg ctggggcctc agtgcccaga aaagaaaatg tcttagaggt atcggcatgg     540
```

```
gcctggagga ggggggacag ggcaggggga ggcatcttcc tcaggacatc gggtcctaga    600
ggggtaccca acgggttacg acacacctac tagtaacccc tccagctggt gatggcaggt    660
ctagggtagg accagtgact ggctcctaat cgagcactct attttcaggg tttgcattcc    720
aaaagggtca ggtccaagag ggacctggag tgccaagtgg aggtgtagag cacggccag     780 tacccatgga gaatggtgga tgtccttagg ggttagcaag tgccgtgtgc taaggagggg    840
gctttggagg ttgggcaggc cctctgtggg gctccatttt tgtggggggtg ggggctggag   900 cattataggg ggtgggaagt gattggggct gtcaccctag ccttccttat ctgacgccca    960
cccatgcctc ctcaggtacc ccctgccccc cacagctcct ctcctgtgcc ttgtttccca   1020
gccatgcgtt ctcctctata aatacccgct ctggtatttg gggttggcag ctgttgctgc   1080
cagggagatg gttgggttga catgcggctc ctgacaaaac acaaacccct ggtgtgtgtg   1140
ggcgtgggtg gtgtgagtag ggggatgaat cagggagggg gcggggggacc caggggcag   1200 gagccacaca aagtctgtgc gggggtggga gcgcacatag caattggaaa ctgaaagctt   1260
atcagaccct ttctggaaat cagcccactg tttataaact tgaggcccca ccctcgacag   1320 taccgggggag gaagagggcc tgcactagtc cagaggaaaa ctgaggctca gggctagctc   1380
gcccatagac atacatggca ggcaggcttt ggccaggatc cctccgcctg ccaggcgtct   1440
ccctgccctc ccttcctgcc tagagacccc caccctcaag cctggctggt ctttgcctga   1500
gacccaaacc tcttcgactt caagagaata tttaggaaca aggtggttta gggccttttcc  1560 tgggaacagg ccttgaccct ttaagaaatg acccaaagtc tctccttgac caaaaggggg   1620
accctcaaac taaagggaag cctctcttct gctgtctccc ctgaccccac tccccccac   1680 cccaggacga ggagataacc agggctgaaa gaggcccgcc tgggggctgc agacatgctt   1740
gctgcctgcc ctggcgaagg attggcaggc ttgcccgtca caggacccc gctggctgac   1800 tcagggcgc aggcctcttg cggggagct ggcctccccg cccccacggc cacgggccgc    1860
cctttcctgg caggacagcg ggatcttgca gctgtcaggg gaggggaggc gggggctgat   1920
gtcaggaggg atacaaatag tgccgacggc tgggggccct gtctcccctc gccgcatcca   1980
ctctccggcc ggccgcctgc ccgccgcctc ctccgtgcgc ccgccagcct cgcccgcgcc   2040
gtcacctcta gaaagaggta agggtttaag ggatggttgg ttggtggggt attaatgttt   2100
aattacctgg agcacctgcc tgaaatcact ttttttcagg ttggaagctt atggaagatg   2160
ccaaaaacat taagaagggc ccagcgccat tctacccact cgaggacggg accgccggcg   2220
agcagctgca caaagccatg aagcgctacg ccctggtgcc cggcaccatc gcctttaccg   2280
acgcacatat cgaggtggac attacctacg ccgagtactt cgagatgagc gttcggctgg   2340
cagaagctat gaagcgctat gggctgaata caaaccatcg gatcgtggtg tgcagcgaga   2400
atagcttgca gttcttcatg cccgtgttgg gtgccctgtt catcggtgtg gctgtggccc   2460
cagctaacga catctacaac gagcgcgagc tgctgaacag catgggcatc agccagccca   2520
ccgtcgtatt cgtgagcaag aaagggctgc aaaagatcct caacgtgcaa agaagctac   2580 cgatcataca aaagatcatc atcatggata gcaagaccga ctaccagggc ttccaaagca   2640
tgtacacctt cgtgacttcc catttgccac ccggcttcaa cgagtacgac ttcgtgcccg   2700
agagcttcga ccgggacaaa accatcgccc tgatcatgaa cagtagtggc agtaccggat   2760
tgcccaaggg cgtagcccta ccgcaccgca ccgcttgtgt ccgattcagt catgcccgcg   2820
accccatctt cggcaaccag atcatccccg acaccgctat cctcagcgtg gtgccatttc   2880
accacggctt cggcatgttc accacgctgg gctacttgat ctgcggcttt cgggtcgtgc   2940
```

```
tcatgtaccg cttcgaggag gagctattct tgcgcagctt gcaagactat aagattcaat    3000
ctgccctgct ggtgcccaca ctatttagct tcttcgctaa gagcactctc atcgacaagt    3060
acgacctaag caacttgcac gagatcgcca gcggcggggc gccgctcagc aaggaggtag    3120
gtgaggccgt ggccaaacgc ttccacctac caggcatccg ccaggctac ggcctgacag     3180
aaacaaccag cgccattctg atcacccccg aagggacga caagcctggc gcagtaggca     3240
aggtggtgcc cttcttcgag gctaaggtgg tggacttgga caccggtaag acactgggtg    3300
tgaaccagcg cggcgagctg tgcgtccgtg gccccatgat catgagcggc tacgttaaca    3360
accccgaggc tacaaacgct ctcatcgaca aggacggctg gctgcacagc ggcgacatcg    3420
cctactggga cgaggacgag cacttcttca tcgtggaccg gctgaagagc ctgatcaaat    3480
acaagggcta ccaggtagcc ccagccgaac tggagagcat cctgctgcaa cccccaaca    3540
tcttcgacgc cggggtcgcc ggcctgcccg acgacgatgc cggcgagctg cccgccgcag    3600
tcgtcgtgct ggaacacggt aaaaccatga ccgagaagga gatcgtggac tatgtggcca    3660
gccaggttac aaccgccaag aagctgcgcg tggtgttgt gttcgtggac gaggtgccta    3720
aaggactgac cggcaagttg gacgcccgca agatccgcga gattctcatt aaggccaaga    3780
agggcggcaa gatcgccgtg taattcgaaa cgttccgtcc atcttgagca tctgacttct    3840
ggctaaataa aagatcttta ttttcattag atctgtgtgt tggttttttg tgtgcgtcga    3900
gatccacggc cgcaggaacc cctagtgatg gagttggcca ctccctctct gcgcgctcgc    3960
tcgctcactg aggccgggcg accaaaggtc gcccgacgcc cgggctttgc ccgggcggcc    4020
tcagtgagcg agcgagcgcg cagctgcctg caggggcgcc tgatgcggta ttttctcctt    4080
acgcatctgt gcggtatttc acaccgcata cgtcaaagca accatagtac gcgccctgta    4140
gcggcgcatt aagcgcggcg ggtgtggtgg ttacgcgcag cgtgaccgct acacttgcca    4200
gcgccctagc gcccgctcct ttcgctttct tcccttcctt tctcgccacg ttcgccggct    4260
ttccccgtca agctctaaat cggggggctcc ctttagggtt ccgatttagt gctttacggc    4320
acctcgaccc caaaaaactt gatttgggtg atggttcacg tagtgggcca tcgccctgat    4380
agacggtttt tcgccctttg acgttggagt ccacgttctt taatagtgga ctcttgttcc    4440
aaactggaac aacactcaac cctatctcgg gctattcttt tgatttataa gggattttgc    4500
cgatttcggc ctattggtta aaaaatgagc tgatttaaca aaaatttaac gcgaatttta    4560
acaaaatatt aacgtttaca attttatggt gcactctcag tacaatctgc tctgatgccg    4620
catagttaag ccagccccga cacccgccaa cacccgctga cgcgccctga cgggcttgtc    4680
tgctcccggc atccgcttac agacaagctg tgaccgtctc cgggagctgc atgtgtcaga    4740
ggttttcacc gtcatcaccg aaacgcgcga cgcgaaggg cctcgtgata cgcctatttt     4800
tataggttaa tgtcatgata ataatggttt cttagacgtc aggtggcact tttcggggaa    4860
atgtgcgcgg aacccctatt tgtttatttt tctaaataca ttcaaatatg tatccgctca    4920
tgagacaata accctgataa atgcttcaat aatattgaaa aaggaagagt atgagtattc    4980
aacatttccg tgtcgccctt attccctttt ttgcggcatt ttgccttcct gttttttgctc    5040
acccagaaac gctggtgaaa gtaaaagatg ctgaagatca gttgggtgca cgagtgggtt    5100
acatcgaact ggatctcaac agcggtaaga tccttgagag ttttcgcccc gaagaacgtt    5160
ttccaatgat gagcactttt aaagttctgc tatgtgcgc ggtattatcc cgtattgacg     5220
ccgggcaaga gcaactcggt cgccgcatac actattctca gaatgacttg gttgagtact    5280
```

```
caccagtcac agaaaagcat cttacggatg gcatgacagt aagagaatta tgcagtgctg    5340
ccataaccat gagtgataac actgcggcca acttacttct gacaacgatc ggaggaccga    5400
aggagctaac cgcttttttg cacaacatgg gggatcatgt aactcgcctt gatcgttggg    5460
aaccggagct gaatgaagcc ataccaaacg acgagcgtga caccacgatg cctgtagcaa    5520
tggcaacaac gttgcgcaaa ctattaactg gcgaactact tactctagct tcccggcaac    5580
aattaataga ctggatggag gcggataaag ttgcaggacc acttctgcgc tcggcccttc    5640
cggctggctg gtttattgct gataaatctg gagccggtga gcgtgggtct cgcggtatca    5700
ttgcagcact ggggccagat ggtaagccct cccgtatcgt agttatctac acgacgggga    5760
gtcaggcaac tatggatgaa cgaaatagac agatcgctga gataggtgcc tcactgatta    5820
agcattggta actgtcagac caagtttact catatatact ttagattgat ttaaaacttc    5880 attttttaatt taaaaggatc taggtgaaga tcctttttga taatctcatg accaaaatcc    5940
cttaacgtga gttttcgttc cactgagcgt cagaccccgt agaaaagatc aaaggatctt    6000
cttgagatcc ttttttttctg cgcgtaatct gctgcttgca acaaaaaaa ccaccgctac    6060 cagcggtggt ttgtttgccg gatcaagagc taccaactct ttttccgaag gtaactggct    6120
tcagcagagc gcagatacca atactgtcc ttctagtgta gccgtagtta ggccaccact    6180
tcaagaactc tgtagcaccg cctacatacc tcgctctgct aatcctgtta ccagtggctg    6240
ctgccagtgg cgataagtcg tgtcttaccg ggttggactc aagacgatag ttaccggata    6300
aggcgcagcg gtcgggctga acggggggtt cgtgcacaca gcccagcttg gagcgaacga    6360
cctacaccga actgagatac ctacagcgtg agctatgaga agcgccacg cttcccgaag    6420 ggagaaaggc ggacaggtat ccggtaagcg gcagggtcgg aacaggagag cgcacgaggg    6480
agcttccagg gggaaacgcc tggtatcttt atagtcctgt cgggtttcgc cacctctgac    6540
ttgagcgtcg atttttgtga tgctcgtcag ggggcggag cctatggaaa aacgccagca    6600
acgcggcctt tttacggttc ctggccttt gctggccttt tgctc                    6645
```

<210> SEQ ID NO 121
<211> LENGTH: 435
<212> TYPE: DNA
<213> ORGANISM: Artificial Sequence
<220> FEATURE:
<223> OTHER INFORMATION: Muscle CRE Sk-SH4

<400> SEQUENCE: 121

```
ttctgagtcc tctaaggtcc ctcactccca actcagcccc atgtcctgtc aattcccact      60
cagtgtctga tctccttctc ctcaccttttc ccatctcccg tttgacccaa gcttcctgag     120
ctctcctccc attcccctttt tggagtcct cctcctctcc cagaacccag taataagtgg     180
gctcctccct ggcctggacc cccgtggtaa ccctataagg cgaggcagct gctgtctgag     240
gcagggaggg gctggtgtgg gaggctaagg gcagctgcta agtttagggt ggctccttct     300
ctcttcttag agacaacagg tggctggggc ctcagtgccc agaaaagaaa atgtcttaga     360
ggtatcggca tgggcctgga ggagggggga cagggcaggg ggaggcatct tcctcaggac     420
atcgggtcct agagg                                                      435
```

<210> SEQ ID NO 122
<211> LENGTH: 454
<212> TYPE: DNA
<213> ORGANISM: Artificial Sequence
<220> FEATURE:
<223> OTHER INFORMATION: Heart-Muscle CRE CSk-SH5

<400> SEQUENCE: 122
cagtttactc accagggatt cagaggcagc actgctgaac cctgagccct tggcacatca 60
ggttggctgt cagaagtcgg cctttgtaca tacacagttc ccttgtgagg cccagctgcg 120
tgtcctagga gcggggcctc tctccacagc agagctcagc ctctcaagtg tatggacagc 180
acgggtgcct gatgggtgga tttagccatg agttgaaggt ggcttgggga gaatgagagt 240
tctagagata gggagaaggg gttgccaata ggagagtgga attcctgagc acctcgtcac 300
aggcagccga cagaacatga gccgcagggc ccaggctatt tatacctcgc ctgtcactat 360
cagggtcccc acagctcccc ccacctccag ccacacacag caggtccttt tgctctttct 420
ggtcccttct ctactcctcc ccctccctac ctaa 454

<210> SEQ ID NO 123
<211> LENGTH: 495
<212> TYPE: DNA
<213> ORGANISM: Artificial Sequence
<220> FEATURE:
<223> OTHER INFORMATION: Heart-Muscle CRE CSk-SH1

<400> SEQUENCE: 123
ctcactcccc gcccaggcag caaggagccc acaccctcat gcccctcagc ttcagccccc 60
acctccagga ggccctaccc acgctcatga ccttgctatt ctgggccttg tgtcctgtag 120
ggagatggac aggagacagc tgggcttcca ggccacccag gcggggggct agccgaggga 180
agcctgctgg ctctcctgct tgctctaatt tctggggctc cccaaacctt ggcctcagga 240
gactggggat aggaccggcc ttgaaagtgg gggaagcttt ggagagccgg gtgctgggtt 300
cttagtgaga tggccagtga aggctgtggt gccccgaggt aagcagggcc tgatcccctc 360
ctaatcttcc agcagcaact ggtgctctga ggctccccct cccccagccc tgccagcctt 420
cagggacctg ccttccaaag atgggcaggg gagggggacg aggacaccca cccactcctc 480
agaccagcat gtctt 495

<210> SEQ ID NO 124
<211> LENGTH: 334
<212> TYPE: DNA
<213> ORGANISM: Artificial Sequence
<220> FEATURE:
<223> OTHER INFORMATION: SPc-5-12 promotor

<400> SEQUENCE: 124
tggccaccgc cttcggcacc atcctcacga cacccaaata tggcgacggg tgaggaatgg 60
tggggagtta tttttagagc ggtgaggaag gtgggcaggc agcaggtgtt ggcgctctaa 120
aaataactcc cgggagttat ttttagagcg gaggaatggt ggacacccaa atatggcgac 180
ggttcctcac ccgtcgccat atttgggtgt ccgccctcgg ccggggccgc attcctgggg 240
gccgggcggt gctcccgccc gcctcgataa aaggctccgg ggccggcggc ggcccacgag 300
ctacccggag gagcgggagg cgccaagctc taga 334

<210> SEQ ID NO 125
<211> LENGTH: 92
<212> TYPE: DNA
<213> ORGANISM: Artificial Sequence
<220> FEATURE:
<223> OTHER INFORMATION: MVM intron

<400> SEQUENCE: 125

```
aagaggtaag ggtttaaggg atggttggtt ggtggggtat taatgtttaa ttacctggag    60
cacctgcctg aaatcacttt ttttcaggtt gg                                 92

<210> SEQ ID NO 126
<211> LENGTH: 134
<212> TYPE: DNA
<213> ORGANISM: Artificial Sequence
<220> FEATURE:
<223> OTHER INFORMATION: SV40 Polyadenylation signal

<400> SEQUENCE: 126
atgctttatt tgtgaaattt gtgatgctat tgctttattt gtaaccatta taagctgcaa    60
taaacaagtt aacaacaaca attgcattca ttttatgttt caggttcagg gggaggtgtg   120
ggaggttttt taaa                                                     134

<210> SEQ ID NO 127
<211> LENGTH: 49
<212> TYPE: DNA
<213> ORGANISM: Artificial Sequence
<220> FEATURE:
<223> OTHER INFORMATION: synthetic Polyadenylation signal

<400> SEQUENCE: 127
aataaaagat ctttattttc attagatctg tgtgttggtt ttttgtgtg               49

<210> SEQ ID NO 128
<211> LENGTH: 20
<212> TYPE: DNA
<213> ORGANISM: Artificial Sequence
<220> FEATURE:
<223> OTHER INFORMATION: forward primer luciferase

<400> SEQUENCE: 128
cccaccgtcg tattcgtgag                                               20

<210> SEQ ID NO 129
<211> LENGTH: 21
<212> TYPE: DNA
<213> ORGANISM: Artificial Sequence
<220> FEATURE:
<223> OTHER INFORMATION: reverse primer luciferase

<400> SEQUENCE: 129
tcagggcgat ggttttgtcc c                                             21

<210> SEQ ID NO 130
<211> LENGTH: 7303
<212> TYPE: DNA
<213> ORGANISM: Artificial Sequence
<220> FEATURE:
<223> OTHER INFORMATION: plasmid pAAVss-CRE04-CSkSH5-SPc5-12GTRM-MVM-
      hGAAco-SynthpA

<400> SEQUENCE: 130
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtaccgg tccttttaga gaatccacac   180
ctgtcccagt tgctgggttc cactaccaaa agtgaattgc aactatttta ggagcactta   240
agcacatccg aaaaatgagt gattctgttc tggcccacac cacatcactg atgtaccccc   300
ttaaagcatg tccctgagtt catcacagaa gactgctcct cctgtgccct ccacaaggtt   360
```

```
agaactgtcc ttgtcttagg gaaaaaggag agagagagag agagagagag agagagagag    420
agagagagag agagagaggg acaggcacca actgggtaac ctctgctgac ccccactcta    480
ctttaccata agtagctcca aatccttcta gaaaatctga aaggcatagc cccatatatc    540
agtgatataa atagaacctg cagcaggctc tggtaaatga tgactacaag gtggactggg    600
aggcagcccg gccttggcag gcatcatcct ctaaatataa agatgagttt gttcagcctt    660
tgcagaagga ggcgcgccac gcgtcagttt actcaccagg gattcagagg cagcactgct    720
gaaccctgag cccttggcac atcaggttgg ctgtcagaag tcggcctttg tacatacaca    780
gttcccttgt gaggcccagc tgcgtgtcct aggagcgggg cctctctcca cagcagagct    840
cagcctctca agtgtatgga cagcacgggt gcctgatggg tggatttagc catgagttga    900
aggtggcttg gggagaatga gagttctaga gataggagag aggggttgcc aataggagag    960
tggaattcct gagcacctcg tcacaggcag ccgacagaac atgagccgca gggcccaggc   1020
tatttatacc tcgcctgtca ctatcagggt ccccacagct ccccccacct ccagccacac   1080
acagcaggtc cttttgctct ttctggtccc ttctctactc ctcccctcc ctacctaagg    1140
tacccaaccc gttacgtggc caccgccttc ggcaccatcc tcacgacacc caaatatggc   1200
gacgggtgag gaatggtggg gagttatttt tagagcggtg aggaaggtgg gcaggcagca   1260
ggtgttggcg ctctaaaaat aactcccggg agttattttt agagcggagg aatggtggac   1320
acccaaatat ggcgacggtt cctcacccgt cgccatattt gggtgtccgc cctcggccgg   1380
ggccgcattc ctgggggccg ggcggtgctc ccgcccgcct cgataaaagg ctccggggcc   1440
ggcggcggcc cacgagctac ccggaggagc gggaggcgcc aagctctaga tctagaacta   1500
gtaagaggta agggtttaag ggatggttgg ttggtggggt attaatgttt aattacctgg   1560
agcacctgcc tgaaatcact tttttttcagg ttggcgtacg gccaccatgg gcgtcagaca   1620
tcctccatgt tctcacagac tgctggccgt gtgtgctctg gtgtctcttg ctacagctgc   1680
cctgctggga catatcctgc tgcacgattt tctgctggtg cccagagagc tgtctggcag   1740
ctctcctgtg ctggaagaaa cacaccctgc acatcagcag ggcgcctcta gacctggacc   1800
tagagatgct caagcccatc ctggcagacc tagagccgtg cctacacagt gtgacgtgcc   1860
acctaacagc agattcgact gcgcccctga caaggccatc acacaagagc agtgtgaagc   1920
cagaggctgc tgctacattc ctgccaaaca aggactgcag ggcgctcaga tgggacagcc   1980
ttggtgcttc ttcccaccat cttaccccag ctacaagctg gaaaacctga gcagcagcga   2040
gatgggctac accgccacac tgaccagaac cacacctaca ttcttcccaa aggacatcct   2100
gacactgcgg ctgacgtga tgatggaaac cgagaaccgg ctgcacttca ccatcaagga   2160
ccccgccaat agaagatacg aggtgccect ggaaacccct cacgtgcact ctagagcccc   2220
atctccactg tacagcgtgg aattcagcga ggaaccctt ggcgtgatcg tgcggagaca   2280
gctggatggc agagtgctgc tgaataccac agtggcccct ctgttcttcg ccgaccagtt   2340
tctgcagctg agcacaagcc tgcctagcca gtatatcaca ggcctggccg aacacctgtc   2400
tccactgatg ctgagcacca gctggaccag aatcaccctg tggaacagag atctggcccc   2460
tacacctggc gccaatctgt acggctctca cccttttat ctggccctgg aagatggcgg   2520
aagcgcccac ggtgtctttc tgctgaacag caacgccatg gacgtggtgc tgcaaccatc   2580
tcctgctctg tcttggagaa gcaccggcgg catcctggac gtgtacatct ttctgggacc   2640
cgagcctaag agcgtggtgc agcagtatct ggatgtcgtg ggctacccct tcatgcctcc   2700
ttattggggc ctgggcttcc acctgtgtag atggggatac agctccaccg ccatcaccag   2760
```

```
acaggtggtg gaaaacatga cccgggctca cttcccactg gatgtgcagt ggaacgacct    2820
ggactacatg gactccagac gggacttcac ctttaacaag gacggcttca gagacttccc    2880
cgccatggtg caagaactgc atcaaggcgg cagacggtac atgatgatcg tggatcctgc    2940
catctcttct agcggccctg ccggaagcta cagaccttat gatgagggcc tgagaagagg    3000
cgtgttcatc accaatgaga caggccagcc tctgatcggc aaagtgtggc ctggaagcac    3060
cgcctttcca gacttcacca atccaaccgc tctggcttgg tgggaagata tggtggccga    3120
gttccacgat caggtgccct tcgatggcat gtggatcgac atgaacgagc ccagcaactt    3180
catcagggga agcgaggatg gctgccccaa caacgaactg gaaaatcctc cttacgtgcc    3240
aggcgttgtc ggaggaacac tgcaggccgc cacaatttgt gccagcagcc atcagtttct    3300
gagcacccac tacaacctgc acaacctgta cggcctgacc gaggccattg cctctcatag    3360
agccctggtt aaggccagag gcacccggcc ttttgtgatc agcagaagca catttgccgg    3420
ccacggcaga tatgccggac attggacagg ggacgtttgg tctagttggg agcagctggc    3480
ctctagcgtg cccgagatcc tgcagtttaa tctgctggga gtgcccctcg tgggagccga    3540
tgtttgtgga tttctgggca acacctccga ggaactgtgc gtcagatgga cacagctggg    3600
cgccttctat cccttcatga gaaaccacaa cagcctgctg agcctgcctc aagagcctta    3660
cagctttagc gaacccgcac agcaggccat gagaaaggcc ctgactctga gatacgctct    3720
gctgccccac ctgtacaccc tgtttcatca agctcatgtg gccggcgaga cagtggccag    3780
accactgttt ctggaattcc ccaaggacag cagcacctgg acagtggatc atcagctgct    3840
ctggggagaa gccctgctca ttacacctgt gctgcaggct ggcaaggccg aagtgacagg    3900
atactttccc ctcggcactt ggtacgacct gcagacagtt cctgtggaag ctctgggatc    3960
tctgcctcca cctcctgctg ctcctagaga gcctgccatt cactctgaag gccagtgggt    4020
tacactgccc gctccactgg acaccatcaa tgtgcacctg agagccggct acatcatccc    4080
tctgcaaggc cctggactga ccacaaccga aagcagacag cagccaatgg ctctggccgt    4140
ggctctgaca aaaggcggag aagctagagg cgaactgttc tgggatgacg gcgagagcct    4200
ggaagtgctg gaacggggag cctacacaca agtgatcttt ctcgcccgga acaacaccat    4260
cgtgaacgaa ctcgtcagag tgaccagtga aggtgccgga ctgcagctcc agaaagtgac    4320
agtgcttgga gtgccacag caccccagca ggttttgtct aatggcgtgc ccgtgtccaa    4380
cttcacatac agccctgaca ccaaggtgct ggacatctgt gtgtctctgc tgatgggcga    4440
gcagttcctg tgtcctggt gttgacctag gaataaaaga tctttatttt cattagatct    4500
gtgtgttggt tttttgtgtg acccgtctga ttttgtaggt aaccacgtgc ggaccgagcg    4560
gccgcaggaa cccctagtga tggagttggc cactccctct ctgcgcgctc gctcgctcac    4620
tgaggccggg cgaccaaagg tcgcccgacg cccgggcttt gcccgggcgg cctcagtgag    4680
cgagcgagcg cgcagctgcc tgcaggggcg cctgatgcgg tattttctcc ttacgcatct    4740
gtgcggtatt tcacaccgca tacgtcaaag caaccatagt acgcgccctg tagcggcgca    4800
ttaagcgcgg cgggtgtggt ggttacgcgc agcgtgaccg ctacacttgc cagcgcccta    4860
gcgcccgctc ctttcgcttt cttcccttcc tttctcgcca cgttcgccgg ctttccccgt    4920
caagctctaa atcgggggct ccctttaggg ttccgattta gtgctttacg gcacctcgac    4980
cccaaaaaac ttgatttggg tgatggttca cgtagtgggc catcgccctg atagacggtt    5040
tttcgccctt tgacgttgga gtccacgttc tttaatagtg gactcttgtt ccaaactgga    5100
```

```
acaacactca accctatctc gggctattct tttgatttat aagggatttt gccgatttcg    5160
gcctattggt taaaaaatga gctgatttaa caaaaattta acgcgaattt taacaaaata    5220
ttaacgttta caattttatg gtgcactctc agtacaatct gctctgatgc cgcatagtta    5280
agccagcccc gacacccgcc aacacccgct gacgcgccct gacgggcttg tctgctcccg    5340
gcatccgctt acagacaagc tgtgaccgtc tccgggagct gcatgtgtca gaggttttca    5400
ccgtcatcac cgaaacgcgc gagacgaaag ggcctcgtga tacgcctatt tttataggtt    5460
aatgtcatga taataatggt ttcttagacg tcaggtggca cttttcgggg aaatgtgcgc    5520
ggaacccta tttgtttatt tttctaaata cattcaaata tgtatccgct catgagacaa    5580
taaccctgat aaatgcttca ataatattga aaaggaaga gtatgagtat tcaacatttc    5640
cgtgtcgccc ttattccctt ttttgcggca ttttgccttc ctgttttgc tcacccagaa    5700
acgctggtga agtaaaaga tgctgaagat cagttgggtg cacgagtggg ttacatcgaa    5760
ctggatctca acagcggtaa gatccttgag agttttcgcc ccgaagaacg ttttccaatg    5820
atgagcactt ttaaagttct gctatgtggc gcggtattat cccgtattga cgccgggcaa    5880
gagcaactcg gtcgccgcat acactattct cagaatgact tggttgagta ctcaccagtc    5940
acagaaaagc atcttacgga tggcatgaca gtaagagaat tatgcagtgc tgccataacc    6000
atgagtgata acactgcggc caacttactt ctgacaacga tcggaggacc gaaggagcta    6060
accgcttttt tgcacaacat gggggatcat gtaactcgcc ttgatcgttg ggaaccggag    6120
ctgaatgaag ccataccaaa cgacgagcgt gacaccacga tgcctgtagc aatggcaaca    6180
acgttgcgca aactattaac tggcgaacta cttactctag cttcccggca acaattaata    6240
gactggatgg aggcggataa agttgcagga ccacttctgc gctcggccct tccggctggc    6300
tggtttattg ctgataaatc tggagccggt gagcgtgggt ctcgcggtat cattgcagca    6360
ctggggccag atggtaagcc ctcccgtatc gtagttatct acacgacggg gagtcaggca    6420
actatggatg aacgaaatag acagatcgct gagataggtg cctcactgat taagcattgg    6480
taactgtcag accaagttta ctcatatata ctttagattg atttaaaact tcattttta    6540
tttaaaagga tctaggtgaa gatcctttt gataatctca tgaccaaaat cccttaacgt    6600
gagttttcgt tccactgagc gtcagacccc gtagaaaaga tcaaaggatc ttcttgagat    6660
cctttttttc tgcgcgtaat ctgctgcttg caaacaaaaa aaccaccgct accagcggtg    6720
gtttgtttgc cggatcaaga gctaccaact cttttttccga aggtaactgg cttcagcaga    6780
gcgcagatac caaatactgt ccttctagtg tagccgtagt taggccacca cttcaagaac    6840
tctgtagcac cgcctacata cctcgctctg ctaatcctgt taccagtggc tgctgccagt    6900
ggcgataagt cgtgtcttac cgggttggac tcaagacgat agttaccgga taaggcgcag    6960
cggtcgggct gaacggggg ttcgtgcaca cagcccagct tggagcgaac gacctacacc    7020
gaactgagat acctacagcg tgagctatga gaaagcgcca cgcttcccga agggagaaag    7080
gcggacaggt atccggtaag cggcagggtc ggaacaggag agcgcacgag ggagcttcca    7140
gggggaaacg cctggtatct ttatagtcct gtcgggtttc gccacctctg acttgagcgt    7200
cgatttttgt gatgctcgtc agggggggcgg agcctatgaa aaacgccag caacgcggcc    7260
ttttacggt tcctggcctt tgctggcct tttgctcaca tgt             7303
```

<210> SEQ ID NO 131
<211> LENGTH: 7224
<212> TYPE: DNA
<213> ORGANISM: Artificial Sequence
<220> FEATURE:
<223> OTHER INFORMATION: plasmid pAAVss-CRE64-SKCRM4-hDES1.4kb-MVM-hMTM1
co-SynthpA

<400> SEQUENCE: 131

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggcgcgc caccggtgtc tccgaacgca ggccccgtcg      180
cgttaagcac aagctggcag ggcctctcct ctcccttctc agatttgctc cttgacattt     240
gcctgctgcc tggcggtggc aacagctggg gcggggcgcg cgcaggaggc cccgtaaccc     300
tatccccgct ccggctccct cgtgaaaccg gagcttccct gccttggccg aggggggagg     360
ctgcggggc cagaccgcct gcgaagacca caggtttttt cctctcgggt tttggctccc      420
gtgggatgga tgtggctgtg cgggggttg gcctgagctt cgcttctaag ccagcagctt      480
ggtcagggaa acctgaaagc attcccagct aatcccccaa gtggtgcaag tctgtgcgcg     540
cccatcccgc tgagtaaggc ggtggggcgc gccacgcgtt tctgagtcct ctaaggtccc     600
tcactcccaa ctcagcccca tgtcctgtca attcccactc agtgtctgat ctccttctcc     660
tcaccttttcc catctcccgt ttgacccaag cttcctgagc tctcctccca ttcccctttt    720
tggagtcctc ctcctctccc agaacccagt aataagtggg ctcctccctg gcctggaccc    780
ccgtggtaac cctataaggc gaggcagctg ctgtctgagg cagggagggg ctggtgtggg    840
aggctaaggg cagctgctaa gtttaggtg gctccttctc tcttcttaga gacaacaggt     900
ggctggggcc tcagtgccca gaaaagaaaa tgtcttagag gtatcggcat gggcctggag     960
gagggggac agggcagggg gaggcatctt cctcaggaca tcgggtccta gaggggtacc    1020
caacgggtta cgacacacct actagtaacc cctccagctg gtgatggcag gtctagggta    1080
ggaccagtga ctggctccta atcgagcact ctattttcag ggtttgcatt ccaaaagggt    1140
caggtccaag agggacctgg agtgccaagt ggaggtgtag aggcacggcc agtacccatg    1200
gagaatggtg gatgtcctta ggggttagca agtgccgtgt gctaaggagg gggctttgga    1260
ggttgggcag gccctctgtg gggctccatt tttgtggggg tggggctgg agcattatag     1320
ggggtgggaa gtgattgggg ctgtcaccct agccttcctt atctgacgcc cacccatgcc    1380
tcctcaggta cccctgccc ccacagctc ctctcctgtg ccttgtttcc cagccatgcg      1440
ttctcctcta taaatacccg ctctggtatt tggggttggc agctgttgct gccagggaga    1500
tggttgggtt gacatgcggc tcctgacaaa acacaaaccc ctggtgtgtg tgggcgtggg    1560
tggtgtgagt aggggatga atcagggagg gggcggggga cccaggggc aggagccaca     1620
caaagtctgt gcggggtgg gagcgcacat agcaattgga aactgaaagc ttatcagacc    1680
ctttctggaa atcagcccac tgtttataaa cttgaggccc caccctcgac agtaccgggg    1740
aggaagaggg cctgcactag tccagaggga aactgaggct cagggctagc tcgcccatag    1800
acatacatgg caggcaggct ttggccagga tccctccgcc tgccaggcgt ctccctgccc    1860
tcccttcctg cctagagacc cccaccctca agcctggctg gtctttgcct gagacccaaa    1920
cctcttcgac ttcaagagaa tatttaggaa caaggtggtt tagggccttt cctgggaaca    1980
ggccttgacc cttttaagaaa tgacccaaag tctctccttg accaaaaagg ggaccctcaa    2040
actaaaggga agcctctctt ctgctgtctc ccctgacccc actccccccc acccaggac    2100
gaggagataa ccagggctga agaggcccg cctgggggct gcagacatgc ttgctgcctg    2160
ccctggcgaa ggattggcag gcttgcccgt cacaggaccc ccgctggctg actcagggc    2220
```

```
gcaggcctct tgcggggag ctggcctccc cgcccccacg ccacgggcc gcccttcct      2280
ggcaggacag cgggatcttg cagctgtcag gggaggggag cgggggctg atgtcaggag    2340
ggatacaaat agtgccgacg gctggggcc ctgtctcccc tcgccgcatc cactctccgg    2400
ccggccgcct gcccgccgcc tcctccgtgc gcccgccagc ctcgcccgcg ccgtcacctc   2460
tagaactagt aagaggtaag ggtttaaggg atggttggtt ggtggggtat taatgtttaa   2520
ttacctggag cacctgcctg aaatcacttt ttttcaggtt ggcgtacggc caccatggcc   2580
agcgccagca caagcaagta caacagccac agcctggaaa acgagagcat caagcggacc   2640
agcagagatg gcgtgaacag agatctgacc gaggccgttc ctagactgcc tggcgagaca   2700
ctgatcaccg acaaagaagt gatctacatc tgccccttca acggccccat caagggaaga   2760
gtgtacatca ccaactaccg gctgtacctg cggtccctgg aaaccgatag cagcctgatt   2820
ctggatgtgc ccctgggcgt gatcagccgg attgaaaaaa tgggcggagc cacctccaga   2880
ggcgagaata gctatggcct ggatatcaca tgcaaggaca tgcggaacct gagattcgcc   2940
ctgaagcaag agggccacag cagacgggac atgttcgaga tcctgaccag atacgccttt   3000
cctctggctc actctctgcc cctgttcgcc ttcctgaacg aagagaagtt caacgtggac   3060
ggctggaccg tgtacaaccc cgtggaagag tatagacggc agggactgcc caatcaccac   3120
tggcggatca ccttcatcaa caagtgctac gagctgtgcg acacataccc cgcactgctg   3180
gtggtgcctt acagagcctc tgacgacgat ctgagaagag tggccacctt tcggagccgg   3240
aacagaatcc ctgtgctgag ctggattcac cccgagaaca gaccgtgat cgtgcggtgt    3300
tctcagcctc tcgtgggcat gagcggcaag agaaacaagg acgacgagaa gtacctggac   3360
gtgatccgcg agacaaacaa gcagatcagc aagctgacca tctacgacgc cagaccttct   3420
gtgaacgccg tggccaacaa agccacaggc ggcggatatg agtccgacga tgcctatcac   3480
aacgccgagc tgttcttcct ggacattcac aacatccatg tgatgcgcga gagcctgaag   3540
aaagtgaagg acatcgtgta ccccaatgtg gaagagagcc actggctgtc tagcctggaa   3600
tccacacact ggctggaaca catcaagctg gtgctgacag cgccatcca ggtggcagac    3660
aaagtgtcta gcggcaagtc tagcgtgctg gtgcactgta cgacggatg ggatagaaca    3720
gcccagctga catccctggc catgctgatg ctggacagct tctacagatc catcgagggc   3780
tttgagatcc tggtgcagaa gaagtggatc agcttcggcc acaagttcgc ctctagaatc   3840
ggacacggcg acaagaacca caccgacgcc gatagaagcc ccatcttcct gcagttcatc   3900
gactgcgtgt ggcagatgtc caagcagttc cctaccgcct tcgagttcaa cgagcagttc   3960
ctgatcatca tcctggacca cctgtactct tgcagattcg gcaccttcct gttcaactgc   4020
gagagcgcca gaaacggca gaaagtgacc gagagaaccg tgtctctgtg gtcccctgatc   4080
aacagcaaca agagaaatt caagaacccc ttctacacca agaaatcaa ccgggtgctg     4140
taccccgtgg ccagcatgag acatctggaa ctgtgggtca actactacat ccggtggaac   4200
cccagaatca agcagcagca gcccaatcct gtggaacagc ggtatatgga actgctggcc   4260
ctgcgggacg agtacatcaa gagactggaa gaactgcagc tggccaacag cgccaagctg   4320
agcgatcctc ctacaagccc tagcagcccc ctctcagatga tgcccatgt gcagacccac    4380
ttttgaccta ggaataaaag atctttattt tcattagatc tgtgtgttgg ttttttgtgt    4440
gacccgtctg atttttgtagg taaccacgtg cggaccgagc ggccgcagga acccctagtg   4500
atggagttgg ccactccctc tctgcgcgct cgctcgctca ctgaggccgg gcgaccaaag   4560
```

-continued

```
gtcgcccgac gcccgggctt tgcccgggcg gcctcagtga gcgagcgagc gcgcagctgc    4620
ctgcaggggc gcctgatgcg gtattttctc cttacgcatc tgtgcggtat ttcacaccgc    4680
atacgtcaaa gcaaccatag tacgcgccct gtagcggcgc attaagcgcg gcgggtgtgg    4740
tggttacgcg cagcgtgacc gctacacttg ccagcgccct agcgcccgct cctttcgctt    4800
tcttcccttc ctttctcgcc acgttcgccg gctttccccg tcaagctcta atcggggc     4860
tcccttagg gttccgattt agtgctttac ggcacctcga ccccaaaaaa cttgatttgg     4920
gtgatggttc acgtagtggg ccatcgccct gatagacggt ttttcgccct ttgacgttgg    4980
agtccacgtt ctttaatagt ggactcttgt tccaaactgg aacaacactc aaccctatct    5040
cgggctattc ttttgattta aagggatttt tgccgatttc ggcctattgg ttaaaaaatg    5100
agctgattta acaaaaattt aacgcgaatt ttaacaaaat attaacgttt acaattttat    5160
ggtgcactct cagtacaatc tgctctgatg ccgcatagtt aagccagccc cgacacccgc    5220
caacacccgc tgacgcgccc tgacgggctt gtctgctccc ggcatccgct tacagacaag    5280
ctgtgaccgt ctccgggagc tgcatgtgtc agaggttttc accgtcatca ccgaaacgcg    5340
cgagacgaaa gggcctcgtg atacgcctat ttttataggt taatgtcatg ataataatgg    5400
tttcttagac gtcaggtggc acttttcggg gaaatgtgcg cggaacccct atttgtttat    5460
ttttctaaat acattcaaat atgtatccgc tcatgagaca ataaccctga taatgcttc     5520
aataatattg aaaaggaag agtatgagta ttcaacattt ccgtgtcgcc cttattccct    5580
tttttgcggc attttgcctt cctgtttttg ctcacccaga aacgctggtg aaagtaaaag    5640
atgctgaaga tcagttgggt gcacgagtgg gttacatcga actggatctc aacagcggta    5700
agatccttga gagttttcgc cccgaagaac gttttccaat gatgagcact tttaaagttc    5760
tgctatgtgg cgcggtatta tcccgtattg acgccgggca agagcaactc ggtcgccgca    5820
tacactattc tcagaatgac ttggttgagt actcaccagt cacagaaaag catcttacgg    5880
atggcatgac agtaagagaa ttatgcagtg ctgccataac catgagtgat aacactgcgg    5940
ccaacttact tctgacaacg atcggaggac cgaaggagct aaccgctttt ttgcacaaca    6000
tgggggatca tgtaactcgc cttgatcgtt gggaaccgga gctgaatgaa gccataccaa    6060
acgacgagcg tgacaccacg atgcctgtag caatggcaac aacgttgcgc aaactattaa    6120
ctggcgaact acttactcta gcttcccggc aacaattaat agactggatg gaggcggata    6180
aagttgcagg accacttctg cgctcggccc ttccggctgg ctggtttatt gctgataaat    6240
ctggagccgg tgagcgtggg tctcgcggta tcattgcagc actggggcca gatggtaagc    6300
cctcccgtat cgtagttatc tacacgacgg ggagtcaggc aactatggat gaacgaaata    6360
gacagatcgc tgagataggt gcctcactga ttaagcattg gtaactgtca gaccaagttt    6420
actcatatat actttagatt gatttaaaac ttcatttta atttaaaagg atctaggtga    6480
agatcctttt tgataatctc atgaccaaaa tcccttaacg tgagttttcg ttccactgag    6540
cgtcagaccc cgtagaaaag atcaaaggat cttcttgaga tcctttttt ctgcgcgtaa    6600
tctgctgctt gcaaacaaaa aaaccaccgc taccagcggt ggtttgtttg ccggatcaag    6660
agctaccaac tctttttccg aaggtaactg gcttcagcag agcgcagata ccaaatactg    6720
tccttctagt gtagccgtag ttaggccacc acttcaagaa ctctgtagca ccgcctacat    6780
acctcgctct gctaatcctg ttaccagtgg ctgctgccag tggcgataag tcgtgtctta    6840
ccgggttgga ctcaagacga tagttaccgg ataaggcgca gcggtcgggc tgaacggggg    6900
gttcgtgcac acagcccagc ttggagcgaa cgacctacac cgaactgaga tacctacagc    6960
```

```
gtgagctatg agaaagcgcc acgcttcccg aagggagaaa ggcggacagg tatccggtaa      7020
gcggcagggt cggaacagga gagcgcacga gggagcttcc aggggaaac gcctggtatc       7080 tttatagtcc tgtcgggttt cgccacctct gacttgagcg tcgattttttg tgatgctcgt     7140 caggggggcg gagcctatgg aaaaacgcca gcaacgcggc cttttttacgg ttcctggcct    7200 tttgctggcc ttttgctcac atgt                                             7224

<210> SEQ ID NO 132
<211> LENGTH: 6780
<212> TYPE: DNA
<213> ORGANISM: Artificial Sequence
<220> FEATURE:
<223> OTHER INFORMATION: plasmid pAAVss-CSkSH5-SPc5-12GTRM-MVM-hGAAco-
      SynthpA

<400> SEQUENCE: 132
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac tagggggttcc tgcggccgca cgcgtaccgg tcagtttact caccagggat     180
tcagaggcag cactgctgaa ccctgagccc ttggcacatc aggttggctg tcagaagtcg     240
gcctttgtac atacacagtt cccttgtgag gcccagctgc gtgtcctagg agcggggcct     300
ctctccacag cagagctcag cctctcaagt gtatggacag cacgggtgcc tgatgggtgg    360
atttagccat gagttgaagg tggcttgggg agaatgagag ttctagagat agggagaagg   420
ggttgccaat aggagagtgg aattcctgag cacctcgtca caggcagccg acagaacatg    480
agccgcaggg cccaggctat ttatacctcg cctgtcacta tcagggtccc cacagctccc    540
cccacctcca gccacacaca gcaggtcctt ttgctctttc tggtcccttc tctactcctc    600
cccctcccta cctaaggtac ccaacccgtt acgtggccac cgccttcggc accatcctca    660
cgacacccaa atatgcgac gggtgaggaa tggtggggag ttatttttag agcggtgagg    720
aaggtgggca ggcagcaggt gttggcgctc taaaaataac tcccgggagt tattttttaga   780 gcggaggaat ggtggacacc caaatatggc gacggttcct cacccgtcgc catatttggg   840
tgtccgccct cggccggggc cgcattcctg ggggccgggc ggtgctcccg cccgcctcga   900
taaaaggctc cggggccggc ggcggcccac gagctacccg gaggagcggg aggcgccaag    960
ctctagatct agaactagta agaggtaagg gtttaaggga tggttggttg gtggggtatt   1020 aatgttttaat tacctggagc acctgcctga aatcactttt tttcaggttg gcgtacggcc   1080
accatgggcg tcagacatcc tccatgttct cacagactgc tggccgtgtg tgctctggtg    1140
tctcttgcta cagctgccct gctgggacat atcctgctgc acgattttct gctggtgccc   1200
agagagctgt ctggcagctc tcctgtgctg aagaaacac accctgcaca tcagcagggc   1260
gcctctagac ctggacctag agatgctcaa gcccatcctg gcagacctag agccgtgcct   1320
acacagtgtg acgtgccacc taacagcaga ttcgactgcg cccctgacaa ggccatcaca    1380
caagagcagt gtgaagccag aggctgctgc tacattcctg ccaaacaagg actgcagggc    1440
gctcagatgg gacagccttg tgtgcttcttc ccaccatctt accccagcta caagctggaa    1500
aacctgagca gcagcgagat gggctacacc gccacactga ccagaaccac acctacattc    1560
ttcccaaagg acatcctgac actgcggctg gacgtgatga tggaaaccga gaaccggctg    1620
cacttccaca tcaaggaccc cgccaataga agatacgagg tgcccctgga aaccctcac    1680 gtgcactcta gagccccatc tccactgtac agcgtggaat tcagcgagga acccttggc    1740
```

```
gtgatcgtgc ggagacagct ggatggcaga gtgctgctga ataccacagt ggcccctctg    1800
ttcttcgccg accagtttct gcagctgagc acaagcctgc ctagccagta tatcacaggc    1860
ctggccgaac acctgtctcc actgatgctg agcaccagct ggaccagaat caccctgtgg    1920
aacagagatc tggcccctac acctggcgcc aatctgtacg gctctcaccc tttttatctg    1980
gccctggaag atggcggaag cgcccacggt gtctttctgc tgaacagcaa cgccatggac    2040
gtggtgctgc aaccatctcc tgctctgtct tggagaagca ccggcggcat cctggacgtg    2100
tacatctttc tgggacccga gcctaagagc gtggtgcagc agtatctgga tgtcgtgggc    2160
tacccccttca tgcctcctta ttggggcctg ggcttccacc tgtgtagatg gggatacagc    2220
tccaccgcca tcaccagaca ggtggtggaa acatgaccc gggctcactt cccactggat    2280
gtgcagtgga acgacctgga ctacatggac tccagacggg acttcacctt taacaaggac    2340
ggcttcagag acttccccgc catggtgcaa gaactgcatc aaggcggcag acggtacatg    2400
atgatcgtgg atcctgccat ctcttctagc ggccctgccg gaagctacag accttatgat    2460
gagggcctga agaggcgt gttcatcacc aatgagacag gccagcctct gatcggcaaa    2520
gtgtggcctg gaagcaccgc cttccagac ttcaccaatc aaccgctct ggcttggtgg    2580
gaagatatgg tggccgagtt ccacgatcag gtgcccttcg atggcatgtg gatcgacatg    2640
aacgagccca gcaacttcat caggggcagc gaggatggct gccccaacaa cgaactggaa    2700
aatcctcctt acgtgccagg cgttgtcgga ggaacactgc aggccgccac aatttgtgcc    2760
agcagccatc agtttctgag cacccactac aacctgcaca acctgtacgg cctgaccgag    2820
gccattgcct ctcatagagc cctggttaag gccagaggca cccggccttt tgtgatcagc    2880
agaagcacat ttgccggcca cggcagatat gccggacatt ggacagggga cgtttggtct    2940
agttgggagc agctggcctc tagcgtgccc gagatcctgc agtttaatct gctgggagtg    3000
cccctcgtgg gagccgatgt tgtggattt ctgggcaaca cctccgagga actgtgcgtc    3060
agatggacac agctgggcgc cttctatccc ttcatgagaa accacaacag cctgctgagc    3120
ctgcctcaag agcttacag ctttagcgaa cccgcacagc aggccatgag aaaggccctg    3180
actctgagat acgctctgct gccccacctg tacaccctgt ttcatcaagc tcatgtggcc    3240
ggcgagacag tggccagacc actgtttctg gaattcccca aggacagcag cacctggaca    3300
gtggatcatc agctgctctg gggagaagcc ctgctcatta cacctgtgct gcaggctggc    3360
aaggccgaag tgacaggata ctttcccctc ggcacttggt acgacctgca gacagttcct    3420
gtggaagctc tgggatctct gcctccacct cctgctgctc ctagagagcc tgccattcac    3480
tctgaaggcc agtgggttac actgcccgct ccactggaca ccatcaatgt gcacctgaga    3540
gccggctaca tcatccctct gcaaggccct ggactgacca caaccgaaag cagacagcag    3600
ccaatggctc tggccgtggc tctgacaaaa ggcggagaag ctagaggcga actgttctgg    3660
gatgacggcg agagcctgga agtgctggaa cgggagcct acacacaagt gatctttctc    3720
gcccggaaca acaccatcgt gaacgaactc gtcagagtga ccagtgaagg tgccggactg    3780
cagctccaga aagtgacagt gcttggagtg gccacagcac cccagcaggt tttgtctaat    3840
ggcgtgcccg tgtccaactt cacatacagc cctgacacca aggtgctgga catctgtgtg    3900
tctctgctga tgggcgagca gttcctggtg tcctggtgtt gacctaggaa taaaagatct    3960
ttatttttcat tagatctgtg tgttggtttt ttgtgtgacc cgtctgattt tgtaggtaac    4020
cacgtgcgga ccgagcggcc gcaggaaccc ctagtgatgg agttggccac tccctctctg    4080
```

```
cgcgctcgct cgctcactga ggccgggcga ccaaaggtcg cccgacgccc gggctttgcc    4140
cgggcggcct cagtgagcga gcgagcgcgc agctgcctgc aggggcgcct gatgcggtat    4200
tttctcctta cgcatctgtg cggtatttca caccgcatac gtcaaagcaa ccatagtacg    4260
cgccctgtag cggcgcatta agcgcggcgg gtgtggtggt tacgcgcagc gtgaccgcta    4320
cacttgccag cgccctagcg cccgctcctt tcgctttctt cccttccttt ctcgccacgt    4380
tcgccggctt tccccgtcaa gctctaaatc ggggctccc tttagggttc cgatttagtg    4440
ctttacggca cctcgacccc aaaaaacttg atttgggtga tggttcacgt agtgggccat    4500
cgccctgata cacggttttt cgccctttga cgttggagtc cacgttcttt aatagtggac    4560
tcttgttcca aactggaaca acactcaacc ctatctcggg ctattctttt gatttataag    4620
ggattttgcc gatttcggcc tattggttaa aaaatgagct gatttaacaa aaatttaacg    4680
cgaattttaa caaaatatta cgttacaa ttttatggtg cactctcagt acaatctgct    4740
ctgatgccgc atagttaagc cagccccgac accgccaac accgctgac gcgccctgac    4800 gggcttgtct gctcccggca tccgcttaca gacaagctgt gaccgtctcc gggagctgca    4860
tgtgtcagag gttttcaccg tcatcaccga acgcgcgag acgaaagggc ctcgtgatac    4920
gcctattttt ataggttaat gtcatgataa taatggtttc ttagacgtca ggtggcactt    4980
ttcggggaaa tgtgcgcgga acccctattt gtttattttt ctaaatacat tcaaatatgt    5040
atccgctcat gagacaataa ccctgataaa tgcttcaata atattgaaaa aggaagagta    5100
tgagtattca acatttccgt gtcgccctta ttcccttttt tgcggcattt gccttcctg    5160 tttttgctca cccagaaacg ctggtgaaag taaaagatgc tgaagatcag ttgggtgcac    5220
gagtgggtta catcgaactg gatctcaaca gcggtaagat ccttgagagt tttcgccccg    5280
aagaacgttt tccaatgatg agcacttta aagttctgct atgtggcgcg gtattatccc    5340
gtattgacgc cgggcaagag caactcggtc gccgcataca ctattctcag aatgacttgg    5400
ttgagtactc accagtcaca gaaaagcatc ttacggatgg catgacagta agagaattat    5460
gcagtgctgc cataaccatg agtgataaca ctgcggccaa cttacttctg acaacgatcg    5520
gaggaccgaa ggagctaacc gcttttttgc acaacatggg ggatcatgta actcgccttg    5580
atcgttggga accggagctg aatgaagcca taccaaacga cgagcgtgac accacgatgc    5640
ctgtagcaat ggcaacaacg ttgcgcaaac tattaactgg cgaactactt actctagctt    5700
cccggcaaca attaatagac tggatggagg cggataaagt tgcaggacca cttctgcgct    5760
cggcccttcc ggctggctgg tttattgctg ataaatctgg agccggtgag cgtgggtctc    5820
gcggtatcat tgcagcactg gggccagatg gtaagccctc ccgtatcgta gttatctaca    5880
cgacggggag tcaggcaact atggatgaac gaaatagaca gatcgctgag ataggtgcct    5940
cactgattaa gcattggtaa ctgtcagacc aagtttactc atatatactt tagattgatt    6000
taaaacttca tttttaattt aaaaggatct aggtgaagat cctttttgat aatctcatga    6060
ccaaaatccc ttaacgtgag ttttcgttcc actgagcgtc agaccccgta gaaaagatca    6120
aaggatcttc ttgagatcct tttttctgc gcgtaatctg ctgcttgcaa acaaaaaaac    6180
caccgctacc agcggtggtt tgtttgccgg atcaagagct accaactctt tttccgaagg    6240
taactggctt cagcagagcg cagataccaa atactgtcct tctagtgtag ccgtagttag    6300
gccaccactt caagaactct gtagcaccgc ctacatacct cgctctgcta atcctgttac    6360
cagtggctgc tgccagtggc gataagtcgt gtcttaccgg gttggactca agacgatagt    6420
taccggataa ggcgcagcgg tcgggctgaa cggggggttc gtgcacacag cccagcttgg    6480
```

```
agcgaacgac ctacaccgaa ctgagatacc tacagcgtga gctatgagaa agcgccacgc    6540
ttcccgaagg gagaaaggcg gacaggtatc cggtaagcgg cagggtcgga acaggagagc    6600
gcacgaggga gcttccaggg ggaaacgcct ggtatcttta tagtcctgtc gggtttcgcc    6660
acctctgact tgagcgtcga ttttgtgat gctcgtcagg ggggcggagc ctatggaaaa    6720
acgccagcaa cgcggccttt ttacggttcc tggccttttg ctggccttt gctcacatgt    6780
```

<210> SEQ ID NO 133
<211> LENGTH: 6780
<212> TYPE: DNA
<213> ORGANISM: Artificial Sequence
<220> FEATURE:
<223> OTHER INFORMATION: plasmid pAAVss-CSkSH5-SPc5-12GTRM-MVM-hGAA-SynthpA

<400> SEQUENCE: 133

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtaccgg tcagtttact caccagggat     180
tcagaggcag cactgctgaa ccctgagccc ttggcacatc aggttggctg tcagaagtcg     240
gcctttgtac atacacagtt cccttgtgag gcccagctgc gtgtcctagg agcggggcct     300
ctctccacag cagagctcag cctctcaagt gtatggacag cacgggtgcc tgatgggtgg     360
atttagccat gagttgaagg tggcttgggg agaatgagag ttctagagat agggagaagg     420
ggttgccaat aggagagtgg aattcctgag cacctcgtca caggcagccg acagaacatg     480
agccgcaggg cccaggctat ttatacctcg cctgtcacta tcagggtccc cacagctccc     540
cccacctcca gccacacaca gcaggtcctt ttgctctttc tggtcccttc tctactcctc     600
cccctcccta cctaaggtac ccaacccgtt acgtggccac cgccttcggc accatcctca     660
cgacacccaa atatggcgac gggtgaggaa tggtggggag ttatttttag agcggtgagg     720
aaggtgggca ggcagcaggt gttggcgctc taaaaataac tcccgggagt tattttaga     780 gcggaggaat ggtggacacc caaatatggc gacggttcct cacccgtcgc catatttggg     840
tgtccgccct cggccggggc cgcattcctg ggggccgggc ggtgctcccg cccgcctcga     900
taaaaggctc cggggccggc ggcggcccac gagctacccg gaggagcggg aggcgccaag     960
ctctagatct agaactagta agaggtaagg gtttaaggga tggttggttg gtggggtatt    1020
aatgtttaat tacctggagc acctgcctga aatcactttt tttcaggttg gcgtacggcc    1080
accatgggag tgaggcaccc gccctgctcc caccggctcc tggccgtctg cgccctcgtg    1140
tccttggcaa ccgctgcact cctggggcac atcctactcc atgatttcct gctggttccc    1200
cgagagctga gtggctcctc cccagtcctg gaggagactc acccagctca ccagcaggga    1260
gccagcagac cagggcccccg ggatgcccag gcacaccccg gccgtcccag agcagtgccc    1320
acacagtgcg acgtcccccc caacagccgc ttcgattgcg cccctgacaa ggccatcacc    1380
caggaacagt gcgaggcccg cggctgttgc tacatccctg caaagcaggg gctgcaggga    1440
gcccagatgg ggcagccctg gtgcttcttc ccacccagct accccagcta caagctggag    1500
aacctgagct cctctgaaat gggctacacg gccaccctga cccgtaccac cccccacttc    1560
ttccccaagg acatcctgac cctgcggctg gacgtgatga tggagactga gaaccgcctc    1620
cacttcacga tcaaagatcc agctaacagg cgctacgagg tgcccttgga gacccgcat    1680 gtccacagcc gggcaccgtc cccactctac agcgtggagt tctccgagga gcccttcggg    1740
```

```
gtgatcgtgc gccggcagct ggacggccgc gtgctgctga acacgacggt ggcgccsctg   1800
ttctttgcgg accagttcct tcagctgtcc acctcgctgc cctcgcagta tatcacaggc   1860
ctcgccgagc acctcagtcc cctgatgctc agcaccagct ggaccaggat caccctgtgg   1920
aaccgggacc ttgcgcccac gcccggtgcg aacctctacg ggtctcaccc tttctacctg   1980
gcgctggagg acggcgggtc ggcacacggg gtgttcctgc taaacagcaa tgccatggat   2040
gtggtcctgc agccgagccc tgcccttagc tggaggtcga caggtgggat cctggatgtc   2100
tacatcttcc tgggcccaga gcccaagagc gtggtgcagc agtacctgga cgttgtggga   2160
tacccgttca tgccgccata ctggggcctg ggcttccacc tgtgccgctg gggctactcc   2220
tccaccgcta tcacccgcca ggtggtggag aacatgacca gggcccactt cccsctggac   2280
gtccagtgga acgacctgga ctacatggac tcccggaggg acttcacgtt caacaaggat   2340
ggcttccggg acttcccggc catggtgcag gagctgcacc agggcggccg gcgctacatg   2400
atgatcgtgg atcctgccat cagcagctcg ggccctgccg ggagctacag gccctacgac   2460
gagggtctgc ggagggggt tttcatcacc aacgagaccg gccagccgct gattgggaag   2520
gtatggcccg ggtccactgc cttccccgac ttcaccaacc ccacagccct ggcctggtgg   2580
gaggacatgg tggctgagtt ccatgaccag gtgcccttcg acggcatgtg gattgacatg   2640
aacgagcctt ccaacttcat caggggctct gaggacggct gccccaacaa tgagctggag   2700
aacccaccct acgtgcctgg ggtggttggg gggaccctcc aggcggccac catctgtgcc   2760
tccagccacc agtttctctc cacacactac aacctgcaca acctctacgg cctgaccgaa   2820
gccatcgcct cccacagggc gctggtgaag ctcgggga cacgcccatt tgtgatctcc   2880
cgctcgacct tgctggcca cggccgatac gccggccact ggacggggga cgtgtgagc   2940
tcctgggagc agctcgcctc ctccgtgcca gaaatcctgc agtttaacct gctgggggtg   3000
cctctggtcg gggccgacgt ctgcggcttc ctgggcaaca cctcagagga gctgtgtgtg   3060
cgctggaccc agctgggggc cttctacccc ttcatgcgga ccacaacag cctgctcagt   3120
ctgccccagg agccgtacag cttcagcgag ccggcccagc aggccatgag gaaggccctc   3180
accctgcgct acgcactcct ccccccacctc tacacactgt tccaccaggc ccacgtcgcg   3240
ggggagaccg tggcccggcc cctcttcctg gagttcccca aggactctag cacctggact   3300
gtggaccacc agctcctgtg gggggaggcc ctgctcatca ccccagtgct ccaggccggg   3360
aaggccgaag tgactggcta cttccccttg ggcacatggt acgacctgca gacggtgcca   3420
gtagaggccc ttggcagcct cccaccccca cctgcagctc cccgtgagcc agccatccac   3480
agcgaggggc agtgggtgac gctgccggcc ccsctggaca ccatcaacgt ccacctccgg   3540
gctgggtaca tcatcccsct gcagggccct ggcctcacaa ccacagagtc ccgccagcag   3600
cccatggccc tggctgtggc cctgaccaag ggtggggagg cccgagggga gctgttctgg   3660
gacgatggag agagcctgga agtgctggag cgaggggcct acacacaggt catcttcctg   3720
gccaggaata acacgatcgt gaatgagctg gtacgtgtga ccagtgaggg agctggcctg   3780
cagctgcaga aggtgactgt cctgggcgtg gccacggcgc cccagcaggt cctctccaac   3840
ggtgtccctg tctccaactt cacctacagc cccgacacca aggtcctgga catctgtgtc   3900
tcgctgttga tgggagagca gtttctcgtc agctggtgtt agcctaggaa taaaagatct   3960
ttattttcat tagatctgtg tgttggtttt ttgtgtgacc cgtctgattt tgtaggtaac   4020
cacgtgcgga ccgagcggcc gcaggaaccc ctagtgatgg agttggccac tccctctctg   4080
```

```
cgcgctcgct cgctcactga ggccgggcga ccaaaggtcg cccgacgccc gggctttgcc    4140
cgggcggcct cagtgagcga gcgagcgcgc agctgcctgc aggggcgcct gatgcggtat    4200
tttctcctta cgcatctgtg cggtatttca caccgcatac gtcaaagcaa ccatagtacg    4260
cgccctgtag cggcgcatta agcgcggcgg gtgtggtggt tacgcgcagc gtgaccgcta    4320
cacttgccag cgccctagcg cccgctcctt tcgctttctt cccttccttt ctcgccacgt    4380
tcgccggctt tccccgtcaa gctctaaatc ggggctccc tttagggttc cgatttagtg    4440
ctttacggca cctcgacccc aaaaaacttg atttgggtga tggttcacgt agtgggccat    4500
cgccctgata cacggttttt cgccctttga cgttggagtc cacgttcttt aatagtggac    4560
tcttgttcca aactggaaca cactcaacc ctatctcggg ctattctttt gatttataag    4620
ggattttgcc gatttcggcc tattggttaa aaaatgagct gatttaacaa aaatttaacg    4680
cgaattttaa caaaatatta acgttacaa ttttatggtg cactctcagt acaatctgct    4740
ctgatgccgc atagttaagc cagccccgac accgccaac accgctgac gcgccctgac    4800
gggcttgtct gctcccggca tccgcttaca gacaagctgt gaccgtctcc gggagctgca    4860
tgtgtcagag gttttcaccg tcatcaccga aacgcgcgag acgaaagggc ctcgtgatac    4920
gcctattttt ataggttaat gtcatgataa taatggtttc ttagacgtca ggtggcactt    4980
ttcggggaaa tgtgcgcgga acccctattt gtttattttt ctaaatacat tcaaatatgt    5040
atccgctcat gagacaataa ccctgataaa tgcttcaata atattgaaaa aggaagagta    5100
tgagtattca acatttccgt gtcgccctta ttccctttt tgcggcattt tgccttcctg    5160
tttttgctca cccagaaacg ctggtgaaag taaaagatgc tgaagatcag ttgggtgcac    5220
gagtgggtta catcgaactg gatctcaaca gcggtaagat ccttgagagt tttcgccccg    5280
aagaacgttt tccaatgatg agcactttta aagttctgct atgtggcgcg gtattatccc    5340
gtattgacgc cgggcaagag caactcggtc gccgcataca ctattctcag aatgacttgg    5400
ttgagtactc accagtcaca gaaaagcatc ttacggatgg catgacagta agagaattat    5460
gcagtgctgc cataaccatg agtgataaca ctgcggccaa cttacttctg acaacgatcg    5520
gaggaccgaa ggagctaacc gcttttttgc acaacatggg ggatcatgta actcgccttg    5580
atcgttggga accggagctg aatgaagcca taccaaacga cgagcgtgac accacgatgc    5640
ctgtagcaat ggcaacaacg ttgcgcaaac tattaactgg cgaactactt actctagctt    5700
cccggcaaca attaatagac tggatggagg cggataaagt tgcaggacca cttctgcgct    5760
cggcccttcc ggctggctgg tttattgctg ataaatctgg agccggtgag cgtgggtctc    5820
gcggtatcat tgcagcactg gggccagatg gtaagccctc ccgtatcgta gttatctaca    5880
cgacggggag tcaggcaact atggatgaac gaaatagaca gatcgctgag ataggtgcct    5940
cactgattaa gcattggtaa ctgtcagacc aagtttactc atatatactt tagattgatt    6000
taaaacttca ttttaatttt aaaaggatct aggtgaagat cctttttgat aatctcatga    6060
ccaaaatccc ttaacgtgag ttttcgttcc actgagcgtc agaccccgta gaaaagatca    6120
aaggatcttc ttgagatcct ttttttctgc gcgtaatctg ctgcttgcaa acaaaaaaac    6180
caccgctacc agcggtggtt tgtttgccgg atcaagagct accaactctt tttccgaagg    6240
taactggctt cagcagagcg cagataccaa atactgtcct tctagtgtag ccgtagttag    6300
gccaccactt caagaactct gtagcaccgc ctacatacct cgctctgcta atcctgttac    6360
cagtggctgc tgccagtggc gataagtcgt gtcttaccgg gttggactca agacgatagt    6420
taccggataa ggcgcagcgg tcgggctgaa cggggggttc gtgcacacag cccagcttgg    6480
```

| agcgaacgac | ctacaccgaa | ctgagatacc | tacagcgtga | gctatgagaa | agcgccacgc | 6540 |
| tcccgaagg | gagaaaggcg | gacaggtatc | cggtaagcgg | cagggtcgga | acaggagagc | 6600 |
| gcacgaggga | gcttccaggg | ggaaacgcct | ggtatcttta | tagtcctgtc | gggtttcgcc | 6660 |
| acctctgact | tgagcgtcga | tttttgtgat | gctcgtcagg | ggggcggagc | ctatggaaaa | 6720 |
| acgccagcaa | cgcggccttt | ttacggttcc | tggccttttg | ctggccttt | gctcacatgt | 6780 |

<210> SEQ ID NO 134
<211> LENGTH: 6355
<212> TYPE: DNA
<213> ORGANISM: Artificial Sequence
<220> FEATURE:
<223> OTHER INFORMATION: plasmid pAAVss-hDES1.4kb-MVM-hMTM1co-SynthpA

<400> SEQUENCE: 134

| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | taggggttcc | tgcggccgcg | gcgcgccacc | ggtacacacc | tactagtaac | 180 |
| ccctccagct | ggtgatggca | ggtctagggt | aggaccagtg | actggctcct | aatcgagcac | 240 |
| tctattttca | gggtttgcat | tccaaaaggg | tcaggtccaa | gagggacctg | gagtgccaag | 300 |
| tggaggtgta | gaggcacggc | cagtacccat | ggagaatggt | ggatgtcctt | aggggttagc | 360 |
| aagtgccgtg | tgctaaggag | ggggctttgg | aggttgggca | ggccctctgt | ggggctccat | 420 |
| ttttgtgggg | gtgggggctg | gagcattata | ggggtgggga | agtgattggg | gctgtcaccc | 480 |
| tagccttcct | tatctgacgc | ccacccatgc | ctcctcaggt | acccctgcc | cccacagct | 540 |
| cctctcctgt | gccttgtttc | ccagccatgc | gttctcctct | ataaataccc | gctctggtat | 600 |
| tgggggttgg | cagctgttgc | tgccagggag | atggttgggt | tgacatgcgg | ctcctgacaa | 660 |
| aacacaaacc | cctggtgtgt | gtgggcgtgg | gtggtgtgag | taggggatg | aatcagggag | 720 |
| ggggcggggg | acccaggggg | caggagccac | acaaagtctg | tgcggggtg | ggagcgcaca | 780 |
| tagcaattgg | aaactgaaag | cttatcagac | cctttctgga | aatcagccca | ctgtttataa | 840 |
| acttgaggcc | ccaccctcga | cagtaccggg | gaggaagagg | gcctgcacta | gtccagaggg | 900 |
| aaactgaggc | tcagggctag | ctcgcccata | gacatacatg | gcaggcaggc | tttggccagg | 960 |
| atccctccgc | ctgccaggcg | tctccctgcc | ctcccttcct | gcctagagac | ccccacccctc | 1020 |
| aagcctggct | ggtctttgcc | tgagacccaa | acctcttcga | cttcaagaga | atatttagga | 1080 |
| acaaggtggt | ttagggcctt | tcctgggaac | aggccttgac | cctttaagaa | atgacccaaa | 1140 |
| gtctctcctt | gaccaaaaag | gggaccctca | aactaaaggg | aagcctctct | tctgctgtct | 1200 |
| cccctgaccc | cactccccc | caccccagga | cgaggagata | accagggctg | aaagaggccc | 1260 |
| gcctgggggc | tgcagacatg | cttgctgcct | gccctggcga | aggattggca | ggcttgcccg | 1320 |
| tcacaggacc | cccgctggct | gactcagggg | cgcaggcctc | ttgcggggga | gctggcctcc | 1380 |
| ccgcccccac | ggccacgggc | cgcccttcc | tggcaggaca | gcgggatctt | gcagctgtca | 1440 |
| ggggagggga | ggcgggggct | gatgtcagga | gggatacaaa | tagtgccgac | ggctgggggc | 1500 |
| cctgtctccc | ctcgccgcat | ccactctccg | gccggccgcc | tgcccgccgc | ctcctccgtg | 1560 |
| cgcccgccag | cctcgcccgc | gccgtcacct | ctagaactag | taagaggtaa | gggtttaagg | 1620 |
| gatggttggt | tggtgggta | ttaatgttta | attacctgga | gcacctgcct | gaaatcactt | 1680 |
| ttttcaggt | tggcgtacgg | ccaccatggc | cagcgccagc | acaagcaagt | acaacagcca | 1740 |

```
cagcctggaa aacgagagca tcaagcggac cagcagagat ggcgtgaaca gagatctgac    1800
cgaggccgtt cctagactgc ctggcgagac actgatcacc gacaaagaag tgatctacat    1860
ctgccccttc aacggcccca tcaagggaag agtgtacatc accaactacc ggctgtacct    1920
gcggtccctg gaaaccgata gcagcctgat tctggatgtg ccctgggcg tgatcagccg     1980 gattgaaaaa atgggcggag ccacctccag aggcgagaat agctatggcc tggatatcac    2040
atgcaaggac atgcggaacc tgagattcgc cctgaagcaa gagggccaca gcagacggga    2100
catgttcgag atcctgacca gatacgcctt tcctctggct cactctctgc ccctgttcgc    2160
cttcctgaac gaagagaagt tcaacgtgga cggctggacc gtgtacaacc ccgtggaaga    2220
gtatagacgg cagggactgc ccaatcacca ctggcggatc accttcatca acaagtgcta    2280
cgagctgtgc gacacatacc ccgcactgct ggtggtgcct tacagagcct ctgacgacga    2340
tctgagaaga gtggccacct tcggagccg gaacagaatc cctgtgctga gctggattca    2400
ccccgagaac aagaccgtga tcgtgcggtg ttctcagcct ctcgtgggca tgagcggcaa    2460
gagaaacaag gacgacgaga agtacctgga cgtgatccgc gagacaaaca gcagatcag    2520 caagctgacc atctacgacg ccagaccttc tgtgaacgcc gtggccaaca aagccacagg    2580
cggcggatat gagtccgacg atgcctatca caacgccgag ctgttcttcc tggacattca    2640
caacatccat gtgatgcgcg agagcctgaa gaaagtgaag gacatcgtgt accccaatgt    2700
ggaagagagc cactggctgt ctagcctgga atccacacac tggctggaac acatcaagct    2760
ggtgctgaca ggcgccatcc aggtggcaga caaagtgtct agcggcaagt ctagcgtgct    2820
ggtgcactgt agcgacggat gggatagaac agcccagctg acatccctgg ccatgctgat    2880
gctggacagc ttctacagat ccatcgaggg cttttgagatc ctggtgcaga agaagtggat    2940
cagcttcggc cacaagttcg cctctagaat cggacacggc gacaagaacc acaccgacgc    3000
cgatagaagc cccatcttcc tgcagttcat cgactgcgtg tggcagatgt ccaagcagtt    3060
ccctaccgcc ttcgagttca acgagcagtt cctgatcatc atcctggacc acctgtactc    3120
ttgcagattc ggcaccttcc tgttcaactg cgagagcgcc agagaacggc agaaagtgac    3180
cgagagaacc gtgtctctgt ggtccctgat caacagcaac aaagagaaat tcaagaaccc    3240
cttctacacc aaagaaatca accgggtgct gtaccccgtg ccagcatga acatctgga    3300 actgtgggtc aactactaca tccggtggaa ccccagaatc aagcagcagc agcccaatcc    3360
tgtggaacag cggtatatgg aactgctggc cctgcgggac gagtacatca agagactgga    3420
agaactgcag ctggccaaca cgccaagct gagcgatcct cctacaagcc ctagcagccc    3480
ctctcagatg atgccccatg tgcagaccca cttttgacct aggaataaaa gatctttatt    3540
ttcattagat ctgtgtgttg gttttttgtg tgaaccgtct gattttgtag gtaaccacgt    3600
gcggaccgag cggccgcagg aaccctagt gatggagttg gccactccct ctctgcgcgc    3660
tcgctcgctc actgaggccg ggcgaccaaa ggtcgcccga cgcccgggct ttgcccgggc    3720
ggcctcagtg agcgagcgag cgcgcagctg cctgcagggg cgcctgatgc ggtatttctc    3780
ccttacgcat ctgtgcggta tttcacaccg catacgtcaa agcaaccata gtacgcgccc    3840
tgtagcggcg cattaagcgc ggcgggtgtg tggttacgc gcagcgtgac cgctacactt    3900
gccagcgccc tagcgcccgc tcctttcgct ttcttccctt cctttctcgc cacgttcgcc    3960
ggctttcccc gtcaagctct aaatcggggg ctccctttag ggttccgatt tagtgcttta    4020
cggcacctcg accccaaaaa acttgatttg ggtgatggtt cacgtagtgg gccatcgccc    4080
tgatagacgg ttttcgccc tttgacgttg gagtccacgt tctttaatag tggactcttg    4140
```

```
ttccaaactg gaacaacact caaccctatc tcgggctatt cttttgattt ataagggatt    4200
ttgccgattt cggccattg gttaaaaaat gagctgattt aacaaaaatt taacgcgaat    4260
tttaacaaaa tattaacgtt tacaattta tggtgcactc tcagtacaat ctgctctgat    4320
gccgcatagt taagccagcc ccgacacccg ccaacacccg ctgacgcgcc ctgacgggct    4380
tgtctgctcc cggcatccgc ttacagacaa gctgtgaccg tctccgggag ctgcatgtgt    4440
cagaggtttt caccgtcatc accgaaacgc gcgagacgaa agggcctcgt gatacgccta    4500 ttttatagg ttaatgtcat gataataatg gtttcttaga cgtcaggtgg cacttttcgg    4560
ggaaatgtgc gcggaacccc tatttgttta tttttctaaa tacattcaaa tatgtatccg    4620
ctcatgagac aataaccctg ataaatgctt caataatatt gaaaaggaa gagtatgagt    4680 attcaacatt tccgtgtcgc ccttattccc ttttttgcgg cattttgcct tcctgttttt    4740
gctcacccag aaacgctggt gaaagtaaaa gatgctgaag atcagttggg tgcacgagtg    4800
ggttacatcg aactggatct caacagcggt aagatccttg agagttttcg ccccgaagaa    4860
cgttttccaa tgatgagcac ttttaaagtt ctgctatgtg gcgcggtatt atcccgtatt    4920
gacgccgggc aagagcaact cggtcgccgc atacactatt ctcagaatga cttggttgag    4980
tactcaccag tcacagaaaa gcatcttacg gatggcatga cagtaagaga attatgcagt    5040
gctgccataa ccatgagtga taacactgcg gccaacttac ttctgacaac gatcggagga    5100
ccgaaggagc taaccgcttt tttgcacaac atggggatc atgtaactcg ccttgatcgt    5160
tgggaaccgg agctgaatga agccatacca aacgacgagc gtgacaccac gatgcctgta    5220
gcaatggcaa caacgttgcg caaactatta actggcgaac tacttactct agcttcccgg    5280
caacaattaa tagactggat ggaggcggat aaagttgcag gaccacttct gcgctcggcc    5340
cttccggctg gctggtttat tgctgataaa tctggagccg gtgagcgtgg gtctcgcggt    5400
atcattgcag cactggggcc agatggtaag ccctcccgta tcgtagttat ctacacgacg    5460
gggagtcagg caactatgga tgaacgaaat agacagatcg ctgagatagg tgcctcactg    5520
attaagcatt ggtaactgtc agaccaagtt tactcatata tactttagat tgatttaaaa    5580 cttcatttt aatttaaaag gatctaggtg aagatccttt ttgataatct catgaccaaa    5640
atcccttaac gtgagttttc gttccactga gcgtcagacc ccgtagaaaa gatcaaagga    5700
tcttcttgag atcctttttt tctgcgcgta atctgctgct tgcaaacaaa aaaaccaccg    5760
ctaccagcgg tggtttgttt gccggatcaa gagctaccaa ctctttttcc gaaggtaact    5820
ggcttcagca gagcgcagat accaaatact gtccttctag tgtagccgta gttaggccac    5880
cacttcaaga actctgtagc accgcctaca tacctcgctc tgctaatcct gttaccagtg    5940
gctgctgcca gtggcgataa gtcgtgtctt accgggttgg actcaagacg atagttaccg    6000
gataaggcgc agcggtcggg ctgaacgggg ggttcgtgca cacagcccag cttggagcga    6060
acgacctaca ccgaactgag atacctacag cgtgagctat gagaaagcgc cacgcttccc    6120
gaagggagaa aggcggacag gtatccggta agcggcaggg tcggaacagg agagcgcacg    6180
agggagcttc caggggggaaa cgcctggtat ctttatagtc ctgtcgggtt tcgccacctc    6240
tgacttgagc gtcgattttt gtgatgctcg tcagggggc ggagcctatg gaaaaacgcc    6300
agcaacgcgg cctttttacg gttcctggcc ttttgctggc cttttgctca catgt         6355

<210> SEQ ID NO 135
<211> LENGTH: 6355
<212> TYPE: DNA
```

<213> ORGANISM: Artificial Sequence
<220> FEATURE:
<223> OTHER INFORMATION: plasmid pAAVss-hDES1.4kb-MVM-hMTM1-SynthpA

<400> SEQUENCE: 135

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgcg cgcgccacc ggtacacacc tactagtaac     180
ccctccagct ggtgatggca ggtctagggt aggaccagtg actggctcct aatcgagcac    240
tctattttca gggtttgcat tccaaaaggg tcaggtccaa gagggacctg gagtgccaag    300
tggaggtgta gaggcacggc cagtacccat ggagaatggt ggatgtcctt aggggttagc    360
aagtgccgtg tgctaaggag ggggcttttgg aggttgggca ggccctctgt ggggctccat   420
ttttgtgggg gtgggggctg gagcattata ggggtggga agtgattggg gctgtcaccc     480
tagccttcct tatctgacgc ccacccatgc ctcctcaggt accccctgcc cccacagct     540
cctctcctgt gccttgtttc ccagccatgc gttctcctct ataaataccc gctctggtat    600
ttggggttgg cagctgttgc tgccagggag atggttgggt tgacatgcgg ctcctgacaa    660
aacacaaacc cctggtgtgt gtgggcgtgg gtggtgtgag taggggatg aatcaggag      720
ggggcggggg acccaggggg caggagccac acaaagtctg tgcggggtg ggagcgcaca     780
tagcaattgg aaactgaaag cttatcagac cctttctgga aatcagccca ctgtttataa    840
acttgaggcc ccaccctcga cagtaccggg gaggaagagg gcctgcacta gtccagaggg   900
aaactgaggc tcagggctag ctcgcccata gacatacatg gcaggcaggc tttggccagg    960
atccctccgc ctgccaggcg tctccctgcc ctcccttcct gcctagagac ccccacctc    1020
aagcctggct ggtctttgcc tgagacccaa acctcttcga cttcaagaga atattagga    1080
acaaggtggt ttagggcctt tcctgggaac aggccttgac cctttaagaa atgacccaaa   1140
gtctctcctt gaccaaaaag gggaccctca aactaaaggg aagcctctct tctgctgtct   1200
cccctgaccc cactcccccc cacccaggga cgaggagata accagggctg aaagaggccc   1260
gcctgggggc tgcagacatg cttgctgcct gccctggcga aggattggca ggcttgcccg    1320
tcacaggacc cccgctggct gactcagggg cgcaggcctc ttgcggggga gctggcctcc    1380
ccgcccccac ggccacgggc cgcccttttcc tggcaggaca gcgggatctt gcagctgtca   1440
ggggagggga ggcgggggct gatgtcagga gggatacaaa tagtgccgac ggctgggggc   1500
cctgtctccc ctcgccgcat ccactctccg gccggccgcc tgcccgccgc ctcctccgtg   1560
cgcccgccag cctcgcccgc gccgtcacct ctagaactag taagaggtaa gggtttaagg   1620
gatggttggt tggtgggta ttaatgttta attacctgga gcacctgcct gaaatcactt    1680
tttttcaggt tggcgtacgg ccaccatggc ttctgcatca acttctaaat ataattcaca   1740
ctccttggag aatgagtcta ttaagaggac gtctcgagat ggagtcaatc gagatctcac   1800
tgaggctgtt cctcgacttc caggagaaac actaatcact gacaaagaag ttatttacat   1860
atgtcctttc aatggcccca ttaagggaag agtttacatc acaaattatc gtctttattt   1920
aagaagtttg gaaacggatt cttctctaat acttgatgtt cctctgggtg tgatctcgag   1980
aattgaaaaa atgggaggcg cgacaagtag aggagaaaat tcctatggtc tagatattac   2040
ttgtaaagac atgagaaacc tgaggttcgc tttgaaacag gaaggccaca gcagaagaga   2100
tatgtttgag atcctcacga gatacgcgtt tcccctggct cacagtctgc cattatttgc   2160
attttttaaat gaagaaaagt ttaacgtgga tgatggaca gtttacaatc cagtggaaga   2220
```

```
atacaggagg cagggcttgc ccaatcacca ttggagaata acttttatta ataagtgcta    2280
tgagctctgt gacacttacc ctgctctttt ggtggttccg tatcgtgcct cagatgatga    2340
cctccggaga gttgcaactt ttaggtcccg aaatcgaatt ccagtgctgt catggattca    2400
tccagaaaat aagacggtca ttgtgcgttg cagtcagcct cttgtcggta tgagtgggaa    2460
acgaaataaa gatgatgaga aatatctcga tgttatcagg gagactaata aacaaatttc    2520
taaactcacc atttatgatg caagacccag cgtaaatgca gtggccaaca aggcaacagg    2580
aggaggatat gaaagtgatg atgcatatca taacgccgaa cttttcttct tagacattca    2640
taatattcat gttatgcggg aatctttaaa aaaagtgaag acattgttt atcctaatgt     2700 agaagaatct cattggttgt ccagtttgga gtctactcat tggttagaac atatcaagct    2760
cgttttgaca ggagccattc aagtagcaga caaagtttct tcagggaaga gttcagtgct    2820
tgtgcattgc agtgacggat gggacaggac tgctcagctg acatccttgg ccatgctgat    2880
gttggatagc ttctatagga gcattgaagg gttcgaaata ctggtacaaa aaaaatggat    2940
aagttttgga cataaatttg catctcgaat aggtcatggt gataaaaacc acaccgatgc    3000
tgaccgttct cctattttc tccagtttat tgattgtgtg tggcaaatgt caaaacagtt     3060
ccctacagct tttgaattca atgaacaatt tttgattata attttggatc atctgtatag    3120
ttgccgattt ggtactttct tattcaactg tgaatctgct cgagaaagac agaaggttac    3180
agaaaggact gtttctttat ggtcactgat aaacagtaat aaagaaaaat tcaaaaaccc    3240
cttctatact aaagaaatca atcgagtttt atatccagtt gccagtatgc gtcacttgga    3300
actctgggtg aattactaca ttagatggaa ccccaggatc aagcaacaac agccgaatcc    3360
agtggagcag cgttacatgg agctcttagc cttacgcgac gaatacataa agcggcttga    3420
ggaactgcag ctcgccaact ctgccaagct ttctgatccc ccaacttcac cttccagtcc    3480
ttcgcaaatg atgcccccatg tgcaaactca cttctgacct aggaataaaa gatctttatt    3540
ttcattagat ctgtgtgttg gttttttgtg tgacccgtct gattttgtag gtaaccacgt    3600
gcggaccgag cggccgcagg aaccctagt gatggagttg ccactccct ctctgcgcgc      3660 tcgctcgctc actgaggccg ggcgaccaaa ggtcgcccga cgcccgggct tgcccgggc     3720 ggcctcagtg agcgagcgag cgcgcagctg cctgcagggg cgcctgatgc ggtattttct    3780
ccttacgcat ctgtgcggta tttcacaccg catacgtcaa agcaaccata gtacgcgccc    3840
tgtagcggcg cattaagcgc ggcgggtgtg gtggttacgc gcagcgtgac cgctacactt    3900
gccagcgccc tagcgcccgc tcctttcgct ttcttccctt cctttctcgc cacgttcgcc    3960
ggctttcccc gtcaagctct aaatcggggg ctcccttag ggttccgatt tagtgcttta    4020
cggcacctcg acccccaaaaa acttgatttg ggtgatggtt cacgtagtgg gccatcgccc    4080
tgatagacgg ttttcgccc tttgacgttg gagtccacgt tctttaatag tggactcttg    4140
ttccaaactg gaacaacact caaccctatc tcggctatt ctttgatttt ataagggatt    4200
ttgccgattt cggcctattg gttaaaaaat gagctgattt aacaaaaatt taacgcgaat    4260
tttaacaaaa tattaacgtt tacaattta tggtgcactc tcagtacaat ctgctctgat    4320
gccgcatagt taagccagcc ccgacacccg ccaacacccg ctgacgcgcc ctgacgggct    4380
tgtctgctcc cggcatccgc ttacagacaa gctgtgaccg tctccgggag ctgcatgtgt    4440
cagaggtttt caccgtcatc accgaaacgc gcgagacgaa agggcctcgt gatacgccta    4500
tttttatagg ttaatgtcat gataataatg gtttcttaga cgtcaggtgg cacttttcgg    4560
```

```
ggaaatgtgc gcggaacccc tatttgttta tttttctaaa tacattcaaa tatgtatccg    4620
ctcatgagac aataaccctg ataaatgctt caataatatt gaaaaaggaa gagtatgagt    4680
attcaacatt tccgtgtcgc ccttattccc ttttttgcgg cattttgcct tcctgttttt    4740
gctcacccag aaacgctggt gaaagtaaaa gatgctgaag atcagttggg tgcacgagtg    4800
ggttacatcg aactggatct caacagcggt aagatccttg agagttttcg ccccgaagaa    4860
cgttttccaa tgatgagcac ttttaaagtt ctgctatgtg gcgcggtatt atcccgtatt    4920
gacgccgggc aagagcaact cggtcgccgc atacactatt ctcagaatga cttggttgag    4980
tactcaccag tcacagaaaa gcatcttacg gatggcatga cagtaagaga attatgcagt    5040
gctgccataa ccatgagtga taacactgcg gccaacttac ttctgacaac gatcggagga    5100
ccgaaggagc taaccgcttt tttgcacaac atgggggatc atgtaactcg ccttgatcgt    5160
tgggaaccgg agctgaatga agccatacca aacgacgagc gtgacaccac gatgcctgta    5220
gcaatggcaa caacgttgcg caaactatta actggcgaac tacttactct agcttcccgg    5280
caacaattaa tagactggat ggaggcggat aaagttgcag gaccacttct gcgctcggcc    5340
cttccggctg gctggtttat tgctgataaa tctggagccg gtgagcgtgg gtctcgcggt    5400
atcattgcag cactggggcc agatggtaag ccctcccgta tcgtagttat ctacacgacg    5460
gggagtcagg caactatgga tgaacgaaat agacagatcg ctgagatagg tgcctcactg    5520
attaagcatt ggtaactgtc agaccaagtt tactcatata cttagatt tgatttaaaa    5580 cttcatttt aatttaaaag gatctaggtg aagatccttt ttgataatct catgaccaaa    5640
atcccttaac gtgagttttc gttccactga gcgtcagacc ccgtagaaaa gatcaaagga    5700
tcttcttgag atccttttt tctgcgcgta atctgctgct tgcaaacaaa aaaaccaccg    5760
ctaccagcgg tggtttgttt gccggatcaa gagctaccaa ctcttttccc gaaggtaact    5820
ggcttcagca gagcgcagat accaaatact gtccttctag tgtagccgta gttaggccac    5880
cacttcaaga actctgtagc accgcctaca tacctcgctc tgctaatcct gttaccagtg    5940
gctgctgcca gtggcgataa gtcgtgtctt accgggttgg actcaagacg atagttaccg    6000
gataaggcgc agcggtcggg ctgaacgggg gttcgtgca cacagcccag cttggagcga    6060
acgacctaca ccgaactgag atacctacag cgtgagctat gagaaagcgc cacgcttccc    6120
gaagggagaa aggcggacag gtatccggta agcggcaggg tcggaacagg agagcgcacg    6180
agggagcttc caggggggaaa cgcctggtat ctttatagtc ctgtcgggtt tcgccacctc    6240
tgacttgagc gtcgattttt gtgatgctcg tcaggggggc ggagcctatg gaaaaacgcc    6300
agcaacgcgg cctttttacg gttcctggcc ttttgctggc cttttgctca catgt         6355
```

<210> SEQ ID NO 136
<211> LENGTH: 6808
<212> TYPE: DNA
<213> ORGANISM: Artificial Sequence
<220> FEATURE:
<223> OTHER INFORMATION: plasmid pAAVss-SKCRM4-hDES1.4kb-MVM-hMTM1co-
      SynthpA

<400> SEQUENCE: 136

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgcg gcgcgccacc ggtttctgag tcctctaagg     180
tccctcactc ccaactcagc cccatgtcct gtcaattccc actcagtgtc tgatctcctt     240
```

```
ctcctcacct ttcccatctc ccgtttgacc caagcttcct gagctctcct cccattcccc      300
ttttggagt cctcctcctc tcccagaacc cagtaataag tgggctcctc cctggcctgg       360
accccgtgg taaccctata aggcgaggca gctgctgtct gaggcaggga ggggctggtg       420
tgggaggcta agggcagctg ctaagtttag ggtggctcct tctctcttct tagagacaac     480
aggtggctgg ggcctcagtg cccagaaaag aaaatgtctt agaggtatcg gcatgggcct     540
ggaggagggg ggacagggca gggggaggca tcttcctcag gacatcgggt cctagagggg     600
tacccaacgg gttacgacac acctactagt aaccctcca gctggtgatg gcaggtctag     660
ggtaggacca gtgactggct cctaatcgag cactctattt tcagggtttg cattccaaaa   720
gggtcaggtc caagagggac ctggagtgcc aagtggaggt gtagaggcac ggccagtacc   780
catggagaat ggtggatgtc cttaggggtt agcaagtgcc gtgtgctaag gagggggctt   840
tggaggttgg gcaggccctc tgtggggctc cattttttgtg ggggtggggg ctggagcatt 900
ataggggtg ggaagtgatt ggggctgtca ccctagcctt ccttatctga cgcccaccca  960
tgcctcctca ggtacccct gccccccaca gctcctctcc tgtgccttgt ttcccagcca  1020
tgcgttctcc tctataaata cccgctctgg tatttggggt tggcagctgt tgctgccagg  1080
gagatggttg ggttgacatg cggctcctga caaaacacaa acccctggtg tgtgtgggcg  1140
tgggtggtgt gagtaggggg atgaatcagg gaggggcgg gggacccagg gggcaggagc   1200
cacacaaagt ctgtgcgggg gtgggagcgc acatagcaat tggaaactga agcttatca    1260
gacccttct ggaaatcagc ccactgttta taaacttgag ccccaccct cgacagtacc    1320
ggggaggaag agggcctgca ctagtccaga gggaaactga ggctcagggc tagctcgccc   1380
atagacatac atggcaggca ggctttggcc aggatccctc cgcctgccag gcgtctccct   1440
gccctccctt cctgcctaga gacccccacc ctcaagcctg gctggtcttt gcctgagacc   1500
caaacctctt cgacttcaag agaatattta ggaacaaggt ggtttagggc ctttcctggg   1560
aacaggcctt gacccttaa gaaatgaccc aaagtctctc cttgaccaaa aggggaccc    1620
tcaaactaaa gggaagcctc tcttctgctg tctcccctga ccccactccc ccccacccca  1680
ggacgaggag ataaccaggg ctgaaagagg cccgcctggg ggctgcagac atgcttgctg   1740
cctgccctgg cgaaggattg gcaggcttgc ccgtcacagg accccgctg gctgactcag    1800
gggcgcaggc ctcttgcggg ggagctggcc tccccgcccc cacggccacg ggccgccctt   1860
tcctggcagg acagcgggat cttgcagctg tcaggggagg ggaggcgggg gctgatgtca   1920
ggagggatac aaatagtgcc gacggctggg ggccctgtct cccctcgccg catccactct   1980
ccggccggcc gcctgcccgc cgcctcctcc gtgcgcccgc cagcctcgcc cgcgccgtca   2040
cctctagaac tagtaagagg taagggttta agggatggtt ggttggtggg gtattaatgt   2100
ttaattacct ggagcacctg cctgaaatca cttttttca ggttggcgta cggccaccat    2160
ggccagcgcc agcacaagca agtacaacag ccacagcctg gaaaacgaga gcatcaagcg   2220
gaccagcaga gatggcgtga acagagatct gaccgaggcc gttcctagac tgcctggcga  2280
gacactgatc accgacaaag aagtgatcta catctgcccc ttcaacggcc ccatcaaggg  2340
aagagtgtac atcaccaact accggctgta cctgcggtcc ctggaaaccg atagcagcct  2400
gattctggat gtgcccctgg gcgtgatcag ccggattgaa aaatgggcg agccacctc    2460
cagaggcgag aatagctatg cctggatat cacatgcaag gacatgcgga acctgagatt   2520
cgccctgaag caagagggcc acagcagacg ggacatgttc gagatcctga ccagatacgc   2580
cttttcctctg gctcactctc tgcccctgtt cgccttcctg aacgaagaga gttcaacgt   2640
```

-continued

```
ggacggctgg accgtgtaca accccgtgga agagtatata cggcagggac tgcccaatca    2700
ccactggcgg atcaccttca tcaacaagtg ctacgagctg tgcgacacat accccgcact    2760
gctggtggtg ccttacagag cctctgacga cgatctgaga agagtggcca cctttcggag    2820
ccggaacaga atccctgtgc tgagctggat tcaccccgag aacaagaccg tgatcgtgcg    2880
gtgttctcag cctctcgtgg gcatgagcgg caagagaaac aaggacgacg agaagtacct    2940
ggacgtgatc cgcgagacaa acaagcagat cagcaagctg accatctacg acgccagacc    3000
ttctgtgaac gccgtggcca acaaagccac aggcggcgga tatgagtccg acgatgccta    3060
tcacaacgcc gagctgttct tcctggacat tcacaacatc catgtgatgc gcgagagcct    3120
gaagaaagtg aaggacatcg tgtaccccaa tgtggaagag agccactggc tgtctagcct    3180
ggaatccaca cactggctgg aacacatcaa gctggtgctg acaggcgcca tccaggtggc    3240
agacaaagtg tctagcggca agtctagcgt gctggtgcac tgtagcgacg gatgggatag    3300
aacagcccag ctgacatccc tggccatgct gatgctggac agcttctaca gatccatcga    3360
gggctttgag atcctggtgc agaagaagtg gatcagcttc ggccacaagt tcgcctctag    3420
aatcggacac ggcgacaaga accacaccga cgccgataga agccccatct tcctgcagtt    3480
catcgactgc gtgtggcaga tgtccaagca gttccctacc gccttcgagt tcaacgagca    3540
gttcctgatc atcatcctgg accacctgta ctcttgcaga ttcggcacct tcctgttcaa    3600
ctgcgagagc gccagagaac ggcagaaagt gaccgagaga accgtgtctc tgtggtccct    3660
gatcaacagc aacaaagaga aattcaagaa ccccttctac accaaagaaa tcaaccgggt    3720
gctgtacccc gtggccagca tgagacatct ggaactgtgg gtcaactact acatccggtg    3780
gaaccccaga atcaagcagc agcagcccaa tcctgtggaa cagcggtata tggaactgct    3840
ggccctgcgg gacgagtaca tcaagagact ggaagaactg cagctggcca acagcgccaa    3900
gctgagcgat cctcctacaa gccctagcag ccctctcag atgatgcccc atgtgcagac    3960
ccacttttga cctaggaata aaagatcttt attttcatta gatctgtgtg ttggttttt    4020 gtgtgacccg tctgattttg taggtaacca cgtgcggacc gagcggccgc aggaacccct    4080
agtgatggag ttggccactc cctctctgcg cgctcgctcg ctcactgagg ccgggcgacc    4140
aaaggtcgcc cgacgcccgg gctttgcccg gcggcctca gtgagcgagc gagcgcgcag    4200
ctgcctgcag gggcgcctga tgcggtattt tctccttacg catctgtgcg gtatttcaca    4260
ccgcatacgt caaagcaacc atagtacgcg ccctgtagcg cgcattaag cgcggcgggt    4320 gtggtggtta cgcgcagcgt gaccgctaca cttgccagcg ccctagcgcc cgctccttc    4380 gctttcttcc cttcctttct cgccacgttc gccggctttc cccgtcaagc tctaaatcgg    4440
gggctccctt tagggttccg atttagtgct ttacggcacc tcgaccccaa aaaacttgat    4500
ttgggtgatg gttcacgtag tgggccatcg ccctgataga cggttttcg cccttgacg    4560 ttggagtcca cgttctttaa tagtggactc ttgttccaaa ctggaacaac actcaaccct    4620
atctcgggct attcttttga tttataaggg attttgccga tttcggccta ttggttaaaa    4680
aatgagctga tttaacaaaa atttaacgcg aattttaaca aaatattaac gtttacaatt    4740
ttatggtgca ctctcagtac aatctgctct gatgccgcat agttaagcca gccccgacac    4800
ccgccaacac ccgctgacgc gccctgacgg gcttgtctgc tcccggcatc cgcttacaga    4860
caagctgtga ccgtctccgg gagctgcatg tgtcagaggt tttcaccgtc atcaccgaaa    4920
cgcgcgagac gaaagggcct cgtgatacgc ctatttttat aggttaatgt catgataata    4980
```

| | | | |
|---|---|---|---|
| atggtttctt | agacgtcagg | tggcactttt | cggggaaatg tgcgcggaac ccctatttgt | 5040 |
| ttattttct | aaatacattc | aaatatgtat | ccgctcatga acaataacc ctgataaatg | 5100 |
| cttcaataat | attgaaaaag | gaagagtatg | agtattcaac atttccgtgt cgcccttatt | 5160 |
| cccttttttg | cggcattttg | ccttcctgtt | tttgctcacc cagaaacgct ggtgaaagta | 5220 |
| aaagatgctg | aagatcagtt | gggtgcacga | gtgggttaca tcgaactgga tctcaacagc | 5280 |
| ggtaagatcc | ttgagagttt | tcgccccgaa | gaacgttttc caatgatgag cacttttaaa | 5340 |
| gttctgctat | gtggcgcggt | attatcccgt | attgacgccg ggcaagagca actcggtcgc | 5400 |
| cgcatacact | attctcagaa | tgacttggtt | gagtactcac cagtcacaga aaagcatctt | 5460 |
| acggatggca | tgacagtaag | agaattatgc | agtgctgcca taaccatgag tgataacact | 5520 |
| gcggccaact | tacttctgac | aacgatcgga | ggaccgaagg agctaaccgc ttttttgcac | 5580 |
| aacatggggg | atcatgtaac | tcgccttgat | cgttgggaac cggagctgaa tgaagccata | 5640 |
| ccaaacgacg | agcgtgacac | cacgatgcct | gtagcaatgg caacaacgtt gcgcaaacta | 5700 |
| ttaactggcg | aactacttac | tctagcttcc | cggcaacaat aatagactg gatggaggcg | 5760 |
| gataaagttg | caggaccact | tctgcgctcg | gcccttccgg ctggctggtt tattgctgat | 5820 |
| aaatctggag | ccggtgagcg | tgggtctcgc | ggtatcattg cagcactggg gccagatggt | 5880 |
| aagccctccc | gtatcgtagt | tatctacacg | acggggagtc aggcaactat ggatgaacga | 5940 |
| aatagacaga | tcgctgagat | aggtgcctca | ctgattaagc attggtaact gtcagaccaa | 6000 |
| gtttactcat | atatacttta | gattgattta | aaacttcatt tttaatttaa aaggatctag | 6060 |
| gtgaagatcc | tttttgataa | tctcatgacc | aaaatccctt aacgtgagtt ttcgttccac | 6120 |
| tgagcgtcag | accccgtaga | aaagatcaaa | ggatcttctt gagatccttt ttttctgcgc | 6180 |
| gtaatctgct | gcttgcaaac | aaaaaaacca | ccgctaccag cggtggtttg tttgccggat | 6240 |
| caagagctac | caactctttt | tccgaaggta | actggcttca gcagagcgca gataccaaat | 6300 |
| actgtccttc | tagtgtagcc | gtagttaggc | caccacttca agaactctgt agcaccgcct | 6360 |
| acatacctcg | ctctgctaat | cctgttacca | gtggctgctg ccagtggcga taagtcgtgt | 6420 |
| cttaccgggt | tggactcaag | acgatagtta | ccggataagg cgcagcggtc gggctgaacg | 6480 |
| gggggttcgt | gcacacagcc | cagcttggag | cgaacgacct acaccgaact gagatacca | 6540 |
| cagcgtgagc | tatgagaaag | cgccacgctt | cccgaaggga gaaaggcgga caggtatccg | 6600 |
| gtaagcggca | gggtcggaac | aggagagcgc | acgagggagc ttccagggg aaacgcctgg | 6660 |
| tatctttata | gtcctgtcgg | gtttcgccac | ctctgacttg agcgtcgatt tttgtgatgc | 6720 |
| tcgtcagggg | ggcggagcct | atggaaaaac | gccagcaacg cggcctttt acggttcctg | 6780 |
| gccttttgct | ggccttttgc | tcacatgt | | 6808 |

<210> SEQ ID NO 137
<211> LENGTH: 6808
<212> TYPE: DNA
<213> ORGANISM: Artificial Sequence
<220> FEATURE:
<223> OTHER INFORMATION: plasmid pAAVss-SKCRM4-hDES1.4kb-MVM-hMTM1-SynthpA

<400> SEQUENCE: 137

| | | | |
|---|---|---|---|
| cctgcaggca | gctgcgcgct | cgctcgctca | ctgaggccgc ccgggcaaag cccgggcgtc | 60 |
| gggcgacctt | tggtcgcccg | gcctcagtga | gcgagcgagc gcgcagagag ggagtggcca | 120 |
| actccatcac | taggggttcc | tgcggccgcg | gcgcgccacc ggtttctgag tcctctaagg | 180 |

```
tccctcactc ccaactcagc cccatgtcct gtcaattccc actcagtgtc tgatctcctt      240
ctcctcacct ttcccatctc ccgtttgacc caagcttcct gagctctcct cccattcccc      300
tttttggagt cctcctcctc tcccagaacc cagtaataag tgggctcctc cctggcctgg      360 accccgtgg taaccctata aggcgaggca gctgctgtct gaggcaggga ggggctggtg       420
tgggaggcta agggcagctg ctaagtttag ggtggctcct tctctcttct tagagacaac      480
aggtggctgg ggcctcagtg cccagaaaag aaaatgtctt agaggtatcg catgggcct       540 ggaggagggg ggacagggca gggggaggca tcttcctcag gacatcgggt cctagagggg      600
tacccaacgg gttacgacac acctactagt aaccccctcca gctggtgatg gcaggtctag    660
ggtaggacca gtgactggct cctaatcgag cactctattt tcagggtttg cattccaaaa     720
gggtcaggtc caagagggac ctggagtgcc aagtggaggt gtagaggcac ggccagtacc     780
catggagaat ggtggatgtc cttaggggtt agcaagtgcc gtgtgctaag gagggggctt     840
tggaggttgg gcaggccctc tgtgggctc cattttttgtg ggggtggggg ctggagcatt     900 ataggggtg ggaagtgatt ggggctgtca ccctagcctt ccttatctga cgcccaccca      960
tgcctcctca ggtacccct gcccccaca gctcctctcc tgtgccttgt ttcccagcca       1020
tgcgttctcc tctataaata cccgctctgg tatttgggt tggcagctgt tgctgccagg     1080
gagatggttg ggttgacatg cggctcctga caaaacacaa acccctggtg tgtgtgggcg    1140
tgggtggtgt gagtaggggg atgaatcagg gaggggcgg gggacccagg gggcaggagc     1200
cacacaaagt ctgtgcgggg gtgggagcgc acatagcaat tggaaactga aagcttatca    1260 gacccttct ggaaatcagc ccactgttta taaacttgag gccccaccct cgacagtacc     1320
ggggaggaag agggcctgca ctagtccaga gggaaactga ggctcagggc tagctcgccc    1380
atagacatac atggcaggca ggctttggcc aggatccctc cgcctgccag gcgtctccct   1440 gccctcccctt cctgcctaga gacccccacc ctcaagcctg gctggtcttt gcctgagacc  1500
caaacctctt cgacttcaag agaatatttta ggaacaaggt ggtttagggc cttcctggg   1560 aacaggcctt gacccttaa gaaatgaccc aaagtctctc cttgaccaaa aaggggaccc    1620
tcaaactaaa gggaagcctc tcttctgctg tctccctga ccccactccc ccccacccca   1680
ggacgaggag ataaccaggg ctgaaagagg cccgcctggg ggctgcagac atgcttgctg   1740
cctgccctgg cgaaggattg gcaggcttgc ccgtcacagg accccgctg gctgactcag   1800 gggcgcaggc ctcttgcggg ggagctggcc tccccgcccc cacggccacg ggccgccctt   1860
tcctggcagg acagcgggat cttgcagctg tcagggagg ggaggcgggg gctgatgtca   1920
ggagggatac aaatagtgcc gacggctggg ggccctgtct cccctcgccg catccactct   1980
ccggccggcc gcctgcccgc cgcctcctcc gtgcgcccgc cagccgcgcc cgcgccgtca    2040
cctctagaac tagtaagagg taagggttta agggatggtt ggttggtggg gtattaatgt    2100 ttaattaccct ggagcacctg cctgaaatca cttttttttca ggttggcgta cggccaccat   2160
ggcttctgca tcaacttcta aatataattc acactccttg gagaatgagt ctattaagag    2220
gacgtctcga gatggagtca atcgagatct cactgaggct gttcctcgac ttccaggaga    2280
aacactaatc actgacaaag aagtattta catatgtcct ttcaatggcc ccattaaggg    2340
aagagtttac atcacaaatt atcgtctta tttaagaagt ttggaaacgg attcttctct    2400
aatacttgat gttcctctgg gtgtgatctc gagaattgaa aaaatgggag gcgcgacaag   2460
tagaggagaa aattcctatg gtctagatat tacttgtaaa gacatgagaa acctgaggtt   2520
cgctttgaaa caggaaggcc acagcagaag agatatgttt gagatcctca cgagatacgc   2580
```

-continued

```
gtttcccctg gctcacagtc tgccattatt tgcattttta aatgaagaaa agtttaacgt    2640
ggatggatgg acagtttaca atccagtgga agaatacagg aggcagggct tgcccaatca    2700
ccattggaga ataacttttta ttaataagtg ctatgagctc tgtgacactt accctgctct    2760
tttggtggtt ccgtatcgtg cctcagatga tgacctccgg agagttgcaa cttttaggtc    2820
ccgaaatcga attccagtgc tgtcatggat tcatccagaa aataagacgg tcattgtgcg    2880
ttgcagtcag cctcttgtcg gtatgagtgg gaaacgaaat aaagatgatg agaaatatct    2940
cgatgttatc agggagacta ataaacaaat ttctaaactc accatttatg atgcaagacc    3000
cagcgtaaat gcagtggcca acaaggcaac aggaggagga tatgaaagtg atgatgcata    3060
tcataacgcc gaacttttct tcttagacat tcataatatt catgttatgc gggaatcttt    3120
aaaaaaagtg aaggacattg tttatcctaa tgtagaagaa tctcattggt tgtccagttt    3180
ggagtctact cattggttag aacatatcaa gctcgttttg acaggagcca ttcaagtagc    3240
agacaaagtt tcttcaggga agagttcagt gcttgtgcat tgcagtgacg gatgggacag    3300
gactgctcag ctgacatcct tggccatgct gatgttggat agcttctata ggagcattga    3360
agggttcgaa atactggtac aaaaaaaatg gataagtttt ggacataaat ttgcatctcg    3420
aataggtcat ggtgataaaa accacaccga tgctgaccgt tctcctattt ttctccagtt    3480
tattgattgt gtgtggcaaa tgtcaaaaca gttccctaca gcttttgaat tcaatgaaca    3540 attttttgatt ataattttgg atcatctgta tagttgccga tttggtactt tcttattcaa    3600
ctgtgaatct gctcgagaaa gacagaaggt tacagaaagg actgtttctt tatggtcact    3660
gataaacagt aataagaaaa aattcaaaaa ccccttctat actaagaaaa tcaatcgagt    3720
tttatatcca gttgccagta tgcgtcactt ggaactctgg gtgaattact acattagatg    3780
gaaccccagg atcaagcaac aacagccgaa tccagtggag cagcgttaca tggagctctt    3840
agccttacgc gacgaataca taaagcggct tgaggaactg cagctcgcca actctgccaa    3900
gctttctgat cccccaactt caccttccag tccttcgcaa atgatgcccc atgtgcaaac    3960
tcacttctga cctaggaata aaagatcttt atttttcatta gatctgtgtg ttggttttt    4020 gtgtgacccg tctgattttg taggtaacca cgtgcggacc gagcggccgc aggaacccct    4080
agtgatggag ttggccactc cctctctgcg cgctcgctcg ctcactgagg ccgggcgacc    4140
aaaggtcgcc cgacgcccgg gctttgcccg ggcggcctca gtgagcgagc gagcgcgcag    4200
ctgcctgcag gggcgcctga tgcggtattt tctccttacg catctgtgcg gtatttcaca    4260
ccgcatacgt caaagcaacc atagtacgcg ccctgtagcg gcgcattaag cgcggcgggt    4320
gtggtggtta cgcgcagcgt gaccgctaca cttgccagcg ccctagcgcc cgctcctttc    4380
gctttcttcc cttcctttct cgccacgttc gccggctttc ccgtcaagc tctaaatcgg    4440 gggctcccct tagggttccg atttagtgct ttacggcacc tcgaccccaa aaaacttgat    4500
ttgggtgatg gttcacgtag tgggccatcg ccctgataga cggttttccg ccctttgacg    4560
ttggagtcca cgttctttaa tagtggactc ttgttccaaa ctggaacaac actcaaccct    4620
atctcgggct attctttga tttataaggg attttgccga tttcggccta ttggttaaaa    4680
aatgagctga tttaacaaaa atttaacgcg aattttaaca aaatattaac gtttacaatt    4740
ttatggtgca ctctcagtac aatctgctct gatgccgcat agttaagcca gccccgacac    4800
ccgccaacac ccgctgacgc gccctgacgg gcttgtctgc tcccggcatc cgcttacaga    4860
caagctgtga ccgtctccgg gagctgcatg tgtcagaggt tttcaccgtc atcaccgaaa    4920
```

```
cgcgcgagac gaaagggcct cgtgatacgc ctatttttat aggttaatgt catgataata    4980
atggtttctt agacgtcagg tggcactttt cggggaaatg tgcgcggaac ccctatttgt    5040
ttatttttct aaatacattc aaatatgtat ccgctcatga caataaacc ctgataaatg     5100 cttcaataat attgaaaaag gaagagtatg agtattcaac atttccgtgt cgcccttatt    5160 ccctttttg cggcattttg ccttcctgtt tttgctcacc cagaaacgct ggtgaaagta     5220
aaagatgctg aagatcagtt gggtgcacga gtgggttaca tcgaactgga tctcaacagc    5280
ggtaagatcc ttgagagttt tcgccccgaa gaacgttttc caatgatgag cacttttaaa    5340
gttctgctat gtggcgcggt attatcccgt attgacgccg ggcaagagca actcggtcgc    5400
cgcatacact attctcagaa tgacttggtt gagtactcac cagtcacaga aaagcatctt    5460
acggatggca tgacagtaag agaattatgc agtgctgcca taaccatgag tgataacact    5520
gcggccaact tacttctgac aacgatcgga ggaccgaagg agctaaccgc ttttttgcac    5580
aacatggggg atcatgtaac tcgccttgat cgttgggaac cggagctgaa tgaagccata    5640
ccaaacgacg agcgtgacac cacgatgcct gtagcaatgg caacaacgtt gcgcaaacta    5700
ttaactggcg aactacttac tctagcttcc cggcaacaat taatagactg gatggaggcg    5760
gataaagttg caggaccact tctgcgctcg gcccttccgg ctggctggtt tattgctgat    5820
aaatctggag ccggtgagcg tgggtctcgc ggtatcattg cagcactggg gccagatggt    5880
aagccctccc gtatcgtagt tatctacacg acggggagtc aggcaactat ggatgaacga    5940
aatagacaga tcgctgagat aggtgcctca ctgattaagc attggtaact gtcagaccaa    6000
gtttactcat atatacttta gattgattta aaacttcatt tttaatttaa aaggatctag    6060
gtgaagatcc ttttttgataa tctcatgacc aaaatccctt aacgtgagtt ttcgttccac    6120
tgagcgtcag accccgtaga aaagatcaaa ggatcttctt gagatccttt ttttctgcgc    6180
gtaatctgct gcttgcaaac aaaaaaacca ccgctaccag cggtggtttg tttgccggat    6240
caagagctac caactctttt tccgaaggta actggcttca gcagagcgca gataccaaat    6300
actgtccttc tagtgtagcc gtagttaggc caccacttca gaactctgt agcaccgcct     6360 acatacctcg ctctgctaat cctgttacca gtggctgctg ccagtggcga taagtcgtgt    6420
cttaccgggt tggactcaag acgatagtta ccggataagg cgcagcggtc gggctgaacg    6480 ggggggttcgt gcacacagcc cagcttggag cgaacgacct acaccgaact gagatacctä   6540 cagcgtgagc tatgagaaag cgccacgctt cccgaaggga gaaaggcgga caggtatccg    6600
gtaagcggca gggtcggaac aggagagcgc acgagggagc ttccagggg aaacgcctgg     6660 tatctttata gtcctgtcgg gtttcgccac ctctgacttg agcgtcgatt tttgtgatgc    6720
tcgtcagggg gcggagcct atggaaaaac gccagcaacg cggcctttt acggttcctg      6780 gccttttgct ggccttttgc tcacatgt                                       6808
```

<210> SEQ ID NO 138
<211> LENGTH: 6308
<212> TYPE: DNA
<213> ORGANISM: Artificial Sequence
<220> FEATURE:
<223> OTHER INFORMATION: plasmid pAAVss-SPc5-12GTRM-MVM-hGAAco-SynthpA

<400> SEQUENCE: 138

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtaccgg ttggccaccg ccttcggcac     180
```

```
catcctcacg acacccaaat atggcgacgg gtgaggaatg gtggggagtt atttttagag     240
cggtgaggaa ggtgggcagg cagcaggtgt tggcgctcta aaataactc  ccgggagtta    300 tttttagagc ggaggaatgg tggacaccca aatatggcga cggttcctca cccgtcgcca    360
tatttgggtg tccgccctcg gccggggccg cattcctggg ggccgggcgg tgctcccgcc    420
cgcctcgata aaaggctccg gggcggcgg  cggcccacga gctacccgga ggagcgggag    480
gcgccaagct ctagatctag aactagtaag aggtaagggt ttaagggatg gttggttggt    540
ggggtattaa tgtttaatta cctggagcac ctgcctgaaa tcactttttt tcaggttggc    600
gtacggccac catgggcgtc agacatcctc catgttctca cagactgctg gccgtgtgtg    660
ctctggtgtc tcttgctaca gctgccctgc tgggacatat cctgctgcac gatttctgc    720 tggtgcccag agagctgtct ggcagctctc ctgtgctgga gaaacacac  cctgcacatc    780 agcagggcgc ctctagacct ggacctagag atgctcaagc ccatcctggc agacctagag    840
ccgtgcctac acagtgtgac gtgccaccta acagcagatt cgactgcgcc cctgacaagg    900
ccatcacaca agagcagtgt gaagccagag gctgctgcta cattcctgcc aaacaaggac    960
tgcagggcgc tcagatggga cagccttggt gcttcttccc accatcttac cccagctaca    1020
agctggaaaa cctgagcagc agcgagatgg gctacaccgc cacactgacc agaaccacac    1080
ctacattctt cccaaaggac atcctgacac tgcggctgga cgtgatgatg aaaccgaga    1140 accggctgca cttcaccatc aaggacccccg ccaatagaag atacgaggtg cccctggaaa    1200
cccctcacgt gcactctaga gccccatctc cactgtacag cgtggaattc agcgaggaac    1260
cctttggcgt gatcgtgcgg agacagctgg atggcagagt gctgctgaat accacagtgg    1320
cccctctgtt cttcgccgac cagtttctgc agctgagcac aagcctgcct agccagtata    1380
tcacaggcct ggccgaacac ctgtctccac tgatgctgag caccagctgg accagaatca    1440
ccctgtggaa cagagatctg gcccctacac ctggcgccaa tctgtacggc tctcacccctt    1500 tttatctggc cctggaagat ggcggaagcg cccacggtgt ctttctgctg aacagcaacg    1560
ccatggacgt ggtgctgcaa ccatctcctg ctctgtcttg gagaagcacc ggcggcatcc    1620
tggacgtgta catctttctg ggacccgagc ctaagagcgt ggtgcagcag tatctggatg    1680
tcgtgggcta ccccttcatg cctccttatt ggggcctggg cttccacctg tgtagatggg    1740
gatacagctc caccgccatc accagacagg tggtggaaaa catgacccgg gctcacttcc    1800
cactggatgt gcagtggaac gacctggact acatggactc cagacgggac ttcacctttta    1860 acaaggacgc cttcagagac ttccccgcca tggtgcaaga actgcatcaa ggcggcagac    1920
ggtacatgat gatcgtggat cctgccatct cttctagcgg ccctgccgga agctacagac    1980
cttatgatga gggcctgaga agaggcgtgt tcatcaccaa tgagacaggc cagcctctga    2040
tcggcaaagt gtggcctgga agcaccgcct ttccagactt caccaatcca accgctctgg    2100
cttggtggga agatatggtg gccgagttcc acgatcaggt gcccttcgat ggcatgtgga    2160
tcgacatgaa cgagcccagc aacttcatca ggggcagcga ggatggctgc cccaacaacg    2220
aactggaaaa tcctccttac gtgccaggcg ttgtcggagg aacactgcag gccgccacaa    2280
tttgtgccag cagccatcag tttctgagca ccccactacaa cctgcacaac ctgtacggcc    2340
tgaccgaggc cattgcctct catagagccc tggttaaggc cagaggcacc cggccttttg    2400
tgatcagcag aagcacattt gccggccacg gcagatatgc cggacattgg acagggacg    2460 tttggtctag ttgggagcag ctggcctcta gcgtgcccga gatcctgcag tttaatctgc    2520
```

```
tgggagtgcc cctcgtggga gccgatgttt gtggatttct gggcaacacc tccgaggaac    2580
tgtgcgtcag atggacacag ctgggcgcct tctatccctt catgagaaac acaacagcc     2640 tgctgagcct gcctcaagag ccttacagct ttagcgaacc cgcacagcag gccatgagaa    2700
aggccctgac tctgagatac gctctgctgc cccacctgta caccctgttt catcaagctc    2760
atgtggccgg cgagacagtg gccagaccac tgtttctgga attccccaag acagcagca    2820 cctggacagt ggatcatcag ctgctctggg gagaagccct gctcattaca cctgtgctgc    2880
aggctggcaa ggccgaagtg acaggatact ttcccctcgg cacttggtac gacctgcaga    2940
cagttcctgt ggaagctctg ggatctctgc ctccacctcc tgctgctcct agagagcctg    3000
ccattcactc tgaaggccag tgggttacac tgcccgctcc actggacacc atcaatgtgc    3060
acctgagagc cggctacatc atccctctgc aaggccctgg actgaccaca accgaaagca    3120
gacagcagcc aatggctctg gccgtggctc tgacaaaagg cggagaagct agaggcgaac    3180
tgttctggga tgacggcgag agcctggaag tgctggaacg gggagcctac acacaagtga    3240
tctttctcgc ccggaacaac accatcgtga acgaactcgt cagagtgacc agtgaaggtg    3300
ccggactgca gctccagaaa gtgacagtgc ttggagtggc cacagcaccc cagcaggttt    3360
tgtctaatgg cgtgccgtg tccaacttca catacagccc tgacaccaag gtgctggaca    3420
tctgtgtgtc tctgctgatg ggcgagcagt tcctggtgtc ctggtgttga cctaggaata    3480
aaagatcttt attttcatta gatctgtgtg ttggttttt gtgtgacccg tctgattttg     3540
taggtaacca cgtgcggacc gagcggccgc aggaacccct agtgatggag ttggccactc    3600
cctctctgcg cgctcgctcg ctcactgagg ccgggcgacc aaaggtcgcc cgacgcccgg    3660
gctttgcccg ggcggcctca gtgagcgagc gagcgcgcag ctgcctgcag ggcgcctga    3720 tgcggtattt tctccttacg catctgtgcg gtatttcaca ccgcatacgt caaagcaacc    3780
atagtacgcg ccctgtagcg gcgcattaag cgcggcgggt gtggtggtta cgcgcagcgt    3840
gaccgctaca cttgccagcg ccctagcgcc cgctcctttc gctttcttcc cttcctttct    3900
cgccacgttc gccggctttc cccgtcaagc tctaaatcgg gggctccctt tagggttccg    3960
atttagtgct ttacggcacc tcgaccccaa aaaacttgat tgggtgatg gttcacgtag     4020 tgggccatcg ccctgataga cggttttttcg ccctttgacg ttggagtcca cgttctttaa   4080
tagtggactc ttgttccaaa ctggaacaac actcaaccct atctcgggct attcttttga    4140
tttataaggg attttgccga tttcggccta ttggttaaaa aatgagctga tttaacaaaa    4200
atttaacgcg aattttaaca aaatattaac gtttacaatt ttatggtgca ctctcagtac    4260
aatctgctct gatgccgcat agttaagcca gccccgacac ccgccaacac ccgctgacgc    4320
gccctgacgg gcttgtctgc tcccggcatc cgcttacaga caagctgtga ccgtctccgg    4380
gagctgcatg tgtcagaggt tttcaccgtc atcaccgaaa cgcgcgagac gaaagggcct    4440
cgtgatacgc ctatttttat aggttaatgt catgataata atggtttctt agacgtcagg    4500
tggcactttt cggggaaatg tgcgcggaac ccctatttgt ttatttttct aaatacattc    4560
aaatatgtat ccgctcatga gacaataacc ctgataaatg cttcaataat attgaaaaag    4620
gaagagtatg agtattcaac atttccgtgt cgcccttatt ccctttttg cggcattttg     4680 ccttcctgtt tttgctcacc cagaaacgct ggtgaaagta aaagatgctg aagatcagtt    4740
gggtgcacga gtgggttaca tcgaactgga tctcaacagc ggtaagatcc ttgagagttt    4800
tcgccccgaa gaacgttttc caatgatgag cacttttaaa gttctgctat gtggcgcggt    4860
attatcccgt attgacgccg ggcaagagca actcggtcgc cgcatacact attctcagaa    4920
```

| | |
|---|---|
| tgacttggtt gagtactcac cagtcacaga aaagcatctt acggatggca tgacagtaag | 4980 |
| agaattatgc agtgctgcca taaccatgag tgataacact gcggccaact tacttctgac | 5040 |
| aacgatcgga ggaccgaagg agctaaccgc ttttttgcac aacatggggg atcatgtaac | 5100 |
| tcgccttgat cgttgggaac cggagctgaa tgaagccata ccaaacgacg agcgtgacac | 5160 |
| cacgatgcct gtagcaatgg caacaacgtt gcgcaaacta ttaactggcg aactacttac | 5220 |
| tctagcttcc cggcaacaat taatagactg gatggaggcg gataaagttg caggaccact | 5280 |
| tctgcgctcg gcccttccgg ctggctggtt tattgctgat aaatctggag ccggtgagcg | 5340 |
| tgggtctcgc ggtatcattg cagcactggg gccagatggt aagccctccc gtatcgtagt | 5400 |
| tatctacacg acggggagtc aggcaactat ggatgaacga aatagacaga tcgctgagat | 5460 |
| aggtgcctca ctgattaagc attggtaact gtcagaccaa gtttactcat atatacttta | 5520 |
| gattgattta aaacttcatt tttaatttaa aaggatctag gtgaagatcc tttttgataa | 5580 |
| tctcatgacc aaaatccctt aacgtgagtt ttcgttccac tgagcgtcag acccgtaga | 5640 |
| aaagatcaaa ggatcttctt gagatccttt ttttctgcgc gtaatctgct gcttgcaaac | 5700 |
| aaaaaaacca ccgctaccag cggtggtttg tttgccggat caagagctac caactctttt | 5760 |
| tccgaaggta actggcttca gcagagcgca gataccaaat actgtccttc tagtgtagcc | 5820 |
| gtagttaggc caccacttca agaactctgt agcaccgcct acatacctcg ctctgctaat | 5880 |
| cctgttacca gtggctgctg ccagtggcga taagtcgtgt cttaccgggt tggactcaag | 5940 |
| acgatagtta ccggataagg cgcagcggtc gggctgaacg gggggttcgt gcacacagcc | 6000 |
| cagcttggag cgaacgacct acaccgaact gagatactta cagcgtgagc tatgagaaag | 6060 |
| cgccacgctt cccgaaggga gaaaggcgga caggtatccg gtaagcggca gggtcggaac | 6120 |
| aggagagcgc acgagggagc ttccaggggg aaacgcctgg tatctttata gtcctgtcgg | 6180 |
| gtttcgccac ctctgacttg agcgtcgatt tttgtgatgc tcgtcagggg ggcggagcct | 6240 |
| atggaaaaac gccagcaacg cggcctttt acggttcctg gccttttgct ggccttttgc | 6300 |
| tcacatgt | 6308 |

<210> SEQ ID NO 139
<211> LENGTH: 6308
<212> TYPE: DNA
<213> ORGANISM: Artificial Sequence
<220> FEATURE:
<223> OTHER INFORMATION: plasmid pAAVss-SPc5-12GTRM-MVM-hGAA-SynthpA

<400> SEQUENCE: 139

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtaccgg ttggccaccg ccttcggcac | 180 |
| catcctcacg acacccaaat atggcgacgg gtgaggaatg gtgggagtt attttttagag | 240 |
| cggtgaggaa ggtgggcagg cagcaggtgt tggcgctcta aaataactc ccgggagtta | 300 |
| ttttttagagc ggaggaatgg tggacaccca aatatggcga cggttcctca cccgtcgcca | 360 |
| tatttgggtg tccgccctcg gccggggccg cattcctggg ggccgggcgg tgctcccgcc | 420 |
| cgcctcgata aaaggctccg gggccggcgg cggcccacga gctacccgga ggagcgggag | 480 |
| gcgccaagct ctagatctag aactagtaag aggtaagggt ttaagggatg gttggttggt | 540 |
| ggggtattaa tgtttaatta cctggagcac ctgcctgaaa tcacttttt tcaggttggc | 600 |

```
gtacggccac catgggagtg aggcacccgc cctgctccca ccggctcctg gccgtctgcg      660
ccctcgtgtc cttggcaacc gctgcactcc tggggcacat cctactccat gatttcctgc      720
tggttccccg agagctgagt ggctcctccc cagtcctgga ggagactcac ccagctcacc      780
agcagggagc cagcagacca gggcccgggg atgcccaggc acaccccggc cgtcccagag      840
cagtgcccac acagtgcgac gtcccccca acagccgctt cgattgcgcc cctgacaagg       900
ccatcaccca ggaacagtgc gaggcccgcg gctgttgcta catccctgca aagcaggggc      960
tgcagggagc ccagatgggg cagccctggt gcttcttccc acccagctac cccagctaca     1020
agctggagaa cctgagctcc tctgaaatgg gctacgggc cacctgacc cgtaccaccc       1080 ccaccttctt ccccaaggac atcctgaccc tgcggctgga cgtgatgatg gagactgaga     1140
accgcctcca cttcacgatc aaagatccag ctaacaggcg ctacgaggtg cccttggaga     1200
ccccgcatgt ccacagccgg gcaccgtccc cactctacag cgtggagttc tccgaggagc     1260
ccttcggggt gatcgtgcgc cggcagctgg acggccgcgt gctgctgaac acgacggtgg     1320
cgcccctgtt ctttgcggac cagttccttc agctgtccac ctcgctgccc tcgcagtata     1380
tcacaggcct cgccgagcac ctcagtcccc tgatgctcag caccagctgg accaggatca     1440
ccctgtggaa ccgggacctt gcgcccacgc ccggtgcgaa cctctacggg tctcacccttt    1500 tctacctggc gctggaggac ggcgggtcgg cacacgggt gttcctgcta aacagcaatg      1560
ccatggatgt ggtcctgcag ccgagccctg cccttagctg gaggtcgaca ggtgggatcc     1620
tggatgtcta catcttcctg ggcccagagc ccaagagcgt ggtgcagcag tacctggacg     1680
ttgtgggata cccgttcatg ccgccatact ggggcctggg cttccacctg tgccgctggg     1740
gctactcctc caccgctatc acccgccagg tggtggagaa catgaccagg gcccacttcc     1800
ccctggacgt ccagtggaac gacctggact acatggactc ccggagggac ttcacgttca     1860
acaaggatgg cttccgggac ttccggcca tggtgcagga gctgcaccag ggcggccggc     1920
gctacatgat gatcgtggat cctgccatca gcagctcggg cctgccgggg agctacaggc    1980
cctacgacga gggtctgcgg aggggggttt tcatcaccaa cgagaccggc cagccgctga    2040
ttgggaaggt atggcccggg tccactgcct tccccgactt caccaacccc acagccctgg    2100
cctggtggga ggacatggtg gctgagttcc atgaccaggt gcccttcgac ggcatgtgga    2160
ttgacatgaa cgagccttcc aacttcatca ggggctctga ggacggctgc cccaacaatg    2220
agctggagaa cccaccctac gtgcctgggg tggttggggg gaccctccag gcggccacca    2280
tctgtgcctc cagccaccag tttctctcca cacactacaa cctgcacaac ctctacggcc    2340
tgaccgaagc catcgcctcc cacagggcgc tggtgaaggc tcgggggaca cgcccatttg    2400
tgatctcccg ctcgacctt gctggccacg gccgatacgc cggccactgg acggggacg      2460 tgtggagctc ctgggagcag ctcgcctcct ccgtgccaga aatcctgcag tttaacctgc    2520
tgggggtgcc tctggtcggg gccgacgtct gcggcttcct gggcaacacc tcagaggagc    2580
tgtgtgtgcg ctggacccag ctgggggcct tctacccctt catgcggaac acaacagcc    2640 tgctcagtct gccccaggag ccgtacagct tcagcgagcc ggcccagcag gccatgagga    2700
aggccctcac cctgcgctac gcactcctcc cccacctcta cactgttc caccaggcc      2760 acgtcgcggg ggagaccgtg gcccggcccc tcttcctgga gttccccaag gactctagca    2820
cctggactgt ggaccaccag ctcctgtggg gggaggccct gctcatcacc ccagtgctcc    2880
aggccgggaa ggccgaagtg actggctact tccccttggg cacatggtac gacctgcaga    2940
cggtgccagt agaggccctt ggcagcctcc cacccccacc tgcagctccc cgtgagccag    3000
```

```
ccatccacag cgaggggcag tgggtgacgc tgccggcccc cctggacacc atcaacgtcc      3060
acctccgggc tgggtacatc atcccctgc agggccctgg cctcacaacc acagagtccc      3120
gccagcagcc catggccctg gctgtggccc tgaccaaggg tggggaggcc cgaggggagc      3180
tgttctggga cgatggagag agcctggaag tgctggagcg aggggcctac acacaggtca      3240
tcttcctggc caggaataac acgatcgtga atgagctggt acgtgtgacc agtgagggag      3300
ctggcctgca gctgcagaag gtgactgtcc tgggcgtggc cacggcgccc cagcaggtcc      3360
tctccaacgg tgtccctgtc tccaacttca cctacagccc cgacaccaag gtcctggaca      3420
tctgtgtctc gctgttgatg ggagagcagt ttctcgtcag ctggtgttag cctaggaata      3480
aaagatcttt attttcatta gatctgtgtg ttggtttttt gtgtgacccg tctgattttg      3540
taggtaacca cgtgcggacc gagcggccgc aggaacccct agtgatggag ttggccactc      3600
cctctctgcg cgctcgctcg ctcactgagg ccggcgacc aaaggtcgcc cgacgcccgg      3660
gctttgcccg ggcggcctca gtgagcgagc gagcgcgcag ctgcctgcag gggcgcctga      3720
tgcggtattt tctccttacg catctgtgcg gtatttcaca ccgcatacgt caaagcaacc      3780
atagtacgcg ccctgtagcg gcgcattaag cgcggcgggt gtggtggtta cgcgcagcgt      3840
gaccgctaca cttgccagcg ccctagcgcc cgctcctttc gctttcttcc cttcctttct      3900
cgccacgttc gccggctttc cccgtcaagc tctaaatcgg gggctccctt tagggttccg      3960
atttagtgct ttacggcacc tcgaccccaa aaaacttgat ttgggtgatg gttcacgtag      4020
tgggccatcg ccctgataga cggttttttcg ccctttgacg ttggagtcca cgttctttaa      4080
tagtggactc ttgttccaaa ctggaacaac actcaaccct atctcgggct attcttttga      4140
tttataaggg attttgccga tttcggccta ttggttaaaa atgagctga tttaacaaaa      4200 atttaacgcg aattttaaca aaatattaac gtttacaatt ttatggtgca ctctcagtac      4260
aatctgctct gatgccgcat agttaagcca gccccgacac ccgccaacac ccgctgacgc      4320
gccctgacgg gcttgtctgc tcccggcatc cgcttacaga caagctgtga ccgtctccgg      4380
gagctgcatg tgtcagaggt tttcaccgtc atcaccgaaa cgcgcgagac gaaagggcct      4440
cgtgatacgc ctatttttat aggttaatgt catgataata atggtttctt agacgtcagg      4500
tggcactttt cggggaaatg tgcgcggaac ccctatttgt ttatttttct aaatacattc      4560
aaatatgtat ccgctcatga acaataaccc tgataaatg cttcaataat attgaaaaag      4620
gaagagtatg agtattcaac atttccgtgt cgcccttatt ccctttttg cggcattttg      4680 ccttcctgtt tttgctcacc cagaaacgct ggtgaaagta aaagatgctg aagatcagtt      4740
gggtgcacga gtgggttaca tcgaactgga tctcaacagc ggtaagatcc ttgagagttt      4800
tcgccccgaa gaacgttttc caatgatgag cacttttaaa gttctgctat gtggcgcggt      4860
attatcccgt attgacgccg ggcaagagca actcggtcgc cgcatacact attctcagaa      4920
tgacttggtt gagtactcac cagtcacaga aaagcatctt acggatggca tgacagtaag      4980
agaattatgc agtgctgcca taaccatgag tgataacact gcggccaact tacttctgac      5040
aacgatcgga ggaccgaagg agctaaccgc ttttttgcac aacatggggg atcatgtaac      5100
tcgccttgat cgttgggaac cggagctgaa tgaagccata ccaaacgacg agcgtgacac      5160
cacgatgcct gtagcaatgg caacaacgtt gcgcaaacta ttaactggcg aactacttac      5220
tctagcttcc cggcaacaat taatagactg gatggaggcg gataaagttg caggaccact      5280
tctgcgctcg gcccttccgg ctggctggtt tattgctgat aaatctggag ccggtgagcg      5340
```

-continued

```
tgggtctcgc ggtatcattg cagcactggg gccagatggt aagccctccc gtatcgtagt    5400
tatctacacg acggggagtc aggcaactat ggatgaacga aatagacaga tcgctgagat    5460
aggtgcctca ctgattaagc attggtaact gtcagaccaa gtttactcat atatacttta    5520
gattgattta aaacttcatt tttaatttaa aaggatctag gtgaagatcc ttttgataa     5580 tctcatgacc aaaatccctt aacgtgagtt ttcgttccac tgagcgtcag accccgtaga    5640
aaagatcaaa ggatcttctt gagatccttt tttttctgcgc gtaatctgct gcttgcaaac   5700
aaaaaaacca ccgctaccag cggtggtttg tttgccggat caagagctac caactctttt   5760
tccgaaggta actggcttca gcagagcgca gataccaaat actgtccttc tagtgtagcc   5820
gtagttaggc caccacttca agaactctgt agcaccgcct acatacctcg ctctgctaat   5880
cctgttacca gtggctgctg ccagtggcga taagtcgtgt cttaccgggt tggactcaag   5940
acgatagtta ccggataagg cgcagcggtc gggctgaacg ggggggttcgt gcacacagcc   6000 cagcttggag cgaacgacct acaccgaact gagataccta cagcgtgagc tatgagaaag   6060
cgccacgctt cccgaaggga gaaaggcgga caggtatccg gtaagcggca gggtcggaac   6120
aggagagcgc acgagggagc ttccaggggg aaacgcctgg tatctttata gtcctgtcgg   6180
gtttcgccac ctctgacttg agcgtcgatt tttgtgatgc tcgtcagggg ggcggagcct   6240
atggaaaaac gccagcaacg cggccttttt acggttcctg gccttttgct ggccttttgc   6300
tcacatgt                                                             6308
```

```
<210> SEQ ID NO 140
<211> LENGTH: 21
<212> TYPE: DNA
<213> ORGANISM: Artificial Sequence
<220> FEATURE:
<223> OTHER INFORMATION: Forward Primer hGAA

<400> SEQUENCE: 140
tgccctcgca gtatatcaca g                                              21

<210> SEQ ID NO 141
<211> LENGTH: 19
<212> TYPE: DNA
<213> ORGANISM: Artificial Sequence
<220> FEATURE:
<223> OTHER INFORMATION: Reverse Primer hGAA

<400> SEQUENCE: 141
gagacccgta gaggttcgc                                                 19

<210> SEQ ID NO 142
<211> LENGTH: 20
<212> TYPE: DNA
<213> ORGANISM: Artificial Sequence
<220> FEATURE:
<223> OTHER INFORMATION: Forward Primer hGAAco

<400> SEQUENCE: 142
accccttcat gcctccttat                                                20

<210> SEQ ID NO 143
<211> LENGTH: 20
<212> TYPE: DNA
<213> ORGANISM: Artificial Sequence
<220> FEATURE:
<223> OTHER INFORMATION: Reverse Primer hGAAco

<400> SEQUENCE: 143
```

```
tccatgtagt ccaggtcgtt                                               20

<210> SEQ ID NO 144
<211> LENGTH: 23
<212> TYPE: DNA
<213> ORGANISM: Artificial Sequence
<220> FEATURE:
<223> OTHER INFORMATION: Forward Primer hMTM1

<400> SEQUENCE: 144
gtttgagatc ctcacgagat acg                                           23

<210> SEQ ID NO 145
<211> LENGTH: 23
<212> TYPE: DNA
<213> ORGANISM: Artificial Sequence
<220> FEATURE:
<223> OTHER INFORMATION: Reverse Primer hMTM1

<400> SEQUENCE: 145
gtccatccat ccacgttaaa ctt                                           23

<210> SEQ ID NO 146
<211> LENGTH: 20
<212> TYPE: DNA
<213> ORGANISM: Artificial Sequence
<220> FEATURE:
<223> OTHER INFORMATION: Forward Primer hMTM1co

<400> SEQUENCE: 146
ggcaagagaa acaaggacga                                               20

<210> SEQ ID NO 147
<211> LENGTH: 20
<212> TYPE: DNA
<213> ORGANISM: Artificial Sequence
<220> FEATURE:
<223> OTHER INFORMATION: Reverse Primer hMTM1co

<400> SEQUENCE: 147
ggcatcgtcg gactcatatc                                               20
```